(12) United States Patent
Bailey et al.

(10) Patent No.: US 9,133,215 B2
(45) Date of Patent: Sep. 15, 2015

(54) MACROCYCLIC DERIVATIVES FOR THE TREATMENT OF DISEASES

(71) Applicant: PFIZER INC., New York, NY (US)

(72) Inventors: Simon Bailey, San Diego, CA (US); Benjamin Joseph Burke, San Diego, CA (US); Michael Raymond Collins, San Diego, CA (US); Jingrong Jean Cui, San Diego, CA (US); Judith Gail Deal, Wildomar, CA (US); Robert Louis Hoffman, San Marcos, CA (US); Qinhua Huang, San Diego, CA (US); Ted William Johnson, Carlsbad, CA (US); Robert Steven Kania, San Diego, CA (US); John Charles Kath, La Mesa, CA (US); Phuong Thi Quy Le, San Diego, CA (US); Michele Ann McTigue, Encinitas, CA (US); Cynthia Louise Palmer, La Mesa, CA (US); Paul Francis Richardson, San Diego, CA (US); Neal William Sach, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/156,144

(22) Filed: Jan. 15, 2014

(65) Prior Publication Data
US 2014/0135339 A1  May 15, 2014

Related U.S. Application Data

(63) Continuation of application No. 13/786,106, filed on Mar. 5, 2013, now Pat. No. 8,680,111.

(60) Provisional application No. 61/607,485, filed on Mar. 6, 2012, provisional application No. 61/759,307, filed on Jan. 31, 2013.

(51) Int. Cl.
| | | |
|---|---|---|
| *C07D 273/02* | (2006.01) | |
| *C07D 413/04* | (2006.01) | |
| *C07D 413/14* | (2006.01) | |
| *C07D 491/08* | (2006.01) | |
| *C07D 491/18* | (2006.01) | |
| *C07D 498/08* | (2006.01) | |
| *C07D 498/18* | (2006.01) | |
| *C07D 498/22* | (2006.01) | |
| *C07D 513/18* | (2006.01) | |

(52) U.S. Cl.
CPC ............ *C07D 498/08* (2013.01); *C07D 491/08* (2013.01); *C07D 491/18* (2013.01); *C07D 498/18* (2013.01); *C07D 498/22* (2013.01); *C07D 513/18* (2013.01); *C07D 273/02* (2013.01); *C07D 413/04* (2013.01); *C07D 413/14* (2013.01)

(58) Field of Classification Search
CPC ............ A61K 31/5025; C07D 413/04; C07D 273/02; C07D 413/14; C07D 491/08; C07D 491/18; C07D 498/08; C07D 498/18; C07D 498/22; C07D 513/18
See application file for complete search history.

(56) References Cited

U.S. PATENT DOCUMENTS

| | | |
|---|---|---|
| 7,230,098 B2 | 6/2007 | Cui |
| 7,825,137 B2 | 11/2010 | Christensen |
| 7,858,643 B2 | 12/2010 | Cui |
| 8,217,057 B2 | 7/2012 | Cui |
| 8,362,236 B2 | 1/2013 | Shimma |
| 8,383,793 B2 | 2/2013 | Morris |
| 2006/0128724 A1 | 6/2006 | Cui |

FOREIGN PATENT DOCUMENTS

| | | |
|---|---|---|
| WO | WO 2004/026881 | 4/2004 |
| WO | WO 2004/076412 | 9/2004 |
| WO | WO 2004/078682 | 9/2004 |
| WO | WO 2006/021881 | 3/2006 |

(Continued)

OTHER PUBLICATIONS

Sakamoto et. al., Cancer Cell, 2011, Elsevier, vol. 19, pp. 679-690.*
Chabner et. al., Nature Reviews Cancer, 2005, Nature Publishing Group, vol. 5, pp. 65-72.*
Leaf, Fortune, Mar. 9, 2004, Time Inc., pp. 1-13.*
Choi Y.L. et al., "EML4-ALK Mutations in Lung Cancer That Confer Resistance to ALK Inhibitors," The New England Journal of Medicine, 2010, 363, 18, 1734-1739.
International Search Report for PCT Application No. PCT/IB2013/051391 mailed on Jun. 3, 2013.
International Written Opinion for PCT Application No. PCT/IB2013/051391 prepared on May 27, 2013.

(Continued)

*Primary Examiner* — Sarah Pihonak
(74) *Attorney, Agent, or Firm* — Leslie A. Robinson

(57) ABSTRACT

The invention relates to compounds of formula (Φ)

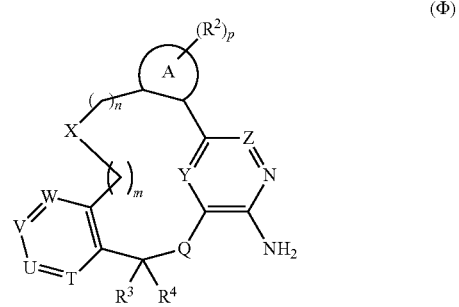

as further defined herein and to the pharmaceutically acceptable salts thereof, to pharmaceutical compositions comprising such compounds and salts, and to the uses thereof. The compounds and salts of the present invention inhibit anaplastic lymphoma kinase (ALK) and/or EML4-ALK and are useful for treating or ameliorating abnormal cell proliferative disorders, such as cancer.

18 Claims, 1 Drawing Sheet

(56) References Cited

FOREIGN PATENT DOCUMENTS

| | | |
|---|---|---|
| WO | WO 2006/021882 | 3/2006 |
| WO | WO 2006/021884 | 3/2006 |
| WO | WO 2006/108695 | 10/2006 |
| WO | WO 2007/066185 | 6/2007 |
| WO | WO 2007/066187 | 6/2007 |
| WO | WO 2008/088881 | 7/2008 |
| WO | WO 2008/105526 | 9/2008 |
| WO | WO 2009/132202 | 10/2009 |
| WO | WO2009132202 | 10/2009 |
| WO | WO 2010/085597 | 7/2010 |
| WO | WO2010085597 | 7/2010 |
| WO | WO 2011/047926 | 4/2011 |
| WO | WO 2011/138751 | 11/2011 |
| WO | WO2012016186 | 2/2012 |
| WO | WO2012125603 | 9/2012 |

OTHER PUBLICATIONS

Iwahara T. et al., "Molecular characterization of ALK, a receptor tyrosine kinase expressed specifically in the nervous system," Oncogene, 1997, 14, 439-449.

Kostich M et al., "Human members of the eukaryotic protein kinase family," Genome Biology, 2002, 3, 1-12.

Kwak et al., "Anaplastic lymphoma kinase inhibition in non-small-cell lung cancer," The New England Journal of Medicine, 2010;363(18):1693-1703.

Meng K. et al., "Pleiotrophin signals increased tyrosine phosphorylation of β-catenin through inactivation of the intrinsic catalytic activity of the receptor-type protein tyrosine phosphatase β/ζ," PNAS, 2000, 97, 2603-2608.

Milkiewicz K. et al., "Inhibitors of anaplastic lymphoma kinase: a patent review," Expert Opin. Ther. Patents, 2010, 20:1653-1681.

Perez-Pinera P. et al., "Anaplastic lymphoma kinase is activated through the pleiotrophin/receptor protein-tyrosine phosphatase beta/zeta signaling pathway: an alternative mechanism of receptor tyrosine kinase activation," J. Biol. Chem., 2007, 282, 28683-28690.

Soda M. et al., "Identification of the transforming EML4-ALK fusion gene in non-small-cell lung cancer," Nature. 2007;448(7153):561-566.

Stoica G.E. et al., "Identification of anaplastic lymphoma kinase as a receptor for the growth factor pleiotrophin," J. Biol. Chem., 2001, 276, 16772-16779.

Stoica G.E. et al., "Midkine binds to anaplastic lymphoma kinase (ALK) and acts as a growth factor for different cell types," J. Biol. Chem., 2002, 277, 35990-35998.

Turner S.D. et al., "The NPM-ALK tyrosine kinase mimics TCR signalling pathways, inducing NFAT and AP-1 by RAS-dependent mechanisms," Cell Signal, 2007, 19, 740-747.

Webb T.R. et al., "Anaplastic lymphoma kinase: role in cancer pathogenesis and small-molecule inhibitor development for therapy," Expert Reviews in Anticancer Therapy, 2009 9 331-355.

Vernersson E. et al., "Characterization of the expression of the ALK receptor tyrosine kinase in mice," Gene Expression Patterns. 2006;6(5):448-461.

Costa Rican Patent Opposition WO2013132376 dated Nov. 25, 2014.

English Translation of Costa Rican Patent Opposition WO2013132376 dated Nov. 25, 2014.

* cited by examiner

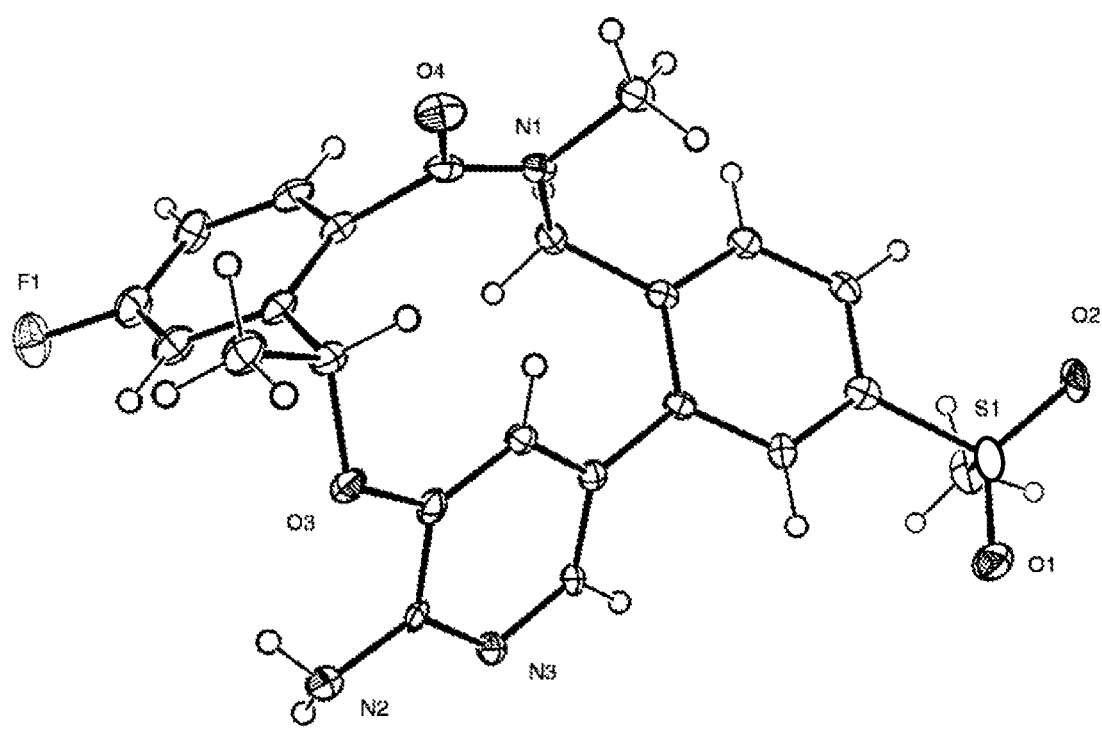

MACROCYCLIC DERIVATIVES FOR THE TREATMENT OF DISEASES

CROSS-REFERENCE TO RELATED APPLICATIONS

This application is a continuation application of U.S. patent application Ser. No. 13/786,106 filed on Mar. 5, 2013, now allowed, which claims the benefit of priority to U.S. Provisional Application No. 61/607,485 filed on Mar. 6, 2012, and U.S. Provisional Application No. 61/759,307 filed on Jan. 31, 2013, the contents of each of which are hereby incorporated by reference in their entirety.

REFERENCE TO SEQUENCE LISTING

This application is being filed electronically via EFS-Web and includes an electronically submitted sequence listing in .txt format. The .txt file contains a sequence listing entitled "PC71904B_SequenceListing.txt" created on Jan. 7, 2014 and having a size of 1 KB. The sequence listing contained in this .txt file is part of the specification and is herein incorporated by reference in its entirety.

FIELD OF THE INVENTION

The present invention relates to compounds of formulae (Φ) and (I)-(XXX) and their pharmaceutically acceptable salts, to pharmaceutical compositions comprising such compounds and salts, and to the uses thereof. The compounds and salts of the present invention inhibit anaplastic lymphoma kinase (ALK) and are useful for treating or ameliorating abnormal cell proliferative disorders, such as cancer.

BACKGROUND OF THE INVENTION

Anaplastic lymphoma kinase (ALK) is a member of the receptor tyrosine kinase superfamily, and at an amino acid sequence level is most closely related to members such as Ros-1, leucocyte tyrosine kinase, the insulin receptor and cMet (hepatic growth factor receptor) (Kostich M et al, Genome Biology, 2002, 3, 1-12). As with all members of this gene family, it possesses an extracellular ligand binding domain, a transmembrane spanning sequence, and an intracellular kinase catalytic region/signalling domain. The identity of the signalling ligand for ALK is not yet elucidated and different mechanisms have been proposed in the literature (Stoica G. E. et al., *J. Biol. Chem.*, 2001, 276, 16772-16779; Stoica G. E. et al., *J. Biol. Chem.*, 2002, 277, 35990-35999; Mewng K. et al., *PNAS*, 2000, 97, 2603-2608; Perez-Pinera P. et al., *J. Biol. Chem.*, 2007, 282, 28683-28690). The stimulation of ALK leads to an intracellular signalling cascade via phopholipase-C, PI3Kinase and STAT3 (amongst other signalling proteins) (Turner S. D. et al., *Cell Signal*, 2007, 19, 740-747).

ALK is largely expressed in the developing nervous system (Iwahara T. et al., *Oncogene*, 1997, 14, 439-449). Its relative abundance does tend to decrease in the adult animal, though its expression is maintained in certain regions of the brain, spinal cord and the eye (Vernersson E. et al., *Gene Expression Patterns*, 2006, 6, 448-461).

ALK has an important role in oncology (Webb T. R. et al., *Expert Reviews in Anticancer Therapy*, 2009 9 331-355). Point mutations in the full length ALK enzyme that lead to activation of the enzyme, and also increase in expression of the full length enzyme, have both been shown to lead to neuroblastoma. In addition, the fusion of ALK with other proteins due to genetic translocation events has also been shown to lead to activated kinase domain associated with cancer. A number of such ALK translocations leading to gene fusions are seen in lymphomas, the most prevalent being the nucleophosmin NPM-ALK fusion seen in anaplastic large cell lymphomas. ALK fusion with EML4 leads to a chimeric protein (EML4-ALK) thought to be responsible for a 3-5% of non small cell lung adenocarcinomas (NSCLC) (Soda M. et al., *Nature*, 2007, 448, 561-567).

Crizotinib is a potent dual tyrosine kinase inhibitor (TKI) targeting c-Met and ALK that has recently found application in the treatment of NSCLC patients harbouring the EML4-ALK fusion event (Kwak et al., *New Eng. J. of Med.*, 2010, 363, 18, 1693-1703). Crizotinib is disclosed in PCT Publication No. WO 2006/021884 and U.S. Pat. No. 7,858,643. Acquired resistance to crizotinib therapy has be reported and attributed to a L1196M and a C1156Y mutation in the EL4-ALK fusion protein (Choi Y. L. et al., *N. Engl. J. Med.*, 2010, 363, 18, 1734-1739). As crizotinib therapy becomes more widely available to patients harbouring the EML4-ALK gene fusion event, it is likely that the L1196M and C1156Y mutations and possibly other mutations will play a more prevalent role in acquired resistance to crizotinib therapy. See, e.g., Morris et al. United States Patent Publication Number 2011/0256546 describing other ALK inhibitor resistance mutations occurring in the ALK kinase domain of the related gene fusion NPM-ALK).

Accordingly, there is a need for ALK inhibitors and EML4-ALK inhibitors that have an appropriate pharmacological profile, for example in terms of potency, selectivity, pharmacokinetics, ability to cross the blood brain barrier and duration of action. More specifically, there is a need for ALK inhibitors that inhibit the EML4-ALK fusion protein having a L1196M and/or C1156Y mutation. In this context, the present invention relates to novel ALK inhibitors.

SUMMARY OF THE INVENTION

The present invention provides, in part, novel compounds and pharmaceutically acceptable salts thereof that can modulate the activity of ALK and/or EML4-ALK, thereby effecting biological functions, including but not limited to inhibiting cell proliferation and cell invasiveness, inhibiting metastasis, inducing apoptosis or inhibiting angiogenesis. Also provided are pharmaceutical compositions and medicaments, comprising the compounds or salts of the invention, alone or in combination with other therapeutic agents or palliative agents. The present invention also provides, in part, methods for preparing the novel compounds, salts and compositions thereof, and methods of using the foregoing.

It will be understood that each embodiment describing the inventive compounds herein may be combined alone or in combination with any other embodiment describing the inventive compounds provided that such embodiments are not inconsistent with each other.

In one aspect, the invention provides a compound of the formula (Φ)

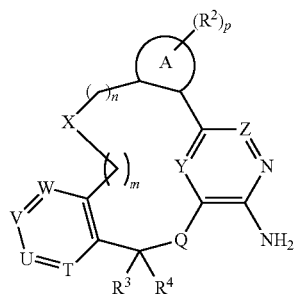

wherein:

X is selected from the group consisting of —(CR$^5$R$^6$)$_q$O(CR$^5$R$^6$)$_r$—, —(CR$^5$R$^6$)$_q$N(R$^1$)(CR$^5$R$^6$)$_r$—, —(CR$^5$R$^6$)$_q$C(O)N(R$^1$)(CR$^5$R$^6$)$_r$— and —(CR$^5$R$^6$)$_q$N(R$^1$)C(O)(CR$^5$R$^6$)$_r$—; or X is a C$_6$-C$_{12}$ arylene or a 5-12 membered heteroarylene, each of which is optionally substituted by 0-4 R$^{12}$ substituents;

Y and Z are each independently N or CH, with the proviso that when Y is N, Z is CH and when Z is N, Y is CH;

T is N or CR$^{11a}$; U is N or CR$^{11b}$; V is N or CR$^{11c}$; and W is N or CR$^{11d}$; provided no more than two of T, U, V and W are N;

Q is O or CH$_2$;

A is a ring selected from the group consisting of C$_6$-C$_{12}$ aryl and 5-12 membered heteroaryl;

R$^1$ is selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^2$ and R$^{12}$ is independently selected from the group consisting of halogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —S(O)$_t$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$C$_3$-C$_6$ cycloalkyl, —(CR$^5$R$^6$)$_q$C$_6$-C$_{12}$ aryl, —(CR$^5$R$^6$)$_q$-3-12 membered heteroalicyclic, —(CR$^5$R$^6$)$_q$ 5-6 membered heteroaryl, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ and R$^4$ are each independently selected from hydrogen, C$_1$-C$_6$ alkyl and C$_3$-C$_6$ cycloalkyl, wherein each hydrogen on C$_1$-C$_6$ alkyl and C$_3$-C$_6$ cycloalkyl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

each R$^{11a}$, R$^{11b}$, R$^{11c}$ and R$^{11d}$ is independently selected from the group consisting of hydrogen, halogen and C$_1$-C$_6$ alkyl;

m is 0, 1, 2 or 3;

n is 0, 1, 2 or 3;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, T is CR$^{11a}$; U is CR$^{11b}$; V is CR$^{11c}$; and W is CR$^{11d}$. In another embodiment of this aspect, T is N; U is CR$^{11b}$; V is CR$^{11c}$; and W is CR$^{11d}$. In another embodiment of this aspect, T is CR$^{11a}$; U is N; V is CR$^{11c}$; and W is CR$^{11d}$. In another embodiment of this aspect, T is CR$^{11a}$; U is CR$^{11b}$; V is N; and W is CR$^{11d}$. In a further embodiment of this aspect, T is CR$^{11a}$; U is CR$^{11b}$; V is CR$^{11c}$; and W is N. In another embodiment of this aspect, T and U are N; V is CR$^{11c}$; and W is CR$^{11d}$. In another embodiment of this aspect, T and V are N; U is CR$^{11b}$; and W is CR$^{11d}$. In another embodiment of this aspect, T and W are N; U is CR$^{11b}$; and V is CR$^{11c}$. In yet another embodiment of this aspect, U and V are N; T is CR$^{11a}$; and W is CR$^{11d}$. In another embodiment of this aspect, U and W are N; T is CR$^{11a}$; and V is CR$^{11c}$. In another embodiment of this aspect, V and W are N; T is CR$^{11a}$; and U is CR$^{11b}$.

In some embodiments, at least one of R$^{11a}$, R$^{11b}$, R$^{11c}$, and R$^{11d}$ is halo, preferably fluoro or chloro. In other embodiments, at least two of R$^{11a}$, R$^{11b}$, R$^{11c}$, and R$^{11d}$ are halo, preferably fluoro or chloro. In some such embodiments, R$^{11b}$ is halo, preferably fluoro. In some embodiments, each of R$^{11a}$, R$^{11c}$, and R$^{11d}$ is hydrogen. In specific embodiments, T is $CR^{11a}$; U is $CR^{11b}$; V is $CR^{11c}$; and W is $CR^{11d}$; $R^{11b}$ is halo, in particular fluoro; and each of $R^{11a}$, $R^{11c}$, and $R^{11d}$ is hydrogen.

In another aspect of this embodiment, Y is CH and Z is CH. In another embodiment, Y is CH and Z is N. In another embodiment, Y is N and Z is CH.

In one embodiment of this aspect, X is —$(CR^5R^6)_qO(CR^5R^6)_r$—. In some such embodiments, when X is —$(CR^5R^6)_qO(CR^5R^6)_r$—, m is 0 and n is 3. In other such embodiments, m is 1 and n is 2. In other such embodiments, m is 2 and n is 1. In still other embodiments, m is 3 and n is 0. In further such embodiments, m is 3 and n is 3. In other such embodiments, m is 2 and n is 2. In another such embodiment, m is 1 and n is 1. In still another such embodiment, m is 0, n is 3, q is 0 and r is 0. In another such embodiment, m is 1, n is 2, q is 0 and r is 0. In another such embodiment, m is 2, n is 1, q is 0 and r is 0. In another such embodiment, m is 3, n is 0, q is 0 and r is 0.

In another embodiment of this aspect, X is selected from the group consisting of —$(CR^5R^6)_qN(R^1)(CR^5R^6)_r$—, —$(CR^5R^6)_qC(O)N(R^1)(CR^5R^6)_r$— and —$(CR^5R^6)_qN(R^1)C(O)(CR^5R^6)_r$—. In some such embodiments, X is —$(CR^5R^6)_qN(R^1)(CR^5R^6)_r$—. In other such embodiments, X is —$(CR^5R^6)_qC(O)N(R^1)(CR^5R^6)_r$—. In other such embodiments of this aspect, X is —$(CR^5R^6)_qN(R^1)C(O)(CR^5R^6)_r$—.

In another embodiment of this aspect, X is —$(CR^5R^6)_qN(R^1)(CR^5R^6)_r$—. In some such embodiments, when X is —$(CR^5R^6)_qN(R^1)(CR^5R^6)_r$—, m is 0 and n is 3. In other such embodiments, m is 1 and n is 2. In other such embodiments, m is 2 and n is 1. In other such embodiments, m is 3 and n is 0. In still other embodiments, m is 3 and n is 3. In further such embodiments, m is 2 and n is 2. In still other such embodiments, m is 1 and n is 1.

In another embodiment of this aspect, X is —$(CR^5R^6)_qC(O)N(R^1)(CR^5R^6)_r$—. In some such embodiments, when X is —$(CR^5R^6)_qC(O)N(R^1)(CR^5R^6)_r$—, m is 0 and n is 1. In other such embodiments, m is 0 and n is 2. In other such embodiments, m is 0 and n is 3. In other such embodiments, m is 2 and n is 0. In still other such embodiments, m is 2 and n is 2. In still another such embodiment, m is 0, n is 1, q is 0 and r is 0. In another such embodiment, m is 0, n is 2, q is 0 and r is 0. In still another such embodiment, m is 0, n is 3, q is 0 and r is 0. In another such embodiment, m is 0, n is 0, q is 0 and r is 1. In another such embodiment, m is 0, n is 0, q is 0 and r is 2. In still another such embodiment, m is 2, n is 0, q is 0 and r is 0.

In another embodiment of this aspect, X is —$(CR^5R^6)_qN(R^1)C(O)(CR^5R^6)_r$—. In some such embodiments, when X is —$(CR^5R^6)_qN(R^1)C(O)(CR^5R^6)_r$—, m is 0 and n is 1. In other such embodiments, m is 0 and n is 2. In other such embodiments, m is 2 and n is 0. In other such embodiments, m is 0 and n is 3. In other such embodiments, m is 2 and n is 0. In still other such embodiments, m is 2 and n is 2. In still another such embodiment, m is 0, n is 1, q is 0 and r is 0. In another such embodiment, m is 0, n is 2, q is 0 and r is 0. In still another such embodiment, m is 0, n is 3, q is 0 and r is 0. In another such embodiment, m is 0, n is 0, q is 0 and r is 1. In another such embodiment, m is 0, n is 0, q is 0 and r is 2. In another such embodiment, m is 2, n is 0, q is 0 and r is 0. In another such embodiment, m is 1, n is 1, q is 0 and r is 0. In another such embodiment, m is 2, n is 1, q is 0 and r is 0.

In still another embodiment, m is 3, n is 0, q is 0 and r is 0.

In another embodiment of this aspect, X is a $C_6$-$C_{12}$ arylene or a 5-12 membered heteroarylene, each of which is optionally substituted by 0-4 $R^{12}$ substituents. In some such embodiments, m is 0 and n is 1. In other such embodiments, m is 0 and n is 2. In some embodiment of this aspect, X is a a $C_6$-$C_{12}$ arylene or a 5-12 membered heteroarylene selected from the group consisting of a 1,2-disubstituted phenyl, pyridine, pyrimidine, pyridazine, pyrazine, triazine, pyrazole, imidazole, triazole, tetrazole, thiazole, isothiazole, oxazole and isoxazole ring, each of which is optionally substituted by 0-4 $R^{12}$ substituents. In some embodiments, m is 0, and n is 1. In other such embodiments, m is 0, and n is 2.

In specific embodiments, X is selected from the group consisting of:

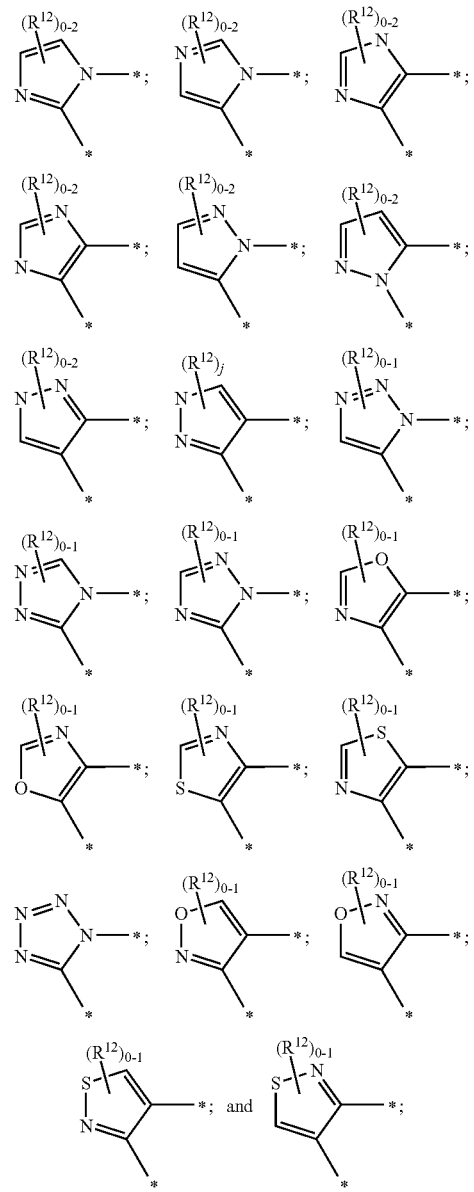

where the asterisks (*) represent the points of attachment to the macrocyclic ring.

In another embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, —OH, —$NH_2$, —$S(O)_rR^9$, —$S(O)_2NR^9R^{10}$, —$S(O)_2OR^9$, —$NO_2$, —CN, —$OR^9$, —$C(O)R^9$, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰.

In another embodiment of this aspect, R¹ is selected from the group consisting of hydrogen, C₁-C₆ alkyl, and C₃-C₆ cycloalkyl. In specific embodiments, R¹ is hydrogen, methyl, ethyl or cyclopropyl. In some embodiments, R¹ is hydrogen. In other embodiments, R¹ is methyl. In other embodiments, R¹ is ethyl. In other embodiments, R¹ is cyclopropyl.

In another embodiment of this aspect, each R² is independently selected from the group consisting of C₁-C₆ alkyl, C₃-C₆ cycloalkyl, —S(O)ᵣR⁷, —S(O)₂NR⁷R⁸, —OR⁷, —O(CR⁵R⁶)(CR⁵R⁶)_qOR⁷, —O(CR⁵R⁶)(CR⁵R⁶)_qR⁷ and —CN; wherein each hydrogen on said C₁-C₆ alkyl and C₃-C₆ cycloalkyl may be independently optionally substituted by halogen, —OH, —NH₂, —S(O)ᵣR⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰.

In another embodiment of this aspect, each R² is independently selected from the group consisting of C₁-C₆ alkyl, C₃-C₆ cycloalkyl, —S(O)ᵣR⁷, —S(O)₂NR⁷R⁸, —OR⁷, —O(CR⁵R⁶)(CR⁵R⁶)_qOR⁷, —O(CR⁵R⁶)(CR⁵R⁶)_qR⁷ and —CN.

In another embodiment of this aspect, R³ and R⁴ are each independently selected from the group consisting of hydrogen and C₁-C₆ alkyl. In frequent embodiments, R³ and R⁴ are each independently hydrogen or methyl. In some such embodiments, each of R³ and R⁴ is hydrogen. In other such embodiments, one of R³ and R⁴ is hydrogen and the other is methyl.

In some embodiments of this aspect, Q is 0. In other embodiments of this aspect, Q is CH₂.

In one embodiment of this aspect, A is a ring selected from the group consisting of C₆-C₁₂ aryl and 5-12 membered heteroaryl. In embodiments of this aspect, ring A is optionally substituted by 0 to 4 substituent groups labelled as —(R²)_p, where p is 0, 1, 2, 3 or 4. It will be understood by those of skill in the art that the number of R² substituents on ring A is limited by the number of open valence positions on ring A, where two of the valence positions are used to incorporate the A-ring into the macrocyclic core.

In another embodiment of this aspect, A is a C₆-C₁₂ aryl or 5-12 membered heteroaryl ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, A is a ring selected from the group consisting of phenyl, pyridine, pyrimidine, pyridazine, pyrazine and triazine. In other such embodiments, A is a ring selected from the group consisting of pyrazole, imidazole, triazole, tetrazole, thiazole, isothiazole, oxazole and isoxazole. In certain embodiments, A is a ring selected from the group consisting of pyrazole, triazole, thiazole, isothiazole, and isoxazole. In specific embodiments, A is a pyrazole ring. In other embodiments, A is triazole ring. In other embodiments, A is isothiazole ring. In still other embodiments, A is isoxazole ring. In further embodiments, A is a phenyl or pyridyl ring.

In some embodiments of this aspect, A is selected from the group consisting of:

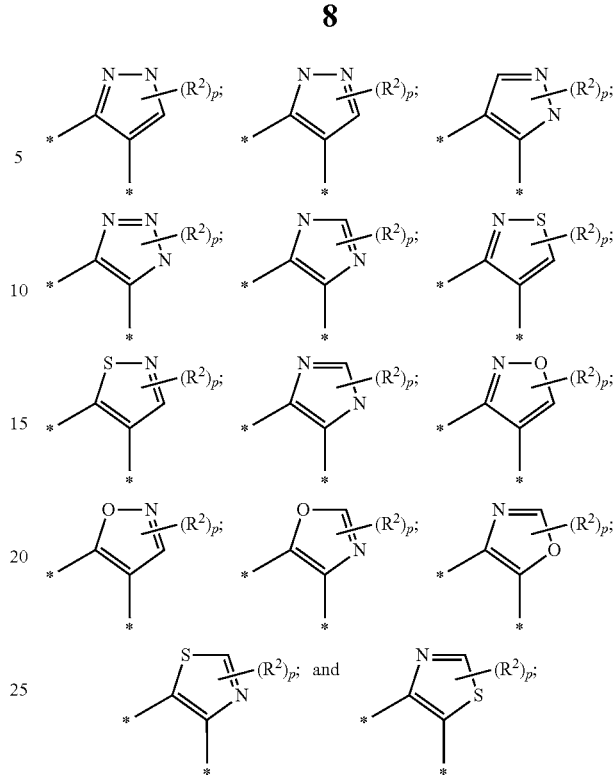

where the asterisks (*) represent the points of attachment to the macrocyclic ring. In some such embodiments, p is 0, 1 or 2, and each R² is independently selected from the group consisting of C₁-C₆ alkyl, C₃-C₆ cycloalkyl, —S(O)ᵣR⁷, —S(O)₂NR⁷R⁸, —OR⁷, —O(CR⁵R⁶)(CR⁵R⁶)_qOR⁷, —O(CR⁵R⁶)(CR⁵R⁶)_qR⁷ and —CN.

In other embodiments of this aspect, A is a ring selected from the group consisting of:

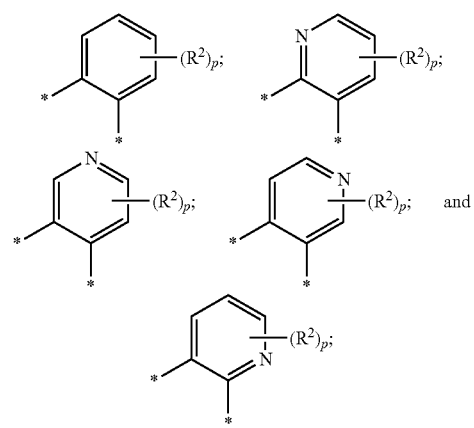

where the asterisks (*) represent the points of attachment to the macrocyclic ring. In some such embodiments, p is 0, 1 or 2, and each R² is independently selected from the group consisting of C₁-C₆ alkyl, C₃-C₆ cycloalkyl, —S(O)ᵣR⁷, —S(O)₂NR⁷R⁸, —OR⁷, —O(CR⁵R⁶)(CR⁵R⁶)_qOR⁷, —O(CR⁵R⁶)(CR⁵R⁶)_qR⁷ and —CN.

In other embodiments of this aspect, A is a ring selected from the group consisting of:

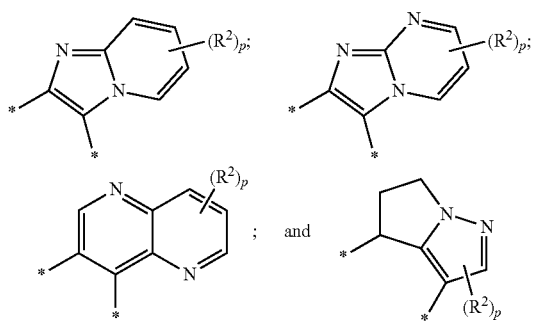

where the asterisks (*) represent the points of attachment to the macrocyclic ring. In some such embodiments, p is 0, 1 or 2, and each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN.

In specific embodiments, A is selected from the group consisting of:

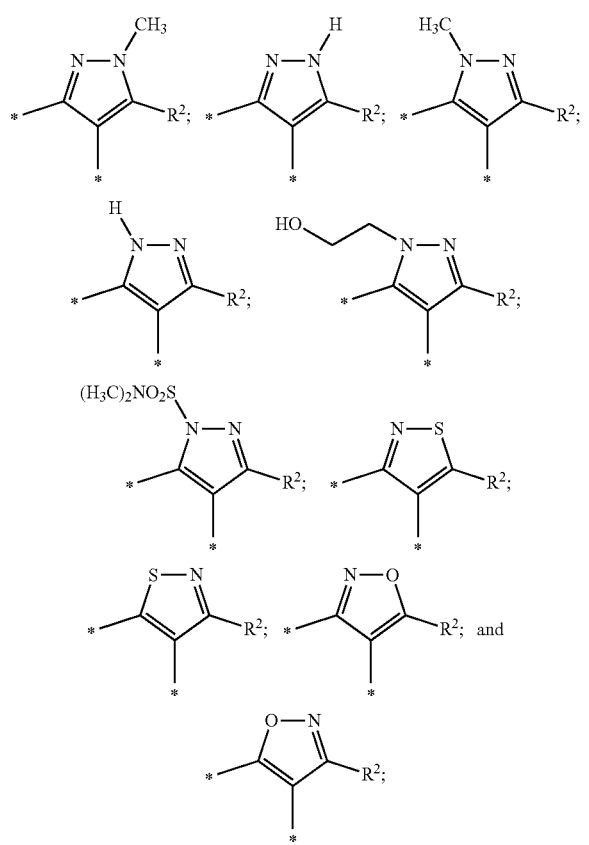

where the asterisks (*) represent the points of attachment to the macrocyclic ring, and wherein $R^2$ is selected from the group consisting of $C_1$-$C_6$ alkyl, $C_3$-$C_6$ cycloalkyl, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, $R^2$ is selected from the group consisting of methyl, ethyl, cyclopropyl, methoxy, ethoxy and —CN.

In other specific embodiments, A is selected from the group consisting of:

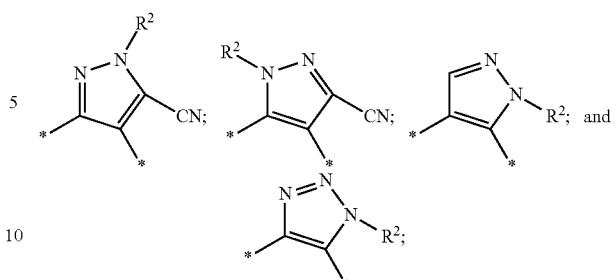

where the asterisks (*) represent the points of attachment to the macrocyclic ring, and wherein $R^2$ is selected from the group consisting of $C_1$-$C_6$ alkyl, and $C_3$-$C_6$ cycloalkyl; and wherein each hydrogen on said $C_1$-$C_6$ alkyl and $C_3$-$C_6$ cycloalkyl may be independently optionally substituted by halogen or —OH. In some such embodiments, $R^2$ is selected from the group consisting of methyl, ethyl, -2-hydroxyethyl, propyl, isopropyl, n-butyl, isobutyl, sec-butyl, difluoroethyl, trifluoroethyl, cyclopropyl and cyclobutyl.

Certain preferred embodiments of formula (Φ), or a pharmaceutically acceptable salt thereof, have one, two or more of the following preferred features, which may occur in combination to the extent they are not inconsistent with each other:

T is CR$^{11a}$; U is CR$^{11b}$; V is CR$^{11c}$; and W is CR$^{11d}$; wherein at least one of R$^{11a}$, R$^{11b}$, R$^{11c}$, and R$^{11d}$ is halo, preferably fluoro or chloro;

R$^{11b}$ is halo, preferably fluoro, and each of R$^{11a}$, R$^{11c}$, and R$^{11d}$ is hydrogen;

X is —(CR$^5$R$^6$)$_q$O(CR$^5$R$^6$)$_r$—, wherein each of R$^5$ and R$^6$ is H; m is 0; and n is 0;

X is —(CR$^5$R$^6$)$_q$N(R$^1$)(CR$^5$R$^6$)$_r$—, wherein each of R$^5$ and R$^6$ is H; m is 0; and n is 0;

X is —(CR$^5$R$^6$)$_q$C(O)N(R$^1$)(CR$^5$R$^6$)$_r$—, wherein each of R$^5$ and R$^6$ is H, m is 0 and n is 0;

q is 1, and r is 1;
q is 0, and r is 1;
Y and Z are each CH;
Y is N and Z is CH;
Q is O;
R$^1$ is selected from the group consisting of hydrogen, $C_1$-$C_6$ alkyl, and $C_3$-$C_6$ cycloalkyl;
R$^1$ is hydrogen, methyl, ethyl or cyclopropyl;
R$^1$ is methyl;
A is a $C_6$-$C_{12}$ aryl or 5-12 membered heteroaryl ring selected from the group consisting of phenyl, pyridine, pyrimidine, pyridazine, pyrazine, triazine, pyrazole, imidazole, triazole, tetrazole, thiazole, isothiazole, oxazole and isoxazole;
A is a $C_6$-$C_{12}$ aryl or 5-12 membered heteroaryl ring of phenyl, pyrazole, imidazole, triazole, thiazole, isothiazole, oxazole and isoxazole;
A is a $C_6$-$C_{12}$ aryl or 5-12 membered heteroaryl ring of phenyl, pyrazole, triazole, isothiazole and isoxazole;
A is a pyrazole;
is 0, 1 or 2;
R$^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN;
R$^3$ and R$^4$ are each independently selected from the group consisting of hydrogen and $C_1$-$C_6$ alkyl;
R$^3$ and R$^4$ are each independently hydrogen or methyl;
one of R$^3$ and R$^4$ is hydrogen and the other is methyl;

$R^5$ and $R^6$ are each independently selected from the group consisting of hydrogen and $C_1$-$C_6$ alkyl;

$R^5$ and $R^6$ are each independently hydrogen or methyl;

each of $R^5$ and $R^6$ is hydrogen;

$R^7$ and $R^8$ are each independently selected from the group consisting of hydrogen and $C_1$-$C_6$ alkyl; wherein each hydrogen on said $C_1$-$C_6$ alkyl may be independently optionally substituted by halogen, —OH, —$NH_2$, —$S(O)_tR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$; and each $R^9$ and $R^{10}$ is independently selected from hydrogen, $C_1$-$C_6$ alkyl, and $C_3$-$C_6$ cycloalkyl.

The embodiments described above as suitable for compounds of formula (Φ), including the combinations of preferred embodiments, are also suitable for compounds of formulae (I) to (XXX), to the extent they are not inconsistent with each other, as further described herein.

The specific aromatic and heteroaromatic groups described above as suitable for ring A in formula Φ are also suitable for ring A in the compounds of formulae (I) to (XXX), as further described herein.

In another aspect, the invention provides a compound of the formula (I)

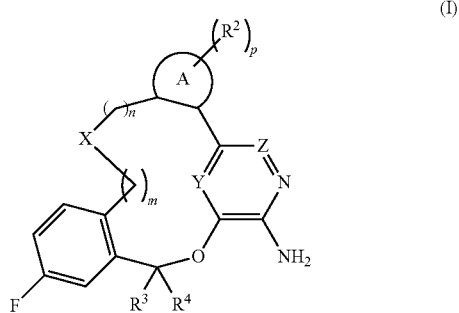

wherein:

X is selected from the group consisting of —$(CR^5R^6)_qO(CR^5R^6)_r$—, —$(CR^5R^6)_qN(R^1)(CR^5R^6)_r$—, —$(CR^5R^6)_qC(O)N(R^1)(CR^5R^6)_r$— and —$(CR^5R^6)_qN(R^1)C(O)(CR^5R^6)_r$—;

Y and Z are each independently N or CH, with the proviso that when Y is N, Z is CH and when Z is N, Y is CH;

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —$S(O)_tR^7$, —$S(O)_2NR^7R^8$, —$S(O)_2OR^7$, —$NO_2$, —$(CR^5R^6)_qNR^7R^8$, —$N(CR^5R^6)(CR^5R^6)_qNR^7R^8$, —$OR^7$, —$O(CR^5R^6)(CR^5R^6)_qOR^7$, —$O(CR^5R^6)(CR^5R^6)_qR^7$, —CN, —$C(O)R^7$, —$OC(O)R^7$, —$O(CR^5R^6)_qR^7$, —$NR^7C(O)R^8$, —$(CR^5R^6)_qC(O)OR^7$, —$(CR^5R^6)_qNR^7R^8$, —$C(=NR^7)NR^7R^8$, —$NR^7C(O)NR^7R^8$, —$NR^7S(O)_2R^8$ and —$(CR^5R^6)_qC(O)NR^7R^8$;

wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ and —$C(O)NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

m is 0, 1, 2 or 3;

n is 0, 1, 2 or 3;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, Y is N. In another embodiment of this aspect, Z is N. In another aspect of this embodiment, Y is CH and Z is CH.

In another embodiment of this aspect, X is —$(CR^5R^6)_qO(CR^5R^6)_r$—. In some such embodiments, when X is —$(CR^5R^6)_qO(CR^5R^6)_r$—, m is 0 and n is 3. In other such embodiments, m is 1 and n is 2. In other such embodiments, m is 2 and n is 1. In other such embodiments, m is 3 and n is 0. In still other such embodiments, m is 3 and n is 3. In other such embodiments, m is 2 and n is 2. In further such embodiments, m is 1 and n is 1. In other such embodiments, m is 0, n is 3, q is 0 and r is 0. In still other such embodiments, m is 1, n is 2, q is 0 and r is 0. In other such embodiments, m is 2, n is 1, q is 0 and r is 0. In still other such embodiments, m is 3, n is 0, q is 0 and r is 0.

In another embodiment of this aspect, X is selected from the group consisting of $-(CR^5R^6)_qN(R^1)(CR^5R^6)_r-$, $-(CR^5R^6)_qC(O)N(R^1)(CR^5R^6)_r-$ and $-(CR^5R^6)_qN(R^1)C(O)(CR^5R^6)_r-$. In one such embodiment of this aspect, X is $-(CR^5R^6)_qN(R^1)(CR^5R^6)_r-$. In another such embodiment of this aspect, X is $-(CR^5R^6)_qC(O)N(R^1)(CR^5R^6)_r-$. In another such embodiment of this aspect, X is $-(CR^5R^6)_qN(R^1)C(O)(CR^5R^6)_r-$.

In another embodiment of this aspect, X is $-(CR^5R^6)_qN(R^1)(CR^5R^6)_r-$. In some such embodiments, when X is $-(CR^5R^6)_qN(R^1)(CR^5R^6)_r-$, m is 0 and n is 3. In other such embodiments, m is 1 and n is 2. In other such embodiments, m is 2 and n is 1. In other such embodiments, m is 3 and n is 0. In still other such embodiments, m is 3 and n is 3. In other such embodiments, m is 2 and n is 2. In further such embodiments, m is 1 and n is 1. In other such embodiments, m is 0, n is 3, q is 0 and r is 0. In still other such embodiments, m is 1, n is 2, q is 0 and r is 0. In other such embodiments, m is 2, n is 1, q is 0 and r is 0. In still other such embodiments, m is 3, n is 0, q is 0 and r is 0. In other such embodiments, m is 1, n is 1, q is 0 and r is 0.

In another embodiment of this aspect, X is $-(CR^5R^6)_qC(O)N(R^1)(CR^5R^6)_r-$. In some such embodiments, when X is $-(CR^5R^6)_qC(O)N(R^1)(CR^5R^6)_r-$, m is 0 and n is 2. In other such embodiments, m is 0 and n is 1. In still other such embodiments, m is 2 and n is 0. In further such embodiments, m is 2 and n is 2. In other such embodiments, m is 0, n is 2, q is 0 and r is 0. In still other such embodiments, m is 0, n is 1, q is 0 and r is 0. In other such embodiments, m is 2, n is 0, q is 0 and r is 0.

In another embodiment of this aspect, X is $-(CR^5R^6)_qN(R^1)C(O)(CR^5R^6)_r-$. In some such embodiments, when X is $-(CR^5, R^6)_qN(R^1)C(O)(CR^5R^6)_r-$, m is 0 and n is 2. In other such embodiments, m is 0 and n is 1. In still other such embodiments, m is 2 and n is 0. In other such embodiments, m is 0, n is 2, q is 0 and r is 0. In other such embodiments, m is 0, n is 1, q is 0 and r is 0. In other such embodiments, m is 2, n is 0, q is 0 and r is 0.

In another embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, $-OH$, $-NH_2$, $-S(O)_rR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$. In another embodiment of this aspect, $R^1$ is selected from the group consisting of hydrogen, $C_1$-$C_6$ alkyl, and $C_3$-$C_6$ cycloalkyl.

In another embodiment of this aspect, $R^1$ is selected from the group consisting of hydrogen, $C_1$-$C_6$ alkyl, and $C_3$-$C_6$ cycloalkyl. In specific embodiments, $R^1$ is hydrogen, methyl, ethyl or cyclopropyl. In some embodiments, $R^1$ is hydrogen. In other embodiments, $R^1$ is methyl. In other embodiments, $R^1$ is ethyl. In other embodiments, $R^1$ is cyclopropyl.

In another embodiment of this aspect, each $R^2$ is independently selected from the group consisting of, $C_1$-$C_6$ alkyl, $C_3$-$C_6$ cycloalkyl, $-S(O)_rR^7$, $-S(O)_2NR^7R^8$, $-OR^7$, $-O(CR^5R^6)(CR^5R^6)_qOR^7$, $-O(CR^5R^6)(CR^5R^6)_qR^7$ and $-CN$; wherein each hydrogen on said $C_1$-$C_6$ alkyl and $C_3$-$C_6$ cycloalkyl may be independently optionally substituted by halogen, $-OH$, $-NH_2$, $-S(O)_rR^9$, $-S(O)_2NR^9R^{10}$, $-S(O)_2OR^9$, $-NO_2$, $-OR^9$, $-CN$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$.

In another embodiment of this aspect, each $R^2$ is independently selected from the group consisting of $C_1$-$C_6$ alkyl, $C_3$-$C_6$ cycloalkyl, $-S(O)_rR^7$, $-S(O)_2NR^7R^8$, $-OR^7$, $-O(CR^5R^6)(CR^5R^6)_qOR^7$, $-O(CR^5R^6)(CR^5R^6)_qR^7$ and $-CN$.

In another embodiment of this aspect, A is a ring selected from phenyl, pyridine, triazine, pyrazole, imidazole, thiazole, isothiazole, oxazole and isoxazole.

In another embodiment of this aspect, A is a ring selected from the group consisting of a phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

Certain preferred embodiments of formula (I), or a pharmaceutically acceptable salt thereof, have one, two or more of the following preferred features, which may occur in combination to the extent they are not inconsistent with each other:

X is $-(CR^5R^6)_qO(CR^5R^6)_r-$, wherein each of $R^5$ and $R^6$ is H; m is 0; and n is 0;

X is $-(CR^5R^6)_qN(R^1)(CR^5R^6)_r-$, wherein each of $R^5$ and $R^6$ is H; m is 0; and n is 0;

X is $-(CR^5R^6)_qC(O)N(R^1)(CR^5R^6)_r-$, wherein each of $R^5$ and $R^6$ is H, m is 0 and n is 0;

q is 1, and r is 1;

q is 0, and r is 1;

Y and Z are each CH;

Y is N and Z is CH;

$R^1$ is selected from the group consisting of hydrogen, $C_1$-$C_6$ alkyl, and $C_3$-$C_6$ cycloalkyl;

$R^1$ is hydrogen, methyl, ethyl or cyclopropyl;

$R^1$ is methyl;

A is a $C_6$-$C_{12}$ aryl or 5-12 membered heteroaryl ring selected from the group consisting of phenyl, pyridine, pyrimidine, pyridazine, pyrazine, triazine, pyrazole, imidazole, triazole, tetrazole, thiazole, isothiazole, oxazole and isoxazole;

A is a $C_6$-$C_{12}$ aryl or 5-12 membered heteroaryl ring of phenyl, pyrazole, imidazole, triazole, thiazole, isothiazole, oxazole and isoxazole;

A is a $C_6$-$C_{12}$ aryl or 5-12 membered heteroaryl ring of phenyl, pyrazole, triazole, isothiazole and isoxazole;

A is a pyrazole;

p is 0, 1 or 2;

$R^2$ is independently selected from the group consisting of $C_1$-$C_6$ alkyl, $C_3$-$C_6$ cycloalkyl, $-S(O)_rR^7$, $-S(O)_2NR^7R^8$, $-OR^7$, $-O(CR^5R^6)(CR^5R^6)_qOR^7$, $-O(CR^5R^6)(CR^5R^6)_qR^7$ and $-CN$;

$R^3$ and $R^4$ are each independently selected from the group consisting of hydrogen and $C_1$-$C_6$ alkyl;

$R^3$ and $R^4$ are each independently hydrogen or methyl;

one of $R^3$ and $R^4$ is hydrogen and the other is methyl;

$R^5$ and $R^6$ are each independently selected from the group consisting of hydrogen and $C_1$-$C_6$ alkyl;

$R^5$ and $R^6$ are each independently hydrogen or methyl;

each of $R^5$ and $R^6$ is hydrogen;

$R^7$ and $R^8$ are each independently selected from the group consisting of hydrogen and $C_1$-$C_6$ alkyl; wherein each hydrogen on said $C_1$-$C_6$ alkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, and $C_3$-$C_6$ cycloalkyl.

In another aspect, the invention provides a compound of the formula (II)

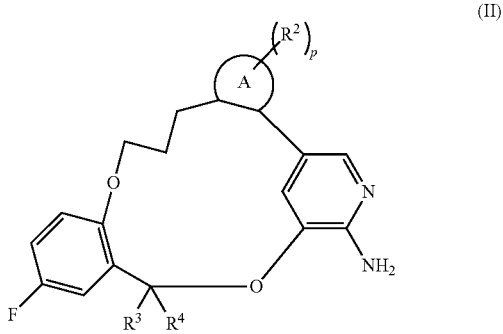

(II)

wherein:

A is a ring selected from $C_6$-$C_{12}$ aryl and 5-6 membered heteroaryl;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^9$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$.

In another aspect of this embodiment, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^9$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole.

In another embodiment of this aspect, A is a ring selected from phenyl, pyridine, triazine, pyrazole, imidazole, thiazole, isothiazole, oxazole and isoxazole; each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, $R^3$ and $R^4$ are each independently selected from the group consisting of hydrogen and $C_1$-$C_6$ alkyl. In other such embodiments, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl.

In another aspect, the invention provides a compound of the formula (III)

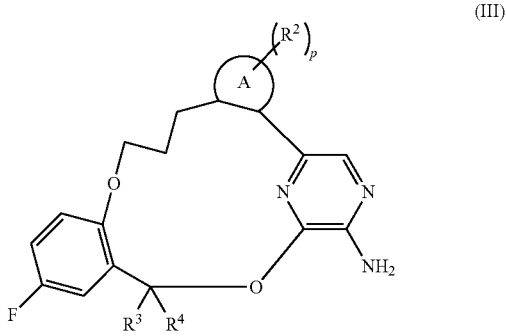

(III)

wherein:

A is a ring selected from $C_6$-$C_{12}$ aryl and 5-6 membered heteroaryl;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, $R^3$ and $R^4$ are each independently selected from the group consisting of hydrogen and $C_1$-$C_6$ alkyl.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

In another embodiment of this aspect, A is a ring selected from phenyl, pyridine, triazine, pyrazole, imidazole, thiazole, isothiazole, oxazole and isoxazole.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl.

In another aspect, the inventions provides a compound of the formula (IV)

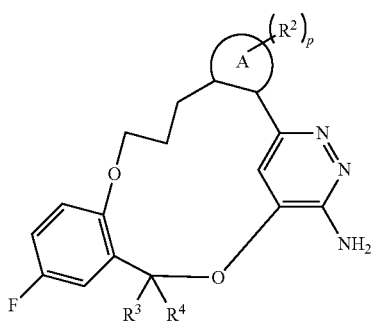

(IV)

wherein:

A is a ring selected from $C_6$-$C_{12}$ aryl and 5-6 membered heteroaryl;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, $R^3$ and $R^4$ are each independently selected from the group consisting of hydrogen and $C_1$-$C_6$ alkyl.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

In another embodiment of this aspect, A is a ring selected from phenyl, pyridine, triazine, pyrazole, imidazole, thiazole, isothiazole, oxazole and isoxazole.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from phenyl, pyridine, triazine, pyrazole, imidazole, thiazole, isothiazole, oxazole and isoxazole; each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl.

In another aspect, the invention provides a compound of the formula (V)

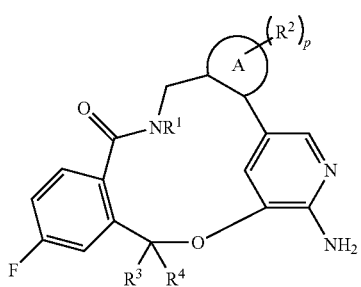

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, —OH, —NH$_2$, —S(O)$_r$R$^9$, —S(O)$_2$ NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$) NR$^9$R$^{10}$, —NR$^9$C(O)NR$^9$R$^{10}$, —NR$^9$S(O)$_2$R$^{10}$ or —C(O) NR$^9$R$^{10}$. In another embodiment of this aspect, $R^1$ is selected from the group consisting of hydrogen, $C_1$-$C_6$ alkyl, and $C_3$-$C_6$ cycloalkyl.

In another aspect of this aspect, $R^1$ is selected from the group consisting of hydrogen, $C_1$-$C_6$ alkyl, and $C_3$-$C_6$ cycloalkyl. In specific embodiments, $R^1$ is hydrogen, methyl, ethyl or cyclopropyl. In some embodiments, $R^1$ is hydrogen. In other embodiments, $R^1$ is methyl. In other embodiments, $R^1$ is ethyl. In other embodiments, $R^1$ is cyclopropyl.

In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^3$R$^6$)(CR$^3$R$^6$)$_q$OR$^7$, —O(CR$^3$R$^6$)(CR$^3$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O) R$^9$, —NR$^9$C(O)R$^{10}$, —C(O)OR$^9$, —C(=NR$^9$)NR$^9$R$^{10}$, —NR⁹C(O)NR⁹R¹⁰, —NR⁹S(O)₂R¹⁰ or —C(O)NR⁹R¹⁰. In another embodiment of this aspect, R² is independently selected from the group consisting of $C_1$-$C_6$ alkyl, $C_3$-$C_6$ cycloalkyl, —S(O)$_r$R⁷, —S(O)₂NR⁷R⁸, —OR⁷, —O(CR⁵R⁶)(CR⁵R⁶)$_q$OR⁷, —O(CR⁵R⁶)(CR⁵R⁶)$_q$R⁷ and —CN. In some such embodiments, R³ and R⁴ are each independently selected from the group consisting of hydrogen and $C_1$-$C_6$ alkyl.

In another embodiment of this aspect, R³ and R⁴ are each independently selected from the group consisting of hydrogen and $C_1$-$C_6$ alkyl. In frequent embodiments, R³ and R⁴ are each independently hydrogen or methyl. In some such embodiments, each of R³ and R⁴ is hydrogen. In other such embodiments, one of R³ and R⁴ is hydrogen and the other is methyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, R³ and R⁴ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, R³ and R⁴ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each R² is independently selected from the group consisting of $C_1$-$C_6$ alkyl, $C_3$-$C_6$ cycloalkyl, —S(O)$_r$R⁷, —S(O)₂NR⁷R⁸, —OR⁷, —O(CR⁵R⁶)(CR⁵R⁶)$_q$OR⁷, —O(CR⁵R⁶)(CR⁵R⁶)$_q$R⁷ and —CN; and R³ and R⁴ are each independently selected from the group consisting of hydrogen and $C_1$-$C_6$ alkyl.

In another aspect, the invention provides a compound of the formula (VI)

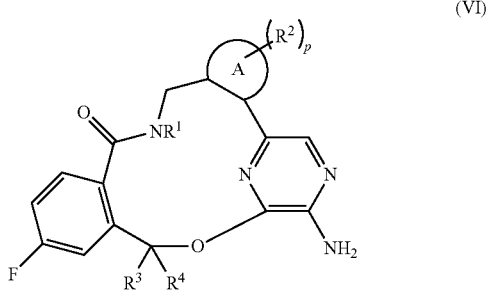

(VI)

wherein:

A is a ring selected from $C_6$-$C_{12}$ aryl and 5-6 membered heteroaryl;

R¹ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH₂, —S(O)$_r$R⁹, —S(O)₂NR⁹R¹⁰, —S(O)₂OR⁹, —NO₂, —CN, —OR⁹, —C(O)R⁹, —OC(O)R⁹, —NR⁹C(O) R¹⁰, —C(O)OR⁹, —C(=NR⁹)NR⁹R¹⁰, —NR⁹C(O) NR⁹R¹⁰, —NR⁹S(O)₂R¹⁰ or —C(O)NR⁹R¹⁰;

each R² is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R⁷, —S(O)₂NR⁷R⁸, —S(O)₂OR⁷, —NO₂, —(CR⁵R⁶)$_q$NR⁷R⁸, —N(CR⁵R⁶) (CR⁵R⁶)$_q$NR⁷R⁸, —OR⁷, —O(CR⁵R⁶)(CR⁵R⁶)$_q$OR⁷, —O(CR⁵R⁶)(CR⁵R⁶)$_q$R⁷, —CN, —C(O)R⁷, —OC(O)R⁷, —O(CR⁵R⁶)$_q$R⁷, —NR⁷C(O)R⁸, —(CR⁵R⁶)$_q$C(O)OR⁷, —(CR⁵R⁶)$_q$NR⁷R⁸, —C(=NR⁷)NR⁷R⁸, —NR⁷C(O) NR⁷R⁸, —NR⁷S(O)₂R⁸ and —(CR⁵R⁶)$_q$C(O)NR⁷R⁸; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH₂, —S(O)$_r$R⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

R³ and R⁴ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH₂, —S(O)$_r$R⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁵ and R⁶ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH₂, —S(O)$_r$R⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O) OR⁹, —C(=NR⁹)NR⁹R¹⁰, —NR⁹C(O)NR⁹R¹⁰, —NR⁹S (O)₂R¹⁰ and —C(O)NR⁹R¹⁰; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH₂, —S(O)$_r$R⁹, —S(O)₂NR⁹R¹⁰, —S(O)₂OR⁹, —NO₂, —CN, —OR⁹, —C(O)R⁹, —OC(O) R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁷ and R⁸ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH₂, —S(O)$_r$R⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁹ and R¹⁰ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;
or a pharmaceutically acceptable salt thereof.

In one embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, $R^1$ is selected from the group consisting of hydrogen, $C_1$-$C_6$ alkyl, and $C_3$-$C_6$ cycloalkyl.

In another embodiment of this aspect, $R^1$ is selected from the group consisting of hydrogen, $C_1$-$C_6$ alkyl, and $C_3$-$C_6$ cycloalkyl. In specific embodiments, $R^1$ is hydrogen, methyl, ethyl or cyclopropyl. In some embodiments, $R^1$ is hydrogen. In other embodiments, $R^1$ is methyl. In other embodiments, $R^1$ is ethyl. In other embodiments, $R^1$ is cyclopropyl.

In another embodiment of this aspect, each $R^2$ is independently selected from the group consisting of $C_1$-$C_6$ alkyl, $C_3$-$C_6$ cycloalkyl, —S(O)$_t$R$^7$, —S(O)$_2$NR$^7$R$^8$, —OR$^7$, —O(CR$^3$R$^6$)(CR$^3$R$^6$)$_q$OR$^7$, —O(CR$^3$R$^6$)(CR$^3$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, each $R^2$ is independently selected from the group consisting of $C_1$-$C_6$ alkyl, $C_3$-$C_6$ cycloalkyl, —S(O)$_t$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, $R^3$ and $R^4$ are each independently selected from the group consisting of hydrogen and $C_1$-$C_6$ alkyl.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

In another embodiment of this aspect, A is a ring selected from phenyl, pyridine, triazine, pyrazole, imidazole, thiazole, isothiazole, oxazole and isoxazole. In another embodiment of this aspect, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each $R^2$ is independently selected from the group consisting of $C_1$-$C_6$ alkyl, $C_3$-$C_6$ cycloalkyl, —S(O)$_t$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl.

In another aspect, the invention provides a compound of the formula (VII)

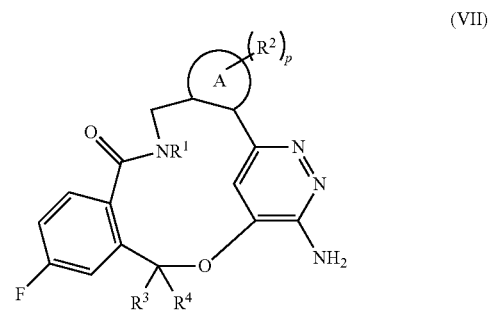

(VII)

wherein:
A is a ring selected from $C_6$-$C_{12}$ aryl and 5-6 membered heteroaryl;
$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_t$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O) OR$^9$, —C(=NR$^9$)NR$^9$R$^{10}$, —NR$^9$C(O)NR$^9$R$^{10}$, —NR$^9$S (O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$) NR$^9$R$^{10}$, —NR$^9$C(O)NR$^9$R$^{10}$, —NR$^9$S(O)$_2$R$^{10}$ or —C(O) NR$^9$R$^{10}$. In another embodiment of this aspect, $R^1$ is selected from the group consisting of hydrogen, $C_1$-$C_6$ alkyl, and $C_3$-$C_6$ cycloalkyl.

In another embodiment of this aspect, $R^1$ is selected from the group consisting of hydrogen, $C_1$-$C_6$ alkyl, and $C_3$-$C_6$ cycloalkyl. In specific embodiments, $R^1$ is hydrogen, methyl, ethyl or cyclopropyl. In some embodiments, $R^1$ is hydrogen. In other embodiments, $R^1$ is methyl. In other embodiments, $R^1$ is ethyl. In other embodiments, $R^1$ is cyclopropyl.

In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, $R^3$ and $R^4$ are each independently selected from the group consisting of hydrogen and $C_1$-$C_6$ alkyl.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

In another embodiment of this aspect, A is a ring selected from phenyl, pyridine, triazine, pyrazole, imidazole, thiazole, isothiazole, oxazole and isoxazole. In another embodiment of this aspect, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$ R$^7$ and —CN; and $R^3$ and $R^4$ are each independently selected from the group consisting of hydrogen and $C_1$-$C_6$ alkyl.

Certain preferred embodiments of formulae (V), (V) and (VI), or a pharmaceutically acceptable salt thereof, have one, two or more of the following preferred features, which may occur in combination to the extent they are not inconsistent with each other:

$R^1$ is selected from the group consisting of hydrogen, $C_1$-$C_6$ alkyl, and $C_3$-$C_6$ cycloalkyl;

$R^1$ is hydrogen, methyl, ethyl or cyclopropyl;

$R^1$ is methyl;

A is a $C_6$-$C_{12}$ aryl or 5-12 membered heteroaryl ring selected from the group consisting of phenyl, pyridine, pyrimidine, pyridazine, pyrazine, triazine, pyrazole, imidazole, triazole, tetrazole, thiazole, isothiazole, oxazole and isoxazole;

A is a $C_6$-$C_{12}$ aryl or 5-12 membered heteroaryl ring of phenyl, pyrazole, imidazole, triazole, thiazole, isothiazole, oxazole and isoxazole;

A is a $C_6$-$C_{12}$ aryl or 5-12 membered heteroaryl ring of phenyl, pyrazole, triazole, isothiazole and isoxazole;

A is a pyrazole;

p is 0, 1 or 2;

$R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN;

$R^3$ and $R^4$ are each independently selected from the group consisting of hydrogen and $C_1$-$C_6$ alkyl;

$R^3$ and $R^4$ are each independently hydrogen or methyl; one of $R^3$ and $R^4$ is hydrogen and the other is methyl;

$R^5$ and $R^6$ are each independently selected from the group consisting of hydrogen and $C_1$-$C_6$ alkyl;

$R^5$ and $R^6$ are each independently hydrogen or methyl; each of $R^5$ and $R^6$ is hydrogen;

$R^7$ and $R^8$ are each independently selected from the group consisting of hydrogen and $C_1$-$C_6$ alkyl; wherein each hydrogen on said $C_1$-$C_6$ alkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, and $C_3$-$C_6$ cycloalkyl.

In another aspect, the invention provides a compound of the formula (VIII)

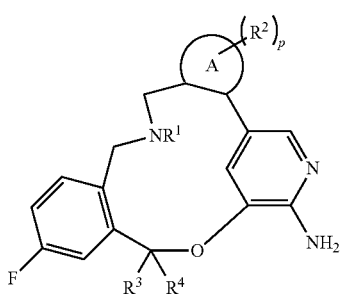

(VIII)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$) (CR$^5$R$^6$)$_q$NR$^7$R$^8$, —O(CR$^5$R$^6$)(CR$^5$R$^6$)$_q$OR$^7$, —O(CR$^5$R$^6$) (CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S (O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$) NR$^9$R$^{10}$, —NR$^9$C(O)NR$^9$R$^{10}$, —NR$^9$S(O)$_2$R$^{10}$ or —C(O) NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O) OR$^9$, —C(=NR$^9$)NR$^9$R$^{10}$, —NR$^9$C(O)NR$^9$R$^{10}$, —NR$^9$S (O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

In one embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$) NR$^9$R$^{10}$, —NR$^9$C(O)NR$^9$R$^{10}$, —NR$^9$S(O)$_2$R$^{10}$ or —C(O) NR$^9$R$^{10}$. In another embodiment of this aspect, $R^1$ is selected from the group consisting of hydrogen, $C_1$-$C_6$ alkyl, and $C_3$-$C_6$ cycloalkyl.

In another embodiment of this aspect, $R^1$ is selected from the group consisting of hydrogen, $C_1$-$C_6$ alkyl, and $C_3$-$C_6$ cycloalkyl. In specific embodiments, $R^1$ is hydrogen, methyl, ethyl or cyclopropyl. In some embodiments, $R^1$ is hydrogen. In other embodiments, $R^1$ is methyl. In other embodiments, $R^1$ is ethyl. In other embodiments, $R^1$ is cyclopropyl.

In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)

R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰. In another embodiment of this aspect, each R² is independently selected from the group consisting of C₁-C₆ alkyl, C₃-C₆ cycloalkyl, —S(O)ᵣR⁷, —S(O)₂NR⁷R⁸, —OR⁷, —O(CR⁵R⁶)(CR⁵R⁶)ᵩOR⁷, —O(CR⁵R⁶)(CR⁵R⁶)ᵩR⁷ and —CN. In some such embodiments, R³ and R⁴ are each independently selected from the group consisting of hydrogen and C₁-C₆ alkyl.

In another embodiment of this aspect, R³ and R⁴ are each independently selected from the group consisting of hydrogen and C₁-C₆ alkyl. In frequent embodiments, R³ and R⁴ are each independently hydrogen or methyl. In some such embodiments, each of R³ and R⁴ is hydrogen. In other such embodiments, one of R³ and R⁴ is hydrogen and the other is methyl.

In another embodiment of this aspect, A is a ring selected from phenyl, pyridine, triazine, pyrazole, imidazole, thiazole, isothiazole, oxazole and isoxazole. In another embodiment of this aspect, R³ and R⁴ are each independently selected from the group consisting of hydrogen and C₁-C₆ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, R³ and R⁴ are each independently selected from the group consisting of hydrogen and C₁-C₆ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, R³ and R⁴ are each independently selected from the group consisting of hydrogen and C₁-C₆ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each R² is independently selected from the group consisting of C₁-C₆ alkyl, C₃-C₆ cycloalkyl, —S(O)ᵣR⁷, —S(O)₂NR⁷R⁸, —OR⁷, —O(CR⁵R⁶)(CR⁵R⁶)ᵩOR⁷, —O(CR⁵R⁶)(CR⁵R⁶)ᵩR⁷ and —CN; and R³ and R⁴ are each independently selected from the group consisting of hydrogen and C₁-C₆ alkyl.

In another aspect, the invention provides a compound of the formula (IX)

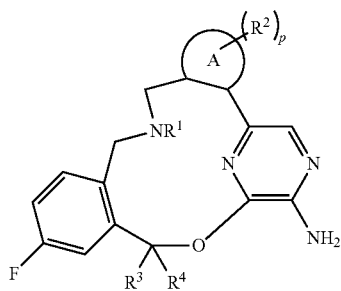

(IX)

wherein:

A is a ring selected from C₆-C₁₂ aryl and 5-6 membered heteroaryl;

R¹ is selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic and 5-6 membered heteroaryl, wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R² is independently selected from the group consisting of halogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, 5-6 membered heteroaryl, —S(O)ᵣR⁷, —S(O)₂NR⁷R⁸, —S(O)₂OR⁷, —NO₂, —(CR⁵R⁶)ᵩNR⁷R⁸, —N(CR⁵R⁶) (CR⁵R⁶)ᵩNR⁷R⁸, —O(CR⁵R⁶)(CR⁵R⁶)ᵩOR⁷, —O(CR⁵R⁶) (CR⁵R⁶)ᵩR⁷, —CN, —C(O)R⁷, —OC(O)R⁷, —O(CR⁵R⁶)ᵩ R⁷, —NR⁷C(O)R⁸, —(CR⁵R⁶)ᵩC(O)OR⁷, —(CR⁵R⁶)ᵩ NR⁷R⁸, —C(=NR⁷)NR⁷R⁸, —NR⁷C(O)NR⁷R⁸, —NR⁷S (O)₂R⁸ and —(CR⁵R⁶)ᵩC(O)NR⁷R⁸; wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl may be independently optionally substituted by halogen, —OH, —NH₂, —S(O)ᵣR⁹, —S(O)₂ NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹) NR⁹R¹⁰, —NR⁹C(O)NR⁹R¹⁰, —NR⁹S(O)₂R¹⁰ or —C(O) NR⁹R¹⁰;

R³ and R⁴ are each independently selected from hydrogen, C₁-C₆ alkyl and C₃-C₆ cycloalkyl, wherein each hydrogen on C₁-C₆ alkyl and C₃-C₆ cycloalkyl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁵ and R⁶ is independently selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, 5-6 membered heteroaryl, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O) OR⁹, —C(=NR⁹)NR⁹R¹⁰, —NR⁹C(O)NR⁹R¹⁰, —NR⁹S (O)₂R¹⁰ and —C(O)NR⁹R¹⁰; wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O) R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁷ and R⁸ is independently selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl, wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

In another embodiment of this aspect, $R^1$ is selected from the group consisting of hydrogen, $C_1$-$C_6$ alkyl, and $C_3$-$C_6$ cycloalkyl, wherein each hydrogen on said $C_1$-$C_6$ alkyl, and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, $R^1$ is selected from the group consisting of hydrogen, $C_1$-$C_6$ alkyl, and $C_3$-$C_6$ cycloalkyl.

In another embodiment of this aspect, $R^1$ is selected from the group consisting of hydrogen, $C_1$-$C_6$ alkyl, and $C_3$-$C_6$ cycloalkyl. In specific embodiments, $R^1$ is hydrogen, methyl, ethyl or cyclopropyl. In some embodiments, $R^1$ is hydrogen. In other embodiments, $R^1$ is methyl. In other embodiments, $R^1$ is ethyl. In other embodiments, $R^1$ is cyclopropyl.

In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, $R^3$ and $R^4$ are each independently selected from the group consisting of hydrogen and $C_1$-$C_6$ alkyl.

In another embodiment of this aspect, $R^3$ and $R^4$ are each independently selected from the group consisting of hydrogen and $C_1$-$C_6$ alkyl. In frequent embodiments, $R^3$ and $R^4$ are each independently hydrogen or methyl. In some such embodiments, each of $R^3$ and $R^4$ is hydrogen. In other such embodiments, one of $R^3$ and $R^4$ is hydrogen and the other is methyl.

In another embodiment of this aspect, A is a ring selected from phenyl, pyridine, triazine, pyrazole, imidazole, thiazole, isothiazole, oxazole and isoxazole. In another embodiment of this aspect, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, $R^3$ and $R^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each $R^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and $R^3$ and $R^4$ are each independently selected from the group consisting of hydrogen and $C_1$-$C_6$ alkyl.

In another aspect, the invention provides a compound of the formula (X)

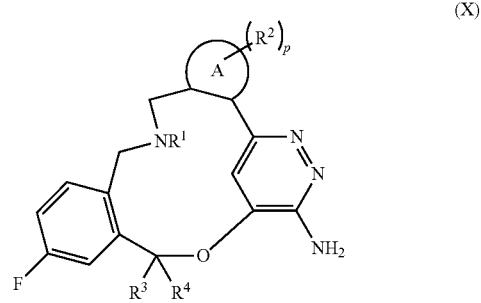

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^3$R$^6$)(CR$^3$R$^6$)$_q$NR$^7$R$^8$, —O(CR$^3$R$^6$)(CR$^5$R$^6$)$_q$OR$^7$, —O(CR$^3$R$^6$)(CR$^3$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^3$R$^6$)$_q$C(O)OR$^7$, —(CR$^3$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

In one embodiment of this aspect, R$^1$ is selected from the group consisting of hydrogen, $C_1$-$C_6$ alkyl, and $C_3$-$C_6$ cycloalkyl, wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, R$^1$ is selected from the group consisting of hydrogen, $C_1$-$C_6$ alkyl, and $C_3$-$C_6$ cycloalkyl.

In another embodiment of this aspect, each R$^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$. In another embodiment of this aspect, each R$^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN. In some such embodiments, R$^3$ and R$^4$ are each independently selected from the group consisting of hydrogen and $C_1$-$C_6$ alkyl.

In another embodiment of this aspect, R$^3$ and R$^4$ are each independently selected from the group consisting of hydrogen and $C_1$-$C_6$ alkyl. In frequent embodiments, R$^3$ and R$^4$ are each independently hydrogen or methyl. In some such embodiments, each of R$^3$ and R$^4$ is hydrogen. In other such embodiments, one of R$^3$ and R$^4$ is hydrogen and the other is methyl.

In another embodiment of this aspect, A is a ring selected from phenyl, pyridine, triazine, pyrazole, imidazole, thiazole, isothiazole, oxazole and isoxazole. In another embodiment of this aspect, R$^3$ and R$^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In specific embodiments of this aspect, A is a ring selected from the group consisting of the specific rings indicated as suitable for compounds of formula Φ, above.

In another embodiment of this aspect, A is a ring selected from phenyl, pyridine, triazine, pyrazole, imidazole, thiazole, isothiazole, oxazole and isoxazole. In some such embodiments, R$^3$ and R$^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole. In some such embodiments, R$^3$ and R$^4$ are each independently selected from the group consisting of hydrogen and $C_1$-$C_6$ alkyl.

In another embodiment of this aspect, A is a ring selected from the group consisting of phenyl, pyridine, pyrimidine, pyridazine, pyrazine, triazine, pyrazole, imidazole, triazole, tetrazole, thiazole, isothiazole, oxazole and isoxazole; each R$^2$ is independently selected from the group consisting of $C_1$-$C_6$ alkyl, $C_3$-$C_6$ cycloalkyl, —S(O)$_r$R$^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$ and —CN; and R$^3$ and R$^4$ are each independently selected from the group consisting of hydrogen and $C_1$-$C_6$ alkyl.

In another aspect, the invention provides a compound of the formula (XI)

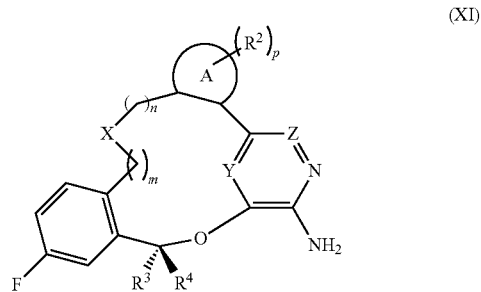

wherein:

X is selected from the group consisting of —(CR$^3$R$^6$)$_q$O(CR$^3$R$^6$)$_r$—, —(CR$^3$R$^6$)$_q$N(R$^1$)(CR$^3$R$^6$)$_r$—, —(CR$^3$R$^6$)$_q$C(O)N(R$^1$)(CR$^5$R$^6$)$_r$— and —(CR$^5$R$^6$)$_q$N(R$^1$)C(O)(CR$^5$R$^6$)$_r$—;

Y and Z are each independently N or CH, with the proviso that when Y is N, Z is CH and when Z is N, Y is CH;

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —$S(O)_tR^7$, —$S(O)_2NR^7R^8$, —$S(O)_2OR^7$, —$NO_2$, —$(CR^5R^6)_qNR^7R^8$, —$N(CR^5R^6)(CR^5R^6)_qNR^7R^8$, —$O(CR^5R^6)(CR^5R^6)_qOR^7$, —$O(CR^5R^6)(CR^5R^6)_qR^7$, —CN, —$C(O)R^7$, —$OC(O)R^7$, —$O(CR^5R^6)_qR^7$, —$NR^7C(O)R^8$, —$(CR^5R^6)_qC(O)OR^7$, —$(CR^5R^6)_qNR^7R^8$, —$C(=NR^7)NR^7R^8$, —$NR^7C(O)NR^7R^8$, —$NR^7S(O)_2R^8$ and —$(CR^5R^6)_qC(O)NR^7R^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ and —$C(O)NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

m is 0, 1, 2 or 3;
n is 0, 1, 2 or 3;
p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The same embodiments described herein as relevant to compounds of formula (I) are also applicable to compounds of formula (XI).

In another aspect, the invention provides a compound of the formula (XII)

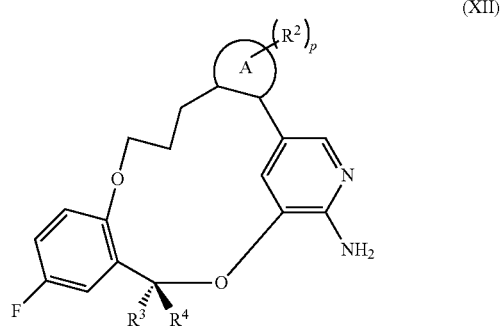

(XII)

wherein:

A is a ring selected from $C_6$-$C_{12}$ aryl and 5-6 membered heteroaryl;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —$S(O)_tR^7$, —$S(O)_2NR^7R^8$, —$S(O)_2OR^7$, —$NO_2$, —$(CR^5R^6)_qNR^7R^8$, —$N(CR^5R^6)(CR^5R^6)_qNR^7R^8$, —$O(CR^5R^6)(CR^5R^6)_qOR^7$, —$O(CR^5R^6)(CR^5R^6)_qR^7$, —CN, —$C(O)R^7$, —$OC(O)R^7$, —$O(CR^5R^6)_qR^7$, —$NR^7C(O)R^8$, —$(CR^5R^6)_qC(O)OR^7$, —$(CR^5R^6)_qNR^7R^8$, —$C(=NR^7)NR^7R^8$, —$NR^7C(O)NR^7R^8$, —$NR^7S(O)_2R^8$ and —$(CR^5R^6)_qC(O)NR^7R^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_tR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —$NH_2$, —$S(O)_tR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ and —$C(O)NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^9$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The same embodiments described herein as relevant to compounds of formula (II) are also applicable to compounds of formula (XII).

In another aspect, the invention provides a compound of the formula (XIII)

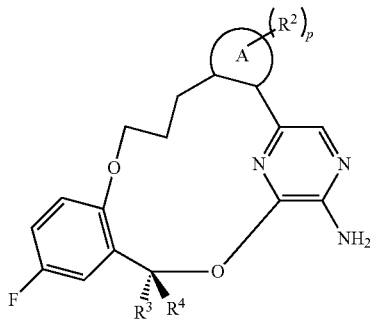

(XIII)

wherein:

A is a ring selected from $C_6$-$C_{12}$ aryl and 5-6 membered heteroaryl;

each R$^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$;
wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is $C_1$-$C_6$ alkyl or $C_3$-$C_6$ cycloalkyl and R$^4$ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The same embodiments described herein as relevant to compounds of formula (III) are also applicable to compounds of formula (XIII).

In another aspect, the inventions provides a compound of the formula (XIV)

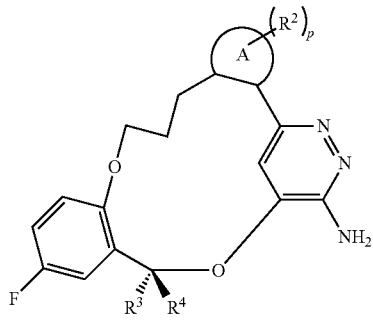

(XIV)

wherein:
A is a ring selected from $C_6$-$C_{12}$ aryl and 5-6 membered heteroaryl;

each R² is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R⁷, —S(O)$_2$NR⁷R⁸, —S(O)$_2$OR⁷, —NO$_2$, —(CR⁵R⁶)$_q$NR⁷R⁸, —N(CR⁵R⁶) (CR⁵R⁶)$_q$NR⁷R⁸, —O(CR⁵R⁶)(CR⁵R⁶)$_q$OR⁷, —O(CR⁵R⁶) (CR⁵R⁶)$_q$R⁷, —CN, —C(O)R⁷, —OC(O)R⁷, —O(CR⁵R⁶)$_q$ R⁷, —NR⁷C(O)R⁸, —(CR⁵R⁶)$_q$C(O)OR⁷, —(CR⁵R⁶)$_q$ NR⁷R⁸, —C(=NR⁷)NR⁷R⁸, —NR⁷C(O)NR⁷R⁸, —NR⁷S (O)$_2$R⁸ and —(CR⁵R⁶)$_q$C(O)NR⁷R⁸; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R⁹, —S(O) $_2$NR⁹R¹⁰, —S(O)$_2$OR⁹, —NO$_2$, —OR⁹, —CN, —C(O)R⁹, —OC(O)R⁹, —NR⁹C(O)R¹⁰, —C(O)OR⁹, —C(=NR⁹) NR⁹R¹⁰, —NR⁹C(O)NR⁹R¹⁰, —NR⁹S(O)$_2$R¹⁰ or —C(O) NR⁹R¹⁰;

R³ is $C_1$-$C_6$ alkyl or $C_3$-$C_6$ cycloalkyl and R⁴ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O)R⁹, —NR⁹C(O) R¹⁰, —C(O)OR⁹, —C(=NR⁹)NR⁹R¹⁰, —NR⁹C(O) NR⁹R¹⁰, —NR⁹S(O)$_2$R¹⁰ or —C(O)NR⁹R¹⁰;

each R⁵ and R⁶ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O)R⁹, —NR⁹C(O)R¹⁰, —C(O) OR⁹, —C(=NR⁹)NR⁹R¹⁰, —NR⁹C(O)NR⁹R¹⁰, —NR⁹S (O)$_2$R¹⁰ and —C(O)NR⁹R¹⁰; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O) R⁹, —NR⁹C(O)R¹⁰, —C(O)OR⁹, —C(=NR⁹)NR⁹R¹⁰, —NR⁹C(O)NR⁹R¹⁰, —NR⁹S(O)$_2$R¹⁰ or —C(O)NR⁹R¹⁰;

each R⁷ and R⁸ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R⁹, —S(O)$_2$NR⁹R¹⁰, —S(O)$_2$OR⁹, —NO$_2$, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)$_2$R¹⁰ or —C(O)NR⁹R¹⁰;

each R⁹ and R¹⁰ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The same embodiments described herein as relevant to compounds of formula (IV) are also applicable to compounds of formula (XIV).

In another aspect, the invention provides a compound of the formula (XV)

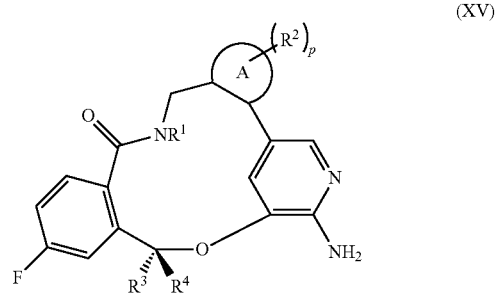

(XV)

wherein:
A is a ring selected from $C_6$-$C_{12}$ aryl and 5-6 membered heteroaryl;

R¹ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O)R⁹, —NR⁹C(O) R¹⁰, —C(O)OR⁹, —C(=NR⁹)NR⁹R¹⁰, —NR⁹C(O) NR⁹R¹⁰, —NR⁹S(O)$_2$R¹⁰ or —C(O)NR⁹R¹⁰;

each R² is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R⁷, —S(O)$_2$NR⁷R⁸, —S(O)$_2$OR⁷, —NO$_2$, —(CR⁵R⁶)$_q$NR⁷R⁸, —N(CR⁵R⁶) (CR⁵R⁶)$_q$NR⁷R⁸, —O(CR⁵R⁶)(CR⁵R⁶)$_q$OR⁷, —O(CR⁵R⁶) (CR⁵R⁶)$_q$R⁷, —CN, —C(O)R⁷, —OC(O)R⁷, —O(CR⁵R⁶)$_q$ R⁷, —NR⁷C(O)R⁸, —(CR⁵R⁶)$_q$C(O)OR⁷, —(CR⁵R⁶)$_q$ NR⁷R⁸, —C(=NR⁷)NR⁷R⁸, —NR⁷C(O)NR⁷R⁸, —NR⁷S (O)$_2$R⁸ and —(CR⁵R⁶)$_q$C(O)NR⁷R⁸; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R⁹, —S(O)$_2$ NR⁹R¹⁰, —S(O)$_2$OR⁹, —NO$_2$, —OR⁹, —CN, —C(O)R⁹, —OC(O)R⁹, —NR⁹C(O)R¹⁰, —C(O)OR⁹, —C(=NR⁹) NR⁹R¹⁰, —NR⁹C(O)NR⁹R¹⁰, —NR⁹S(O)$_2$R¹⁰ or —C(O) NR⁹R¹⁰;

R³ is $C_1$-$C_6$ alkyl or $C_3$-$C_6$ cycloalkyl and R⁴ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O)R⁹, —NR⁹C(O) R¹⁰, —C(O)OR⁹, —C(=NR⁹)NR⁹R¹⁰, —NR⁹C(O) NR⁹R¹⁰, —NR⁹S(O)$_2$R¹⁰ or —C(O)NR⁹R¹⁰;

each R⁵ and R⁶ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O)R⁹, —NR⁹C(O)R¹⁰, —C(O) OR⁹, —C(=NR⁹)NR⁹R¹⁰, —NR⁹C(O)NR⁹R¹⁰, —NR⁹S (O)$_2$R¹⁰ and —C(O)NR⁹R¹⁰; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R⁹, —S(O)$_2$NR⁹R¹⁰, —S(O)$_2$OR⁹, —NO$_2$, —CN, —OR⁹, —C(O)R⁹, —OC(O)

$R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_rR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The same embodiments described herein as relevant to compounds of formula (V) are also applicable to compounds of formula (XV).

In another aspect, the invention provides a compound of the formula (XVI)

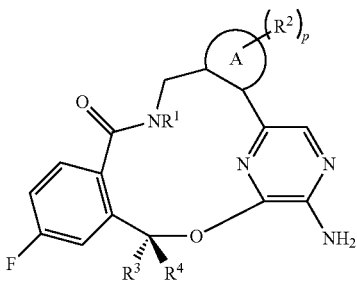

(XVI)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_rR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —$S(O)_rR^7$, —$S(O)_2NR^7R^8$, —$S(O)_2OR^7$, —$NO_2$, —$(CR^5R^6)_qNR^7R^8$, —$N(CR^5R^6)(CR^5R^6)_qNR^7R^8$, —$O(CR^5R^6)(CR^5R^6)_qOR^7$, —$O(CR^5R^6)_q$ $(CR^5R^6)_qR^7$, —CN, —$C(O)R^7$, —$OC(O)R^7$, —$O(CR^5R^6)_q$ $R^7$, —$NR^7C(O)R^8$, —$(CR^5R^6)_qC(O)OR^7$, —$(CR^5R^6)_q$ $NR^7R^8$, —$C(=NR^7)NR^7R^8$, —$NR^7C(O)NR^7R^8$, —$NR^7S$ $(O)_2R^8$ and —$(CR^5R^6)_qC(O)NR^7R^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_rR^9$, —$S(O)_2$ $NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)$ $NR^9R^{10}$, —$NR^9C(O)NR^9R^{10}$, —$NR^9S(O)_2R^{10}$ or —$C(O)$ $NR^9R^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, —OH, —$NH_2$, —$S(O)_rR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)$ $R^{10}$, —$C(O)OR^9$, —$C(=NR^9)NR^9R^{10}$, —$NR^9C(O)$ $NR^9R^{10}$, —$NR^9S(O)_2R^{10}$ or —$C(O)NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —$NH_2$, —$S(O)_rR^9$, —$S(O)_2NR^9R^{10}$, —$S(O)_2OR^9$, —$NO_2$, —CN, —$OR^9$, —$C(O)R^9$, —$OC(O)R^9$, —$NR^9C(O)R^{10}$, —$C(O)$ $OR^9$, —$C(=NR^9)NR^9R^{10}$, —$NR^9C(O)NR^9R^{10}$, —$NR^9S$ $(O)_2R^{10}$ and —$C(O)NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —$S(O)_rR^9$, —$S(O)_2NR^9R^{10}$, —$S(O)_2OR^9$, —$NO_2$, —CN, —$OR^9$, —$C(O)R^9$, —$OC(O)$ $R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —$S(O)_rR^9$, —$S(O)_2NR^9R^{10}$, —$S(O)_2OR^9$, —$NO_2$, —$OR^9$, —CN, —$C(O)R^9$, —$OC(O)R^9$, —$NR^9C(O)R^{10}$, —$C(O)OR^9$, —$C(=NR^9)NR^9R^{10}$, —$NR^9C(O)NR^9R^{10}$, —$NR^9S(O)_2R^{10}$ or —$C(O)NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The same embodiments described herein as relevant to compounds of formula (VI) are also applicable to compounds of formula (XVI).

In another aspect, the invention provides a compound of the formula (XVII)

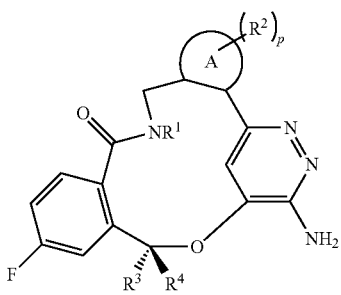

(XVII)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The same embodiments described herein as relevant to compounds of formula (VII) are also applicable to compounds of formula (XVII).

In another aspect, the invention provides a compound of the formula (XVIII)

(XVIII)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)

$(CR^5R^6)_qNR^7R^8$, $-O(CR^5R^6)(CR^5R^6)_qOR^7$, $-O(CR^5R^6)(CR^5R^6)_qR^7$, $-CN$, $-C(O)R^7$, $-OC(O)R^7$, $-O(CR^5R^6)_qR^7$, $-NR^7C(O)R^8$, $-(CR^5R^6)_qC(O)OR^7$, $-(CR^5R^6)_qNR^7R^8$, $-C(=NR^7)NR^7R^8$, $-NR^7C(O)NR^7R^8$, $-NR^7S(O)_2R^8$ and $-(CR^5R^6)_qC(O)NR^7R^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, $-OH$, $-NH_2$, $-S(O)_tR^9$, $-S(O)_2NR^9R^{10}$, $-S(O)_2OR^9$, $-NO_2$, $-OR^9$, $-CN$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, $-OH$, $-NH_2$, $-S(O)_tR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, $-OH$, $-NH_2$, $-S(O)_tR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ and $-C(O)NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, $-OH$, $-NH_2$, $-S(O)_tR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, $-OH$, $-NH_2$, $-S(O)_tR^9$, $-S(O)_2NR^9R^{10}$, $-S(O)_2OR^9$, $-NO_2$, $-OR^9$, $-CN$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The same embodiments described herein as relevant to compounds of formula (VIII) are also applicable to compounds of formula (XVIII).

In another aspect, the invention provides a compound of the formula (XIX)

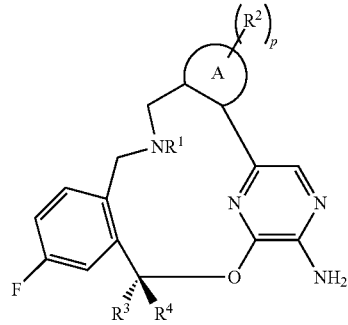

(XIX)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, $-OH$, $-NH_2$, $-S(O)_tR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, $-S(O)_tR^7$, $-S(O)_2NR^7R^8$, $-S(O)_2OR^7$, $-NO_2$, $-(CR^5R^6)_qNR^7R^8$, $-N(CR^5R^6)(CR^5R^6)_qNR^7R^8$, $-O(CR^5R^6)(CR^5R^6)_qOR^7$, $-O(CR^5R^6)(CR^5R^6)_qR^7$, $-CN$, $-C(O)R^7$, $-OC(O)R^7$, $-O(CR^5R^6)_qR^7$, $-NR^7C(O)R^8$, $-(CR^5R^6)_qC(O)OR^7$, $-(CR^5R^6)_qNR^7R^8$, $-C(=NR^7)NR^7R^8$, $-NR^7C(O)NR^7R^8$, $-NR^7S(O)_2R^8$ and $-(CR^5R^6)_qC(O)NR^7R^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, $-OH$, $-NH_2$, $-S(O)_tR^9$, $-S(O)_2NR^9R^{10}$, $-S(O)_2OR^9$, $-NO_2$, $-OR^9$, $-CN$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, $-OH$, $-NH_2$, $-S(O)_tR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ or $-C(O)NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, $-OH$, $-NH_2$, $-S(O)_tR^9$, $-S(O)_2NR^9R^{10}$, $-S(O)_2OR^9$, $-NO_2$, $-CN$, $-OR^9$, $-C(O)R^9$, $-OC(O)R^9$, $-NR^9C(O)R^{10}$, $-C(O)OR^9$, $-C(=NR^9)NR^9R^{10}$, $-NR^9C(O)NR^9R^{10}$, $-NR^9S(O)_2R^{10}$ and $-C(O)NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, $-OH$, $-NH_2$, $-S(O)_tR^9$, $-S(O)_2NR^9R^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The same embodiments described herein as relevant to compounds of formula (IX) are also applicable to compounds of formula (XIX).

In another aspect, the invention provides a compound of the formula (XX)

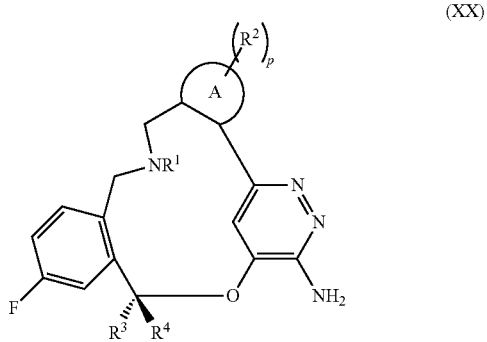

(XX)

wherein:

A is a ring selected from C$_6$-C$_{12}$ aryl and 5-6 membered heteroaryl;

R$^1$ is selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^2$ is independently selected from the group consisting of halogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is C$_1$-C$_6$ alkyl or C$_3$-C$_6$ cycloalkyl and R$^4$ is hydrogen, wherein each hydrogen on C$_1$-C$_6$ alkyl or C$_3$-C$_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The same embodiments described herein as relevant to compounds of formula (X) are also applicable to compounds of formula (XX).

In another aspect, the invention provides a compound of the formula (XXI)

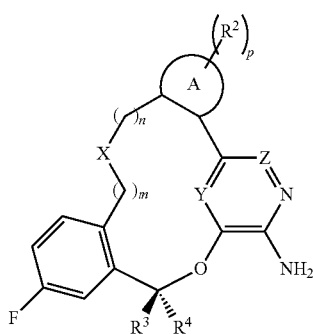

(XXI)

wherein:

X is selected from the group consisting of —(CR$^5$R$^6$)$_q$O(CR$^5$R$^6$)$_r$—, —(CR$^5$R$^6$)$_q$N(R$^1$)(CR$^5$R$^6$)$_r$—, —(CR$^5$R$^6$)$_q$C(O)N(R$^1$)(CR$^5$R$^6$)$_r$— and —(CR$^5$R$^6$)$_q$N(R$^1$)C(O)(CR$^5$R$^6$)$_r$—;

Y and Z are each independently N or CH, with the proviso that when Y is N, Z is CH and when Z is N, Y is CH;

A is a ring selected from C$_6$-C$_{12}$ aryl and 5-6 membered heteroaryl;

R$^1$ is selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^2$ is independently selected from the group consisting of halogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —S(O)$_t$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is C$_1$-C$_6$ alkyl or C$_3$-C$_6$ cycloalkyl and R$^4$ is hydrogen, wherein each hydrogen on C$_1$-C$_6$ alkyl or C$_3$-C$_6$ cycloalkyl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_t$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

m is 0, 1, 2 or 3;
n is 0, 1, 2 or 3;
p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The embodiments described herein as relevant to compounds of formula (I) and (XI) are also applicable to compounds of formula (XXI), to the extent they are compatible with the definition of R$^3$ and R$^4$ in formula (XXI).

In another aspect, the invention provides a compound of the formula (XXII)

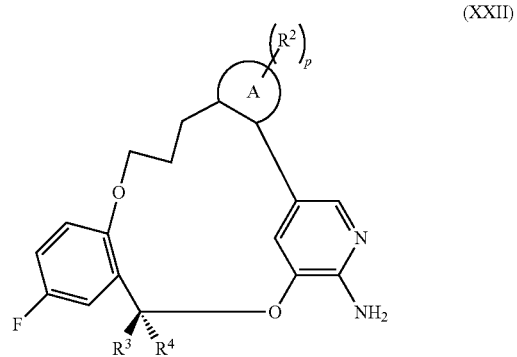

(XXII)

wherein:

A is a ring selected from C$_6$-C$_{12}$ aryl and 5-6 membered heteroaryl;

each R$^2$ is independently selected from the group consisting of halogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —S(O)$_t$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S $(O)_2R^8$ and $-(CR^5R^6)_qC(O)NR^7R^8$; wherein each hydrogen on said $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is $C_1-C_6$ alkyl or $C_3-C_6$ cycloalkyl and R$^4$ is hydrogen, wherein each hydrogen on $C_1-C_6$ alkyl or $C_3-C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl, wherein each hydrogen on said $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ are independently selected from hydrogen, $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The embodiments described herein as relevant to compounds of formula (II) and (XII) are also applicable to compounds of formula (XXII), to the extent they are compatible with the definition of R$^3$ and R$^4$ in formula (XXII).

In another aspect, the invention provides a compound of the formula (XXIII)

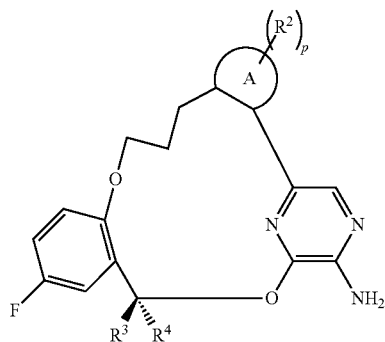

(XXIII)

wherein:

A is a ring selected from $C_6-C_{12}$ aryl and 5-6 membered heteroaryl;

each R$^2$ is independently selected from the group consisting of halogen, $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is $C_1-C_6$ alkyl or $C_3-C_6$ cycloalkyl and R$^4$ is hydrogen, wherein each hydrogen on $C_1-C_6$ alkyl or $C_3-C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic, and 5-6 membered heteroaryl, wherein each hydrogen on said $C_1-C_6$ alkyl, $C_2-C_6$ alkenyl, $C_2-C_6$ alkynyl, $C_3-C_6$ cycloalkyl, $C_6-C_{12}$ aryl, 3-12 membered heteroalicyclic and 5-6 membered heteroaryl may be independently optionally substituted by halogen, —OH, —NH$_2$, —S(O)$_r$R$^9$, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁹ and R¹⁰ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The embodiments described herein as relevant to compounds of formula (III) and (XIII) are also applicable to compounds of formula (XXIII), to the extent they are compatible with the definition of R³ and R⁴ in formula (XXIII).

In another aspect, the inventions provides a compound of the formula (XXIV)

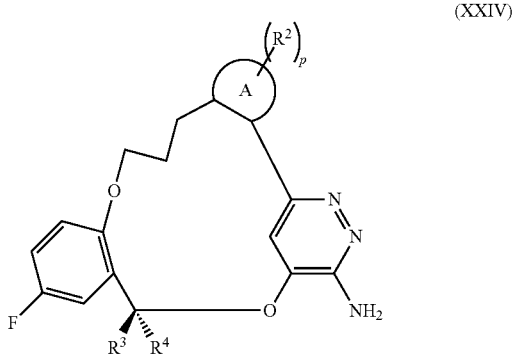

(XXIV)

wherein:
A is a ring selected from $C_6$-$C_{12}$ aryl and 5-6 membered heteroaryl;

each R² is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)ₜR⁷, —S(O)₂NR⁷R⁸, —S(O)₂OR⁷, —NO₂, —(CR⁵R⁶)ₑNR⁷R⁸, —N(CR⁵R⁶) (CR⁵R⁶)ₑNR⁷R⁸, —O(CR⁵R⁶)(CR⁵R⁶)ₑOR⁷, —O(CR⁵R⁶)ₑ (CR⁵R⁶)ₑR⁷, —CN, —C(O)R⁷, —OC(O)R⁷, —O(CR⁵R⁶)ₑ R⁷, —NR⁷C(O)R⁸, —(CR⁵R⁶)ₑC(O)OR⁷, —(CR⁵R⁶)ₑ NR⁷R⁸, —C(=NR⁷)NR⁷R⁸, —NR⁷C(O)NR⁷R⁸, —NR⁷S (O)₂R⁸ and —(CR⁵R⁶)ₑC(O)NR⁷R⁸; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH₂, —S(O)ₜR⁹, —S(O)₂ NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹) NR⁹R¹⁰, —NR⁹C(O)NR⁹R¹⁰, —NR⁹S(O)₂R¹⁰ or —C(O) NR⁹R¹⁰;

R³ is $C_1$-$C_6$ alkyl or $C_3$-$C_6$ cycloalkyl and R⁴ is hydrogen, wherein each hydrogen on $C_1$-$C_6$ alkyl or $C_3$-$C_6$ cycloalkyl may be independently optionally substituted by halogen, —OH, —NH₂, —S(O)ₜR⁹, —S(O)₂NR⁹R¹⁰, —S(O)₂OR⁹, —NO₂, —CN, —OR⁹, —C(O)R⁹, —OC(O)R⁹, —NR⁹C(O) R¹⁰, —C(O)OR⁹, —C(=NR⁹)NR⁹R¹⁰, —NR⁹C(O) NR⁹R¹⁰, —NR⁹S(O)₂R¹⁰ or —C(O)NR⁹R¹⁰;

each R⁵ and R⁶ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH₂, —S(O)ₜR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O) OR⁹, —C(=NR⁹)NR⁹R¹⁰, —NR⁹C(O)NR⁹R¹⁰, —NR⁹S (O)₂R¹⁰ and —C(O)NR⁹R¹⁰; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH₂, —S(O)ₜR⁹, —S(O)₂NR⁹R¹⁰, —S(O)₂OR⁹, —NO₂, —CN, —OR⁹, —C(O)R⁹, —OC(O) R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁷ and R⁸ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH₂, —S(O)ₜR⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁹ and R¹⁰ are independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The embodiments described herein as relevant to compounds of formula (IV) and (XIV) are also applicable to compounds of formula (XXIV), to the extent they are compatible with the definition of R³ and R⁴ in formula (XXIV).

In another aspect, the invention provides a compound of the formula (XXV)

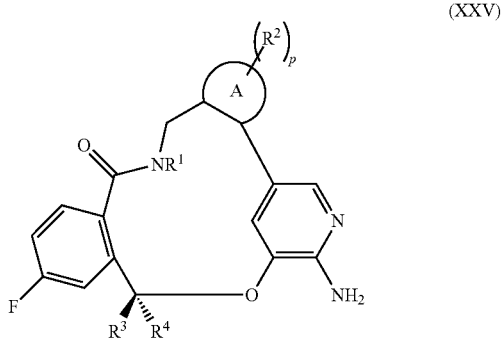

(XXV)

wherein:
A is a ring selected from $C_6$-$C_{12}$ aryl and 5-6 membered heteroaryl;

R¹ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH₂, —S(O)ₜR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R² is independently selected from the group consisting of halogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, 5-6 membered heteroaryl, —S(O)ᵣR⁷, —S(O)₂NR⁷R⁸, —S(O)₂OR⁷, —NO₂, —(CR⁵R⁶)qNR⁷R⁸, —N(CR⁵R⁶)(CR⁵R⁶)qNR⁷R⁸, —O(CR⁵R⁶)(CR⁵R⁶)qOR⁷, —O(CR⁵R⁶)(CR⁵R⁶)qR⁷, —CN, —C(O)R⁷, —OC(O)R⁷, —O(CR⁵R⁶)qR⁷, —NR⁷C(O)R⁸, —(CR⁵R⁶)qC(O)OR⁷, —(CR⁵R⁶)qNR⁷R⁸, —C(=NR⁷)NR⁷R⁸, —NR⁷C(O)NR⁷R⁸, —NR⁷S(O)₂R⁸ and —(CR⁵R⁶)qC(O)NR⁷R⁸; wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

R³ is C₁-C₆ alkyl or C₃-C₆ cycloalkyl and R⁴ is hydrogen, wherein each hydrogen on C₁-C₆ alkyl or C₃-C₆ cycloalkyl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁵ and R⁶ is independently selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, 5-6 membered heteroaryl, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ and —C(O)NR⁹R¹⁰; wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁷ and R⁸ is independently selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl, wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁹ and R¹⁰ is independently selected from hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The embodiments described herein as relevant to compounds of formula (V) and (XV) are also applicable to compounds of formula (XV), to the extent they are compatible with the definition of R³ and R⁴ in formula (XV).

In another aspect, the invention provides a compound of the formula (XXVI)

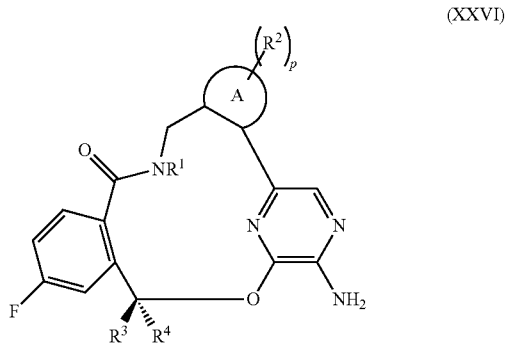

(XXVI)

wherein:
A is a ring selected from C₆-C₁₂ aryl and 5-6 membered heteroaryl;

R¹ is selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic and 5-6 membered heteroaryl, wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R² is independently selected from the group consisting of halogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, 5-6 membered heteroaryl, —S(O)ᵣR⁷, —S(O)₂NR⁷R⁸, —S(O)₂OR⁷, —NO₂, —(CR⁵R⁶)qNR⁷R⁸, —N(CR⁵R⁶)(CR⁵R⁶)qNR⁷R⁸, —O(CR⁵R⁶)(CR⁵R⁶)qOR⁷, —O(CR⁵R⁶)(CR⁵R⁶)qR⁷, —CN, —C(O)R⁷, —OC(O)R⁷, —O(CR⁵R⁶)qR⁷, —NR⁷C(O)R⁸, —(CR⁵R⁶)qC(O)OR⁷, —(CR⁵R⁶)qNR⁷R⁸, —C(=NR⁷)NR⁷R⁸, —NR⁷C(O)NR⁷R⁸, —NR⁷S(O)₂R⁸ and —(CR⁵R⁶)qC(O)NR⁷R⁸; wherein each hydrogen on said C₁-C₆ alkyl, C₂-C₆ alkenyl, C₂-C₆ alkynyl, C₃-C₆ cycloalkyl, C₆-C₁₂ aryl, 3-12 membered heteroalicyclic, and 5-6 membered heteroaryl may be independently optionally substituted by halogen, —OH, —NH₂, —S(O)ᵣR⁹, —S(O)₂NR⁹R¹⁰, —S(O)₂OR⁹, —NO₂, —OR⁹, —CN, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

R³ is C₁-C₆ alkyl or C₃-C₆ cycloalkyl and R⁴ is hydrogen, wherein each hydrogen on C₁-C₆ alkyl or C₃-C₆ cycloalkyl may be independently optionally substituted by halogen, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S(O)₂R¹⁰ or —C(O)NR⁹R¹⁰;

each R⁵ and R⁶ is independently selected from the group consisting of hydrogen, C₁-C₆ alkyl, C₂-C₆ alkenyl, C₂-C₆ alkynyl, C₃-C₆ cycloalkyl, C₆-C₁₂ aryl, 3-12 membered heteroalicyclic, 5-6 membered heteroaryl, —OH, —NH₂, —S(O)ᵣR⁹, —S(O)₂NR⁹R¹⁰, —S(O)₂OR⁹, —NO₂, —CN, —OR⁹, —C(O)R⁹, —OC(O)R⁹, —NR⁹C(O)R¹⁰, —C(O)OR⁹, —C(=NR⁹)NR⁹R¹⁰, —NR⁹C(O)NR⁹R¹⁰, —NR⁹S (O)$_2$R$^{10}$ and —C(O)NR$^9$R$^{10}$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The embodiments described herein as relevant to compounds of formula (VI) and (XVI) are also applicable to compounds of formula (XVI), to the extent they are compatible with the definition of R$^3$ and R$^4$ in formula (XVI).

In another aspect, the invention provides a compound of the formula (XXVII)

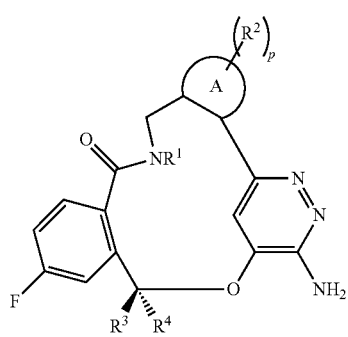

(XXVII)

wherein:
A is a ring selected from C$_6$-C$_{12}$ aryl and 5-6 membered heteroaryl;
R$^1$ is selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^2$ is independently selected from the group consisting of halogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —S(O)$_t$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$) (CR$^5$R$^6$)$_q$NR$^7$R$^8$, —O(CR$^5$R$^6$)(CR$^5$R$^6$)$_q$OR$^7$, —O(CR$^5$R$^6$) (CR$^5$R$^6$)$_q$R$^7$, —CN, —C(O)R$^7$, —OC(O)R$^7$, —O(CR$^5$R$^6$)$_q$ R$^7$, —NR$^7$C(O)R$^8$, —(CR$^5$R$^6$)$_q$C(O)OR$^7$, —(CR$^5$R$^6$)$_q$ NR$^7$R$^8$, —C(=NR$^7$)NR$^7$R$^8$, —NR$^7$C(O)NR$^7$R$^8$, —NR$^7$S (O)$_2$R$^8$ and —(CR$^5$R$^6$)$_q$C(O)NR$^7$R$^8$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$ NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$) NR$^9$R$^{10}$, —NR$^9$C(O)NR$^9$R$^{10}$, —NR$^9$S(O)$_2$R$^{10}$ or —C(O) NR$^9$R$^{10}$;

R$^3$ is C$_1$-C$_6$ alkyl or C$_3$-C$_6$ cycloalkyl and R$^4$ is hydrogen, wherein each hydrogen on C$_1$-C$_6$ alkyl or C$_3$-C$_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O) R$^{10}$, —C(O)OR$^9$, —C(=NR$^9$)NR$^9$R$^{10}$, —NR$^9$C(O) NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O) OR$^9$, —C(=NR$^9$)NR$^9$R$^{10}$, —NR$^9$C(O)NR$^9$R$^{10}$, —NR$^9$S (O)$_2$R$^{10}$ and —C(O)NR$^9$R$^{10}$; wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O) R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3;
each t is independently 0, 1 or 2; or a pharmaceutically acceptable salt thereof.

The embodiments described herein as relevant to compounds of formula (VII) and (XVII) are also applicable to compounds of formula (XVII), to the extent they are compatible with the definition of R$^3$ and R$^4$ in formula (XVII).

In another aspect, the invention provides a compound of the formula (XXVIII)

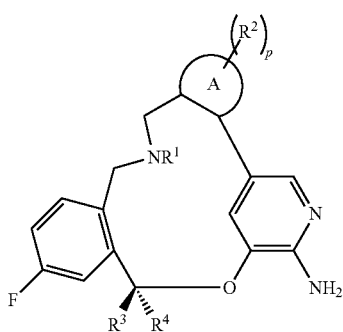

(XXVIII)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The embodiments described herein as relevant to compounds of formula (VIII) and (XVIII) are also applicable to compounds of formula (XVIII), to the extent they are compatible with the definition of $R^3$ and $R^4$ in formula (XVIII).

In another aspect, the invention provides a compound of the formula (XXIX)

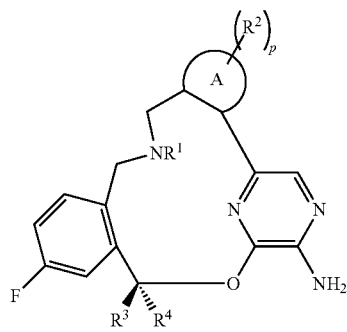

(XXIX)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)

$(CR^5R^6)_qR^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is $C_1$-$C_6$ alkyl or $C_3$-$C_6$ cycloalkyl and R$^4$ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3;

each r is independently 0, 1, 2 or 3; and each t is independently 0, 1 or 2;

or a pharmaceutically acceptable salt thereof.

The embodiments described herein as relevant to compounds of formula (IX) and (XIX) are also applicable to compounds of formula (XXIX), to the extent they are compatible with the definition of R$^3$ and R$^4$ in formula (XXIX).

In another aspect, the invention provides a compound of the formula (XXX)

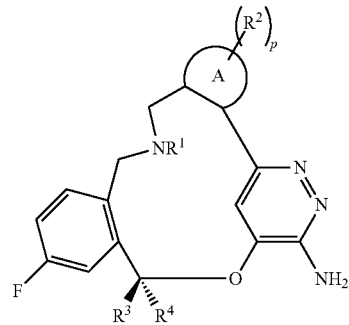

(XXX)

wherein:

A is a ring selected from $C_6$-$C_{12}$ aryl and 5-6 membered heteroaryl;

R$^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NR$^7$R$^8$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

R$^3$ is $C_1$-$C_6$ alkyl or $C_3$-$C_6$ cycloalkyl and R$^4$ is hydrogen, wherein each hydrogen on $C_1$-$C_6$ alkyl or $C_3$-$C_6$ cycloalkyl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^5$ and R$^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^7$ and R$^8$ is independently selected from the group consisting of hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl, wherein each hydrogen on said C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic and 5-6 membered heteroaryl may be independently optionally substituted by halogen, —OH, —NH$_2$, —S(O)$_r$R$^9$, —S(O)$_2$NR$^9$R$^{10}$, —S(O)$_2$OR$^9$, —NO$_2$, —OR$^9$, —CN, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$ or —C(O)NR$^9$R$^{10}$;

each R$^9$ and R$^{10}$ is independently selected from hydrogen, C$_1$-C$_6$ alkyl, C$_2$-C$_6$ alkenyl, C$_2$-C$_6$ alkynyl, C$_3$-C$_6$ cycloalkyl, C$_6$-C$_{12}$ aryl, 3-12 membered heteroalicyclic, and 5-6 membered heteroaryl;

p is 0, 1, 2, 3 or 4;
each q is independently 0, 1, 2 or 3;
each r is independently 0, 1, 2 or 3; and
each t is independently 0, 1 or 2;
or a pharmaceutically acceptable salt thereof.

The embodiments described herein as relevant to compounds of formula (X) and (XX) are also applicable to compounds of formula (XXX), to the extent they are compatible with the definition of R$^3$ and R$^4$ in formula (XXX).

In one embodiment, the invention provides one or more compounds selected from the group consisting of the compounds of Example 1 to Example 137, or a pharmaceutically acceptable salt thereof.

In another embodiment, the invention provides a compound selected from:

(5R)-8-amino-3-fluoro-5,17-dimethyl-13-(methylsulfonyl)-16,17-dihydro-7,11-(metheno)dibenzo[g,l][1,4,10]oxadiazacyclotetradecin-18(5H)-one;
(10R)-7-amino-12-fluoro-2,10,16-trim ethyl-15-oxo-10,15,16,17-tetrahydro-2H-8,4-(metheno)pyrazolo[4,3-h][2,5,11]benzoxadiazacyclotetradecine-3-carbonitrile;
(10R)-7-amino-12-fluoro-3-methoxy-10,16-dimethyl-16,17-dihydro-8,4-(metheno)isothiazolo[4,3-h][2,5,11]benzoxadiazacyclotetradecin-15(10H)-one;
7-amino-12-fluoro-2,16-dimethyl-15-oxo-10,15,16,17-tetrahydro-2H-8,4-(metheno)pyrazolo[4,3-h][2,5,11]benzoxadiazacyclotetradecine-3-carbonitrile;
8-amino-3-fluoro-17-methyl-13-(methylsulfonyl)-16,17-dihydro-7,11-(metheno)dibenzo[g,l][1,4,10]oxadiazacyclotetradecin-18(5H)-one;
7-amino-12-fluoro-1,3,16-trimethyl-16,17-dihydro-1H-8,4-(metheno)pyrazolo[4,3-h][2,5,11]benzoxadiazacyclotetradecin-15(10H)-one;
8-amino-3-fluoro-17-methyl-16,17-dihydro-7,11-(metheno)dibenzo[g,l][1,4,10]oxadiazacyclotetradecin-18(5H)-one;
8-amino-3-fluoro-5,17-dimethyl-16,17-dihydro-7,11-(metheno)dibenzo[g,l][1,4,10]-oxadiazacyclotetradecin-18(5H)-one;
7-amino-16-ethyl-12-fluoro-1,3,10-trimethyl-16,17-dihydro-1H-8,4-(metheno)pyrazolo[4,3-h][2,5,11]benzoxadiazacyclotetradecin-15(10H)-one;
7-amino-16-cyclopropyl-12-fluoro-1,3,10-trimethyl-16,17-dihydro-1H-8,4-(metheno)pyrazolo[4,3-h][2,5,11]benzoxadiazacyclotetradecin-15(10H)-one;
7-amino-12-fluoro-1,3,10,16-tetramethyl-16,17-dihydro-1H-8,4-(metheno)pyrazolo[4,3-h][2,5,11]benzoxadiazacyclotetradecin-15(10H)-one;
7-amino-3-cyclopropyl-12-fluoro-2,10,16-trimethyl-16,17-dihydro-2H-8,4-(metheno)pyrazolo[4,3-h][2,5,11]benzoxadiazacyclotetradecin-15(10H)-one;
7-amino-3-cyclopropyl-12-fluoro-1,10,16-trimethyl-16,17-dihydro-1H-8,4-(metheno)pyrazolo[4,3-h][2,5,11]benzoxadiazacyclotetradecin-15(10H)-one;
7-amino-12-fluoro-3-methoxy-2,10,16-trinnethyl-16,17-dihydro-2H-8,4-(metheno)pyrazolo[4,3-h][2,5,11]benzoxadiazacyclotetradecin-15(10H)-one;
7-amino-12-fluoro-3-methoxy-1,10,16-trimethyl-16,17-dihydro-1H-8,4-(metheno)pyrazolo[4,3-h][2,5,11]benzoxadiazacyclotetradecin-15(10H)-one;
7-amino-10-ethyl-12-fluoro-3-methoxy-1,16-dimethyl-16,17-dihydro-1H-8,4-(metheno)pyrazolo[4,3-h][2,5,11]benzoxadiazacyclotetradecin-15(10H)-one;
7-amino-10-cyclopropyl-12-fluoro-3-methoxy-1,16-dimethyl-16,17-dihydro-1H-8,4-(metheno)pyrazolo[4,3-h][2,5,11]benzoxadiazacyclotetradecin-15(10H)-one;
(10R)-7-amino-3-ethyl-12-fluoro-10,16-dimethyl-16,17-dihydro-3H-8,4-(metheno)pyrazolo[3,4-h][2,5,11]benzoxadiazacyclotetradecin-15(10H)-one;
7-amino-12-fluoro-1,3,10,16-tetramethyl-16,17-dihydro-1H-8,4-(azeno)pyrazolo[4,3-h][2,5,11]benzoxadiazacyclotetradecin-15(10H)-one;
8-amino-13-fluoro-4-methoxy-11,17-dimethyl-17,18-dihydro-9,5-(azeno)pyrido[3,4-h][2,5,11]benzoxadiazacyclotetradecin-16(11H)-one;
7-amino-12-fluoro-2,10,16-trimethyl-15-oxo-10,15,16,17-tetrahydro-2H-8,4-(azeno)pyrazolo[4,3-h][2,5,11]benzoxadiazacyclotetradecine-3-carbonitrile;
(11R)-8-amino-13-fluoro-4-methoxy-11,17-dimethyl-17,18-dihydro-9,5-(metheno)pyrido[3,4-h][2,5,11]benzoxadiazacyclotetradecin-16(11H)-one;
(5R)-3-fluoro-5,17-dimethyl-13-(methylsulfonyl)-5,16,17,18-tetrahydro-7,11-(metheno)dibenzo[g,l][1,4,10]oxadiazacyclotetradecin-8-amine;
(10R)-7-amino-12-fluoro-2,10,16-trimethyl-10,15,16,17-tetrahydro-2H-4,8-(metheno)pyrazolo[4,3-h][2,5,11]benzoxadiazacyclotetradecine-3-carbonitrile;
12-fluoro-3-methyl-3,16,17,18-tetrahydro-10H-8,4-(metheno)pyrazolo[4,3-e][1,12,9]benzodioxazacyclopentadecin-7-amine;
12-fluoro-3-methyl-1,16,17,18-tetrahydro-10H-8,4-(metheno)pyrazolo[3,4-e][1,12,9]benzodioxazacyclopentadecin-7-amine;
7-amino-12-fluoro-2,16,17,18-tetrahydro-10H-8,4-(metheno)pyrazolo[3,4-e][1,12,9]benzodioxazacyclopentadecine-3-carbonitrile;
7-amino-12-fluoro-16,17-dihydro-1H,10H-8,4-(metheno)pyrazolo[3,4-d][1,11,8]benzodioxazacyclotetradecine-3-carbonitrile; and
(10R)-7-amino-12-fluoro-10,16-dimethyl-3-propyl-16,17-dihydro-3H-8,4-(metheno)[1,2,3]triazolo[4,5-h][2,5,11]benzoxadiazacyclotetradecin-15(10H)-one;
or a pharmaceutically acceptable salt thereof.

In another aspect, the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In another aspect, the invention provides a compound of one of the formulae described herein, or a pharmaceutically acceptable salt thereof, for use as a medicament. In one embodiment, the medicament is for use in the treatment of abnormal cell growth in a mammal. In frequent embodiments, the abnormal cell growth is cancer. In one embodiment, the medicament is for use in the treatment of abnormal cell growth mediated by ALK in a mammal. In another embodiment, the medicament is for use in the treatment of abnormal cell growth mediated by an EML4-ALK fusion protein in a mammal. In some such embodiments, the EML4-ALK fusion protein has at least one mutation. In one embodiment, the mutation is L1196M. In another embodiment, the mutation is C1156Y.

In one embodiment, the invention provides a compound of one of the formulae described herein, or a pharmaceutically acceptable salt thereof, for use in the treatment of abnormal cell growth in a mammal. In frequent embodiments, the abnormal cell growth is cancer. In one embodiment, the abnormal cell growth is mediated by ALK. In another embodiment, the abnormal cell growth is mediated by an EML4-ALK fusion protein. In some such embodiments, the EML4-ALK fusion protein has at least one mutation. In one embodiment, the mutation is L1196M. In another embodiment, the mutation is C1156Y.

The invention also provides therapeutic methods and uses comprising administering a compound of the invention, or a pharmaceutically acceptable salt thereof, alone or in combination with another therapeutic or palliative agent to a mammal in need of such treatment.

In a preferred embodiment, the mammal is a human. In other embodiments, the mammal is a dog or cat.

In one aspect, the invention provides a method for the treatment of abnormal cell growth in a mammal comprising administering to a mammal a therapeutically effective amount of a compound of the invention, or a pharmaceutically acceptable salt thereof.

In another aspect, the invention provides a method for the treatment of abnormal cell growth in a mammal comprising administering to a mammal an amount of a compound of the invention, or a pharmaceutically acceptable salt thereof, in combination with an amount of an anti-tumor agent, which amounts are together effective in treating said abnormal cell growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In one embodiment, the invention provides a method for the treatment of abnormal cell growth in a mammal, comprising administering to said mammal a therapeutically effective amount of a compound of one of the formulae described herein, or a pharmaceutically acceptable salt thereof. In frequent embodiments, the abnormal cell growth is cancer. In one embodiment, the abnormal cell growth is mediated by ALK. In another embodiment, the abnormal cell growth is mediated by an EML4-ALK fusion protein. In some such embodiments, the EML4-ALK fusion protein has at least one mutation. In one embodiment, the mutation is L1196M. In another embodiment, the mutation is C1156Y.

In another aspect, the invention provides a method for the treatment of a disorder mediated by ALK in a mammal comprising administering to the mammal a compound of the invention, or a pharmaceutically acceptable salt thereof, in an amount that is effective for treating said disorder.

The compounds and salts of the present invention inhibit wild-type ALK and/or certain mutant forms of ALK, including EML4-ALK fusion proteins, including EML4-ALK fusion proteins having at least one mutation. In one embodiment, the mutation is L1196M. In one embodiment, the mutation is C1156Y.

In one embodiment, the invention provides a method of treating abnormal cell proliferation in a mammal, comprising administering to said mammal a therapeutically effective amount of a compound of the invention or a pharmaceutically acceptable salt thereof. In some such embodiments, the abnormal cell proliferation is cancer. In one embodiment, the cancer is mediated by ALK. In another embodiment, the cancer is mediated by an EML4-ALK fusion protein. In further such embodiments, the EML4-ALK fusion protein has at least one mutation. In one such embodiment, the mutation is L1196M. In another such embodiment, the mutation is C1156Y.

In another aspect, the invention provides a compound of one of the formulae described herein, or pharmaceutically acceptable salt thereof, for use in the treatment of abnormal cell growth in a mammal. In a further aspect, the invention provides the use of a compound of one of the formulae described herein, or pharmaceutically acceptable salt thereof, for the treatment of abnormal cell growth in a mammal.

In yet another aspect, the invention provides the use of a compound of one of the formulae described herein, or a pharmaceutically acceptable salt thereof, for the preparation of a medicament for the treatment of abnormal cell growth.

In frequent embodiments of the methods and uses described herein, the abnormal cell growth is cancer. In some embodiments, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

In another embodiment, the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

In some embodiments, the methods described herein further comprise administering to the mammal an amount of an anti-cancer therapeutic agent or a palliative agent, which amounts are together effective in treating said abnormal cell growth. In some such embodiments, one or more anti-cancer therapeutic agent are selected from anti-tumor agents, anti-angiogenesis agents, signal transduction inhibitors and anti-proliferative agents, which amounts are together effective in treating said abnormal cell growth.

In other embodiments, the uses described herein comprise the use of a compound of one of the formulae described herein or pharmaceutically acceptable salt thereof, in combination with one or more substances selected from anti-tumor agents, anti-angiogenesis agents, signal transduction inhibitors and antiproliferative agents.

In some embodiments, the medicaments described herein are adapted for use in combination with one or more substances selected from anti-tumor agents, anti-angiogenesis agents, signal transduction inhibitors and antiproliferative agents.

Each of the embodiments of the compounds of the present invention described herein can be combined with one or more other embodiments of the compounds of the present invention described herein not inconsistent with the embodiment(s) with which it is combined. In addition, each of the embodiments describing the invention envisions within its scope the pharmaceutically acceptable salts of the compounds of the invention. Accordingly, the phrase "or a pharmaceutically acceptable salt thereof" is implicit in the description of all compounds described herein.

BRIEF DESCRIPTION OF THE DRAWINGS

FIG. 1: X-ray crystal structure of Example 1 demonstrating absolute stereochemistry of an (R)-configuration for the compound of Example 1.

DETAILED DESCRIPTION OF THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

"Alkyl" refers to a saturated, monovalent aliphatic hydrocarbon radical including straight chain and branched chain groups having the specified number of carbon atoms. Alkyl substituents typically contain 1 to 20 carbon atoms ("$C_1$-$C_{20}$ alkyl"), preferably 1 to 12 carbon atoms ("$C_1$-$C_{12}$ alkyl"), more preferably 1 to 8 carbon atoms ("$C_1$-$C_8$ alkyl"), or 1 to 6 carbon atoms ("$C_1$-$C_6$ alkyl"), or 1 to 4 carbon atoms ("$C_1$-$C_4$ alkyl"). Examples of alkyl groups include methyl, ethyl, n-propyl, isopropyl, n-butyl, iso-butyl, tert-butyl, n-pentyl, isopentyl, neopentyl, n-hexyl, n-heptyl, n-octyl and the like. Alkyl groups may be substituted or unsubstituted. In particular, unless otherwise specified, alkyl groups may be substituted by one or more halo groups, up to the total number of hydrogen atoms present on the alkyl moiety. Thus, $C_1$-$C_4$ alkyl includes halogenated alkyl groups, e.g., trifluoromethyl or difluoroethyl (i.e., $CF_3$ and —$CH_2CHF_2$).

As used herein, "$C_1$-$C_6$ alkyl" denotes a straight-chain or branched group containing 1, 2, 3, 4, 5 or 6 carbon atoms. This also applies if they carry substituents or occur as substituents of other radicals, for example in O—($C_1$-$C_6$)alkyl radicals. Examples of suitable $C_1$-$C_6$ alkyl radicals are methyl, ethyl, n-propyl, iso-propyl, n-butyl, iso-butyl, sec-butyl, tert-butyl, n-pentyl, sec-pentyl, neopentyl, n-hexyl, sec-hexyl, and the like. Examples of suitable O—($C_1$-$C_6$)alkyl radicals are methoxy, ethoxy, n-propyloxy, iso-propyloxy, n-butyloxy, iso-butyloxy, sec-butyloxy and tert-butyloxy, n-pentyloxy, neopentyloxy, hexyloxy, and the like.

Alkyl groups described herein as optionally substituted may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents.

Optional substituent groups suitable for alkyl include, but are not limited to $C_3$-$C_8$ cycloalkyl, 3-12 membered heterocyclyl, $C_6$-$C_{12}$ aryl and 5-12 membered heteroaryl, halo, =O (oxo), =S (thiono), =N—CN, =N—$OR^x$, =$NR^x$, —CN, —C(O)$R^x$, —$CO_2R^x$, —C(O)$NR^xR^y$, —$SR^x$, —$SOR^x$, —$SO_2R^x$, —$SO_2NR^xR^y$, —$NO_2$, —$NR^xR^y$, —$NR^xC(O)R^y$, —$NR^xC(O)NR^xR^y$, —$NR^xC(O)OR^x$, —$NR^xSO_2R^y$, —$NR^xSO_2NR^xR^y$, —$OR^x$, —OC(O)$R^x$ and —OC(O)$NR^xR^y$; wherein each $R^x$ and $R^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or $R^x$ and $R^y$ may be taken together with the N atom to which they are attached to form a 3-12 membered heterocyclyl or 5-12 membered heteroaryl, each optionally containing 1, 2 or 3 additional heteroatoms selected from O, N and S;

each $R^x$ and $R^y$ is optionally substituted with 1 to 3 substituents independently selected from the group consisting of halo, =O, =S, =N—CN, =N—OR', =NR', —CN, —C(O)R', —$CO_2$R', —C(O)NR'$_2$, —SR', —SOR', —$SO_2$R', —$SO_2$NR'$_2$, —$NO_2$, —NR'C(O)R', —NR'C(O)NR'$_2$, —NR'C(O)OR', —NR'$SO_2$R', —NR'$SO_2$NR'$_2$, —OR', —OC(O)R' and —OC(O)NR'$_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or $C_5$-$C_{12}$ heteroaryl; and wherein each said $C_3$-$C_8$ cycloalkyl, 3-12 membered heterocyclyl, $C_6$-$C_{12}$ aryl and 5-12 membered heteroaryl is optionally substituted as further defined herein.

Typical substituent groups on alkyl include halo, —OH, $C_1$-$C_4$ alkoxy, —O—$C_6$-$C_{12}$ aryl, —CN, =O, —COO$R^x$, —OC(O)$R^x$, —C(O)$NR^xR^y$, —$NR^xC(O)R^y$, $NR^xR^y$, $C_3$-$C_8$ cycloalkyl, $C_6$-$C_{12}$ aryl, 5-12 membered heteroaryl and 3-12 membered heterocyclyl; where each $R^x$ and $R^y$ is independently H or $C_1$-$C_4$ alkyl, or $R^x$ and $R^y$ may be taken together with the N to which they are attached form a 3-12 membered heterocyclyl or 5-12 membered heteroaryl ring, each optionally containing 1, 2 or 3 additional heteroatoms selected from O, N and S; wherein each said $C_3$-$C_8$ cycloalkyl, $C_6$-$C_{12}$ aryl, 5-12 membered heteroaryl and 3-12 membered heterocyclyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl), and —N($C_1$-$C_4$ alkyl)$_2$.

In some embodiments, alkyl is optionally substituted by one or more substituents, and preferably by 1 to 3 substituents, which are independently selected from the group consisting of halo, —OH, $C_1$-$C_4$ alkoxy, —O—$C_6$-$C_{12}$ aryl, —CN, =O, —COO$R^x$, —OC(O)$R^x$, —C(O)$NR^xR^y$, —$NR^xC(O)R^y$, $NR^xR^y$, $C_3$-$C_8$ cycloalkyl, $C_6$-$C_{12}$ aryl, 5-12 membered heteroaryl and 3-12 membered heterocyclyl; where each $R^x$ and $R^y$ is independently H or $C_1$-$C_4$ alkyl, or $R^x$ and $R^y$ may be taken together with the N to which they are attached form a 3-12 membered heterocyclyl or 5-12 membered heteroaryl ring, each optionally containing 1, 2 or 3 additional heteroatoms selected from O, N and S; and each said $C_3$-$C_8$ cycloalkyl, $C_6$-$C_{12}$ aryl, 5-12 membered heteroaryl and 3-12 membered heterocyclyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$.

In other embodiments, alkyl is optionally substituted by one or more substituent, and preferably by 1 to 3 substituents, independently selected from the group consisting of halo, —OH, $C_1$-$C_4$ alkoxy, —CN, NR$^x$R$^y$, $C_3$-$C_8$ cycloalkyl, 3-12 membered heterocyclyl, $C_6$-$C_{12}$ aryl and 5-12 membered heteroaryl; where each R$^x$ and R$^y$ is independently H or $C_1$-$C_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and where each said cycloalkyl, heterocyclyl, aryl or heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$.

In some instances, substituted alkyl groups may be specifically named with reference to the substituent group. For example, "haloalkyl" refers to an alkyl group having the specified number of carbon atoms that is substituted by one or more halo substituents, and typically contain 1-6 carbon atoms and 1, 2 or 3 halo atoms (i.e., "$C_1$-$C_6$ haloalkyl"). Thus, a $C_1$-$C_6$ haloalkyl group includes trifluoromethyl (—CF$_3$) and difluoromethyl (—CF$_2$H).

Similarly, "hydroxyalkyl" refers to an alkyl group having the specified number of carbon atoms that is substituted by one or more hydroxy substituents, and typically contain 1-6 carbon atoms and 1, 2 or 3 hydroxy (i.e., "$C_1$-$C_6$ hydroxyalkyl"). Thus, $C_1$-$C_6$ hydroxyalkyl includes hydroxymethyl (—CH$_2$OH) and 2-hydroxyethyl (—CH$_2$CH$_2$OH).

"Alkoxyalkyl" refers to an alkyl group having the specified number of carbon atoms that is substituted by one or more alkoxy substituents. Alkoxyalkyl groups typically contain 1-6 carbon atoms in the alkyl portion and are substituted by 1, 2 or 3 $C_1$-$C_4$ alkyoxy substituents. Such groups are sometimes described herein as $C_1$-$C_4$ alkyoxy-$C_1$-$C_6$ alkyl.

"Aminoalkyl" refers to alkyl group having the specified number of carbon atoms that is substituted by one or more substituted or unsubstituted amino groups, as such groups are further defined herein. Aminoalkyl groups typically contain 1-6 carbon atoms in the alkyl portion and are substituted by 1, 2 or 3 amino substituents. Thus, a $C_1$-$C_6$ aminoalkyl group includes, for example, aminomethyl (—CH$_2$NH$_2$), N,N-dimethylamino-ethyl (—CH$_2$CH$_2$N(CH$_3$)$_2$), 3-(N-cyclopropylamino)propyl (—CH$_2$CH$_2$CH$_2$NH-$^c$Pr) and N-pyrrolidinyl-ethyl (—CH$_2$CH$_2$N-pyrrolidinyl).

"Alkenyl" refers to an alkyl group, as defined herein, consisting of at least two carbon atoms and at least one carbon-carbon double bond. Typically, alkenyl groups have 2 to 20 carbon atoms ("$C_2$-$C_{20}$ alkenyl"), preferably 2 to 12 carbon atoms ("$C_2$-$C_{12}$ alkenyl"), more preferably 2 to 8 carbon atoms ("$C_2$-$C_8$ alkenyl"), or 2 to 6 carbon atoms ("$C_2$-$C_6$ alkenyl"), or 2 to 4 carbon atoms ("$C_2$-$C_4$ alkenyl"). Representative examples include, but are not limited to, ethenyl, 1-propenyl, 2-propenyl, 1-, 2-, or 3-butenyl, and the like. A "$C_2$-$C_6$ alkenyl" denotes a straight-chain or branched group containing 1 to 6 carbon atoms and at least one double bond between two sp$^2$ hybridized carbon atoms. This also applies if they carry substituents or occur as substituents of other radicals, for example in O—($C_1$-$C_6$)alkenyl radicals. Examples of suitable $C_1$-$C_6$ alkyl radicals are n-propenyl, iso-propenyl, n-butenyl, iso-butenyl, n-pentenyl, sec-pentenyl, n-hexenyl, sec-hexenyl, and the like. Alkenyl groups may be unsubstituted or substituted by the same groups that are described herein as suitable for alkyl.

"Alkynyl" refers to an alkyl group, as defined herein, consisting of at least two carbon atoms and at least one carbon-carbon triple bond. Alkynyl groups have 2 to 20 carbon atoms ("$C_2$-$C_{20}$ alkynyl"), preferably 2 to 12 carbon atoms ("$C_2$-$C_{12}$ alkynyl"), more preferably 2 to 8 carbon atoms ("$C_2$-$C_8$ alkynyl"), or 2 to 6 carbon atoms ("$C_2$-$C_6$ alkynyl"), or 2 to 4 carbon atoms ("$C_2$-$C_4$ alkynyl"). Representative examples include, but are not limited to, ethynyl, 1-propynyl, 2-propynyl, 1-, 2-, or 3-butynyl, and the like. Alkynyl groups may be unsubstituted or substituted by the same groups that are described herein as suitable for alkyl. A "$C_2$-$C_6$ alkynyl" denotes a straight-chain or branched group containing 1 to 6 carbon atoms and at least one triple bond between two sp hybridized carbon atoms. This also applies if they carry substituents or occur as substituents of other radicals, for example in O—($C_1$-$C_6$)alkynyl radicals. Examples of suitable $C_1$-$C_6$ alkynyl radicals are propynyl, butynyl, pentynyl, hexynyl, and the like.

"Alkylene" as used herein refers to a divalent hydrocarbyl group having the specified number of carbon atoms which can link two other groups together. Sometimes it refers to —(CH$_2$)$_n$— where n is 1-8, and preferably n is 1-4. Where specified, an alkylene can also be substituted by other groups and may include one or more degrees of unsaturation (i.e., an alkenylene or alkynlene moiety) or rings. The open valences of an alkylene need not be at opposite ends of the chain. Thus —CH(Me)— and —C(Me)$_2$— are also included within the scope of the term 'alkylenes', as are cyclic groups such as cyclopropan-1,1-diyl and unsaturated groups such as ethylene (—CH=CH—) or propylene (—CH$_2$—CH=CH—). Where an alkylene group is described as optionally substituted, the substituents include those typically present on alkyl groups as described herein.

"Heteroalkylene" refers to an alkylene group as described above, wherein one or more non-contiguous carbon atoms of the alkylene chain are replaced by —N(R)—, —O— or —S(O)$_q$—, where R is H or $C_1$-$C_4$ alkyl and q is 0-2. For example, the group —O—(CH$_2$)$_{1-4}$— is a '$C_2$-$C_5$'— heteroalkylene group, where one of the carbon atoms of the corresponding alkylene is replaced by O.

"Alkoxy" refers to a monovalent —O-alkyl group, wherein the alkyl portion has the specified number of carbon atoms. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes —OCH$_3$, —OCH$_2$CH$_3$, —OCH(CH$_3$)$_2$, —OC(CH$_3$)$_3$, and the like. Such groups may also be referred to herein as methoxy, ethoxy, isopropoxy, tert-butyloxy, etc. Alkoxy groups may be unsubstituted or substituted on the alkyl portion by the same groups that are described herein as suitable for alkyl. In particular, alkoxy groups may be substituted by one or more halo groups, up to the total number of hydrogen atoms present on the alkyl portion. Thus, $C_1$-$C_4$ alkoxy includes halogenated alkoxy groups, e.g., trifluoromethoxy and 2,2-difluoroethoxy (i.e., —OCF$_3$ and —OCH$_2$CHF$_2$).

Similarly, "thioalkoxy" refers to a monovalent —S-alkyl group, wherein the alkyl portion has the specified number of carbon atoms, and may be optionally substituted on the alkyl portion by the same groups that are described herein as suitable for alkyl. For example, a $C_1$-$C_4$ thioalkoxy includes SCH$_3$ and —SCH$_2$CH$_3$.

"Halogen" or "halo" refers to fluoro, chloro, bromo and iodo (F, Cl, Br, I). Preferably, halo refers to fluoro or chloro (F or Cl).

"Heteroaryl" or "heteroaromatic" refer to monocyclic or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl") or 5 to 6 ring atoms ("5-6 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. The heteroaryl group may be unsubstituted or substituted as further described herein. As used herein, "5-6 membered heteroaryl" refers to a monocyclic group of 5 or 6 ring atoms containing one, two or three ring heteroatoms selected from N, O, and S, the remaining ring atoms being C, and, in addition, having a completely conjugated pi-electron system. Substituents on adjacent ring atoms of a 5- or 6-membered heteroaryl may combine to form a fused 5- or 6-membered carbocyclic ring optionally substituted by one or more substituents, such as oxo, $C_1$-$C_6$ alkyl, hydroxyl, amino and halogen, or a fused 5- or 6-membered heterocyclic ring containing one, two or three ring heteroatoms selected from N, O and $S(O)_p$ (where p is 0, 1 or 2) optionally substituted by one or more substituents, such as oxo, $C_1$-$C_6$ alkyl, hydroxyl, amino and halogen. A pharmaceutically acceptable heteroaryl is one that is sufficiently stable to be attached to a compound of the invention, formulated into a pharmaceutical composition and subsequently administered to a patient in need thereof.

Examples of 5-membered heteroaryl rings containing 1, 2 or 3 heteroatoms independently selected from O, N and S, include pyrrolyl, thienyl, furanyl, pyrazolyl, imidazolyl, oxazolyl, isoxazolyl, thiazolyl, isothiazolyl, triazolyl, tetrazolyl, oxadiazolyl and thiadiazolyl. Preferred 6-membered heteroaryl rings contain 1 or 2 nitrogen atoms. Examples of 6-membered heteroaryl are pyridyl, pyridazinyl, pyrimidinyl and pyrazinyl. Examples of fused heteroaryl rings include benzofuran, benzothiophene, indole, benzimidazole, indazole, quinoline, isoquinoline, purine, triazine, naphthyridine and carbazole.

Examples of typical monocyclic heteroaryl groups include, but are not limited to:

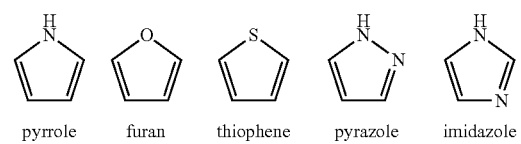

pyrrole (pyrrolyl)   furan (furanyl)   thiophene (thiophenyl)   pyrazole (pyrazolyl)   imidazole (imidazolyl)

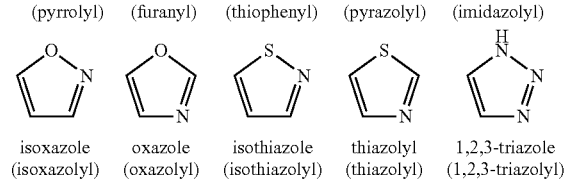

isoxazole (isoxazolyl)   oxazole (oxazolyl)   isothiazole (isothiazolyl)   thiazolyl (thiazolyl)   1,2,3-triazole (1,2,3-triazolyl)

-continued

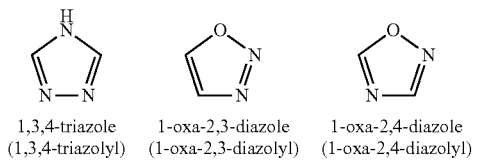

1,3,4-triazole (1,3,4-triazolyl)   1-oxa-2,3-diazole (1-oxa-2,3-diazolyl)   1-oxa-2,4-diazole (1-oxa-2,4-diazolyl)

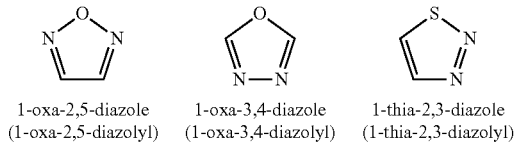

1-oxa-2,5-diazole (1-oxa-2,5-diazolyl)   1-oxa-3,4-diazole (1-oxa-3,4-diazolyl)   1-thia-2,3-diazole (1-thia-2,3-diazolyl)

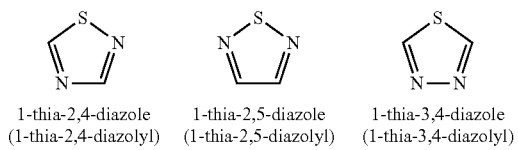

1-thia-2,4-diazole (1-thia-2,4-diazolyl)   1-thia-2,5-diazole (1-thia-2,5-diazolyl)   1-thia-3,4-diazole (1-thia-3,4-diazolyl)

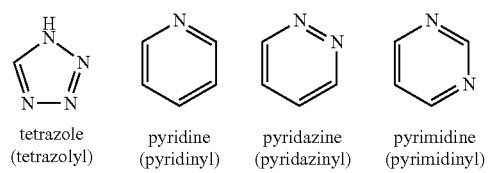

tetrazole (tetrazolyl)   pyridine (pyridinyl)   pyridazine (pyridazinyl)   pyrimidine (pyrimidinyl)

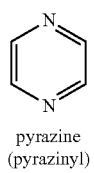

pyrazine (pyrazinyl)

Examples of 6-membered heteroaryl groups having adjacent ring atoms that form a fused heterocyclic ring or a carbocyclic ring include, but are not limited to

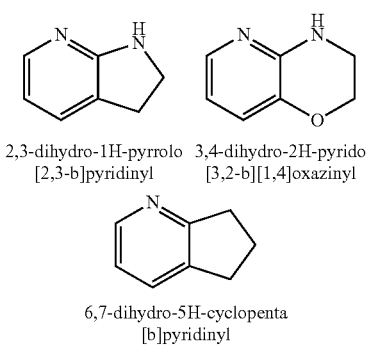

2,3-dihydro-1H-pyrrolo [2,3-b]pyridinyl   3,4-dihydro-2H-pyrido [3,2-b][1,4]oxazinyl 6,7-dihydro-5H-cyclopenta [b]pyridinyl Illustrative examples of fused ring heteroaryl groups include, but are not limited to:

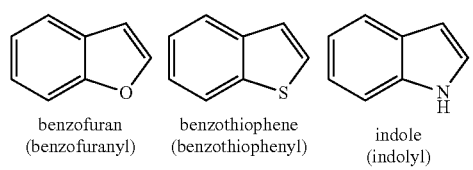

benzofuran (benzofuranyl)   benzothiophene (benzothiophenyl)   indole (indolyl)

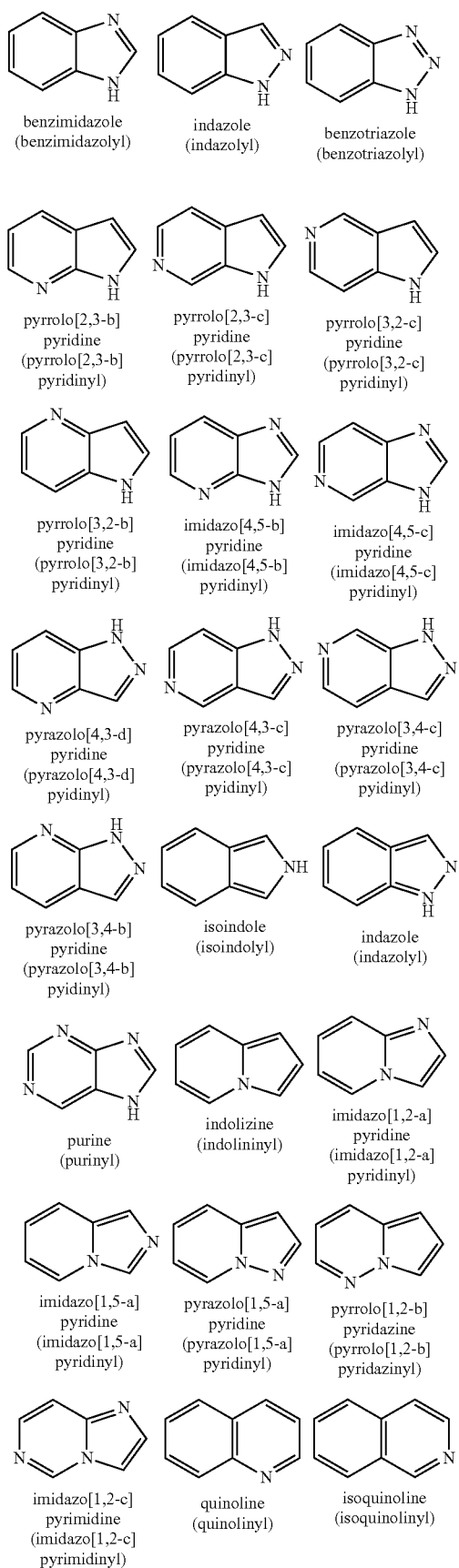
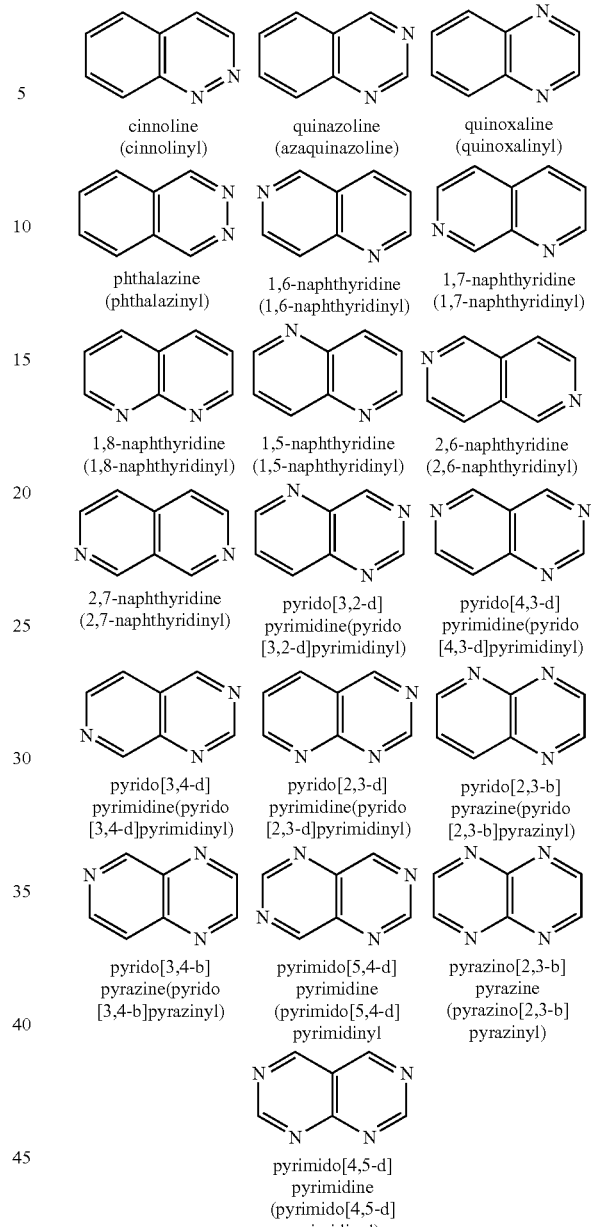

The terms "heteroalicyclic", "heterocyclyl", or "heterocyclic" may be used interchangeably herein to refer to a non-aromatic, saturated or partially unsaturated ring system containing the specified number of ring atoms, including at least one heteroatom selected from N, O and S as a ring member, wherein the heterocyclic ring is connected to the base molecule via a ring atom, which may be C or N. Heteroalicyclic rings may be fused to one or more other heteroalicyclic or carbocyclic rings, which fused rings may be saturated, partially unsaturated or aromatic. Preferably, heteroalicyclic rings contain 1 to 4 heteroatoms selected from N, O, and S as ring members, and more preferably 1 to 2 ring heteroatoms, provided that such heteroalicyclic rings do not contain two contiguous oxygen atoms. Heteroalicyclic groups may be unsubstituted or substituted by the same groups that are described herein as suitable for alkyl, aryl or heteroaryl. In addition, ring N atoms may be optionally substituted by groups suitable for an amine, e.g., alkyl, acyl, carbamoyl, sulfonyl substituents, etc., and ring S atoms may be optionally substituted by one or two oxo groups (i.e., S(O)$_p$, where p is 0, 1 or 2). Preferred heteroalicyclic groups include 3-12 membered heteroalicyclic groups in accordance with the definition herein. As used herein, "3-12 membered heteroalicyclic" refers to a monocyclic or bicyclic group having 3 to 12 ring atoms, in which one, two, three or four ring atoms are heteroatoms selected from N, O and S(O)$_p$ (where p is 0, 1, 2) the remaining ring atoms being C. The ring may also have one or more double bonds. However, the ring does not have a completely conjugated pi-electron system. Substituents on two ring carbon atoms may combine to form a 5- or 6-membered bridged ring that is either carbocyclic or heteroalicyclic containing one, two or three ring heteroatoms selected from N, O and S(O)$_p$ (where p is 0, 1 or 2). The heteroalicyclic group is optionally substituted by oxo, hydroxyl, amino, $C_1C_6$-alkyl and the like.

Examples of suitable partially unsaturated heteroalicyclic groups include, but are not limited to:

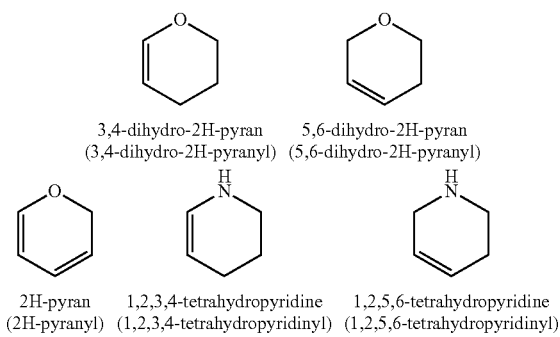

Examples of suitable saturated heteroalicyclic groups include, but are not limited to:

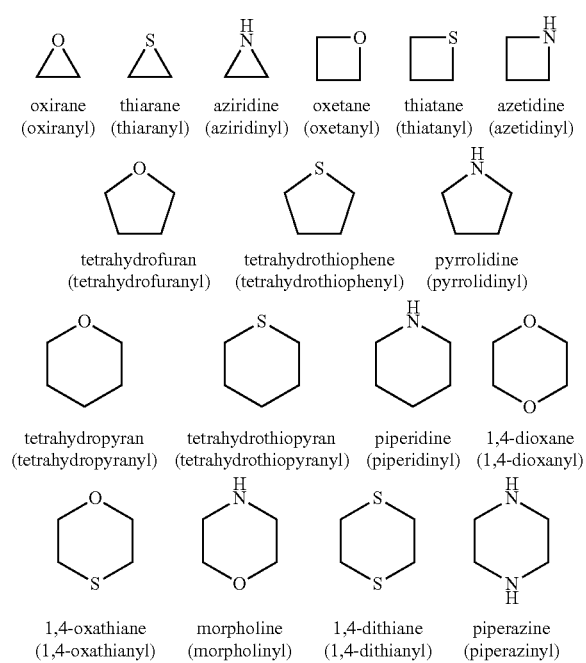

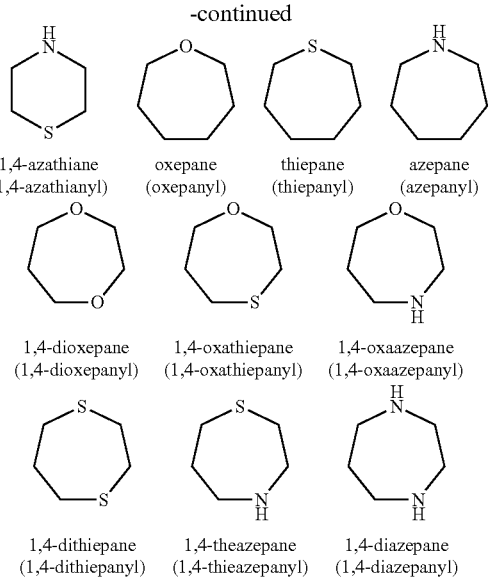

In frequent embodiments, heteroalicyclic groups contain 3-12 ring members, including both carbon and non-carbon heteroatoms, and preferably 4-6 ring members. In certain preferred embodiments, substituent groups comprising 3-12 membered heteroalicyclic groups are selected from azetidinyl, pyrrolidinyl, piperidinyl, piperazinyl, morpholinyl and thiomorpholinyl rings, each of which may be optionally substituted to the extent such substitution makes chemical sense.

It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

The term "heterocyclylalkyl" may be used to describe a heterocyclic group of the specified size that is connected to the base molecule through an alkylene linker of the specified length. Typically, such groups contain an optionally substituted 3-12 membered heterocycle attached to the base molecule through a $C_1$-$C_4$ alkylene linker. Where so indicated, such groups may be optionally substituted on the alkylene portion by the same groups that are described herein as suitable for alkyl groups and on the heterocyclic portion by groups described as suitable for heterocyclic rings.

As used herein, "$C_6$-$C_{12}$ aryl" refers to an all-carbon monocyclic or fused-ring polycyclic groups of 6 to 12 carbon atoms having a completely conjugated pi-electron system. Examples of aryl groups are phenyl and naphthalenyl. The aryl group may be substituted or unsubstituted. Substituents on adjacent ring carbon atoms of a $C_6$-$C_{12}$ aryl may combine to form a 5- or 6-membered carbocyclic ring optionally substituted by one or more substituents, such as oxo, $C_1$-$C_6$ alkyl, hydroxyl, amino and halogen, or a 5- or 6-membered heterocyclic ring containing one, two or three ring heteroatoms selected from N, O and S(O)$_p$ (where p is 0, 1 or 2) optionally substituted by one or more substituents, such as oxo, $C_1$-$C_6$ alkyl, hydroxyl, amino and halogen. Examples, without limitation, of aryl groups include phenyl, biphenyl, naphthyl, anthracenyl, phenanthrenyl, indanyl, indenyl, and tetrahydronaphthyl. The aryl group may be unsubstituted or substituted as further described herein. Additional examples of $C_6$-$C_{10}$ aryl having two ring carbon atoms that form a fused heterocyclic or carbocyclic ring include but are not limited to:

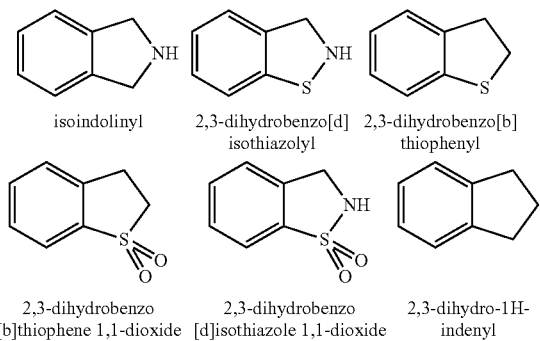

isoindolinyl    2,3-dihydrobenzo[d]    2,3-dihydrobenzo[b]
                isothiazolyl            thiophenyl 2,3-dihydrobenzo    2,3-dihydrobenzo    2,3-dihydro-1H-
[b]thiophene 1,1-dioxide  [d]isothiazole 1,1-dioxide  indenyl Aryl, heteroaryl and heteroalicyclic moieties described herein as optionally substituted may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl, heteroaryl or heterocyclyl groups typically contain from 1 to 5 optional substituents, sometimes 1 to 4 optional substituents, preferably 1 to 3 optional substituents, or more preferably from 1 to 2 optional substituents.

An "arylene" as used herein refers to a bivalent radical derived from an aromatic hydrocarbon by removal of a hydrogen atom from each of two carbon atoms of the nucleus. In frequent embodiments, the arylene ring is a 1,2-disubstituted or a 1,3-disubstituted arylene. The aryl ring of the arylene moiety may be optionally substituted on open valence positions with groups suitable for an aryl ring, to the extent such substitution is indicated. Preferably, the arylene ring is a $C_6$-$C_{12}$ arylene ring, for example a 1,2-phenylene or 1,3-phenylene moiety.

Similarly, a "heteroarylene" as used herein refers to a bivalent radical derived from a heteroaromatic ring by removal of a hydrogen atom from each of two carbon or nitrogen atoms of the nucleus. In frequent embodiments, the heteroarylene ring is a 1,2-disubstituted or a 1,3-disubstituted heteroarylene. The heteroaryl ring of the heteroarylene moiety is optionally substituted with groups suitable for an heteroaryl ring, to the extent such substitution is indicated. Preferably, the heteroarylene ring is a 5-12 membered heteroarylene ring, more preferably a 5-6 membered heteroarylene ring, each of which may be optionally substituted.

Optional substituent groups suitable for aryl, heteroaryl and heteroalicyclic rings include, but are not limited to: $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl; and halo, =O, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^x$, —NR$^x$SO$_2$R$^y$, —NR$^x$SO$_2$NR$^x$R$^y$, —OR$^x$, —OC(O)R$^x$ and —OC(O)NR$^x$R$^y$; where each R$^x$ and R$^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or R$^x$ and R$^y$ may be taken together with the N atom to which they are attached to form a 3-12 membered heterocyclyl or 5-12 membered heteroaryl, each optionally containing 1, 2 or 3 additional heteroatoms selected from O, N and S; each R$^x$ and R$^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC (O)NR'$_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl; and each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted as further defined herein.

In typical embodiments, optional substitution on aryl, heteroaryl and heteroalicyclic rings includes one or more substituents, and preferably 1 to 3 substituents, independently selected from the group consisting of halo, $C_1$-$C_8$ alkyl, —OH, $C_1$-$C_8$ alkoxy, —CN, =O, —C(O)R$^x$, —COOR$^x$, —OC(O)R$^x$, —C(O)NR$^x$R$^y$, —NR$^x$C(O)R$^y$, —SR$^x$, —SOR$^x$, —SO$_2$R$^x$, —SO$_2$NR$^x$R$^y$, —NO$_2$, NR$^x$R$^y$, —NR$^x$C (O)R$^y$, —NR$^x$C(O)NR$^x$R$^y$, —NR$^x$C(O)OR$^y$NR$^x$SO$_2$R$^y$, —NR$^x$SO$_2$NR$^x$R$^y$, —OC(O)R$^x$, OC(O)NR$^x$R$^y$, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl); where each R$^x$ and R$^y$ is independently H or $C_1$-$C_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and wherein each said $C_1$-$C_8$ alkyl, $C_1$-$C_8$ alkoxy, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl) that is described as an optional substituent or is part of R$^x$ or R$^y$ is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl), —N($C_1$-$C_4$ alkyl)$_2$ and N-pyrrolidinyl.

"Cycloalkyl" refers to a non-aromatic, saturated or partially unsaturated carbocyclic ring system containing the specified number of carbon atoms, which may be a monocyclic, bridged or fused bicyclic or polycyclic ring system that is connected to the base molecule through a carbon atom of the cycloalkyl ring. Typically, the cycloalkyl groups of the invention contain 3 to 12 carbon atoms ("$C_3$-$C_{12}$ cycloalkyl"), preferably 3 to 8 carbon atoms ("$C_3$-$C_8$ cycloalkyl"). Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups may be unsubstituted or substituted by the same groups that are described herein as suitable for alkyl. As used herein, "$C_3$-$C_6$ cycloalkyl" refers to an all-carbon, monocyclic or fused-ring polycyclic group of 3 to 6 carbon atoms.

"Cycloalkylalkyl" may be used to describe a cycloalkyl ring, typically a $C_3$-$C_8$ cycloalkyl, which is connected to the base molecule through an alkylene linker, typically a $C_1$-$C_4$ alkylene. Cycloalkylalkyl groups are described by the total number of carbon atoms in the carbocyclic ring and linker, and typically contain from 4-12 carbon atoms ("$C_4$-$C_{12}$ cycloalkylalkyl"). Thus a cyclopropylmethyl group is a $C_4$-cycloalkylalkyl group and a cyclohexylethyl is a $C_8$-cycloalkylalkyl. Cycloalkylalkyl groups may be unsubstituted or substituted on the cycloalkyl and/or alkylene portions by the same groups that are described herein as suitable for alkyl groups.

An "arylalkyl" group refers to an aryl group as described herein which is linked to the base molecule through an alkylene or similar linker. Arylalkyl groups are described by the total number of carbon atoms in the ring and linker. Thus a benzyl group is a $C_7$-arylalkyl group and a phenylethyl is a $C_8$-arylalkyl. Typically, arylalkyl groups contain 7-16 carbon atoms ("$C_7$-$C_{16}$ arylalkyl"), wherein the aryl portion contains 6-12 carbon atoms and the alkylene portion contains 1-4 carbon atoms. Such groups may also be represented as —$C_1$-$C_4$ alkylene-$C_6$-$C_{12}$ aryl.

"Heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "$C_7$"-heteroarylalkyl. Typically, unsubstituted heteroarylalkyl groups contain 6-20 non-hydrogen atoms (including C, N, S and O atoms), wherein the heteroaryl portion typically contains 5-12 atoms and the alkylene portion typically contains 1-4 carbon atoms. Such groups may also be represented as —$C_1$-$C_4$ alkylene-5-12 membered heteroaryl.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined. Thus, —O—$CH_2$-phenyl and —O—$CH_2$-pyridinyl groups would be referred to as $C_8$-arylalkoxy and $C_8$-heteroarylalkoxy groups, respectively.

Where an arylalkyl, arylalkoxy, heteroarylalkyl or heteroarylalkoxy group is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

"Hydroxy" refers to an —OH group.

"Acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acyloxy includes an —OC(O)$C_1$-$C_4$ alkyl substituent, e.g., —OC(O)$CH_3$.

"Acylamino" refers to a monovalent group, —NHC(O) alkyl or —NRC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acylamino includes an —NHC(O)$C_1$-$C_4$alkyl substituent, e.g., —NHC(O)$CH_3$.

"Aryloxy" or "heteroaryloxy" refer to optionally substituted —O-aryl or —O-heteroaryl, in each case where aryl and heteroaryl are as further defined herein.

"Arylamino" or "heteroarylamino" refer to optionally substituted —NH-aryl, —NR-aryl, —NH-heteroaryl or —NR-heteroaryl, in each case where aryl and heteroaryl are as further defined herein and R represents a substituent suitable for an amine, e.g., an alkyl, acyl, carbamoyl or sulfonyl group, or the like.

"Cyano" refers to a —C≡N group.

"Unsubstituted amino" refers to a group —$NH_2$. Where the amino is described as substituted or optionally substituted, the term includes groups of the form —$NR^xR^y$, where each or $R^x$ and $R^y$ is independently H, alkyl, alkenyl, alkynyl, cycloalkyl, heterocyclyl, acyl, thioacyl, aryl, heteroaryl, cycloalkylalkyl, arylalkyl or heteroarylalkyl, in each case having the specified number of atoms and optionally substituted as described herein. For example, "alkylamino" refers to a group —$NR^xR^y$, wherein one of $R^x$ and $R^y$ is an alkyl moiety and the other is H, and "dialkylamino" refers to $NR^xR^y$ wherein both of $R^x$ and $R^y$ are alkyl moieties, where the alkyl moieties having the specified number of carbon atoms (e.g., —NH—$C_1$-$C_4$ alkyl or —N($C_1$-$C_4$ alkyl)$_2$). Typically, alkyl substituents on amines contain 1 to 8 carbon atoms, preferably 1 to 6 carbon atoms, or more preferably 1 to 4 carbon atoms. The term also includes forms wherein $R^x$ and $R^y$ are taken together with the N atom to which they are attached to form a 3-12 membered heterocyclyl or 5-12 membered heteroaryl ring, each of which may itself be optionally substituted as described herein for heterocyclyl or heteroaryl rings, and which may contain 1 to 3 additional heteroatoms selected from N, O and S as ring members, provided that such rings do not contain two contiguous oxygen atoms.

"Optional" or "optionally" means that the subsequently described event or circumstance may but need not occur, and the description includes instances where the event or circumstance occurs and instances in which it does not.

The terms "optionally substituted" and "substituted or unsubstituted" may be used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described, to the extent that such substitution makes chemical sense. Where an optional substituent is attached via a double bond, such as an oxo (=O) substituent, the group occupies two available valences, so the total number of other substituents that may be included is reduced by two. In the case where optional substituents are selected independently from a list of alternatives, the selected groups may be the same or different.

A "pharmaceutical composition" refers to a mixture of one or more of the compounds described herein, or a pharmaceutically acceptable salt, solvate, hydrate or prodrug thereof as an active ingredient, and at least one pharmaceutically acceptable carrier or excipient. The purpose of a pharmaceutical composition is to facilitate administration of a compound to a mammal.

In one aspect, the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional an anti-cancer therapeutic agent or a palliative agent. In some such embodiments, the at least one additional medicinal or pharmaceutical agent is an anti-cancer agent as described below. In some such embodiments, the combination provides an additive, greater than additive, or synergistic anti-cancer effect. In some such embodiments, the one or more additional anti-cancer therapeutic agent is selected from the group consisting of anti-tumor agents, anti-angiogenesis agents, signal transduction inhibitors and antiproliferative agents.

In one aspect, the invention provides a method for the treatment of abnormal cell growth in a mammal comprising administering to the mammal a therapeutically effective amount of a compound of the invention, or a pharmaceutically acceptable salt thereof.

In another aspect, the invention provides a method for the treatment of abnormal cell growth in a mammal comprising administering to the mammal an amount of a compound of the invention, or a pharmaceutically acceptable salt thereof, in combination with an amount of an anti-tumor agent, which amounts are together effective in treating said abnormal cell growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In frequent embodiments of the methods provided herein, the abnormal cell growth is cancer. In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by ALK or by an EML4-ALK fusion protein in a mammal, comprising administering to the mammal a compound of the invention, or a pharmaceutically acceptable salt thereof, in an amount that is effective for treating said disorder. In some such embodiments, the EML4-ALK fusion protein has at least one mutation.

The term "mammal" as used herein refers to a human or a non-human animal classified as a mammal. More particularly, the term mammal includes humans, domestic and farm animals, and research, zoo, sports and companion animals, such as household pets and other domesticated animals including, but not limited to, cattle, sheep, ferrets, swine, horses, rabbits, goats, dogs, cats, and the like. In frequent embodiments, the mammal is a human. In some embodiments, the term "subject" may be used to refer to a human. In some other embodiments, the mammal is a dog or cat.

The ALK fusion proteins of particular interest for the present invention are the mutated forms of EML4-ALK. Of particular interest are compounds capable of inhibiting the L1196M mutant EML4-ALK fusion protein and the C1156Y mutant EML4-ALK fusion protein.

The compounds, compositions and methods provided herein are useful for the treatment of cancers including but not limited to cancers of the circulatory system, respiratory tract, gastrointestinal system, genitourinary tract, liver, bone, nervous system, reproductive system, hematologic system, oral cavity, skin, adrenal glands, and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of cancer when used herein in connection with the present invention include cancer selected from lung cancer, preferably non small cell lung carcinoma (NSCLC), lymphoma, preferably Anaplastic large cells lymphoma, neuroblastoma or soft tissue cancer such as inflammatory myofibroblastic tumor.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methanesulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

Pharmaceutically acceptable salts of compounds of the invention may be prepared by one or more of the following methods:

(i) by reacting the compound of the invention with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see Haleblian, J. Pharm. Sci., 1975, 64 (8):1269-1288, the disclosure of which is incorporated herein by reference in its entirety.

Hereinafter all references to compounds of the invention include references to salts, solvates and complexes thereof and to solvates and complexes of salts thereof.

The compounds of the invention include compounds of the invention as hereinbefore defined, including all polymorphs and crystal habits thereof, prodrugs and isomers thereof (including optical, geometric and tautomeric isomers) as hereinafter defined and isotopically-labeled compounds of the invention.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:
(i) where the compound contains a carboxylic acid functionality (—COOH), an ester thereof, for example, replacement of the hydrogen with $(C_1-C_8)$alkyl;
(ii) where the compound contains an alcohol functionality (—OH), an ether thereof, for example, replacement of the hydrogen with $(C_1-C_6)$alkanoyloxymethyl; and
(iii) where the compound contains a primary or secondary amino functionality (—NH$_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the invention, that is, compounds formed in vivo upon administration of the drug. Some examples of metabolites in accordance with the invention include
(i) where the compound of the invention contains a methyl group, an hydroxymethyl derivative thereof (—CH$_3$→—CH$_2$OH):
(ii) where the compound of the invention contains an alkoxy group, an hydroxy derivative thereof (—OR→—OH);
(iii) where the compound of the invention contains a tertiary amino group, a secondary amino derivative thereof (—NR$^1$R$^2$→—NHR$^1$ or —NHR$^2$);
(iv) where the compound of the invention contains a secondary amino group, a primary derivative thereof (—NHR$^1$→—NH$_2$);
(v) where the compound of the invention contains a phenyl moiety, a phenol derivative thereof (—Ph→—PhOH); and
(vi) where the compound of the invention contains an amide group, a carboxylic acid derivative thereof (—CONH$_2$→COOH).

The compounds of the formulae provided herein may have asymmetric carbon atoms. The carbon-carbon bonds of the compounds of the invention may be depicted herein using a solid line ( ——— ), a solid wedge ( ◢ ), or a dotted wedge ( ·······||||| ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention containing one or more asymmetric carbon atoms can exist as two or more stereoisomers, such as racemates, enantiomers, or diastereomers. Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

"Enantiomerically pure" as used herein, describes a compound that is present as a single enantiomer and which is described in terms of enantiomeric excess (e.e.). Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, "diastereomerically pure" as used herein, describes a compound that is present as a diastereomer and which is described in terms of diasteriomeric excess (d.e.). Preferably, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of the invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent. Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutic Methods and Uses

The invention further provides therapeutic methods and uses comprising administering the compounds of the invention, or pharmaceutically acceptable salts thereof, alone or in combination with other therapeutic agents or palliative agents.

In one aspect, the invention provides a method for the treatment of abnormal cell growth in a mammal comprising administering to the mammal a therapeutically effective amount of a compound of the invention, or a pharmaceutically acceptable salt thereof.

In another aspect, the invention provides a method for the treatment of abnormal cell growth in a mammal comprising administering to the mammal an amount of a compound of the invention, or a pharmaceutically acceptable salt thereof, in combination with an amount of an anti-tumor agent, which amounts are together effective in treating said abnormal cell growth. In some such embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

Compounds of the invention include compounds of any of the formulae described herein, including formulae (Φ) and (I)-(XXX), or a pharmaceutically acceptable salt thereof.

In another aspect, the invention provides a method for the treatment of abnormal cell growth in a mammal comprising administering to the mammal an amount of a compound of the invention, or a pharmaceutically acceptable salt thereof, that is effective in treating abnormal cell growth.

In still another aspect, the invention provides a method of inhibiting cancer cell proliferation in a mammal, comprising administering to the mammal a compound of the invention, or pharmaceutically acceptable salt thereof, in an amount effective to inhibit cell proliferation.

In another aspect, the invention provides a method of inhibiting cancer cell invasiveness in a mammal, comprising administering to the mammal a compound of the invention, or pharmaceutically acceptable salt thereof, in an amount effective to inhibit cell invasiveness.

In another aspect, the invention provides a method of inducing apoptosis in cancer cells in a mammal, comprising administering to the mammal a compound of the invention, or pharmaceutically acceptable salt thereof, in an amount effective to induce apoptosis.

In a further aspect, the invention provides a method of inducing apoptosis in a mammal, comprising administering to the mammal a therapeutically effective amount of a compound of one of the formulae described herein, or pharmaceutically acceptable salt thereof.

In frequent embodiments of the methods provided herein, the abnormal cell growth is cancer, wherein said cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

The compounds of the invention, their pharmaceutically acceptable salts and/or derived forms or composition thereof, are valuable pharmaceutically active compounds, which are suitable for the therapy of numerous disorders in which ALK receptor and/or an ALK fusion protein, e.g., EML4-ALK, is involved or in which inhibition of ALK activity may induce benefit, in particular, cancer.

A further aspect of the invention relates to a compound of the invention, or pharmaceutically acceptable salts, derived forms or compositions thereof, for use as a medicament, and in particular for use in the treatment of diseases where the inhibition of ALK and/or an ALK fusion protein, e.g., EML4-ALK, activity may induce benefit, such as cancer.

A still further aspect of the present invention also relates to the use of the compounds of the invention, or pharmaceutically acceptable salts, derived forms or compositions thereof, for the manufacture of a drug having an ALK inhibitory activity for the treatment of ALK-mediated diseases and/or conditions, in particular the diseases and/or conditions listed above.

A another aspect of the present invention also relates to the use of the compounds of the invention, or pharmaceutically acceptable salts, derived forms or compositions thereof, for the manufacture of a drug having an EML4-ALK inhibitory activity for the treatment of EML4-ALK mediated diseases and/or conditions, in particular the diseases and/or conditions listed above.

The compounds of the invention, their pharmaceutically acceptable salts and/or derived forms or composition thereof, are valuable pharmaceutically active compounds, which are suitable for the treatment of pain, including acute pain; chronic pain; neuropathic pain; inflammatory pain (including e.g. osteoarthritis pain, rheumatoid arthritis pain); visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

A further aspect of the invention relates to a compound of the invention, or pharmaceutically acceptable salts, derived forms or compositions thereof, for use as a medicament, and in particular for use in the treatment of pain, including acute pain; chronic pain; neuropathic pain; inflammatory pain (including e.g. osteoarthritis pain, rheumatoid arthritis pain); visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

A still further aspect of the present invention also relates to the use of the compounds of the invention, or pharmaceutically acceptable salts, derived forms or compositions thereof, for the manufacture of a drug for treatment of the diseases and/or conditions listed above.

As a consequence, the present invention provides a method to treat a mammal, including a human, with a therapeutically effective amount of a compound of the invention, or a pharmaceutically acceptable salt, derived form or pharmaceutical composition thereof. More precisely, the present invention provides a method for the treatment of ALK-mediated cancers in a mammal, including a human, in particular the cancers listed above, comprising administering said mammal with a therapeutically effective amount of a compound of the invention, its pharmaceutically acceptable salts and/or derived forms, or a pharmaceutical composition thereof.

Another embodiment of the present invention of particular interest relates to a method for the treatment of lung cancer in a human in need of such treatment, comprising administering to said human an amount of a compound of the invention, in combination with one or more (preferably one to three) anticancer agents selected from the group consisting of capecitabine, bevacizumab, gemcitabine, docetaxel, paclitaxel, premetrexed disodium, erlotinib, gefitinib, vinorelbine, irinotecan, etoposide, vinblastine, and carboplatin, wherein the amounts of the active agent together with the amounts of the combination anticancer agents is effective in treating lung cancer.

Preferably, the compounds of the invention are selective ALK inhibitors. Preferably, the compounds of the invention are selective inhibitors of the EML4-ALK mutant L1196M. Preferably, the compounds of the invention are selective inhibitors of the EML4-ALK mutant C1156Y.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a mammal.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). This includes the abnormal growth of: (1) tumor cells (tumors) that proliferate by expressing ALK or an ALK fusion protein, e.g., EML4-ALK; (2) benign and malignant cells of other proliferative diseases in which ALK or an ALK fusion protein occurs; (3) any tumors that proliferate by aberrant ALK or ALK fusion protein activation; and (4) benign and malignant cells of other proliferative diseases in which aberrant ALK or ALK fusion protein activation occurs.

As used herein "cancer" refers to any malignant and/or invasive growth or tumor caused by abnormal cell growth, including solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

The compounds of the invention inhibit ALK, and thus are all adapted to therapeutic use as antiproliferative agents (e.g., cancer) or antitumor agent (e.g., effect against solid tumors) in mammals, particularly in humans. In particular, the compounds of the invention are useful in the prevention and treatment of a variety of human hyperproliferative disorders including both malignant and benign abnormal cell growth.

The compounds, compositions and methods provided herein are useful for the treatment of cancers including but not limited to cancers of the:

circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of cancer when used herein in connection with the present invention include cancer selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

Still more specifically, examples of cancer when used herein in connection with the present invention include cancer selected from lung cancer (NSCLC and SCLC), breast cancer, ovarian cancer, colon cancer, rectal cancer, cancer of the anal region, or a combination of one or more of the foregoing cancers.

In one embodiment of the present invention the non-cancerous conditions include such hyperplastic conditions such as benign hyperplasia of the skin (e.g., psoriasis) and benign hyperplasia of the prostate (e.g., BPH).

In another aspect, the invention provides a method for inhibiting cell proliferation, comprising contacting cells with a compound of the invention or a pharmaceutically acceptable salt thereof in an amount effective to inhibit proliferation of the cells.

In another aspect, the invention provides methods for inducing cell apoptosis, comprising contacting cells with a compound described herein in an amount effective to induce apoptosis of the cells.

"Contacting" refers to bringing a compound or pharmaceutically acceptable salt of the invention and a cell expressing ALK together in such a manner that the compound can affect the activity of ALK, either directly or indirectly. Contacting can be accomplished in vitro (i.e., in an artificial environment such as, e.g., without limitation, in a test tube or culture medium) or in vivo (i.e., within a living organism such as, without limitation, a mouse, rat or rabbit.)

In some embodiments, the cells are in a cell line, such as a cancer cell line. In other embodiments, the cells are in a tissue or tumor, and the tissue or tumor may be in a mammal, including a human.

Dosage Forms and Regimens

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian mammals to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular mammal, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the mammal being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents which are described below. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which can be used in conjunction with a compound of the invention and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzumab (Herceptin™), sunitinib (Sutent™), imatinib (Gleevec™), and PD325901 (Pfizer).

Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitor include PF-2341066 (Pfizer), PF-299804 (Pfizer), canertinib (CI 1033), pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), lapatinib (Tycerb™), PF-299804 (Pfizer), pelitinib (EKB 569), and pertuzumab (Omnitarg™).

Other examples of signal transduction inhibitors include ARRY 142886 (Array Biopharm), everolimus (Certican™), zotarolimus (Endeavor™), temsirolimus (Torisel™), AP 23573 (ARIAD), and VX 680 (Vertex).

Additionally, other signal transduction inhibitors include XL 647 (Exelixis), sorafenib (Nexavar™), LE-AON (Georgetown University), and Gl-4000 (Globelmmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), and AG 024322 (Pfizer).

This invention contemplates the use of compounds of the invention together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, episteride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with compounds of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

The invention also contemplates the use of the compounds of the invention together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound of the invention, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy)), bexarotene (Targretin™), Tesmilifene (DPPE—enhances efficacy of cytotoxics)), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof.

Further examples of classical antineoplastic agents used in combination therapy with a compound of the invention, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P(C4P), Oxi-4503, AVE-8062, ZD-6126, TZT-1027, Atorvastatin (Lipitor, Pfizer Inc.), Provastatini (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Another embodiment of the present invention of particular interest relates to a method for the treatment of breast cancer in a human in need of such treatment, comprising administering to said human an amount of a compound of the invention, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

In one embodiment the invention provides a method of treating colorectal cancer in a mammal, such as a human, in need of such treatment, by administering an amount of a compound of the invention, in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615)epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (Cl-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCl 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Another embodiment of the present invention of particular interest relates to a method for the treatment of renal cell carcinoma in a human in need of such treatment, comprising administering to said human an amount of a compound of the invention, in combination with one or more (preferably one to three) anti-cancer agents selected from the group consisting of axitinib (AG 13736), capecitabine (Xeloda), interferon alpha, interleukin-2, bevacizumab (Avastin), gemcitabine (Gemzar), thalidomide, cetuximab (Erbitux), vatalanib (PTK-787), sunitinib (Sutent™), AG-13736, SU-11248, Tarceva, Iressa, Lapatinib and Gleevec, wherein the amounts of the active agent together with the amounts of the combination anticancer agents is effective in treating renal cell carcinoma.

Another embodiment of the present invention of particular interest relates to a method for the treatment of melanoma in a human in need of such treatment, comprising administering to said human an amount of a compound of the invention, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325, 901, axitinib (AG 13736), bevacizumab (Avastin), thalidomide, sorafanib, vatalanib (PTK-787), sunitinib (Sutent™), CpG-7909, AG-13736, Iressa, Lapatinib and Gleevec, wherein the amounts of the active agent together with the amounts of the combination anticancer agents is effective in treating melanoma.

Another embodiment of the present invention of particular interest relates to a method for the treatment of lung cancer in a human in need of such treatment, comprising administering to said human an amount of a compound of the invention, in combination with one or more (preferably one to three) anti-cancer agents selected from the group consisting of capecitabine (Xeloda), axitinib (AG 13736), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, sunitinib (Sutent™), and Paraplatin (carboplatin), wherein the amounts of the active agent together with the amounts of the combination anticancer agents is effective in treating lung cancer.

According to another embodiment of the present invention, the compounds of the invention, or pharmaceutically acceptable salts, derived forms or compositions thereof, can also be used as a combination with one or more additional therapeutic agents to be co-administered to a patient to obtain some particularly desired therapeutic end result such as the treatment of central nervous system diseases, cancer and cancer. The second and more additional therapeutic agents may also be a compound of the formula (1), or a pharmaceutically acceptable salt, derived forms or compositions thereof, or may be selected from a different class of therapeutic agents.

As used herein, the terms "co-administration", "co-administered" and "in combination with", referring to the compounds of the invention and one or more other therapeutic agents, is intended to mean, and does refer to and include the following:

i. simultaneous administration of such combination of compound(s) of the invention and therapeutic agent(s) to a patient in need of treatment, when such components are formulated together into a single dosage form which releases said components at substantially the same time to said patient,
ii. substantially simultaneous administration of such combination of compound(s) of the invention and therapeutic agent(s) to a patient in need of treatment, when such components are formulated apart from each other into separate dosage forms which are taken at substantially the same time by said patient, whereupon said components are released at substantially the same time to said patient,
iii. sequential administration of such combination compound(s) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and
iv. sequential administration of such combination of compound(s) of the invention and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Synthetic Methods

The compounds of the invention can be prepared by a variety of synthetic methods, as further described and illustrated herein. It will be understood by those of skill in the art that the following general synthetic methods are representative and not intended to be limiting.

Method A

In a general synthetic process, compounds of the general structure represented by compound VI are prepared according to Method A.

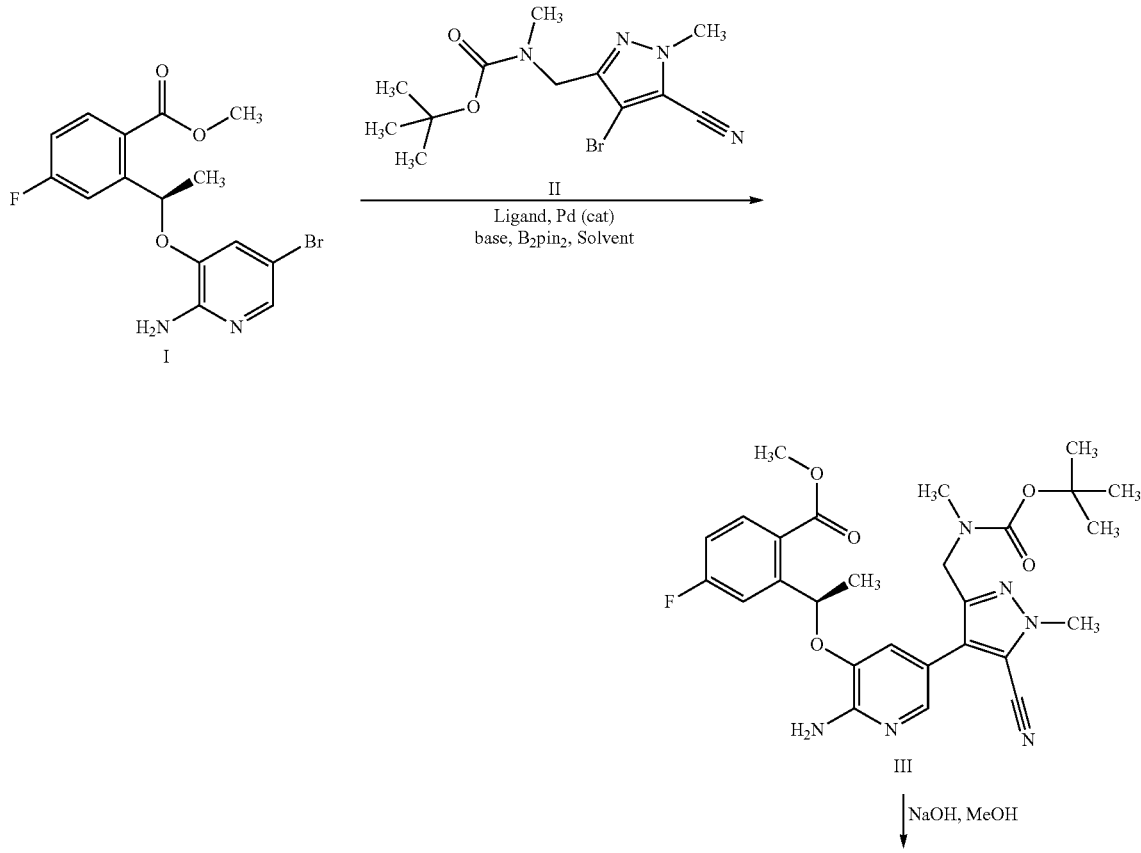

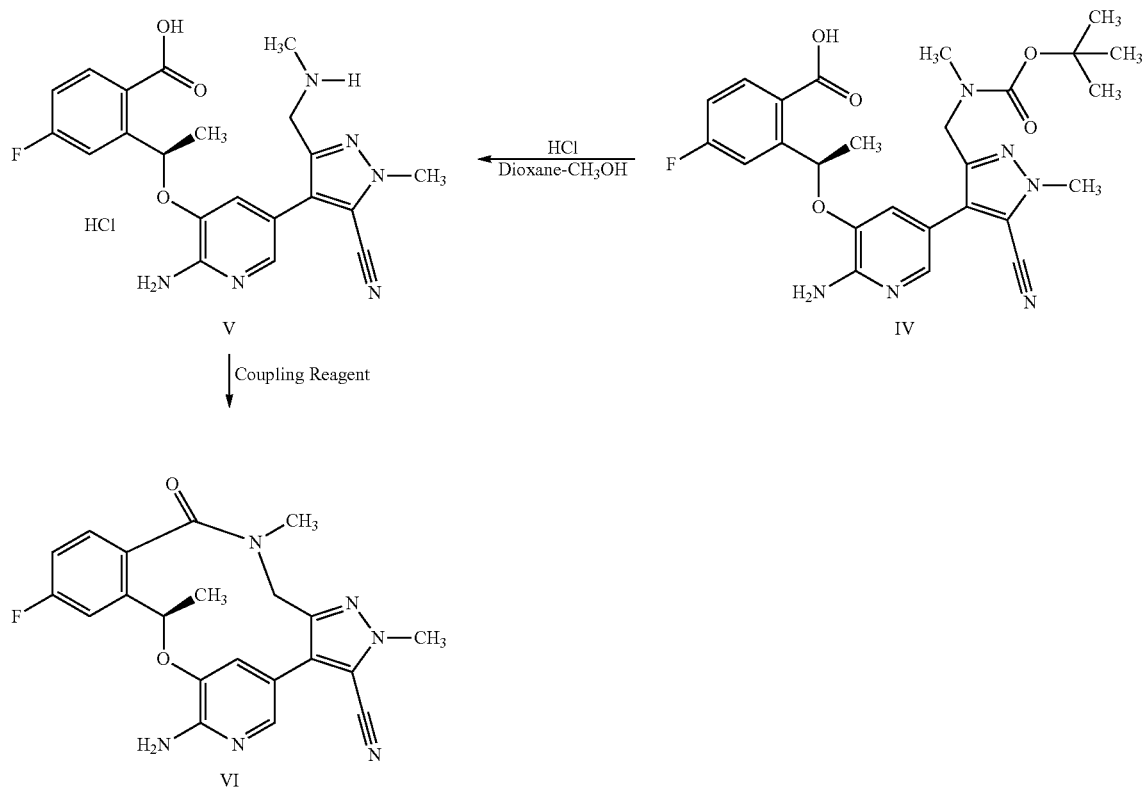

The aryl halide (I) may be coupled with aryl halide (II) using the Suzuki coupling conditions, where the in situ generated boronic acid reacts with the aryl halide to give compound (III). The ester group of compound (III) may be hydrolyzed using an appropriate base, such as sodium hydroxide, to provide compound (IV), and the BOC protecting group may be removed using HCl or TFA to yield compound (V). Finally, formation of the lactam may be achieved by using the appropriate coupling reagent such as HATU to yield compound (VI).

Method B

In a general synthetic process, compounds of the general structure represented by compound (IX) are prepared according to Method B.

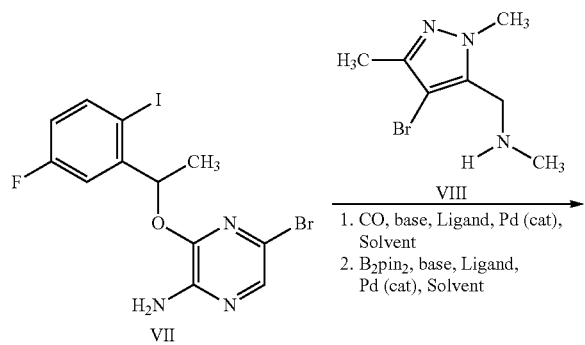

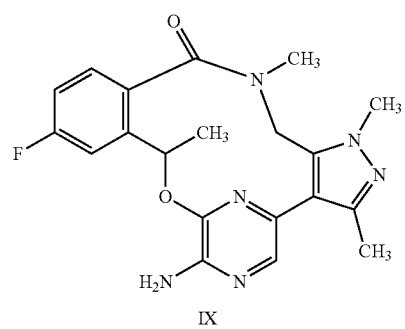

In the first step of a two step sequence, regioselective carboamidation of aryl dihalide (VII) may be accomplished with amine (VIII) in the presence of carbon monoxide and an appropriate palladium catalyst and base. In the second step, Suzuki coupling of the crude amide may be accomplished using diboron pinacol ester and the appropriate palladium catalyst and base to provide the macrocycle (IX).

Method C

In a general synthetic process, compounds of the general structure represented by compound (XI) are prepared according to Method C.

111
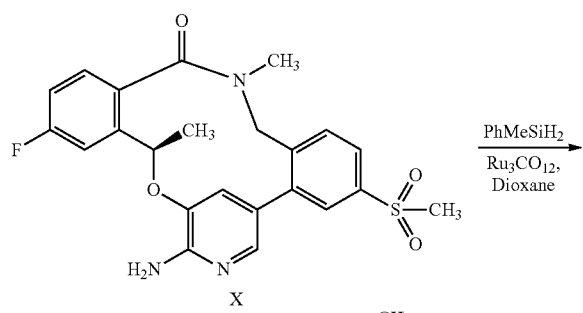
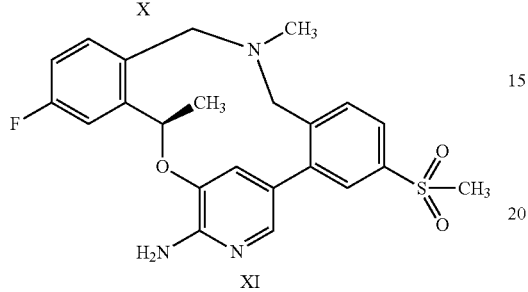
The amide (X) is reduced by the appropriate reducing reagent, such as a PhMeSiH₂ in the presence of a ruthenium catalyst to give compound (XI).
Method D
In a general synthetic process, compounds of the general structure represented by compound (XII) are prepared according to Method D.
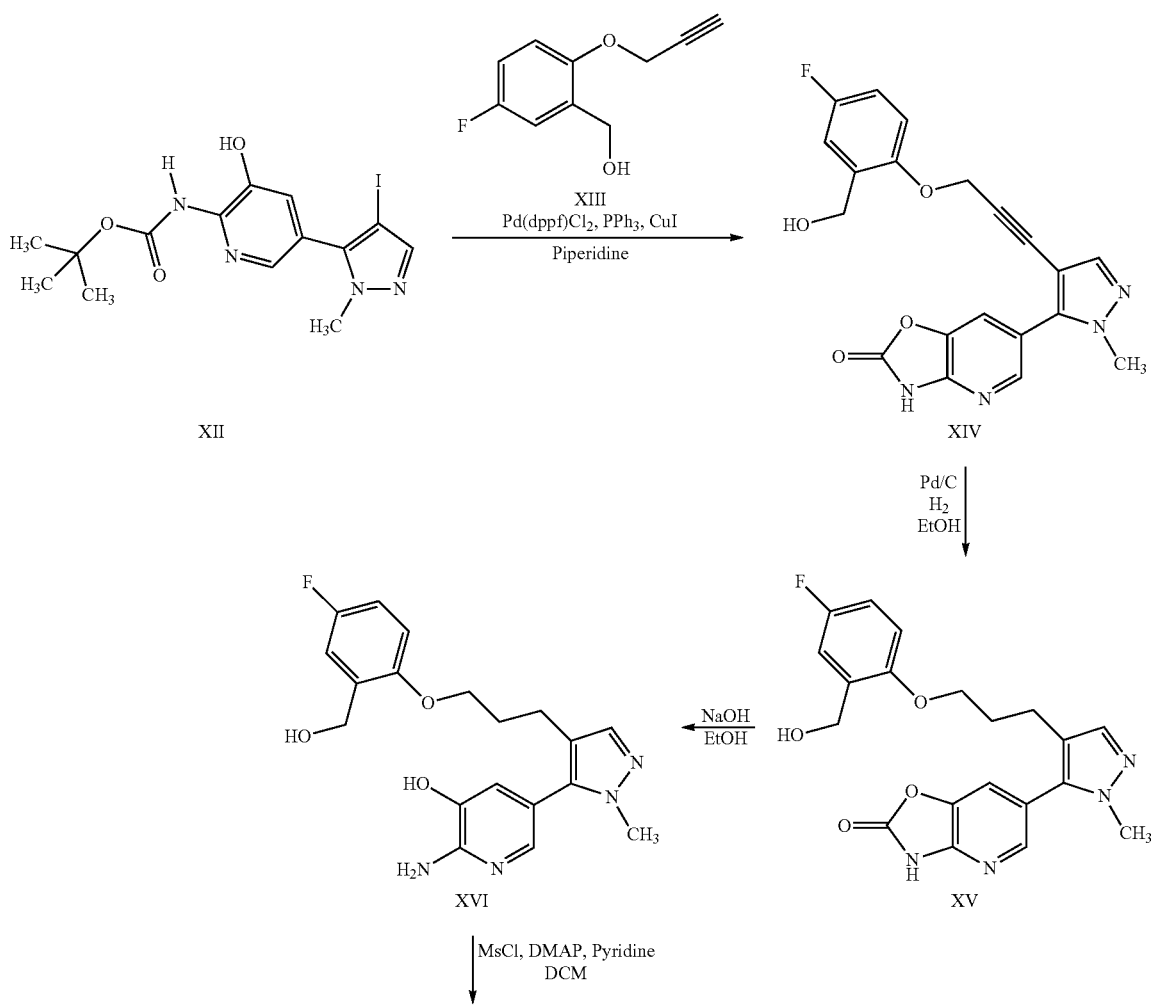

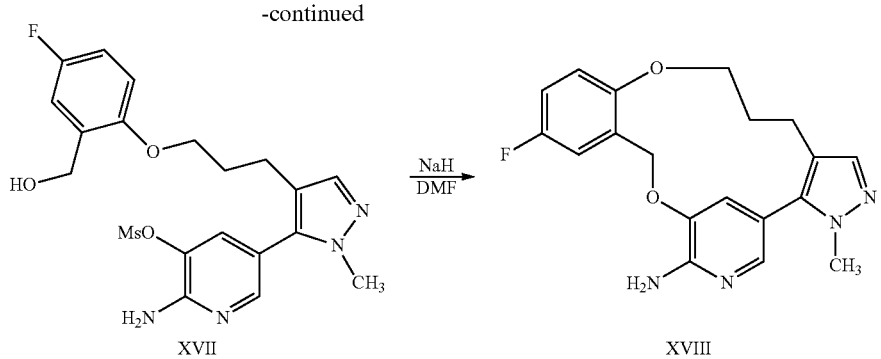

The Sonagashira cross-coupling between aryl halide (XII) and alkyne (XIII) was accomplished in the presence of the appropriate palladium and copper catalysts and base to provide compound (XIV). The alkyne (XIV) may be reduced in an atmosphere of hydrogen in the presence of the appropriate palladium catalyst to provide compound (XV). Compound (XV) may be deprotected using a suitable base, such as sodium hydroxide, to provide compound (XVI). The hydroxyl group of compound (XVI) may be converted to a reactive agent, followed by an intramolecular displacement by the phenoxide to generated macrocycle (XVIII). Thus, compound (XVI) may be treated with mesyl chloride in the presence of a base to provide compound (XVII). The addition of a suitable base, such as sodium hydride, to compound (XV11) provides macrocycle (XVIII).

Method E

In a general synthetic process, compounds of the general structure represented by compound (XXI) are prepared according to Method E.

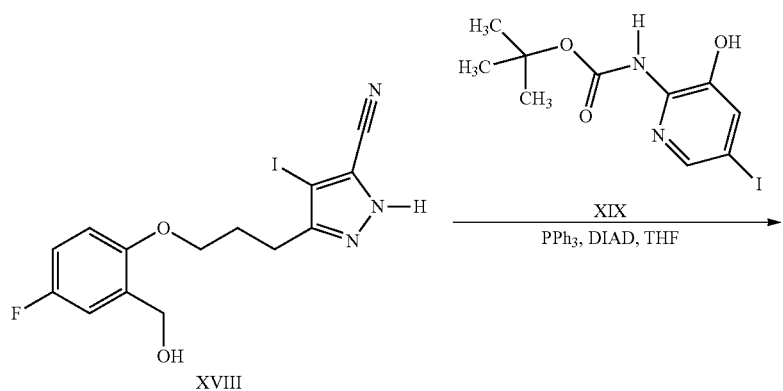

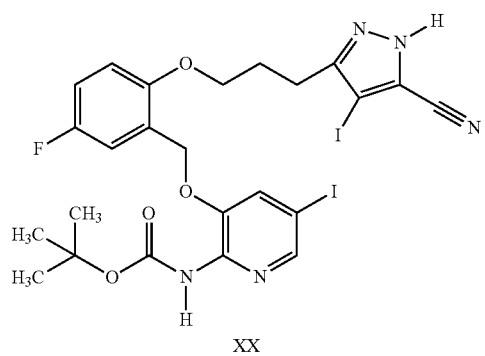

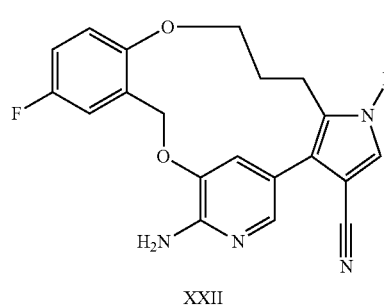

XXII

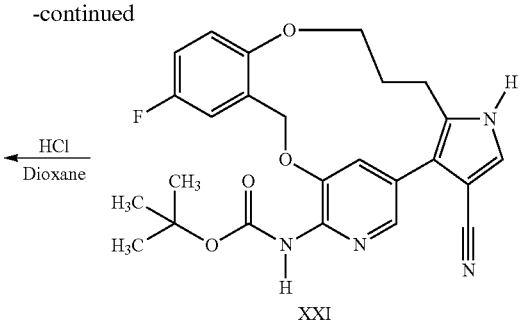

XXI

The phenol (XIX) may be coupled with compound (XVIII) using the Mitsunobu conditions to provide compound (XX). In the second step, intramolecular Suzuki coupling of compound (XX) may be accomplished using diboron pinacol ester and the appropriate palladium catalyst and base to provide the macrocycle (XXI). The BOC protecting group of compound (XXI) may be removed using HCl to provide compound (XXII).

Method F

In a general synthetic process, compounds of the general structure represented by compound (XXV) are prepared according to Method F.

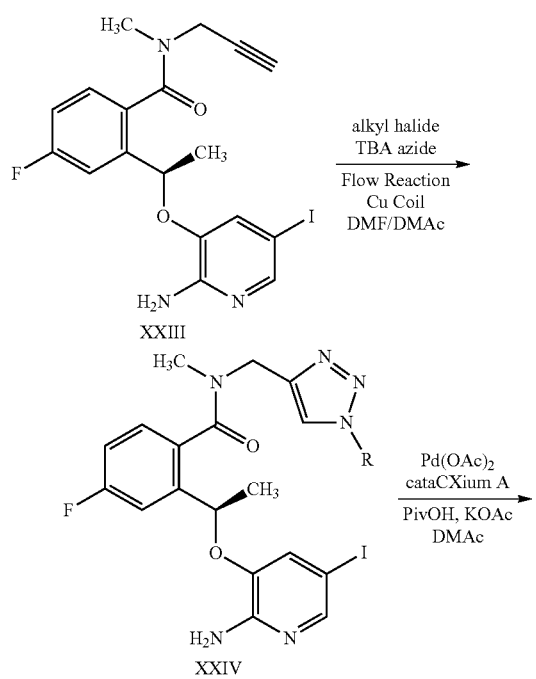

An alkyl halide may be converted to an alkyl azide, followed by the addition of the alkyne (XXIII) and copper to provide compound (XXIV). The 1,4-disubstituted triazole (XXIV) may be treated with a palladium catalyst to provide macrocycle (XXV).

Method G

In a general synthetic process, compounds of the general structure represented by compound (IX) are prepared according to Method G.

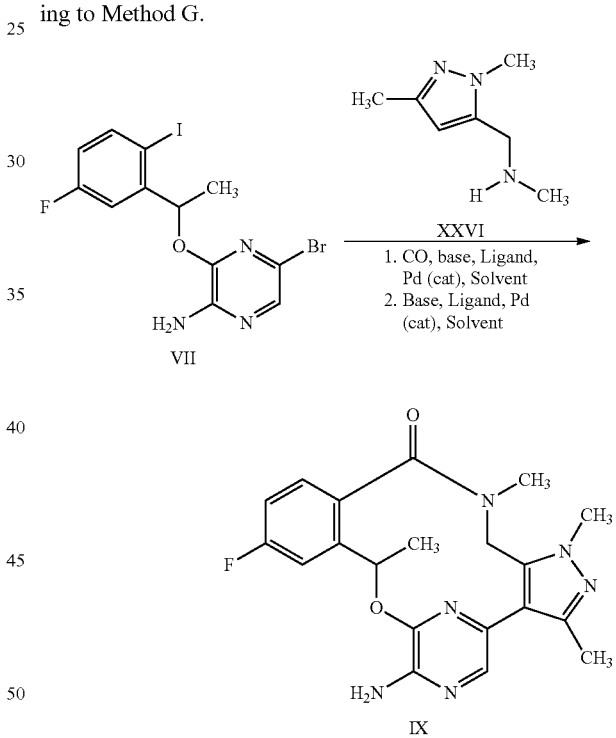

In the first step of a two step sequence, regioselective carboamidation of aryl dihalide (VII) may be accomplished with amine (XXVI) in the presence of carbon monoxide and an appropriate palladium catalyst and base. In the second step, a C—H activation reaction on the amide (either crude or purified) may be accomplished using the appropriate palladium catalyst and base to provide the macrocycle (IX).

Method H

In a general synthetic process, compounds of the general structure represented by compound (XXI) are prepared according to Method H.

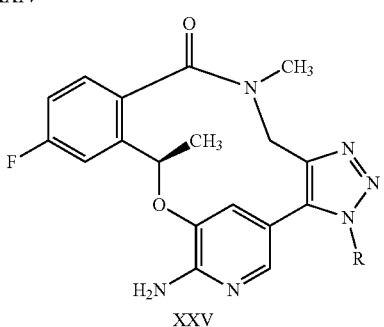

XXV

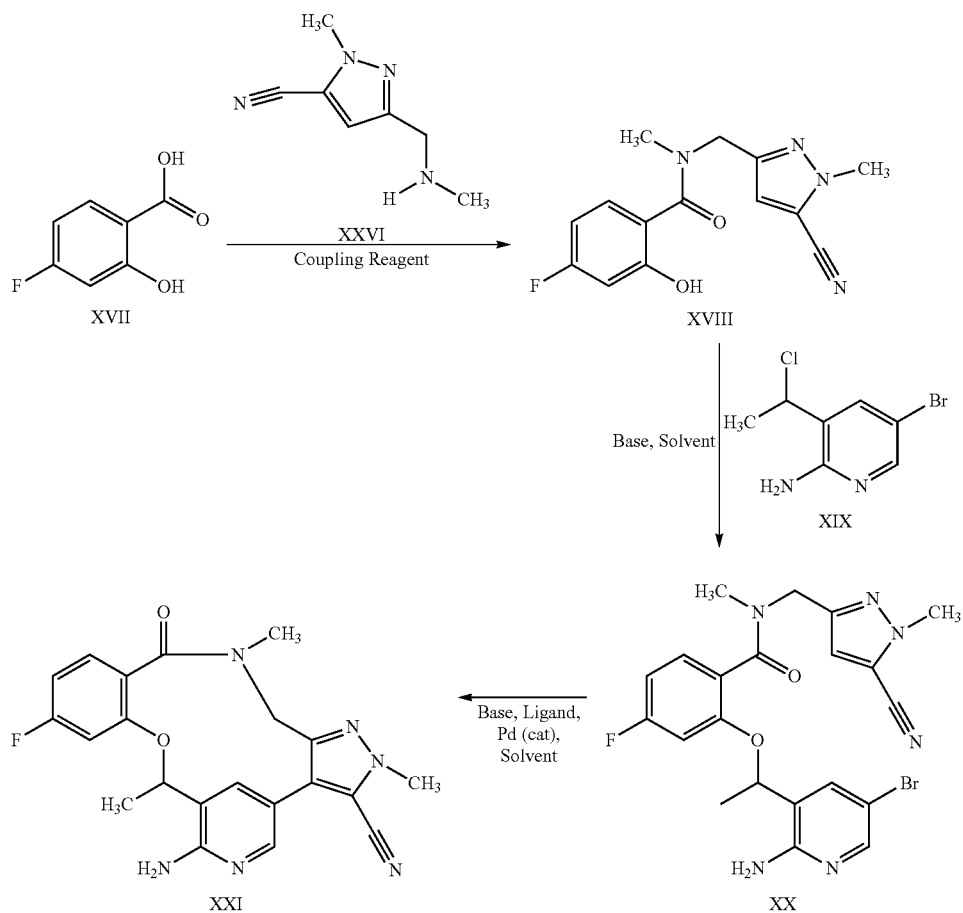

In the first of a three step sequence, amide bond formation of acid (XVII) and amine (XVI) may be accomplished using a suitable coupling agent, such as HATU, to provide compound (XVIII). Nucleophilic displacement of (XVIII) with compound (XIX) to obtain compound (XX) may occur in the presence of a suitable base, such as potassium carbonate. In the final step, a C—H activation reaction on the amide (XX) may be accomplished using the appropriate palladium catalyst and base to provide the macrocycle (XXI).

Method I

In a general synthetic process, compounds of the general structure represented by compound (XXVII) are prepared according to Method I.

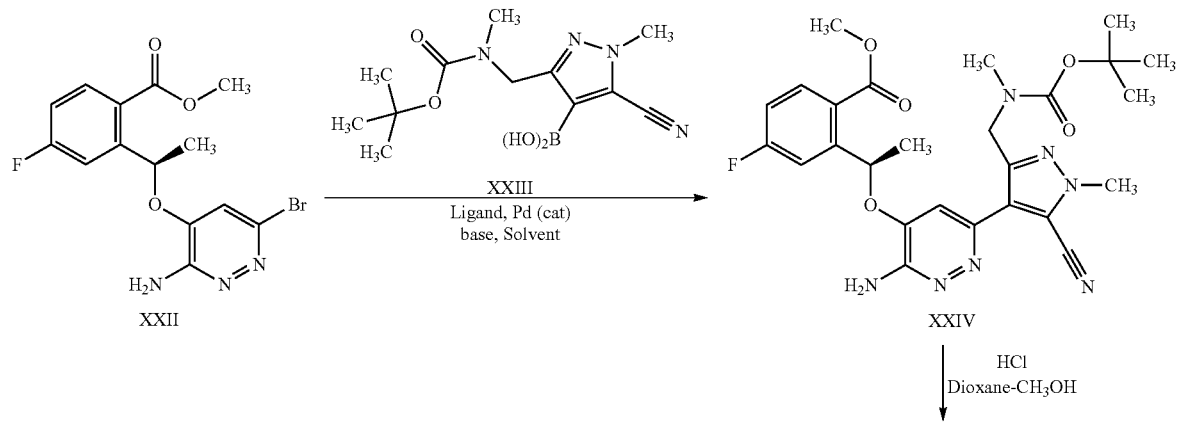

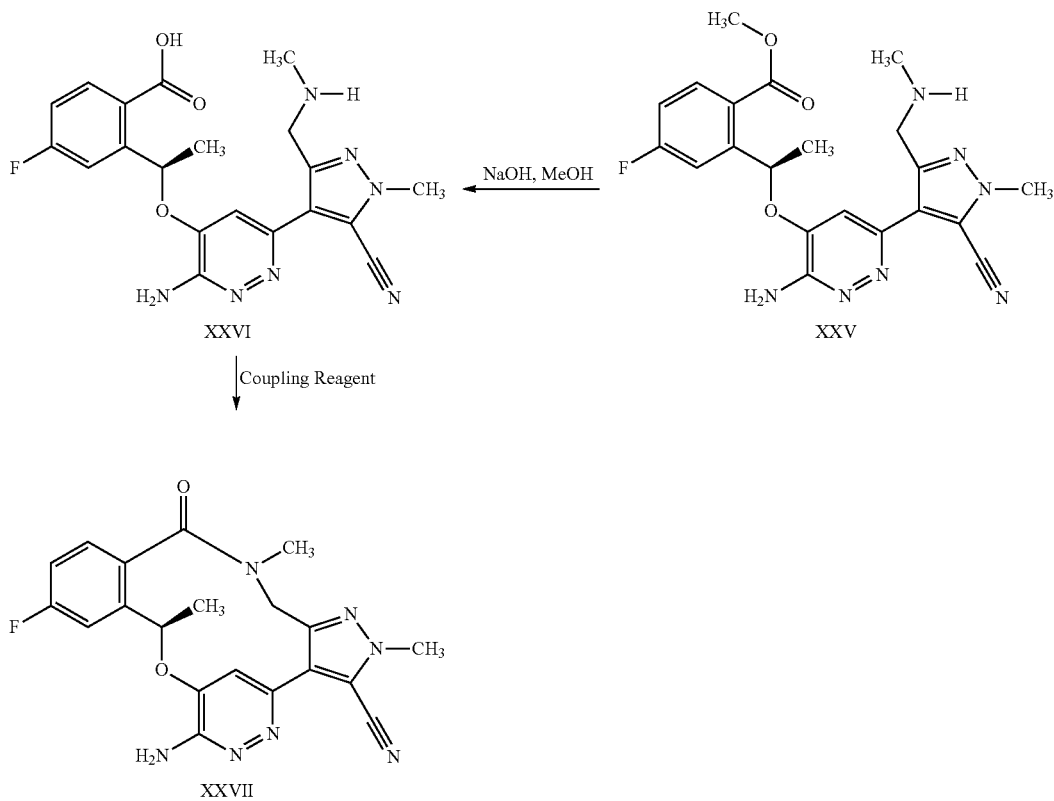

The aryl halide (XXII) may be coupled with boronic acid (XXIII) using the Suzuki coupling conditions to give compound (XXIV). The BOC protecting group may removed using HCl or TFA to yield compound (XXV), and the ester group of compound (XXV) may be hydrolyzed using an appropriate base, such as sodium hydroxide, to provide compound (XXVI), Finally, formation of the lactam may be achieved by using the appropriate coupling reagent such as HATU to yield compound (XXVII).

Method J

In a general synthetic process, compounds of the general structure represented by compound (XXXIV) are prepared according to Method J.

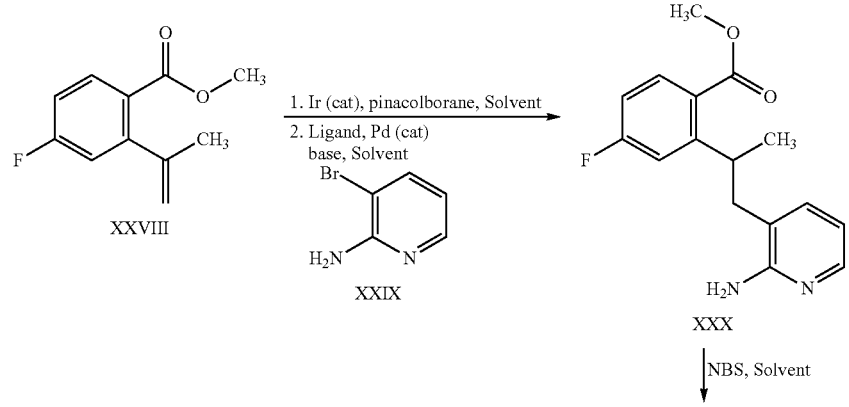

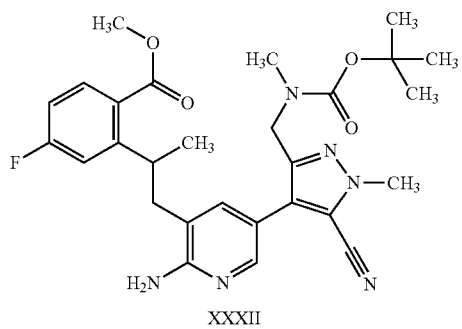

XXXII

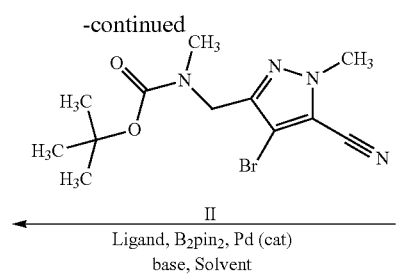

II
Ligand, B₂pin₂, Pd (cat)
base, Solvent

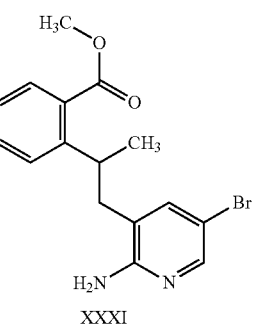

XXXI

1. NaOH, CH₃OH
2. HCl, Dioxane-CH₃OH

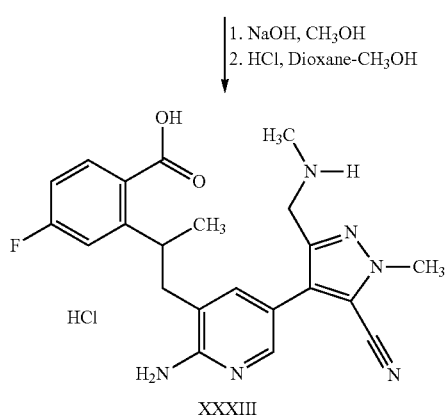

XXXIII

Coupling Reagent

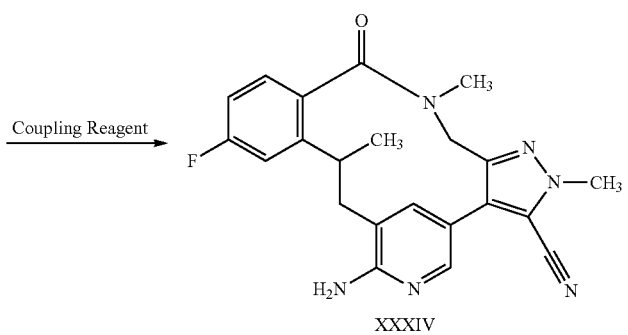

XXXIV

Regioselective hydroboration of the alkene (XXVIII) may be achieved using pinacol borane, and a suitable catalyst. The boronate species formed may be directly coupled to an aryl halide (XXIX) using the Suzuki coupling conditions to give compound (XXX). Regioselective halogenation of compound (XXX) may be accomplished using a reagent such as NBS to give compound (XXXI). The aryl halide (XXXI) may be coupled with aryl halide (II) using the Suzuki coupling conditions, where the in situ generated boronic acid reacts with the aryl halide to give compound (XXXII). The ester group of compound (XXXII) may be hydrolyzed using an appropriate base, such as sodium hydroxide and then without purification, the BOC protecting group may be removed using HCl or TFA to yield compound (XXXIII). Finally, formation of the lactam may be achieved by using the appropriate coupling reagent such as HATU to yield compound (XXXIV).

Method K

In a general synthetic process, compounds of the general structure represented by compound (XXXIX) are prepared according to Method K.

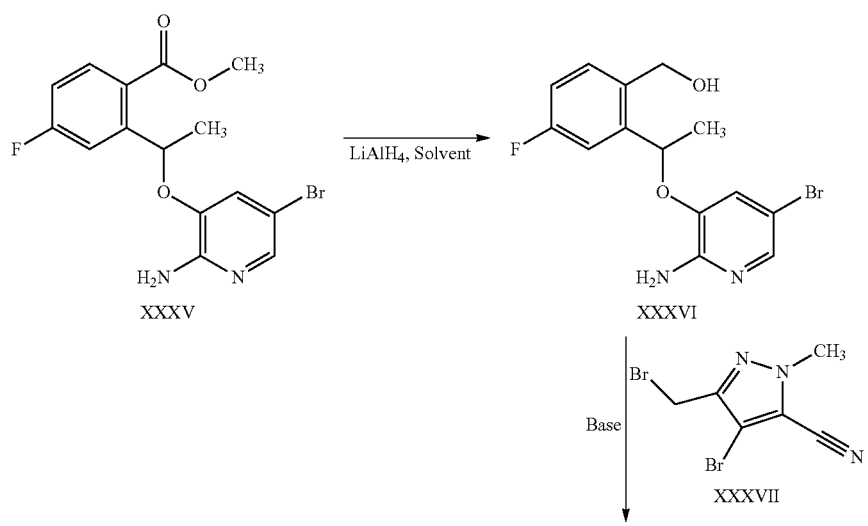

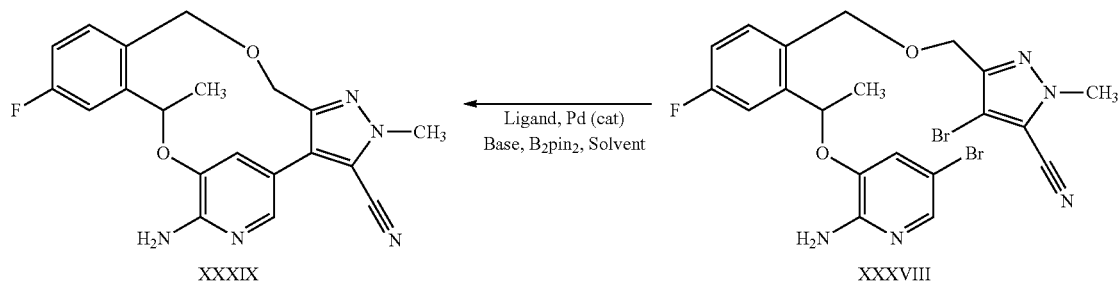

Reduction of the ester (XXXV) to the alcohol (XXXVI) may be accomplished with a reducing agent such as LAH. Ether bond formation between alcohol (XXXVI) and aryl halide (XXXVII) may occur mediated by a base such as NaH. The aryl dihalide (XXXVIII) may be coupled in an intramolecular fashion using the Suzuki coupling conditions, where the in situ generated boronic acid generated at one halide reacts with the other halide in the molecule to give compound (XXXIX).

Method L

In a general synthetic process, compounds of the general structure represented by compound (XLV) are prepared according to Method L.

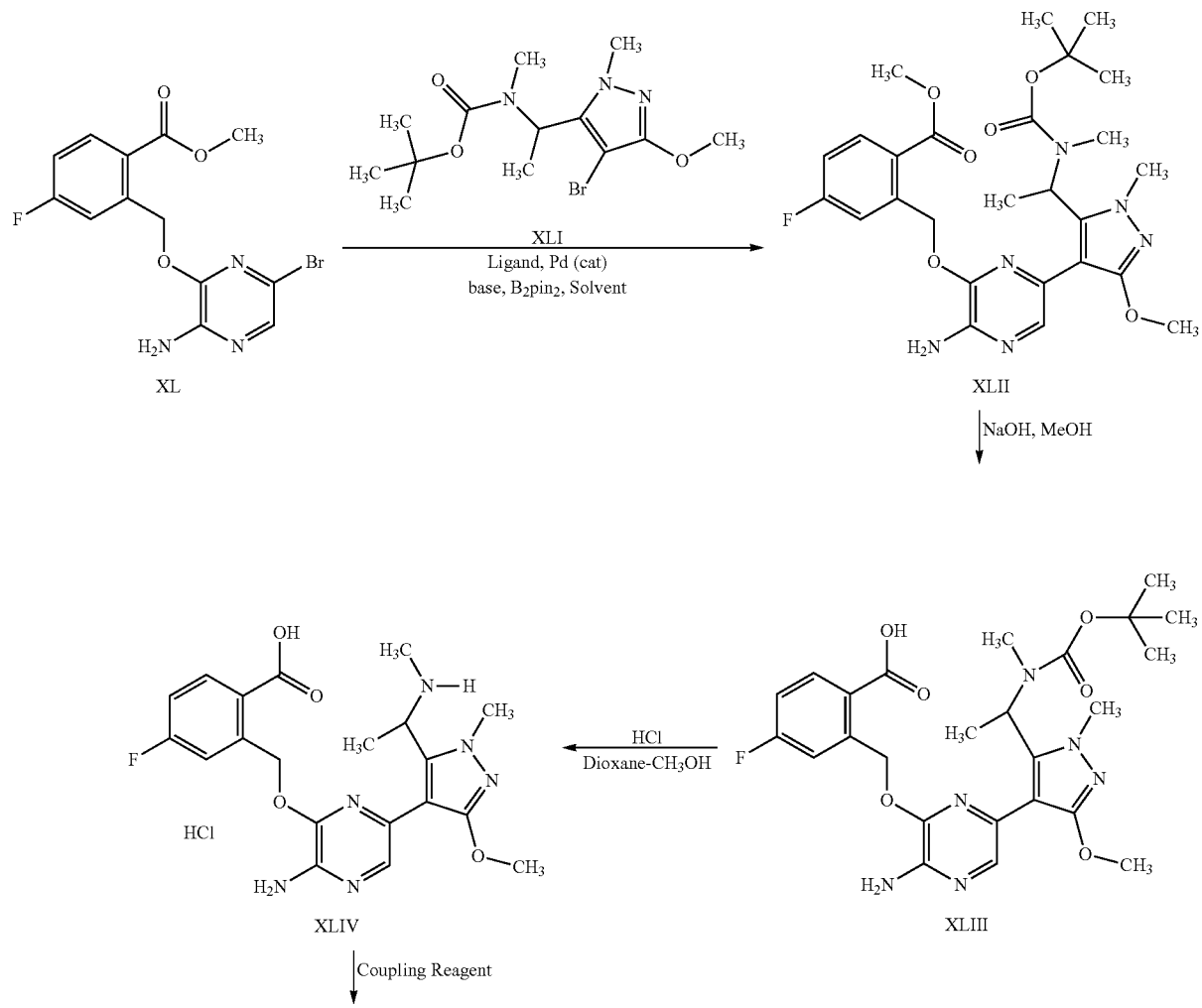

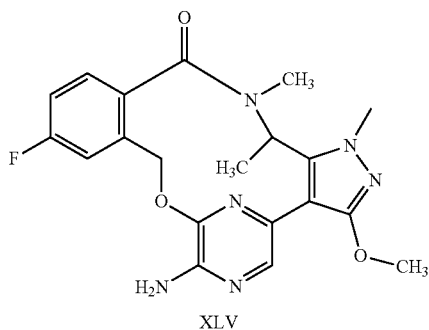

XLV

Method M

In a general synthetic process, compounds of the general structure represented by compound (XLIX) are prepared according to Method M.

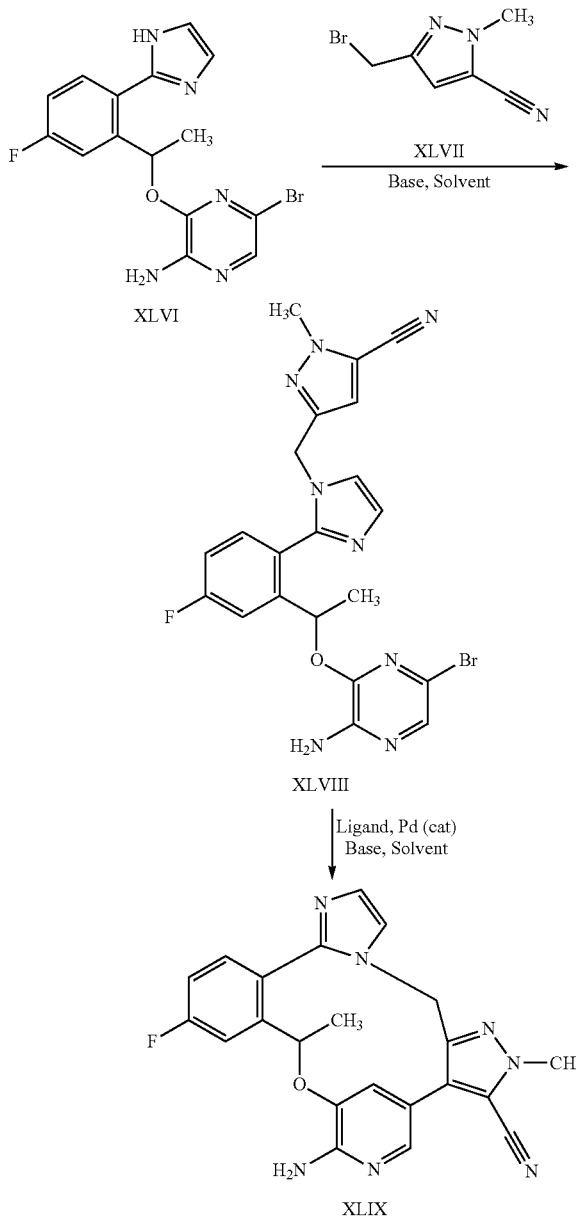

The symmetrical imidazole (XLVI) may be alkylated with the benzylic halide (XLVII) in the presence of a suitable base such as $K_2CO_3$. In the final step, a C—H activation reaction on the amide (XLVIII) may be accomplished using the appropriate palladium catalyst and base to provide the macrocycle (XLIX).

Method N

In a general synthetic process, compounds of the general structure represented by compound (LII) are prepared according to Method N.

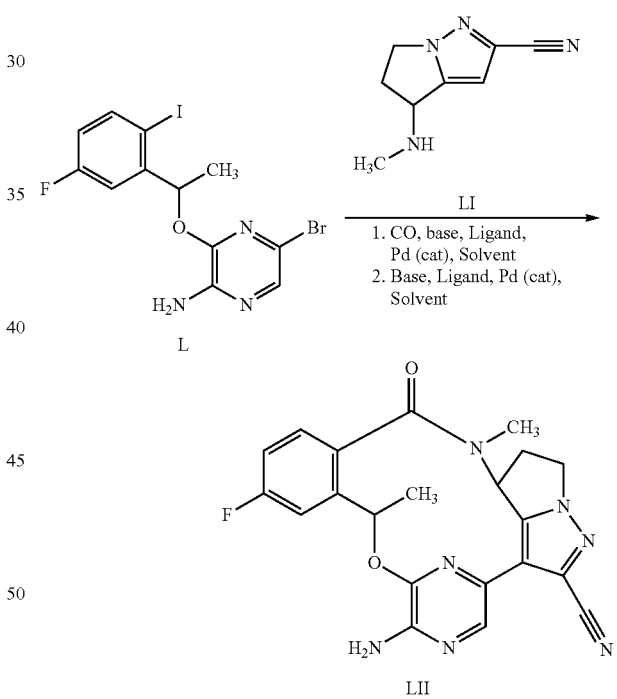

In the first step of a two step sequence, regioselective carboamidation of aryl dihalide (L) may be accomplished with a bicyclic amine (LII) in the presence of carbon monoxide and an appropriate palladium catalyst and base. In the second step, a C—H activation reaction on the amide (either crude or purified) may be accomplished using the appropriate palladium catalyst and base to provide the macrocycle (LII).

Method O

In a general synthetic process, compounds of the general structure represented by compound (LVIII) are prepared according to Method N.

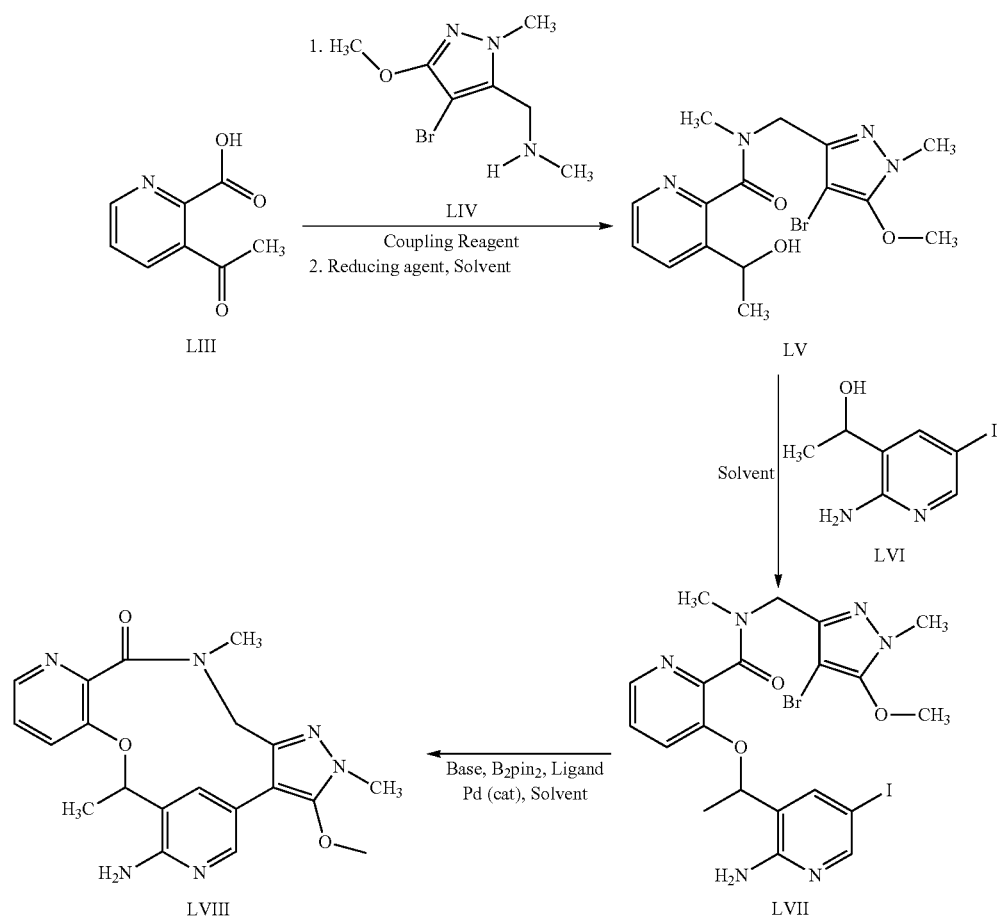

Amide bond formation between acid (LIII) and amine (LIV) may be accomplished using a suitable coupling agent, such as HATU. Subsequent reduction of the acetophenone functionality to the alcohol (LV) may be accomplished using a reagent such as NaBH4. Ether bond formation between (LV) and the alcohol (LVI) may be accomplished using methodology such as a Mitsunobu reaction to give compound (LVII). The aryl dihalide (LVII) may be coupled in an intramolecular fashion using the Suzuki coupling conditions, where the in situ generated boronic acid generated at one halide reacts with the other halide in the molecule to give compound (LVIII).

For some of the steps of the here above described process of preparation of the compounds of the invention, it may be necessary to protect potential reactive functions that are not wished to react, and to cleave said protecting groups in consequence. In such a case, any compatible protecting radical can be used. In particular methods of protection and deprotection such as those described by T.W. GREENE (*Protective Groups in Organic Synthesis*, A. Wiley-Interscience Publication, 1981) or by P. J. Kocienski (Protecting groups, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto. The compounds of the invention as well as intermediates for the preparation thereof can be purified according to various well-known methods, such as for example crystallization or chromatography.

EXAMPLES

The Preparations and Examples that follow illustrate the invention but do not limit the invention. All starting materials are available commercially or are described in the literature. All temperatures are in 0° C. Flash column chromatography was carried out using Merck silica gel 60 (9385). Thin layer chromatography (TLC) was carried out on Merck silica gel 60 plates (5729). "$R_f$" represents the distance travelled by a compound divided by the distance travelled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

The invention is illustrated by the following non-limiting examples in which the following abbreviations and definitions are used:

"Et" means ethyl, "Ac" means acetyl, "Me" means methyl, "Ph" means phenyl, "Boc", "BOC", "t-Boc", or "t-BOC" means tert-butoxycarbonyl, "EtOAc" means ethyl acetate, "TEA", "NEt$_3$," or "Et$_3$N" means triethylamine, "THF" means tetrahydrofuran, "MeTHF" means methyltetrahydrofuran, "MeOH" means methanol, "DMSO" means dimethylsulfoxide, "CDCl$_3$," means deuterated chloroform, "TBME" or "MTBE" means methyl t-butyl ether, "DMF" means dimethyl formamide, "DMAP" means 4-dimethylaminopyridine, "dppf" means diphenylphosphino ferrocene, "DME" means ethylene glycol dimethyl ether, "TLC" means thin layer chromatography, "SFC" means supercritical fluid chromatography, "h", "hr" or "hrs" means hours, "min." or "mins." means minutes, "DCM" or "CH$_2$Cl$_2$" means methylene chloride, "Et$_2$O" means diethyl ether, "LC-MS" or "LCMS" means liquid chromatography-mass spectrometry, "MS" means mass spectrometry, "rt" or "RT" means room temperature, "NBS" means N-bromosuccinimide, "MeCN" or "CH$_3$CN" means acetonitrile, "brine" means saturated aqueous sodium chloride, "HATU" means 2-(7-Aza-1H-benzotriazole-1-yl)-1,1,3,3-tetramethyluronium hexafluorophosphate, "APCI" means atmospheric pressure chemical ionization, "CD$_3$OD" means deuterated methanol, "(CD$_3$)$_2$SO" means deuterated dimethyl sulphoxide, "δ" means chemical shift, "d" means doublet, "DAD" means diode array detector, g means grams, "ESCI" means electrospray chemical ionization, "HPLC" means high pressure liquid chromatography, "LRMS" means low resolution mass spectrum, "M" means molar, "m" means multiplet, "mg" or "mgs" means milligrams, "MHz" means mega hertz, "mL" means milliliters, "μL" means microliters, "mmol" means millimoles, "mol" means moles, "NMR" means nuclear magnetic resonance, "q" means quartet, "Rt" means retention time, "s" means singlet, "t" means triplet, "TFA" means trifluoroacetic acid, "SFC" means supercritritcal fluid chromatography, "MeMgBr" means methyl magnesium bromide, "DMSO-d$_6$" means deuterated dimethylsulfoxide, "DiBAL" or "DIBAL-H" means diisobutylaluminium hydride, "CH$_3$I" means methyl iodide, "ppm" means parts per million, "mCPBA" means meta-chloroperoxybenzoic acid, "DIPCl" means β-chlorodiisopinocamphenylborane (DIP-Chloride®), "N$_2$" means nitrogen gas, "MeI" means methyl iodide, "NBS" means N-bromosuccinimide", "NIS" means N-iodosuccinimide, "DIAD" means diisopropyl azodicarboxylate, "DCE" means 1,2-dichloroethane, "HOBt" means hydroxybenzotriazole, "EDCI" means 1-ethyl-3-(3-dimethylaminopropyl) carbodiimide, "CDI" means 1,1'-carbonyldiimidazole, "DMS" means dimethyl sulfide, "DIEA", "DIPEA" or "Hunig's base" means N,N-diisopropylethylamine, "MsCl" means methanesulfonyl chloride, "AIBN" means azobisisobutyronitrile, "cataCXium" means di(1-adamantyl)-n-butylphosphine, "HATU" means 2-(7-Aza-1H-benzotriazole-1-yl)-1,1,3,3-tetramethyluronium hexafluorophosphate, "AgOTf" means trifluoromethanesulfonic acid silver salt, "TFAA" means trifluoroacetic acid, "SCX cartridge" means strong cation-exchange column cartridge, and "DMAc" means dimethylacetamide Preparation of Synthetic Intermediates Preparation of (R)-methyl 2-(1-((2-amino-5-bromopyridin-3-yl)oxy)ethyl)-4-fluorobenzoate (7)

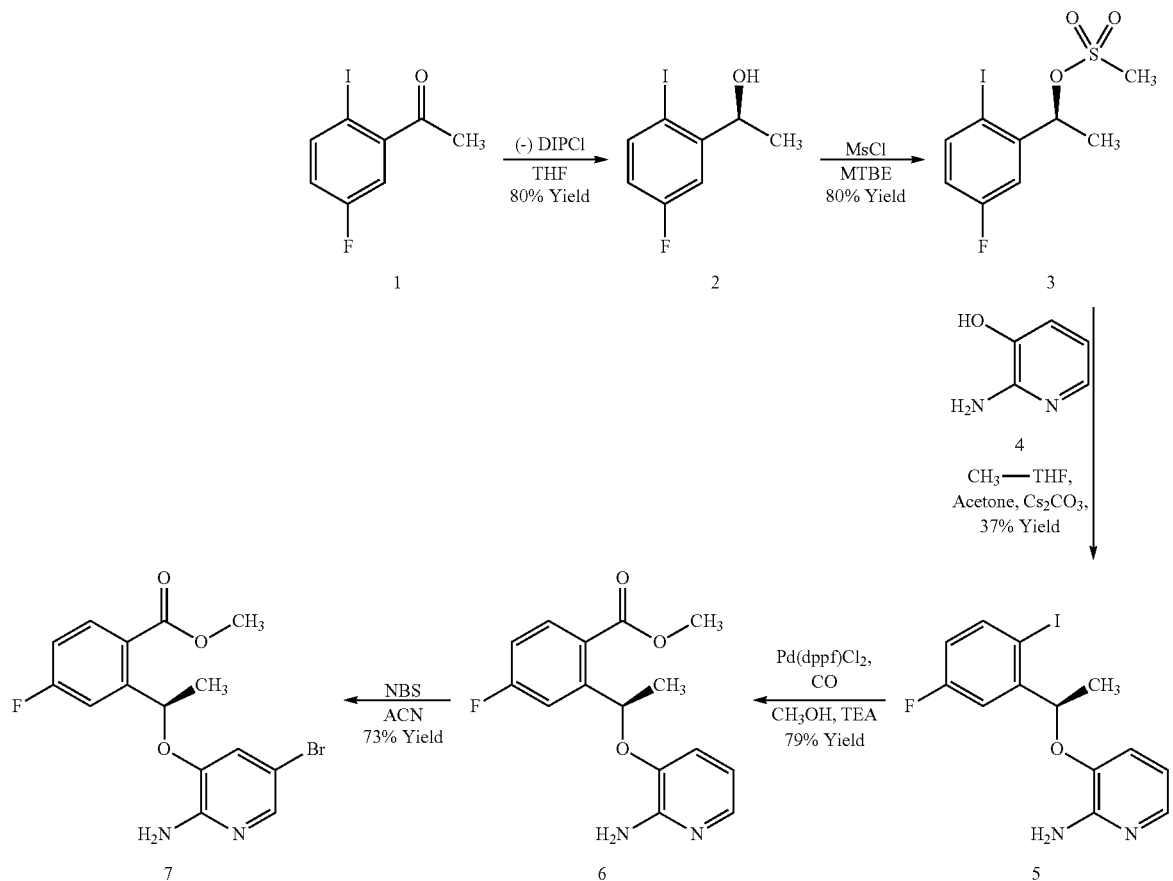

Step 1:

A solution of (−)-DIPCI (57.1 g, 178 mmol) in THF (100 ml) was cooled to −20 to −30° C. A solution of compound 1 (31.3 g, 119 mmol) in THF (100 ml) was then added dropwise, via addition funnel (30 min addition). The reaction was left to warm up to RT. After 2 h, the reaction was cooled to −30° C. and another portion of (−)-DIPCI (38.0 g, 119 mmol) was added. After 30 min, the reaction was allowed to warm to RT and after 1 h, the solvents were removed in vacuo and the residue re-dissolved in MTBE (200 ml). A solution of diethanolamine (31 g, 296 mmol) in ethanol/THF (15 ml/30 ml) was added via addition funnel, to the reaction mixture under an ice bath. The formation of a white precipitate was observed. The suspension was heated at reflux for 2 hours then cooled to room temperature, filtered and the mother liquids concentrated in vacuo. The residue was suspended in heptane/EtOAc (7:3, 200 ml) and again filtered. This procedure was repeated until no more solids could be observed after the liquids were concentrated. The final yellow oil was purified by column chromatography (eluent: cyclohexane/EtOAc-99:1 to 96:4). The resulting colorless oil was further purified by recrystallisation from heptanes, to give alcohol compound 2 (25 g, 80% yield, 99% purity and 96% ee) as white crystals. $^1$H NMR (400 MHz, CDCl$_3$) δ 7.73 (dd, 1 H), 7.32 (dd, 1 H), 6.74 (ddd, 1 H), 4.99-5.04 (m, 1 H), 2.01 (d, 1 H), 1.44 (d, 3 H). LCMS-ES: No ionization, Purity 99%. Chiral GC (column CP-Chirasil-DexnCB): 96% ee; Rt (minor) 17.7 minutes and Rt (major) 19.4 minutes.

Step 2:

A solution of compound 2 (22 g, 83 mmol) in MTBE (350 mL) was cooled under an ice bath and triethylamine (23 mL, 166 mmol) followed by mesyl chloride (9.6 mL, 124 mmol) were added drop-wise. The reaction was then warmed to RT and stirred for 3 h. The reaction mixture was filtered and the solids washed with EtOAc. The mother liquids were concentrated in vacuo to give compound 3 (35 g, 80% yield) as a pale yellow oil. This material was taken into the following step without further purification. $^1$H NMR (400 MHz, CDCl$_3$) δ 7.78 (dd, 1 H), 7.24 (dd, 1 H), 6.82 (ddd, 1 H), 2.92 (s, 3 H), 1.64 (d, 3 H). LCMS-ES no ionization.

Step 3:

A suspension of Cs$_2$CO$_3$ (65 g, 201 mmol) and compound 4 (13.3 g, 121 mmol) in CH$_3$-THF (600 mL) and acetone (300 mL) was stirred at RT for 30 minutes then heated at 40° C. before drop-wise addition of a solution of compound 3 (34.4 g, 80 mmol) in CH$_3$-THF (300 mL) via addition funnel. The resulting mixture was left stirring at 75-80° C. for 24 h. The reaction was then filtered through celite with MTBE, the solvents removed in vacuo and the residue purified by column chromatography over silica gel which was eluted with cyclohexane/EtOAc (9:1 to 1:1) to give compound 5 (14.3 g, 39% yield, 90% ee) as a white solid. The solids were then recrystallised from heptane/EtOAc to give compound 5 (10.8 g, 37% yield, 95% ee). $^1$H NMR (400 MHz, CDCl$_3$) δ 7.38 (dd, 1 H), 7.62 (dd, 1 H), 7.10 (dd, 1 H), 6.75 (ddd, 1 H), 6.44-6.51 (m, 2 H), 5.34-5.39 (m, 1 H), 4.73 (br s, 2 H), 1.61 (d, 3 H). LCMS-ES m/z 359 [M+H]$^+$. HPLC (Chiralpak IC 4.6×250 mm): 95% ee; Rt (minor) 10.4 minutes; Rt (major) 14.7 minutes; eluent: Heptane 80%/IPA 20% with 0.2% DEA, 0.7 mL/min.

Step 4:

Compound 5 (20 g, 57 mmol) was dissolved in methanol (300 mL), and sequentially treated with triethylamine (15.4 mL, 113 mmol) and PdCl$_2$(dppf) (4.1 g, 5.7 mmol). This mixture was heated at 100° C. for 16 hours, under a 100 psi carbon monoxide atmosphere. LCMS indicated consumption of starting material. The reaction mixture was filtered through a pad of Celite, and the filtrate evaporated to a brown oil. The crude product was purified by flash chromatography over silica gel which was eluted with 50% to 75% ethyl acetate in cyclohexane, affording the pure product 6 as a brick-red solid (13.0 g, 79% yield). $^1$H NMR (400 MHz, CDCl$_3$) δ 1.65 (d, 3 H), 3.94 (s, 3 H), 4.75 (br s, 2 H), 6.32 (q, 1 H), 6.42 (dd, 1 H), 6.61 (dd, 1 H), 7.00 (ddd, 1 H), 7.28 (dd, 1 H), 7.60 (dd, 1 H), 8.03 (dd, 1 H). LCMS ES m/z 291 for [M+H]$^+$.

Step 5:

Compound 6 (13.0 g, 45 mmol) was dissolved in acetonitrile (195 mL), and cooled to <10° C. in an ice water bath. NBS (7.9 g, 45 mmol) was added drop-wise to the cooled reaction mixture as a solution in acetonitrile (195 mL), monitoring the internal temperature to ensure it did not rise above 10° C. After addition was complete, the mixture was stirred for 15 minutes. TLC (1:1 cyclohexane/ethyl acetate) showed consumption of starting material. The reaction mixture was evaporated, and the residue redissolved in ethyl acetate (400 mL), and washed with 2M aqueous NaOH (2×300 mL), and 10% aqueous sodium thiosulfate solution (300 mL). The organic extracts were dried over MgSO$_4$, and evaporated to a red oil (17.6 g). The crude product was purified over silica gel, which was eluted with 10% to 50% ethyl acetate in cyclohexane, which gave compound 7 (12.0 g, 73% yield). $^1$H NMR (400 MHz, CDCl$_3$)δ 1.65 (d, 3 H), 3.96 (s, 3 H), 4.74-4.81 (br s, 2 H), 6.33 (q, 1 H), 6.75 (d, 1 H), 7.03 (ddd, 1 H), 7.25 (dd, 1 H), 7.66 (d, 1 H), 8.06 (dd, 1 H). LCMS ES m/z 369/371 [M+H]$^+$. A Chiralpak AD-H (4.6×100 mm, 5 micron) column was eluted with 10% MeOH (0.1% DEA) in CO$_2$ at 120 bar. A flow rate of 5.0 mL/min gave the minor isomer Rt 0.6 minutes and the major isomer Rt 0.8 minutes (99% ee). Optical rotation: $[α]_d^{20}$=−92.4 deg (c=1.5, MeOH).

Preparation of 1-(5-fluoro-2-iodophenyl)ethyl methanesulfonate (11)

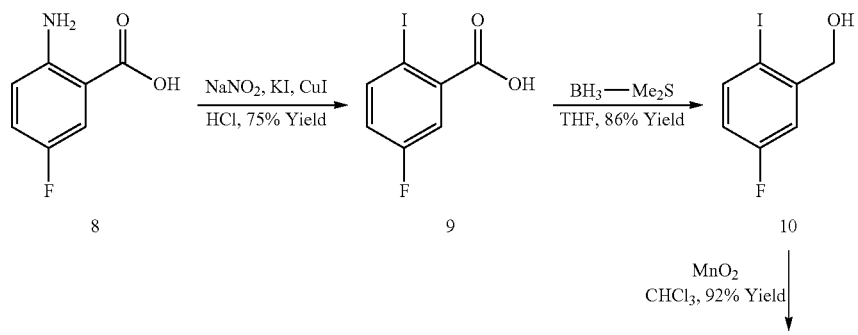

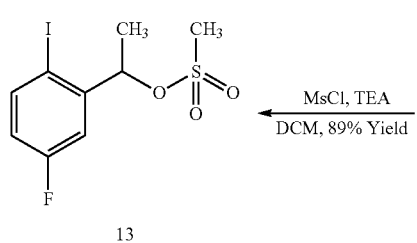 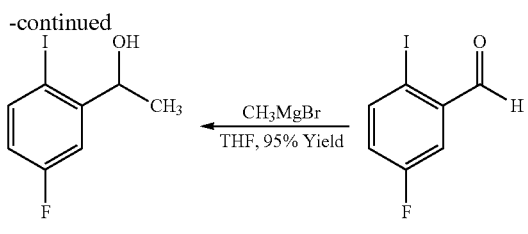

Step 1:

To a solution of compound 8 (25 g, 0.162 mol) in 2 N HCl solution (350 mL) was added a solution of sodium nitrite (11.2 g, 0.16 mol) in $H_2O$ (150 mL) drop-wise while maintaining the temperature between 0-5° C. After the addition was completed, the mixture was stirred at 0~5° C. for 90 minutes. Then, the mixture was added to a solution of potassium iodide (53 g, 0.32 mol) and copper (I) iodide (15.2 g, 0.081 mol) in $H_2O$ (150 mL) drop-wise with the temperature maintained at ~5° C. After addition was completed, the mixture was stirred at room temperature for 18 hours after which TLC (EtOAc) indicated that the reaction was complete. The mixture was filtered and the cake dried. The residue was diluted with MTBE (500 mL), refluxed for 20 minutes, and filtered. The filtrate was concentrated to afford compound 9 as a yellow solid (30 g, 75% yield). $^1$H NMR (400 MHz, Methanol-$d_4$) δ 8.04-8.00 (m, 1 H), 7.59-7.56 (m, 1 H), 7.08-7.03 (m, 1 H).

Step 2:

To a solution of compound 9 (67 g, 0.26 mol) in anhydrous THF (500 mL) was added a solution of $BH_3 \cdot SMe_2$ (50.9 mL, 0.51 mol, 1.0 M) in dry THF (150 mL) drop-wise at 0° C. under $N_2$. After addition was completed, the mixture was stirred at 0° C. for 30 min, and then refluxed for 2 hours. TLC (petroleum ether/EtOAc 1/1) indicated that the reaction was completed. The mixture was quenched with saturated aqueous $NH_4Cl$ solution (300 mL). The volatiles were removed in vacuo, and the residue extracted with EtOAc (200 mL×3). The combined organic layers were washed with brine (200 mL), dried over $Na_2SO_4$ and concentrated to give a residue, which was purified by silica gel chromatography eluting with petroleum ether:EtOAc (50/1 to 25/1) and gave compound 10 as a white solid (55 g, 86% yield). $^1$H NMR (400 MHz, $CDCl_3$) δ 7.69-7.66 (m, 1 H), 7.20-7.17 (m, 1 H), 6.72-6.67 (m, 1 H), 4.57 (d, 2 H), 1.98 (t, 1 H).

Step 3:

To a mixture of compound 10 (55 g, 221 mmol) in $CHCl_3$ (500 mL) was added $MnO_2$ (115 g, 1.33 mol), and the mixture was refluxed for 18 hours. TLC (petroleum ether:EtOAc=10: 1) indicated the reaction was completed. The mixture was filtered, and the filtrate was concentrated to afford compound 11 as a yellow solid (50 g, 97% yield).

Step 4:

To a solution of compound 11 (50 g, 200 mmol) in anhydrous THF (500 mL) was added $CH_3MgBr$ (200 mL, 600 mmol, 3 M in diethyl ether) drop-wise at −60° C. under $N_2$. Once addition was completed, the mixture was warmed to room temperature and stirred for a further 2 hours. TLC (petroleum ether:EtOAc 10:1) indicated the reaction was completed. The mixture was quenched with saturated aqueous $NH_4Cl$ solution (300 mL), and extracted with EtOAc (200 mL×3). The combined organic extracts were washed with brine (200 mL), dried over $Na_2SO_4$ and concentrated in vacuo and afforded compound 12 as a yellow solid (50 g, 95% yield). $^1$H NMR (400 MHz, $CDCl_3$) δ 7.69-7.64 (m, 1 H), 7.27-7.24 (m, 1 H), 6.71-6.65 (m, 1 H), 4.96-4.94 (m, 1 H), 1.38 (d, 3 H).

Step 5:

To a stirred solution of compound 12 (57 g, 0.213 mol) and TEA (38.5 mL, 0.277 mol) in dry DCM (1 L) was added drop-wise MsCl (35.7 g, 0.213 mol) with the temperature maintained at 0° C. After the addition was completed, the reaction mixture was stirred at this temperature for 30 minutes and then the mixture was allowed to warm and stirred at room temperature for 3 hours. TLC (petroleum ether/EtOAc 10:1) indicated the reaction was complete. The reaction mixture was washed sequentially with 1 N HCl (200 mL×3), saturated aqueous $NaHCO_3$ solution (200 mL×3) and brine (100 mL×3), dried over $Na_2SO_4$ and concentrated in vacuo and afforded compound 13 as yellow oil (65 g, 89% yield). $^1$H-NMR (400 MHz, $CDCl_3$) δ 7.79 (1 H, dd), 7.24 (1 H, dd), 6.82 (1 H, td), 5.88 (1 H, q), 2.92 (3 H, s), 1.64 (3 H, d).

Preparation of methyl 2-(1-((2-amino-5-bromopyridin-3-yl)oxy)ethyl)-4-fluorobenzoate (16)

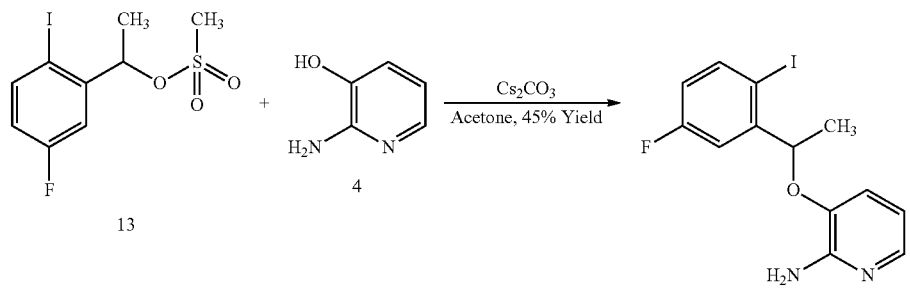

Carbon Monoxide
TEA, Pd(dppf)Cl$_2$
CH$_3$OH, 93% Yield

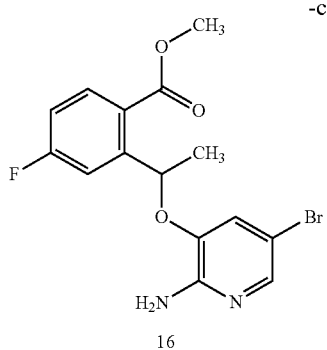

16

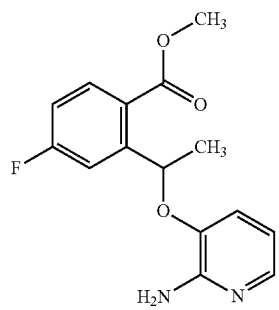

15

NBS
CH₃CN, 66% Yield

Step 1:

To a stirred suspension of compound 13 (57 g, 0.16 mol) and compound 4 (18.1 g, 0.16 mol) in acetone (1 L) was added Cs₂CO₃ (70 g, 0.21 mol) in portions at room temperature. After the addition was completed, the reaction mixture was stirred at room temperature for 15 minutes and then stirred at 45° C. for 18 hours. TLC (petroleum ether/EtOAc=3:1) indicated that the reaction was complete. The reaction mixture was filtered and the filtrate was concentrated in vacuo to yield a residue, which was purified by silica gel column chromatography eluting with petroleum ether/EtOAc (10:1 to 3:1) and gave compound 14 as a brown solid (47 g, 65% yield). ¹H NMR (400 MHz, CDCl₃) δ 7.73-7.69 (m, 1 H), 7.54 (d, 1 H), 7.03 (dd, 1 H), 6.71-6.68 (m, 1H), 6.44-6.37 (m, 2 H), 5.32-5.27 (m, 1 H), 4.68 (br s, 2 H), 1.54 (d, 3 H).

Step 2:

The procedure described in step 4 for compound 6 was used to prepare compound 15 (35.5 g, 93% yield). ¹H-NMR (400 MHz, CDCl₃) δ 7.77 (1 H, dd), 7.61 (1 H, d), 7.10 (1 H, dd), 6.75 (1 H, td), 6.51-6.44 (2 H, m), 5.36 (1 H, q), 4.75 (2 H, br s), 1.61 (3 H, d).

Step 3:

The procedure described in step 5 for compound 7 was used to prepare compound 16 (29 g, 66% yield). ¹H-NMR (400 MHz, CDCl₃) δ 8.06 (1 H, dd), 7.67 (1 H, d), 7.25 (1 H, dd), 7.03 (1 H, td), 6.75 (1 H, d), 6.33 (1 H, q), 4.76 (2 H, br s), 3.96 (3 H, s), 1.65 (3 H, d). LCMS m/z 181 (styrene fragment from cleavage at the ether bond).

Preparation of (S)-methyl 2-(1-((2-amino-5-bromopyridin-3-yl)oxy)ethyl)-4-fluorobenzoate (17) and (R)-methyl 2-(1-((2-amino-5-bromopyridin-3-yl)oxy)ethyl)-4-fluorobenzoate (7)

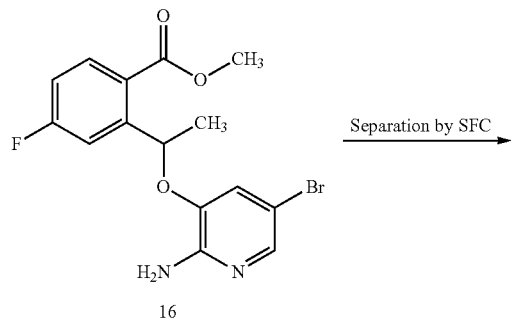

16

Separation by SFC

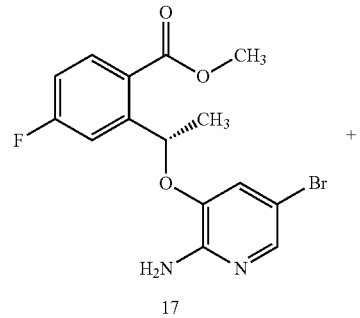

17

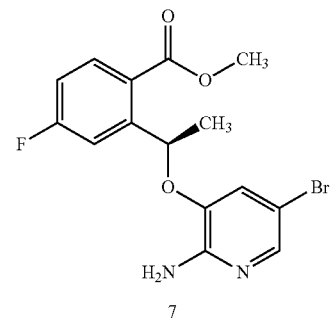

7

Compound 16 (24 g) was resolved by SFC and gave compound 17 (Peak 1) (10.6 g, 88% yield) and compound 7 (Peak 2) (10.2 g, 85% yield) as yellow solids. A Chiralpak AD-H (250×4.6 mm I.D., 5 micron particle size) column was eluted with 5% to 40% ethanol (0.05% DEA) in CO₂ at a flow rate of 2.3 mL/min and gave Peak 1 retention time of 4.1 minutes and Peak 2 retention time of 5.8 minutes.

Compound 17 (Peak 1): 99% ee. ¹H NMR (400 MHz, CDCl₃) δ 7.99 (dd, 1 H), 7.60 (d, 1 H), 7.18 (t, 1 H), 6.99-6.94 (m, 1 H), 6.68 (d, 1 H), 6.28-6.24 (dd, 1 H), 4.69 (s, 2 H), 3.89 (s, 3 H), 1.58 (d, 3 H). LCMS m/z 369/371 [M+H]⁺. [α]$_d$=+108.0 deg (c=0.5, MeOH).

Compound 7 (Peak 2): 100% ee. ¹H NMR (400 MHz, CDCl₃) δ 7.99 (dd, 1 H), 7.60 (d, 1 H), 7.18 (t, 1 H), 6.99-6.95 (m, 1 H), 6.68 (d, 1 H), 6.24 (dd, 1 H), 4.69 (s, 2 H), 3.89 (s, 3 H), 1.58 (d, 3 H). LCMS m/z 369/371 [M+H]⁺. [α]$_d$=−100.0 deg (c=0.5, MeOH).

Preparation of methyl 2-(1-((2-amino-5-bromopyridin-3-yl)oxy)propyl)-4-fluorobenzoate (23)

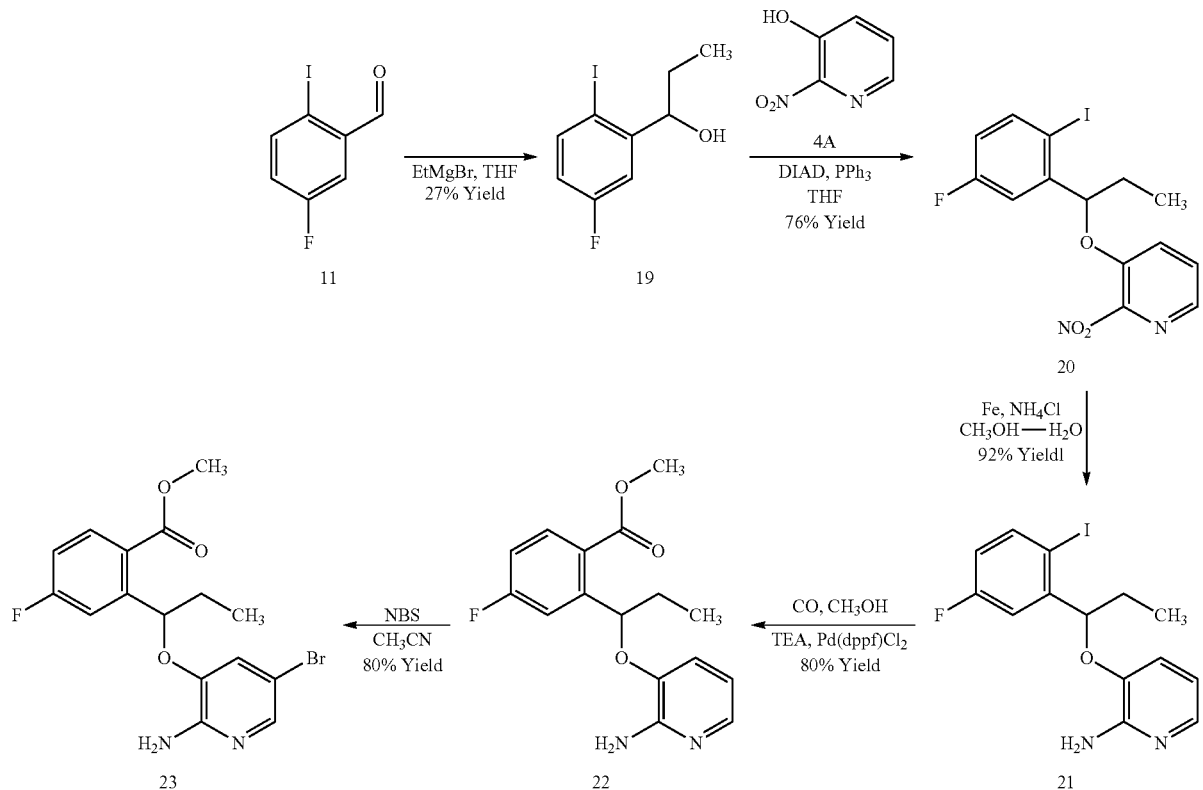

Step 1:
To a solution of compound 11 (40 g, 0.16 mol) in dry THF (400 mL) was added drop-wise EtMgBr (320 mL, 1 M in THF) at 0° C. After the addition, the resulting mixture was stirred at this temperature for 2 hours. TLC (petroleum ether/EtOAc=10:1) indicated the reaction was complete. The reaction mixture was quenched with saturated $NH_4Cl$ (200 mL) at 0° C. and the mixture was extracted with EtOAc (300 mL×2). The combined organic layers were washed with brine (500 mL×2), dried over $Na_2SO_4$ and concentrated. The residue was purified by Biotage (petroleum ether/EtOAc 20:1 to 10:1) to give compound 19 as light yellow oil (12 g, 27% yield). $^1H$ NMR (400 MHz, $CDCl_3$) δ 7.67-7.64 (m, 1 H), 7.20-7.17 (m, 1 H), 6.66 (t, 1 H), 4.72-4.70 (m, 1 H), 2.20 (s, 1 H), 1.77-1.69 (m, 1 H), 1.61-1.52 (m, 1 H), 0.98 (t, 3 H).

Step 2:
To a stirred solution of compound 19 (11 g, 0.039 mol), the compound 4A (5.5 g, 0.039 mol) and $PPh_3$ (14 g, 0.055 mol) in anhydrous THF (200 mL) was added drop-wise DIAD (11 g, 0.055 mol) at 0° C. After the addition, the reaction mixture was stirred at room temperature for 16 hours. TLC (petroleum ether/EtOAc 10:1) indicated the reaction was complete. The reaction mixture was concentrated in vacuo and the residue was purified by column chromatography on silica gel (petroleum ether/EtOAc 10:1 to 3:1) to give as a yellow solid compound 20 (12 g, 76% yield). $^1H$ NMR (400 MHz, $CDCl_3$) δ 8.11 (d, 1 H), 7.83-7.81 (m, 1 H), 7.47-7.42 (m, 1 H), 7.22-7.19 (m, 1 H), 7.09-7.07 (m, 1 H), 6.85-6.82 (m, 1 H), 5.36-5.32 (m, 1 H), 1.88-1.85 (m, 1 H), 1.09 (t, 3 H).

Step 3:
A suspension of compound 20 (12 g, 0.029 mol) and Fe (10 g, 0.18 mol) in methanol (100 mL) and saturated aqueous $NH_4Cl$ (100 mL) was stirred at 80° C. for 2 hours. TLC (petroleum ether/EtOAc=1:1) showed the reaction was complete. The reaction mixture was filtered and the filtrate was concentrated in vacuo to give an aqueous solution, which was extracted with EtOAc (150 mL×2). The combined organic layers were washed with brine (100 mL), dried over $Na_2SO_4$ and concentrated in vacuo to give compound 21 as a pale brown solid (10 g, 92% yield). $^1H$ NMR (400 MHz, DMSO-$d_6$) δ 7.96-7.93 (m, 1 H), 7.50 (d, 1 H), 7.34 (d, 1 H), 7.02 (t, 1 H), 6.59-6.57 (m, 1 H), 6.41-6.40 (m, 1 H), 5.94 (s, 2 H), 5.24 (t, 1 H), 1.96-1.85 (m, 2 H), 1.08 (t, 3 H).

Step 4:
A mixture of compound 21 (10 g, 0.027 mol), Pd(dppf)$Cl_2$ (2.6 g, 0.0027 mol) and TEA (10 mL, 0.08 mol) in methanol (250 mL) was sealed under CO (2 MPa) at 100° C. for 16 hours. TLC (petroleum ether/EtOAc=1:1) indicated the reaction was complete. The reaction mixture was filtered and the filtrate was concentrated in vacuo to give residue, which was purified by column chromatography on silica gel, (petroleum ether/EtOAc from 5:1 to 2:1) to give compound 22 as a pale yellow solid (6.5 g, 80% yield).

Step 5:
To a stirred solution of compound 22 (6.5 g, 0.02 mol) in $CH_3CN$ (50 mL) was added drop-wise a solution of NBS (3.8 g, 0.02 mol) in $CH_3CN$ (40 mL) at 0° C. during a period of 30 minutes. After the addition, the reaction mixture was stirred at this temperature for 30 minutes. TLC (petroleum ether/EtOAc=1:1) indicted the reaction was complete. The mixture was diluted with EtOAc (200 mL), washed with saturated $NaHCO_3$ (100 mL), brine (100 mL), dried over $Na_2SO_4$ and concentrated. The residue was purified by column chromatography over silica gel, which was eluted with petroleum ether/EtOAc (10:1 to 3:1) to give compound 23 as a pale yellow solid (5.8 g, 76% yield). $^1H$ NMR (400 MHz, $CDCl_3$) δ 8.01-7.98 (m, 1 H), 7.59 (s, 1 H), 7.12 (d, 1 H), 6.96-6.94 (m, 1 H), 6.69 (s, 1 H), 6.09-6.06 (m, 1 H), 4.74 (s, 2 H), 3.89 (s, 3 H), 1.88-1.82 (m, 2 H), 1.02-096 (m, 3 H). LCMS m/z 383/385 [M+H]+.

Preparation of methyl 2-(((2-amino-5-bromopyridin-3-yl)oxy)(cyclopropyl)methyl)-4-fluorobenzoate (28)

43% yield). $^1$H NMR (400 MHz, CDC$_3$) δ 8.01-7.98 (m, 1 H), 7.49-7.45 (m, 2 H), 7.16-7.11 (m, 1 H), 6.99 (d, 1 H), 5.90 (q, 1 H), 3.96 (s, 3 H), 1.42-1.41 (m, 1 H), 0.69-0.68 (m, 1 H), 0.56-0.49 (m, 3 H). LCMS m/z 395/397 [M+H]+.

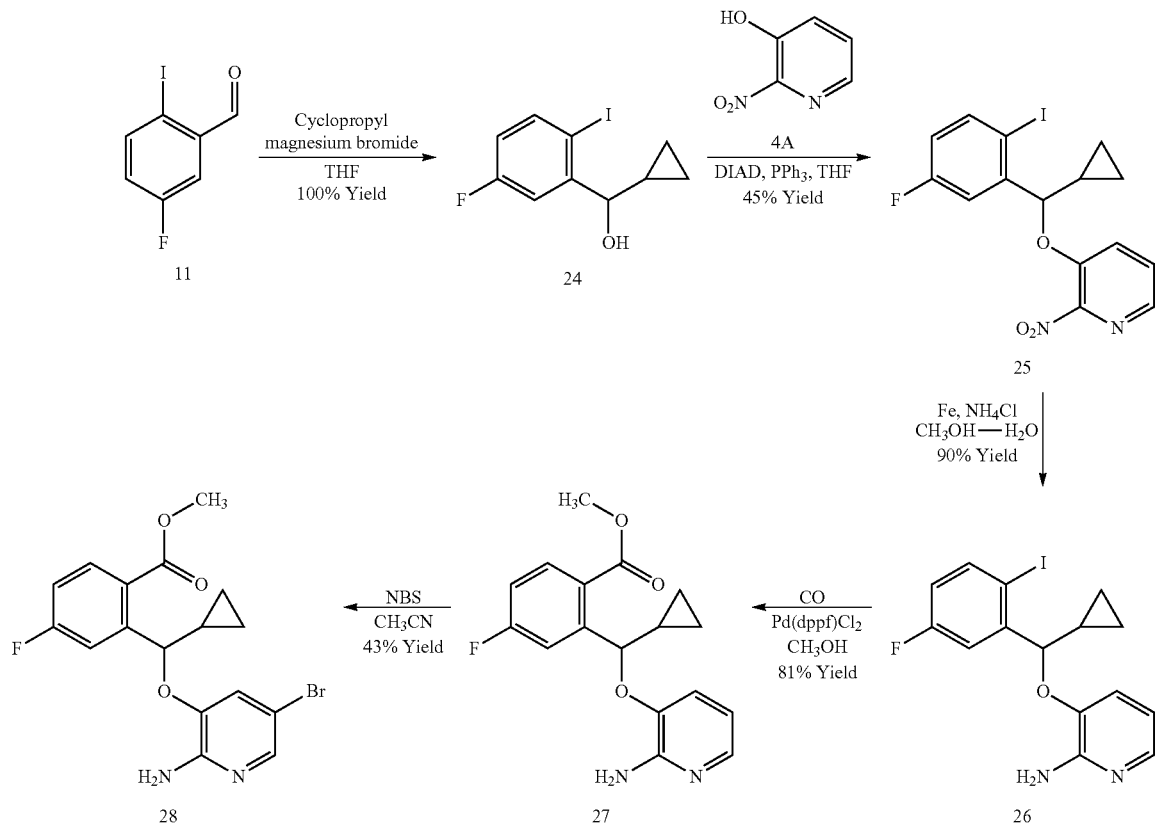

Step 1:
The procedure described in step 1 for compound 23 was used to prepare compound 24 as a light yellow oil (29 g, 100% yield). $^1$H NMR (400 MHz, CDCl$_3$) δ 7.68 (dt, 1 H), 7.21 (dd, 1 H), 6.68 (dt, 1 H), 4.45 (d, 1 H), 4.10-4.00 (m, 1 H), 1.97 (s, 1 H), 1.20-1.11 (m, 1 H), 0.56-0.36 (m, 4 H).

Step 2:
The procedure described in step 2 for compound 23 was used to prepare compound 25 as a yellow solid (18 g, 44% yield). $^1$H NMR (400 MHz, CDCl$_3$) δ 7.96 (d, 1 H), 7.74 (dd, 1 H), 7.32-7.29 (m, 1 H), 7.16-7.07 (m, 2 H), 6.76-6.68 (m, 1 H), 5.22 (d, 1 H), 1.38-1.19 (m, 1 H), 0.71-0.56 (m, 4 H).

Step 3:
The procedure described in step 3 for compound 23 was used to prepare compound 26 as a pale brown solid (15 g, 90% yield).

Step 4:
The procedure described in step 4 for compound 23 was used to prepare compound 27 as a yellow solid (10 g, 81% yield). $^1$H NMR (400 MHz, CDCl$_3$) δ 7.98 (q, 1 H), 7.59 (d, 1 H), 7.32-7.26 (m, 1 H), 7.03-6.99 (m, 1 H), 6.74-6.72 (m, 1 H), 6.44-6.40 (m, 1 H), 6.04 (d, 1 H), 4.73 (s, 2 H), 3.94 (s, 3 H), 1.35-1.28 (m, 1 H), 0.62-0.52 (m, 4 H).

Step 5:
The procedure described in step 5 for compound 23 was used to prepare compound 28 as a pale yellow solid (5.3 g, Preparation of 5-bromo-3-(1-(5-fluoro-2-iodophenyl)ethoxy)pyrazin-2-amine (30)

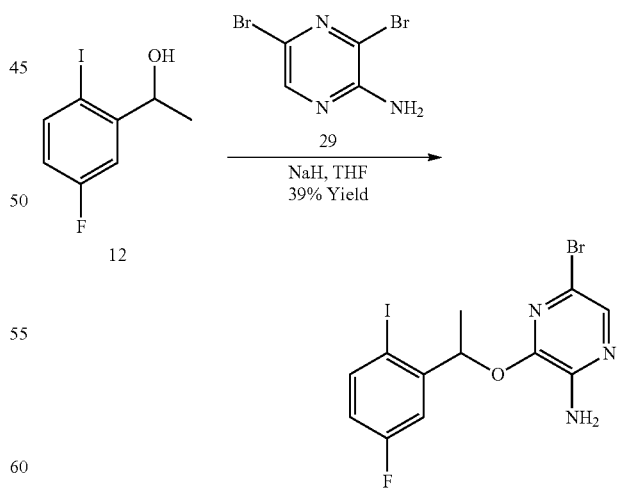

To a solution of compound 12 (17.8 g, 67.9 mmol) in anhydrous THF (350 mL) was added NaH (2.7 g, 67.9 mmol, 60% in oil) at 0° C. under nitrogen. The mixture was stirred for a further 30 minutes. A solution of compound 29 (17.1 g, 67.9 mmol) in anhydrous THF (150 mL) was added to the above mixture at 0° C., and the mixture was refluxed for 18 hours. LCMS indicated that 90% of the starting alcohol had been consumed. The volatiles were removed under reduced pressure, and the residue was diluted with a mixture of $H_2O$ (100 mL) and EtOAc (100 mL). The mixture was filtered, the organic layer removed, and the aqueous layer further extracted with EtOAc (100 mL×3). The combined organic layers were washed with brine (100 mL), dried over $Na_2SO_4$ and concentrated to give a residue, which was purified by silica gel column eluting with petroleum ether:EtOAc (30/1 to 20/1) to give compound 30 as a yellow solid (11.5 g, 39% yield). $^1$H NMR (400 MHz, $CDCl_3$) δ 7.69-7.73 (m, 1 H), 7.55 (s, 1 H), 7.04 (d, J=6.8 Hz, 1 H), 6.65-6.71 (m, 1 H), 6.10 (q, J=6.4 Hz, 1 H), 4.81 (br s, 2 H), 1.55 (d, J=6.4 Hz, 3 H). LCMS m/z 438/440 $[M+H]^+$.

Preparation of methyl 2-(((2-amino-5-bromopyridin-3-yl)oxy)methyl)-4-fluorobenzoate (35)

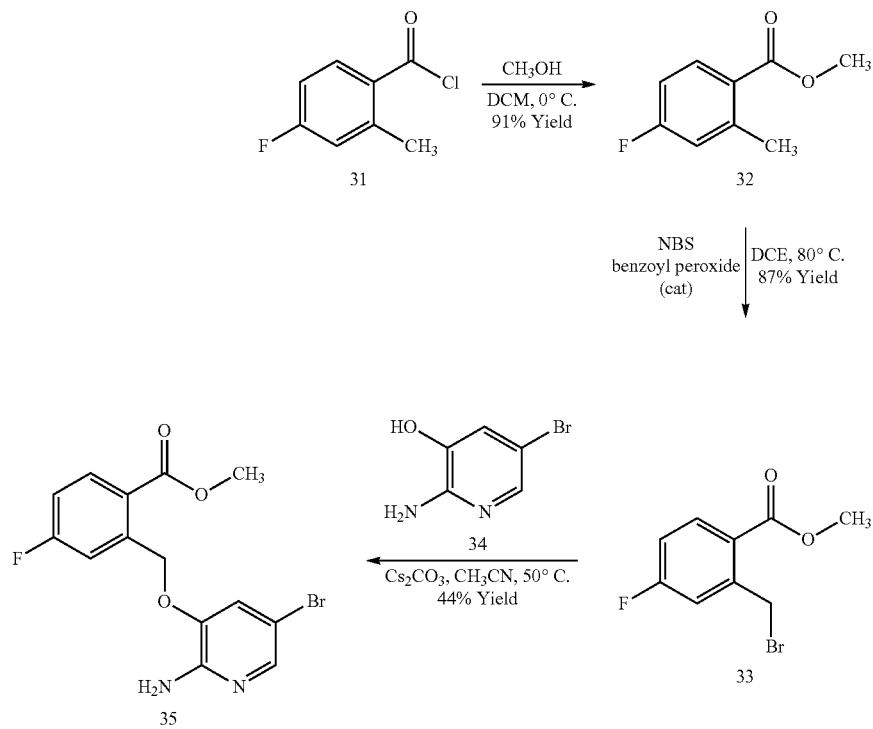

Step 1:

To an ice-cooled solution of compound 31 (24.3 g, 141 mmol) in DCM (300 mL) was added methanol (100 mL) drop-wise over 20 minutes. The reaction mixture was then allowed to warm to room temperature and stirred at room temperature for 2 hours. The reaction was then concentrated in vacuo and the residue was dissolved in DCM (200 mL) and then washed with saturated aqueous sodium bicarbonate (150 mL). The organics were then dried over $MgSO_4$, filtered and concentrated in vacuo to give compound 32 as a colorless oil (19.5 g, 91% yield). $^1$H NMR (400 MHz, $CDCl_3$) δ 7.95 (1 H, m), 6.95-6.85 (2 H, m), 3.90 (3 H, s), 2.60 (3 H, s). LCMS ES no ionization.

Step 2:

To a solution of compound 32 (6.3 g, 41.4 mmol) in DCE (100 mL) was added NBS (8.1 g, 46 mmol) followed by a catalytic amount of benzoyl peroxide (200 mg, 0.82 mmol). The reaction was then heated at 80° C. for 8 hrs. The reaction was cooled to room temperature and the precipitated solid was removed by filtration and washed with MTBE. The filtrate was concentrated in vacuo and the residue was partitioned between 2 N NaOH (150 mL) and MTBE (150 mL). The organic layer was separated, dried over $MgSO_4$, filtered and concentrated to give compound 33 (8.9 g, 87% yield). $^1$H NMR (400 MHz, $CDCl_3$) δ 8.05 (1 H, m), 7.20 (1 H, m), 7.10 (1 H, m), 4.90 (2 H, s), 3.95 (3 H, s).

Step 3:

To compound 33 (15.0 g, 61 mmol) in acetonitrile (150 mL) at room temperature was added compound 34 (10.9 g, 58 mmol) followed by cesium carbonate (23 g, 69 mmol). The mixture was then heated at 50° C. for 5 hours before cooling to room temperature. The mixture was then concentrated in vacuo to remove ~80% of the acetonitrile before the residue was partitioned between water (400 mL) and ethyl acetate (400 mL). The two layers were separated and the aqueous layer was re-extracted with ethyl acetate (400 mL). The combined organics were then concentrated in vacuo to give a dark brown solid. (Note that the aqueous layer was still very dark and contained insoluble solids—yield likely to be compromised by the lack of solubility of the product in organic solvents). The solid residue was then slurried in MTBE (300 mL) for 20 minutes and compound 35 was collected as a dark grey solid (11.5 g, 52% yield. This product was then purified further by column chromatography on silica gel eluting with ethyl acetate and cyclohexane (33% EtOAc to neat EtOAc) to give compound 35 (9.5 g, 44% yield) as an off-white solid. $^1$H NMR (400 MHz, $CDCl_3$) δ 8.10 (1 H, m), 7.75 (1 H, s), 7.35 (1 H, m), 7.10 (1 H, m), 7.05 (1 H, s), 5.50 (2 H, s), 4.75 (1 H, br s), 3.90 (3 H, s). LCMS ES m/z 355/357 $[M+H]^+$.

Preparation of tert-butyl 2-bromo-4-(methylsulfonyl)benzyl(methyl)carbamate (40)

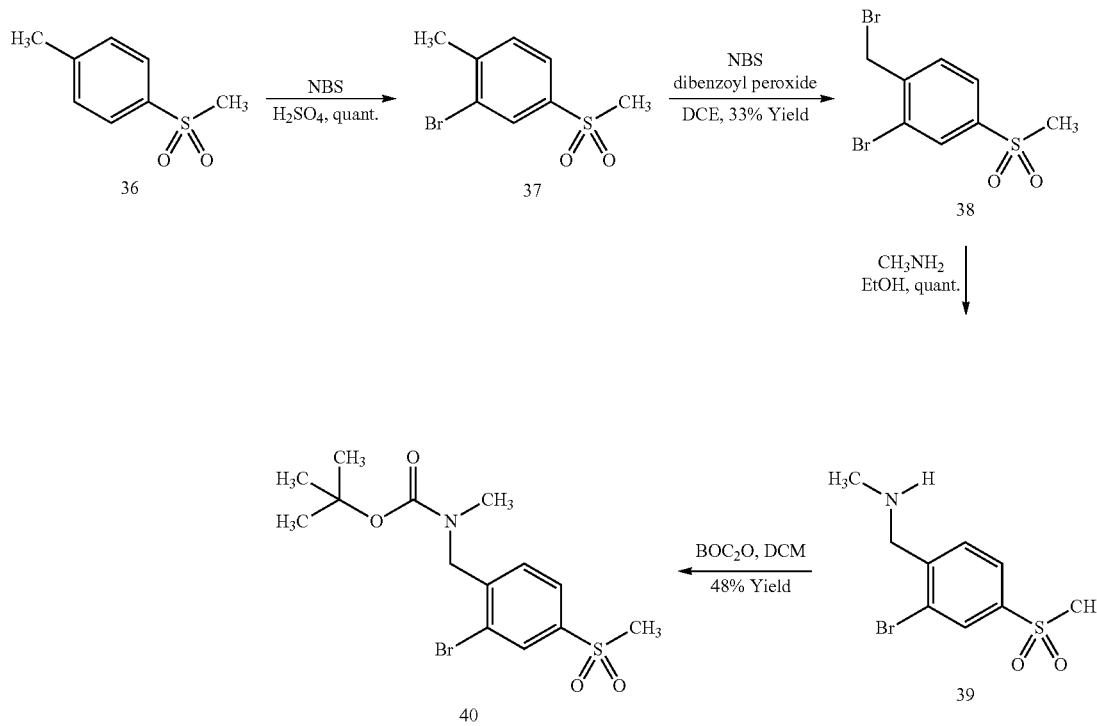

Step 1:

To a stirred mixture of NBS (12.0 g, 68 mmol), and compound 36 (10.0 g, 58 mmol) was added concentrated sulfuric acid (50 mL). The solution initially turned green, after which a pale yellow color persisted. The solution was stirred for 16 hours at room temperature. The mixture was carefully poured onto ice (400 mL), and then extracted with ethyl acetate (500 mL). The organic layer was washed with 2 M aqueous sodium hydroxide (2×300 mL), then dried over magnesium sulfate, and evaporated to give compound 37 as a white solid (14.7 g, quantitative yield). $^1$H NMR (400 MHz, CDCl$_3$) δ 2.48 (s, 3 H), 3.05 (s, 3 H), 7.43 (d, 1 H), 7.77 (dd, 1 H), 8.10 (d, 1 H).

Step 2:

Compound 37 (10.0 g, 40 mmol) was dissolved in 1,2-dichloroethane (250 mL), followed by addition of NBS (7.1 g, 40 mmol) and dibenzoyl peroxide (970 mg, 4.0 mmol), in small portions. After stirring at 85° C. for 2 hours, TLC (8:2 cyclohexane/ethyl acetate) indicated near-consumption of starting material, and the emergence of a minor spot for dibrominated material. The mixture was allowed to cool, diluted to 500 mL with dichloromethane, and washed with water (2×250 mL). The organic layer was dried over MgSO$_4$, and evaporated to a yellow oil. The viscous oil was cooled in an ice bath which gave a solid. Trituration of the solid with diethyl ether gave compound 38 (4.4 g, 33% yield). $^1$H NMR (400 MHz, CDCl$_3$) δ 3.05 (s, 3 H), 4.60 (s, 2 H), 7.66 (d, 1 H), 7.87 (dd, 1 H), 8.15 (d, 1 H). LCMS ES No ionization of compound 11 evident.

Step 3:

Compound 38 (4.3 g, 13 mmol) was dissolved in methylamine solution (33% solution in ethanol, 100 mL), and stirred at RT for 16 hours. TLC (ethyl acetate) and LCMS indicated consumption of starting material, and the major peak for the product. The mixture was evaporated to compound 39 as a white solid (3.7 g, quantitative yield). $^1$H NMR (400 MHz, methanol-d$_4$) δ 2.49 (s, 3 H), 3.15 (s, 3 H), 3.97 (s, 2 H), 7.71 (d, 1 H), 7.94 (dd, 1 H), 8.16 (d, 1H). LCMS m/z 278/280 [M+H]$^+$.

Step 4:

Compound 39 (3.7 g, 13 mmol) was dissolved in dichloromethane (40 mL), and the mixture cooled to 0° C. A solution of di(tert-butyl)dicarbonate (3.5 g, 16 mmol) in dichloromethane (35 mL) was added dropwise. The ice bath was removed and the mixture stirred for 18 hours at room temperature. LCMS and TLC (1:1 cyclohexane/ethyl acetate) showed consumption of compound 12, so the reaction was diluted to 150 mL with dichloromethane, and washed with water (2×100 mL). Organic extracts were dried over magnesium sulfate, and evaporated to a pale yellow oil. The crude product was purified over silica gel, which was eluted with a gradient of 10% to 20% ethyl acetate in cyclohexane, gave compound 40 (2.4 g, 48% yield). $^1$H NMR (400 MHz, methanol-d$_4$) δ 1.36-1.52 (br, 9 H, t-Bu rotamers), 2.95 (s, 3 H), 3.15 (s, 3 H), 4.58 (s, 2 H), 7.40 (d, 1 H), 7.95 (d, 1 H), 8.15 (d, 1 H). LCMS ES m/z 378/380 [M+H]$^+$.

Preparation of tert-butyl ((4-bromo-5-cyano-1-methyl-1H-pyrazol-3-yl)methyl)-(methyl)carbamate (47)

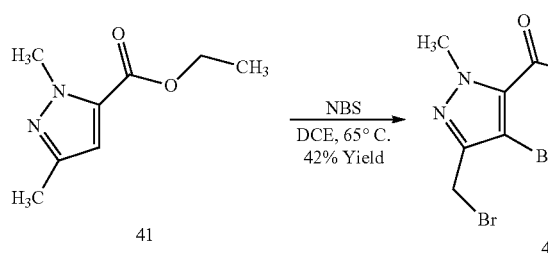

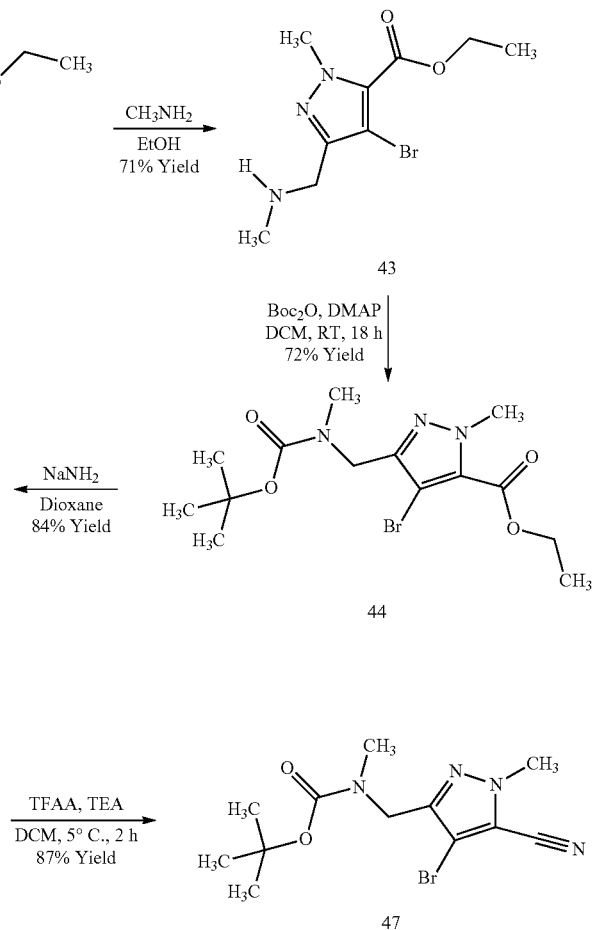

Step 1:
The procedure described in step 2 for compound 40 was used to prepare compound 42 (4.1 g, 42% yield). TLC (EtOAc/Cyclohexane; 1:10; KMnO$_4$): Rf ~0.3. $^1$H NMR (400 MHz, CDCl$_3$) δ 4.47 (s, 2 H), 4.41 (q, 2 H), 4.15 (s, 3 H), 1.42 (t, 3 H). LCMS ES m/z 324/326/328 [M+H]$^+$.

Step 2:
The procedure described in step 3 for compound 40 was used to prepare compound 43 (1.8 g, 71% yield). $^1$H NMR (400 MHz, CDCl$_3$) δ 4.39 (q, 2 H), 4.14 (s, 3 H), 4.05 (s, 2 H), 2.62 (d, 3 H), 1.41 (t, 3 H). LCMS ES m/z 276/278 [M+H]$^+$.

Step 3:
The procedure described in step 4 for compound 40 was used to prepare compound 44 (1.8 g, 72% yield). $^1$H NMR (400 MHz, CDCl$_3$) δ 4.48-4.44 (m, 2 H), 4.41 (q, 2 H), 4.12 (s, 3 H), 2.82-2.79 (m, 3 H), 1.47 (s, 9 H), 1.41 (t, 3 H). LCMS ES m/z 376/378 [M+H]$^+$ and 276/278 [M−BOC]$^+$.

Step 4:
Compound 44 (4 g, 11 mmol) was dissolved in dioxane (43 mL). Sodium amide (1 g, 27 mmol) was added in one portion. The reaction mixture was stirred at 100° C. for 24 h. After this time, the solvent was removed under reduced pressure to give a white solid. The material was suspended in EtOAc (100 mL) and washed with 5% citric acid solution (100 mL). The organic phase was separated and washed with water (100 mL), dried over MgSO$_4$, filtered and the solvent removed in vacuo to give compound 45 as a yellow gum (3.1 g, 84% yield). $^1$H NMR (400 MHz, DMSO-d$_6$) δ 4.27 (s, 2 H), 3.92 (s, 3 H), 2.70 (s, 3 H), 1.40 (s, 9 H). LCMS ES m/z 348/350 [M+H]$^+$ and 248/250 [M−BOC]+.

Step 5:
Compound 45 (3 g, 8.6 mmol) was dissolved in DMF (43 mL, 0.2 M). HOBt (1.2 g, 8.6 mmol) was added, followed by ammonium chloride (0.9 g, 17.2 mmol). EDCI (2.5 g, 13 mmol) was then added, followed by TEA (2.4 mL, 17 mmol). The reaction mixture was stirred at room temperature. After 18 h, the solvent was removed under reduced pressure to give a yellow oil (8.0 g). The residue was dissolved in EtOAc (75 mL). The organic phase was washed with NaHCO$_3$ (sat. solution, 70 mL) and then brine (100 mL). The combined organic layers were dried over MgSO$_4$ and the solvent removed in vacuo to give compound 46 as a dark yellow oil (2.7 g, 91% yield). This material was used directly in the next step without further purification. $^1$H NMR (400 MHz, CDCl$_3$) δ 6.74 (br s, 1 H), 5.95 (br s, 1 H), 4.49 (br s, 2 H), 4.16 (s, 3 H), 2.81 (br s, 3 H), 1.47 (s, 9 H). LCMS ES m/z 347/349 [M+H]$^+$ and 247/249 [M−BOC]$^+$.

Step 6:
Compound 46 (2.7 g, 7.9 mmol) was dissolved in DCM (80 mL, 0.1 M). TEA (3.3 mL, 23.8 mmol) was then added and the reaction mixture cooled down to −5° C. Trifluoroacetic anhydride (2.2 mL, 15.8 mmol) in DCM (15 mL) was added dropwise over 30 min. After addition, the reaction mixture was stirred at 0° C. for 1 h. After this time, the solvents were removed under reduced pressure to give a dark yellow oil. This residue was diluted in DCM (100 mL), washed with 5% citric acid, sat. NaHCO$_3$ and brine, dried over MgSO$_4$, filtered and the solvents removed in vacuo to give a dark yellow oil (2.6 g). The crude product was purified by reverse phase chromatography to give compound 47 as a yellow oil (2.3 g, 87% yield). $^1$H NMR (400 MHz, CDC$_3$) δ 4.46 (br s, 2 H), 4.01 (s, 3 H), 2.83 (br s, 3 H), 1.47 (s, 9 H). LCMS ES m/z 331/329 [M+H]$^+$ and 229/231 [M−BOC]$^+$ as the base ion.

Preparation of tert-butyl ((4-bromo-5-methoxy-isothiazol-3-yl)methyl)(methyl)carbamate (52)

phy over silica gel, which was eluted with 5% EtOAc in heptanes, giving 50 g of an inseparable mixture consisting of starting material 49 and product 50 and dibromomethyl side product in an approximate ratio of 1:2.7:1 respectively. Compound 50 was obtained in 48% yield. $^1$H NMR (CDCl$_3$, 400 MHz) δ 6.77 (s, 1 H, corresponds to dibromomethyl side product); 4.59 (s, 2 H, corresponds to compound 31); 2.55 (s, 3 H, corresponds to starting material 30). LCMS ES no ionization.

Step 3:

A solution of the mixture obtained from step 2 (50 g, calculated to contain 28 g, 83 mmol of pure compound 31) in THF (20 mL) was added slowly to a solution of CH$_3$NH$_2$ (33% in EtOH, 200 mL, 2.1 mol) diluted with additional EtOH (200 mL) at 0° C. over 10 minutes. After complete addition, the reaction was stirred at 0° C. for 25 minutes. The

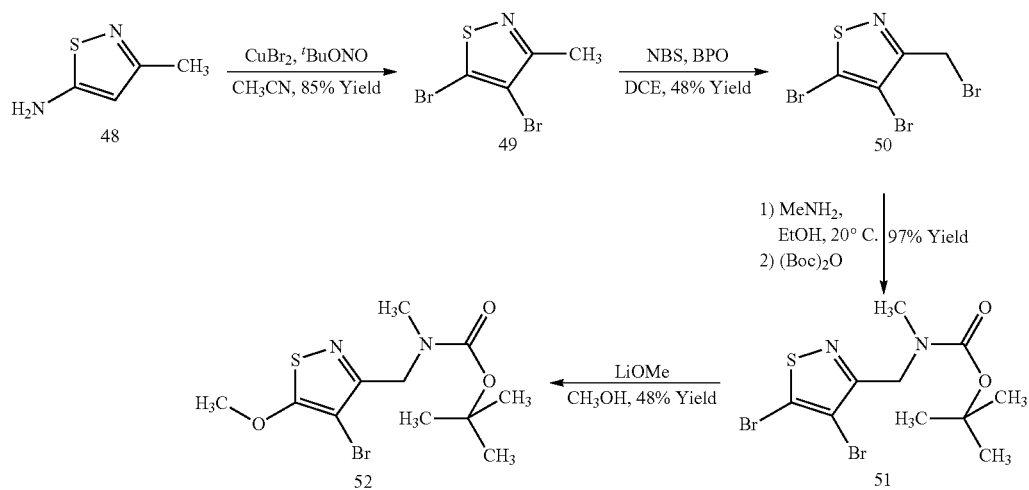

Step 1:

Tert-butyl nitrite (47.4 g, 0.46 mol) was added slowly to a stirred mixture of CuBr$_2$ (103 g, 0.46 mol) and CH$_3$CN (900 mL) at 0° C. over 2 minutes. After stirring for 5 minutes, the HCl salt of compound 48 (35 g, 0.23 mol) was added portion-wise as a solid over 20 minutes. During the addition a slight exotherm of 10° C. was noticed but quickly subsided on complete addition of compound 48. After complete addition of compound 48, the reaction was stirred while slowly warming to room temperature over 20 minutes. HCl (aq, 1 M, 2.5 L) was slowly added with stirring (some frothing and NO$_2$ gas given-off). The mixture was extracted into diethyl ether (2×800 mL). The combined organics were washed with HCl (aq, 1 M, 2×1 L), then brine (1 L), dried over Na$_2$SO$_4$, and the solvent was removed under reduced pressure, giving compound 49 as a yellow/orange solid (45 g, 76% yield). TLC: R$_f$=0.75 (10% EtOAc in heptanes). $^1$H NMR (400 MHz, CDCl$_3$) δ 2.46 (s, 3 H). LCMS ES no ionization detected.

Step 2:

A mixture of compound 49 (45 g, 175 mmol), NBS (47 g, 265 mmol) and di-benzoyl peroxide (70% in H$_2$O, 9.7 g, 40 mmol) in DCE (400 mL) was stirred at reflux for 12 hours. TLC (10% DCM in heptanes) showed approx 50% starting material (R$_f$=0.50) and 50% product (R$_f$=0.55). An additional portion of NBS (10 g, 56 mmol) was added and the reaction was stirred at reflux for 6 hours. After cooling, the mixture was filtered to remove succinimide and the filtrate was concentrated. The residue was purified by column chromatograreaction was then concentrated in vacuo to approximately 300 mL volume. Ethanol (150 mL) was added and the mixture was again concentrated to approximately 300 mL in volume. The resulting solution was then cooled to 0° C. and (BOC)$_2$O (33 g, 150 mmol) was added portion-wise over 5 minutes (CO$_2$ evolution). After complete addition the mixture was left to stir at 20° C. overnight. The reaction mixture was concentrated in vacuo and the residue was purified by column chromatography over silica gel, which was eluted with 10% EtOAc in heptanes, giving compound 51 as a cream colored solid (32 g, 97% yield). TLC (R$_f$=0.30, 10% EtOAc in heptanes). $^1$H NMR (400 MHz, CDCl$_3$) δ 4.50-4.60 (m, 2 H), 2.90-2.99 (m, 3 H), 1.35-1.55 (m, 9 H). LCMS ES m/z 287 ES [M−Boc]$^+$.

Step 4:

Lithium (40 mg, 5.7 mmol) was cautiously added to methanol (6 mL), with stirring, in a reaction flask fitted with a reflux condenser. After the lithium dissolved, compound 51 (350 mg, 0.91 mmol), dissolved in methanol (2 mL), was added in one portion and the resulting solution was stirred at 60° C. for 20 hours. TLC (10% EtOAc in heptanes) showed a major new spot (R$_f$=0.20), along with approximately 20% compound 51 (Rf=0.30) and traces of two other products (R$_f$'s=0.25 and baseline). After cooling, the reaction (now containing a suspension) was added to water (30 mL) and the mixture was extracted into EtOAc (20 mL). The organic layer was separated, washed with brine (20 mL), dried over Na$_2$SO$_4$ and evaporated. The residue was purified by column chromatography over silica gel, which was eluted with 10% EtOAc in heptanes, giving compound 52 as a pale yellow oil (150 mg, 48% yield). TLC: $R_f$=0.20 (10% EtOAc in heptanes). $^1$H NMR (400 MHz, CDCl$_3$) δ 4.40-4.55 (m, 2 H), 4.04 (s, 3 H), 2.85-2.95 (m, 3 H), 1.40-1.50 (m, 9 H). LCMS ES m/z 237/239 [M−Boc]$^+$.

Preparation of tert-butyl ((4-bromo-1,3-dimethyl-1H-pyrazol-5-yl)methyl)(methyl)carbamate (57)

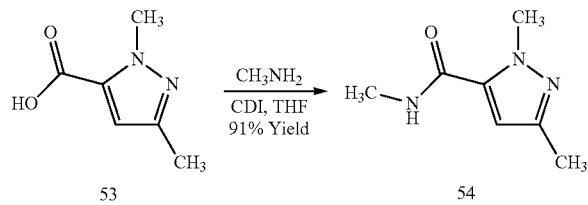

Step 1:

CDI (2.8 g, 17 mmol) was added to a suspension of compound 53 (2.0 g, 14 mmol) in THF (25 mL) at 20° C. The mixture was then warmed to 50° C. with stirring for 30 mins (gas evolution).

The mixture was then cooled to −10° C. and MeNH$_2$ (2 M in THF, 20 mL, 40.0 mmol) was added in one portion. The ice bath was removed and the reaction was stirred at room temperature for 60 minutes. The mixture was then concentrated and purified by column chromatography over silica gel, which was eluted with 100% EtOAc, giving compound 54 (2.0 g, 91% yield) as a clear oil. TLC: $R_f$=0.60 (100% EtOAc). $^1$H NMR (400 MHz, CDCl$_3$) δ 2.23 (s, 3 H), 2.93 (d, 3H), 4.09 (s, 3 H), 6.00 (br s, 1 H), 6.12 (s, 1 H). LCMS ES m/z 154 [M+H]$^+$.

Step 2:

BH$_3$DMS (8.0 g, 105 mmol) was added slowly to a solution of compound 54 (2.0 g, 13.0 mmol) in THF at −5° C. After complete addition, the mixture was stirred at 50° C. for 3 hrs, before cooling and stirring at room temperature overnight. The reaction was then cooled to 0° C. and 6 M HCl (30 mL) was added slowly (frothing occurred). After complete addition the mixture was stirred at 70° C. for 30 mins, before cooling to 0° C. and basified with NaOH (30% aq solution) to pH 13 (pH paper). The mixture was concentrated under reduced pressure to remove THF and then extracted into DCM (5×40 mL). The combined organic layers were dried over Na$_2$SO$_4$ and evaporated, which gave compound 55 (1.5 g, 83% yield). TLC: $R_f$=0.20 (98% EtOAc and 2% 7 M NH$_3$ in MeOH). $^1$H NMR (400 MHz, CDCl$_3$) δ 2.20 (s, 3 H), 2.40 (s, 3 H), 3.68 (s, 2 H), 3.78 (s, 3 H), 5.91 (s, 1 H).

Step 3:

To a solution of compound 55 (1.5 g, 10.7 mmol) in DCM (30 mL) was added (BOC)$_2$O (3.27 g, 15 mmol). The mixture was stirred overnight, concentrated under reduced pressure and the residue purified by flash chromatography over silica gel, which was eluted with 30-50% EtOAc in cyclohexane, and gave compound 56 (2.0 g, 78% yield) as a colorless oil. TLC: Rf=0.50 (1:1 EtOAc/cyclohexane). $^1$H NMR (400 MHz, CDCl$_3$) δ 1.48 (s, 9 H), 2.20 (s, 3 H), 2.78 (s, 3 H), 3.78 (s, 3 H), 4.61 (s, 2 H), 5.94 (s, 1 H).

Step 4:

Compound 56 (2.1 g, 8.8 mmol) was dissolved in acetonitrile (31 mL), sodium bicarbonate (0.88 g, 10 mmol) was added and the mixture was cooled to 0° C. NBS (1.6 g, 9.2 mmol) was added and the reaction mixture was stirred for 1 hour at ~5° C. LCMS showed consumption of compound 56. The reaction mixture was warmed to RT, filtered and concentrated under vacuum to give a yellow oil. MTBE was added and a white solid was observed and filtered. The mother liquors were concentrated and MTBE was added again. The white solid formed was filtered and the mother liquors were washed with a diluted aqueous solution of sodium thiosulfate, water then brine. The solution was dried over MgSO$_4$, filtered and concentrated under vacuum to give compound 57 as a white solid (2.7 g, 95% yield). $^1$H NMR (400 MHz, CDCl$_3$) δ 4.50 (s, 2 H), 3.79 (s, 3 H), 2.70 (s, 3 H), 2.20 (s, 3 H), 1.45 (s, 9 H). LCMS ES m/z 318/320 [M+H]$^+$.

Preparation of tert-butyl 2-bromobenzyl(methyl)carbamate (59)

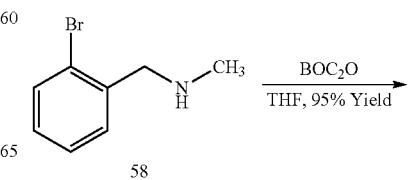

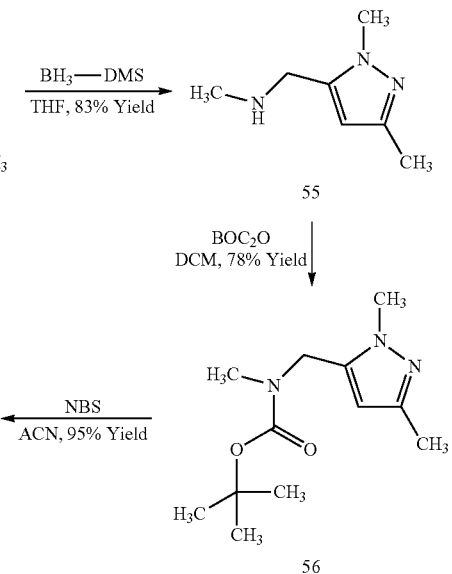

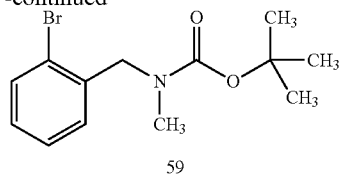

59

A solution of compound 58 (2.0 g, 10.0 mmol) and Boc$_2$O (2.29 g, 10.5 mmol) in THF (40 mL) was stirred at RT for 16 hours. The mixture was then concentrated in vacuo. The crude product was purified by flash column chromatography over silica gel, which was eluted with 10% EtOAc in heptanes, and yielded compound 59 as a colorless oil (2.8 g, 95% yield). $^1$H NMR (400 MHz, CDCl$_3$) δ 7.54 (d, 1 H), 7.30 (t, 1 H), 7.13 (m, 2 H), 4.53 (br d, 2 H), 2.87 (br s, 3 H), 1.46 (br d, 9 H).

Preparation of tert-butyl ((4-bromo-1,3-dimethyl-1H-pyrazol-5-yl)methyl)-(cyclopropyl)carbamate (63)

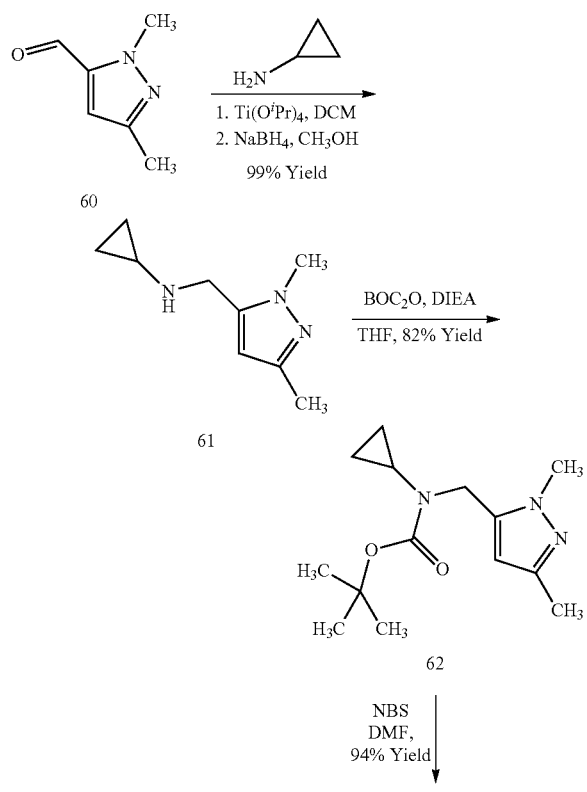

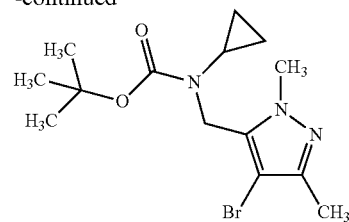

63

Step 1:

To a solution of compound 60 (1.00 g, 8.06 mmol) in DCM (80 mL) was added cyclopropyl amine (0.850 mL, 12 mmol) then Ti(Oi-Pr)$_4$ (4.7 mL, 16 mmol). The solution was stirred at room temperature overnight then MeOH (20 mL) was added followed by NaBH$_4$ (610 mg, 16 mmol) portion wise (gas evolved). The reaction was quenched with saturated NaHCO$_3$, forming white solids. The mixture was filtered through celite then the mother liquor was extracted with EtOAc (2×). The combined organics were washed with brine, dried over MgSO$_4$, filtered and concentrated and gave to give compound 61 (1.38 g). $^1$H NMR (400 MHz, DMSO-d$_6$) δ 5.88 (s, 1 H), 3.68-3.66 (m, 2 H), 3.65 (s, 3 H), 2.57 (br. s., 1 H), 2.07 (s, 3 H), 2.06-2.01 (m, 1 H), 0.40-0.30 (m, 2 H), 0.25-0.18 (m, 2 H).

Step 2:

A solution of compound 61 (1.33 g, 8.06 mmol), DIEA (2.81 mL, 16.1 mmol) and Boc$_2$O (2.64 g, 12.1 mL) in THF (27 mL) was stirred at room temperature for 2 days. The solution was concentrated and purified by flash chromatography eluting with heptanes/EtOAc (0-50%) to afford compound 62 (1.75 g, 82% yield over 2 steps). $^1$H NMR (400 MHz, DMSO-d$_6$) δ 5.85 (s, 1 H), 4.34 (s, 2 H), 3.68 (s, 3 H), 2.36 (br s, 1 H), 2.08 (s, 3 H), 1.40 (s, 9 H), 0.68 (d, J=6.0 Hz, 2 H), 0.61 (br s, 2 H).

Step 3:

To a solution of compound 62 (1.75 g, 6.60 mmol) in DMF (44 mL) was added NBS (1.2 g, 6.6 mmol). After 1 hour the solution was diluted with EtOAc, washed with 50% saturated Na$_2$CO$_3$ (2×) and brine, dried (MgSO$_4$), filtered and concentrated to give compound 63 as a yellow gum (2.14 g, 94% yield). $^1$H NMR (400 MHz, DMSO-d$_6$) δ 4.45 (s, 2 H), 3.73 (s, 3 H), 2.23-2.14 (m, 1 H), 2.09 (s, 3 H), 1.41 (s, 9 H), 0.70-0.52 (m, 4 H).

Preparation of tert-butyl ((4-bromo-5-cyclopropyl-1-methyl-1H-pyrazol-3-yl)methyl)-(methyl)carbamate (70)

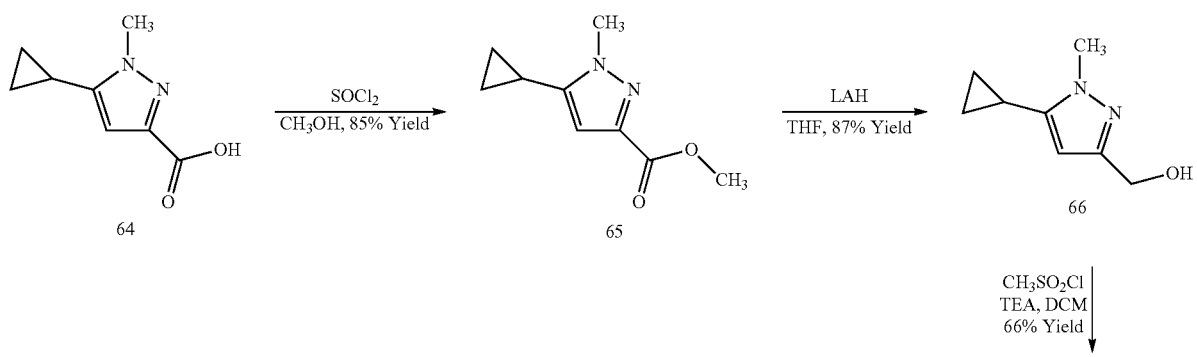

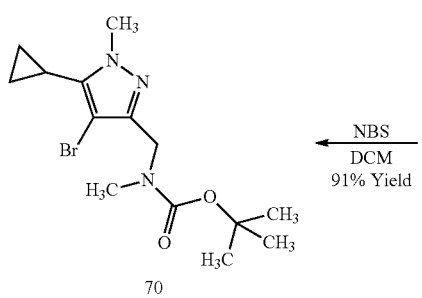
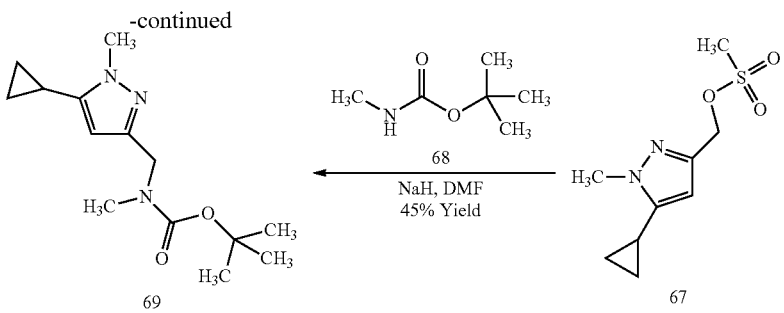

Step 1:

To a solution of compound 64 (2.9 g, 17.4 mmol) in dry methanol (100 mL) was drop-wise SOCl$_2$ (20 mL) at 0° C. After addition, the reaction solution was stirred at room temperature for 48 hours. TLC (dichloromethane/methanol 10/1) showed the reaction was completed. The reaction mixture was concentrated in vacuo and gave a residue, which was dissolved with EtOAc (200 mL). The organic layer was washed with saturated NaHCO$_3$ (100 mL×3), brine (100 mL), dried over Na$_2$SO$_4$ and concentrated in vacuo and gave compound 65 as pale yellow oil (2.7 g, 85% yield). $^1$H NMR (400 MHz, CDCl$_3$) δ 6.63 (s, 1 H), 4.19 (s, 3 H), 4.12 (s, 3 H), 1.99-1.92 (m, 1 H), 1.27-1.23 (m, 2 H), 0.94-0.91 (m, 2 H).

Step 2:

To a mixture of LiAlH$_4$ (0.85 g, 22.5 mmol) in dry THF (40 mL) was added drop-wise compound 65 (2.7 g, 15 mmol) in THF (10 mL) at −10~0° C. After addition, the reaction mixture was stirred at room temperature for 2 hours. TLC (petroleum ether/EtOAc 1/1) showed the reaction mixture was completed. The reaction was quenched with 20% aq. NaOH (4 mL). The mixture was filtered and the filtrate was concentrated under reduced pressure. The crude product was purified flash chromatography over silica gel which was eluted with petroleum ether/EtOAc (3/1) and gave compound 66 as a white solid (2.3 g, 87% yield).

Step 3:

To a solution of compound 66 (2.5 g, 16.4 mmol) and Et$_3$N (2.48 g, 24.6 mmol) in dry DCM (100 mL) was added drop-wise MsCl (2.13 g, 18.1 mmol) at 0° C. After addition, the reaction mixture was stirred at room temperature for 3 hours. TLC (petroleum ether/EtOAc 3/1) showed the reaction was complete. The reaction mixture was washed with water (100 mL×3), saturated NaHCO$_3$ (100 mL×3), brine (100 mL), dried over Na$_2$SO$_4$ and concentrated in vacuo and gave compound 67 as red oil (2.5 g, 66% yield).

Step 4:

To a solution of the compound 68 (2.8 g, 21.3 mmol) in dry DMF (40 mL) was added NaH (60% in oil, 0.96 g, 121 mmol) at 0° C. in small portions. After addition, the reaction mixture was stirred at room temperature for 1 hour. Compound 67 (2.5 g, 10.8 mmol) in DMF (10 mL) was then added drop-wise to the anion at 0° C. The resulting mixture was then stirred at room temperature overnight. None of compound 67 was detected by TLC (petroleum ether/EtOAc 3/1). The reaction mixture was poured into ice water (100 mL). The mixture was then extracted with EtOAc (50 mL×3). The combined organic extracts were washed with brine (100 mL), dried over Na$_2$SO$_4$ and concentrated under reduced pressure. The crude product was purified by flash column chromatography over silica gel, which was eluted with petroleum ether/EtOAc (3/1) and gave compound 69 as an off-white solid (1.3 g, 45% yield). $^1$H NMR (400 MHz, CDCl$_3$) δ 6.32 (d, 1 H), 4.30 (s, 2 H), 3.84 (s, 3 H), 2.82 (s, 3 H), 1.62-1.54 (m, 1 H), 1.48 (s, 9 H), 0.96-0.94 (m, 2 H), 0.64-0.63 (m, 2 H).

Step 5:

To a solution of compound 69 (1.2 g, 4.14 mmol) in DCM (50 mL) was incrementally added NBS (0.77 g, 4.35 mmol) at 0° C. After addition, the reaction mixture was stirred at room temperature for 2 hours. None of compound 69 was detected by TLC (petroleum ether/EtOAc 3/1). The reaction mixture was washed with saturated NaHCO$_3$ (50 mL×3), brine (100 mL), dried over Na$_2$SO$_4$ and concentrated under reduced pressure. The crude product was purified by column chromatography over silica gel which was eluted with petroleum ether/EtOAc (4/1) and gave compound 70 as pale yellow oil (1.3 g, 91% yield). $^1$H NMR (400 MHz, CDCl$_3$) δ 4.35-4.33 (s, 2 H), 3.79 (s, 3 H), 2.71 (s, 3 H), 1.62-1.54 (m, 1 H), 1.41 (s, 9 H), 0.96-0.94 (m, 2 H), 0.80-0.78 (m, 2 H).

Preparation of tert-butyl ((4-bromo-3-cyclopropyl-1-methyl-1H-pyrazol-5-yl)methyl)(methyl)carbamate (76)

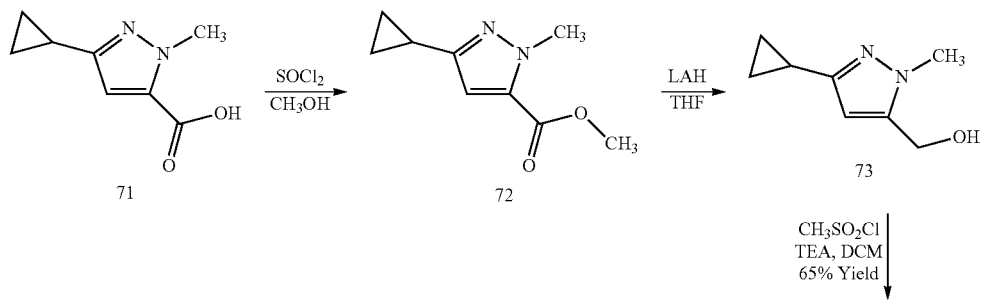

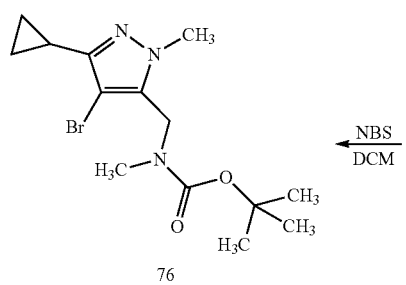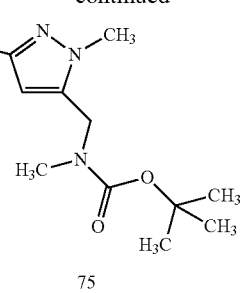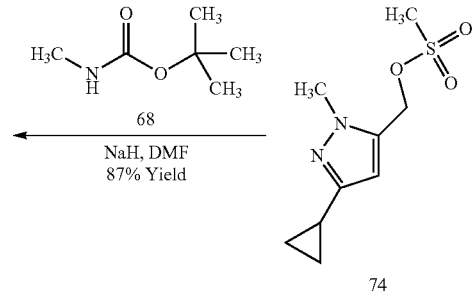

Step 1:
The procedure described in step 1 for compound 70 was used to prepare compound 72. ¹H NMR (400 MHz, CDCl$_3$) δ 6.43 (s, 1 H), 4.05 (s, 3 H), 3.78 (s, 3 H), 1.83-1.81 (m, 1 H), 0.87-0.83 (m, 2 H), 0.65-0.62 (m, 2 H).
Step 2:
The procedure described in step 2 for compound 70 was used to prepare compound 73. ¹H NMR (400 MHz, CDCl$_3$) δ 5.87-5.77 (d, 1 H), 4.53 (s, 3 H), 3.74-3.71 (t, 3 H), 1.83-1.77 (m, 3 H), 1.60 (s, 1 H), 0.84-0.80 (m, 2 H), 0.61-0.57 (m, 2 H).
Step 3:
The procedure described in step 2 for compound 70 was used to prepare compound 74 (1.7 g, 65% yield).
Step 4:
The procedure described in step 4 for compound 70 was used to prepare compound 75 (1.6 g, 87% yield).
Step 5:
The procedure described in step 5 for compound 70 was used to prepare compound 76. ¹H NMR (400 MHz, CDCl$_3$) δ 4.43 (s, 2 H), 4.06-4.04 (s, 3 H), 2.66 (s, 3 H), 1.77-1.76 (m, 1 H), 1.41 (s, 9 H), 0.83-0.79 (m, 4 H).

Step 1:
The procedure described in step 1 for compound 70 was used to prepare compound 78. ¹H NMR (400 MHz, CDCl$_3$) δ 6.08 (s, 1 H), 3.94-3.92 (m, 6 H), 3.75-3.72 (m, 3 H).

Step 2:
The procedure described in step 2 for compound 70 was used to prepare compound 79 (0.6 g, 87% yield).

Step 3:
The procedure described in step 3 for compound 70 was used to prepare compound 80.

Step 4:
The procedure described in step 4 for compound 70 was used to prepare compound 81. ¹H NMR (400 MHz, CDCl$_3$) δ 5.47 (s, 1 H), 4.27 (s, 2 H), 3.83 (s, 3 H), 3.57 (s, 3 H), 2.82 (s, 3 H), 1.48 (s, 9 H).

Step 5:
The procedure described in step 5 for compound 70 was used to prepare compound 82 (3.9 g, 79% yield). LCMS m/z 333 [M+H]⁺.

Preparation of tert-butyl ((4-bromo-5-methoxy-1-methyl-1 H-pyrazol-3-yl)methyl)(methyl)carbamate (82)

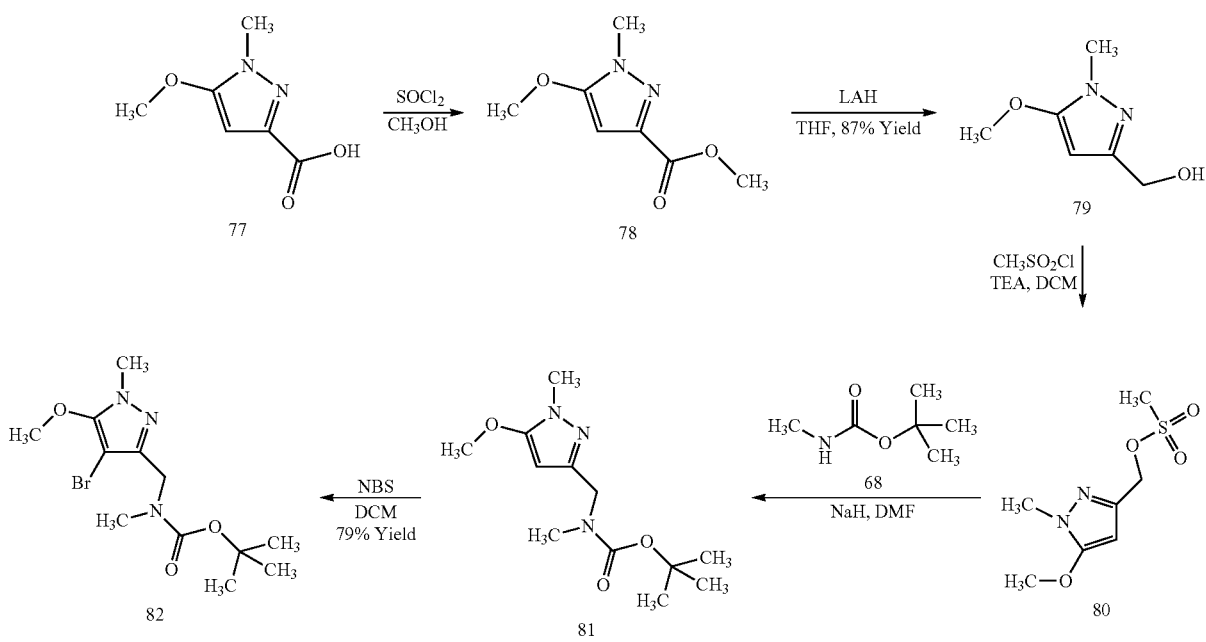

Preparation of tert-butyl ((4-bromo-3-methoxy-1-methyl-1H-pyrazol-5-yl)methyl)(methyl)-carbamate (91)

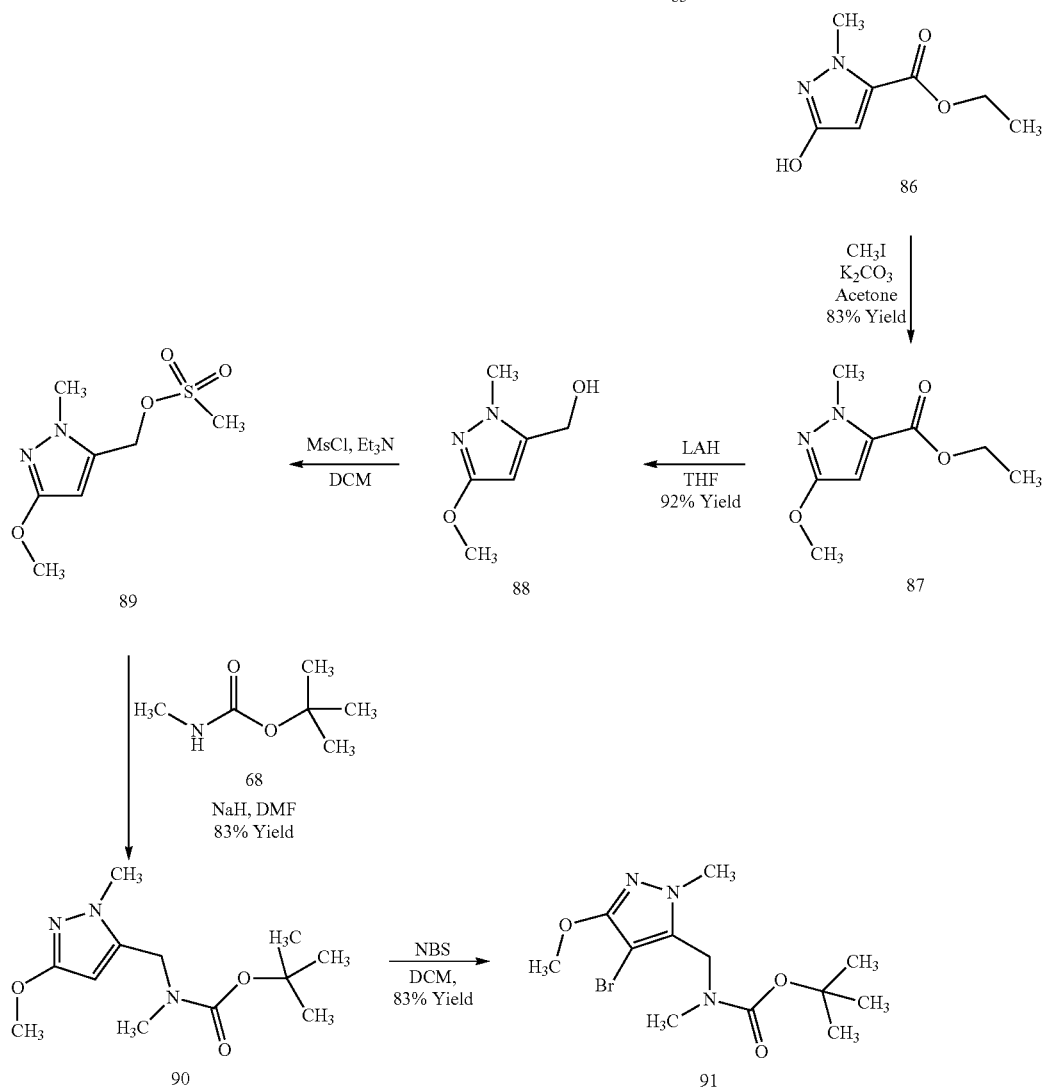

Step 1:
To a mixture of compound 83 (10.7 mL, 0.067 mol) in 1:1 EtOH/H$_2$O (120 mL) was slowly added at 0° C. a solution of compound 84 (7.72 g, 0.08 mol) and NaOH (3.2 g, 0.08 mol) in 1:1 EtOH/H$_2$O (40 mL). The solution was stirred at 0° C. for 30 min, and warmed to room temperature over for 1 hour. The mixture was concentrated and the residue was partitioned between water (100 mL) and EtOAc (100 mL). The aqueous layer was concentrated and gave compound 85 as a brown oil (7.6 g, 62% yield).

Step 2:
A mixture of compound 85 (7.6 g, 41 mmol) in 1 N HCl (75 mL) was stirred at room temperature for 1.5 hours. The mixture was extracted with DCM (50 mL), the aqueous layer was concentrated and gave a residue. The crude product was purified by flash chromatography over silica gel, which was eluted with petroleum ether/EtOAc 6:1) and gave compound 86 as a white solid (2.2 g, 32% yield).

Step 3:
A mixture of compound 86 (1.6 g, 9.1 mmol), K$_2$CO$_3$ (3.7 g, 27.5 mmol) and methyl iodide (6.5 g, 46 mmol) was heated at reflux for 3 hours. TLC (petroleum ether/EtOAc=6:1) showed the reaction was complete. The mixture was filtered and the filtrate was concentrated to give a residue. The crude product was purified by flash chromatography over silica gel, which was eluted with petroleum ether/EtOAc (20:1) and gave compound 87 as a yellow oil (1.4 g, 83% yield). $^1$H NMR (400 MHz, CDCl$_3$) δ 6.18 (s, 1 H), 4.30 (q, 2 H), 4.05 (s, 3 H), 3.83 (s, 3 H), 1.36 (t, 3 H).
Step 4:
The procedure described in step 2 for compound 70 was used to prepare compound 88 (1.0 g, 92% yield).
Step 5:
The procedure described in step 3 for compound 70 was used to prepare compound 89.
Step 6:
The procedure described in step 4 for compound 70 was used to prepare compound 90 (1.5 g, 83% yield). $^1$H NMR (400 MHz, CDCl$_3$) δ 5.57 (s, 1 H), 4.36 (s, 2 H), 3.84 (s, 3 H), 3.67 (s, 3 H), 2.77 (s, 3 H), 1.47 (s, 9 H).
Step 7:
The procedure described in step 5 for compound 70 was used to prepare compound 91 (1.3 g, 83% yield). $^1$H NMR (400 MHz, CDCl$_3$) δ 4.47 (s, 2 H), 3.93 (s, 3 H), 3.75 (s, 3 H), 2.73 (s, 3 H), 1.32 (s, 9 H). LCMS m/z 335 [M+H]$^+$.

Preparation of 1-(3-bromo-2-methoxypyridin-4-yl)-N-methylmethanamine (98)

was removed and the reaction mixture was heated at 70° C. overnight. The majority of the POCl$_3$ was removed in vacuo. Ice was slowly added to the residue followed by the careful addition of 1 N Na$_2$CO$_3$. Once the release of CO$_2$ was complete, the solution was extracted with EtOAc (3×). The combined organic extracts were dried over MgSO$_4$, filtered and concentrated. The crude product was purified by flash chromatography over silica gel which was eluted with heptanes/EtOAc (0-20%) to yield compound 94 as a white solid (1.65 g, 38% yield). $^1$H NMR (400 MHz, DMSO-d$_6$) δ 8.27 (d, J=4.8 Hz, 1 H), 7.42 (d, J=4.8 Hz, 1 H), 2.48-2.38 (m, 3 H).
Step 3:
In a sealed tube, NaOMe (25% in MeOH, 3.1 mL, 13 mmol) was added to a solution of compound 94 (1.8 g, 8.7 mmol) in MeOH (17 mL). The reaction was heated at 75° C. for 3 days. The reaction mixture was cooled to room temperature, diluted with EtOAc, washed with saturated NH$_4$Cl and brine, dried over MgSO$_4$, filtered and concentrated. The crude product was purified by flash chromatography over silica gel, which was eluted with heptanes/EtOAc (0-15%) to afford compound 95 as a clear oil (991 mg, 56% yield). $^1$H NMR (400 MHz, DMSO-d$_6$) δ 8.00 (d, J=5.0 Hz, 1 H), 6.98 (d, J=4.8 Hz, 1 H), 3.90 (s, 3 H), 2.35 (s, 3 H).

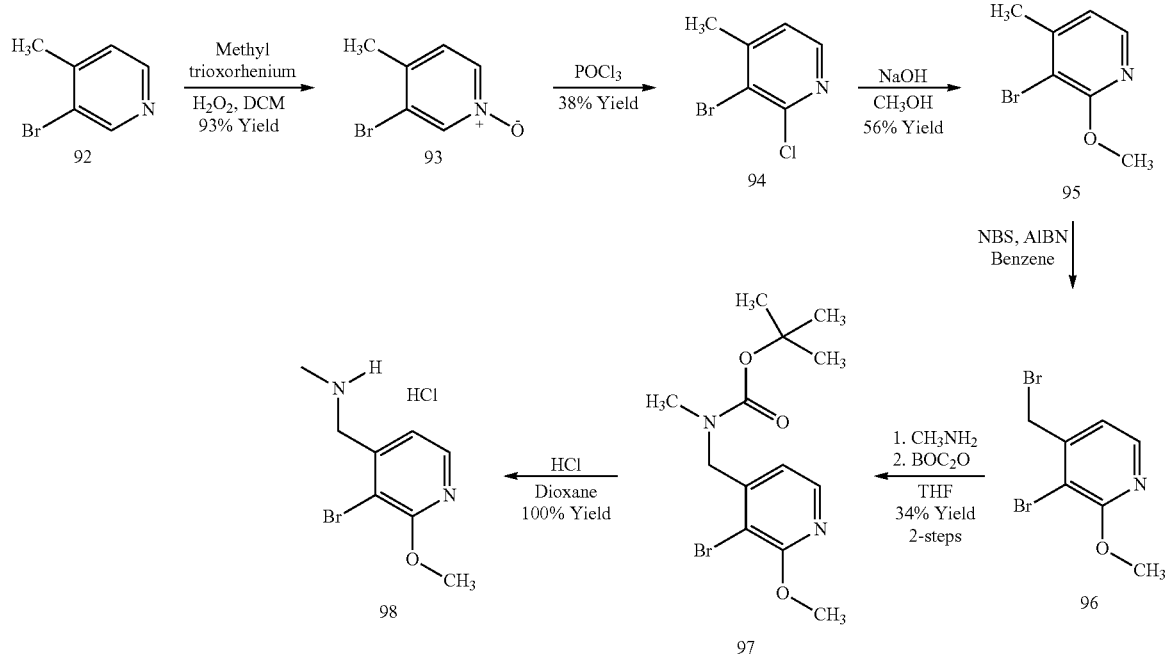

Step 1:
To a solution of the compound 92 (5.0 g, 29 mmol) in DCM (15 mL) was added methyl trioxorhenium (73 mg, 0.29 mmol) followed by H$_2$O$_2$(50% in water, 3.6 mL, 58 mmol). The yellow biphasic mixture was stirred at room temperature overnight. The reaction mixture was diluted with water and extracted with DCM (2×). The combined organic extracts were washed with brine, dried over MgSO$_4$, filtered and concentrated to give compound 93 as a white solid (5.1 g, 93% yield). $^1$H NMR (400 MHz, DMSO-d$_6$) δ 8.53 (s, 1 H), 8.15 (d, J=6.5 Hz, 1 H), 7.40 (d, J=6.5 Hz, 1 H), 2.35-2.27 (m, 3 H).
Step 2:
Compound 93 (4.0 g, 21 mmol) was added portion-wise to neat POCl$_3$ (14 mL) at 0° C. resulting in a slurry. The ice bath Step 4:
To a solution of compound 95 (990 mg, 4.9 mmol) in benzene (33 mL) was added NBS (870 mg, 4.9 mmol) followed by AIBN (40 mg, 0.25 mmol). The mixture was placed in an 80° C. oil bath. After six hours, the reaction was diluted with EtOAc, washed with 1 M Na$_2$CO$_3$ and brine, dried over MgSO$_4$, filtered and concentrated. The crude product was purified by flash chromatography eluting with heptanes/EtOAc (0-10%) to afford compound 96 as an oil (669 mg, 70% pure by NMR). $^1$H NMR (400 MHz, DMSO-d$_6$) δ 8.14 (d, J=5.0 Hz, 1 H), 7.22 (d, J=5.0 Hz, 1 H), 4.68 (s, 2 H), 3.93 (s, 3 H).

Step 5:

To a solution of compound 96 (665 mg, 70% pure) in THF (12 mL) was added methyl amine (2 M in THF, 3.5 mL, 6.9 mmol). After 2 hours, Boc$_2$O (1.5 g, 6.9 mmol) was added. After another 2 hours, the reaction was diluted with EtOAc, washed with water and brine, dried over MgSO$_4$, filtered and concentrated under reduced pressure. The crude product was purified by flash chromatography eluting with heptanes/EtOAc (0-20%) to afford compound 97 as a clear gum (552 mg, 34% over 2 steps). $^1$H NMR (400 MHz, DMSO-d$_6$) δ 8.13 (d, J=5.0 Hz, 1 H), 6.71 (br s, 1 H), 4.42 (s, 2 H), 3.93 (s, 3 H), 2.87 (s, 3 H), 1.56-1.16 (m, 9 H).

Step 6:

To a cooled (0° C.) solution of compound 97 (530 mg, 1.6 mmol) in DCM (8.0 mL) was added HCl (4 N in dioxane, 8 mL). The ice bath was removed and a white precipitate formed. Once complete by LCMS, the mixture was concentrated to afford compound 98 as a white solid (quantitative).

Preparation of tert-butyl ((5-bromo-1-ethyl-1H-pyrazol-4-yl)methyl)(methyl)carbamate (108)

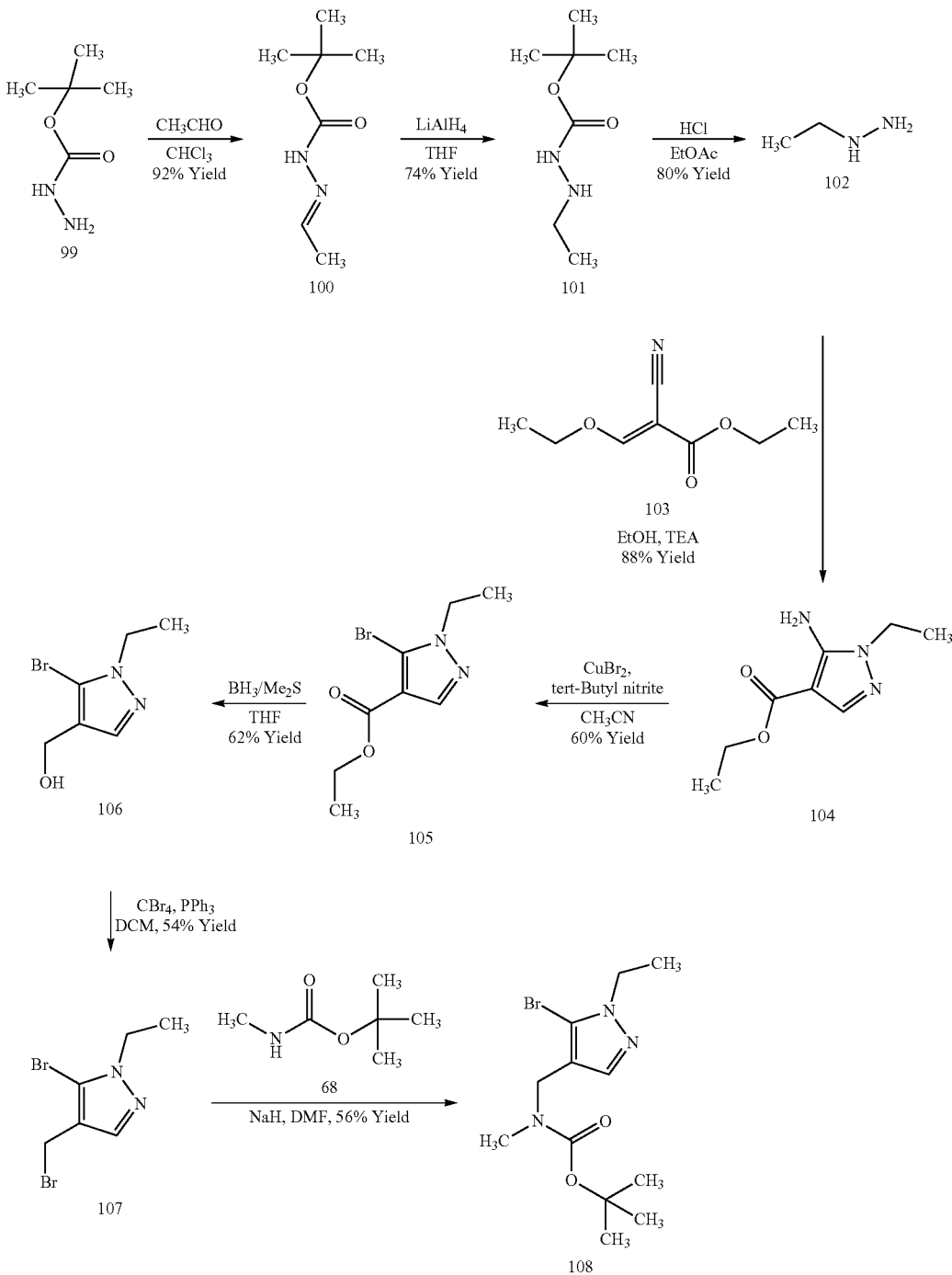

Step 1:

To a stirred solution of compound 99 (145 g, 1.1 mol) in $CHCl_3$ (1.4 L) was added drop-wise MeCHO (40% in water, 500 g, 4.5 mol) at room temperature. After the addition, the reaction was stirred at room temperature for 24 hours. TLC (petroleum ether/EtOAc=1/1) showed the reaction was complete. The reaction mixture was filtered and the filtrate was concentrated in vacuo to give compound 100 as light yellow oil (160 g, 92% yield).

Step 2:

To a stirred suspension of $LiAH_4$ (22.5 g, 0.505 mol) in dry THF (1 L) was added drop-wise a solution of compound 100 (80 g, 0.505 mol) at −10° C. After the addition, the reaction mixture was stirred at room temperature for 2 hours. TLC (petroleum ether/EtOAc=3/1) showed the reaction mixture was complete. The reaction mixture was quenched with saturated $NH_4Cl$ (100 mL) below 0° C., EtOAc (500 mL) was poured into the above reaction and stirred for 10 minutes.

The reaction mixture was filtered and the filtrate was washed with brine (100 mL×3), dried over $Na_2SO_4$, concentrated in vacuo and gave a residue, which was purified by column chromatography (on silica gel petroleum ether/EtOAc 20/1~10/1) to give compound 101 as colorless oil (60 g, 74% yield).

Step 3:

To a stirred solution of compound 101 (60 g, 0.375 mol) in EtOAc (100 mL) was added drop-wise 4 N HCl in EtOAc (200 mL) at 0° C. After addition, the reaction mixture was stirred at room temperature for 10 hours. TLC (petroleum ether/EtOAc=3/1) showed the reaction was complete. The reaction mixture was filtered, the cake was collected and dried under reduced pressure to give compound 102 as a white solid (40 g, 80% yield).

Step 4:

A mixture of compound 102 (40 g, 0.3 mol) and compound 103 (56 g, 0.33 mol) and TEA (105 mL, 0.76 mol) in EtOH (500 mL) was refluxed for 24 hours. TLC (petroleum ether/EtOAc=3/1) showed the reaction was complete. The reaction mixture was concentrated in vacuo to get a residue, which was diluted with EtOAc (500 mL). The solution was washed with brine (100 mL×3), dried over $Na_2SO_4$ and concentrated in vacuo to give a residue, which was purified by column chromatography over silica gel, which was eluted with petroleum ether/EtOAc (10/1-3/1) to give compound 104 as a white solid (48 g, 88% yield).

Step 5:

To a stirred solution of tert-butyl nitrite (35 mL, 0.31 mol) and $CuBr_2$ (56.3 g, 0.252 mol) in $CH_3CN$ (1 L) was added drop-wise a solution of compound 104 (38 g, 0.21 mol) at 0° C. After the addition, the reaction mixture was stirred at room temperature for 3 hours. TLC (petroleum ether/EtOAc=3/1) showed the reaction was complete. The reaction mixture was poured into 6 N aq. HCl (400 mL) and extracted with DCM (200 mL×3). The combined organic layers were washed with brine (100 mL×3), dried over $Na_2SO_4$ and concentrated in vacuo to give a residue, which was purified by column chromatography over silica gel, which was eluted with petroleum ether/EtOAc (20/1-1/1) to give compound 105 as light yellow oil (35 g, 60% yield).

Step 6:

To a stirred solution of compound 105 (20 g, 81 mmol) in dry THF (200 mL) was added drop-wise $BH_3/Me_2S$ (1 N, 81 mL, 0.81 mol) at 0° C. After the addition, the reaction mixture was stirred at room temperature for 1 hour and subsequently refluxed for 4 hours. TLC (petroleum ether/EtOAc=3/1) showed the reaction was complete. The reaction mixture was quenched with saturated aqueous $NH_4Cl$ (100 mL) at 0° C.

The mixture was filtered and the filtrate was extracted with EtOAc (100 mL×3). The combined organic layers were washed with brine (50 mL×3), dried over $Na_2SO_4$ and concentrated in vacuo to give a residue, which was purified by column chromatography over silica gel, which was eluted with petroleum ether/EtOAc (6/1-3/1) to give compound 106 as light yellow oil (10 g, 62% yield).

Step 7:

To a stirred solution of compound 106 (10 g, 48.8 mmol) and $PPh_3$ (15.4 g, 58.5 mmol) in dry DCM (200 mL) was added drop-wise a solution of $CBr_4$ (19.3 g, 58.8 mmol) in DCM at 0° C. After the addition, the reaction mixture was stirred at room temperature for 24 hours. TLC (petroleum ether/EtOAc=3/1) showed the reaction complete. The reaction mixture was concentrated in vacuo to give a residue, which was purified by column chromatography over silica gel, which was eluted with petroleum ether/EtOAc (50/1~10/1) to give compound 107 as a white solid (7.0 g, 54% yield).

Step 8:

The procedure described in step 4 for compound 70 was used to prepare compound 108 as a colorless oil (4.8 g, 56% yield). $^1$H NMR (400 MHz, $CD_3OD$) δ 7.53 (s, 1 H), 4.28-4.25 (m, 2 H), 4.23 (d, 2 H), 2.83 (s, 3 H), 1.50 (s, 9 H), 1.44-1.38 (m, 3 H). LCMS m/z 318/320 $[M+H]^+$.

Preparation of 4-bromo-1-methyl-3-[(methylamino) methyl]-1H-pyrazole-5-carbonitrile (109)

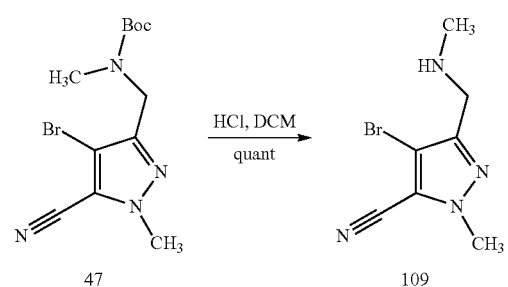 [SMILES: CN(Cc1nn(C)c(C#N)c1Br)C(=O)OC(C)(C)C ; CNCc1nn(C)c(C#N)c1Br]

To a 0° C. solution of compound 47 (1.0 g, 3.0 mmol) in DCM (15 mL) was added 4 N HCl in dioxane (3.8 mL, 15 mmol). Allowed to stir at room temperature for 3 hours, then concentrated under vacuum to give compound 109 (810 mg, quantitative) as a white solid.

Preparation of tert-butyl (3-hydroxy-5-(4-iodo-1-methyl-1H-pyrazol-5-yl)pyridin-2-yl)carbamate (113)

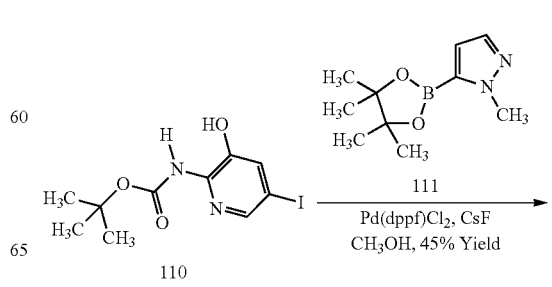

Preparation of (5-fluoro-2-(prop-2-yn-1-yloxy)phenyl)methanol (117)

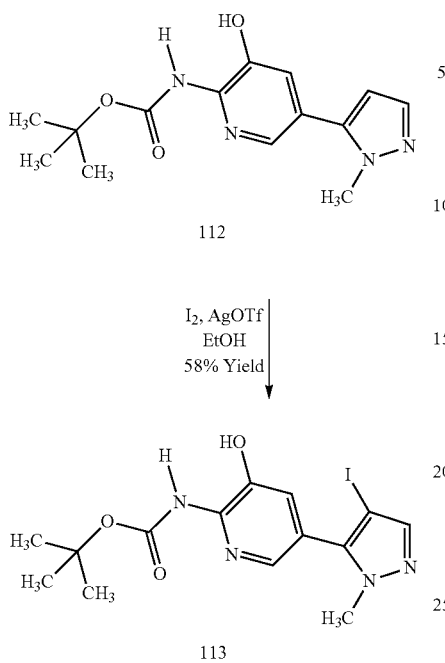

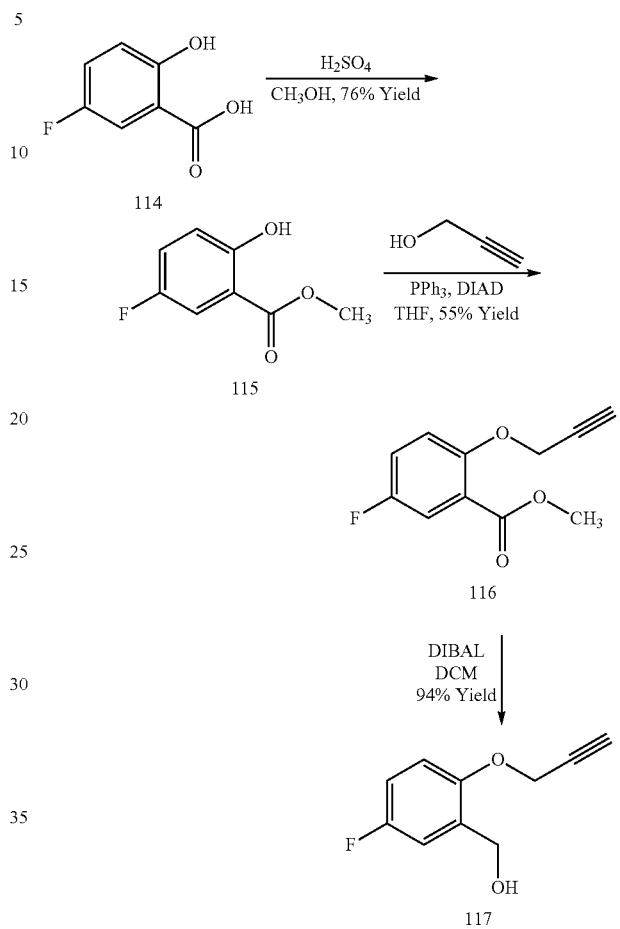

Step 1:

To a mixture of compound 110 and compound 111 in MeOH was added 2 M CsF in water. The mixture was bubbled with nitrogen for 5 minutes then PdCl₂dppf 1:1 with CH₂Cl₂ was added. The reaction was heated at 60° C. overnight then diluted with EtOAc, washed with water and brine, dried (MgSO₄), filtered and concentrated. The crude product was purified by flash chromatography eluting with heptanes/EtOAc (0-75%). The fractions containing the desired product were concentrated and the product was crashed out using DCM/Et₂O to give compound 112 (960 mg, 45% yield). $^1$H NMR (400 MHz, DMSO-$d_6$) δ 1.46 (s, 9 H) 3.85 (s, 3 H) 6.44 (s, 1 H) 7.31 (s, 1 H) 7.48 (s, 1 H) 7.99 (s, 1 H) 9.02 (s, 1 H) 10.12 (s, 1 H).

Step 2:

To a mixture of compound 112 (960 mg, 3.3 mmol) and AgOTf (850 mg, 3.3 mmol) in EtOH (30 mL) was added a solution of I₂ (0.25 M in EtOH, 13 mL, 3.31 mmol). After 1 hour, additional AgOTf (425 mg, 1.66 mmol) and I₂ (0.25 M in EtOH, 6.6 mL, 1.66 mmol) were added. Once LCMS showed the reaction was complete, the mixture was filtered and the mother liquor was diluted with EtOAc, washed with 1 N Na₂CO₃, saturated Na₂S2O₃/water, and brine. The combined aqueous layers were neutralized with 4 N HCl and extracted with DCM (2×). The combined organic extracts were dried (MgSO₄), filtered and concentrated. The crude product was purified by flash chromatography of silica gel, which was eluted with heptanes/EtOAc (0-100%) and gave compound 113 as a cream solid (800 mg, 58% yield). $^1$H NMR (400 MHz, DMSO-$d_6$) δ 1.47 (s, 9 H), 3.80 (s, 3 H), 7.25 (d, J=2.0 Hz, 1 H), 7.63 (s, 1 H), 7.89 (d, J=2.0 Hz, 1 H), 9.02 (s, 1 H), 10.28 (br s, 1 H).

Step 1:

To a solution of compound 114 (2.5 g, 16 mmol) in methanol (32 mL) was added sulfuric acid (2.0 mL, 21 mmol). The solution was heated at reflux overnight, cooled to room temperature and concentrated. The residue was dissolved in EtOAc, washed with saturated NaHCO₃ (3×), brine, dried (MgSO₄), filtered and concentrated to give compound 115 as to a cream solid (2.1 g, 76% yield). $^1$H NMR (400 MHz, DMSO-$d_6$) δ 3.89 (s, 3 H), 7.01 (dd, J=9.1, 4.5 Hz, 1 H), 7.40 (td, J=8.6, 3.2 Hz, 1 H), 7.45-7.54 (m, 1 H), 10.28 (s, 1 H).

Step 2:

To a solution of compound 115 (2.1 g, 12 mmol), propargyl alcohol (830 μL, 14 mmol), and triphenylphosphine (4.8 g, 18 mmol) in THF (31 mL) was added TEA (1.7 mL, 12 mmol) followed by DIAD (3.7 mL, 18 mmol). The solution was stirred at room temperature overnight and concentrated. The residue was purified by flash chromatography eluting with heptanes/EtOAc (0-30%) to give compound 116 as a needle like solid (1.4 g, 55% yield). $^1$H NMR (400 MHz, DMSO-$d_6$) δ 3.51-3.64 (m, 1 H), 3.80 (s, 3 H), 4.86 (d, J=2.3 Hz, 2 H), 7.25 (dd, J=9.1, 4.3 Hz, 1 H), 7.38-7.55 (m, 2 H).

Step 3:

To a cooled (−78° C.) solution of compound 116 (1.4 g, 6.7 mmol) in DCM (34 mL) was added DiBAL (1 M in hexanes, 18.5 mL, 18.5 mmol) drop-wise via a syringe pump at ~1 mL/min. The reaction was quenched with MeOH (10 mL) at −78° C. The dry ice bath was removed, then saturated sodium potassium tartrate (40 mL) was added and the reaction mixture was diluted with EtOAc (50 mL). The mixture was stirred at room temperature for 2 hours then diluted with EtOAc, washed with brine, dried over MgSO$_4$, filtered and concentrated to give compound 117 as a clear oil (1.1 g, 94% yield). $^1$H NMR (400 MHz, DMSO-d$_6$) δ 3.55 (t, J=2.4 Hz, 1 H), 4.48 (d, J=5.8 Hz, 2 H), 4.79 (d, J=2.3 Hz, 2 H), 5.20 (t, J=5.7 Hz, 1 H), 7.03 (dd, J=6.2, 1.6 Hz, 2 H), 7.13-7.21 (m, 1 H).

Preparation of (2-(but-3-yn-1-yloxy)-5-fluorophenyl)methanol (120)

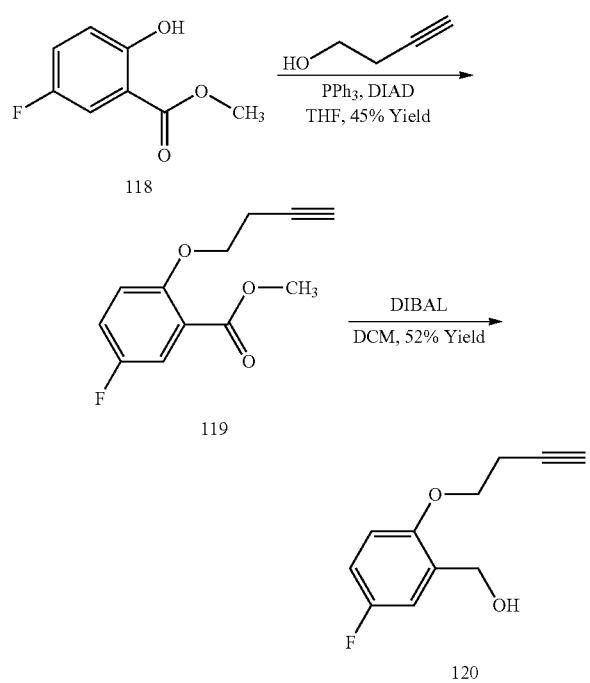

Step 1:

The procedure described in step 2 for compound 117 was used to prepare compound 119 (13 g, 45% yield).

Step 2:

The procedure described in step 3 for compound 117 was used to prepare compound 120 (13 g, 52% yield). $^1$H NMR (400 MHz, DMSO-d$_6$) δ 7.20-7.17 (m, 1 H), 7.05-6.96 (m, 2 H), 5.20 (t, 1 H), 4.54 (t, 2 H), 4.08 (t, 2 H), 2.90 (t, 1 H), 2.66-2.62 (m, 2 H). LCMS m/z 176 [M−OH]$^+$.

Preparation of (3-Hydroxy-5-iodo-pyridin-2-yl)-carbamic acid tert-butyl ester (123)

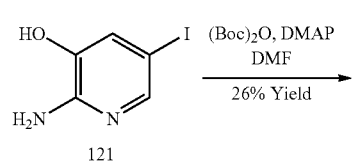

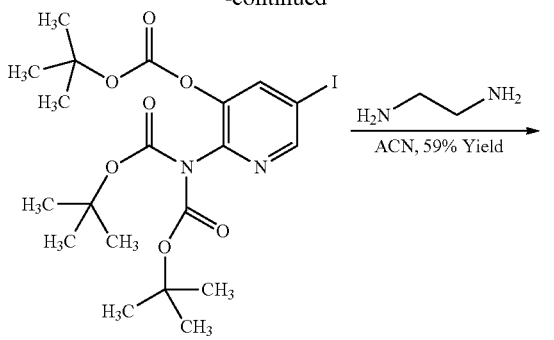

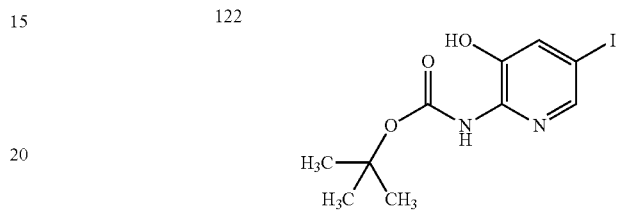

Step 1:

A mixture of 2-amino-5-iodopyridin-3-ol compound 121 (623 mg, 2.64 mmol), 4-dimethaminopyridine (64.5 mg, 0.528 mmol), and Di-tert-butyl dicarbonate (1.73 g, 7.92 mmol) in DMF (7.5 mL) was stirred at RT overnight. The mixture was diluted with EtOAc, washed with saturated aq. bicarbonate (2×), brine, dried over magnesium sulfate, filtered and concentrated to dryness. The residue was Purified by flash chromatography (ISCO 40 g cartridge) using a gradient to 0-35% EtOAc/heptane as eluent to give compound 122 (372 mg, 26.3%) as a gum. $^1$H NMR (400 MHz, DMSO-d6) δ ppm 8.62 (d, J=1.77 Hz, 1 H) 8.36 (d, J=1.77 Hz, 1 H), 1.48 (2, 9H), 1.39 (s, 18 H)

Step 2:

A mixture of compound 122 (106 mg, 0.98 mmol) and N,N-diethylenediamine (30.6 μL, 0.218 mmol)) in Acetonitrile (1 mL) was stirred at RT for 5 hr. Starting material was still evident by LCMS. More N,N-diethylenediamne (28 μL, 0.198 mmol) was added. After stirring at RT for another 1 hr, LCMS indicated reaction was complete. The mixture was concentrated to dryness and the residue purified by flash chromatography using a gradient of 0-50% dichloromethane/heptane as eluent to obtain compound 123 as a white solid in 59% yield. $^1$H NMR (400 MHz, DMSO-d6) δ ppm 10.29 (br. s., 1 H), 8.83 (s, 1 H), 8.00 (d, J=1.52 Hz, 1 H), 7.48 (d, J=1.77 Hz, 1 H), 1.43 (s, 9 H).

Preparation of (5-fluoro-2-(pent-4-yn-1-yloxy)phenyl)methanol (125)

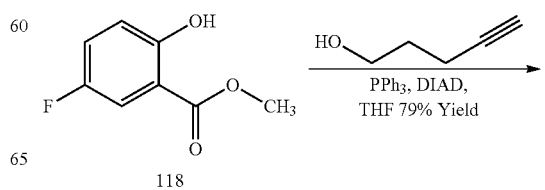

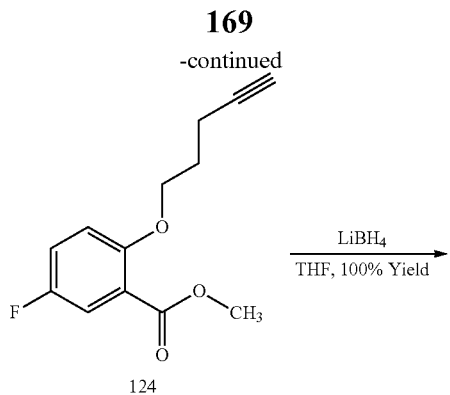

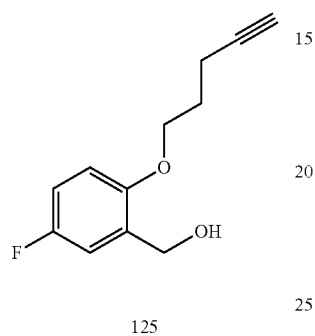

Step 1:

The procedure described in step 2 for compound 117 was used to prepare compound 124 (10.0 g, 79% yield).

Step 2:

To a stirred solution of compound 124 (9.0 g, 38.1 mmol) in dry THF (180 mL) was added portion-wise LiBH₄ (2.1 g, 95.2 mmol) at 0° C. under nitrogen. After the addition, the mixture was stirred at 50° C. for 5 hours. TLC (petroleum ether/EtOAc=6:1) indicated the reaction was complete. The mixture was cooled to 0° C., and water (50 mL) was added drop-wise. The aqueous layer was extracted with EtOAc (150 mL×2). The combined organic extracts were washed with brine (150 mL×2), dried over Na₂SO₄ and concentrated to give a residue, which was purified by column chromatography on silica gel (petroleum ether/EtOAc=15:1) to give compound 125 as yellow oil (9.0 g, 100% yield). ¹H NMR (400 MHz, DMSO-d₆) δ 7.22-7.19 (m, 1 H), 7.08-6.98 (m, 2 H), 5.23 (t, 1 H), 4.55 (t, 2 H), 4.08 (t, 2 H), 2.88 (t, 1 H), 2.40-2.38 (m, 2 H), 1.97-1.91 (m, 2 H). LCMS m/z 191 [M−OH]⁺.

SFC separation of 5-bromo-3-[1-(5-fluoro-2-iodophenyl)ethoxy]pyrazin-2-amine (30) into 5-bromo-3-[(1R)-1-(5-fluoro-2-iodophenyl)ethoxy]pyrazin-2-amine (126) and 5-bromo-3-[(1S)-1-(5-fluoro-2-iodophenyl)ethoxy]pyrazin-2-amine (127)

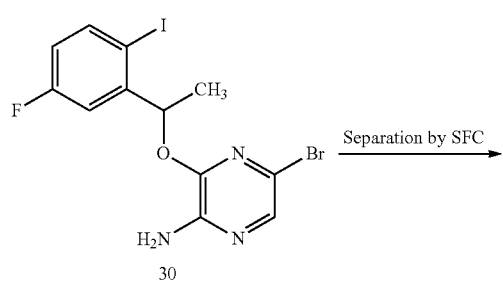

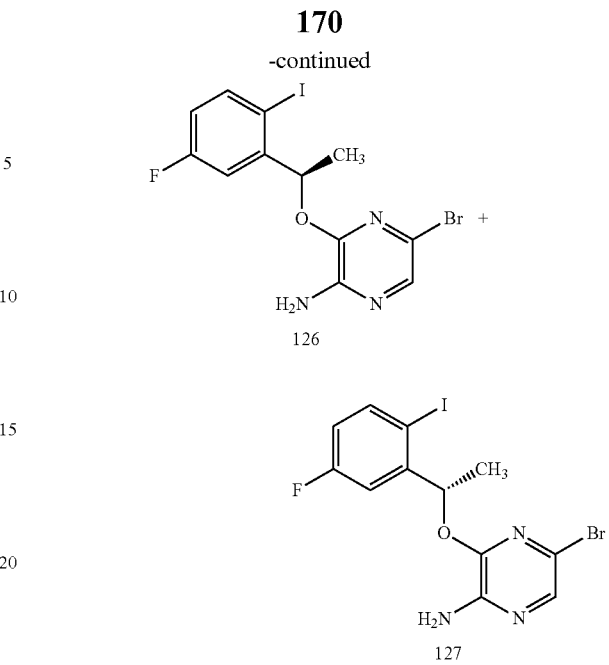

Compound 30 (18 g) was resolved by SFC and gave compound 126 (Peak 1) (7.75 g, 86%) and compound 127 (Peak 2) (7.72 g, 85%) as yellow solids. A Chiralpak AD-H (250× 4.6 mm I.D., 5 micron particle size) column was eluted with 15% methanol in CO₂ @140 bar at a flow rate of 3 mL/min and gave Peak 1 retention time of 3.76 minutes and Peak 2 retention time of 4.51 minutes.

Compound 126 (Peak 1): 99% ee. ¹H NMR (400 MHz, DMSO-d₆) δ 7.87 (dd, J=5.8, 8.8 Hz, 1 H), 7.61-7.54 (m, 2 H), 6.98 (dt, J=3.0, 8.6 Hz, 1 H), 6.71 (s, 2 H), 6.18-6.04 (m, 1 H), 1.53 (d, J=6.3 Hz, 1 H). LCMS m/z 437/439 [M+H]⁺.

Compound 127 (Peak 2): >98% ee. ¹H NMR (400 MHz, DMSO-d₆) δ 7.86 (dd, J=5.8, 8.8 Hz, 1 H), 7.62-7.54 (m, 2 H), 6.97 (dt, J=3.1, 8.5 Hz, 1 H), 6.71 (s, 2 H), 6.17-6.04 (m, 1 H), 1.52 (d, J=6.5 Hz, 3 H). LCMS m/z 437/439 [M+H]⁺.

Preparation of (3-{[(tert-butoxycarbonyl)(methyl)amino]methyl}-5-cyano-1-methyl-1H-pyrazol-4-yl)boronic acid (128)

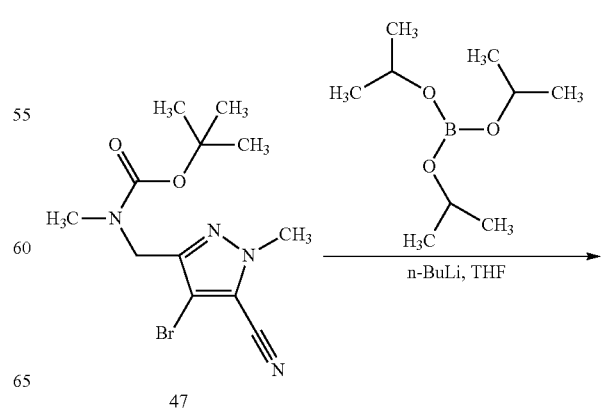

171

-continued

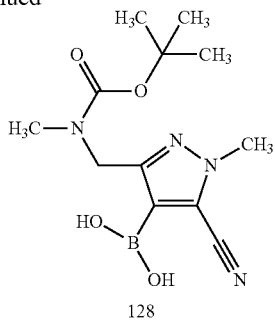
128

To a solution of compound 47 (800 mg, 2.43 mmol) in anhydrous THF (30 mL) at −78° C. was added n-BuLi (1.2 mL, 2.5M in hexanes, 3.2 mmol) dropwise via a syringe. The mixture turned orange in color and was stirred at −78° C. for 30 minutes. A solution of triisopropyl borate (0.85 mL, 3.64 mmol) in THF (5 mL) was added dropwise via an addition funnel. The resulting mixture was stirred at −78° C. for 30 minutes. 1N HCl (6 mL) was added dropwise and the cooling bath removed. The mixture was allowed to warm to room temperature. The mixture was partitioned between EtOAc/brine, and extracted with EtOAc. The combined organics were dried (MgSO$_4$) and reduced to minimum volume to give 738 mg of a residue, which was taken up in MeOH (17.2 mL) to provide a 0.14M solution of compound 128, which was used without further purification.

Preparation of 4-(methylamino)-5,6-dihydro-4H-pyrrolo[1,2-b]pyrazole-2-carbonitrile (135)

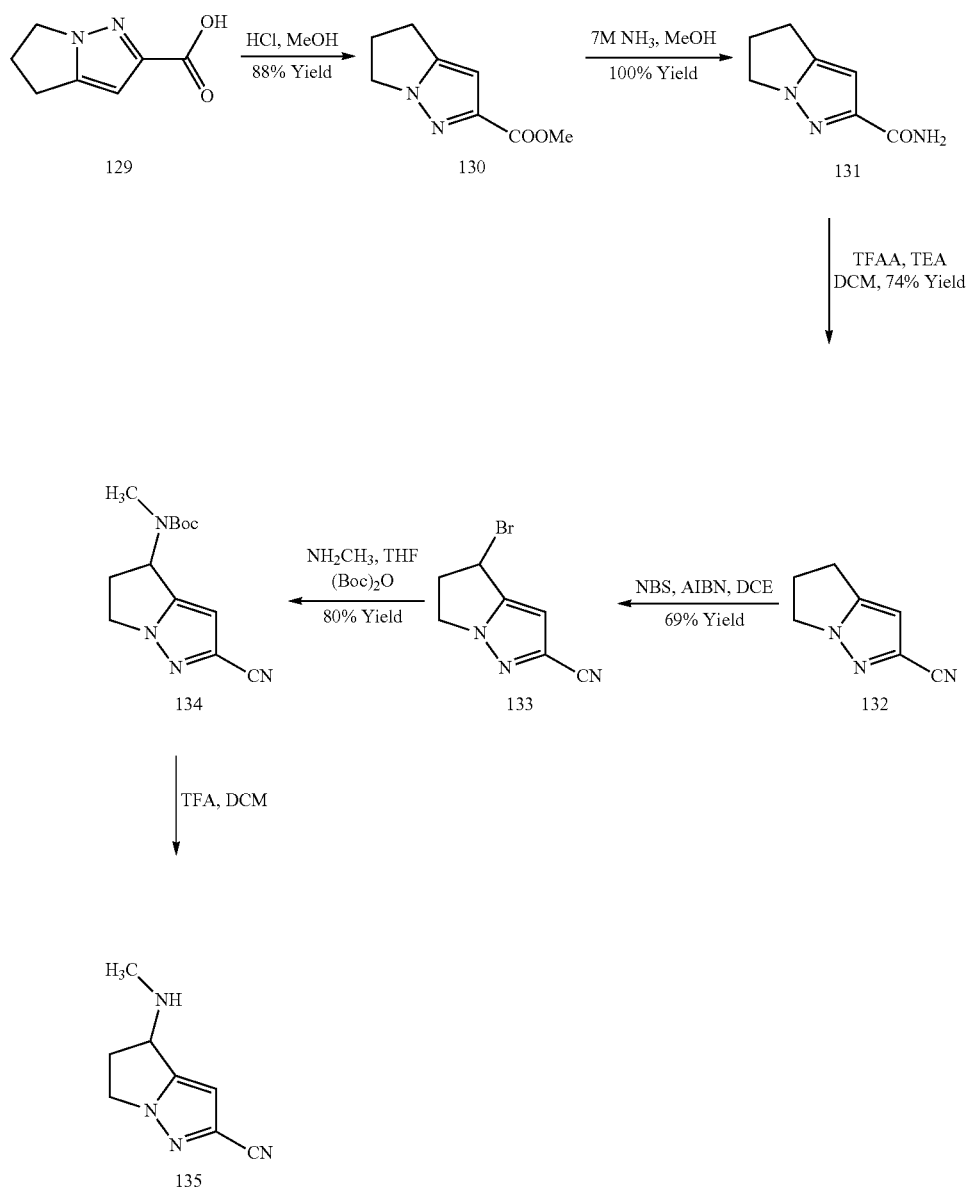

Step 1:

A solution of compound 129 (284 mg, 1.87 mmol) in MeOH (10 mL) was treated with 4 drops of conc. HCl. The reaction was heated at 50° C. for 24 hours. The reaction was concentrated, and partitioned between EtOAc and saturated aqueous NaHCO$_3$. The reaction was extracted with EtOAc, and the combined organics dried (Na$_2$SO$_4$), and concentrated to give compound 130 (273 mg, 88%) as an off white solid. LCMS ES m/z 167 [M+H]$^+$.

Step 2:

A mixture of compound 130 (273 mg, 1.64 mmol) in 7M NH3 in MeOH (5 mL) was heated at 80° C. in a sealed tube for 20 hours. The reaction was concentrated to an off-white solid, which was re-dissolved in 7M NH3 in MeOH (5 mL), and heated for a further 60 hours. The reaction was concentrated to give compound 131 (276 mg, 100%) as a brownish solid, which was used in the next step without further purification. LCMS ES m/z 152 [M+H]$^+$.

Step 3:

To a suspension of compound 131 (248 mg, 1.64 mmol) in DCM (10 mL) was added TEA (0.686 mL, 4.92 mmol). The resulting mixture was cooled to 0° C. and TFAA (0.456 mL, 3.28 mmol) was added. After 1.5 hours, LCMS showed the reaction was completed. The reaction was concentrated, and purified by column chromatography over silica gel (0-50% EtOAc/heptane) to give 5,6-dihydro-4H-pyrrolo[1,2-b]pyrazole-2-carbonitrile, compound 132 (168 mg, 74%) as a white solid. $^1$H NMR (400 MHz, DMSO-d$_6$) δ 6.70 (s, 1 H) 4.13-4.21 (m, 2 H) 2.89 (t, J=7.33 Hz, 2 H), 2.53-2.62 (m, 2 H).

Step 4:

Compound 132 (165 mg, 1.24 mmol), NBS (451 mg, 2.51 mmol), and AIBN (10.2 mg, 0.062 mmol) were combined in DCE (8 mL), and the reaction was heated at 85° C. for 60 hours. The reaction was concentrated to give a cream solid. Water (10 mL) was added, and the aqueous extracted with EtOAc (2×). The organics were dried (Na2SO4), concentrated and purified by column chromatography over silica gel (0-30% EtOAc/heptanes) to give compound 133 (182 mg, 69%) as a thick orange oil. $^1$H NMR (400 MHz, CDCl$_3$) δ 6.59 (s, 1 H) 5.35 (dd, J=6.82, 1.77 Hz, 1 H) 4.35-4.46 (m, 1 H) 4.21-4.29 (m, 1 H) 3.28 (ddt, J=14.81, 8.32, 8.32 Hz, 1 H) 2.95 (ddt, J=14.59, 6.76, 1.96 Hz, 1 H).

Step 5:

To a cooled solution of compound 133 (182 mg, 0.858 mmol) in THF (8 mL) was added 2M NH$_2$CH$_3$ in THF (1.27 mL). The mixture was stirred at 50° C. for 14 hours. LCMS shows ~50% completion. A further 4 mL of 2M NH$_2$CH$_3$ in THF was added, and the resulting mixture was heated at 50° C. for 16 hours. The reaction was allowed to cool, (Boc)$_2$O (281 mg, 1.29 mmol) was added, and the reaction stirred at room temperature for 18 hours. The reaction was concentrated, and partitioned between water and EtOAc. The organic phase separated, dried (Na$_2$SO$_4$), and concentrated to give a brown residue, which was purified by column chromatography over silica gel (0-50% EtOAc/heptane) to give compound 134 (180 mg, 80%) as a colorless oil. $^1$H NMR (400 MHz, CDCl$_3$) δ 6.44 (d, J=0.76 Hz, 1 H) 5.53-5.82 (m, 1 H) 4.33 (ddd, J=11.68, 9.28, 4.55 Hz, 1 H) 4.13 (ddd, J=11.75, 8.72, 6.82 Hz, 1 H) 2.98 (dtd, J=13.58, 8.94, 4.67 Hz, 1 H) 2.64 (br. s., 3 H) 2.49 (d, J=5.56 Hz, 1 H) 1.43 (s, 9 H). LCMS ES m/z 263 [M+H]$^+$.

Step 6:

To a solution of compound 134 (180 mg, 0.686 mmol) in DCM (2 mL) was added TFA (2 mL). The reaction was complete after 1 hour. It was concentrated to give compound 135 (237 mg) as a thick yellow oil, which was used without further purification. LCMS ES m/z 163 [M+H]$^+$.

Preparation of 1-Methyl-3-((methylamino)methyl)-1H-pyrazole-5-carbonitrile (137)

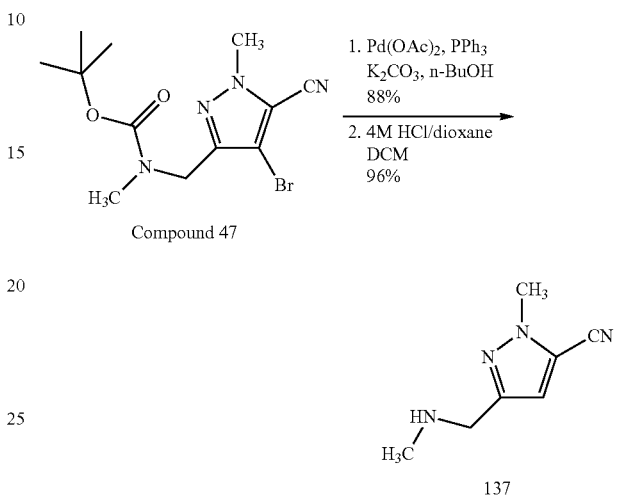

Compound 47

137

Step 1:

A suspension of compound 47 (118 g, 358 mmol) in n-butanol (1.20 L) was degassed and placed under nitrogen. K$_2$CO$_3$ (99.0 g, 716 mmol), triphenylphosphine (18.7 g, 71.3 mmol) and palladium (II) acetate (4.00 g, 17.8 mmol) were then added and the mixture was heated for 4 hours, reaching 80° C. after 1 hour, and achieving reflux after 3 hours. The mixture was allowed to cool to room temperature then diluted with EtOAc (1 L) and washed with water (1 L) and brine (1 L). The organic layer was dried (MgSO$_4$) and filtered. On standing overnight a small amount of precipitate was given and so the mixture was filtered and then concentrated in vacuo to give 117.4 g of brown oil. Purification by column chromatography over silica gel (10-30% EtOAc/heptane) gave Boc-protected intermediate compound 137A as a yellow oil (74.8 g, 83.5%). Impure fractions were combined to give 5.98 g of yellow oil that were purified further by column chromatography over silica gel eluting with 10% EtOAc in heptane increasing polarity to pure EtOAc. This gave a further 3.92 g of compound 137A as a yellow oil (4.4%). $^1$H NMR (400 MHz, CDCl$_3$) δ 6.68 (s, 1 H), 4.38 (s, 2 H), 4.01 (s, 3 H), 2.84 (s, 3 H), 1.47 (s, 9 H). LCMS ES m/z 251 [M+H]+.

Step 2:

A solution of compound 137 (78.7 g, 314 mmol) in dichloromethane (400 mL) was cooled to 0° C. under nitrogen and a 4M solution of HCl in dioxane (400 mL, 1.6 mol) was added over 5 minutes. After stirring at 0° C. for 30 minutes the mixture was allowed to warm to room temperature and stirred for a further 3 hours. The reaction mixture was concentrated to approximately 150 mL, cooled and filtered, washing with TBME (100 mL). The residue was air dried to give compound 137 as a colourless crystalline solid (56.12 g, 96%). $^1$H NMR (400 MHz, DMSO-d$_6$) δ 9.50 (s, 2 H), 7.31 (s, 1 H), 4.13 (s, 2 H), 4.03 (s, 3 H), 2.52 (s, 3 H). LCMS ES m/z 151[M+H]$^+$.

Preparation of N-[(5-cyano-1-methyl-1H-pyrazol-3-yl)methyl]-4-fluoro-2-hydroxy-N-methylbenzamide (138)

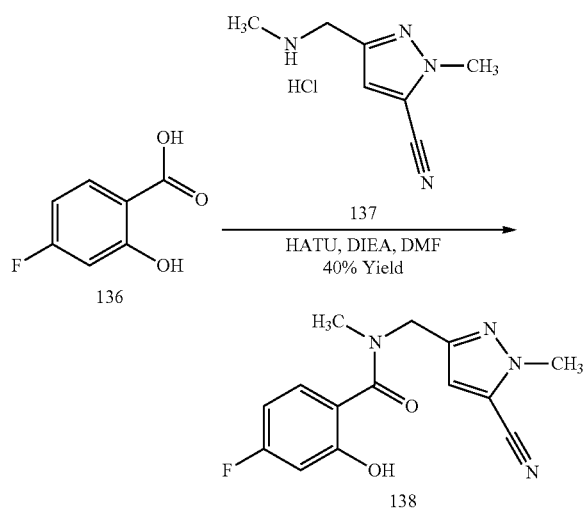

To a solution of 4-fluoro-2-hydroxybenzoic acid 136 (500 mg, 3.2 mmol), (5-cyano-1-methyl-1H-pyrazol-3-yl)-N-methylmethanaminium chloride 137 (600 mg, 3.2 mmol), and HATU (1.4 g, 3.5 mmol) in DMF (21 mL) was added DIEA (2.8 mL, 16 mmol). After stirring at room temperature for 14 hours, the solution was concentrated and purified by column chromatography over silica gel eluting with heptane/ethyl acetate(0-75%) to afford compound 138 (370 mg, 40%) as a semi-solid. $^1$H NMR (400 MHz, 80° C., DMSO-$d_6$) δ 10.08 (s, 1 H) 7.19 (m, 1 H) 6.94 (s, 1 H) 6.70-6.59 (m, 2 H) 4.52 (s, 2 H) 3.98 (d, J=0.8 Hz, 3 H) 2.86 (s, 3 H). LCMS APCI m/z 298 [M+H]$^+$.

Preparation of 1-methyl-3-[1-(methylamino)ethyl]-1H-pyrazole-5-carbonitrile (144)

Step 1:

To a stirred suspension of compound 139 (200 mg, 1.3 mmol), potassium carbonate (450 mg, 3.26 mmol) in DMF (5 mL) was added methyl iodide (456 mg, 3.21 mmol) in a dropwise fashion at room temperature. The vessel was sealed, and the mixture was heated at 50° C. for 1 hour. LCMS indicates complete consumption of starting material and 2 products in a ~3:1 ratio. The mixture was partitioned between EtOAc/brine. The aqueous layer was extracted with EtOAc. The combined organics were washed with water (2×), brine (1×), dried over MgSO$_4$ and reduced to minimum volume. The residue was purified by column chromatography over silica gel using a gradient of 10-75% EtOAc/heptane as eluent. Two isomers were isolated with the major isomer being compound 140 (146 mg white solid, 62%) as a white solid. $^1$H NMR (400 MHz, CDCl$_3$) δ 7.32 (s, 1 H) 4.25 (s, 3 H) 3.91 (s, 3 H) 2.59 (s, 3 H). Minor regioisomer (49 mg, 21%) $^1$H NMR (400 MHz, CDCl$_3$) δ 7.38 (s, 1 H) 4.24 (s, 3 H) 3.96 (s, 3 H) 2.56 (s, 3 H).

Step 2:

To a solution of compound 140 (1.13 g, 6.2 mmol) in methanol (50 mL) was added methylamine solution (3.8 mL, 2 M in THF, 7.6 mmol). was allowed to stir at room temperature for 20 hours. To the reaction mixture was added NaBH$_4$ (235 mg, 6.21 mmol). A vigorous gas evolution was initially observed, which ceased after ~30 minutes. LCMS indicated complete conversion to the amine. To the resulting mixture was added (Boc)$_2$O (2 g, 9.1 mmol) and the mixture was stirred at room temperature for 18 hours. The mixture was concentrated to dryness. The residue was purified by column chromatography over silica gel using a gradient of 10-75% EtOAc/heptane as eluent. The desired fractions were combined and concentrated to give compound 141 (1.6 g, ~85% pure) as an oil. This material was carried directly into the next step without further purification. $^1$H NMR (400 MHz, 80° C., DMSO-$d_6$) δ 6.67 (s, 1 H) 5.26 (q, J=7.05 Hz, 1 H) 4.05 (s, 3 H) 3.84 (s, 3 H) 2.60 (s, 3 H) 1.43 (d, J=7.30 Hz, 12 H).

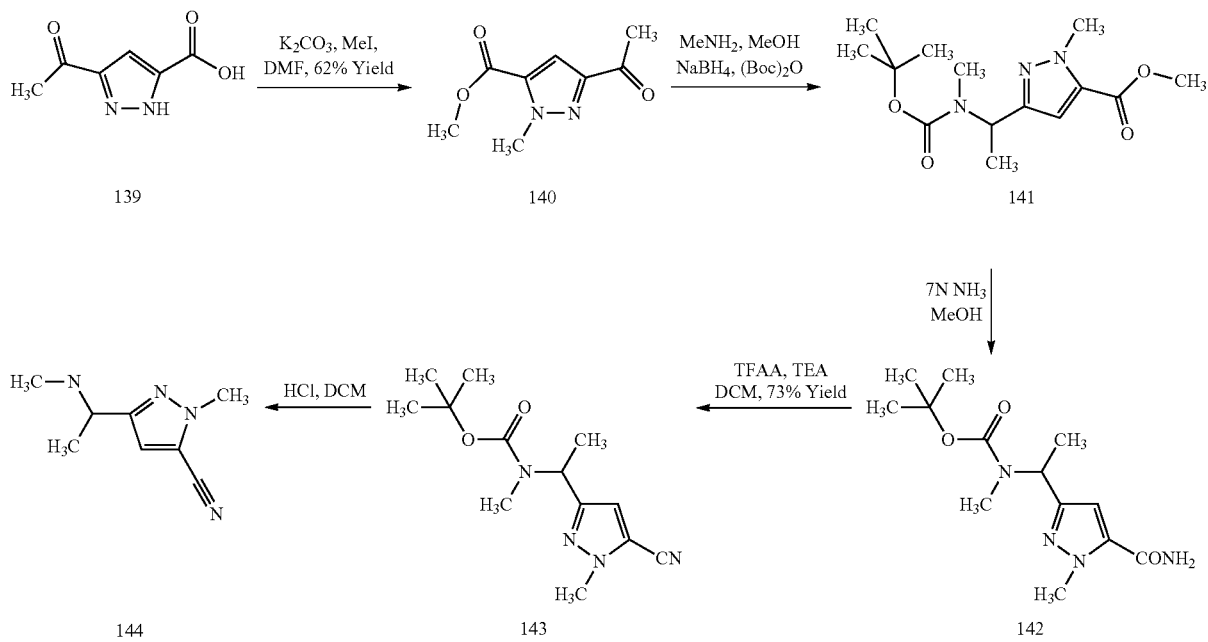

Step 3:

Compound 141 (1.6 g, 5.4 mmol) was dissolved in 7M ammonia in methanol (20 mL). The vessel was sealed, and the mixture was heated at 50° C. for 5 days. LCMS indicated complete conversion to the desired product. The mixture was concentrated to give compound 142 (1.496 g ~85% pure) as a gum. This material was carried directly into the next step without further purification. $^1$H NMR (400 MHz, 80° C., DMSO-$d_6$) δ 7.38 (br. s., 2 H) 6.69 (s, 1 H) 5.26 (q, J=6.97 Hz, 1 H) 4.01 (s, 3 H) 2.60 (s, 3 H) 1.44 (s, 9 H) 1.41 (d, J=7.05 Hz, 3 H).

Step 4:

To a suspension of compound 142 (1.496 g, 5.3 mmol) in dichloromethane (20 mL) was added triethylamine (2.2 mL, 15.9 mmol). The resulting suspension was cooled to −10° C. and a solution of trifluoroacetic anhydride (1.5 mL, 10.6 mmol) in dichloromethane (10 mL) was added dropwise over 20 minutes. After the addition was complete, the reaction mixture was stirred at 0° C. for 1 hour. The mixture was partitioned between dichloromethane and aqueous NaHCO$_3$. The aqueous layer was extracted with dichloromethane (2×). The combined organics were washed with brine, dried over MgSO$_4$ and concentrated to give a dark yellow oil. The residue was purified by column chromatography over silica gel using a gradient of 10-75% EtOAc/heptane as eluent. The desired fractions were concentrated to give compound 143 (1.026 g, 73%) as a white solid. $^1$H NMR (400 MHz, 80° C., DMSO-$d_6$) δ 6.90 (s, 1 H) 5.27 (q, J=7.13 Hz, 1 H) 3.97 (s, 3 H) 2.61 (s, 3 H) 1.37-1.51 (m, 12 H).

Step 5:

To a solution of compound 143 (300 mg, 1.14 mmol) in dichloromethane (4.5 mL) was added a solution of HCl in dioxane (4M, 4.5 mL). After stirring at room temperature for 1 hour, the resulting solution was reduced to minimum volume. The residue was concentrated from toluene and dried at 50° C. in a vacuum oven for 1.5 hours to give compound 144 (228 mg, quant) as a white solid. The material was carried directly into the next step without purification. $^1$H NMR (400 MHz, 80° C., DMSO-$d_6$) δ 9.39 (br. s., 2 H) 7.30 (s, 1 H) 4.42 (q, J=6.88 Hz, 1 H) 4.03 (s, 3H) 2.46 (s, 3 H) 1.59 (d, J=6.80 Hz, 3 H).

Preparation of tert-butyl [(4-chloro-1,5-naphthyridin-3-yl)methyl]methylcarbamate (153)

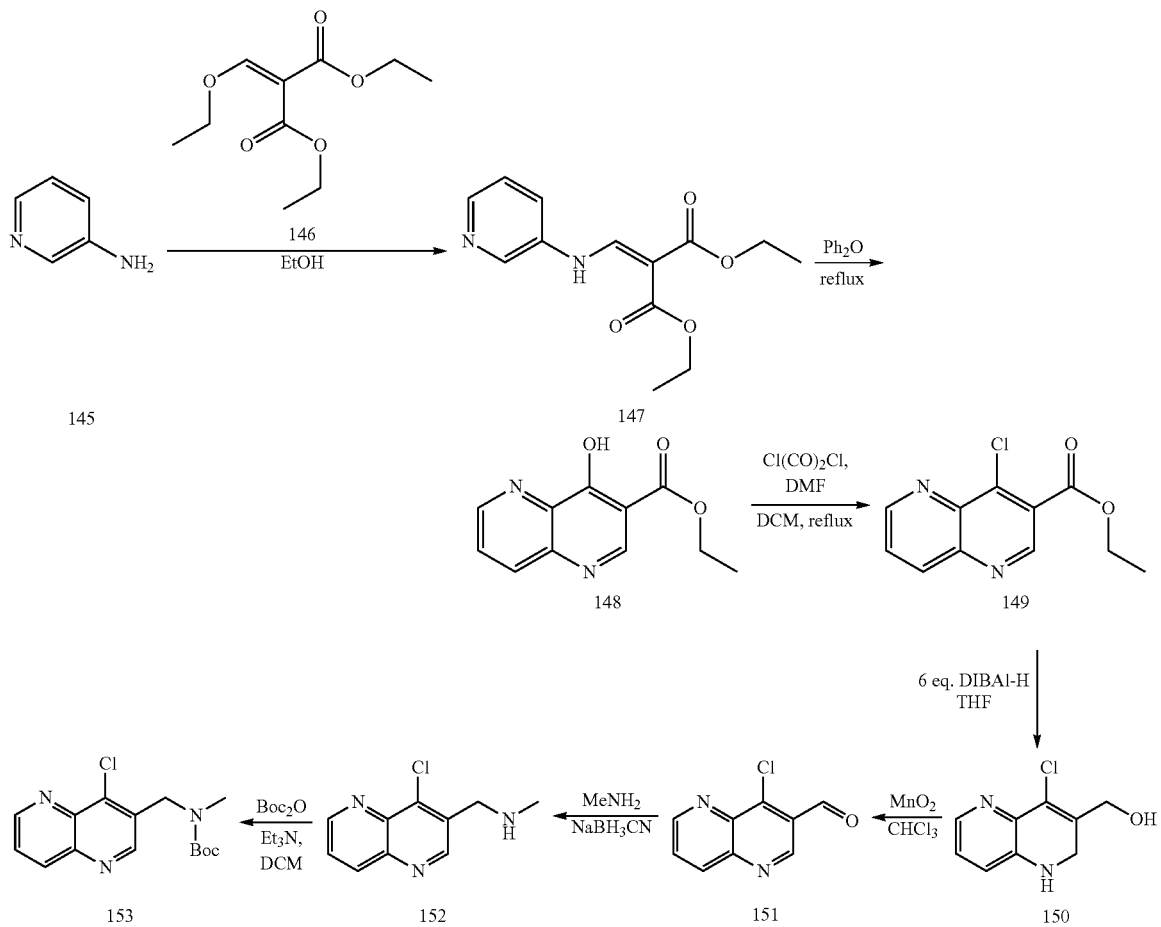

Step 1:

A mixture of compound 145 (35 g, 0.372 mol) and compound 146 (96.5 g, 0.447 mol) in EtOH (300 mL) was refluxed overnight. TLC (PE/EtOAc 1/1) showed the reaction was completed. The reaction mixture was concentrated in vacuo to give residue. Petroleum ether (200 mL) was added, and then stirred at room temperature for 30 minutes. The mixture was filtered to give compound 147 (95 g, 97%) as an off-white solid. $^1$H NMR (400 MHz, CDCl$_3$) δ 11.03-11.00 (d, 1H), 8.50-8.41 (m, 3H), 7.49-7.47 (d, 1H), 7.34-7.30 (m, 1H), 4.35-4.20 (m, 4H), 1.62-1.18 (m, 6H).

Step 2:

To a refluxing solvent of Ph$_2$O (200 mL) was added in portions compound 147 (30 g, 0.113 mol). After addition, the resulting mixture was stirred between 250-260° C. for 30 minutes. TLC (PE/EtOAc 1/1) showed the starting material was consumed completely. The reaction mixture was cooled to room temperature, and then poured into EtOAc (200 mL). The mixture was filtered and the wet cake was washed with EtOH (50 mL), EtOAc (50 mL) and petroleum ether (50 mL) to give compound 148 (11 g, 45%) as a brown solid.

Step 3:

To a suspension of compound 148 (12 g, 55 mmol) and DMF (5 mL) in DCM (200 mL) was added dropwise oxalyl chloride (20 mL) below 0° C. After addition, the resulting mixture was refluxed for three hours. TLC (PE/EtOAc 3/1) showed the reaction was completed. The reaction mixture was poured into ice-water carefully. The mixture was concentrated in vacuo to remove DCM. The mixture was extracted with MTBE (500 mL×3). The combined organic layers were washed with brine (100 mL×2), dried over Na$_2$SO$_4$ and concentrated in vacuo to give a residue, which was purified via column chromatography (silica gel, PE/EtOAc 5/1) to give compound 149 (6 g, 46%) as a yellow solid. $^1$H NMR (400 MHz, CDCl$_3$) δ 9.26 (s, 1H), 9.17-9.16 (d, 1H), 8.49-8.16 (d, 1H), 7.81-7.78 (t, 1H), 4.56-4.51 (q, 2H), 1.50-1.47 (m, 3H).

Step 4:

To a solution of compound 149 (4 g, 16.9 mmol) in dry THF (100 mL) was added dropwise DIBAL-H (101.4 mL, 101.4 mmol, 1M in toluene) below 0° C. After addition, the resulting mixture was stirred at this temperature for 3 hours. TLC (PE/EtOAc 1/1) showed the reaction was completed. The reaction mixture was quenched with saturated aq. Na$_2$SO$_4$ (100 mL) below 0° C. and stirred at this temperature for 30 minutes and then at room temperature for 30 minutes. The mixture was filtered. The wet cake was washed with EtOAc (100 mL×5). The combined filtrates were washed with brine (100 mL), dried over Na$_2$SO$_4$ and concentrated in vacuo to give a residue, which was purified via crystallization from DCM (10 mL) to give compound 150 (2.5 g, 75.1%) as a yellow solid. $^1$H NMR (400 MHz, CDCl$_3$) δ 7.96-7.95 (d, 1H), 6.94-6.91 (m, 1H), 6.75-6.68 (t, 1H), 4.51 (s, 2H), 4.42 (s, 2H), 3.79-3.71 (brs, 1H), 1.70-1.63 (brs, 1H)

Step 5:

A mixture of compound 150 (2.5 g, 12.7 mmol) and MnO$_2$ (10 g, 115 mmol) in CHCl$_3$ (100 mL) was refluxed overnight. TLC (PE/EtOAc 1/1) showed the reaction was completed. The reaction mixture was filtered and the wet cake was washed with DCM (20 mL×5). The combined filtrates were dried over Na$_2$SO$_4$ and concentrated in vacuo to give compound 151 (2.1 g, 86%) as an off-white solid. $^1$H NMR (400 MHz, CDCl$_3$) δ 10.80 (s, 1H), 9.45 (s, 1H), 9.19-9.11 (m, 1H), 8.51-8.44 (m, 1H), 7.86-7.79 (m, 1H).

Step 6:

A mixture of compound 151 (2.7 g, 14.02 mmol), MeNH$_2$.HCl (1.9 g, 28.04 mmol), MgSO$_4$ (5 g) and Et$_3$N (2.83 g, 158.04 mmol) in methanol (50 mL) was stirred at room temperature overnight. NaBH$_3$CN (2.5 g, 42.06 mmol) was then added to above mixture and then stirred at room temperature for 4 hours. TLC (PE/EtOAc 1/1) showed the reaction was completed. The reaction mixture was concentrated in vacuo to give crude compound 152, which was used for next step without any further purification. $^1$H NMR (400 MHz, CDCl$_3$) δ 9.11-9.10 (d, 1H), 9.02 (s, 1H), 8.46-8.44 (d, 1H), 7.73-7.70 (m, 1H), 4.19 (s, 2H), 2.55 (s, 3H).

Step 7:

To a solution of crude compound 152 (~14.02 mmol) and (Boc)$_2$O (6.1 g, 28.06 mmol) in DCM (100 mL) was added dropwise Et$_3$N (2.86 g, 28.04 mmol) at room temperature overnight. After addition, the resulting mixture was stirred at room temperature for 1 hour. TLC (PE/EtOAc 3/1) showed the reaction was completed. The reaction mixture was concentrated in vacuo to give residue, which was purified by column chromatography over silica gel (PE/EtOAc 3/1, Rf, 0.15) to give compound 153 (1.7 g, 36% over two steps) as a yellow solid. $^1$H NMR (400 MHz, CDCl$_3$) δ 9.10-9.09 (d, 1H), 8.88-8.86 (d, 1H), 8.45-8.43 (d, 1H), 7.72-7.71 (m, 1H), 4.87-4.83 (d, 2H), 2.99-2.93 (d, 3H), 1.51-1.47 (d, 9H). LCMS m/z 308 [M+H]$^+$.

Preparation of 3-(bromomethyl)-1-methyl-1H-pyrazole-5-carbonitrile (158)

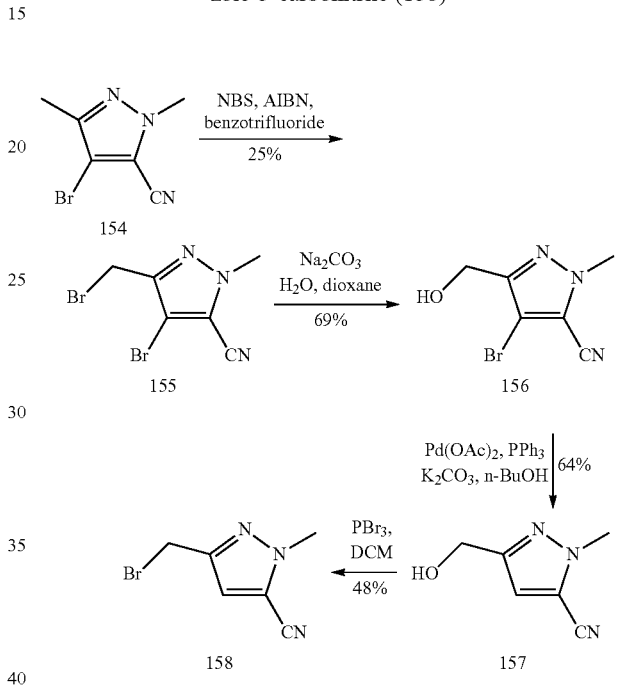

Step 1:

Compound 154 (25.0 g, 124.9 mmol) was dissolved in benzotrifluoride (300 mL) and NBS (31.1 g, 174.9 mmol) and AIBN (0.25 g, 1.53 mmol) were added at 45° C. The temperature was then increased to 80° C. and heated for one hour. Additional AIBN (0.25 g, 1.53 mmol) was added and heating continued overnight. The reaction was cooled to room temperature and the solvent removed under vacuum to give a yellow gum. The gum was taken up in DCM (300 mL) and the remaining solids removed by filtration. The filtrate was concentrated and cold MeOH added to the yellow oil. After standing at 0° C. for two hours, the resultant colorless solid was collected by filtration and washed with cold MeOH (2×20 mL). The solid was then recrystallised from methylcyclohexane to give compound 155 as a colorless solid (9.4 g, 25% yield). $^1$H NMR (400 MHz, CDCl$_3$) δ 4.42 (s, 2H), 4.05 (s, 3H).

Step 2:

Compound 155 (16.0 g, 57.36 mmol) was dissolved in dioxane (200 mL) and a solution of Na$_2$CO$_3$ (30.4 g, 286.8 mmol) in H$_2$O (200 mL) added, and the biphasic mixture heated at 60° C. for 16 hours. The reaction mixture was cooled to room temperature and the dioxane removed under vacuum. The residue was partitioned between DCM (150 mL) and brine (100 mL) and the phases separated. The aqueous phase was extracted with DCM (3×50 mL) and the combined organic extracts dried over MgSO₄ and concentrated to give a yellow oil. The crude oil was purified by column chromatography over silica gel (1:3 EtOAc:heptane to 1:1 EtOAc:heptane) to give compound 156 as a colorless solid (8.60 g, 69% yield). ¹H NMR (400 MHz, CDCl₃) δ 4.68 (d, J=6.1 Hz, 2H), 4.04 (s, 3H), 1.99 (t, J=6.1 Hz, 1H).

Step 3:

Compound 156 (8.60 g, 39.81 mmol) was dissolved in n-butanol (90 mL) and PPh₃ (2.09 g, 7.97 mmol), Pd(OAc)₂ (440 mg, 1.96 mol) and K₂CO₃ (11.0 g, 79.6 mmol) were added, and the reaction mixture heated at reflux for 4 hours. After cooling to room temperature, the reaction mixture was diluted with EtOAc (150 mL) and washed with saturated NaHCO₃ solution (100 mL) and brine (100 mL). The organic phase was dried over MgSO₄, and concentrated to give a yellow oil. The crude oil was purified by column chromatography over silica gel (1:1 EtOAc:heptane) to give compound 157 as a colorless solid (3.49 g, 64%). ¹H NMR (400 MHz, CDCl₃) δ 4.68 (d, J=6.1 Hz, 2H), 4.04 (s, 3H), 1.99 (t, J=6.1 Hz, 1H).

Step 4:

Compound 157 (3.47 g, 25.30 mmol) was dissolved in DCM (50 mL) and cooled to 0° C. PBr₃ (3.12 mL, 32.89 mmol) was added dropwise to give a white suspension which was stirred at room temperature overnight. The resultant solution containing a pale yellow gum was diluted with DCM (30 mL) and quenched by the careful addition of H₂O (20 mL) and neutralized with saturated NaHCO₃ solution. The phases were separated and the aqueous phase extracted with DCM (2×60 mL). The combined DCM extracts were dried over MgSO₄ and concentrated to give a yellow oil. The crude oil was purified by column chromatography over silica gel (1:1 DCM:heptane) to give compound 158 as a colorless oil (2.43 g, 48% yield). ¹H NMR (400 MHz, CDCl₃) δ 6.82 (s, 1H), 4.43 (s, 2H), 4.03 (s, 3H).

Preparation of 5-bromo-3-{1-[5-fluoro-2-(1-{[2-(trimethylsilyl)ethoxy]methyl}-1H-imidazol-2-yl)phenyl]ethoxy}pyrazin-2-amine (166)

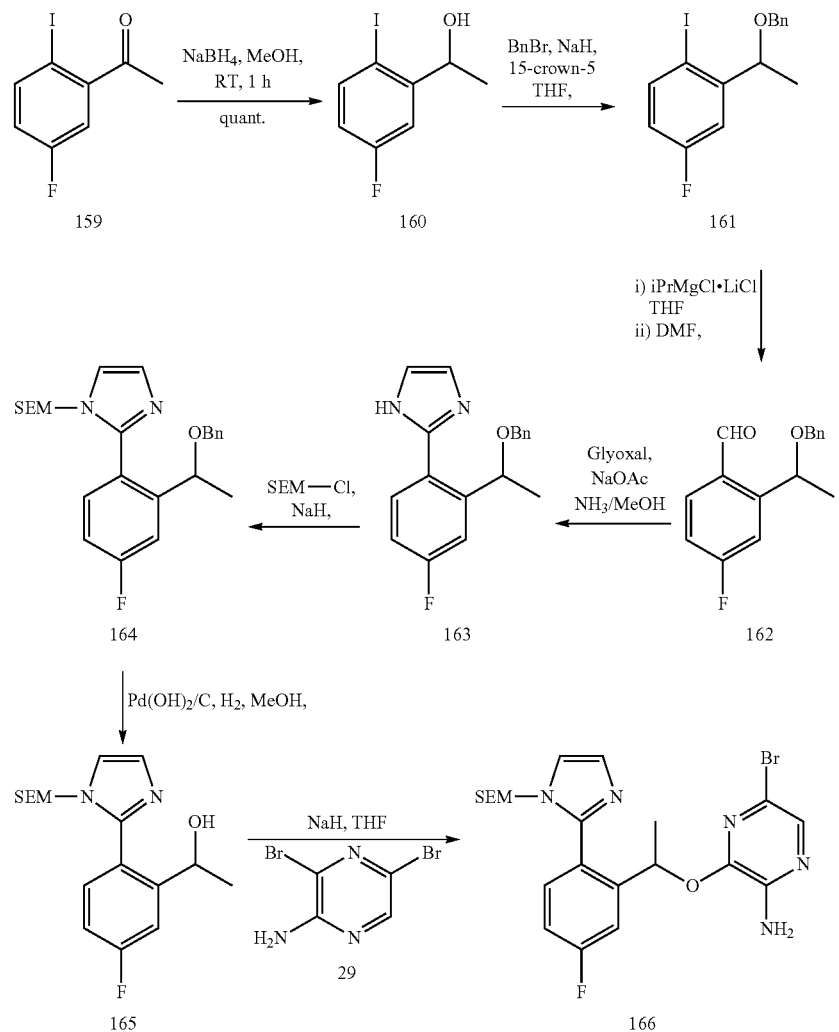

Step 1:

The reaction was performed in 2 batches of 50 g each for portionwise addition of NaBH₄. To a cooled (ice bath) solution of compound 159 (100 g, 379 mmol) in THF (800 ml) and MeOH (400 mL), NaBH₄ (28.7 g, 757 mmol) was added portionwise (2 g each) during a 2 hour period (strong gas evolution was observed). The reaction was stirred at room temperature for 3 hours. TLC analysis indicated completion. The reaction was quenched with aqueous NH$_4$Cl (300 mL). The mixture was extracted with EtOAc (500 mL), the organics separated and again washed with NH$_4$Cl (300 mL), water (1×300 mL) then brine (1×400 mL). The combined organics were dried (MgSO$_4$), and the solvents removed in vacuo to give compound 160 (104.1 g, quant) as a pale yellow oil. $^1$H NMR (400 MHz, DMSO-d$_6$) δ 7.80 (dd, J=8.6, 5.7 Hz, 1H), 7.31 (dd, J=10.4, 3.2 Hz, 1H), 6.92 (td, J=8.4, 3.2 Hz, 1H), 5.55 (d, J=4.1 Hz, 1H), 4.71-4.76 (m, 1H), 1.26 (d, J=6.3 Hz, 3H).

Step 2:

A solution of compound 160 (119.7 g, 450 mmol) in THF (300 mL) was added via addition funnel to an ice-cooled suspension of NaH (60% wt, 19.8 g, 495 mmol) in THF (500 mL) (time of addition—~1 hour). 15-crown-5 r (13.3 ml, 67.5 mmol) was added and the reaction allowed to warm to room temperature. After 2 hours, a solution of BnBr (51 mL, 427 mmol) in THF (300 mL) was added (~20 min, small exotherm observed up to ~40° C.). The reaction mixture was left stirring at room temperature overnight then quenched with NH$_4$Cl (200 mL). The mixture was diluted with EtOAc (200 mL), the organics were separated then again washed with NH$_4$Cl (200 mL), water (300 mL) then brine (2×300 mL). The combined organics were dried (MgSO$_4$), the solvents removed in vacuo to give an orange oil that was purified by column chromatography (eluent:Heptane/EtOAc-99:1 to 8:2) to give compound 161 (144.3 g, 90%) as a colorless liquid. $^1$H NMR (400 MHz, DMSO-d$_6$) δ 7.87 (dd, J=8.7, 5.7 Hz, 1H), 7.53-7.24 (m, 6H), 7.00 (td, J=8.5, 3.1 Hz, 1H), 4.63 (qd, J=6.4, 1.5 Hz, 1H), 4.40 (d, J=12.0 Hz, 1H), 4.32 (d, J=11.9 Hz, 1H), 1.34 (d, J=6.4 Hz, 3H).

Step 3:

A solution of compound 161 (50 g, 140 mmol) in THF (500 mL) was cooled to −45° C. (internal T). A solution of i-PrMg-Cl.LiCl (1.3 M in THF, 121 mL, 160 mmol) was added via addition funnel (~20 min addition period) keeping the reaction internal T between −40 and −50° C. After stirring for 1 hour, a white suspension had formed. After another hour, a solution of DMF (15.5 mL, 201 mmol) in THF (100 mL) was added (~30 min addition). The resulting clear reaction mixture was allowed to warm slowly to room temperature. After 16 hours, the reaction was diluted with EtOAc (200 mL), washed with NH$_4$Cl (3×300 mL) then brine (2×400 mL). The combined organics were dried with MgSO$_4$ and the solvents removed in vacuo to give 2-(1-(benzyloxy)ethyl)-4-fluorobenzaldehyde compound 162 (37.9 g, quant) as a pale yellow oil that was used in the following step without further purification. $^1$H NMR (400 MHz, DMSO-d$_6$) δ 10.19 (s, 1H), 8.02 (dd, J=8.6, 5.9 Hz, 1H), 7.62-7.16 (m, 8H), 5.61-5.38 (m, 1H), 4.41 (s, 2H), 1.42 (d, J=6.4 Hz, 3H).

Step 4:

Glyoxal (88.2 mL, 771.6 ml) followed by NaOAc (95.5 g, 701.5 mmol) were added to a cooled (ice bath) solution of compound 162 (38.22 g, 140.3 mmol) in MeOH (100 mL). After stirring for 5 min, a 7N NH$_3$ in MeOH solution (425 mL) was added and the resulting mixture stirred at 0° C. for another 10 min before being sealed in an autoclave and heated at 120° C. for 5 hours. The reaction was then cooled to room temperature, the solvents removed in vacuo to give a black paste that was redissolved in DCM (600 mL) then washed with a 1:1 NH$_4$Cl/1M HCl aqueous solution (2×500 mL) then brine (1×500 mL). The combined organics were dried (MgSO$_4$), the solvents removed in vacuo and the residue (adsorbed on celite) was purified by column chromatography (eluent: Heptane/EtOAc-9:1 to 1:1). The brown solids isolated were further purified by slurring in minimum amount of EtOAc followed by filtration. After drying in vacuo, compound 163 (16.2 g, 39%) was isolated as off-white solids. $^1$H NMR (400 MHz, DMSO-d$_6$) δ 12.47 (s, 1H), 7.62 (s, 1H), 7.40 (dd, J=10.4, 2.7 Hz, 1H), 7.35-7.19 (m, 8H), 5.47 (s, 1H), 4.43-4.12 (m, 2H), 1.40 (d, J=5.1 Hz, 3H). LCMS ES m/z 297 [M+H]$^+$.

Step 5:

NaH (60% wt, 2.23 g, 55.7 mmol) was added portionwise to a cooled (ice bath) solution of compound 163 (14 g, 47.2 mmol) in THF (250 mL). The mixture was stirred for 30 minutes before SEM-Cl (9.28 mL, 55.7 mmol) was added dropwise. The resulting mixture was allowed to warm to room temperature. After 6 hours, the reaction was placed under an ice bath then quenched by slow addition of water (150 mL) then diluted with EtOAc. The phases were separated and the aqueous layer again extracted with EtOAc (2×100 mL). The combined organics were dried (MgSO$_4$) and the solvents removed in vacuo to give a residue that was purified by column chromatography (eluent:Heptane/EtOAc-7:3 to 1:1) to give compound 164 (32 g, 70%) as a yellow oil. $^1$H NMR (400 MHz, DMSO-d$_6$) δ 7.36-7.49 (m, 2H), 7.34-7.18 (m, 7H), 7.04 (d, J=1.3 Hz, 1H), 5.22-5.05 (m, 2H), 4.57 (qd, J=6.4, 1.6 Hz, 1H), 4.37-4.12 (m, 2H), 3.54-3.38 (m, 2H), 1.33 (d, J=6.4 Hz, 3H), 0.85-0.63 (m, 2H), −0.08 (s, 9H). LCMS APCI m/z 427 [M+H]$^+$.

Step 6:

To a stirred solution of compound 164 (24 g, 56.3 mmol) in MeOH (375 mL) was added 20% wt. Pd(OH)$_2$/C (5 g), and the resulting mixture was heated at 50° C. under an atmosphere of H$_2$ (30 psi) for 6 hours then at room temperature for 16 hours. The reaction mixture was filtered through a pad of celite washing the filtrates with MeOH. The mother liquids were concentrated in vacuo and the resulting residue was purified by column chromatography (eluent:Heptane/EtOAc-3:1 to 1:1) to give compound 165 (18.19 g, 96%) as a pale yellow oil. This material was taken into the following step without further purification. $^1$H NMR (400 MHz, DMSO-d$_6$) δ 7.45 (d, J=1.4 Hz, 1H), 7.44-7.37 (m, 2H), 7.16 (td, J=8.4, 2.8 Hz, 1H), 7.05 (d, J=1.3 Hz, 1H), 5.40 (d, J=4.5 Hz, 1H), 4.68-4.74 (m, 1H), 3.41 (dd, J=9.0, 7.3 Hz, 2H), 1.15 (d, J=6.4 Hz, 3H), 0.83-0.73 (m, 2H), −0.06 (s, 9H). LCMS APCI m/z 337 [M+H]$^+$.

Step 7:

A solution of compound 165 (18.19 g, 54.06) in THF (200 mL) was cooled under an ice bath before NaH (60% wt, 2.59 g, 64.87 mmol) was added (in 3 portions). After stirring for 30 minutes, the reaction was allowed to warm to room temperature. A solution of compound 29 (16.4 mmol, 64.87 mmol) in THF (50 mL) was added via addition funnel. The reaction mixture was heated at 60° C. for 16 hours then cooled to room temperature. The mixture was diluted with EtOAc (300 mL) then washed with water (2×300 mL). The organics were dried (MgSO$_4$) and the solvents removed in vacuo to give crude dark solids. These were purified by column chromatography over silica gel (eluent:Heptane/EtOAc-9:1 to 1:1) to give compound 166 (19.36 g, 70%) as an off-white solid. $^1$H NMR (400 MHz, DMSO-d$_6$) δ 7.71 (dd, J=10.3, 2.8 Hz, 1H), 7.63-7.49 (m, 3H), 7.29 (td, J=8.5, 2.8 Hz, 1H), 7.15 (d, J=1.3 Hz, 1H), 6.71 (s, 2H), 6.08-5.89 (m, 1H), 5.32 (d, J=10.9 Hz, 1H), 5.16 (d, J=10.9 Hz, 1H), 3.66-3.48 (m, 2H), 1.65 (d, J=6.4 Hz, 3H), 0.85 (ddd, J=10.1, 6.2, 2.5 Hz, 2H), −0.00 (s, 9H). LCMS APCI m/z 508/509 [M+H]$^+$.

185

Preparation of methyl 2-{1-[(2-amino-5-bromopyridin-3-yl)oxy]-2-fluoroethyl}-4-fluorobenzoate (174)

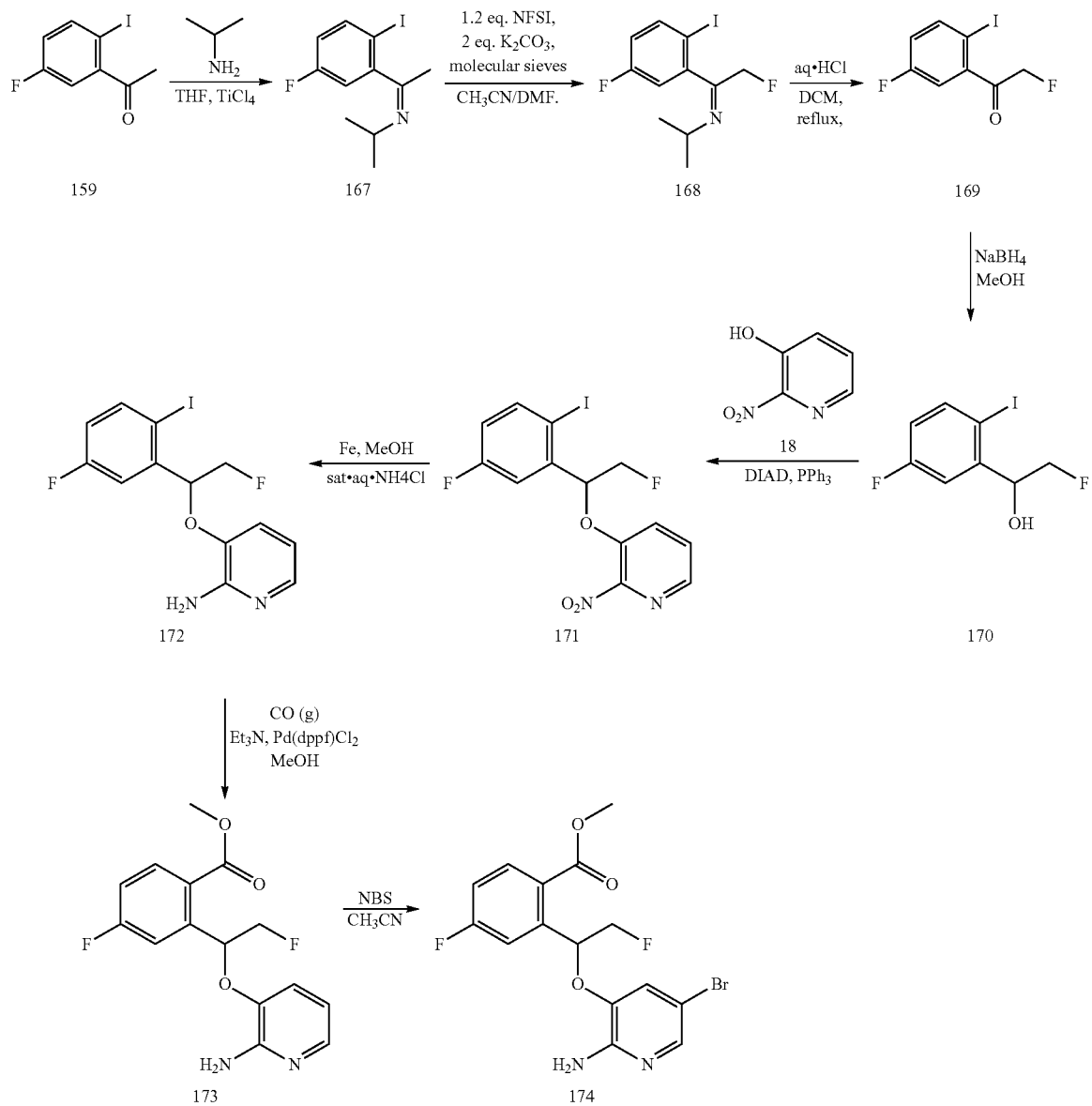

Step 1:
To a solution of compound 159 (40 g, 0.153 mol) and isopropylamine (36.2 g, 0.613 mol) in dry THF (500 mL) was added TiCl₄ (10 mL) drop-wise at 0° C. After addition the mixture was stirred at room temperature for 2 hours. TLC (petroleum ether/EtOAc 10/1) showed the reaction was complete. The mixture was filtered. The filtrate was poured into 0.5 M NaOH solution (500 mL).

The organic layer was separated, and the aqueous layer was extracted with EtOAc (200 mL×3). The combined organic layers were washed with brine (200 mL), dried over Na₂SO₄, and concentrated to give compound 167 (43 g, 93.5%) as yellow oil.

Step 2:
To a mixture of NFSI (25 g, 79.4 mmol) K₂CO₃ (18.4 g, 132.4 mmol) and 4 Å molecular sieves (25 g) in dry CH₃CN/DMF (250 mL/50 mL) was stirred at 0° C. under nitrogen for 15 minutes.

186

Compound 167 (20 g, 66.2 mmol) was added to the mixture. After addition, the reaction mixture was stirred at room temperature for two days. TLC (petroleum ether/EtOAc=10:1) indicated 90% of compound 167 was consumed. Et₃N (5 mL) was added to reaction mixture at 0° C., and the mixture was stirred for another 15 minutes. The mixture was filtered. The filtrate was poured to 0.5 M NaOH solution (300 mL). The organic layer was separated, and the aqueous layer was extracted with EtOAc (100 mL×3). The combined organic layers were washed with brine (100 mL×3), dried over Na₂SO₄, and concentrated to give compound 168 (20 g, 95%) as brown oil which was used directly without further purification.

Step 3:
To a solution of compound 168 (27.8 g, 86.3 mmol) in CH₂Cl₂/H₂O (250 mL/200 mL) was added concentrated HCl (50 mL). After addition the mixture was refluxed for 1 hour. TLC (petroleum ether:EtOAc=50:1) showed the reaction was complete. The mixture was cooled to room temperature. The organic layer was separated, and the aqueous layer was extracted with CH$_2$Cl$_2$ (200 mL×3). The combined organic layers were washed with brine (100 mL), dried over Na$_2$SO$_4$, and concentrated. The residue was purified by reverse phase preparative HPLC to give compound 169 (13 g, 54%) as a yellow solid.

Step 4:

To a solution of compound 169 (13 g, 45.9 mmol) in MeOH (100 mL) was added NaBH$_4$ (3.4 g, 91.9 mol) in portions at 0° C. After addition, the mixture was stirred at room temperature for 2 hours. TLC (petroleum ether:EtOAc=10:1) showed the reaction was complete. The mixture was concentrated The residue was diluted with H$_2$O (100 mL) and extracted with EtOAc (100 mL×3). The combined organic layers were washed with brine (100 mL×3), dried over Na$_2$SO$_4$, and concentrated to give compound 170 (13 g, 100%) as yellow oil.

Step 5:

To a stirred solution of compound 170 (4.5 g, 15.8 mmol), compound 18 (2.23 g, 15.8 mmol) and PPh$_3$ (5.59 g, 22 mmol) in anhydrous THF (80 mL) was added drop-wise DIAD (4.4 g, 0.22 mmol) at 0° C. After the addition, the reaction mixture was stirred at room temperature for 2 hours. TLC (petroleum ether/EtOAc 3:1) indicated the reaction was complete. The reaction mixture was concentrated in vacuo and the residue was purified by column chromatography on silica gel (petroleum ether/EtOAc 20:1 to 10:1) to give compound 171 (5 g, 78%) as a yellow solid.

Step 6:

A suspension of compound 171 (6 g, 14.7 mmol) and Fe (3.3 g, 59 mmol) in MeOH (80 mL) and saturated aqueous NH$_4$Cl (80 mL) was refluxed for 2 hours. TLC (petroleum ether/EtOAc=2:1) showed the reaction was complete. The reaction mixture was filtered and the filtrate was concentrated to give an aqueous solution, which was extracted with EtOAc (100 mL×3). The combined organic layers were washed with brine (50 mL), dried over Na$_2$SO$_4$ and concentrated.

The residue was purified by column chromatography over silica gel eluting with petroleum ether/EtOAc 6/1~3/1 to give compound 172 (5 g, 91%) as a yellow solid.

Step 7:

A mixture of compound 172 (5 g, 13.3 mmol), Pd(dppf)Cl$_2$ (1.15 g, 1.33 mmol) and TEA (2.65 g, 26.5 mmol) in methanol (100 mL) was sealed under CO (4 bar) at 100° C. for 16 hours. TLC (petroleum ether/EtOAc=1:1) indicated the reaction was complete. The reaction mixture was filtered and the filtrate was concentrated to give a residue, which was purified by column chromatography on silica gel, (petroleum ether/EtOAc from 8:1 to 6:1) to give compound 173 (3.5 g, 84%) as a pale brown solid.

Step 8:

To a stirred solution of compound 173 (3.5 g, 11.3 mmol) in CH$_3$CN (50 mL) was added dropwise a solution of NBS (2 g, 11.3 mmol) in CH$_3$CN (30 mL) at 0° C. After the addition, the reaction mixture was stirred at this temperature for 30 minutes. TLC (petroleum ether/EtOAc=1:1) indicted the reaction was complete. The mixture was diluted with EtOAc (200 mL), washed with saturated aqueous NaHCO$_3$ (50 mL). The aqueous layer was extracted with EtOAc (50 mL). The combined organic layers were washed with brine (50 mL), dried over Na$_2$SO$_4$ and concentrated. The residue was purified by column chromatography over silica gel (petroleum ether/EtOAc 3:1) to give compound 174 (3.5 g, 79%) as a pale brown solid. $^1$H NMR (400 MHz, CDCl$_3$) δ 8.17-8.22 (m, 1H), 7.77 (s, 1H), 7.37-7.40 (d, 1H), 7.14-7.19 (m, 1H), 6.78 (s, 1H), 6.45-6.51 (m, 1H), 4.85-4.9 (s, 2H), 4.59-4.76 (m, 2H), 4.01 (s, 3H). LCMS m/z 388 [M+H]$^+$.

Preparation of methyl 2-[(1R)-1-{[2-amino-5-(4,4,5, 5-tetramethyl-1,3,2-dioxaborolan-2-yl)pyridin-3-yl] oxy}ethyl]-4-fluorobenzoate (175)

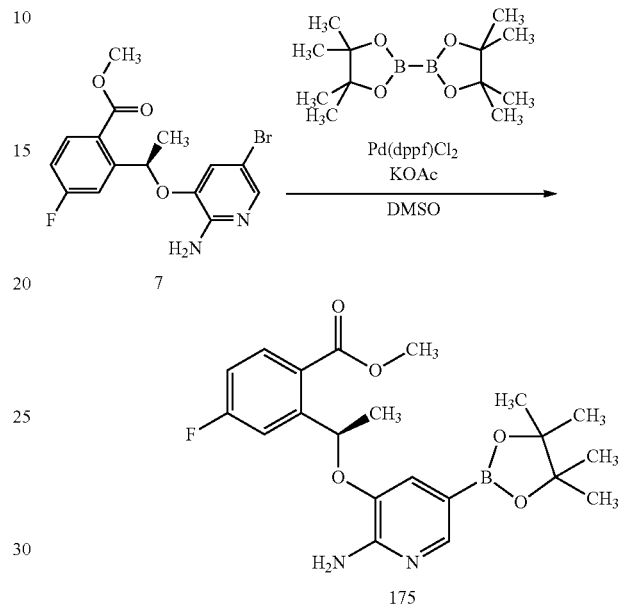

The procedure described in step 1 for Example 45 was used to prepare compound 175. $^1$H NMR (600 MHz, DMSO-d$_6$) δ 7.94 (dd, J=8.80, 5.87 Hz, 1 H), 7.74 (s, 1 H), 7.68 (dd, J=10.56, 2.35 Hz, 1 H), 7.25 (td, J=8.36, 2.64 Hz, 1 H), 6.87 (s, 1 H), 6.36 (s, 2 H), 6.26 (q, J=6.46 Hz, 1 H), 3.91 (s, 3 H), 1.57 (d, J=5.87 Hz, 3 H), 1.21 (d, J=5.87 Hz, 12 H).

Preparation of tert-butyl [(3-bromoimidazo[1,2-a] pyridin-2-yl)methyl]methylcarbamate (177)

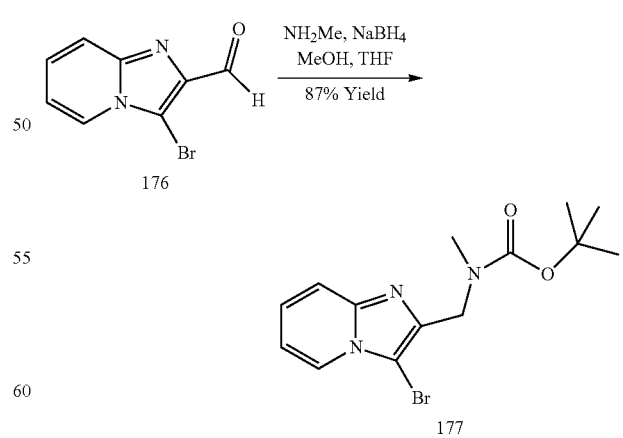

To a solution of compound 176 (0.5 g, 2.22 mmol), in MeOH (20 mL) was added a methyl amine solution (2M in THF, 1.33 mL, 2.67 mmol). The resulting mixture was stirred at RT for 1 hr. To the reaction mixture was added NaBH$_4$ (84 mg, 2.22 mmol). Vigorous gas evolution was observed. Gas evolution ceased after 30 minutes. LCMS indicates complete conversion to the amine. Di-tert-butyl dicarbonate (735 mg, 3.33 mmol) was added and mixture was stirred at RT for 18 h. LCMS shows complete conversion to desired product. The solution was concentrated, and the residue was purified by Biotage (40+S cartridge) using a gradient of 10-75% EtOAc/heptane as eluent to give compound 177 (654 mg, 86.5%) as an oil. $^1$H NMR taken at 80° C. $^1$H NMR (400 MHz. 80° C., DMSO-$d_6$) δ ppm 8.21-8.44 (m, 1 H), 7.50-7.64 (m, 1 H), 7.27-7.43 (m, 1 H), 6.96-7.14 (m, 1 H), 4.54 (s, 2 H), 2.86 (s, 3 H), 1.42 (s, 8 H).

Preparation of 1-(5-methoxy-1,2-thiazol-3-yl)-N-methylmethanamine (178)

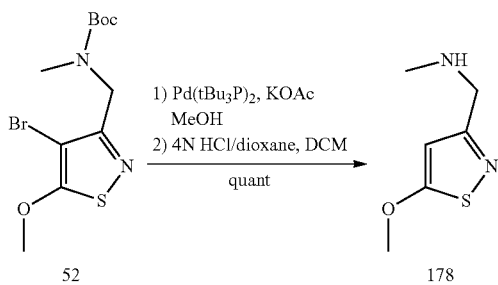

In a sealed 20 ml microwave vial, a solution of compound 52 (340 mg, 1.01 mmol), KOAc (297 mg, 3.02 mmol) and Pd(P$^t$Bu$_3$)$_2$ (52.7 mg, 0.101 mmol) in MeOH (5 mL) was heated in the microwave for 45 min at 100° C. Diluted with EtOAc, washed with water and brine, dried (MgSO$_4$), filtered and concentrated under vacuum. The residue was dissolved in DCM (2.50 mL) then 4 N HCl in dioxane (2.52 mL, 10.1 mmol) was added. The reaction was stirred at room temperature and concentrated under vacuum to give compound 178 (196 mg, quantitative) as a solid. $^1$H NMR (400 MHz, DMSO-d6) δ 9.46 (br. s., 2 H), 6.92 (s, 1 H), 4.15 (s, 2 H), 4.00 (s, 3 H), 2.58 (s, 3 H).

Preparation of 3-[(cyclopropylamino)methyl]-1-methyl-1H-pyrazole-5-carbonitrile (181)

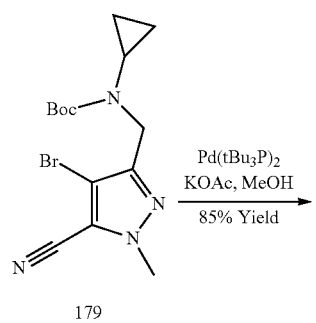

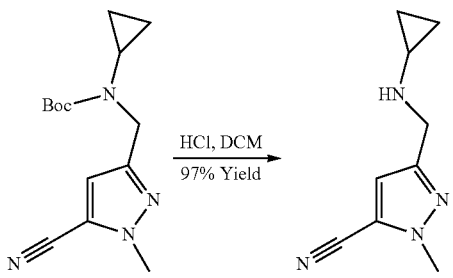

Step 1:

To a solution of compound 179 (1.50 g, 4.22 mmol) in degassed MeOH was added KOAc (1.24 g, 3.00 mmol) and Pd(tBu$_3$P)$_2$ (220 mg, 0.10 mmol). Heated to 120° C. in the microwave for 1 hour. The reaction mixture was filtered and concentrated under vacuum. The residue was purified by column chromatography (0-40% EtOAc/heptanes) to give compound 180 (990 mg, 85%) as a clear oil. $^1$H NMR (400 MHz, DMSO-d6) δ 6.91 (s, 1 H), 4.31 (s, 2 H), 3.96 (s, 3 H), 2.49-2.43 (m, 1 H), 1.39 (s, 9 H), 0.72-0.53 (m, 4 H)

Step 2:

To a solution of compound 180 (990 mg, 3.58 mmol) in DCM (9 mL) was added 4 N HCl in dioxane (8.96 mL, 35.8 mmol). The suspension was stirred for 2 hours at room temperature, then the reaction mixture concentrated under vacuum to give compound 181 (739 mg, 97%) as a white solid $^1$H NMR (400 MHz, DMSO-d6) δ 9.72 (br. s., 2 H), 7.33 (s, 1 H), 4.22 (s, 2 H), 4.03 (s, 3 H), 2.66 (tt, J=3.8, 7.4 Hz, 1 H), 0.95-0.83 (m, 2 H), 0.77-0.66 (m, 2 H).

Preparation of tert-butyl [(4-bromo-5-cyano-1-methyl-1H-pyrazol-3-yl)methyl]cyclopropyl-carbamate (183)

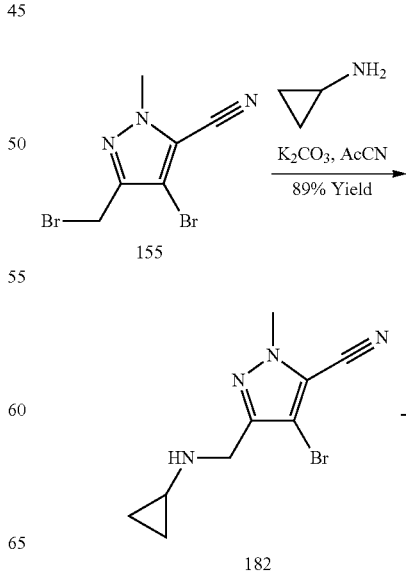

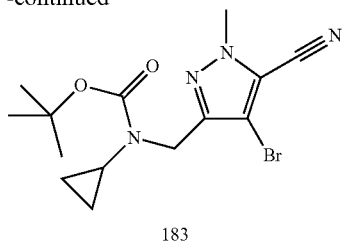

183

Step 1:
Cyclopropylamine (31.07 g, 544 mmol) was diluted in acetonitrile (30 ml) then potassium carbonate (8.4 g, 61 mmol) was added, followed by compound 155 (8.5 g, 279 mmol) dissolved in acetonitrile (30 ml). The reaction mixture was stirred at room temperature during 18 hours. To the reaction mixture was added EtOAc (400 ml) and water (80 ml). The phases were separated then the organic phase was evaporated to remove the excess of cyclopropylamine. To the crude compound was added EtOAc (400 ml) and an aqueous solution of HCl 1 M (80 ml). The aqueous phase was put to pH 7 with an aqueous solution of NaOH 1M and extracted with EtOAc (3*400 ml). The organic phases were combined, dried over MgSO4, filtered and the solvents were removed under reduced pressure to give compound 182 as a pale yellow solid (6.95 g, 89% yield). $^1$H NMR (400 MHz, DMSO-d6) δ 3.99 (s, 3H), 3.68 (s, 2H), 2.05 (tt, 1H, J=6.65, 3.53 Hz), 0.34 (td, 2H, J=4.06, 6.43 Hz), 0.23-0.19 (m, 2H), [M+H]+=257.06-258.14 (1/1)

Step 2:
Compound 182 (6.95 g, 27.2 mmol, 1 eq.) was dissolved in dichloromethane (90 ml, 0.3 M) then Boc anhydride (5.94 g, 27.2 mmol, 1 eq.) was added in small portion. The reaction mixture was stirred at room temperature during 60 hours. The solvents were removed in vacuo. The crude material was combined with the smaller scale reaction (792 mg) and purified by flash chromatography to give compound 183 as a white solid (10.29 g, 96% yield, 97% purity by LC-MS). $^1$H NMR (400 MHz, DMSO-d6) δ 4.35 (s, 2H), 3.99 (s, 3H), 2.42 (tt, J=6.6, 4.0 Hz, 1H), 1.37 (s, 8H), 0.63 (ddt, J=5.1, 3.4, 2.1 Hz, 4H). [M+H-Boc]=255.01-256.99 (1/1).

Preparation of tert-butyl((3-bromo-6-methylimidazo[1,2-a]pyrimidin-2-yl)methyl)(methyl)-carbamate (189)

Step 1:
To a solution of compound 184 (10.0 g, 77.79 mmol) in IMS (100 mL) was added aqueous ammonia (35%, 100 ml). The reaction mixture was transferred to a sealed bomb and heated at 200° C. for 4 h. The reaction mixture was allowed to cool to room temperature and was concentrated to remove most of the solvent and water (25 mL) added. The solid obtained was filtered and dried under vacuum to give the desired compound 185 as off-white solid (7.85 g, 92% yield). $^1$H NMR (400 MHz, DMSO-d6) δ 8.06 (s, 2H), 6.30 (s, 2H), 2.03 (s, 3H). LCMS m/z 110 [M+H]+.

Step 2:
The reaction was done in two batches using 1 g and 9.36 g of compound 185 and the crude material obtained from both batches was combined for purification. To a slurry of compound 185 (9.36 g, 85.82 mmol) in dry THF (250 mL) was added dichloroacetone (21.80 g, 171.64 mmol) and 4A° molecular sieves (25 g). The reaction mixture was heated at 90° C. for 3 days, then the reaction mixture was concentrated and the resulting residue dissolved in water (200 mL). The solution was treated with solid $K_2CO_3$ (10 g) and stirred for 10 min before extraction with ethyl acetate (3×400 mL). The combined ethyl acetate extracts were washed with brine (100 mL) and concentrated to give the crude product as thick brown oil. The aqueous phase was subjected to liquid-liquid extraction with DCM (500 mL) and the resulting product obtained was combined with the crude oil obtained from the ethyl acetate extractions for purification. Purification by silica gel column chromatography using 0.5%-1% MeOH in DCM furnished compound 186 as off-white solid (4.2 g, 24% yield). $^1$H NMR (400 MHz, Chloroform-d) δ 8.44 (d, J=2.4 Hz, 1H), 8.23 (dd, J=2.4, 1.2 Hz, 1H), 7.56 (d, J=0.8 Hz, 1H), 4.79 (d, J=0.8 Hz, 2H), 2.37 (d, J=1.1 Hz, 3H). LCMS m/z 182 [M+H]+.

Step 3:
The reaction was done in two batches using 2.0 g and 2.2 g of compound 186 and the crude material obtained from both batches was combined for purification. To a solution of compound 186 (2.0 g, 11.01 mmol) in acetonitrile (30 mL) was added NBS (2.14 g, 12.0 mmol) and the reaction stirred at room temperature overnight. The solvent was removed under vacuum and the combined crude product was dissolved in EtOAc (100 mL). The solid which precipitated was removed by filtration and the filtrate was evaporated to give the crude

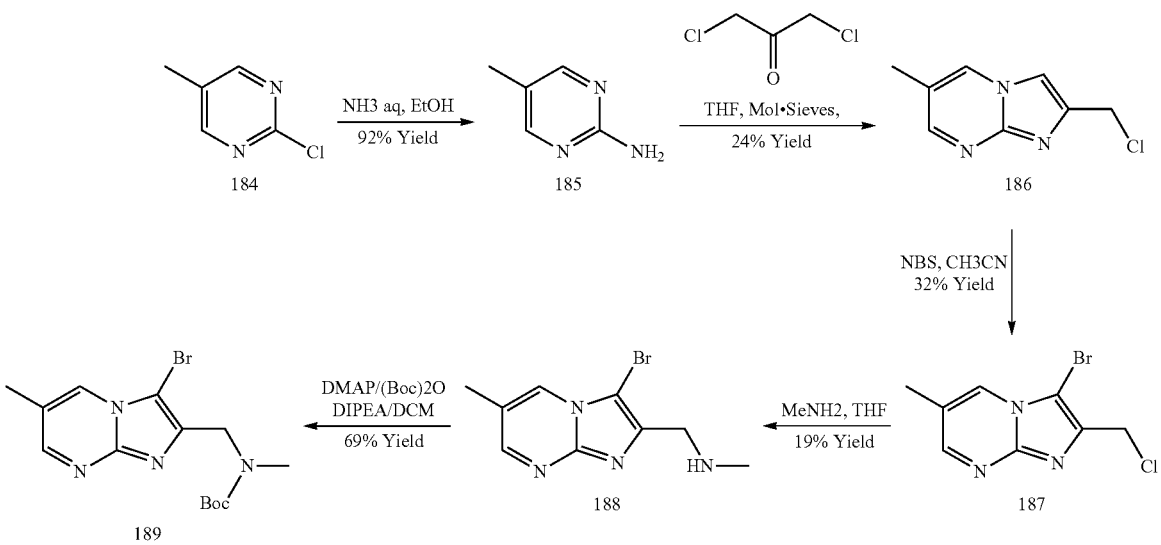

product as light yellow gum. Purification of the crude by silica gel column chromatography using 0.5% MeOH in DCM furnished the pure compound 187 as an off-white solid (1.9 g, 32% yield). ¹H NMR (400 MHz, Chloroform-d) δ 8.47 (d, J=2.4 Hz, 1H), 8.14 (dd, J=2.4, 1.2 Hz, 1H), 4.78 (s, 2H), 2.44 (s, 3H). LCMS m/z 260/262 [M+H]⁺.

Step 4:

To a suspension of compound 187 (1.68 g, 6.45 mmol) in THF (20 mL) being heated at 60° C., was slowly added a solution of methyl amine in THF (2M, 53.2 mL, 96.75 mmol) over a period of 30 min using a syringe pump. Once the addition was complete, the reaction was heated at 60° C. for 4 h. The crude product obtained after concentration of the reaction mixture, was purified by flash silica gel column chromatography using 10% MeOH in DCM along with 0.1% of 35% aqueous ammonia. The product obtained was found to contain a small amount of undesired dimer and so was further purified by reverse phase using a CH₃CN/H₂O solvent gradient. The product thus obtained was contaminated with a trace of impurity and was purified again by flash silica gel column chromatography using 4% MeOH in DCM (containing 7N ammonia) to furnish compound 188 as a yellow solid (254 mg, 15% yield). ¹H NMR (400 MHz, Methanol-d4) δ 8.89-8.22 (m, 2H), 3.88 (s, 2H), 2.45 (d, J=1.1 Hz, 3H), 2.42 (s, 3H). LCMS m/z 255/257 [M+H]⁺.

Step 5:

To a solution of compound 188 (250 mg, 0.980 mmol), DIEA (0.512 mL, 2.94 mmol) and DMAP (23.9 mg, 0.196 mmol) in DCM (4 mL) was added (Boc)₂O (856 mg, 3.92 mmol) at 0° C. The mixture was stirred at RT for overnight. It was concentrated and purified by ISCO (24 g) using 0%-75% EtOAc/Heptanes to give compound 189 as a gum (241 mg, 69% yield). ¹H NMR (400 MHz, DMSO-d6) δ 8.59 (s, 1H), 8.48 (d, J=2.3 Hz, 1H), 4.52 (s, 2H), 2.85 (br. s., 3H), 2.37 (s, 3H), 1.39 (d, J=15.9 Hz, 9H). LCMS m/z 355/357 [M+H]⁺.

Preparation of 1-[1-(2-{[tert-butyl(dimethyl)silyl]oxy}ethyl)-3-methyl-1H-pyrazol-5-yl]-N-methyl-methanamine (195)

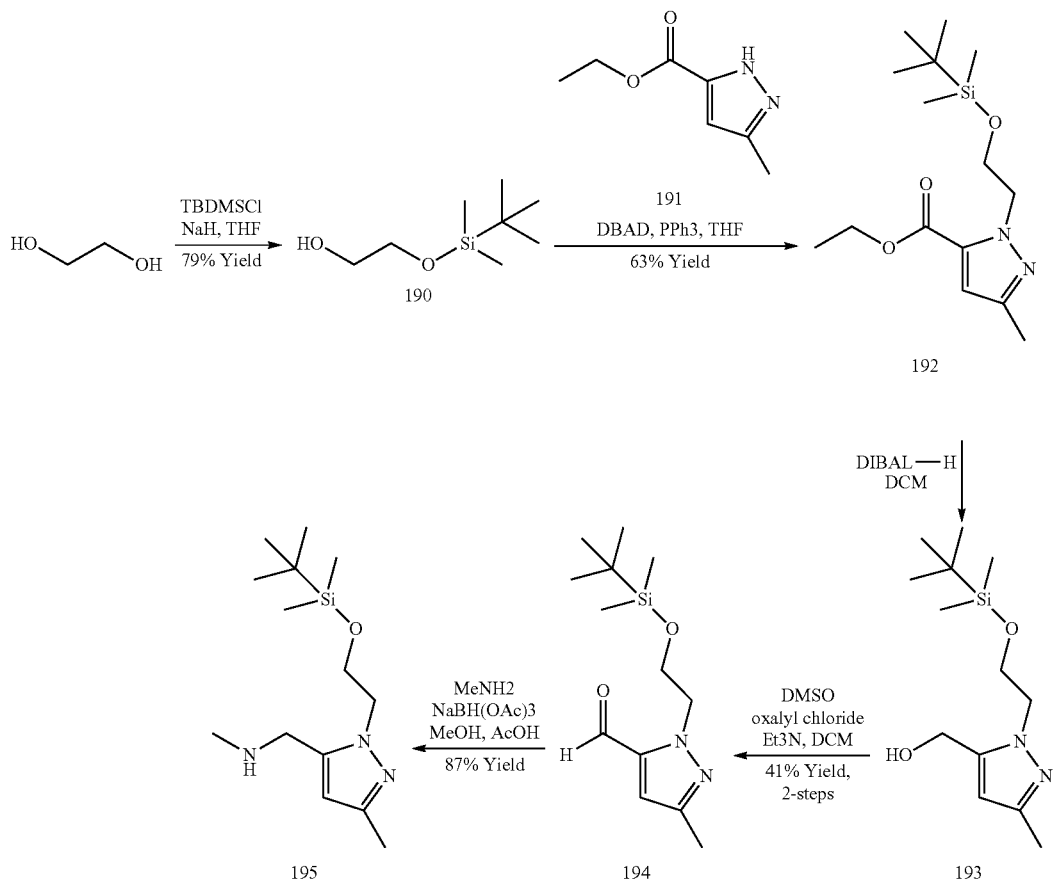

Step 1:

Under inert atmosphere at 0° C. (ice/water bath), to a suspension of NaH (60% in mineral oil, 6.44 g, 0.161 mol) (internal T=4° C.) was added ethylene glycol (10.0 g, 0.161 mol). The internal temperature after addition was 6° C. The reaction was stirred for 45 minutes in ice/water bath (internal T=4° C.). tert-butylchlorodimethylsilane (29.121 g, 0.161 mol) was added portionwise over 15 minutes keeping the temperature below 10° C. After addition of tert-butylchlorodimethylsilane the reaction mixture was allowed to warm to room temperature and stirred for 2.5 hours. The reaction was then quenched by addition of NaHCO3 sat solution (250 mL) and water (100 mL). The mixture was extracted with TBME (250 mL×2), the combined organics were washed with brine (250 mL), dried over Na₂SO₄, filtered and reduced to dryness to give a yellow oil. The crude was purified by filtration on silica pad using heptanes/EtOAc (gradient elution 95/5 then 9/1, 8/2, 7/3). The correct fractions were combined and reduced to dryness to give compound 190 as colorless oil (22.5 g, 79%). ¹H NMR (400 MHz, CDCl₃) δ 0.00 (s, 6H), 0.82 (s, 9H), 2.00 (t, 1H), 3.54-3.58 (m, 2H), 3.62-3.64 (m, 2H).

Step 2:

Under an inert atmosphere, to a solution of compound 191 (20.00 g, 129.7 mmol), 2-((tert-butyldimethylsilyl)oxy)ethanol 190 (27.45 g, 155.7 mmol) and triphenylphosphine (40.83 g, 155.7 mmol) in THF (400 mL) cooled to 0° C. was added dropwise a solution of DBAD (35.85 g, 155.7 mmol) in THF (200 mL) over 1 hour. After stirring for 3 hours at room temperature, 0.1 equiv of 2-((tert-butyldimethylsilyl)oxy)ethanol (2.2 g, 12.48 mmol) was added. The reaction mixture was stirred for another 18 hours then concentrated. The resulting yellow oil was triturated with heptane (1 L) forming a white solid which was removed by filtration. The filtrate was concentrated and the oily residue was purified by column chromatography (silica, 2% to 6% EtOAc in heptane) yielding compound 192 as a pale yellow oil (25.47 g, 63%). ¹H NMR (400 MHz, CDCl₃) δ 0.11 (s, 6H), 0.78 (s, 9H), 1.33 (t, 3H), 2.25 (s, 3H), 3.89 (t, 2H), 4.29 (q, 2H), 4.63 (t, 2H), 6.57 (s, 1H), [MH]+ 313.

Step 3:

Under an inert atmosphere, to a solution of compound 192 (24.8 g, 79.4 mmol) in DCM (600 mL) cooled to −78° C. was added dropwise DIBAL-H (1M solution in DCM, 250 mL, 250 mmol). After stirring for 1 hour at −78° C., the reaction mixture was quenched with methanol (60 mL) then warmed to room temperature. Water and brine were added forming a grey precipitate. Attempt at performing an extraction was not successful as both phases were hard to visualize. The reaction mixture was then filtered over celite and washed with large amounts of DCM (4 L). The water layer was separated and the organic phase was dried (Na₂SO₄) and concentrated to give compound 193 as an oil (20 g) which was used as it is in the next step. ¹H NMR (400 MHz, CDCl₃) δ 0.04 (s, 6H), 0.79 (s, 9H), 2.23 (s, 3H), 3.96 (t, 2H), 4.22 (t, 2H), 4.55 (d, 2H), 5.97 (s, 1H), [MH]+ 271.

Step 4:

Under an inert atmosphere, to a solution of oxalyl chloride (8.70 mL, 103 mmol) in DCM (188 mL) cooled to −78° C. was added over 30 min a solution of DMSO (14.4 mL, 205 mmol) in DCM (75 mL). The reaction mixture was stirred for 30 min at −78° C. then a solution of compound 193 (20 g) in DCM (188 mL) was added dropwise. The reaction mixture was stirred for 1.25 hours at −78° C. followed by the dropwise addition of triethylamine (66.0 mL, 474 mmol). The reaction was warmed to room temperature and water (600 mL) was added. The phases were separated and the aqueous layer was extracted with DCM (3×500 mL). The combined organics were dried (Na₂SO₄) and concentrated. The resulting oily residue was purified by column chromatography (silica, 0% to 2% EtOAc in DCM) to give compound 194 as a pale yellow oil (8.75 g, 41% over two steps). ¹H NMR (400 MHz, CDCl₃) δ 0.11 (s, 6H), 0.78 (s, 9H), 2.29 (s, 3H), 3.90 (t, 2H), 4.56 (t, 2H), 6.63 (s, 1H), 9.80 (s, 1H), [MH]+ 269.

Step 5:

Under an inert atmosphere, to a solution of compound 194 (11.15 g, 41.54 mmol) and methylamine (33% w/w in EtOH, 14.77 g, 157.22 mmol) in methanol (280 mL) was added acetic acid (2.50 mL, 41.54 mmol) dropwise. The reaction mixture was stirred at room temperature for 1.3 hours, cooled to 0° C., treated with NaBH(OAc)₃ (13.2 g, 62.31 mmol) then stirred at room temperature for 18 hours. After this time, some amine (3.90 mg, 41.92 mmol) was added followed by NaBH(OAc)₃ (8.80 g, 41.5 mmol) 30 minutes later. The reaction mixture was stirred for another 40 minutes, concentrated, taken up in EtOAc (375 mL) and washed with sat. aq. NaHCO₃ (275 mL) and brine (200 mL). The organic layer was dried (Na₂SO₄) and concentrated. The resulting oily residue was purified by column chromatography (neutralized silica, 0% to 6% 7N NH₃/MeOH in DCM) to give compound 195 (10.3 g, 87%). ¹H NMR (400 MHz, CDCl₃) δ 0.10 (s, 6H), 0.80 (s, 9H), 1.60 (br, 1H), 2.20 (s, 3H), 2.42 (s, 3H), 3.71 (s, 2H), 3.92 (t, 2H), 4.11 (t, 2H), 5.88 (s, 1H), MH]+ 284.

Preparation of 1-(4-bromo-3-methoxy-1-methyl-1H-pyrazol-5-yl)-N-methylmethanamine (196)

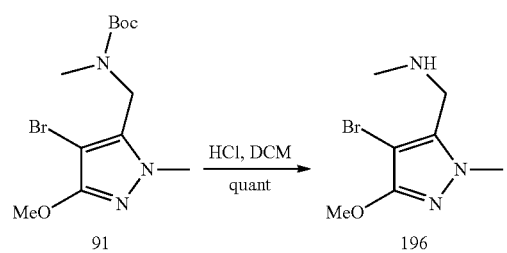 [SMILES: COc1nn(C)c(CN(C)C(=O)OC(C)(C)C)c1Br ; CNCc1c(Br)c(OC)nn1C]

To a solution of compound 91 (1613 mg, 4.826 mmol) in DCM (10 ml) was added 4N HCl in dioxane.(10 ml). The solution was allowed to stir at room temperature for 2 hours, then the reaction mixture was concentrated to give compound 196 (1357 mg, 104%) as a yellow solid.

Preparation of 5-((methylamino)methyl)isoxazole-3-carboxamide (200)

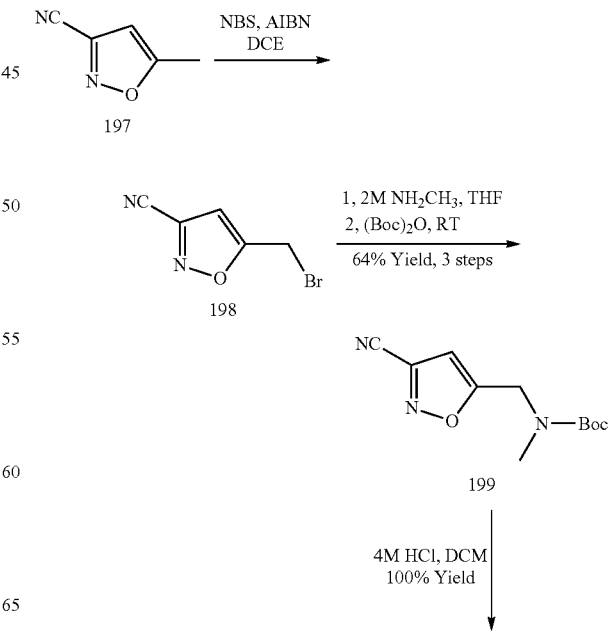

-continued

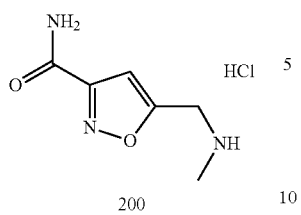
200

Step 1:

To a solution of compound 197 (800 mg, 7.40 mmol) in DCE (30 mL) was added NBS (2.79 g, 15.5 mmol) and AIBN (60.8 mg, 0.375 mmol). The reaction stirred at 85° C. for overnight. Concentrate to give the cream solid. Water (20 mL) was added, and extracted with EtOAc (30 mL×2). The combined organic layers were washed with brine (20 mL), dried over $Na_2SO_4$ and concentrated to give compound 198 (1.44 g, 2.90 mmol) as an off-white semi-solid, which was taken into the next step without further purification.

Step 2:

To a solution of compound 198 (1.44 g, 2.90 mmol) in THF (15 mL) was cooled to 0° C., 2M $NH_2CH_3$ in THF (4.36 mL, 8.73 mmol) was added. The mixture was stirred at 0° C. for 2.5 h. $(Boc)_2O$ (635 mg, 2.91 mmol) was added. Let it go for overnight at RT. LCMS shows the new peak and the staring material. 380 mg of $(Boc)_2O$ was added. The resulting mixture was stirred at RT for 3 h. LCMS shows the new peak was growing. After another 2 h, no any progress was found by LCMS. 283 mg of $(Boc)_2O$ was added. It was stirred at RT for overnight. Solvent removed in vacuo and the reaction partitioned between water and EtOAc (50 ml/50 ml). The organic phase separated, dried over $Na_2SO_4$, and concentrated. It was purified by ISCO with 0-40% EtOAc/Heptane to give compound 199 as a colorless oil (445 mg, 64% yield). $^1$H NMR (400 MHz, $CDCl_3$) δ 1.47 (br. s., 9 H) 2.98 (s, 3 H) 4.60 (br. s., 2 H) 6.56 (br. s., 1 H).

Step 3:

To a solution of compound 199 (445 mg, 1.88 mmol) in DCM (5 mL) was added 4M HCl in dioxane (5 mL) dropwise. The reaction was complete after 2 hours by LCMS. It was concentrated and dried over a vacuum oven at 60° C. for overnight to give compound 200HCl salt as a white solid (333 mg, 100% yield). $^1$H NMR (400 MHz, DMSO-d6) δ 2.59 (s, 3 H) 4.44 (s, 2 H) 7.00 (s, 1 H) 7.90 (br. s., 1 H) 8.21 (br. s., 1 H) 9.77 (br. s., 2 H). LCMS m/z 156 $[M+H]^+$.

Preparation of 5-[(methylamino)methyl]-1,2-oxazole-3-carbonitrile (201)

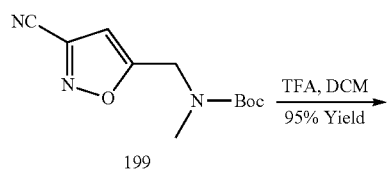
199

-continued

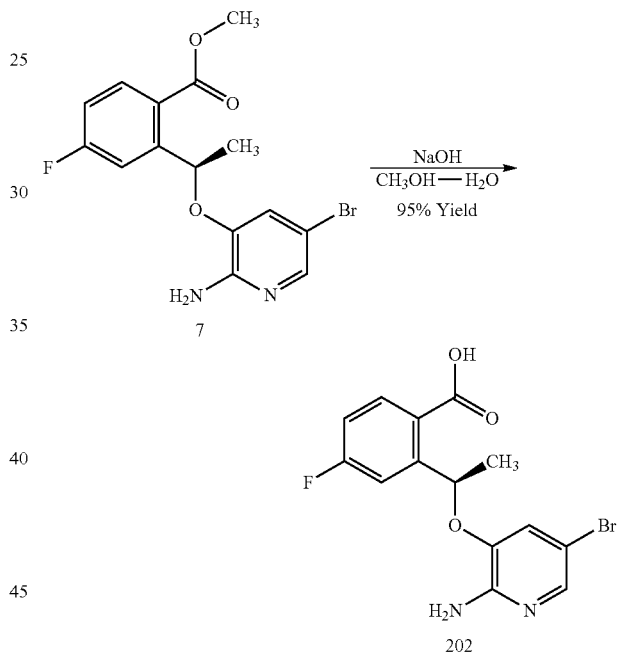

To a solution of compound 199 (850 mg, 2.90 mmol) in DCM (3 mL) was added TFA (3 mL, 38.9 mmol) dropwise. The reaction was complete after 1.5 hours by LCMS. It was concentrated and dried over a vacuum oven at 60° C. overnight to give compound 201 as a brown gum (686 mg, 95% yield).

Preparation of 2-{(1R)-1-[(2-amino-5-bromopyridin-3-yl)oxy]ethyl}-4-fluorobenzoic acid (202)

The procedure described in step 2 for Example 41 was used to prepare compound 202 (731 mg, 95%). $^1$H NMR (400 MHz, DMSO-$d_6$) δ 13.43 (br. s., 1H) 7.97 (dd, J=8.59, 6.06 Hz, 1 H) 7.47-7.64 (m, 2 H) 7.18-7.30 (m, 1 H) 6.87 (s, 1 H) 6.20-6.48 (m, 3 H) 1.58 (d, J=6.32 Hz, 3 H).

Preparation of tert-butyl [(4-bromo-5-ethyl-1,2-oxazol-3-yl)methyl]methylcarbamate (205)

199

-continued

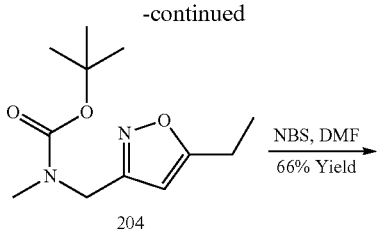

Step 1:

To a 0° C. suspension of compound 203 (1.81 g, 12.9 mmol), TEA (9.10 mL, 64.6 mmol), and DMAP (0.315 g, 2.58 mmol) in ACN (50 mL) was added di-t-butyl-dicarbonate (3.38 g, 15.5 mmol). The reaction mixture was allowed to stir at room temperature for 2 hours. Water and EtOAc were added to the reaction mixture. The aqueous layer was extracted by 2× EtOAc. The organic layer was washed by brine, dried over $Na_2SO_4$, filtered, and concentrated under vacuum. The residue was purified by column chromatography (2 to 30% EtOAc/Heptane) to give compound 204 (2.09 g, 67%) as a colorless oil. $^1$H NMR (400 MHz, METHANOL-d4) δ 1.28 (t, J=7.58 Hz, 3 H) 1.47 (br. s., 9 H) 2.77 (q, J=7.58 Hz, 2 H) 2.88 (s, 3 H) 4.42 (s, 2 H) 6.04 (s, 1 H).

Step 2:

To a solution of compound 204 (500 mg, 2.08 mmol) in DMF (2.2 mL) was added N-bromosuccinimide (444 mg, 2.50 mmol). The reaction mixture was heated to 60° C. for 1 hour. EtOAc (22 mL) was added to the reaction mixture, then washed with water (1×22 mL), and brine (22 mL). The organic layer was dried over $Na_2SO_4$, filtered, and concentrated under vacuum. The residue was purified by column chromatography (3% to 30% EtOAc/Heptane) to give compound 205 (441 mg, 66%) as a colorless oil. $^1$H NMR (400 MHz, METHANOL-$d_4$) δ 1.28 (t, J=7.71 Hz, 3 H) 1.48 (s, 4 H) 1.43 (s, 5 H) 2.82 (q, J=7.66 Hz, 2 H) 2.89 (s, 3 H) 4.50 (s, 2 H).

Synthesis of tert-butyl ((4-bromo-5-cyano-1-((-2-(trimethylsilyl)ethoxy)methyl)-1H-pyrazol-3-yl)methyl)carbamate (Compound 214)

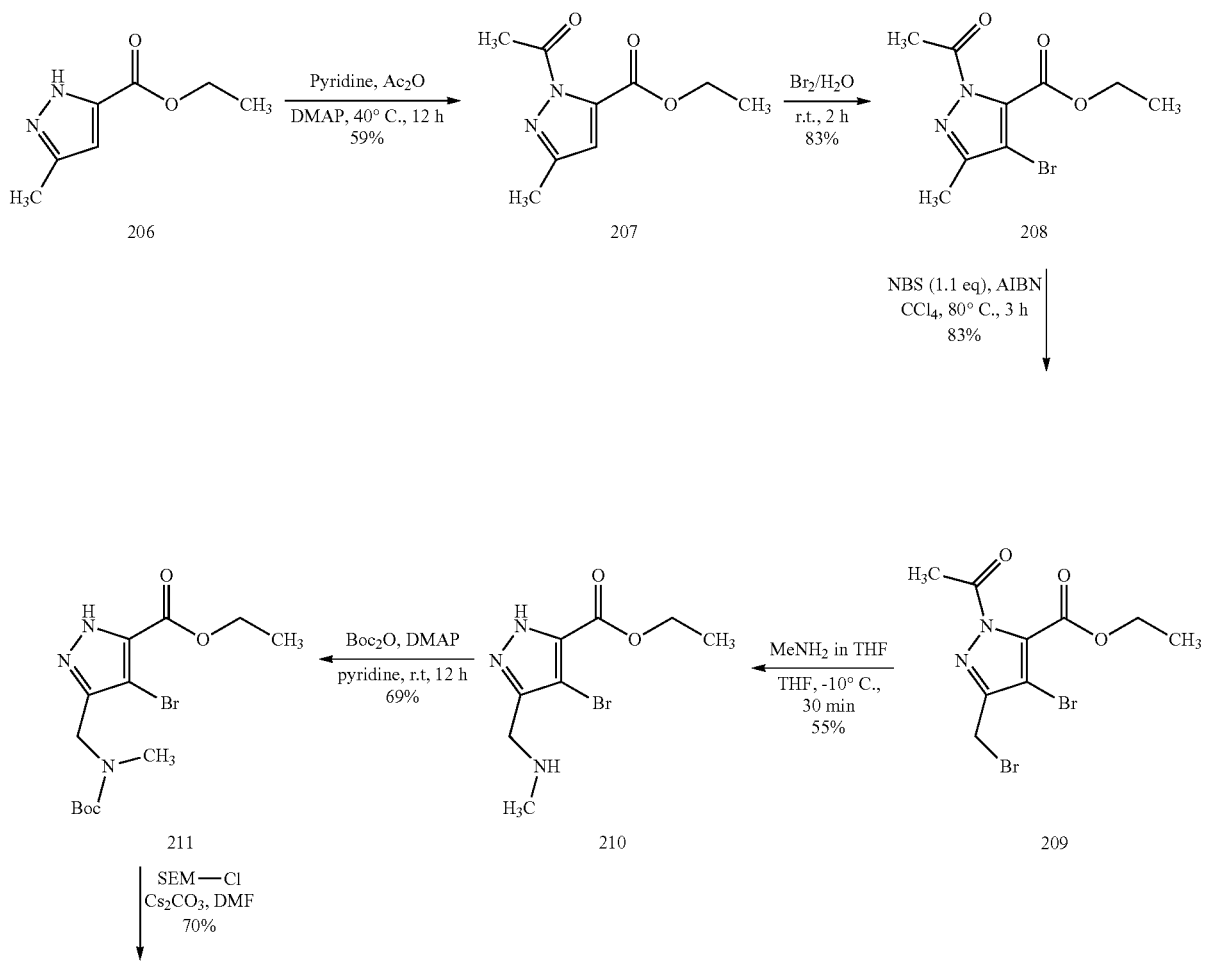

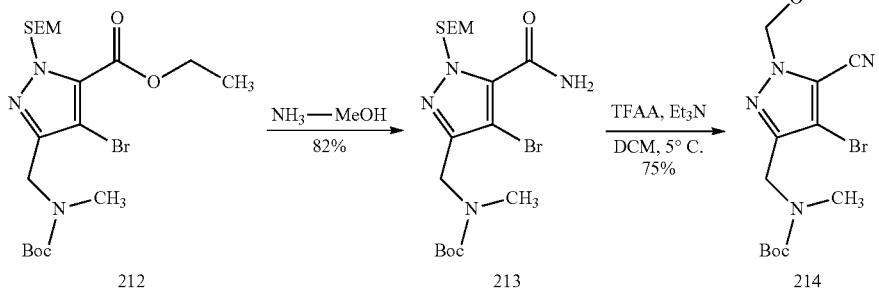

Step 1:

To a solution of compound 206 (120 g, 0.779 mol) in pyridine (800 mL) was added Ac$_2$O (400 mL) and then a catalytic amount of DMAP (13 g, 0.106 mol) at room temperature. The resulting mixture was stirred at room temperature for 12 hours. TLC (Petroleum ether/EtOAc=3:1) showed the reaction was complete. The mixture was concentrated in vacuo to give the residue, which was partitioned between CH$_2$Cl$_2$ (1 L) and H$_2$O (200 mL). The organic layer was separated, washed with brine (100 mL) and dried over Na$_2$SO$_4$, concentrated in vacuo to give the crude product. The crude product was purified by column chromatography over silica gel (Petroleum ether/EtOAc=10:1) to obtain compound 207 (90 g, 59%) as a white solid. $^1$H NMR (400 MHz, CDCl$_3$) δ 6.57 (s, 1H), 4.40-4.35 (q, 2H), 2.74 (s, 3H), 2.57 (s, 3H), 1.39-1.35 (t, 3H).

Step 2:

To a suspension of compound 207 (50 g, 0.255 mol) in H$_2$O (1.5 L) was added dropwise Br$_2$ (44 g, 0.281 mol) at room temperature. The resulting mixture was stirred at room temperature for 3 hours. TLC (Petroleum ether/EtOAc=5:1) showed the reaction was complete. The mixture was extracted with EtOAc (500 mL×3). The organic layers were combined, washed with saturated aqueous NaHCO$_3$ (200 mL), H$_2$O (100 mL) and brine (100 mL), dried over Na$_2$SO$_4$ and concentrated in vacuo give the crude product, which was purified by re-crystallization from petroleum ether/EtOAc (5:1, 120 mL) to obtain compound 208 (58 g, 83%) as a yellow solid. $^1$H NMR (400 MHz, CDCl$_3$) δ 4.47-4.42 (q, 2H), 2.77 (s, 3H), 2.63 (s, 3H), 1.44-1.40 (t, 3H)

Step 3:

To a suspension of compound 208 (56 g, 0.204 mol) in CCl$_4$ (800 mL) was added NBS (40 g, 0.225 mol) and AIBN (9.6 g) at room temperature under a nitrogen atmosphere. The resulting mixture was heated at reflux for 3 hours. TLC (Petroleum ether/EtOAc=3:1) showed the reaction was complete. The mixture was cooled to room temperature and then filtered, and the solids washed with CH$_2$Cl$_2$ (200 mL). The filtrate was washed with saturated aqueous NaHCO$_3$ solution (100 mL×2), H$_2$O (100 mL) and brine (100 mL), dried over Na$_2$SO$_4$ and concentrated in vacuo to give the crude product, which was re-crystallized from petroleum ether/EtOAc (5:1, 120 mL) to obtain compound 209 (60 g, 83%) as a yellow solid. $^1$H NMR (400 MHz, CDCl$_3$) 4.88 (s, 2H), 4.48-4.42 (q, 2H), 2.80 (s, 3H), 1.45-1.41 (t, 3H)

Step 4:

To a solution of compound 209 (59 g, 0.167 mol) in THF (300 mL) was added dropwise CH$_3$NH$_2$ in THF (2 N, 419 mL, 0.835 mol) at −10° C. The resulting mixture was stirred at −10° C. for 30 minutes. TLC (Petroleum ether/EtOAc=3:1) showed the reaction was complete. The mixture was filtered, and the filtrate was concentrated in vacuo at 25° C. for 20 minutes and then at higher temperature to give the crude product, which was purified by column chromatography over silica gel (CH$_2$Cl$_2$/MeOH=100:1-20:1, R$_f$=0.3 in CH$_2$Cl$_2$/MeOH=10:1) to obtain compound 210 (24 g, 55%) as a yellow oil. $^1$H NMR (400 MHz, CDCl$_3$) δ 7.90-7.55 (br, 2H), 6.85 (s, 1H), 5.29 (s, 0.62H, residual CH$_2$Cl$_2$), 4.36-4.31 (q, 2H), 4.21 (s, 2H), 3.49 (s, 1.56H, residual MeOH), 2.68 (s, 3H), 1.37-1.24 (t, 3H).

Step 5:

To a solution of compound 210 (24 g, 0.092 mol) in pyridine (300 mL) was added DMAP (5.66 g, 0.046 mol) and Boc$_2$O (29.81 g, 0.138 mol) at room temperature. The resulting mixture was stirred at room temperature overnight. TLC (Petroleum ether/EtOAc=3:1) showed the reaction was complete. The mixture was concentrated in vacuo to give the crude product, which was purified by column chromatography over silica gel (Petroleum ether/EtOAc=10:1~2:1) to give compound 211 (23 g, 69%) as yellow oil. $^1$H NMR (400 MHz, CDCl$_3$) δ 4.44-4.38 (m, 4H), 2.91 (s, 3H), 1.49 (s, 9H), 1.25-1.24 (t, 3H)

Step 6:

To a suspension of compound 211 (23 g, 0.0637 mol) in anhydrous DMF (400 mL) was added Cs$_2$CO$_3$ (46.8 g, 0.14 mol) at room temperature. The resulting mixture was stirred at room temperature for 30 minutes. After 30 minutes, SEM-Cl (24.39 g, 0.146 mol) was added into the mixture. The resulting mixture was stirred at room temperature for 2 hours. TLC (Petroleum ether/EtOAc=3:1) showed the reaction was complete. The mixture was diluted with EtOAc (1 L) and brine (200 mL). The organic layer was separated and washed with H$_2$O (200 mL×2), brine (100 mL), dried over Na$_2$SO$_4$ and concentrated in vacuo to give the crude product, which was purified by column chromatography over silica gel (Petroleum ether/EtOAc=10:1) to obtain compound 212 (22 g, 70%) as a yellow oil. $^1$H NMR (400 MHz, CDCl$_3$) δ 5.90-5.76 (s, 1H), 4.72-4.65 (m, 2H), 4.47-4.40 (q, 2H), 3.55-3.51 (m, 2H), 2.95-2.76 (m, 3H), 1.49 (s, 9H), 1.43-1.39 (t, 3H), 0.96-0.85 (m, 2H), 0-0.05 (m, 9H).

Step 7:

A solution of compound 212 (22 g, 0.0448 mol) in NH$_3$-MeOH (5 N, 350 mL) was heated at 60° C. for 12 hours in a sealed tube. TLC (Petroleum ether/EtOAc=1:1) showed the reaction was complete. The mixture was concentrated in vacuo to give the residue, which was partitioned between CH$_2$Cl$_2$ (200 mL) and citric acid (2 N, 30 mL). The organic layer was separated and washed with aqueous NaHCO$_3$ (2 N, 30 mL), brine (20 mL) and dried over Na$_2$SO$_4$, filtered and concentrated in vacuo to give the crude product, which was purified by column chromatography over silica gel (Petroleum ether/EtOAc=5:1~3:1) to obtain compound 213 (17 g, 82%) as a yellow oil. $^1$H NMR (400 MHz, CDCl$_3$) δ 6.89 (s, 1H), 5.80 (s, 1H), 5.75 (s, 1H), 4.53-4.48 (m, 2H), 3.62-3.55 (m, 2H), 2.83-2.77 (m, 2H), 1.48 (s, 9H), 0.93-0.87 (m, 2H), 0 (s, 9H)

Step 8:

To a solution of compound 213 (16 g, 0.0346 mol) in anhydrous CH$_2$Cl$_2$ (250 mL) was added Et$_3$N (14.4 mL, 0.104 mol) and then TFAA (9.6 mL) at 0° C. The resulting mixture was stirred at 0° C. for 2 hours. TLC (Petroleum ether/EtOAc=3:1) showed the reaction was complete. The mixture was concentrated in vacuo to give the crude product, which was partitioned between CH$_2$Cl$_2$ (150 mL) and citric acid (40 mL, 2 N). The organic layer was separated, washed with aqueous NaHCO$_3$ (2 N, 50 mL), brine (20 mL) and dried over Na$_2$SO$_4$, filtered and concentrated in vacuo to give the crude product, which was purified by column chromatography over silica gel (Petroleum ether/EtOAc=50:1) to give compound 214 (11.5 g, 74.8%) as a yellow oil. $^1$H NMR (400 MHz, CDCl$_3$) δ 5.52 (s, 2H), 4.61-4.42 (m, 2H), 3.63-3.51 (m, 2H), 2.83-2.79 (m, 2H), 1.47 (s, 9H), 0.95-0.86 (m, 2H), 0 (s, 9H). LC-MS m/z 468 [M+Na]$^+$.

Preparation of tert-butyl {[4-bromo-5-cyano-1-(2,2-difluoroethyl)-1H-pyrazol-3-yl]methyl}methylcarbamate (225)

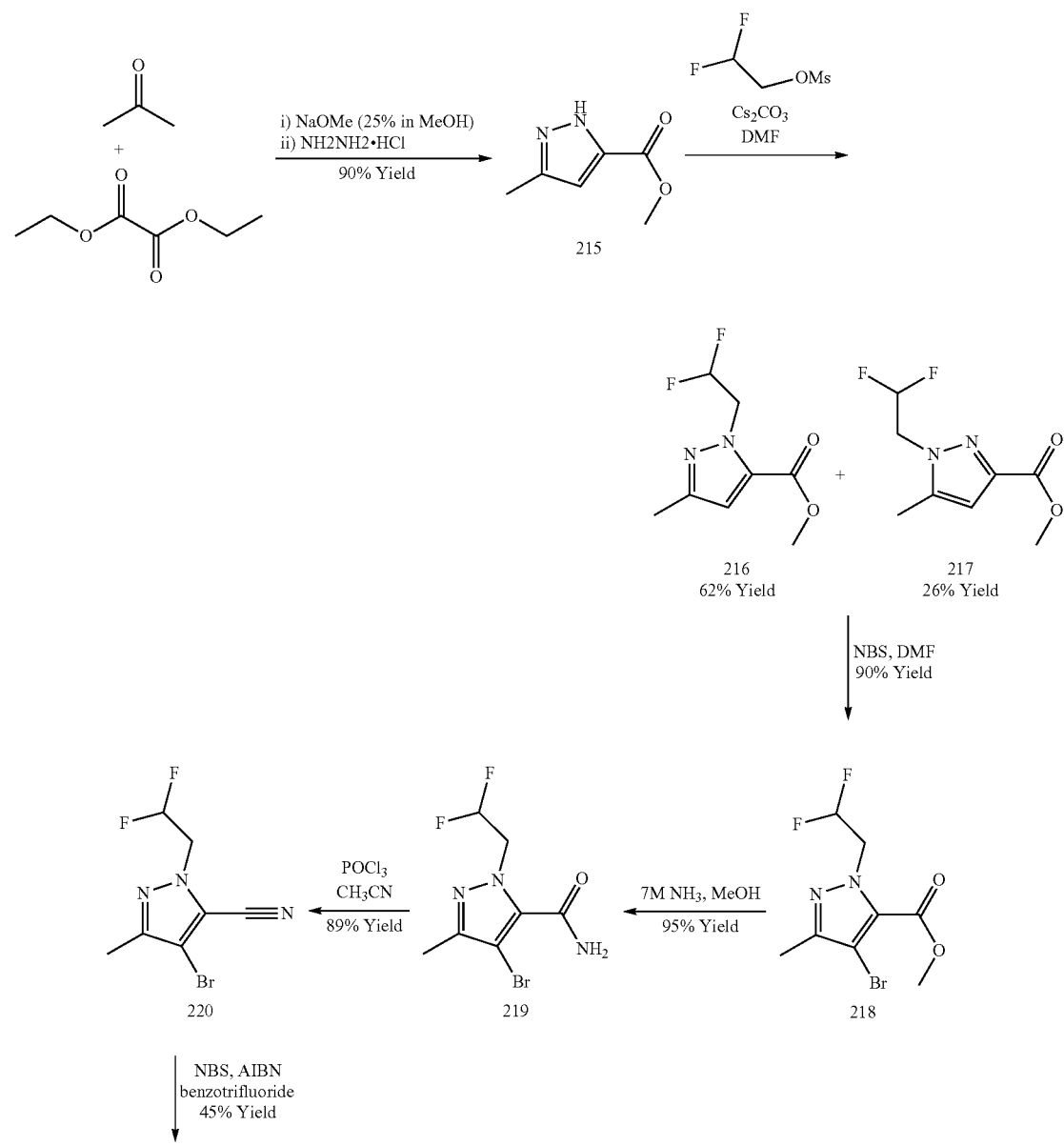

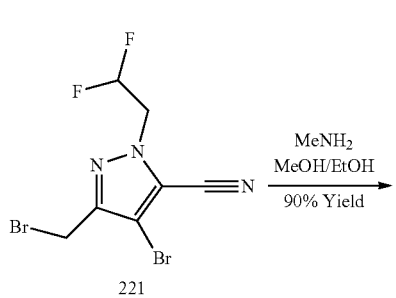
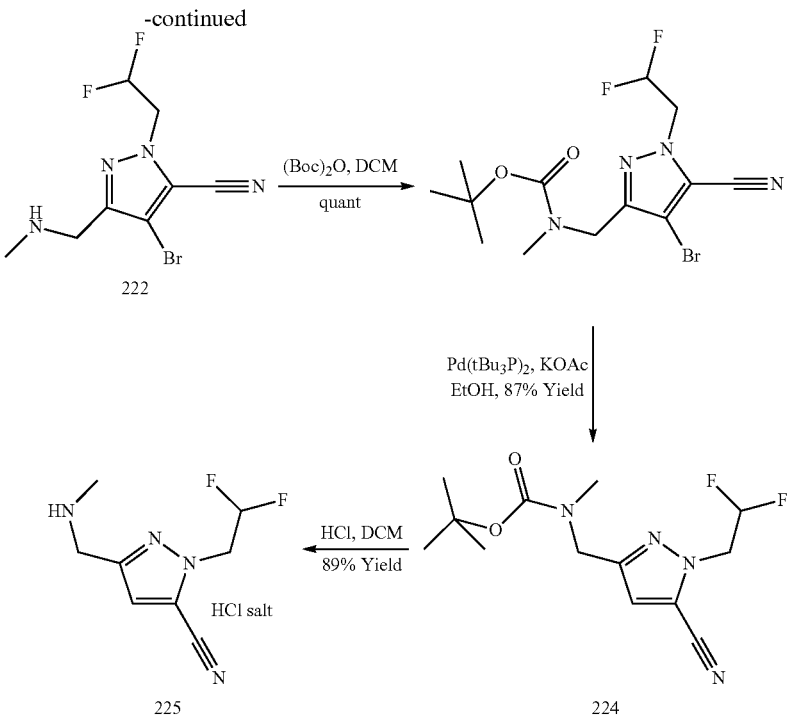

Step 1:

To a 5 liter flask fitted with an overhead stirrer was added NaOMe solution (25% in MeOH, 500 mL, 2.31 mol) under an $N_2$ atmosphere. To this was added MeOH (1.50 L) followed by a solution of diethyl oxalate (337 g, 2.31 mol) in acetone (168 mL, 2.31 mol) slowly over 50 mins (after 35 mins the reaction had set solid so a further 500 mL of MeOH was added). On complete addition the thick pale yellow reaction mixture was allowed to stand at room temperature for 2 days under $N_2$. The reaction was then cooled to 0° C. with stirring and conc. 37% aq HCl (190 mL, 2.31 mol) was slowly added followed by slow addition hydrazine monohydrate (112 mL, 2.31 mol) over 60 mins, maintaining a internal reaction temperature of less than 20° C. The reaction was then stirred at room temperature overnight. The reaction was then filtered through celite, washing the pad with MeOH (200 mL). The solvent was removed to a very low volume and the residue was partitioned between EtOAc (2.5 L) and water/brine (2.0 L, 1:1). The organic phase was collected and the aq phase extracted with additional EtOAc (500 mL). The combined organics were washed with brine 1.0 L), dried over $Na_2SO_4$ and evaporated to dryness, giving compound 215 (226 g, 70%) as a cream colored solid. $^1$H NMR (400 MHz, Chloroform-d) δ 11.64 (s, 1H), 6.58 (d, J=0.8 Hz, 1H), 3.89 (s, 3H), 2.37 (d, J=0.7 Hz, 3H), [MH]+ 140.99.

Step 2:

A mixture of compound 215 (30.8 g, 0.22 mol), 2,2-difluoroethyl methanesulfonate (38.0 g, 0.24 mol) and $Cs_2CO_3$ (94.3 g, 0.29 mol) in DMF (150 mL) was stirred at 80° C. for 3.5 hours. After cooling, the reaction was diluted with EtOAc (200 mL) and water (800 mL). The organic was collected and the aqueous was extracted with EtOAc (2×300 mL). The combined organics were washed with water (500 mL), brine (500 mL), dried ($Na_2SO_4$) and evaporated. Purification by flash chromatography (20% to 50% EtOAc in heptanes) gave compound 216 (28 g, 62%) and compound 217 (12 g, 26%).

Compound 216: $^1$H NMR (400 MHz, Chloroform-d) δ 6.64 (s, 1H), 6.09 (tt, J=55.9, 4.5 Hz, 1H), 4.87 (td, J=13.1, 4.5 Hz, 2H), 3.86 (s, 3H), 2.26 (s, 3H).

Compound 217: $^1$H NMR (400 MHz, Chloroform-d) 6.55 (s, 1H), 6.09 (tt, J=55.5, 4.5 Hz, 1H), 4.41 (td, J=13.1, 4.5 Hz, 2H), 3.86 (s, 3H), 2.30 (s, 3H), [MH]+ 205.06.

Step 3:

NBS (32.0 g, 180 mmol) was added to a solution of compound 216 (35.0 g, 172 mmol) in DMF (100 mL) and stirred at 20° C. for 20 hr. Water (200 mL) and 2% aq $NaHSO_4$ (150 mL) was added and the mixture was stirred for 10 mins, then extracted into EtOAc/heptanes (2:1, 400 mL). The organic layer was separated and washed with brine (200 mL), dried ($Na_2SO_4$) and evaporated, giving compound 218 (41 g, 90%) as an oil. $^1$H NMR (400 MHz, DMSO-d6) δ 6.36 (tt, J=55.0, 3.8 Hz, 1H), 4.90 (td, J=14.6, 3.8 Hz, 2H), 3.88 (s, 3H), 2.20 (s, 3H), [MH]+ 283 and 285 (100%).

Step 4:

A mixture of compound 218 (41 g, 0.145 mol) and 7M $NH_3$ in MeOH (500 mL) was stirred at 25° C. for 5 days. The reaction mixture was then evaporated giving compound 219 (37 g, 95%) as a white solid. $^1$H NMR (400 MHz, DMSO-d6) δ 8.04 (s, 1H), 7.77 (s, 1H), 6.31 (tt, J=55.1, 3.7 Hz, 1H), 4.74 (td, J=15.0, 3.7 Hz, 2H), 2.16 (s, 3H), [MH]+ 268 and 270 (100%).

Step 5:

POCl3 (74 g, 0.483 mol) was added to a solution of compound 219 (37 g, 0.138 mol) in acetonitrile (250 mL) at 25° C. The reaction was then stirred at reflux for 6 hours. After cooling, the reaction was slowly poured into water (1000 mL) while controlling the exotherm by keeping the mixture below 40° C. by addition of ice to the aqueous as needed. After stirring for 5 minutes and no further exotherm was noted, the mixture was extracted into EtOAc/heptanes (1:1, 500 mL). The organic layer was separated and washed with saturated aq $NaHCO_3$ (200 mL), dried ($Na_2SO_4$) and evaporated, giving compound 220 (27 g, 78%) as a light brown solid. $^1$H NMR (400 MHz, DMSO-d6) δ 6.43 (tt, J=53.9, 2.9 Hz, 1H), 4.81 (td, J=15.9, 2.8 Hz, 2H), 2.23 (s, 3H).

Step 6:

A mixture of compound 220 (15 g, 60 mmol), NBS (14.95 g, 84 mmol) and AIBN (492 mg, 3.0 mmol) in benzotrifluoride (200 mL) was stirred at 80° C. for 12 hours. After cooling, the mixture was filtered through a short pad of silica gel and the filter cake was washed with toluene (20 mL). The filtrate was evaporated, giving compound 221 (9.0 g, 45% yield) as a pale yellow oil. $^1$H NMR (400 MHz, DMSO-d6) δ 6.72-6.21 (m, 1H), 5.03-4.72 (m, 2H), 4.64 (s, 2H).

Step 7:

A solution of compound 221 (18 g, 27.4 mmol) in EtOH (50 mL) was slowly added to a solution of MeNH$_2$ (40% in MeOH, 56 mL, 0.55 mol) in additional EtOH (50 mL) at 0° C. over 15 mins. After complete addition the reaction was stirred at 0° C. for 2 hours. The mixture was then concentrated under vacuo to approx 50 mL in volume. EtOH (50 mL) was added and the mixture was again concentrated under vacuo to approx 40 mL volume. 1M aq HCl (90 mL) was added, followed by TBME (150 mL) and the mixture was stirred vigorously for 5 minutes. The aqueous layer was collected and washed once more with TBME (100 mL). The aqueous layer was collected and basified to approx pH 12-13 (pH paper) using conc. aq NH$_3$. The resulting mixture was extracted into DCM (3×150 mL). The organics were dried (Na$_2$SO$_4$) and evaporated, giving compound 222 (6.8 g, 90%) as a pale brown oil which solidified on standing. $^1$H NMR (400 MHz, DMSO-d6) δ 6.44 (tt, J=53.8, 2.8 Hz, 1H), 4.84 (td, J=15.9, 2.8 Hz, 2H), 3.63 (s, 2H), 2.24 (s, 3H), [MH]$^+$ 279.0 and 281.0 (60%).

Step 8:

Di-tert-butyl dicarbonate (5.6 g, 25.6 mmol) was added portionwise (solid) to a solution of compound 222 (6.8 g, 24.4 mmol) in DCM (100 mL) at 20° C. over 5 minutes. The mixture was then concentrated under vacuo and the residue purified by flash chromatography (20% EtOAc in heptane) giving compound 223 (9.24 g, quant) as an oil. $^1$H NMR (400 MHz, DMSO-d6) δ 6.44 (tt, J=53.7, 2.7 Hz, 1H), 4.86 (td, J=16.0, 2.7 Hz, 2H), 4.42 (s, 2H), 2.78 (s, 3H), 1.47-1.28 (m, 9H), [MH-Boc]+268 and 270 (40%).

Step 9:

Pd(t-Bu$_3$P)$_2$ (240 mg) was added in one portion to a mixture of compound 223 (1.80 g, 4.75 mmol), KOAc (1.39 g, 14.3 mmol) and de-gassed IMS (95% EtOH, 18.0 mL). The mixture was then stirred under microwave irradiation (120° C.) for 60 mins. After cooling, the mixture was concentrated and purified by column chromatography (30% EtOAc in heptanes) giving compound 224 (1.25 g, 87%) as an oil. $^1$H NMR (400 MHz, DMSO-d6) δ 7.08 (s, 1H), 6.42 (tt, J=54.0, 2.9 Hz, 1H), 4.80 (td, J=15.8, 2.9 Hz, 2H), 4.36 (s, 2H), 2.79 (s, 3H), 1.38 (s, 9H), [MH-Boc]+201.06.

Step 10:

HCl (4M in dioxane, 5.0 mL) was added to a solution of compound 224 (1.40 g, 4.66 mmol) and the mixture was stirred at 25° C. overnight. The mixture was concentrated under vacuum and the residue was slurried with EtOAc (10 mL) and collected by filtration. Compound 225 (980 mg, 89%) was obtained as the hydrochloride salt (cream colored solid). $^1$H NMR (400 MHz, DMSO-d6) δ 9.47 (s, 2H), 7.44 (s, 1H), 6.46 (tt, J=53.8, 2.8 Hz, 1H), 4.88 (td, J=16.0, 2.7 Hz, 2H), 4.18 (s, 2H), 2.54 (s, 3H), [MH]+ 201.11.

Preparation of tert-butyl {[4-bromo-5-cyano-1-(2,2-difluoroethyl)-1H-pyrazol-3-yl]methyl}methylcarbamate (226)

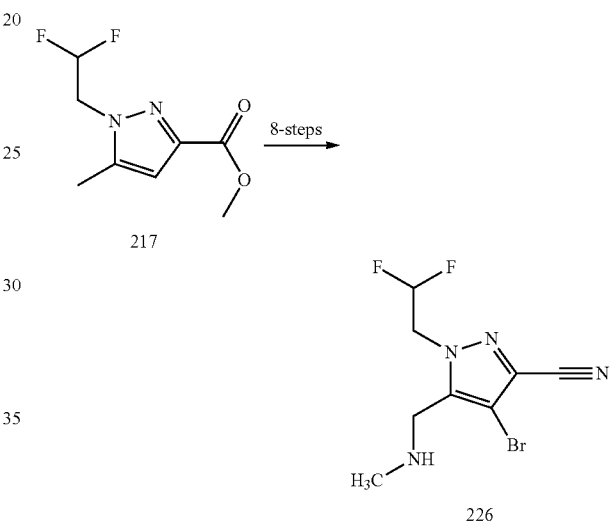

The procedures described in steps 3-10 for compound 225 were used to prepare compound 226 (30% yield). $^1$H NMR (400 MHz, DMSO-d6) δ 9.57 (s, 2H), 7.30 (s, 1H), 6.47 (tt, J=54.2, 3.4 Hz, 1H), 4.96 (td, J=15.2, 3.4 Hz, 2H), 4.36 (s, 2H), 2.59 (s, 3H), [MH+CH3CN]+242.04.

Synthesis of tert-butyl ((5-cyano-1-oxetan-3-yl)-1H-pyrazol-3-yl)methyl)(methyl)carbamate (Compound 234)

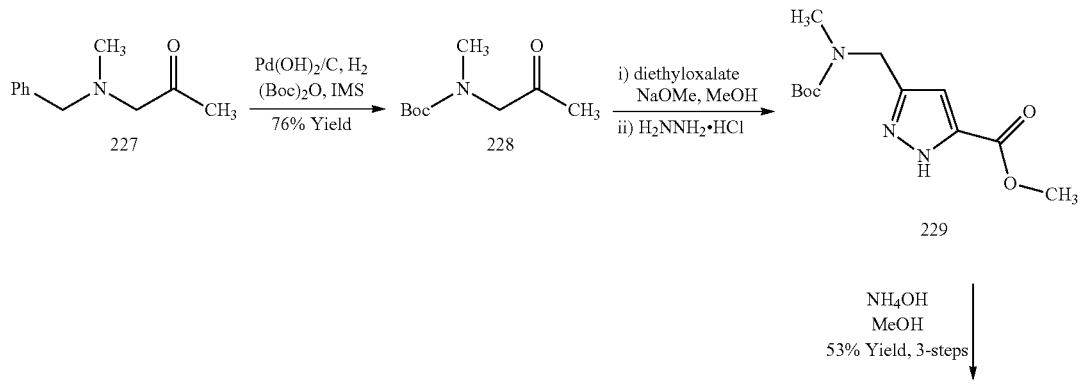

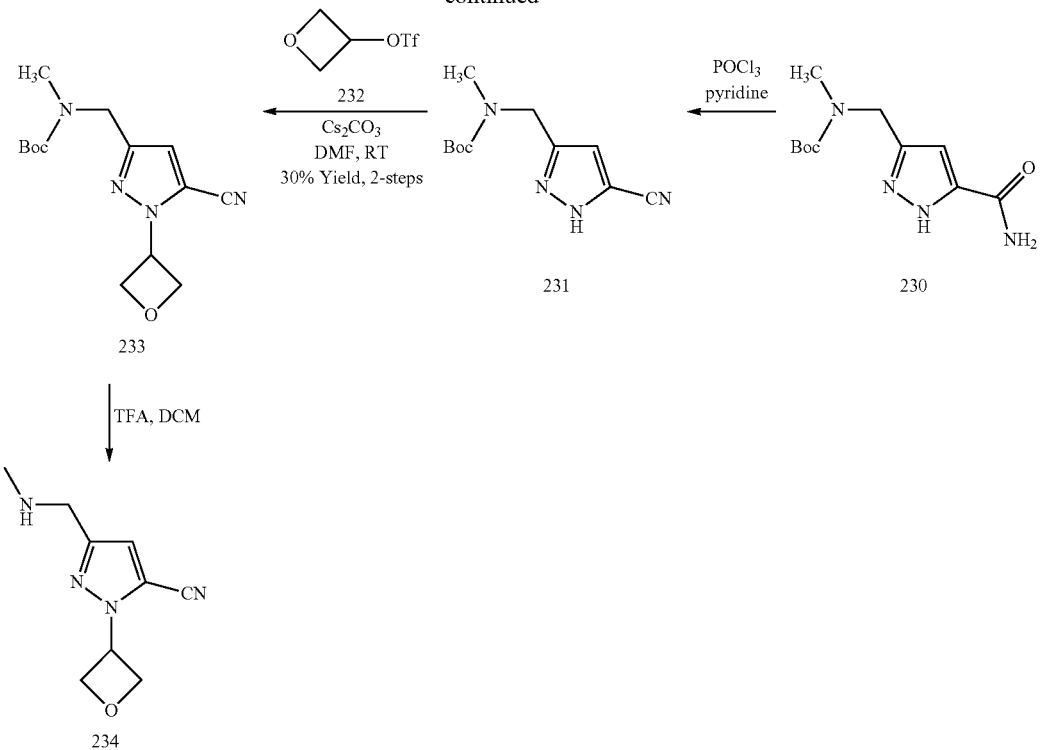

Step 1:

Compound 227 (45.3 g, 0.256 mol) was dissolved in IMS (475 mL) and (Boc)$_2$O (58.6 g, 0.269 mol) and Pd(OH)$_2$/C (4.0 g, 9 wt %) were added. The reaction mixture was then stirred at room temperature under a hydrogen atmosphere (50 psi) for three hours before being heated at 50° C. for a further two hours. After cooling to room temperature the reaction mixture was filtered through celite, eluting with additional IMS and the filtrate concentrated to give a brown oil. The majority of the crude material (43.2 g) was purified by flash chromatography over silica gel (10% to 30% EtOAc in heptanes) to give compound 228 as a yellow oil (29.5 g, 76% yield, >95% purity by $^1$H NMR). 1H NMR indicates a ~1:1.1 mixture of tautomers. $^1$H NMR (400 MHz, CDCl$_3$) δ 4.01 (s, 2H), 3.90 (s, 2H), 2.92 (s, 3H), 2.89 (s, 3H), 2.12 (s, 6H), 1.47 (s, 9H), 1.42 (s, 9H).

Step 2:

A solution of 5.4M NaOMe in MeOH (29.2 mL, 0.157 mol) was diluted with further MeOH (150 mL) and stirred at room temperature under nitrogen. A solution of compound 228 (29.5 g, 0.157 mol) and diethyloxalate (21.3 mL, 0.157 mol) in MeOH (40 mL) was added from a dropping funnel over 10 minutes and the resultant yellow reaction mixture heated to 50° C. After 3 hours, additional diethyloxalate (2 mL, 0.015 mol) and NaOMe solution (2 mL, 0.011 mol) were added and heating continued for a further 30 minutes. The reaction was cooled to 5-10° C. and hydrazine monohydrochloride (10.7 g, 0.157 mol) added in portions over 10 minutes, maintaining the temperature in this range. The reaction was then left to warm to room temperature and was stirred for 60 hours. H2O (200 mL) and brine (100 mL) were added to the reaction mixture before being extracted with EtOAc (3×200 mL). The combined organic extracts were washed with brine (100 mL), dried over MgSO4 and concentrated to give compound 229 as a yellow oil, which was used without purification (43.2 g). $^1$H NMR (400 MHz, CDCl$_3$) δ 6.72 (s, 1H), 4.47-4.32 (m, 2H), 3.91 (s, 3H), 2.86 (s, 3H), 1.47 (s, 9H). LC-MS ES m/z 268 [M+H]+.

Step 3:

Compound 229 (21.1 g, 78.3 mmol) was dissolved in MeOH (60 mL) and 33% aqueous NH$_3$ solution (100 mL) added before the reaction solution was stirred at room temperature overnight. The volume of MeOH was reduced under vacuum, until a precipitate just started to form. The mixture was left to crystallize and the precipitate collected by filtration, washed with H$_2$O (2×30 mL) and thoroughly dried in a vacuum oven (40° C., overnight) to give a tautomeric mixture (~1:1) of compound 230 as an off-white solid (10.4 g, 53% yield over two steps). $^1$H NMR indicates a ~1:1.2 mixture of tautomers. $^1$H NMR (400 MHz, DMSO-d$_6$) δ 13.27 (s, 1H), 13.11 (s, 1H), 7.91 (s, 1H), 7.55-7.33 (m, 2H), 7.15 (s, 1H), 6.68 (d, J=2.0 Hz, 1H), 6.43 (d, J=1.9 Hz, 1H), 4.37 (s, 2H), 4.30 (s, 2H), 2.79 (s, 3H), 2.75 (s, 3H), 1.41 (s, 18H). LC-MS ES m/z 252 [M+H]$^+$.

Step 4:

Compound 230 (10.5 g, 41.3 mmol) was dissolved in pyridine (105 mL) and POCl$_3$ (9.6 mL, 103.2 mmol) was added slowly from a dropping funnel, maintaining the temperature around 15° C. using an ice/H$_2$O cooling bath. The reaction mixture was stirred for 90 minutes, during which time it turned yellow and then a darker brown color. In portions, the mixture was then poured into H$_2$O (250 mL), maintaining the temperature around 30° C. by the addition of ice. Once hydrolyzed, the mixture was extracted with EtOAc (3×100 mL) and the combined organic extracts washed with saturated aqueous NaHCO$_3$ solution (150 mL) before being dried over MgSO$_4$ and concentrated. The residue was azeotroped with toluene (3×100 mL) and then heptanes (3×100 mL) to remove residual pyridine to give compound 231 as a brown gum which was used without purification (9.1 g, >85% purity by ¹H NMR). ¹H NMR (400 MHz, CDCl₃) δ 6.56 (s, 1H), 4.31 (s, 2H), 2.89 (s, 3H), 1.48 (s, 9H). LC-MS ES m/z 235 [M+H]⁺.

Step 5:

Crude compound 231 (9.1 g) was dissolved in DMF (85 mL) under nitrogen and Cs₂CO₃ (37.6 g) was added. A solution of oxetan-3-yl trifluoromethanesulfonate 232 (9.5 g) in DMF (15 mL) was then added slowly from a dropping funnel, maintaining the temperature between 15-20° C. After complete addition, the reaction mixture was stirred for 90 minutes before being diluted with H₂O (100 mL) and extracted with EtOAc (3×100 mL). The combined organic extracts were washed with brine (100 mL), dried over MgSO₄ and concentrated to give a brown residue. The crude material was purified by flash chromatography over silica gel (1:2 EtOAc: heptanes then 1:1 EtOAc:heptanes) to give compound 233 as a yellow oil (4.00 g, 30% yield over two steps). ¹H NMR (400 MHz, DMSO-d₆) 7.14-6.89 (m, 1H), 5.71 (tt, J=7.6, 6.0 Hz, 1H), 4.96 (t, J=7.2 Hz, 2H), 4.88 (t, J=6.5 Hz, 2H), 4.41 (s, 2H), 2.81 (s, 3H), 1.47-1.34 (m, 9H). Further elution afforded the regioisomeric pyrazole as a colorless solid (3.28 g, 25% yield over two steps). ¹H NMR (400 MHz, DMSO-d₆) δ 6.93 (s, 1H), 5.77 (s, 1H), 4.91-4.81 (m, 4H), 4.47 (s, 2H), 2.72 (s, 3H), 1.41 (s, 9H).

Step 6:

Compound 233 (0.50 g, 1.71 mmol) was dissolved in DCM (5 mL) and cooled in an ice-water bath under nitrogen. TFA (5 mL) was then added and the reaction mixture was stirred for two hours, during which it warmed to room temperature. The reaction was concentrated and residual TFA removed from the residue by co-evaporation with DCM (2×10 mL) and then toluene (2×10 mL). The TFA salt of compound 234 was obtained as a yellow gum (0.85 g). ¹H NMR (400 MHz, DMSO-d6) δ 9.00 (s, 2H), 7.25 (s, 1H), 5.78 (tt, J=7.6, 5.9 Hz, 1H), 5.00 (t, J=7.2 Hz, 2H), 4.89 (t, J=6.4 Hz, 2H), 4.27 (t, J=5.6 Hz, 2H), 2.61 (t, J=5.2 Hz, 3H).

Preparation of 3-[(methylamino)methyl]-1-(propan-2-yl)-1H-pyrazole-5-carbonitrile hydrochloride (1:1) (239)

Step 1:

Di tert-butylazodicarboxylate (6.5 g, 28.2 mmol) was added portionwise (solid) to a solution of compound 229 (8.0 g, 28.2 mmol), Ph₃P (7.4 g, 28.2 mmol) and isopropanol (2.55 g, 42.5 mmol) in THF (80 mL) at 0° C. over 5 minutes. The reaction was then stirred at 0° C. to 20° C. over 2 hours. The reaction was then concentrated and the residue purified by flash chromatography (10% to 40% EtOAc in heptanes) giving compound 235 (7.1 g, 77%). ¹H NMR (400 MHz, DMSO-d6) δ 6.63 (d, J=15.6 Hz, 1H), 5.36 (hept, J=6.6 Hz, 1H), 4.37-4.23 (m, 4H), 2.76 (s, 3H), 1.39 (t, J=5.6 Hz, 15H), 1.29 (t, J=7.1 Hz, 3H), [MH]+ 326.12.

Step 2:

NaOH (3.4 g, 87.3 mmol) was dissolved in water (6.0 mL) and the solution was added to a solution of compound 235 in MeOH and the reaction was stirred at 25° C. for 2 hours. The mixture was then diluted with water (250 mL) and acidified to approx pH 2 (pH paper) using 5% aq NaHSO₄. The mixture was then extracted into EtOAc (2×120 mL). The organic layers were washed with brine (100 mL), dried (Na₂SO₄) and evaporated, giving compound 236 (6.0 g, 92%) as a white solid. ¹H NMR (400 MHz, DMSO-d6) δ 13.26 (s, 1H), 6.58 (d, J=11.4 Hz, 1H), 5.42 (hept, J=6.6 Hz, 1H), 4.30 (s, 2H), 2.76 (s, 3H), 1.38 (m, 15H), [MH]+ 298.07.

Step 3:

Carbonyldiimidazole (3.56 g, 22.0 mmol) was added to a solution of compound 236 in DMF (35 mL) at room temperature. After stirring for 45 minutes, the reaction was cooled to 0° C. and ammonia gas was bubbled through the mixture for 10 minutes. The reaction was then allowed to stir for 2 hours at room temperature, before dilution with water (250 mL). The mixture was extracted into EtOAc (2×100 mL). The combined organics were washed with brine (200 mL), dried (Na₂SO₄) and evaporated, giving compound 237 (4.9 g, 83%) as an oil which set to a solid on standing. ¹H NMR (400 MHz, DMSO-d6) δ 7.92 (s, 1H), 7.44 (s, 1H), 6.65 (s, 1H), 5.51 (hept, J=6.6 Hz, 1H), 4.38-4.24 (m, 2H), 2.76 (s, 3H), 1.40 (d, J=4.1 Hz, 9H), 1.34 (d, J=6.6 Hz, 6H), [MH]+ 297.11.

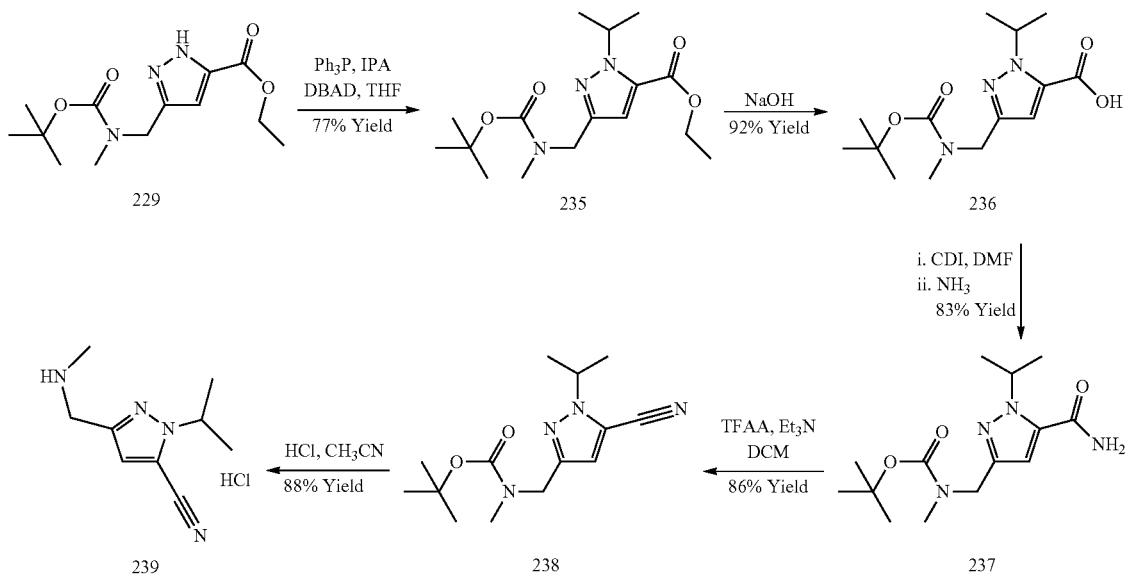

Step 4:

A solution of trifluoroacetic anhydride in DCM (50 mL) was added slowly to a solution of compound 237 (4.90 g, 16.55 mmol) and Et₃N (5.10 g, 50.0 mmol) in DCM (50 mL) at 0° C. over minutes. The reaction was stirred at 0° C. for 60 minutes, before addition of water (100 mL) and stirred for 10 minutes. The organic layer was separated, dried (Na₂SO₄) and evaporated. The residue was purified by flash chromatography (20% EtOAc in heptanes), giving compound 238 (3.95 g, 86%) as a colorless oil. ¹H NMR (400 MHz, DMSO-d6) δ 6.95 (d, J=15.2 Hz, 1H), 4.72 (hept, J=6.6 Hz, 1H), 4.34 (s, 2H), 2.78 (s, 3H), 1.45 (d, J=6.6 Hz, 6H), 1.43-1.34 (m, 9H), [MH-Boc]+179.14.

Step 5:

HCl (4M in dioxane, 5.0 mL) was added to a solution of compound 238 (3.90 g, 14.0 mmol) in CH₃CN and stirred at 50° C. for 60 mins. After cooling, the reaction was concentrated, then EtOAc (35 mL) was added and the mixture was filtered to collect compound 239 (2.20 g, 88%) as a white solid. ¹H NMR (400 MHz, DMSO-d6) δ 9.49 (s, 2H), 7.34 (s, 1H), 4.79 (hept, J=6.6 Hz, 1H), 4.16 (s, 2H), 2.53 (s, 3H), 1.47 (d, J=6.6 Hz, 6H), [MH]+ 179.14.

Preparation of 5-bromo-3-[(1R)-2-fluoro-1-(5-fluoro-2-iodophenyl)ethoxy]pyrazin-2-amine (241)

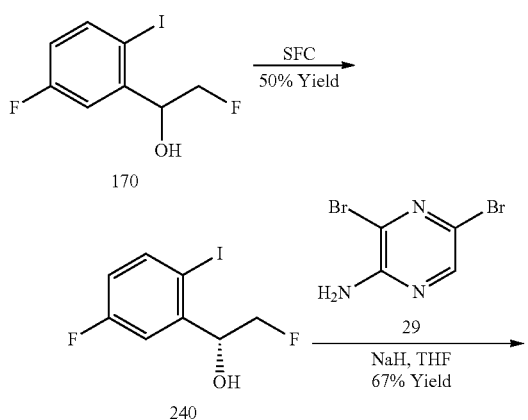

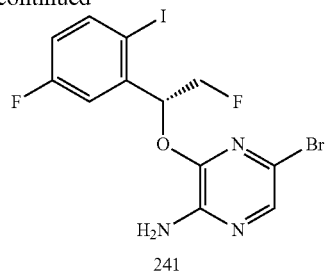

Step 1:

Compound 170 was separated by preparative SFC to give pure compound 240 (4 g, 50%) as yellow oil. ¹H NMR (400 MHz, CDCl3): δ 7.75-7.78 (m, 1H), 7.34-7.37 (m, 1H), 6.79-6.84 (m, 1H), 5.17-5.24 (m, 1H), 4.57-4.70 (m, 1H), 4.17-4.34 (m, 1H), 2.652-2.658 (s, 1H).

Step 2:

To a solution of compound 240 (3 g, 10.6 mmol) in anhydrous THF (100 mL) was added NaH (464 mg, 11.6 mmol, 60% in oil) at 0° C. under N2, and the mixture was stirred for another 30 min. A solution of compound 12 (2.141 g, 8.5 mmol) in dry THF (10 mL) was added to the above mixture at 0° C., and the mixture was refluxed for 10 hours. THF was remover under reduced pressure, and the residue was dilute with H₂O (100 mL)/EtOAc (100 mL). The mixture was filtered, and the filtrated was extracted with EtOAc (100 mL×3). The combined organic layers were washed with brine (100 mL), dried over Na₂SO₄ and concentrated to give residue which was purified by silica gel column eluting with petroleum ether:EtOAc=60/1~10/1 to give compound 241 (2.6 g, 67%) as a yellow solid. ¹H NMR (400 MHz, CDCl₃): δ 7.81-7.84 (m, 1H), 7.67 (s, 1H), 7.09-7.12 (d, 1H), 6.79-6.84 (t, 1H), 6.35-6.42 (q, 1H), 4.91 (s, 2H), 4.59-4.81 (m, 2H), [M+H]+ 457.8.

Synthesis of N-methyl-1-(6-methylimidazo[1,2-a]pyrimidin-2-yl)methanamine (Compound 246)

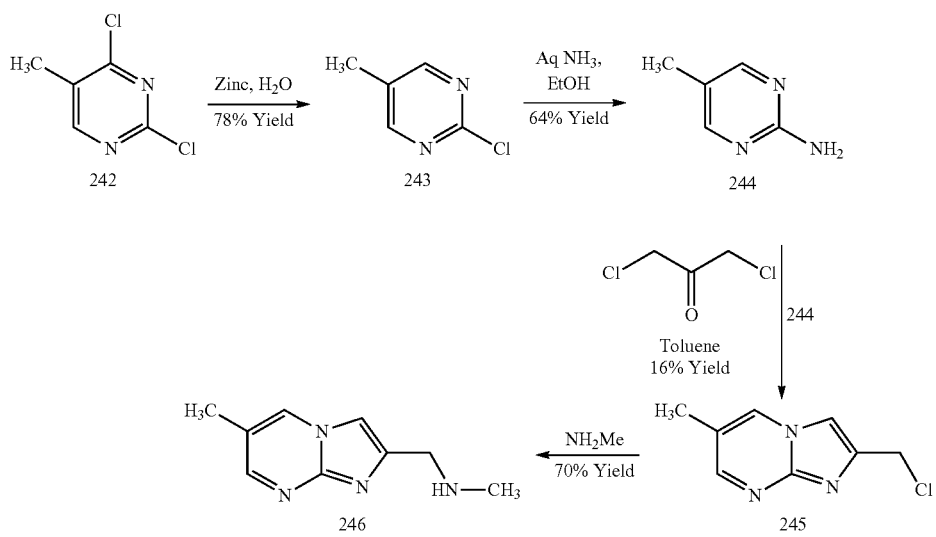

Step 1:
A suspension of compound 242 (50.0 g, 307 mmol) and freshly activated (acid washed) Zn (59.8 g, 920 mmol) in water (500 mL) was heated at reflux for 3 hours. TLC showed consumption of SM. The reaction mixture was cooled to room temperature, filtered through a pad of celite, and rinsed with $CH_2Cl_2$ (500 mL). The phases of the filtrate were separated and the organic phase was washed with brine (300 mL), dried over $MgSO_4$, filtered and concentrated under vacuum carefully to give compound 243 as a beige powder (30.6 g, 78% yield, 95% purity by $^1$H NMR). $^1$H NMR (400 MHz, DMSO-$d_6$) δ 8.63 (d, J=0.9 Hz, 2H), 2.27 (t, J=0.8 Hz, 3H).
Step 2:
Compound 243 (30.6 g, 239 mmol) was dissolved in ethanol (300 mL) and aqueous ammonia (35%, 300 mL). The solution was set in a reaction bomb and heated at 200° C. for 6 hours, cooled at room temperature, then left opened at this temperature for 72 hours. The ethanol had evaporated, and aqueous ammonia was added again (35%, 200 mL). The solution was heated at 200° C. for 22 hours then cooled to room temperature. The mixture was concentrated under vacuum then water (50 mL) was added and the suspension obtained filtered. The beige powder obtained was dried in a vacuum oven for 20 hours to give pure compound 244 (16.7 g, 64% yield, >95% purity by $^1$H NMR). $^1$H NMR (400 MHz, DMSO-$d_6$) δ 8.07 (s, 2H), 6.33 (s, 2H), 2.03 (s, 3H). LC-MS m/z 109 [M+H]$^+$.

1.1 Hz, 1H), 8.45 (d, J=2.4 Hz, 1H), 7.88 (s, 1H), 4.85 (d, J=0.6 Hz, 2H), 2.29 (d, J=1.1 Hz, 3H). LC-MS m/z 182/184 [M+H]$^+$.
Step 4:
Compound 245 (1.4 g, 7.7 mmol) was dissolved in $CH_2Cl_2$ (70 mL) and this solution was added to a solution of N-methylamine in MeOH/THF (2 M, 145 mL, MeOH/THF=1:4). The flask was sealed and the yellow solution was stirred at room temperature for 24 hours. TLC showed consumption of SM. A solution of HCl in dioxane (1 mL, 4 M) was added dropwise to the solution. The mixture was concentrated then $CH_2Cl_2$ (10 mL) was added. The suspension obtained was filtered to give a beige solid containing the hydrochloride salt of both the expected amine and of N-methyl amine. The solids were dissolved in MeOH (150 mL) and Amberlyst A-26 (40 mL) was added. The mixture was concentrated in vacuo, and then filtered. The filtrate was concentrated to give compound 246 (500 mg, 37% yield, 99% purity by LC-MS). $^1$H NMR (400 MHz, DMSO-$d_6$) δ 8.73 (dq, J=2.3, 1.1 Hz, 1H), 8.35 (d, J=2.4 Hz, 1H), 7.65 (s, 1H), 3.73 (d, J=0.8 Hz, 2H), 2.32 (s, 3H), 2.28 (d, J=1.0 Hz, 3H). LC-MS m/z 177 [M+H]$^+$.

Preparation of
tert-butyl-2-bromo-3-cyanobenzyl(methyl)carbamate
(Compound 252)

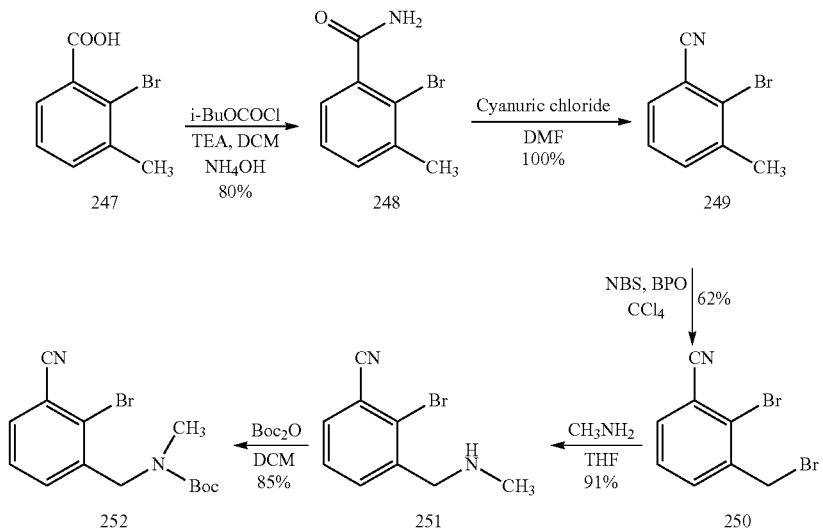

Step 3:
Compound 244 (5.0 g, 45.9 mmol) and dichloroacetone (29.1 g, 229.3 mmol) were mixed with toluene (1 L). The flask was equipped with a Dean-Stark apparatus and the mixture was heated at 155° C. for 1 hour (as soon as refluxing toluene was observed on top of the Dean-Stark). The reaction was cooled to room temperature and $CH_2Cl_2$ (500 mL) and silica were added. The mixture obtained was put directly on top of a column chromatography and purified by this way (eluents $CH_2Cl_2$/MeOH from 100:0 to 80:20). The fractions containing compound 245 were combined, concentrated under vacuum and purified by SCX-2 column. The fractions containing the expected compound 245 were purified again by column chromatography over silica gel (eluents $CH_2Cl_2$/MeOH from 100:0 to 95:5) to give the expected compound 245 as pale yellow oil (1.4 g, 16% yield, 95% purity by LC-MS). $^1$H NMR (400 MHz, DMSO-$d_6$) δ 8.76 (dq, J=2.3, Step 1:
To a solution of compound 247 (15 g, 69.8 mmol) in $CH_2Cl_2$ (100 mL) was added TEA (7.76 g, 76.7 mol) and iso-butylchloroformate (10.4 g, 76.7 mmol) at 0° C. After the addition, the mixture was stirred at 0° C. for 30 minutes, TLC($CH_2Cl_2$/MeOH=10:1) showed the reaction was completed. Then, $NH_3 \cdot H_2O$ (27.9 g, 0.28 mol, 35% in $H_2O$) was added to the mixture 0° C. The resulting mixture was stirred at this temperature for 30 minutes. TLC (petroleum ether/EtOAc=8:1) showed the reaction was completed. The mixture was poured into ice-water (200 mL). The solid was filtered and the wet cake was washed with $H_2O$ (50 mL), dried to give compound 248 (12 g, 80%) as a white solid. $^1$H NMR (400 MHz, DMSO-$d_6$) δ 7.70 (brs, 1H), 7.55 (brs, 1H), 7.35 (m, 1H), 7.30 (m, 1H), 7.15 (m, 1H), 2.38 (s, 3H).
Step 2:
To a solution of compound 248 (12 g, 56.1 mmol) in DMF (100 mL) was added a solution of cyanuric chloride (15.47 g, 84.1 mol) in DMF (50 mL) at 0° C. under a nitrogen atmosphere. After the addition, the mixture was stirred at room temperature overnight. TLC (petroleum ether/EtOAc=1:1) showed the reaction was completed. The mixture was poured into water (500 mL) and extracted with EtOAc (200 mL×2). The combined organic layers were washed with saturated aqueous $Na_2CO_3$ (200 mL×2), brine (200 mL×4), dried over $Na_2SO_4$ and concentrated to give compound 249 (11 g, 100%). as an off-white solid. $^1$H NMR (400 MHz, $CDCl_3$): δ 7.51-7.45 (m, 2H), 7.33-7.29 (m, 1H), 2.47 (s, 3H)

Step 3:

A mixture of compound 249 (11 g, 56.1 mmol), NBS (10 g, 56.1 mmol) and BPO (81 mg, 0.34 mmol) in $CCl_4$ (150 mL) was heated at reflux overnight. TLC (petroleum ether/EtOAc=5:1) showed the reaction was completed. The mixture was filtered and the filtrate was concentrated. The residue was purified by column chromatography over silica gel (petroleum ether/EtOAc=20:1) to yield compound 250 (9.6 g, 62%) as a white solid. $^1$H NMR (400 MHz, $CDCl_3$) δ 7.69-7.67 (d, 1H), 7.63-7.61 (d, 1H), 7.45-7.41 (t, 1H), 4.61 (s, 2H)

Step 4:

To a solution of compound 250 (11.9 g, 43.3 mmol) in THF (100 mL) was added a solution of methylamine (2M in THF, 215 mL, 0.43 mol) at −10° C.~0° C. under a nitrogen atmosphere. After the addition, the mixture was allowed to warm to room temperature and stirred for 2 hours. TLC (petroleum ether/EtOAc=5:1) showed the reaction was completed. The mixture was diluted with water (200 mL), and extracted with EtOAc (200 mL×2). The combined organic layers were washed with brine (200 mL), dried over $Na_2SO_4$, and concentrated to give compound 251 (8.9 g, 91%). as a yellow solid. $^1$H NMR (400 MHz, $CDCl_3$) δ 7.67-7.65 (d, 1H), 7.58-7.56 (d, 1H), 7.43-7.39 (t, 1H), 3.87 (s, 2H), 2.47 (s, 3H).

Step 5:

To a solution of compound 251 (8.7 g, 38.6 mmol) in $CH_2Cl_2$ (100 mL) were added TEA (11.7 g, 0.11 mol) and $Boc_2O$ (8.9 g, 40.5 mmol) at room temperature. The mixture was stirred at room temperature for 3 hours. TLC($CH_2Cl_2$/MeOH=10:1) showed the reaction was completed. The mixture was concentrated and purified by column chromatography over silica gel (petroleum ether/EtOAc=40:1) to yield compound 252 (10.71 g, 85%) as a colorless gum. $^1$H NMR (400 MHz, $CDCl_3$) δ 7.58 (m, 1H), 7.45-7.38 (m, 2H), 4.56-4.50 (m, 2H), 2.93-2.89 (m, 3H), 1.52-1.40 (m, 9H). MS m/z 347 $[M+Na]^+$.

Preparation of 2-{(1R)-1-[(3-amino-6-bromopyrazin-2-yl)oxy]ethyl}-4-fluorobenzoic acid (254)

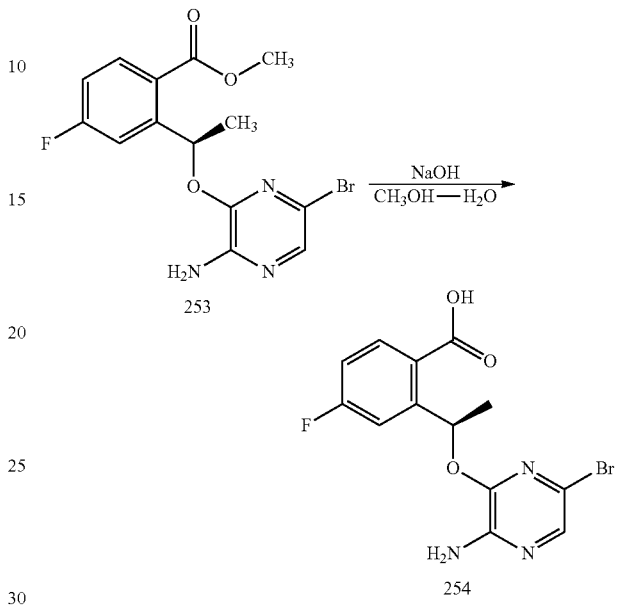

The procedure described in step 2 for Example 41 was used to prepare compound 254 (0.56 g, 89% yield). $^1$H NMR (400 MHz, DMSO-d6) δ 7.92 (dd, J=8.7, 6.0 Hz, 1H), 7.67 (dd, J=10.5, 2.7 Hz, 1H), 7.52 (s, 1H), 7.19 (td, J=8.4, 2.7 Hz, 1H), 6.88 (q, J=6.4 Hz, 1H), 6.68 (s, 2H), 1.57 (d, J=6.3 Hz, 3H), [MH]+ 356.03 (8%) and 357.95 (8%).

Preparation of 2-((methylamino)methyl)imidazo[1,2-a]pyridine-6-carbonitrile (264)

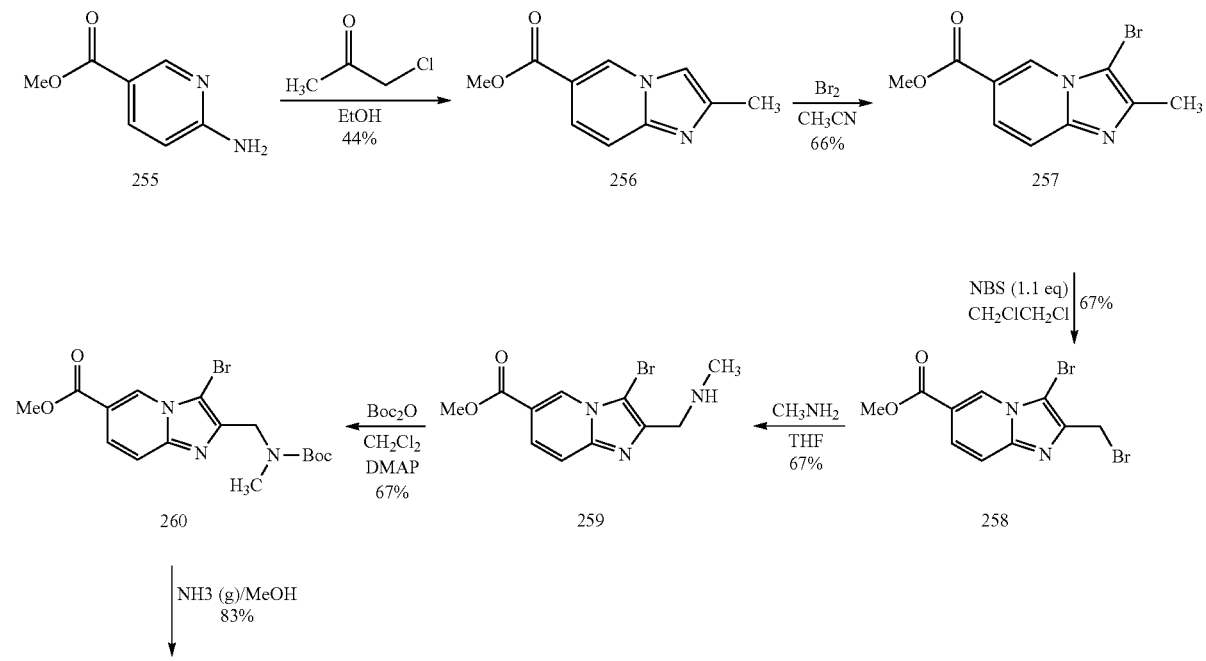

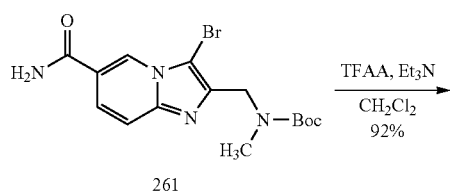
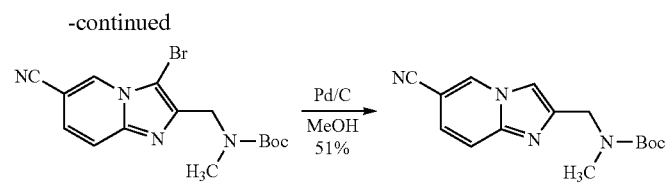
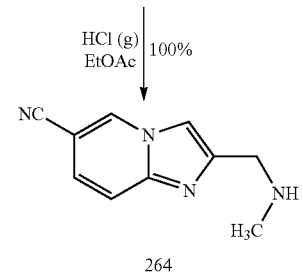

Step 1:

A mixture of compound 255 (50 g, 0.329 mmol) and 1-chloropropane-2-one (448.4 g, 4.87 mol) in EtOH (150 mL) was heated at reflux for 24 hours. TLC (Petroleum ether/EtOAc=1:1) showed that approximately half of compound 255 remained. No change was observed after reflux for a further 12 hours. The mixture was concentrated in vacuo to give the residue, which was dissolved in $CH_2Cl_2$ (200 mL), washed with aqueous $NaHCO_3$ solution (2 N, 50 mL) and brine (50 mL), dried over $Na_2SO_4$ and concentrated in vacuo to give the crude product, which was purified by column chromatography over silica gel (petroleum ether/EtOAc=2:1-1:1) to obtain compound 256 (18 g, 44%) as a yellow solid. $^1H$ NMR (400 MHz, $CDCl_3$) δ 8.82 (s, 1H), 7.67-7.65 (m, 1H), 7.81-7.48 (m, 1H), 7.41 (s, 1H), 3.94 (s, 1H), 2.47 (s, 1H)

Step 2:

To a solution of compound 256 (16 g, 0.089 mol) in $CH_3CN$ (400 mL) was added $Br_2$ (15.62 g, 0.098 mol) at room temperature. The resulting mixture was stirred at room temperature for 1 hour. TLC (EtOAc) showed the reaction was complete. The mixture was diluted with $CH_2Cl_2$ (500 mL) and then washed with saturated aqueous $NaHCO_3$ solution (100 mL), brine (100 mL), dried over $Na_2SO_4$ and concentrated in vacuo to give the crude product, which was purified by column chromatography over silica gel (petroleum ether/$CH_2Cl_2$=2:1-1:1) to obtain compound 257 (15 g, 66%) as a yellow solid. $^1H$ NMR (400 MHz, $CDCl_3$) δ 9.02 (s, 1H), 8.44-8.42 (m, 1H), 8.37-8.34 (m, 1H), 4.07 (s, 3H), 2.74 (s, 3H).

Step 3:

To a mixture of compound 257 (16 g, 0.0625 mol) and NBS (9.95 g, 0.05625 mol) in $CH_2ClCH_2Cl$ (375 mL) was added AIBN (1.025 g, 0.00625 mol) at room temperature under a nitrogen atmosphere. The resulting mixture was heated at reflux for 2 hours. TLC (Petroleum ether/EtOAc=3:1) showed most of compound 257 had been consumed. The mixture was cooled to room temperature and washed with saturated aqueous $NaHCO_3$ solution (50 mL), brine (50 mL) and dried over $Na_2SO_4$, concentrated in vacuo to give the crude product, which was purified by column chromatography over silica gel (petroleum ether/EtOAc=4:1~1:1) and then re-crystallized from petroleum ether/EtOAc (5:1, 30 mL) to compound 258 (14 g, 67%) as a yellow solid. $^1H$ NMR (400 MHz, $CDCl_3$) δ 8.85-8.75 (m, 1H), 7.88-7.80 (m, 1H), 7.62-7.55 (m, 1H), 4.67 (s, 2H), 4.00 (s, 3H).

Step 4:

To a solution of compound 258 (14 g, 41.92 mmol) in anhydrous THF (200 mL) was added methylamine in THF (520 mL, 1.048 mol, 2 M in THF) over one minute. The resulting mixture was stirred at 0° C. for 1 hour and then at room temperature for 1 hour. TLC (Petroleum ether/EtOAc=3:1) showed most of compound 258 had been consumed. The mixture was concentrated in vacuo at 25° C. for 20 minutes and then at higher temperature to give the crude product, which was purified by column chromatography over silica gel, (petroleum ether/EtOAc=1:1~$CH_2Cl_2$/MeOH=50:1) to obtain compound 259 (8.4 g, 67%) as a yellow solid. $^1H$ NMR (400 MHz, $CDCl_3$) δ 8.85 (m, 1H), 7.84-7.81 (m, 1H), 7.60-7.52 (m, 1H), 4.18-4.15 (s, 2H), 4.00 (s, 3H), 2.65 (s, 3H)

Step 5:

To a suspension of compound 259 (8.4 g, 28.28 mmol) in $CH_2Cl_2$ (250 mL) was added $Boc_2O$ (12.5 g, 56.56 mmol) and DMAP (3.47 g, 28.28 mmol) at room temperature. The resulting mixture was stirred at room temperature for 12 hours. TLC($CH_2Cl_2$/MeOH=20:1) showed the reaction was complete. The mixture was concentrated in vacuo to give the crude product, which was purified by column chromatography over silica gel (petroleum ether/EtOAc=10:1-5:1) to obtain compound 260 (7.5 g, 67%) as a yellow solid. $^1H$ NMR (400 MHz, $CDCl_3$) δ 8.86 (s, 1H), 7.80-7.78 (m, 1H), 7.59-7.56 (m, 1H), 4.68 (s, 2H), 4.00 (s, 3H), 3.95 (s, 3H), 1.50 (s, 9H)

Step 6:

The reaction was run in 3×1 g batches: A solution of compound 260 (1 g, 2.519 mmol) in $NH_3(g)$/MeOH (7 N, 70 mL) was sealed and heated at 80° C. for 12 hours. TLC (Petroleum ether/EtOAc=1:1) showed the reaction was complete. The reactions were combined, and concentrated in vacuo to give the crude product, which was purified by column chromatography over silica gel (petroleum ether/EtOAc=5:1-1:1) to obtain compound 261 (2.4 g, 83%) as a yellow solid. $^1H$ NMR (400 MHz, Methanol-$d_4$) δ 8.90 (s, 1H), 7.90-7.82 (m, 1H), 7.65-7.55 (m, 1H), 4.65 (s, 2H), 2.95-2.84 (m, 3H), 1.45 (s, 9H)

Step 7:

To a solution of compound 261 (2.4 g, 6.28 mmol) in anhydrous $CH_2Cl_2$ (50 mL) was added $Et_3N$ (2.6 mL, 18.85 mmol) and then in a dropwise manner TFAA (1.73 mL, 12.57 mmol) at 0° C. The resulting mixture was stirred at 0° C. for 2 hours. TLC (Petroleum ether/EtOAc=1:1) showed the reaction was complete. The mixture was concentrated in vacuo to give the residue, which was partitioned between $CH_2Cl_2$ (100 mL) and brine (20 mL). The organic layer was separated, washed with critic acid (1 N, 10 mL), saturated aqueous $NaHCO_3$ solution (10 mL) and brine (10 mL), dried over $Na_2SO_4$ and concentrated in vacuo to give the crude product, which was purified by column chromatography over silica gel (petroleum ether/EtOAc=5:1-1:1) to obtain compound 262 (2.1 g, 92%) as a yellow solid. $^1H$ NMR (400 MHz, $CDCl_3$) δ 8.55 (s, 1H), 7.68-7.65 (m, 1H), 7.35-7.26 (m, 1H), 4.66 (s, 2H), 2.93 (s, 3H), 1.47 (s, 9H). LCMS m/z 308 [M−55]⁺.

solid. $^1H$ NMR (400 MHz, Methanol-$d_4$) δ 8.52 (s, 1H), 7.64-7.50 (m, 2H), 7.27 (s, 1H), 4.59 (s, 2H), 2.98 (s, 3H), 1.50 (s, 9H)

Step 9:

To a solution of compound 263 (0.18 g, 0.627 mmol) in $CH_2Cl_2$ (10 mL) was added HCl (g)/EtOAc (7 N, 20 mL) at room temperature. The resulting mixture was stirred at room temperature for 12 h. The mixture was concentrated in vacuo to give compound 264 (0.15 g, 100%) as a white solid. $^1H$ NMR (400 MHz, Methanol-$d_4$) δ 9.48 (s, 1H), 8.48 (s, 1H), 8.15-8.05 (m, 2H), 4.58 (s, 2H), 2.85 (s, 3H)

Preparation of
3-((methylamino)methyl)isoxazole-5-carbonitrile
(Compound 272)

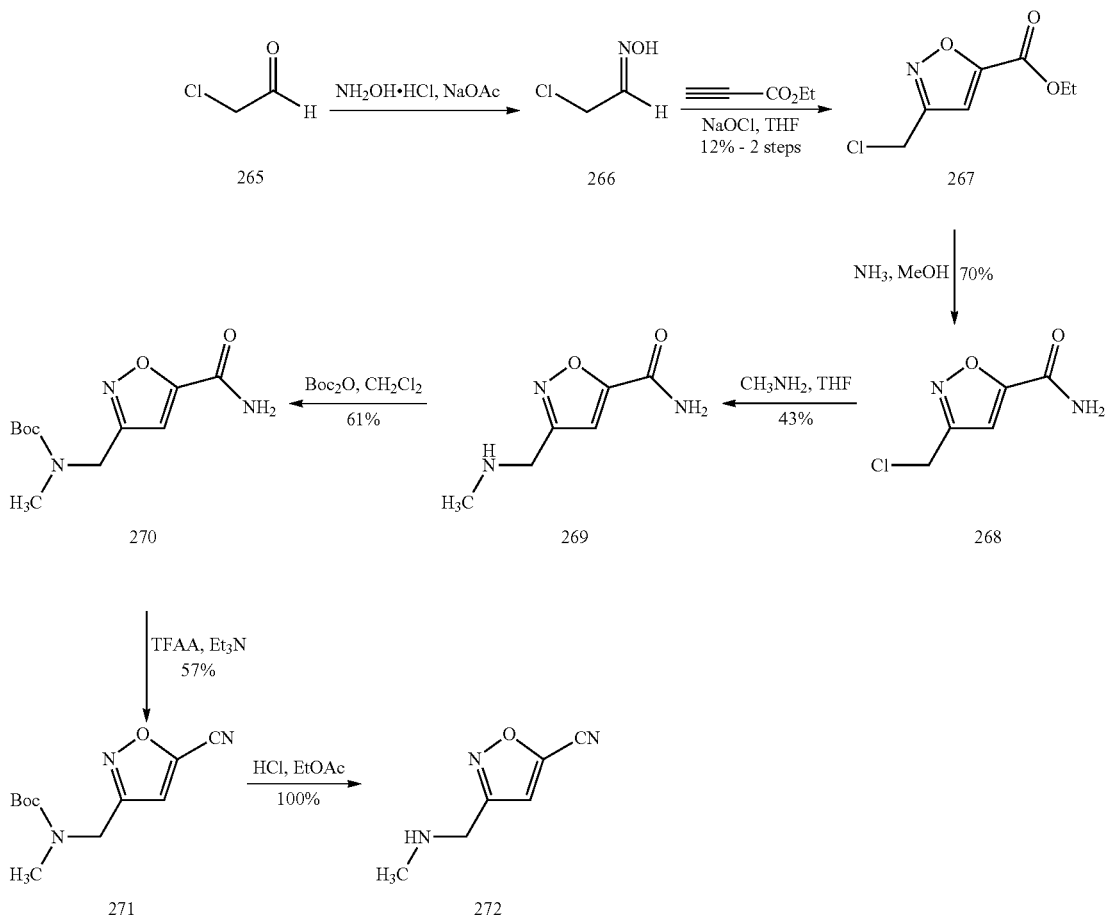

Step 8:

To a solution of compound 262 (0.45 g, 1.23 mmol) in MeOH (80 mL) was added Pd/C (150 mg) at room temperature. The resulting mixture was purged with $H_2$ three times and stirred under a pressure of $H_2$ (15 psi) at room temperature for 2 hours. TLC (Petroleum ether/EtOAc=3:1) showed the reaction was complete. The mixture was filtered and washed with MeOH (30 mL). The filtrate was concentrated in vacuo to give the crude product, which was purified by column chromatography over silica gel, (petroleum ether/EtOAc=5:1) to give compound 263 (0.18 g, 51%) as a white Step 1:

To a stirred solution of compound 265 (52 g, 0.64 mol) in $H_2O$ (830 mL) was added $NH_2OH·HCl$ (50 g, 0.71 mol) and NaOAc (59 g, 0.71 mol) at room temperature. After the addition, the mixture was stirred at room temperature for 1 hour. Then, the solution was extracted with MTBE (2×500 mL), the combined organic layers washed with brine (200 mL×3), dried over $Na_2SO_4$, and concentrated to give crude compound 266 (40 g) as a light yellow oil, which was used in the next step without purification.

Step 2:

To a stirred solution of compound 266 (40 g, 0.437 mol) in THF (150 mL) was added dropwise ethyl propiolate (50 mL, 0.5 mol) at 0° C. NaOCl (10%, 1.5 L) was added dropwise to the above mixture at 0° C. After the addition, the mixture was stirred at room temperature for 18 hours. The mixture was concentrated to remove THF, extracted with EtOAc (2×500 mL). The combined organic layers were washed with brine (200 mL×3), dried over $Na_2SO_4$, and concentrated to give a residue, which was purified by column chromatography over silica gel. (Rf~0.5, petroleum ether/EtOAc=10:1-5:1) to give compound 267 (11 g, 12.2%) as a light yellow solid. $^1$H NMR (400 MHz, $CDCl_3$) δ 7.05 (s, 1H), 4.64 (s, 2H), 4.49-4.41 (m, 2H), 11.46-1.43 (t, 3H).

Step 3:

To a stirred solution of $NH_3$ (g) in MeOH (12N, 100 mL) was added compound 267 (11 g, 0.058 mol) at 0° C. After the addition, the mixture was stirred at room temperature for 10 minutes. TLC (Petroleum ether/EtOAc=1:1) indicated the reaction was complete. The mixture was concentrated to give a residue, which was purified by column chromatography over silica. gel (Rf=0.2, petroleum ether/EtOAc=1:1-2:1) to give compound 268 (6.5 g, 70%) as a white solid. $^1$H NMR (400 MHz, $CDCl_3$) δ 7.06 (s, 1H), 6.2 (s, 1H), 5.74 (s, 1H), 4.63 (s, 2H), Step 4:

This reaction was run in 3×2 g batches. A mixture of compound 268 (2 g, 13 mmol) and methylamine (2M in THF, 15 mL) was heated in a sealed vessel at 110° C. for 18 hours. TLC (EtOAc) indicated the reaction was complete. The reactions were combined, filtered and the filtrates were concentrated to give crude compound 269 (2.5 g, 43%) as a yellow solid. $^1$H NMR (400 MHz, Methanol-$d_4$) δ 7.00 (s, 1H), 3.89-3.88 (s, 1H), 2.44 (s, 3H)

Step 5:

To a stirred solution of compound 269 (2.5 g, 16 mmol) and $Boc_2O$ (5.2 g, 24 mmol) in dry THF (30 mL) was added TEA (3.2 g, 32 mol) at 0° C. After the addition, the mixture was stirred at room temperature for 2 hours. TLC (petroleum ether/EtOAc=1:1) indicated the reaction was complete. The mixture was concentrated to give a residue, which was purified by column chromatography over silica. Gel (Rf=0.46, petroleum ether/EtOAc=3:1) to give compound 270 (2.5 g, 61%) as yellow oil. $^1$H NMR (400 MHz, $CDCl_3$) δ 6.96 (s, 1H), 6.51 (s, 1H), 6.02 (s, 1H), 4.52 (s, 2H), 2.89-2.86 (s, 3H), 1.47 (s, 9H)

Step 6:

To a stirred solution of compound 270 (2.5 g, 10 mmol) and TEA (4.2 mL, 30 mmol) in dry DCM (30 mL) was added TFAA (4.32 g, 20 mol) at 0° C. under a nitrogen atmosphere. After the addition, the mixture was stirred at 0° C. for 12 hours. TLC (petroleum ether/EtOAc=3:1) indicated the reaction was complete. The mixture was washed with saturated aqueous $NaHCO_3$ solution (50 mL) and brine (50 mL×2), dried over $Na_2SO_4$, and concentrated to give a residue, which was purified by column chromatography over silica. gel (Rf=0.4, petroleum ether/EtOAc=10:1) to give compound 271 (1.3 g, 56.5%) as a light yellow oil. $^1$H NMR (400 MHz, $CDCl_3$) δ 6.96 (s, 1H), 4.52 (s, 2H), 2.87 (s, 3H), 1.47 (s, 9H)

Step 7:

To a stirred solution of compound 271 (1.3 g, 5.5 mmol) in EtOAc (2 mL) was added HCl (g)/EtOAc (6N, 10 mL) at room temperature. After the addition, the mixture was stirred at room temperature for 2 hours. TLC (petroleum ether/EtOAc=1:1) indicated the reaction was complete. The mixture was concentrated to give compound 272 (1 g, 100%) as the hydrochloride salt. $^1$H NMR (400 MHz, DMSO-$d_6$) δ 9.72 (s, 2H), 7.85 (s, 1H), 4.43 (s, 2H), 2.63 (s, 3H).

Preparation of (1R)-1-(3,5-difluoro-2-iodophenyl)ethanol (Compound 279)

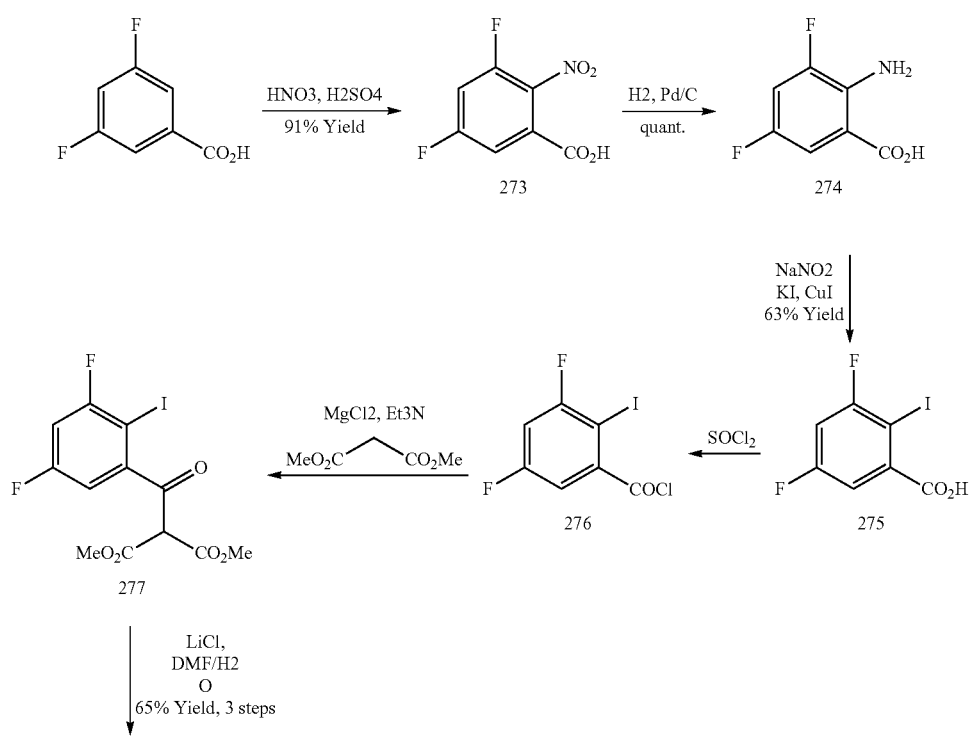

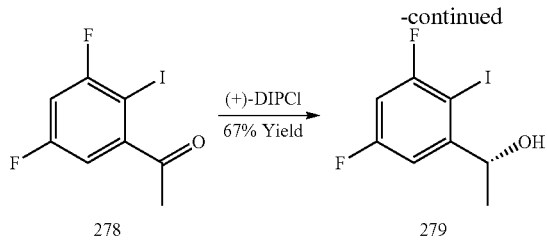

Step 1:
3,5-difluorobenzoic acid (80 g, 506 mmol) and sulfuric acid (250 ml) were stirred at room temperature for one hour. Then nitric acid (90 ml) was added, keeping the internal temperature below 45 C with a water bath. The mixture was left at room temperature overnight. The reaction was poured slowly into ice and the resulting solid was filtered and washed with cold water to give compound 273 as a white solid (93.0 g, 91% yield). This material was taken into the next step without further purification. $^1$H NMR (400 MHz, DMSO-d6) δ 8.01 (ddd, J=10.9, 8.5, 2.8 Hz, 1H), 7.71 (dt, J=8.4, 2.2 Hz, 1H).

Step 2:
Compound 273 (80 g, 394 mmol) and palladium on carbon (9 g, 10% wt) in EtOAc (900 ml) were stirred at room temperature under an atmosphere of H2 (50 bar) for 4 hours. The reaction mixture was filtered on a pad of silica and celite and the solvent removed in vacuo to give compound 274 as a pale yellow solid (67.39 g, 99% yield, ~95% purity-NMR). This material was taken into the next step without further purification. $^1$H NMR (400 MHz, DMSO-d6) δ 7.39 (ddd, J=11.5, 8.4, 3.0 Hz, 1H), 7.3 (ddd, J=9.6, 3.0, 1.8 Hz, 1H)

Step 3:
The compound 274 (53.8 g, 311 mmol) was dissolved in an aqueous solution of HCl (2M, 800 ml) and cooled to 0-5 C. Sodium nitrite (21.44 g, 311 mmol) was dissolved in water (344 ml) and added to the previous solution over a period of 15 minutes. This mixture was stirred at 0-5 C for 2 hours then transferred to a conical flask and kept cold. In a new round bottom flask was added potassium iodide (103.25 g, 622 mmol) and copper iodide (29.61 g, 156 mmol) in water (344 ml). This mixture was cooled at 0-5 C then the previous mixture was added slowly. After the addition, the reaction mixture was allowed to warm to room temperature and stirred for 16 hours. The suspension was filtered and the resulting solid was slurried in ethyl acetate (860 ml) for 1 hour. This solution was filtered again and the mother liquors were washed with sodium metabisulfate (10%, 4*600 ml) and brine (600 ml). After drying on MgSO4 and removal of the solvents in vacuo, Compound 275 was isolated as a pale yellow solid (55.35 g, 63% yield, 90% purity-NMR). $^1$H NMR (400 MHz, CDCl$_3$) δ 7.60 (ddd, J=8.5, 2.9, 1.5 Hz, 1H), 7.07 (J=7.8, 2.8 Hz, 1H), [M−H+]−282.74.

Step 4:
Thionyl chloride (142 ml, 1940 mmol) was added to compound 275 (55.0 g, 194 mmol) and the mixture was heated at 80° C. for 3.5 hours. The reaction was then cooled to room temperature and thionyl chloride was removed under reduced pressure and then azeotroped with toluene. compound 276 was isolated as an orange oil (56 g, quantitative). $^1$H NMR (400 MHz, CDCl$_3$) δ 7.6 (ddd, J=8.4, 2.8, 1.4 Hz, 1H), 7.09 (td, J=7.7, 2.8 Hz, 1H), [M+H+]−298.

Step 5:
This reaction was set up in 7 batches of 5 g each of compound 276. Magnesium chloride (2.35 g, 24.6 mmol) and diethyl malonate (3.95 g, 24.6 mmol) were suspended in acetonitrile (50 ml). The resulting mixture was cooled to 0 C then triethylamine (3.42 ml, 24.6 mmol) was added dropwise at 0 C and the reaction stirred during 45 min at 0 C. A solution of compound 276 (5 g, 16.4 mmol) in acetonitrile (20 ml) was added quickly to this mixture at 0 C. The solution was warmed to room temperature and stirred for 3 hours. The solvents were removed under reduced pressure and the residue was diluted with EtOAc (350 ml) and an aqueous solution of HCl (1M, 300 ml). The aqueous phase was washed with EtOAc (3*300 ml) then the organic phases were combined, dried over MgSO4, filtered and the solvents removed under reduced pressure to give compound 277 as an orange oil (combined crude 68.9 g) $^1$H NMR (400 MHz, DMSO-d6) δ 7.49-7.43 (m, 1H), 7.22 (ddd, J=8.5, 2.7, 1.2 Hz, 1H), 4.11-3.99 (m, 4H), 1.99 (s, 1H), 1.20 (m, 6H); [M<H+]=424.89, 426.14, 426.92 (10/1).

Step 6:
This reaction was set up in 2 batches which were combined prior to work up (37.6 g+31.34 g). Compound 277 (37.6 g, 88.2 mol) and lithium chloride (3.74 g, 88.2 mmol) were dissolved in DMF (170 ml) and water (17 ml) and heated at 100 C for 4 hours. The reaction was allowed to cool to RT then water (150 ml) and TBME (150 ml) were added. The phases were separated and the aqueous layer was washed with TBME (3*150 ml). The organic phases were combined and washed with water (500 ml), dried over MgSO4, filtered then evaporated under reduced pressure. The residue was purified by dry flash chromatography (eluent:Hept/EtOAc 98:2 to 9:1) to give compound 278 as an orange solid (21.34 g, 65% yield over 3 steps, 88% pure by LCMS). $^1$H NMR (400 MHz, DMSO-d6) δ 7.53-7.51 (m, 1H), 7.50-7.48 (m, 1H), 2.57 (s, 3H), [M−F+MeCN]=293.03, 293.79(1/10).

Step 7:
A solution of (+)DIP-Cl (17.1 g, 53.2 mmol) in THF (24 ml) was cooled to −35° C. Then a solution of compound 278 (7.5 g, 26.5 mmol) in THF (20 ml) was added dropwise keeping the internal temperature of the reaction between −35 and −30 C. The reaction was allowed to warm to room temperature and stirred for 12 hours. TLC analysis confirmed the reaction was complete. The solvents were removed in vacuo and the residue was diluted in TBME (64.5 ml). A mixture of diethanolamine (9.16 g, 87.45 mmol) in ethanol/THF (3.75 ml/7.5 ml) was added. The reaction mixture was stirred for 3 hours at reflux then cooled to room temperature and filtered. The mother liquids were concentrated in vacuo and the resulting residue was purified by column chromatography (eluent: Hep/EtOAc 99:1 to 9:1). The colorless oil obtained was further purified by recrystallisation from heptane to give compound 279 as a white solid (5.02 g, 67% yield, 95% pure by NMR, 99% ee-chiral GC analysis). $^1$HNMR (400 MHz, d6-DMSO) δ 7.28-7.12 (m, 2H), 5.64 (d, J=4.2 Hz, 1H), 4.86 (q, J=6.4 Hz, 1H), 1.27 (d, J+6.4 Hz, 3H), [M−F+H2O−H+]−

279.12/280.92 (1:1), HPLC (CP-chiralsil-dex-CB column): 99% ee; Rt(minor)-18.23 min; Rt(major)-18.55 min; 40 C to 225 C at 6 C per minute.

Preparation of di-tert-butyl [(4-bromo-5-cyano-1-methyl-1H-pyrazol-3-yl)methyl]imido-dicarbonate (Compound 282)

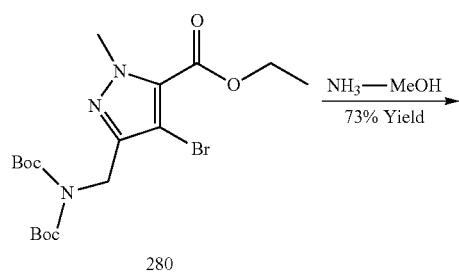
280

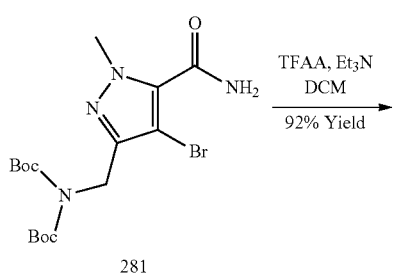
281

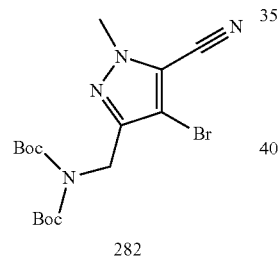
282

Step 1:

A solution of compound 280 (10 g, 0.21 mol) in NH$_3$ (g)/MeOH (150 mL) was stirred at 45° C. overnight in a sealed tube. TLC (petroleum ether/EtOAc=3:1) indicated the consumption of compound 9. The reaction mixture was concentrated. The residue was re-crystallized from CH$_2$Cl$_2$/petroleum ether to give compound 281 (6.6 g, 72.6%) as a pale brown solid. $^1$H NMR (400 MHz, DMSO) δ 8.00 (s, 1H), 7.82 (s, 1H), 4.64 (s, 2H), 3.85 (s, 3H), 1.38 (s, 18H)

Step 2:

To a mixture of compound 281 (58 g, 20.5 mol) and Et$_3$N (4.6 g, 45.6 mmol) in dry CH$_2$Cl$_2$ (100 mL) was added TFAA (6.4 g, 30.5 mol) drop-wise at 0-1-5° C. After addition, the mixture was stirred at 0° C. for 1.5 hour. TLC (petroleum ether:EtOAc=1:1) showed the reaction was complete. The mixture was diluted with CH$_2$Cl$_2$ (100 mL), Washed with 5% citric acid (50 mL), sat. NaHCO$_3$ (50 mL), and brine (50 mL), dried over sodium sulfate and concentrated. The residue was purified by biotage (petroleum ether/EtOAc 6/1, Rf=0.5) to give compound 282 (5.8 g, 92.2%) as a white solid. $^1$H NMR (400 MHz, CDCl$_3$) δ 4.797 (s, 2H), 3.988 (s, 3H), 1.481 (s, 18H). LC-MS: m/z for C16HBrN4O4 [M+Na]+439.2.

Preparation of methyl 2-{1-[(3-amino-6-bromopyrazin-2-yl)oxy]ethyl}-4-fluorobenzoate (283)

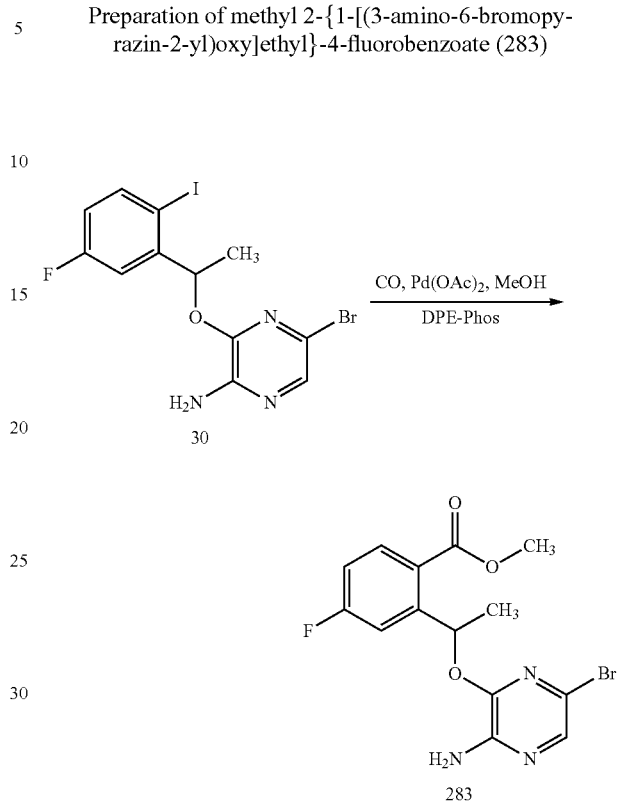

The procedure described in step 1 for Example 89 was used to prepare compound 283.

Preparation of methyl 2-{[(3-amino-6-bromopyrazin-2-yl)oxy]methyl}-4-fluorobenzoate (Compound 287)

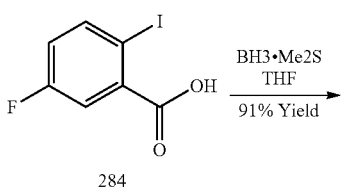
284

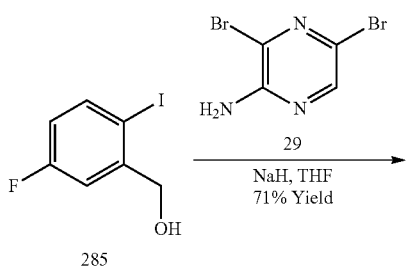
285

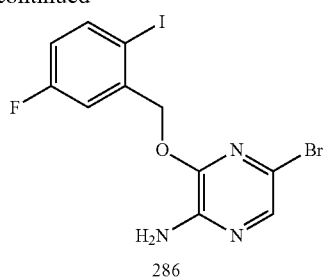

286

Pd(OAc)2, DPE-Phos
DIPEA, CO 60 psi,
MeOH—THF
73% Yield

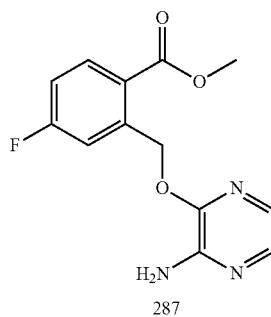

287

Step 1:

Compound 284 (5.00 g, 18.80 mmol) was dissolved in THF (50 mL) and cooled to 0° C. under nitrogen. Borane-dimethylsulphide (3.57 mL, 37.60 mmol) was added dropwise with stirring and the reaction mixture warmed to room temperature. Stirred at room temperature for 16 hours. The reaction mixture was carefully quenched by pouring onto ice and adding 10% aqueous K₂CO₃ solution (50 mL). The mixture was extracted with DCM (2×50 mL) and the combined organic extracts dried over MgSO₄ and concentrated in vacuo to give compound 285 as a colorless solid (4.80 g, 91% yield).

¹H NMR (400 MHz, CDCl₃): δ 7.68 (dd, 1H, J=Hz), 7.19 (dd, 1H, J=Hz), 6.70 (td, 1H, J=Hz), 4.57 (d, 2H, J=Hz), 1.95 (t, 1H, J=Hz).

Step 2:

Compound 285 (4.80 g, 19.05 mmol) was dissolved in dry THF (80 mL) and cooled to 0° C. under nitrogen. NaH (60% dispersion in mineral oil, 831 mg, 20.77 mmol) was added in portions and the mixture stirred for 30 minutes room temperature. Cooled back down to 0° C. and added a solution of 3,5-dibromopyrazin-2-amine (4.38 g, 17.31 mmol) in THF (40 mL). The reaction mixture was then heated at reflux for 18 hours. After cooling to room temperature, the mixture was evaporated in vacuum to give a dark brown oil. To this oil was added 10% aq. K₂CO₃ solution (100 mL) and extracted with EtOAc (3×100 mL). The combined organic extracts were washed with brine (100 mL), dried over MgSO₄ and evaporated in vacuum to give a fawn solid. This was purified by flash chromatography eluting with DCM:heptanes 3:1 and then DCM to give compound 286 as a pale yellow solid (5.80 g, 79% yield). ¹H NMR (400 MHz, CDCl₃): δ 7.84 (dd, 1H, J=8.7, 5.5 Hz), 7.70 (s, 1H), 7.21 (dd, 1H, J=9.7, 3.0 Hz), 6.84 (td, 1H, J=8.3, 3.0 Hz), 5.38 (s, 2H), 4.82 (br. s, 2H); [MH+]–425.80.

Step 3:

Compound 286 (5.20 g, 12.26 mmol) was partially suspended in MeOH (50 mL) and THF (25 mL) added to dissolve in a reaction bomb. DIPEA (10.61 mL, 61.30 mmol), DPE-Phos (792 mg, 12 mol %) and Pd(OAc)₂ (165 mg, 6 mol %) were added. The reaction bomb was filled with CO (60 psi) and the reaction mixture heated to 40° C. for 3 hours. The reaction was cooled to ambient and then evaporated in vacuum to give a mauve solid. This solid was triturated in hot DCM, then cooled before filtering off a yellow solid of essentially pure compound 4 (2.65 g, 61% yield). The filtrate was purified by flash chromatography eluting with 25-33% EtOAc in heptanes to give more of compound 287 as a pale brown solid (540 mg 12% yield). A total of 3.19 g was obtained (73% yield). ¹H NMR (400 MHz, CDCl₃): δ 8.06 (dd, 1H, J=8.7, 5.9 Hz), 7.69 (s, 1H), 7.24 (dd, 1H, J=9.9, 2.6 Hz), 7.08 (ddd, 1H, J=8.7, 7.8, 2.7 Hz), 5.82 (s, 2H), 4.81 (br. s, 2H), 3.90 (s, 3H), [MH+]–358.02.

Preparation of 1-(5-ethyl-1,2-thiazol-3-yl)-N-methylmethanamine (293)

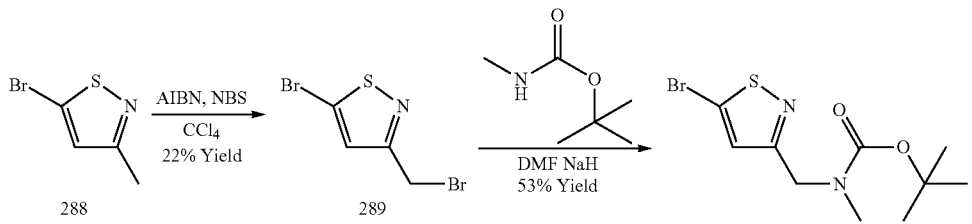

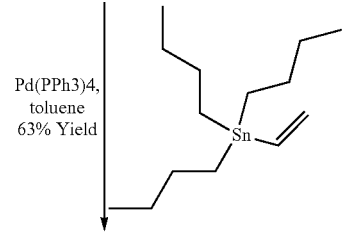

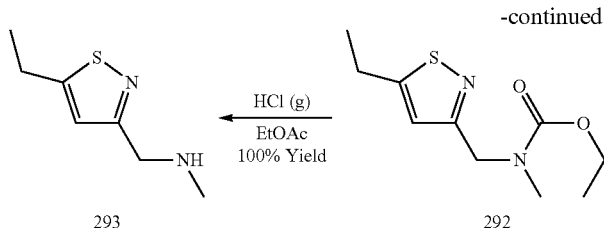
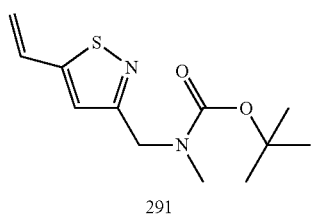

Step 1:

A mixture of compound 288 (13 g, 73 mmol), AIBN (1.19 g, 7.3 mmol) and NBS (32.5 g, 182.5 mmol) in chloroform (200 mL) was refluxed under nitrogen for 24 hours. The reaction mixture was concentrated in vacuo to give the residue, which was purified by column chromatography on silica gel eluting with petroleum ether/EtOAc 200/1 to give compound 289 (4 g, 21.5%) as yellow oil.

Step 2:

To a stirred solution of tert-butyl methylcarbamate (2.4 g, 18.7 mmol) in DMF (30 mL) was added NaH (0.75 g, 17.8 mmol, 60% in mineral oil) at 0° C. under nitrogen. After addition, the reaction mixture was stirred at 0° C. for 1 hour. Compound 289 (4 g, 15.6 mmol) was added to the mixture at 0° C. and the mixture was stirred at room temperature for 16 hours. The reaction mixture was diluted with H2O (100 mL) and extracted with EtOAc (100 mL×3). The combined organic layers were washed with brine (100 mL×3), dried over Na2SO4 and concentrated. The residue was purified by column chromatography on silica gel eluting with petroleum ether/EtOAc 20/1 to give compound 290 (2.5 g, 53.2%) as yellow oil.

Step 3:

A mixture of compound 290 (2.5 g, 8.2 mmol), tributyl (ethenyl)stannane (3.7 g, 12.3 mmol) and Pd(PPh3)4 (0.474 g, 0.41 mmol) in dry toluene (30 mL) was refluxed under nitrogen for 4 hours. The reaction mixture was concentrated in vacuo to give the residue, which was purified by column chromatography on silica gel eluting with petroleum ether/EtOAc 50/1~10/1 to give compound 291 (1.6 g, 62.5%) as yellow oil.

Step 4:

A mixture of compound 291 (1.6 g, 6.3 mmol) and Pd/C (180 mg) in EtOAc (30 mL) was stirred at 30° C. under hydrogen for 16 hours. The reaction mixture was filtered and the filtrate was concentrated in vacuum to give a residue, which was purified by column chromatography on silica gel eluting with petroleum ether/EtOAc 50/1~10/1 to give compound 292 (1.0 g, 62.1%) as light yellow oil. $^1$H NMR (400 MHz, MeOD): δ 6.973 (s, 1H), 4.50 (s, 2H), 2.96-3.0 (q, 2H), 2.93-2.91 (t, 3H), 1.53 (s, 9H), 1.35-1.28 (t, 3H) LC-MS: 127144-146-P m/z for C12HN2O2S [M-boc+H]+ 157.0

Step 5:

To a solution of compound 292 (0.42 g, 1.6 mmol) in EtOAc (10 mL) was added dropwise HCl (g)/EtOAc (5 mL) and stirred at room temperature for 5 hours. The mixture was concentrated to give compound 293 as a yellow solid (0.32 g, 100%). $^1$H NMR (400 MHz, D$_2$O): δ 7.17 (s, 1H), 4.33 (s, 2H), 2.98-2.92 (q, 2H), 2.77 (s, 3H), 1.32-1.29 (t, 3H).

Preparation of tert-butyl [(4-bromo-3-methoxy-1,2-oxazol-5-yl)methyl]methylcarbamate (299)

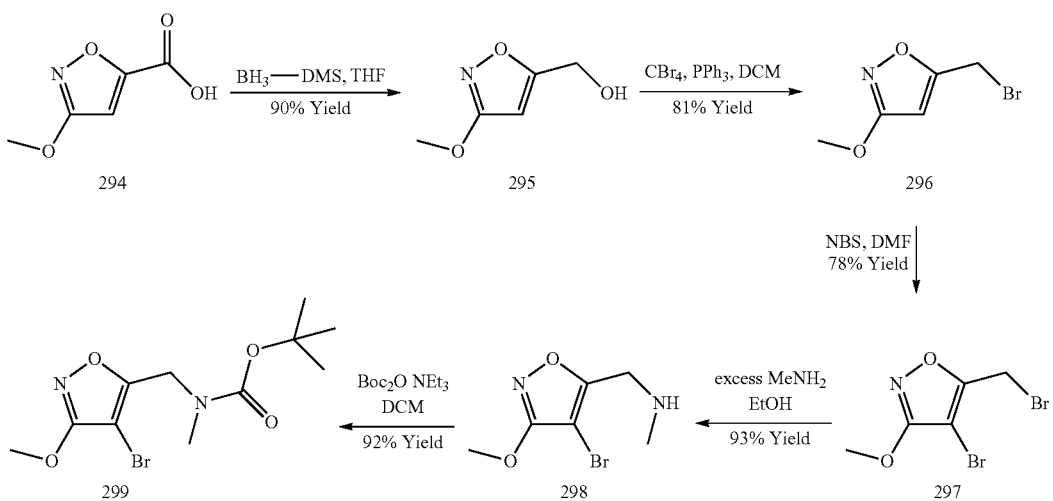

Step 1:

To a solution of 3-methoxyisoxazole-5-carboxylic acid 294 (7.6 g, 53.14 mmol) in anhydrous tetrahydrofuran (80 ml) at 0° C. under nitrogen, was added dropwise over 10 minutes a solution of borane-dimethylsulfide complex (5.18 g, 6.47 ml, 69.0 mmol) in THF (30 ml). The mixture was allowed to warm to room temperature, and then heated to 60° C. for 2 hours, then cooled to room temperature. The mixture was carefully quenched by the dropwise addition of 10 ml water, stirred for 10 minutes, then extracted with EtOAc (2×80 ml), dried over Na$_2$SO$_4$, filtered and the solvent removed under vacuum to afford compound 295 as a pale yellow oil (6.0 g, 88%). $^1$H NMR (400 MHz, d6-DMSO): δ 6.087 (s, 1H), 4.438 (s, 2H), 5.60 (br.s, 1H), 3.867 (s, 3H), [M+H 130.03].
Step 2:
To a solution of compound 295 (411 mg, 3.18 mmol) in dichloromethane (5 ml) at 0° C. under nitrogen, was added triphenylphosphine (833 mg, 3.18 mmol) and carbontetrabromide (1.029 g, 3.10 mmol) (which had been freshly dried by azeotroping 3 times with toluene). The mixture, which had turned orange, was stirred at 0° C. for 1 hour, then allowed to warm to room temperature. The mixture was concentrated by the removal of solvent under vacuum, and then purified by flash column chromatography eluting with 3:1 heptane:EtOAc which yielded the compound 296 as a colorless oil (486 mg, 81%). $^1$H NMR (400 MHz, d6-DMSO): δ 6.350 (s, 1H), 4.696 (s, 2H), 3.889 (s, 3H, [M+H 192.2 and 194.2].
Step 3:
To a solution of compound 296 (4.4 g, 23 mmol) in anhydrous dimethylformamide (20 ml) was added at room temperature N-bromosuccinimide (4.1 g, 23.1 mmol), and mixture warmed to 45° C. for 2 hours. Further N-bromosuccinimide (2.0 g, 11.3 mmol) was added, and mixture stirred at 45° C. for 2 hours. Further N-bromosuccinimide (1.3 g, 7.4 mmol) was added, and mixture stirred overnight at room temperature. Further N-bromosuccinimide (1.1 g, 11.3 mmol) was added, and mixture stirred at 45° C. overnight. The mixture was concentrated by the removal of solvent under vacuum, then extracted with EtOAc (2×100 ml), the organic layer was washed with water (50 ml), brine (20 ml), dried over Na$_2$SO$_4$, filtered and the solvent removed under vacuum. The residue was added to 0.9 g of impure product from another identical reaction and was purified by flash column chromatography eluting with 100:0-80:20 heptane:EtOAc, which yielded the compound 297 as a colorless oil, which later crystallized on standing to a colorless solid (5.66 g, 91%—however taking into account added material to column, calculated yield 78%). $^1$H NMR (400 MHz, d6-DMSO): δ 4.72 (s, 2H), 3.98 (s, 3H).
Step 4:
To a solution of methylamine 33% in ethanol (77 ml, 653 mmol) at 0° C. under nitrogen, was added dropwise over 10 minutes a solution of compound 297 in ethanol (20 ml), and the mixture was allowed to warm to room temperature overnight. The mixture was concentrated by the removal of solvent under vacuum, then saturated aqueous sodium hydrogen carbonate was added (20 ml), then the mixture extracted with EtOAc (100 ml), dried over Na$_2$SO$_4$, filtered and the solvent removed under vacuum to give compound 298 as pale yellow oil 4.5 g (93.5%). $^1$H NMR (400 MHz, d6-DMSO): δ 3.956 (s, 3H), 3.686 (s, 2H), 2.287 (br.s, 1H), 2.234 (s, 3H), [M+H 220.95 and 222.95].
Step 5:
To a solution of compound 298 (4.5 g, 20.4 mmol) in dichloromethane at room temperature under nitrogen was added triethylamine (2.12 g, 2.92 ml, 21 mmol), then portionwise over 3 minutes di-tert-butyldicarbonate (4.58 g, 21 mmol). Very mild effervescence was observed. The mixture was stirred at room temperature under nitrogen for 3 hours. The mixture was concentrated by the removal of solvent under vacuum, azeotroped with 150 ml heptane, then the residue was partitioned between EtOAc (100 ml) and water (20 ml). The organic layer was dried over Na$_2$SO$_4$, filtered and the solvent removed under vacuum to give compound 299 (6 g, 92% yield).

Preparation of 1-(3-ethyl-1,2-thiazol-5-yl)-N-methylmethanamine (305)

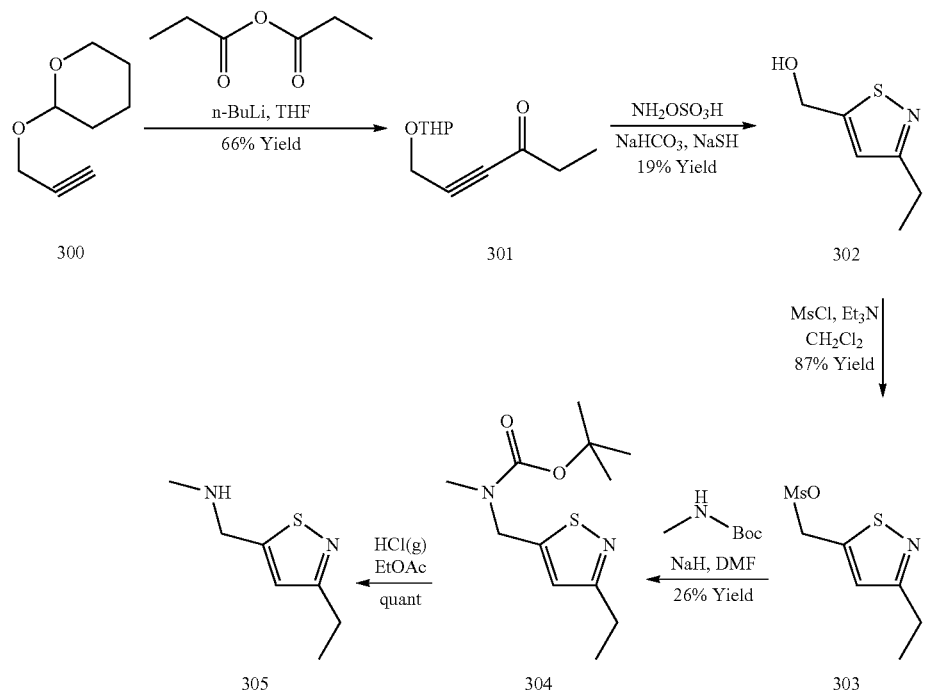

Step 1:
A solution of compound 300 (55 g, 0.39 mol) in dry THF (600 mL) was added n-BuLi (157 mL, 0.39 mol, 2.5 M) drop wise at −70° C. under N2. After addition, the mixture was stirred at −70° C. for 1 hour. The mixture was warmed to −20° C., and stirred at this temperature for 20 min. The reaction mixture was cooled to −70° C., and transferred via a double-ended needle to a solution of propanoic anhydride (61.3 g, 0.47 mol) in dry THF (400 mL) also kept at −70° C. The reaction mixture was allowed to warm to room temperature slowly, and stirred at room temperature overnight. The reaction mixture was diluted with saturated NH$_4$Cl solution (500 mL) and EtOAc (500 mL), and separated. The aqueous layer was extracted with EtOAc (500 mL×3). The combined organic layers were washed with brine (500 mL), dried over Na$_2$SO$_4$, and concentrated. The residue was distilled under reduced pressure to give compound 301 (50 g, 65.7%) as yellow oil.

Step 2:

To a mixture of compound 301 (58 g, 0.296 mol) in H$_2$O (1 L) was added NH$_2$OSO$_3$H (36.78 g, 0.326 mol) at 0° C., and the mixture was stirred at room temperature for 4 hours. NaHCO$_3$ (27.38 g, 0.326 mol) was added to the mixture carefully. Then NaSH (24.86 g, 0.444 mol) was added, and the mixture was refluxed overnight. TLC (petroleum ether:EtOAc=3:1) showed the reaction was complete. The mixture was filtered. The filtrate was extracted with EtOAc (500 mL×3). The combined organic layers were washed with brine (500 mL), dried over Na$_2$SO$_4$, and concentrated. The residue was purified with silica gel column eluting with petroleum ether/EtOAc 15/1~10/1 to give compound 302 (8 g, 19%) as brown oil.

Step 3:

To a solution of compound 302 (8 g, 55.9 mmol) and Et$_3$N (16.9 g, 0.168 mol) in dry CH$_2$Cl$_2$ (100 mL) was added MsCl (8.32 g, 72.7 mmol) drop-wise at 0° C. After addition the mixture was stirred at room temperature for 2 hours. TLC (petroleum ether:EtOAc=3:1) showed the reaction was complete. The mixture was diluted with EtOAc (250 mL), and filtered. The filtrate was washed with brine (50 mL), dried over Na$_2$SO$_4$, and concentrated to give compound 303 (11 g, 87%) as brown liquid.

Step 4:

To a solution of tert-butyl methylcarbamate (11 g, 90.5 mmol) in dry DMF (100 mL) was added NaH (3.6 g, 90.5 mmol, 60% in oil) in portions at 0° C. under N$_2$. After addition, the reaction mixture was stirred at 0° C. for 30 min. Compound 303 (10 g, 45.2 mmol) was added to the mixture at 0° C., and the mixture was stirred at room temperature for 4 hours. The reaction mixture was diluted with H$_2$O (100 mL)), and extracted with EtOAc (100 mL×3). The combined organic layers were washed with brine (100 mL×3), dried over Na$_2$SO$_4$ and concentrated. The residue was purified by prep. HPLC under basic conditions to give compound 304 (3 g, 26%) as a yellow oil. $^1$H NMR (400 MHz, CDCl$_3$): δ 6.926 (s, 1H), 4.626 (s, 2H), 2.94 (s, 3H), 2.84-2.86 (q, 2H), 1.53 (s, 9H), 1.33-1.36 (t, 3H), [M+H]+ 257.

Step 5:

To a solution of compound 304 (0.42 g, 1.6 mmol) in EtOAc (10 mL) was added dropwise HCl (g)/EtOAc (5 mL) and stirred at room temperature for 8 hours. The mixture was concentrated to give compound 305 (0.32 g, 100%) as a white solid. $^1$H NMR (400 MHz, D$_2$O): δ 7.30 (s, 1H), 4.51 (s, 2H), 2.81-2.75 (q, 2H), 2.72 (s, 3H), 1.222-1.18 (t, 3H).

Preparation of tert-butyl [2-(4-bromo-5-methoxypyridin-2-yl)ethyl]methyl-carbamate (314)

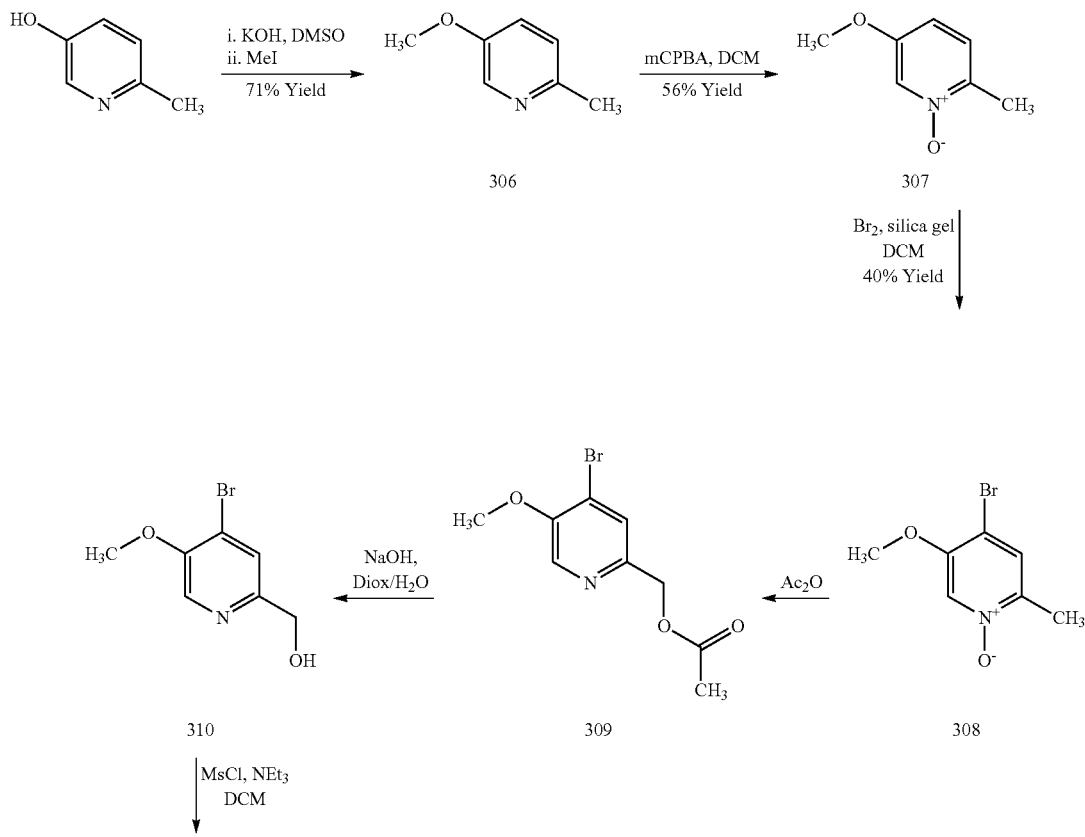

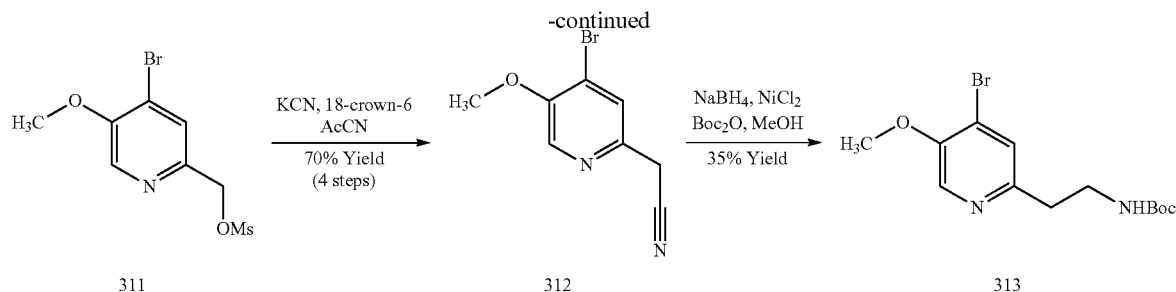

Step 1:

KOH (141 g, 2.52 mol) was added to a solution of 2-methyl-3-hydroxy pyridine (55.0 g, 0.50 mol) in DMSO (840 mL). The mixture was stirred at room temperature for 1 hour (KOH not fully dissolved) then was cooled at 0° C. MeI (34.6 mL, 0.55 mol) was added drop wise then the reaction was stirred at room temperature for 18 hours. Water (1.25 L) was added slowly to the reaction mixture. The aqueous phase was extracted with MTBE (3×500 mL) then EtOAc (3×400 mL). The aqueous phase was saturated with NaCl then extracted again with EtOAc (3×200 mL). Organic phases were combined, dried over $MgSO_4$, filtered and concentrated carefully under vacuum (product is volatile). The oil obtained was purified by column chromatography (eluent:heptanes:EtOAc form 1:1 to 0:1) to give compound 306 (44.1 g, 71% yield). $^1$H NMR (400 MHz, DMSO-$d_6$) δ 8.14 (d, J=3.1 Hz, 1H), 7.27 (dd, J=8.5, 3.1 Hz, 1H), 7.16 (d, J=8.5 Hz, 1H), 3.78 (s, 3H), 2.38 (s, 3H).

Step 2:

To a solution of compound 306 (44.1 g, 358 mmol) in DCM (890 mL) was added $Na_2SO_4$ (76.2 g, 537 mmol). The mixture was stirred at room temperature for 15 min then mCPBA (88.0 g, 358 mmol) was added portion wise (exothermic process). The reaction was stirred at room temperature for 20 hours. An additional amount of mCPBA (8.0 g, 36 mmol) was added and the mixture was stirred at room temperature for 3 hours. The reaction was filtered then washed with 1 M KOH (500 mL). The aqueous phase was extracted with DCM (3×200 mL) then the organic phases were combined, dried over $MgSO_4$, filtered and concentrated under vacuum. The oil obtained was dissolved in DCM (600 mL) then $Na_2SO_4$ (17 g) was added followed by the addition of mCPBA (8.0 g). The mixture was stirred at room temperature for 20 hours then washed with an 1 M KOH (500 mL). The aqueous phase was saturated with NaCl and extracted with DCM (3×300 mL). The organic phases were combined, dried over $MgSO_4$, filtered and concentrated under vacuum to give compound 307 as a white solid (28.7 g, 56% yield). $^1$H NMR (400 MHz, DMSO-$d_6$) δ 8.07 (d, J=2.4 Hz, 1H), 7.36 (d, J=8.8 Hz, 1H), 6.96 (dd, J=8.8, 2.5 Hz, 1H), 3.78 (s, 3H), 2.27 (s, 3H).

Step 3:

Water (100 mL) was added drop wise to silica gel (280 g). The mixture was stirred 30 min at RT to obtain a fluffy powder. DCM (420 mL) was added, the mixture was stirred to obtain an homogeneous suspension then a solution of compound 307 (27.7 g, 199 mmol) in DCM (275 mL) was added. After obtaining an homogeneous suspension, a solution of $Br_2$ in DCM (1 M, 285 mL, 199 mmol) was added drop wise over 30 min. The mixture was stirred at room temperature for 18 hours. An additional portion of silica gel (100 g) and a solution of $Br_2$ in DCM (1 M, 142 mL, 100 mmol) were added. The mixture was stirred at room temperature for 8 hours then the same amount of silica gel and of $Br_2$ solution were added. The mixture was stirred at room temperature for 18 hours then filtered. The pad of silica was rinsed with EtOAc (500 mL) then with a mixture DCM/MeOH (8:2, 400 mL). The mother liquors were concentrated under vacuum, redissolved into DCM (500 mL) and this solution was washed with a 10% aqueous solution of sodium metabisulfite (250 mL). The phases were separated. The aqueous phase was saturated with NaCl then carefully extracted with DCM (8×150 mL). The organic phases were combined, dried over $MgSO_4$, filtered and concentrated. The oil obtained was purified quickly by column chromatography (eluents:EtOAc/MeOH from 15:1 to 8:1). The solids isolated (27 g, mixture between 4-bromo and 2-bromo pyridine ~6:4) were suspended in EtOAc (100 mL) and triturated for 1 hour. The solid was filtered (white powder, 24 g) then slurried in DCM (100 mL) and stirred at reflux for 2 hours. The suspension was cooled to room temperature and the solid was filtered to give compound 308. The mother liquors were concentrated and slurried in DCM and the trituration was repeated to give a second batch of compound 308 (white powder, 14.9 g, 34% yield). The remaining mix fractions (8.0 g, 1:1 mixture) was purified by column chromatography (eluents:EtOAc/MeOH from 15:1 to 8:1) to give an additional compound 308 as a white powder (2.6 g, 6% yield). $^1$H NMR (400 MHz, DMSO-$d_6$) δ 8.23 (d, J=2.3 Hz, 1H), 7.79 (d, J=2.6 Hz, 1H), 3.88 (s, 3H), 2.27 (s, 3H).

Step 4:
Compound 308 (2.8 g, 13 mmol) was dissolved in Ac$_2$O (24 mL) and the solution was heated at 60° C. for 18 hours. The mixture was concentrated under vacuum. Cyclohexane (50 mL) was added and the mixture was concentrated under vacuum. This was repeated 3 times. The oil obtained was dissolved in EtOAc (150 mL) and the solution was washed with a saturated aqueous solution of NaHCO$_3$ (100 mL). The phases were separated and the aqueous phase was extracted with EtOAc (2×100 mL). The organic phases were combined, dried over MgSO$_4$, filtered and concentrated under vacuum to give crude compound 309 which was used in the next step without further purification (light brown crystals, 3.18 g). $^1$H NMR (400 MHz, DMSO-d$_6$) δ 8.36 (s, 1H), 7.70 (s, 1H), 5.06 (s, 2H), 3.97 (s, 3H), 2.09 (s, 3H).

Step 5:
Compound 309 (3.2 g, 12 mmol) was dissolved in dioxane (86 mL) then an aqueous solution of NaOH (2 M, 28 mL) was added. The mixture was stirred at room temperature for 18 hours. The solution was acidified with a 1 M aqueous HCl solution until pH 7. The aqueous phase was extracted with EtOAc (3×150 mL). The organic phases were combined, dried over MgSO$_4$, filtered and concentrated to give compound 310 as a pale yellow oil (2.5 g) which was used in the next step without further purification. $^1$H NMR (400 MHz, DMSO-d$_6$) δ 8.28 (s, 1H), 7.64 (s, 1H), 5.43 (t, J=6.0 Hz, 1H), 4.49 (d, J=5.6 Hz, 2H), 3.95 (s, 3H).

Step 6:
Compound 310 (2.5 g, 12 mmol) was dissolved in DCM (80 mL) then triethylamine (2.0 mL, 15 mmol) was added and the solution was cooled at 0° C. Methanesulfonyl chloride (1.0 mL, 13 mmol) was added drop wise and the mixture was stirred at 0° C. for 1 hour. Water (100 mL) was added carefully to the cooled solution. After leaving it to room temperature for 30 min, the phases were separated and the aqueous phase was extracted with DCM (2×100 mL). The organic phases were combined, dried over MgSO$_4$, filtered and concentrated under vacuum (rotavapor bath at RT) to give compound 311 as a brown oil (3.4 g) which was used directly in the next step (degradation observed if kept at room temperature for 24 hours). $^1$H NMR (400 MHz, DMSO-d$_6$) δ 8.42 (s, 1H), 7.83 (s, 1H), 5.23 (s, 2H), 4.00 (s, 3H), 3.27 (s, 3H).

Step 7:
Compound 311 (3.4 g, 12 mmol) was dissolved in ACN (8.5 mL) and 18-crown-6 (4.8 g, 18 mmol) then KCN (1.0 g, 15 mmol) were added. The mixture was heated at 50° C. for 1.5 hour then was cooled to RT. An aqueous solution of NaOH (1 M, 200 mL) was added. The phases were separated and the aqueous phase was extracted with EtOAc (3×100 mL). Organic phases were combined, dried over MgSO$_4$, filtered and concentrated under vacuum. The oil obtained was purified by column chromatography (eluents heptane/EtOAc from 3:1 to 1:1) to give compound 312 as a beige solid (2.5 g, 70% yield over 4 steps). $^1$H NMR (400 MHz, DMSO-d$_6$) δ 8.37 (s, 1H), 7.71 (s, 1H), 4.13 (s, 2H), 3.97 (s, 3H).

Step 8:
Compound 312 (2.0 g, 8.8 mmol) was dissolved in MeOH (135 mL) and NiCl$_2$.6H$_2$O (0.21 g, 0.88 mmol) then Boc$_2$O (3.9 g, 18 mmol) were added. The mixture was cooled at −10° C. then NaBH$_4$ (1.0 g, 27 mmol) was added portion wise over 9 hours. Diethylenetriamine (2 mL) was added and the mixture was stirred at room temperature for 18 hours. The mixture was concentrated under vacuum then EtOAc (100 mL) was added. The solution was washed with a saturated aqueous solution of NaHCO$_3$ (100 mL). Phases were separated and the aqueous phase was extracted with EtOAc (3×100 mL). The organic phases were combined, dried over MgSO$_4$, filtered and concentrated under vacuum. The oil obtained was purified by reverse phase chromatography (eluents H$_2$O/AcCN from 95:5 to 5:95). Compound 313 was obtained as colorless oil (1.0 g, 35% yield). $^1$H NMR (400 MHz, DMSO-d$_6$) δ 8.35 (s, 1H), 7.51 (s, 1H), 6.85-6.81 (m, 1H), 3.96 (s, 3H), 3.24-3.20 (m, 2H), 2.80-2.76 (m, 2H), 1.38 (s, 9H).

Step 9:
Compound 313 (1.0 g, 3.0 mmol) was dissolved in DMF (135 mL). The solution was cooled at 0° C. then NaH (60% in oil, 180 mg, 4.5 mmol) was added portion wise over 10 min. The mixture was stirred at 0° C. for 1 hour then MeI (0.19 mL, 3.0 mmol) was added drop wise over 10 min. The mixture was stirred at room temperature for 3 hours. The solution was cooled again at 0° C. then H$_2$O (100 mL) was added carefully. The mixture was extracted with Et$_2$O (3×150 mL). The organic phases were combined, dried over MgSO$_4$, filtered and concentrated. The oil obtained was combined with two other samples (starting from 100 mg each) and was purified by column chromatography (eluents heptanes/EtOAc from 3:1 to 1:1). 10% of SM was observed so the previous sample was dissolved in DMF (30 mL), the solution was cooled to 0° C. then NaH (37 mg, 1.0 mmol) was added portion wise. The mixture was stirred at 0° C. for 1 hour then MeI (29 µL, 0.45 mmol) was added. The mixture was stirred at room temperature for 2 hours then was cooled at 0° C. Water (50 mL) was added carefully and was extracted with Et$_2$O (3×100 mL). The organic phases were combined, dried over MgSO$_4$, filtered and concentrated to give compound 314 as a pale yellow oil (920 mg, 75% yield). $^1$H NMR (400 MHz, DMSO-d$_6$) δ 8.28 (s, 1H), 7.54 (s, 1H), 3.92 (s, 3H), 3.54-3.36 (m, 2H), 2.84 (t, J=6.8 Hz, 2H), 2.74 (s, 3H), 1.48-1.11 (m, 9H).

Preparation of tert-butyl [1-(4-bromo-3-methoxy-1-methyl-1H-pyrazol-5-yl)ethyl]methylcarbamate (325)

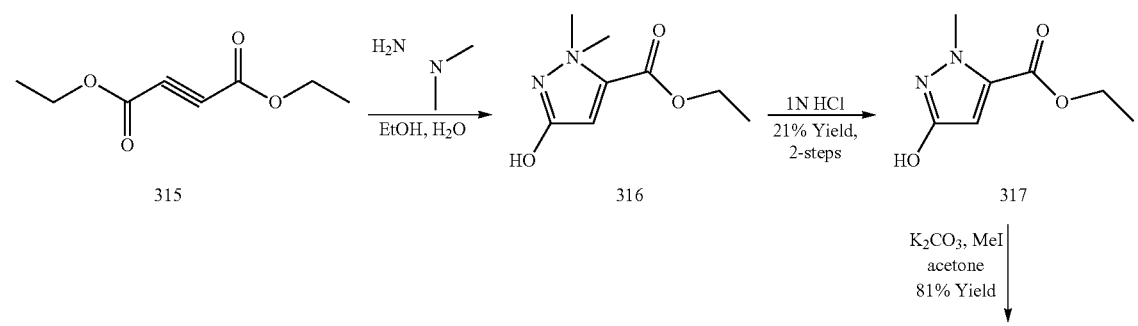

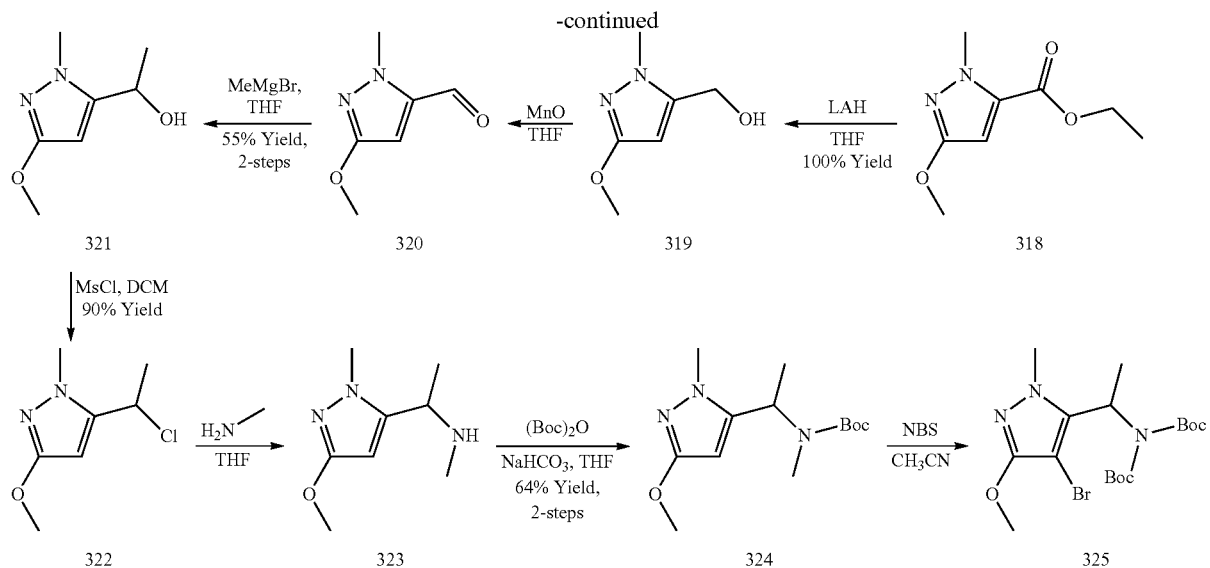

Step 1:

A mixture of compound 315 (55 mL, 0.35 mol) in 1:1 EtOH/H2O (600 mL) was slowly added at 0° C. a solution of 1,1-dimethylhydrazine (25.74 g, 0.44 mol w/w 40% in water) in 1:1 EtOH/H2O (200 mL). The solution was stirred at 0° C. for 30 mins, then allowed to warm to room temperature for 1 h. The mixture was concentrated and the residue was partitioned between water (300 mL) and EtOAc (300 mL). The aqueous layer was concentrated to give compound 316, which was used for next step directly.

Step 2:

A mixture of compound 316 in 1N HCl (200 mL) was stirred at room temperature for 1.5 h. The mixture was extracted with DCM (150 mL), the aqueous layer was concentrated to give the residue, which was purified by column chromatography (silica gel, petroleum ether/EtOAc=6:1) to yield compound 317 (13 g, 21%) as a white solid. $_1$H NMR (400 MHz, CDCl$_3$): δ 6.148 (s, 1H), 4.34-4.26 (m, 2H), 3.99 (s, 3H), 1.38-1.30 (m, 3H)

Step 3:

A mixture of compound 317 (4 g, 23.5 mmol), K2CO3 (9.7 g, 70.5 mmol) and MeI (16.8 g, 0.11 mol) were heated to reflux for 3 hours. TLC (petroleum ether/EtOAc=6:1) showed the reaction was complete. The mixture was filtered and the filtrate was concentrated to give the residue, which was purification by column chromatography (silica gel, petroleum ether/EtOAc=20:1) to yield compound 318 (3.5 g, 81%) as a yellow oil. $^1$H NMR (400 MHz, CDC$_3$): δ 6.18 (s, 1H), 4.34-4.29 (q, 2H), 4.05 (s, 3H), 3.83 (s, 3H), 1.38-1.34 (t, 3H).

Step 4:

To a mixture of compound 318 (2 g, 11.5 mmol) in THF (50 mL) was added LiAlH4 (0.52 g, 13.8 mmol) in portions at 0° C. After the addition, the reaction mixture was stirred at room temperature overnight. TLC (petroleum ether/EtOAc 1/1) showed the reaction mixture was complete. The reaction mixture was quenched with 20% aq. NaOH (4 mL). The mixture was filtered and the filtrate was concentrated in vacuo to give compound 319 (1.7 g, ~100%) as colorless oil. $^1$H NMR (400 MHz, CDCl$_3$): δ 5.58 (s, 1H), 4.55 (s, 2H), 4.83 (s, 3H), 3.65 (s, 3H).

Step 5:

A solution of compound 319 (2 g, 14.3 mmol), MnO2 (6.2 g, 71.4 mmol) in dry THF (50 mL) was heated to reflux overnight. TLC (petroleum ether/EtOAc 6/1) showed the reaction mixture was complete. The reaction mixture was filtered and the filtrate (compound 320) was used for next step directly.

Step 6:

To a solution of compound 320 (~14.3 mmol) in dry THF (100 mL) was added MeMgBr (24 mL, 71.4 mmol, 3.0M) at −50° C. After the addition, the reaction mixture was stirred at room temperature for 15 hours. TLC (petroleum ether/EtOAc 6/1) showed the reaction mixture was completed. The reaction mixture was quenched with sat.NH4Cl (20 mL). The mixture was then extracted with EtOAc (100 mL×3). The combined extracts were washed with brine (100 mL×2), dried over Na2SO4 and concentrated in vacuo to give the residue, which was purified via column chromatography (silica gel, petroleum ether/EtOAc 10/1) to give compound 321 (1.2 g, 55%) as a yellow oil. $^1$H NMR (400 MHz, CDCl$_3$): δ 5.58-5.57 (d, 1H), 4.84-4.80 (q, 1H), 3.83 (s, 3H), 3.73-3.72 (d, 3H), 2.03-2.02 (bs, 1H), 1.55-1.53 (d, 3H).

Step 7:

To a solution of compound 321 (1.2 g, 7.6 mmol) and Et3N (1.1 g, 11.4 mmol) in dry DCM (30 mL) was added dropwise MsCl (1.3 g, 11.4 mmol) at 0° C. After addition, the reaction mixture was stirred at room temperature for 12 hours. TLC (petroleum ether/EtOAc 1/1) showed the reaction mixture was complete. The reaction mixture was washed with brine (20 mL), dried over Na2SO4 and concentrated in vacuo to give crude the residue, which was purified by column chromatography (silica gel, petroleum ether/EtOAc 20/1) to give compound 322 (1.2 g, 90%) as a yellow oil. $^1$H NMR (400 MHz, CDCl$_3$): δ 5.61 (s, 1H), 5.04-4.99 (q, 1H), 3.85 (s, 3H), 3.76 (s, 3H), 1.88-1.86 (d, 3H).

Step 8:

A solution of compound 322 (0.3 g, 1.72 mmol) in a solution of CH3NH2 (20 mL, 2M in THF) was heated to 80° C. in a sealed tube for 12 hours. TLC (petroleum ether/EtOAc 6/1) showed the reaction mixture was complete. The compound 323 was used for next step directly.

Step 9:

To a mixture of compound 323 in DCM (20 mL) was added Et3N (347 mg, 3.44 mmol) and (Boc)2O (743 mg, 3.44 mmol), the mixture was stirred at room temperature overnight. TLC (petroleum ether/EtOAc 6/1) showed the reaction mixture was complete. The reaction mixture was partitioned between water (20 mL) and DCM (50 mL). The separated organic layer was washed with brine (50 mL), dried over Na2SO4 and concentrated in vacuo to give the residue, which was purified by column chromatography (silica gel, petroleum ether/EtOAc 20/1) to give compound 324 (300 mg, 64% in two steps) as colorless oil. $^1$H NMR (400 MHz, CDCl$_3$): δ 5.59 (s, 1H), 5.47 (br, 1H), 3.83 (s, 3H), 3.62 (s, 3H), 2.54 (s, 3H), 1.48 (s, 9H); LCMS: m/z for C13HN3O3 270.3 [M+H]+.

Step 10:

To a solution of compound 324 (2.1 g, 7.78 mmol) in DCM (20 mL) was added in portions NBS (1.46 g, 8.16 mmol) at 0° C. After addition, the reaction mixture was stirred at room temperature for 2 hours. TLC (petroleum ether/EtOAc 6/1) showed the reaction mixture was completed. The reaction mixture was washed with sat. NaHCO3 (30 mL×4), brine (30 mL), dried over Na2SO4 and concentrated in vacuo to give compound 325 (2.5 g, 91%) as yellow oil. $^1$H NMR (400 MHz, CDCl$_3$): δ 5.79 (s, 1H), 3.92 (s, 3H), 3.68 (s, 3H), 2.70 (s, 3H), 1.66-1.64 (d, 3H), 1.47 (s, 9H).

Preparation of 5-bromo-3-[2-fluoro-1-(5-fluoro-2-iodophenyl)ethoxy]pyrazin-2-amine (326)

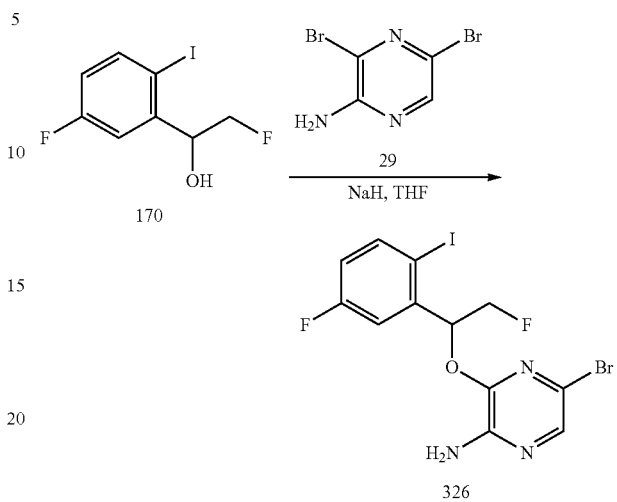

The procedure described in step 2 for compound 241 was used to prepare compound 326.

Preparation of 1-methyl-5-[(methylamino)methyl]-1H-pyrazole-3-carbonitrile (333)

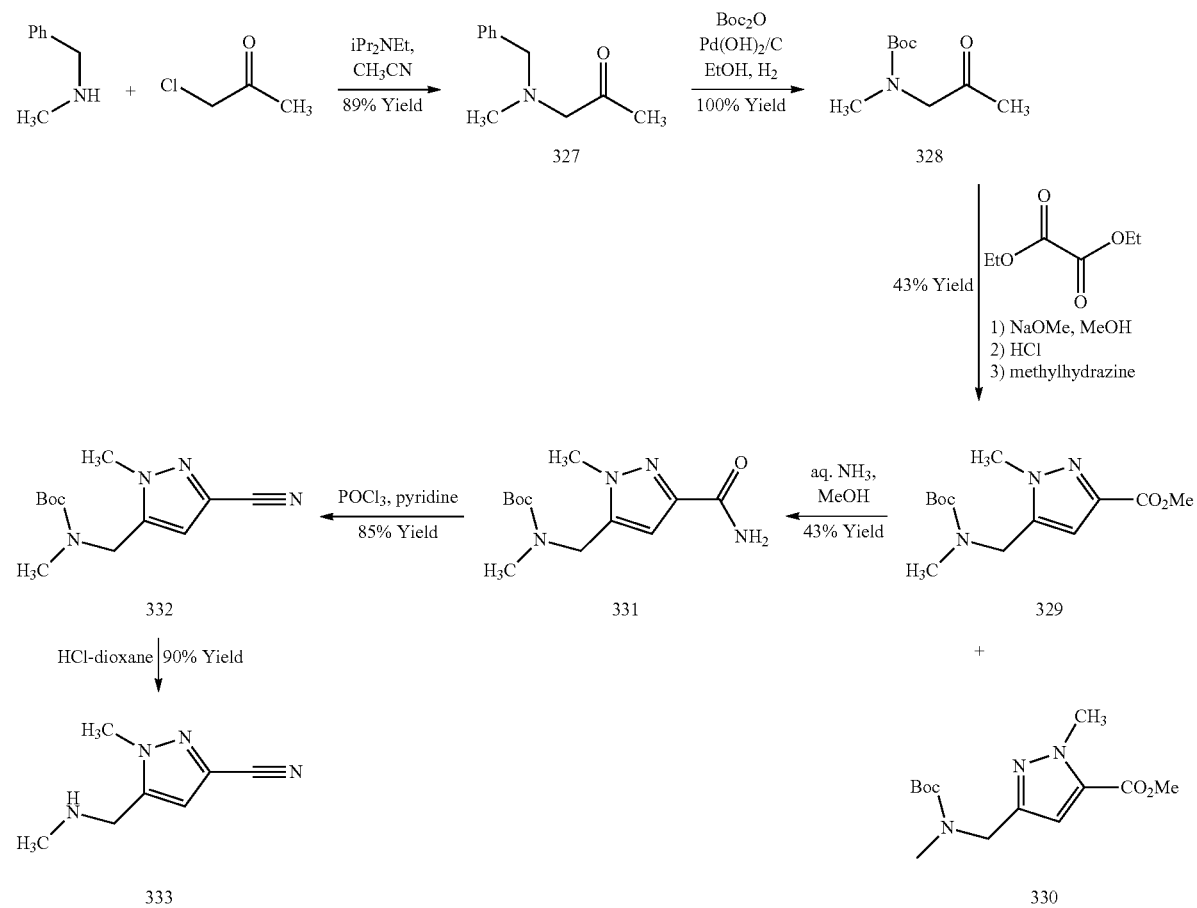

Step 1:

Chloroacetone (207 mL, 2.59 mol) was added drop wise over 45 min to a solution of DIEA (410 mL, 310 g, 2.40 mol) and N-methylbenzylamine (286 g, 2.36 mol) in acetonitrile (1500 mL), maintaining the temperature at between 18 and 20° C. by gentle cooling with a cold water bath. Once addition was complete the cooling bath was left in place for a further 30 min before being removed. Stirring was continued for a further 5.5 h, during which time the internal reaction temperature rose to 27° C. over 1 hour, plateaued for 2 hours and then slowly dropped. The reaction mixture was concentrated in vacuo to approximately 1 L then left to stand overnight. Crystalline precipitate was removed by filtration, washing with acetonitrile (50 mL) and the filtrate was concentrated in vacuo. The concentrated filtrate was taken up in EtOAc (1 L) and filtered through a short silica pad (1200 mL silica) washing with further EtOAc (2×1 L). The filtrate was concentrated in vacuo to give compound 327 as an orange-brown oil (374 g, 89%). $^1$H NMR (400 MHz, Chloroform-d) δ 7.39-7.22 (m, 5H), 3.59 (s, 2H), 3.16 (s, 2H), 2.30 (s, 3H), 2.14 (s, 3H).

Step 2:

Palladium hydroxide on carbon (20%, 36 g) and di-tertbutyl dicarbonate (565 g, 2.59 mol) were added to a solution of compound 327 (439 g, 2.48 mol) in ethanol (3.25 L) and the mixture was hydrogenated at 50° C. and 50 psi pressure of $H_2$ for 8 hours. Heating was stopped and the reaction was left under hydrogen over the weekend. Catalyst was removed by filtering through Celite, washing with methanol, and the solvent was removed in vacuo to give compound 328 as a brown oil containing a small amount of suspended solid (476.5 g). This material was used without further purification. $^1$H NMR (400 MHz, Chloroform-d) 2 rotamers δ 4.00 and 3.90 (2×s, 2H), 2.92 and 2.88 (2×s, 2H), 2.12 (s, 3H), 1.47 and 1.42 (2×s, 9H).

Step 3:

A mixture of diethyl oxalate (187 mL, 1.38 mol) and compound 328 (258 g, 1.38 mol) in MeOH (200 mL) was added drop wise over 30 min to a solution of NaOMe in MeOH (5.38 M, 257 mL, 1.38 mol) in MeOH (1800 mL). Once then addition was complete the reaction was heated to 55° C. and stirred for 2 hours. The reaction was then heated at 65° C. for 30 min before being cooled to −7° C. A solution of methylhydrazine hydrochloride in MeOH (preformed by the dropwise addition of conc. HCl [115 mL, 1.38 mol] to an ice cooled solution of methylhydrazine [72.7 mL, 63.6 g, 1.38 mol] in MeOH [100 mL]) was then added drop wise so that the temperature was kept below −5° C. Once addition was complete the reaction was allowed to warm slowly to room temperature and stirred overnight. The reaction mixture was filtered and concentrated in vacuo. The brown semi-solid mass was then taken up in 10% DCM in heptane (500 mL+250 mL to wash) filtered and combined with the material from a second reaction (207 g tert-butyl methyl(2-oxopropyl) carbamate, 1.10 mol). The combined filtrates were applied to the top of a dry flash column (3.7 L silica) and the column was eluted with heptanes/EtOAc (5-25%) to give compounds 329 and 330 (1:3 ratio). Compound 329: (191 g, 66% purity, 18%). $^1$H NMR (400 MHz, CDCl$_3$) δ 6.69 (s, 1H), 4.46 (s, 2H), 3.89 (s, 6H), 2.77 (s, 3H), 1.45 (s, 9H). LCMS [MH+]− 284.16. Compound 330: (302 g, 43%). $^1$H NMR (400 MHz, DMSO-d6) δ 6.65 (s, 1H), 4.30 (s, 2H), 4.04 (s, 3H), 3.82 (s, 3H), 2.76 (s, 3H), 1.40 (s, 9H).

Step 4:

Compound 329 (7.55 g, 26.6 mmol) was dissolved in MeOH (7 mL) then an aqueous solution of ammonia (35%, 70 mL) was added. The solution was stirred at room temperature for 18 hours. The suspension formed was filtered and the white solid isolated was dried to give compound 331 (3.4 g, 43% yield). $^1$H NMR (400 MHz, DMSO-d$_6$) δ 7.42 (s, 1H), 7.17 (s, 1H), 6.49 (s, 1H), 4.46 (s, 2H), 3.81 (s, 3H), 2.76 (s, 3H), 1.41 (s, 9H).

Step 5:

Compound 331 (3.4 g, 13 mmol) was dissolved in pyridine (34 mL) and the solution was cooled at 0° C. POCl$_3$ (2.32 mL, 25.4 mmol) was added drop wise maintaining the temperature less than 25° C. The mixture was then stirred at 0° C. for additional 5 minutes and then at RT for 20 minutes. The reaction was quenched by adding water (200 mL) slowly. The temperature of the mixture was kept below 30° C. by adding ice. At the end of the addition, the mixture was stirred at RT for 40 minutes then extracted with EtOAc (3×200 mL). The organic phases were combined, washed with an aqueous saturated solution of NaHCO$_3$ (200 mL) then brine (200 mL), dried over MgSO$_4$, filtered and concentrated under vacuum. The brown oil obtained was purified by column chromatography to give compound 332 as yellow oil (2.71 g, 85% yield). $^1$H NMR (400 MHz, DMSO-d$_6$) δ 6.84 (s, 1H), 4.49 (s, 2H), 3.87 (s, 3H), 2.77 (s, 3H), 1.40 (s, 9H).

Step 6:

Compound 332 (2.71 g, 10.8 mmol) was dissolved in DCM (15 mL) and the solution was cooled at 0° C. HCl (4 M in dioxane, 15 mL, 60 mmol) was added drop wise, the solution was stirred at 0° C. for 10 minutes then at room temperature for 3 hours. The suspension obtained was concentrated under vacuum until obtaining half of the initial volume. The suspension was filtered, the solids were rinsed with DCM (10 mL) and dried to give compound 333 hydrochloride as a white solid (1.80 g, 90% yield). $^1$H NMR (400 MHz, Methanol-d$_4$) δ 6.99 (s, 1H), 4.42 (s, 2H), 4.03 (s, 3H), 2.81 (s, 3H).

Preparation of 1-[5-fluoro-2-(pent-4-yn-1-yloxy)phenyl]ethanol (336)

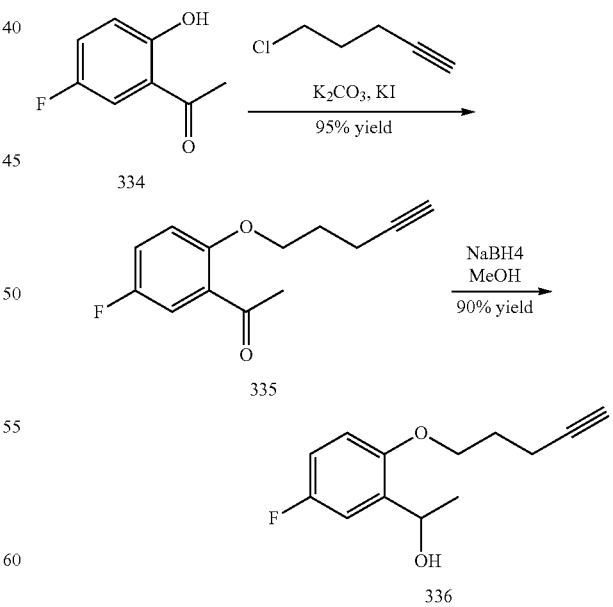

Step 1:

1-(5-fluoro-2-hydroxyphenyl)ethanone 334 (5.0 g, 32.5 mmol), K$_2$CO$_3$ (8.96 g, 64.9 mmol) and KI (8.08 g, 48.7 mmol) were mixed in DMF (150 mL). 5-chloropent-1-yne (5.15 mL, 48.7 mmol) was added and the mixture was heated at 80° C. for 18 hours. LC-MS showed full conversion. The mixture was cooled at RT and EtOAc (1 L) was added then washed with water (6×200 mL). The organic phase was dried over MgSO4, filtered and concentrated under vacuum. The oil obtained was purified by column chromatography (eluents heptanes/EtOAc from 6:1 to 3:1) to give compound 335 as pale yellow oil (6.82 g, 95% yield, 100% purity by LC-MS). $^1$H NMR (400 MHz, DMSO-d6) δ 7.45-7.31 (m, 2H), 7.20 (dd, J=9.1, 4.2 Hz, 1H), 4.15 (t, J=6.1 Hz, 2H), 2.83 (t, J=2.7 Hz, 1H), 2.55 (s, 3H), 2.37 (td, J=7.1, 2.7 Hz, 2H), 2.10-1.85 (m, 2H).

Step 2:

Compound 335 (6.62 g, 30.1 mmol) was dissolved in MeOH (120 mL). The solution was cooled at 0° C. and NaBH4 (1.47 g, 39.1 mmol) was added portion wise. The mixture was stirred at 0° C. for 1 hour the RT for 30 minutes. TLC showed full completion. Water (300 mL) was added slowly to the mixture and was extracted with EtOAc (2×200 mL). The organic phases were combined, dried over MgSO4, filtered and concentrated under vacuum. The oil obtained was purified by column chromatography (eluents heptanes/EtOAc from 9:1 to 3:1) to give compound 336 as pale yellow oil (6.04 g, 90% yield, 97% purity by LC-MS). $^1$H NMR (400 MHz, DMSO-d6) δ 7.17 (dd, J=9.7, 3.1 Hz, 1H), 7.05-6.85 (m, 2H), 5.13 (d, J=3.9 Hz, 1H), 4.95 (p, J=6.2 Hz, 1H), 4.12-3.91 (m, 2H), 2.81 (t, J=2.7 Hz, 1H), 2.34 (td, J=7.1, 2.7 Hz, 2H), 1.96-1.84 (m, 2H), 1.26 (d, J=6.3 Hz, 3H).

EXAMPLES

Preparation of (5R)-8-amino-3-fluoro-5,17-dimethyl-13-(methylsulfonyl)-16,17-dihydro-7,11-(metheno)dibenzo[g,l][1,4,10]oxadiazacyclotetradecin-18(5H)-one (Example 1)

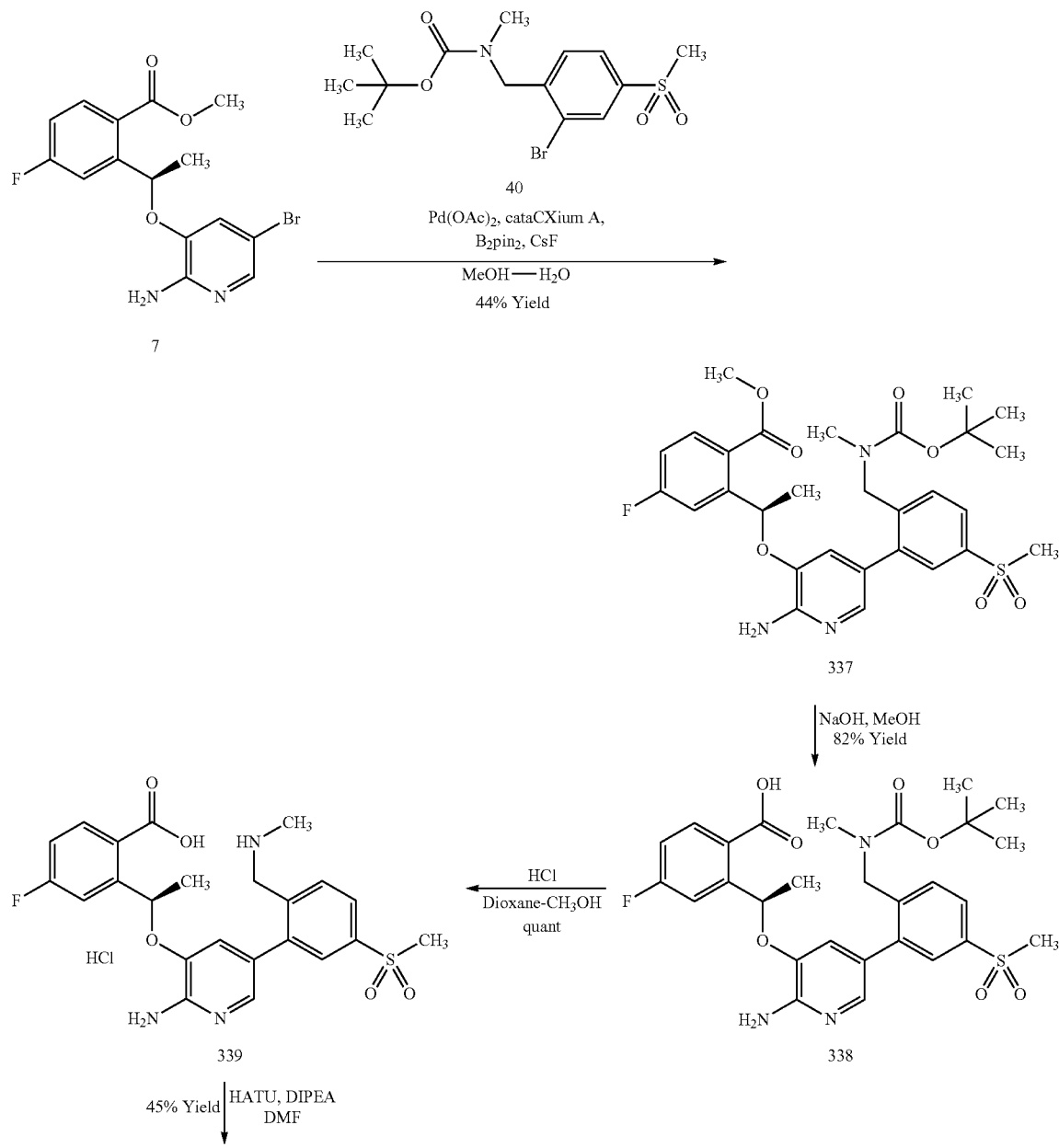

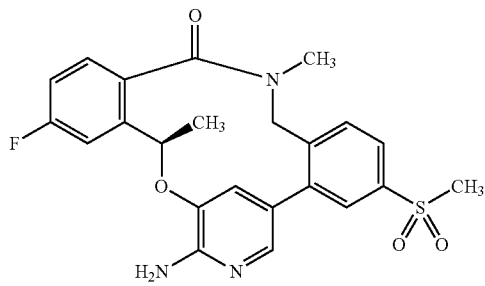

Example 1

Step 1:

Palladium (II) acetate (70 mg, 0.31 mmol) and cat-aCXium® A (221 mg, 0.62 mmol) were mixed together in toluene (2.5 mL, de-gassed) and the resulting solution was added via pipette to a stirred solution of compound 7 (1.10 g, 3.1 mmol), bis-pinacolato diboron (1.6 g, 6.2 mmol) and CsF (1.87 g, 12.4 mmol) in MeOH/H2O (4:1, 24 mL, de-gassed) at 50° C. After 4-5 minutes, the reaction became dark grey/brown in color and a solution of compound 40 (900 mg, 2.4 mmol) in methanol (5 mL, de-gassed) was added all at once. The resulting mixture was then stirred at reflux for 3 hrs, by which time TLC (EtOAc/cyclohexane 6:4) had shown complete consumption of both aryl bromides and conversion to a major new more polar spot (Rf=0.35). After cooling to room temperature, the mixture was diluted with EtOAc (150 mL) and washed with water (100 mL), then brine (100 mL), dried ($Na_2SO_4$) and evaporated. The residue was purified by flash chromatography over silica gel, which was eluted with 6:4 EtOAc/cyclohexane, and gave compound 110 as a light brown foam (950 mg). TLC: Rf=0.35 (EtOAc/cyclohexane 6:4). $^1$H NMR (400 MHz, $CDCl_3$) δ 8.00 (dd, 1 H, J=9.1, 6.1 Hz), 7.83-7.84 (m, 1 H), 7.63 (d, 1 H, J=2.1 Hz), 7.56-7.59 (m, 1 H), 7.34-7.37 (m, 1 H), 6.97-7.04 (m, 2 H), 6.58-6.61 (m, 1 H), 6.39-6.45 (m, 1 H), 4.98 (br s, 2 H), 4.05-4.30 (m, 2 H), 3.84 (br s, 3 H), 3.05 (br s, 3 H), 2.54-2.68 (m, 3 H), 1.67 (d, 3 H, J=6.3 Hz), 1.32-1.51 (m, 9 H). LCMS ES m/z 588 $[M+H]^+$.

Step 2:

To a solution of compound 337 (65% purity, 1.1 g, assumed 1.2 mmol) in MeOH (25 mL) was added NaOH (1.2 g, 30 mmol) and the mixture was stirred at room temperature overnight. The reaction was diluted with water (60 mL) and washed with MTBE (60 mL). The aqueous layer was then acidified carefully with 1 M aq HCl to approx pH 4 (pH paper). Sodium chloride (10 g) was added to the mixture and the mixture was extracted with EtOAc (80 mL). The organic layer was separated, dried ($Na_2SO_4$) and evaporated. The residue was purified by flash chromatography over silica gel which was eluted with 2% AcOH in EtOAc, giving compound 338 (550 mg, 82% yield) as an off white foam. TLC: Rf=0.5 (2% AcOH in EtOAc). $^1$H NMR (400 MHz, $CD_3OD$) δ 7.98 (dd, 1 H, J=8.2, 5.8 Hz), 7.88 (dd, 1 H, J=8.0, 1.7 Hz), 7.62 (s, 1 H), 7.40-7.44 (m, 2 H), 7.34 (dd, 1 H, J=10.1, 2.7 Hz), 7.05-7.09 (m, 1 H), 6.90-6.83 (m, 1 H), 6.53 (br s, 1 H), 4.00-4.33 (m, 2 H), 3.12 (s, 3 H), 2.55-2.75 (m, 3 H), 1.70 (d, 3 H, J=6.55 Hz), 1.25-1.48 (m, 9 H). LCMS ES m/z 574 $[M+H]^+$.

Step 3:

A solution of HCl in dioxane (4 M, 5.0 mL) was added to a solution of compound 338 (550 mg, 0.96 mmol) in dioxane/MeOH (4:1, 15 mL) and the reaction was stirred at room temperature overnight. The reaction mixture was then concentrated to dryness under reduced pressure. The residue was taken-up in MeOH (50 mL) and toluene (100 mL) was added and the mixture was then again evaporated to dryness, which gave compound 339 as an off white solid (500 mg, assumed quantitative yield). $^1$H NMR (400 MHz, $CD_3OD$) δ 8.10 (dd, 1 H, J=8.0, 2.0 Hz), 8.06 (dd, 1 H, J=8.9, 5.9 Hz), 7.85 (d, 1 H, J=8.0 Hz), 7.78 (d, 1 H, J=2.0 Hz), 7.56 (d, 1 H, J=1.7 Hz), 7.48 (dd, 1 H, J=9.9, 2.7 Hz), 7.26 (d, 1 H, J=1.7 Hz), 7.19 (dt, 1 H, J=8.31, 2.85 Hz), 6.70 (q, 1 H, J=6.5 Hz), 4.19 (d, 1 H, J=14.5 Hz), 4.13 (d, 1 H, J=14.6 Hz), 3.17 (s, 3 H), 2.61 (s, 3 H), 1.76 (d, 3 H, J=6.0 Hz). LCMS ES m/z 474 $[M+H]^+$.

Step 4:

A solution of compound 339 (500 mg, assumed 0.96 mmol) as the HCl salt and DIPEA (2.0 g, 15.5 mmol) in DMF (6.0 mL) and THF (1.0 mL) was added drop-wise to a solution of HATU (510 mg, 1.34 mmol) in DMF (6.0 mL) at 0° C. over 35 minutes. After complete addition, the mixture was stirred at 0° C. for a further 60 mins. Water (100 mL) was added and the mixture was extracted into EtOAc (2×50 mL). The combined organics were washed with saturated aqueous $NaHCO_3$ (100 mL), brine (100 mL), dried over $Na_2SO_4$, and evaporated. The residue was purified by column chromatography over silica gel, which was eluted with 100% EtOAc, giving a sticky solid. The solids were dissolved in acetonitrile (2.5 mL) and MTBE (30 mL) was added slowly with good stirring to precipitate the product. After stirring for 20 minutes, the mixture was filtered, and Example 1 was collected as a cream colored solid (200 mg, 45% yield). TLC: $R_f$=0.5 (100% EtOAc). $^1$H NMR (400 MHz, DMSO-$d_6$) δ 7.84-7.92 (m, 3 H), 7.69 (dd, 1 H, J=10.4, 2.8 Hz), 7.51 (d, 1 H, J=2.0 Hz), 7.36 (dd, 1 H, J=8.8, 6.0 Hz), 7.14 (dt, 1 H, J=8.4, 2.4 Hz), 7.09 (d, 1 H, 2.0 Hz), 6.13 (s, 2 H), 5.71-5.67 (m, 1 H), 4.45 (d, 1 H, J=13.2 Hz), 4.22 (d, 1 H, J=13.2 Hz), 3.29 (s, 3 H), 3.01 (s, 3 H), 1.69 (d, 3 H, J=6.4 Hz). LCMS ES m/z 456 $[M+H]^+$.

Crystals of Example 1 were grown by vapor diffusion of pentane into an ethanol solution, and data were collected in a nitrogen gas stream at 120(2) K. See FIG. 1.

Preparation of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Example 2)
Step 1:
Palladium (II) acetate (53 mg, 0.24 mmol) and cataCXium® A (180 mg, 0.5 mmol) were mixed together in toluene (1.5 mL, de-gassed) and the resulting solution was
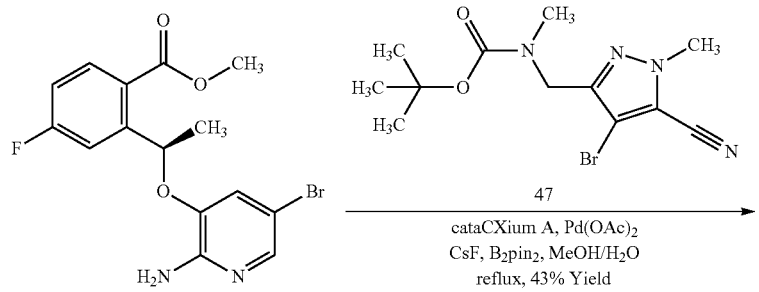
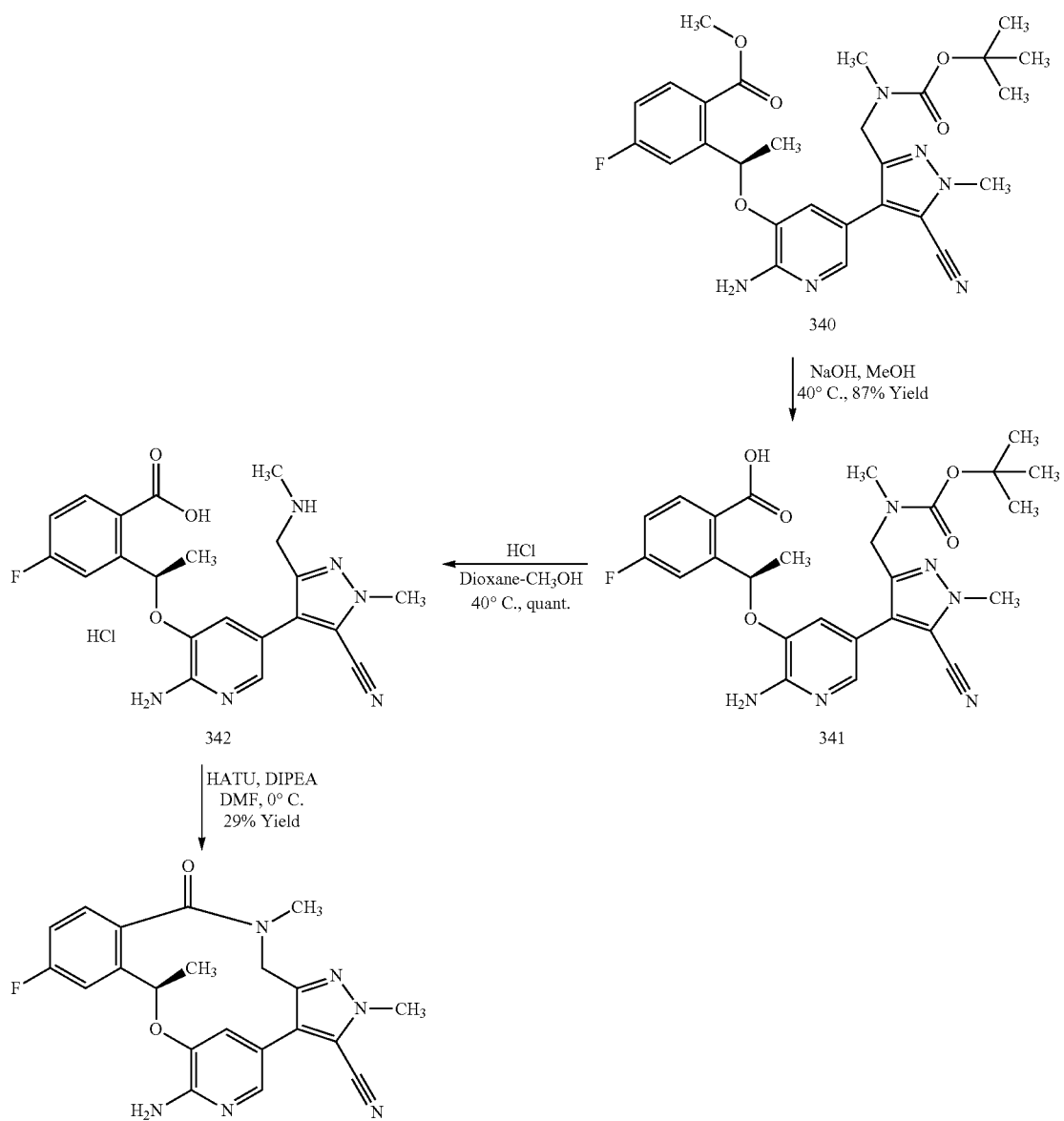

added via pipette to a stirred solution of compound 7 (0.9 g, 2.4 mmol), compound 47 (1.0 g, 3.0 mmol) bis-pinacolato diboron (0.9 g, 3.6 mmol) and CsF (1.9 g, 12.6 mmol) in MeOH/H$_2$O (9:1, 12 mL, de-gassed) at 60° C. The resulting mixture was then stirred at reflux for 3 hrs. A further portion of Palladium (II) acetate (26 mg, 0.12 mmol) and cataCXium® A (90 mg, 0.25 mmol) in toluene (1.5 mL, de-gassed) was added, and the yellow reaction mixture stirred at 60° C. overnight. After cooling to room temperature, the mixture was diluted with EtOAc (150 mL) and filtered through celite. The filtrate was washed with water (100 mL), then brine (100 mL), dried (Na$_2$SO$_4$) and evaporated. The residue was purified by flash chromatography over silica gel, which was eluted with 1:1 EtOAc/cyclohexane, and gave compound 340 as a yellow oil (570 mg, 43% yield). TLC (Rf=0.40, 1:1 EtOAc/cyclohexane). $^1$H NMR (400 MHz, CDCl$_3$) δ 8.03 (m, 1 H), 7.65 (s, 1 H), 7.27 (dd, 1 H, J=9.9, 2.7 Hz), 7.01 (m, 1 H), 6.68 (m, 1 H), 6.40 (m, 1 H), 4.90 (br s, 2 H), 4.20-4.30 (m, 2 H), 3.96 (s, 3 H), 3.94 (s, 3 H), 2.55-2.85 (m, 3 H), 1.68 (d, 3 H, J=6.6 Hz), 1.24 (s, 9 H). LCMS ES m/z 539 [M+H]$^+$.

Step 2:

To a solution of compound 340 (69% purity, 0.95 g, assumed 1.05 mmol) in MeOH (20 mL) was added a solution NaOH (1.0 g, 25 mmol) in water (2 mL). The mixture was stirred at 40° C. for 3.5 hours. The reaction was diluted with water (80 mL), concentrated by 20 mL to remove MeOH on the rotovap, and washed with MTBE (100 mL). The aqueous layer was then acidified carefully with 1 M aq HCl to approx pH 2 (pH paper). Sodium chloride (15 g) was added to the mixture and the mixture was extracted with EtOAc (100 mL). The organic layer was separated, dried (Na$_2$SO$_4$) and evaporated to give compound 341 as a pale yellow solid (480 mg, 87% yield). $^1$H NMR (400 MHz, CD$_3$OD) δ 8.05 (m, 1 H), 7.45 (s, 1 H), 7.37 (dd, 1 H, J=10.4, 2.8 Hz), 7.10 (dt, 1 H, J=8.5, 2.4 Hz), 6.50-6.60 (m, 2 H), 4.05-4.30 (m, 2 H), 3.99 (s, 3 H), 2.60-2.80 (m, 3 H), 1.72 (d, 3 H, J=6.5 Hz). LCMS ES m/z 525 [M+H]$^+$.

Step 3:

A solution of HCl in dioxane (4 M, 6.0 mL) was added to a solution of compound 341 (480 mg, 0.91 mmol) in MeOH (6 mL) and the reaction was stirred at 40° C. for 2.5 hours. The reaction mixture was then concentrated to dryness under reduced pressure. The residue was taken-up in MeOH (50 mL) and acetonitrile (100 mL) was added and the mixture was then again evaporated to dryness, to give compound 342 as an off white solid (400 mg, 87% yield). $^1$H NMR (400 MHz, CD$_3$OD) δ 8.07 (dd, 1 H, J=8.9. 5.9 Hz), 7.51 (d, 1 H, J=1.7 Hz), 7.42 (dd, 1 H, J=9.8, 2.6 Hz), 7.23 (d, 1 H, J=1.6 Hz), 7.16 (dt, 1 H, J=8.5, 2.7 Hz), 6.73 (dd, 1 H, J=11.9, 6.9 Hz), 4.22 (d, 1 H, J=14.7 Hz), 4.14 (d, 1 H, J=14.7 Hz), 4.07 (s, 3 H), 2.75 (s, 3 H), 1.75 (d, 3 H, J=5.5 Hz). LCMS ES m/z 425 [M+H]$^+$.

Step 4:

A solution of compound 342 (400 mg, assumed 0.91 mmol) as the HCl salt and DIPEA (1.17 g, 9.1 mmol) in DMF (5.0 mL) and THF (0.5 mL) was added drop-wise to a solution of HATU (482 mg, 1.27 mmol) in DMF (10.0 mL) at 0° C. over 30 minutes. After complete addition, the mixture was stirred at 0° C. for a further 30 mins. Water (70 mL) was added and the mixture was extracted into EtOAc (2×60 mL). The combined organics were washed with saturated aqueous NaHCO$_3$ (2×100 mL), brine (100 mL), dried over Na$_2$SO$_4$, and evaporated. The residue was purified by column chromatography over silica gel, which was eluted with 70% EtOAc/ cyclohexane giving 205 mg of a pale yellow residue (semi-solid). The solids were dissolved in MTBE (7 mL) and cyclohexane (20 mL) was added slowly with good stirring to precipitate the product. After stirring for 30 minutes, the mixture was filtered, and Example 2 was collected as a white solid (110 mg, 29% yield). TLC (Rf=0.40, 70% EtOAc in cyclohexane). $^1$H NMR (400 MHz, CDCl$_3$) δ 7.83 (d, 1 H, J=2.0 Hz), 7.30 (dd, 1 H, J=9.6, 2.4 Hz), 7.21 (dd, 1 H, J=8.4, 5.6 Hz), 6.99 (dt, 1 H, J=8.0, 2.8 Hz), 6.86 (d, 1 H, J=1.2 Hz), 5.75-5.71 (m, 1 H), 4.84 (s, 2 H), 4.45 (d, 1 H, J=14.4 Hz), 4.35 (d, 1 H, J=14.4 Hz), 4.07 (s, 3 H), 3.13 (s, 3 H), 1.79 (d, 3 H, J=6.4 Hz). LCMS ES m/z 407 [M+H]$^+$.

Preparation of (10R)-7-amino-12-fluoro-3-methoxy-10,16-dimethyl-16,17-dihydro-8,4-(metheno)isothia-zolo[4,3-h][2,5,11]benzoxadiazacyclotetradecin-15(10H)-one (Example 3)

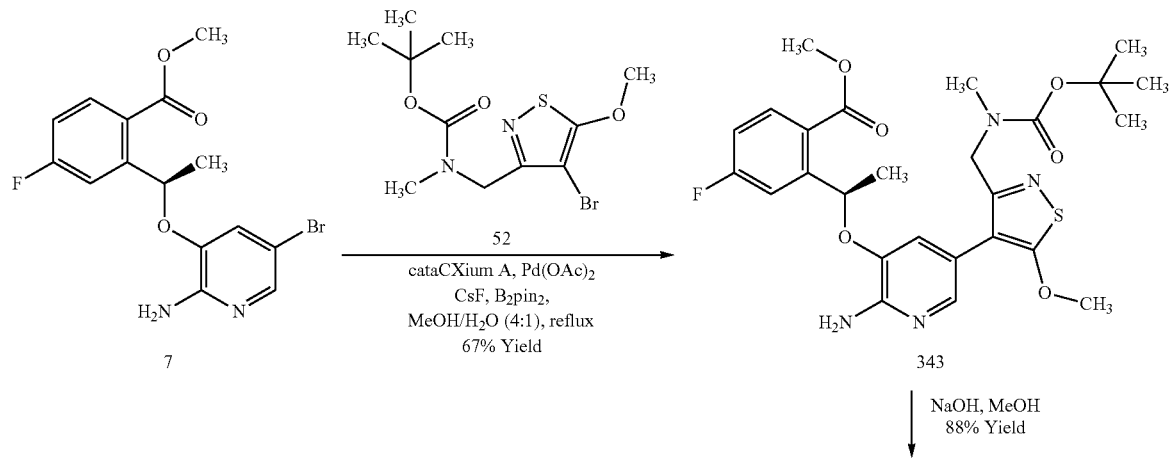

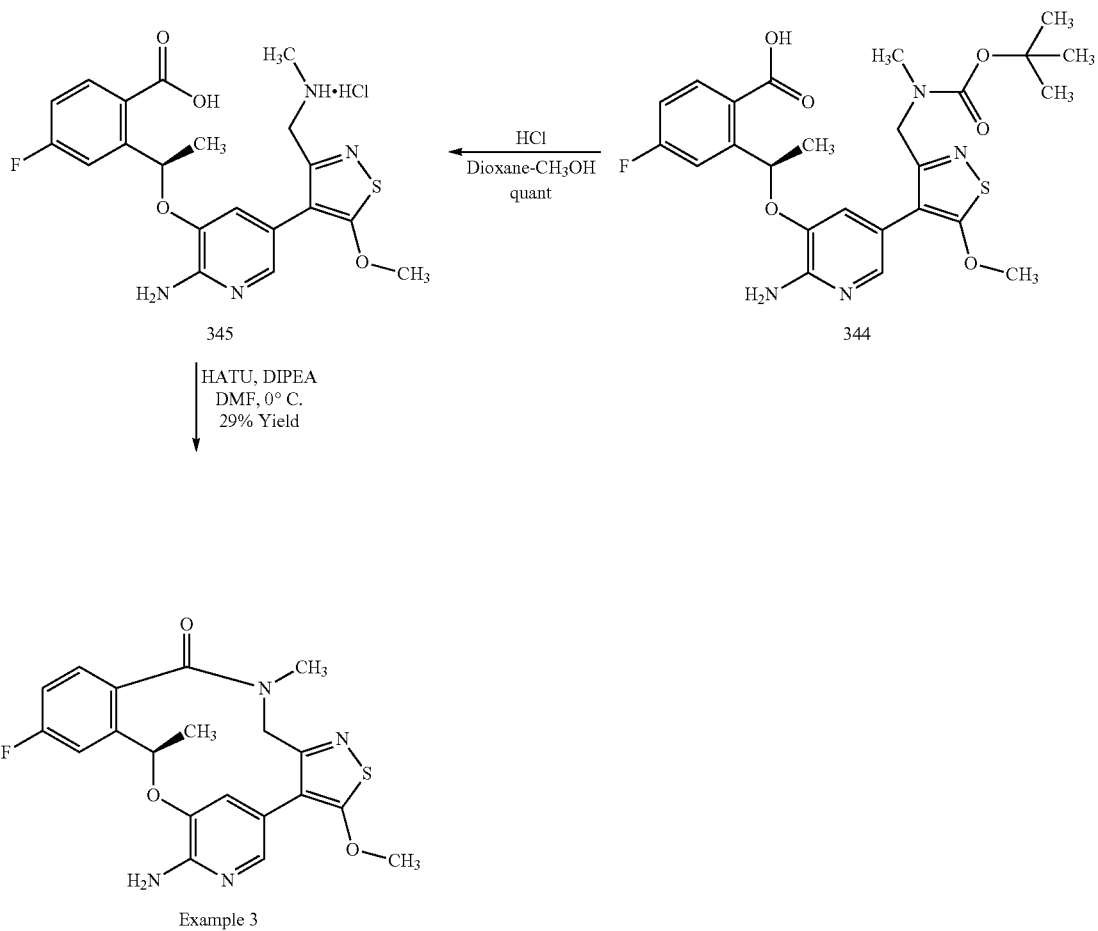

Step 1:

The procedure described in step 1 for Example 1 was used to prepare compound 343 (1.3 g, 67% Yield). TLC (R$_f$=0.30, 1:1 EtOAc/cyclohexane). $^1$H NMR (400 MHz, DMSO-d$_6$) δ 7.95 (m, 1 H), 7.52 (dd, 1 H, J=10.4, 3.0 Hz), 7.41 (m, 1 H), 7.25 (m, 1 H), 6.60 (m, 1 H), 6.20 (m, 1 H), 6.00-6.05 (m, 2 H), 4.00-4.25 (m, 2 H), 3.89 (s, 3 H), 3.85 (s, 3 H), 2.70-2.78 (m, 3 H), 1.60 (d, 3 H, J=6.7 Hz), 1.08-1.38 (m, 9 H). LCMS ES m/z 547 [M+H]$^+$.

Step 2:

The procedure described in step 2 for Example 1 was used to prepare compound 344 (600 mg, 88% yield). TLC: R$_f$=0.25 (EtOAc+1% AcOH). $^1$H NMR (400 MHz, DMSO-d$_6$) δ 7.95-8.10 (m, 3 H), 7.50-7.60 (m, 2 H), 7.25 (m, 1 H), 6.95-7.10 (m, 1 H), 6.52 (m, 1 H), 4.10-4.40 (m, 2 H), 3.91 (s, 3 H), 2.50-2.75 (m, 3 H), 1.65 (d, 3 H), 1.08-1.30 (m, 9 H). LCMS ES m/z 533 [M+H]$^+$.

Step 3:

The procedure described in step 3 for Example 1 was used to prepare compound 345 (540 mg, quantitative yield). $^1$H NMR (400 MHz, DMSO-d$_6$) δ 9.29 (br s, 2 H), 8.10-8.30 (m, 2 H), 8.03 (dd, 1 H, J=9.4, 6.8 Hz), 7.65 (m, 1 H), 7.56 (dd, 1 H, J=11.1, 2.6 Hz), 7.28 (dt, 1 H, J=7.9, 2.8 Hz), 7.10 (s, 1 H), 6.52 (q, 1 H, J=6.7 Hz), 4.00-4.20 (m, 2 H), 3.94 (s, 3 H), 2.54-2.57 (m, 3 H), 1.66 (d, 3 H, J=6.1 Hz). LCMS ES m/z 433 [M+H]$^+$.

Step 4:

The procedure described in step 4 for Example 1 was used to prepare Example 3 (130 mg, 29% yield). TLC (R$_f$=0.40, 100% EtOAc). $^1$H NMR (400 MHz, DMSOd$_6$) δ 7.63 (dd, 1 H, J=12.0, 4.0 Hz), 7.50 (d, 1 H, J=1.6 Hz), 7.42 (dd, 1 H, J=8.4, 5.6 Hz), 7.13 (dt, 1 H, J=8.4, 2.8 Hz), 6.82 (d, 1 H, J=1.6 Hz), 5.96 (s, 2 H), 5.66-5.62 (m, 1 H), 4.31 (d, 1 H, J=13.5 Hz), 4.18 (d, 1 H, J=13.5 Hz), 4.05 (s, 3 H), 3.03 (s, 3 H), 1.67 (d, 3 H, J=6.4 Hz). LCMS ES m/z 415 [M+H]$^+$.

Preparation of 7-amino-12-fluoro-2,16-dimethyl-15-oxo-10,15,16,17-tetrahydro-2H-8,4-(metheno)pyrazolo[4,3-h][2,5,11]benzoxadiazacyclotetradecine-3-carbonitrile (Example 4)

Step 2:

The procedure described in step 2 for Example 1 was used to prepare compound 347, where LiOH was used instead of NaOH (210 mg, quantitative yield). LCMS ES m/z 511 [M+H]+.

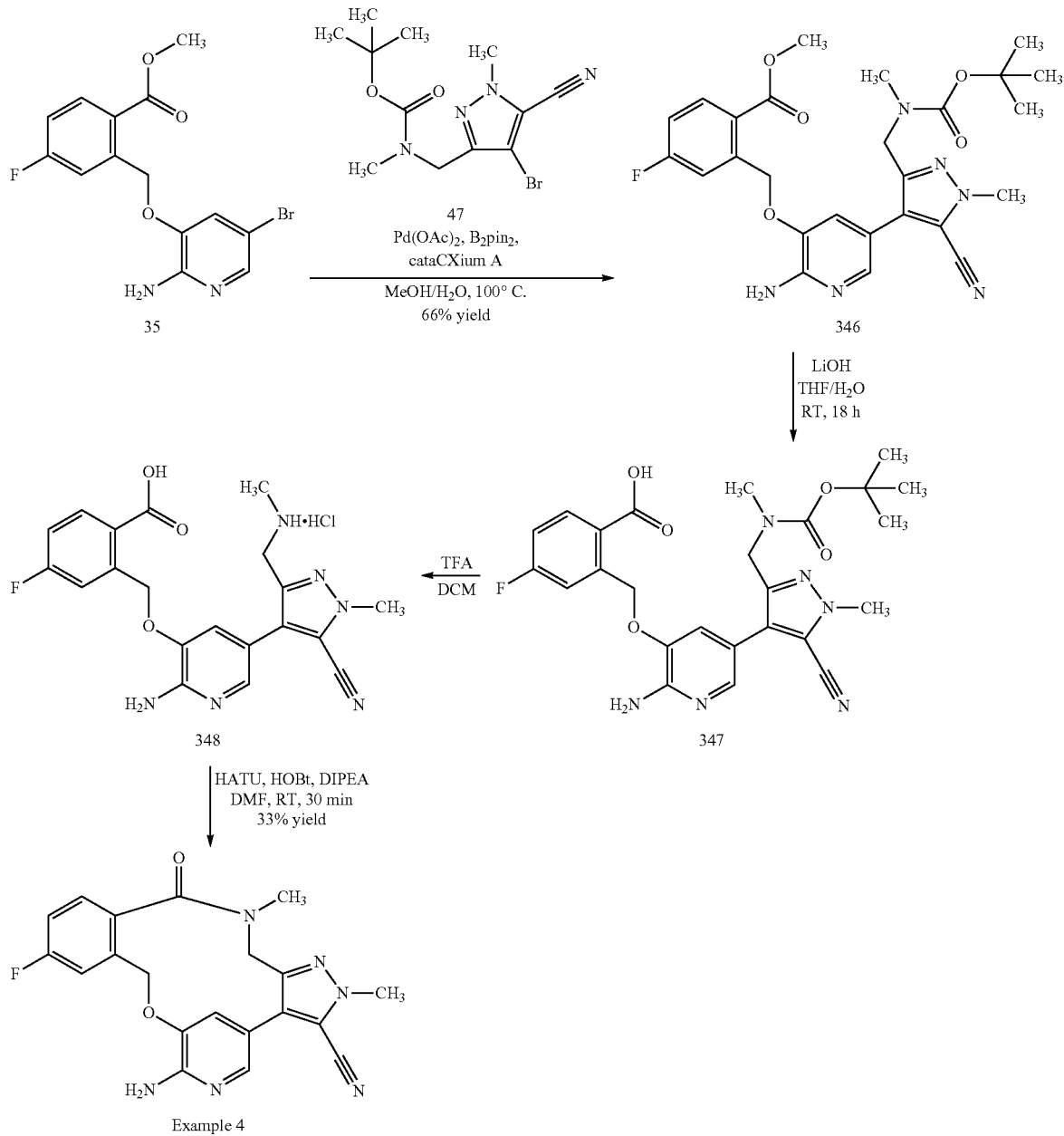

Step 1:

The procedure described in step 1 for Example 1 was used to prepare compound 346 (232 mg, 54% Yield). $^1$H NMR (400 MHz, CDCl$_3$) δ 8.03-8.12 (m, 2 H), 7.69-7.75 (m, 1 H), 7.36 (dd, 1 H), 7.07 (td, 1 H), 5.56 (br s, 2 H), 5.07 (br s, 0.2; H), 4.94 (br s, 1.8 H), 4.50 (br s, 2 H), 4.02 (s, 3 H), 3.90 (s, 3 H), 2.71 (br s, 3 H), 1.35 (br s, 9 H). LCMS ES m/z 525 [M+H]+.

Step 3:

Compound 347 (210 mg, ~0.44 mmol) was dissolved in DCM (6 mL) and TFA (0.12 mL, 1.6 mmol) was added. The mixture was stirred at RT for 18 hours. TFA (0.06 mL, 0.8 mmol) was added and the mixture was stirred at RT for 2 hours. LCMS showed consumption of compound 347. The reaction was concentrated under vacuum and diethyl ether (3 mL) and MTBE (3 mL) were added. The mixture was stirred at RT for 1 hour and decanted. The mother liquors were removed and the white solids obtained were dried under vacuum to give compound 348 (216 mg, quantitative yield).

¹H NMR (400 MHz, CD₃OD) δ 8.23-8.13 (m, 1 H), 7.66 (br s, 1 H), 7.58-7.49 (m, 2 H), 7.26-7.18 (m, 1 H), 5.80-5.77 (m, 2 H), 4.30 (s, 1 H), 4.11 (s, 2 H), 4.05 (s, 1 H), 3.21 (s, 3 H), 2.77 (s, 3 H). LCMS ES m/z 411 [M+H]⁺.

Step 4:
HATU (380 mg, 0.99 mmol) and HOBt (20 mg, cat.) were dissolved in DMF (10 mL). A solution of compound 348 (210 mg, ~0.33 mmol) and DIPEA (0.42 mL, 2.31 mmol) in DMF (10 mL) was added dropwise over 25 min. At the end of the addition, LCMS showed consumption of the SM. Brine (100 mL) was added and extracted with ethyl acetate (6×50 mL). The organics were combined, dried over MgSO₄, filtered and evaporated. Purification by column chromatography over silica gel, which was eluted with cyclohexane and ethyl acetate (1:1 to 0:1), gave Example 4 (45 mg, 35% yield over 3 steps). ¹H NMR (400 MHz, CDCl₃) δ 7.84 (d, 1 H, J=1.6 Hz), 7.34 (dd, 1 H, J=9.2, 2.4 Hz), 7.22-7.27 (m, 1 H), 7.02 (td, 1 H, J=8.4, 2.8 Hz), 6.84 (d, 1 H, J=2.0 Hz), 5.49 (dd, 1 H, J=13.6, 1.6 Hz), 5.23 (d, 1 H, J=13.6 Hz), 4.88 (br s, 2 H), 4.48 (d, 1 H, J=14.4 Hz), 4.38 (d, 1 H, J=14.4 Hz), 4.07 (s, 3 H), 3.12 (s, 3 H). LCMS ES m/z 393 [M+H]⁺. The analytical chiral separation by SFC was performed using a Chiralpak OD-H (4.6 mm×250 mm column, 5 micron particle size), which was eluted with 30% MeOH in CO₂ held at 35° C. at 140 bar. A flow rate of 3 mL/minutes gave Rt$_{(Peak\ 1)}$=4.3 minutes ($[\alpha]_d^{20}$=−121.4° (C=0.23, MeOH) and Rt$_{(Peak\ 2)}$=5.4 minutes ($[\alpha]_d^{20}$=103.30 (C=0.23, MeOH).

Example 4a (Atropisomer Peak 1): 91.6% ee. ¹H NMR (600 MHz, DMSO-d₆) δ 7.45-7.63 (3 H, m), 7.17-7.27 (1 H, m), 6.77 (1 H, s), 6.20 (2 H, br s), 5.29 (1 H, d, J=14.3 Hz), 5.24 (1 H, d, J=13.2 Hz), 4.46 (1 H, d, J=14.2 Hz), 4.23 (1 H, d, J=15.3 Hz), 4.02 (3 H, s), 2.97 (3 H, s).

Example 4b (Atropisomer Peak 2): 89.6% ee. ¹H NMR (600 MHz, DMSO-d₆) δ 7.45-7.62 (3 H, m), 7.18-7.27 (1 H, m), 6.77 (1 H, s), 6.20 (2 H, br s), 5.30 (1 H, d, J=14.3 Hz), 5.24 (1 H, d, J=13.2 Hz), 4.46 (1 H, d, J=14.2 Hz), 4.23 (1 H, d, J=14.2 Hz), 4.02 (3 H, s), 2.97 (3 H, s).

Preparation of 8-amino-3-fluoro-17-methyl-13-(methylsulfonyl)-16,17-dihydro-7,11-(metheno)dibenzo[g,l][1,4,10]oxadiazacyclotetradecin-18(5H)-one
(Example 5)

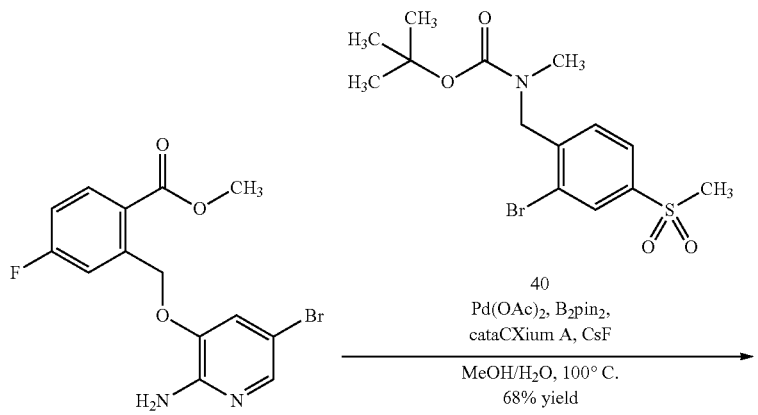

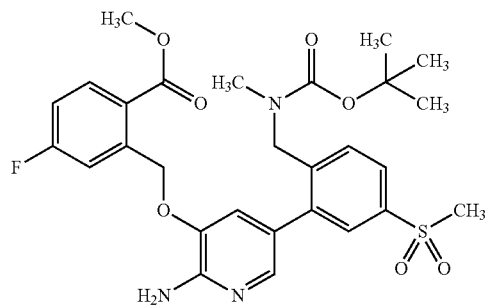

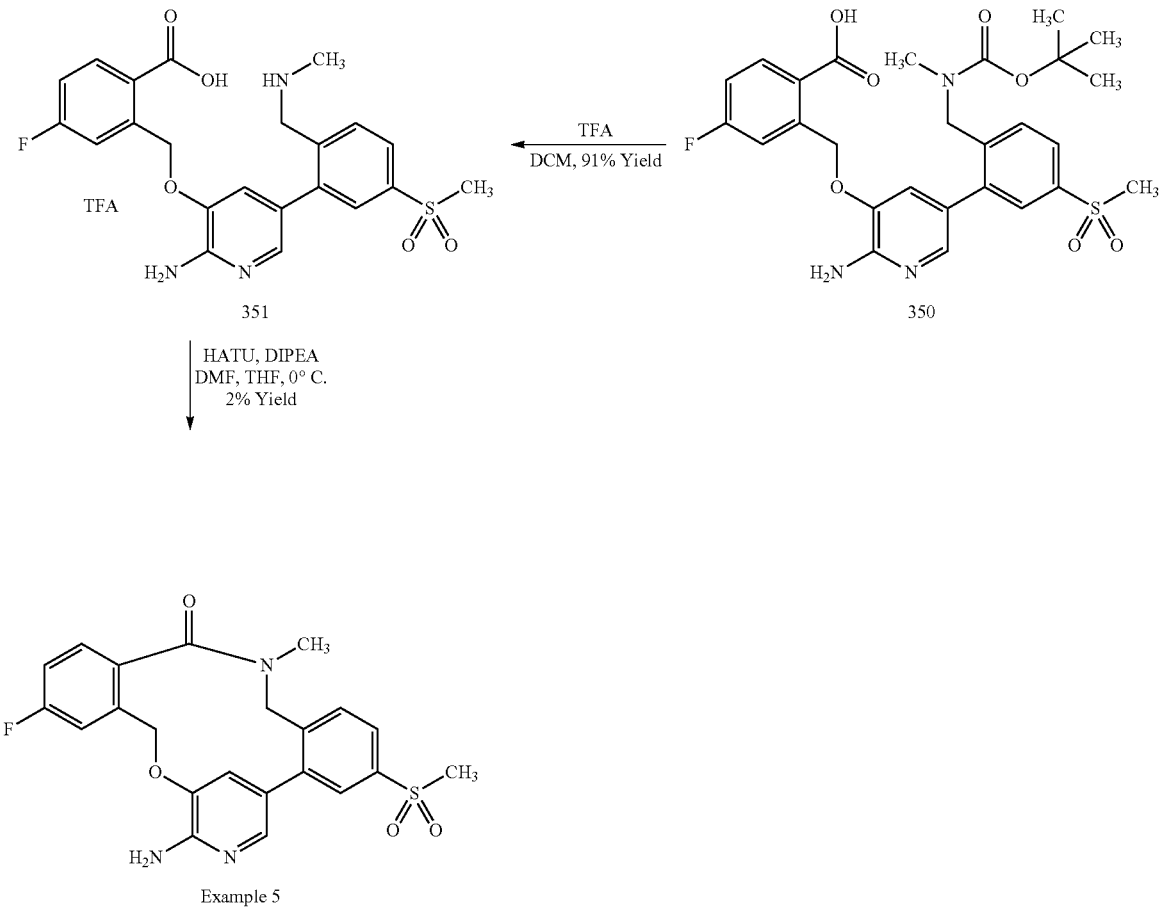

Step 1:

The procedure described in step 1 for Example 1 was used to prepare compound 349 (312 mg, 68% yield). $^1$H NMR (400 MHz, CDCl$_3$) δ 8.09 (dd, 1 H, J=8.4, 5.8 Hz), 7.89 (dd, 1 H, J=8.0, 1.6 Hz), 7.77 (d, 1 H, J=2.0 Hz), 7.63 (br s, 1 H), 7.43 (d, 1 H, J=8.4 Hz), 7.39 (br d, 1 H, J=10.0 Hz), 7.08 (dt, 1 H, J=8.4, 2.4 Hz), 6.86-6.89 (m, 1 H), 5.55 (s, 2 H), 4.92 (br s, 2 H), 4.34-4.42 (m, 2 H), 3.89 (s, 3 H), 3.08 (s, 3 H), 2.68-2.76 (m, 3 H), 1.38-1.47 (m, 9 H). LCMS ES m/z 574 [M+H]$^+$.

Step 2:

The procedure described in step 2 for Example 1 was used to prepare compound 350, where KOH was used instead of NaOH (200 mg, 67% yield). $^1$H NMR (400 MHz, DMSO-d$_6$) δ 8.05 (dd, 1 H, J=8.8, 6.0 Hz), 7.98 (dd, 1 H, J=7.6, 2.0 Hz), 7.78 (d, 1 H, J=2.0 Hz), 7.63-7.70 (m, 2 H), 7.46-7.50 (m, 2 H), 7.29 (dt, 1 H, J=2.8, 8.4 Hz), 5.65 (s, 2 H), 5.39-4.41 (m, 2 H), 3.25 (s, 3 H), 2.66 (br s, 3 H), 1.25-1.36 (m, 9 H). LCMS ES m/z 560 [M+H]$^+$.

Step 3:

The procedure described in step 3 for Example 4 was used to prepare compound 351 (170 mg, 91% yield). $^1$H NMR (400 MHz, DMSO-d$_6$) δ 9.31-9.32 (m, 2 H), 8.02-8.09 (m, 3 H), 7.88 (d, 1 H, J=2.0 Hz), 7.70-7.73 (m, 2 H), 7.54 (s, 1 H), 7.30-7.33 (m, 1 H), 5.65 (s, 2 H), 4.13-4.15 (m, 2 H), 3.30 (s, 3 H), 3.17 (s, 3 H). LCMS ES m/z 460 [M+H]$^+$.

Step 4:

A solution of compound 351 (527 mg, 1.1 mmol) and DIPEA (2.24 mL, 15.9 mmol) in DMF (9 mL) and THF (1 mL) at −10° C. was added drop-wise over 10 minutes to a stirred solution of HATU (566 mg, 1.5 mmol) in DMF (9 mL) cooled under an ice/NaCl/MeOH bath. LCMS showed complete consumption of compound 351. Water (30 mL) and EtOAc (30 mL) were added and the mixture saturated by addition of NaCl. The phases were separated and the aqueous layer was again extracted with EtOAc (3×30 mL). The organic layers were combined, dried over MgSO$_4$, and the solvent was removed in vacuo. The residue was purified by column chromatography over silica gel, which was eluted with EtOAc/heptane (8:2 to 1:0 then EtOAc/MeOH 9:1) to give a fraction containing Example 5 (110 mg, ~70% purity but contaminated with DMF) and a more polar fraction (major component of the crude mixture, 83 mg, white solid, [M+H]$^+$ 883) likely to be the cyclised dimer. The former fraction was further purified by reverse phase chromatography to give Example 5 as a white solid (10 mg, 2% yield). $^1$H NMR (400 MHz, CDCl$_3$) δ 8.01 (d, 1 H, J=2.0 Hz), 7.92 (dd, 1 H, J=8.0, 2.0 Hz), 7.65 (d, 1 H, J=8.0 Hz), 7.59 (d, 1 H, J=2.0 Hz), 7.33 (dd, 1 H, J=9.2, 2.8 Hz), 7.21 (dd, 1 H, J=8.6, 5.4 Hz), 7.11 (d, 1 H, J=1.6 Hz), 7.00 (dt, 1 H, J=8.4, 2.4 Hz), 5.59 (dd, 1 H, J=13.6, 2.0 Hz), 5.22 (d, 1 H, J=13.6 Hz), 4.84 (br s, 2 H), 4.63 (d, 1 H, J=13.2 Hz), 4.28 (d, 1 H, J=13.2 Hz), 3.12 (s, 3 H), 3.11 (s, 3 H).

Preparation of 7-amino-12-fluoro-1,3,16-trimethyl-16,17-dihydro-1H-8,4-(metheno)pyrazolo[4,3-h][2,5,11]benzoxadiazacyclotetradecin-15(10H)-one (Example 6)

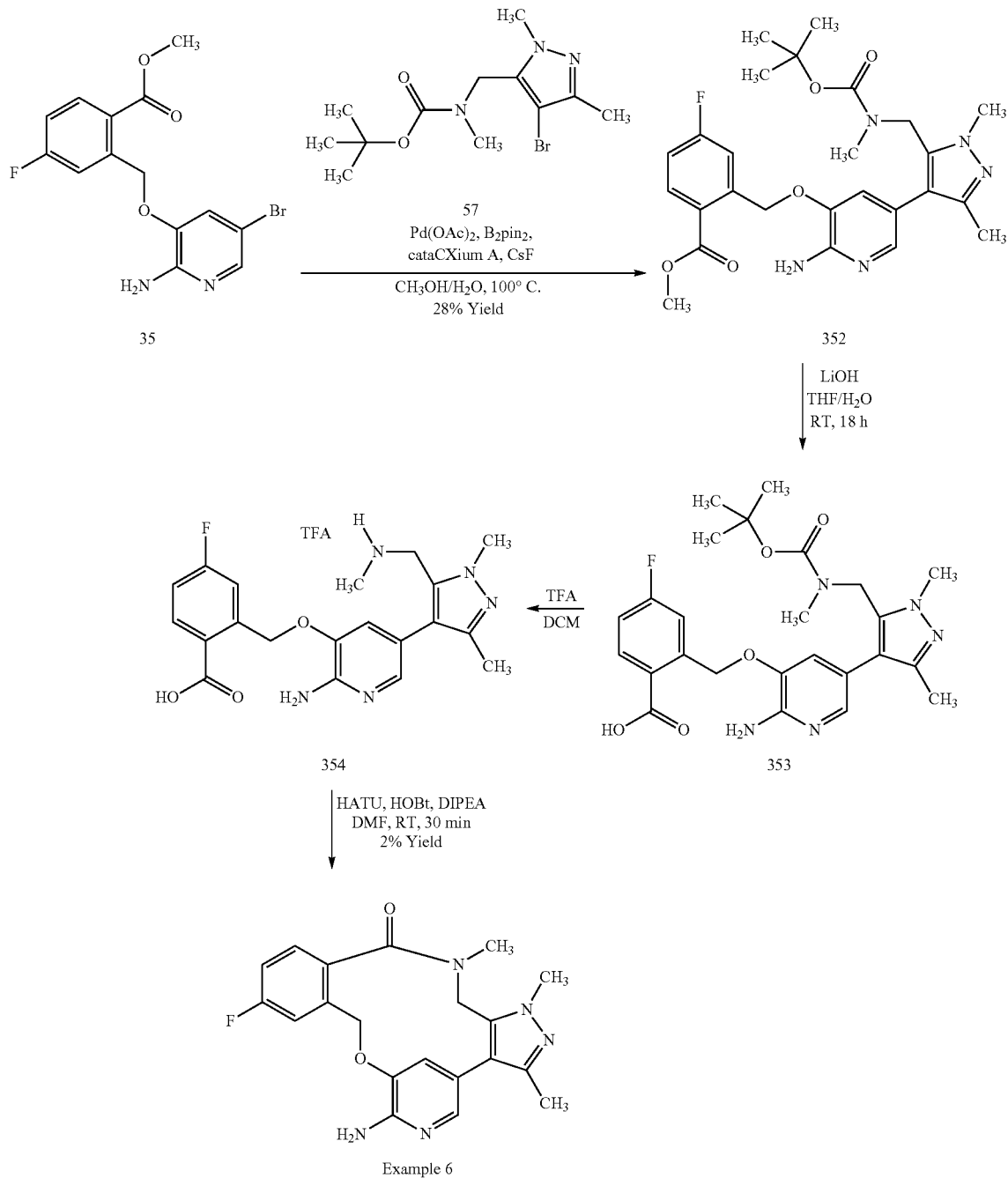

Example 6

Step 1:

The procedure described in step 1 for Example 1 was used to prepare compound 352 (350 mg, 28% yield). $^1$H NMR (400 MHz, CDC$_3$) δ 8.09 (dd, 1 H, J=8.8, 6.0 Hz), 7.55 (s, 1 H), 7.35 (dd, 1 H, J=10.0, 2.8 Hz), 7.06 (td, 1 H, J=8.4, 2.4 Hz), 6.74 (d, 1 H, J=1.6 Hz), 5.54 (s, 2 H), 4.81 (s, 2 H), 4.40 (s, 2 H), 3.89 (s, 3 H), 3.79 (s, 3 H), 2.45 (s, 3 H), 2.10 (s, 3 H), 1.45 (s, 9 H). LCMS ES m/z 514 [M+H]$^+$.

Step 2:

The procedure described in step 2 for Example 1 was used to prepare compound 353, where LiOH was used instead of NaOH (310 mg, 88% yield). $^1$H NMR (400 MHz, CD$_3$OD) δ 7.90-7.85 (m, 1 H), 7.36 (s, 1 H), 7.24 (dd, 1 H, J=10.0, 2.4 Hz), 6.99 (td, 1 H, J=8.4, 2.4 Hz), 6.87 (s, 1 H), 5.60 (s, 2 H), 4.37 (s, 2 H), 3.75 (s, 3 H), 2.40 (s, 3 H), 2.04-2.00 (m, 3 H), 1.42 (s, 9 H). LCMS ES m/z 500 [M+H]$^+$.

Step 3:

The procedure described in step 3 for Example 4 was used to prepare compound 354 (408 mg, quantitative yield). $^1$H NMR (400 MHz, DMSO-d$_6$) δ 8.75 (br s, 2 H), 8.06 (dd, 1 H, J=8.4, 6.0 Hz), 7.67 (dd, 1 H, J=10.0, 2.4 Hz), 7.57 (d, 1 H, J=1.6 Hz), 7.26-7.35 (m, 2 H), 5.65 (s, 2 H), 4.20 (br s, 2 H), 3.86 (s, 3 H), 2.44 (br s, 3 H), 2.05 (s, 3 H). LCMS ES m/z 400 [M+H]⁺.

Step 4:

The procedure described in step 4 for Example 4, performed at 0° C., was used to prepare compound Example 6 (130 mg, 29% yield). ¹H NMR (400 MHz, DMSO-$d_6$) δ 7.56 (dd, 1 H, J=9.6, 2.4 Hz), 7.44-7.38 (m, 2 H), 7.22 (td, 1 H, J=8.4, 2.8 Hz), 6.73 (d, 1 H, J=1.6 Hz), 5.82 (br s, 2 H), 5.30 (d, 1 H, J=13.6 Hz), 5.17 (d, 1 H, J=13.6 Hz), 4.65 (d, 1 H, J=15.2 Hz), 4.20 (d, 1 H, J=15.2 Hz), 3.89 (s, 3 H), 2.97 (s, 3 H), 2.54 (s, 1 H), 2.22 (s, 3 H). LCMS ES m/z 382 [M+H]⁺.

Preparation of 8-amino-3-fluoro-17-methyl-16,17-dihydro-7,11-(metheno)dibenzo[g,l]-[1,4,10]oxadiazacyclotetradecin-18(5H)-one (Example 7)

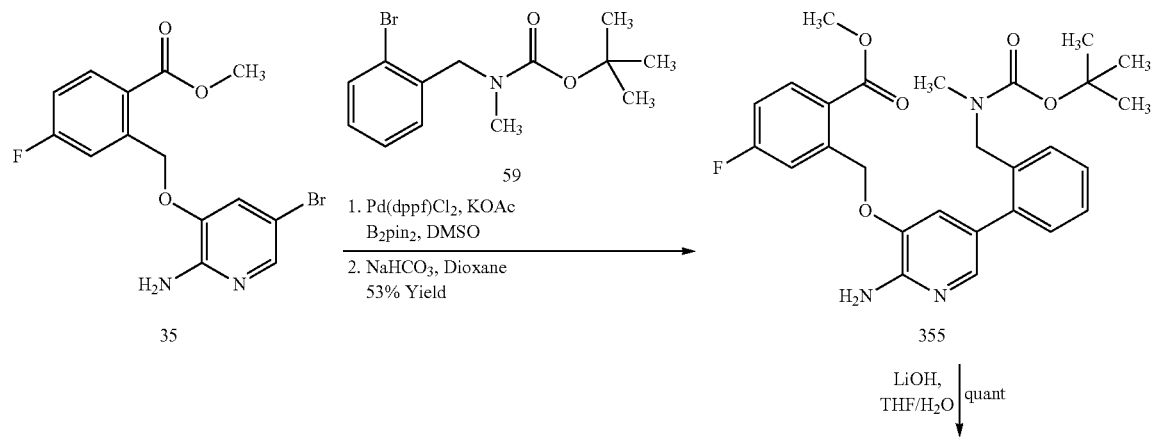

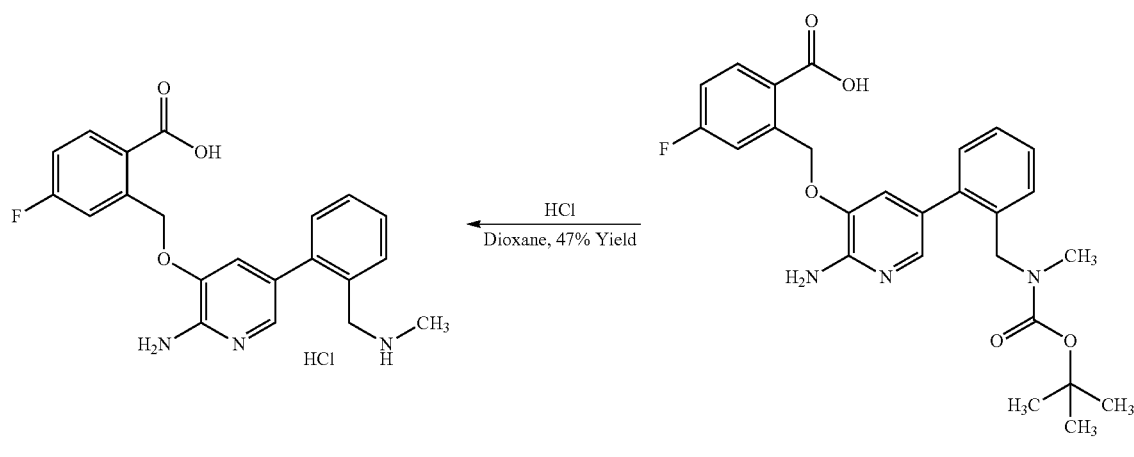

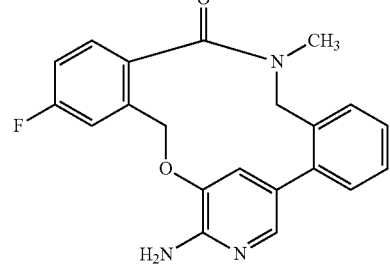

Example 7

Step 1:
To a degassed solution of compound 35 (350 mg, 0.99 mmol), bis(neopentylglycolato)diboron (289 mg, 1.3 mmol) and KOAc (339 mg, 3.4 mmol) in DMSO (10 mL) was added Pd(dppf)Cl$_2$ (80 mg, 0.1 mmol). The resulting mixture was stirred at 75° C. for 1 h. LCMS analysis indicated that the boronic acid intermediate was formed. After cooling to RT, compound 59 (311 mg, 1.03 mmol) and NaHCO$_3$ (aq) (1 M solution, 3.0 mL, 3.0 mmol) and dioxane (10 mL) were added. The mixture was degassed, followed by the addition of Pd(dppf)Cl$_2$ (80 mg, 0.1 mmol). The resulting mixture was stirred at 80° C. for 2 hours and concentrated in vacuo, ethyl acetate (100 mL) and water (150 mL) were added and then partitioned. The aqueous was extracted with EtOAc (2×100 mL), and the combined organic layers were washed with brine (400 mL), dried over MgSO$_4$, and then concentrated in vacuo. Purification by flash column chromatography over silica gel, which was eluted with 1% MeOH and 10% heptane in DCM, gave compound 355 as a yellow solid (260 mg, 53% yield). $^1$H NMR (400 MHz, CDCl$_3$) δ 8.06 (dd, 1 H), 7.66 (s, 1 H), 7.16-7.30 (m, 5 H), 7.05 (ddd, 1 H), 6.86 (d, 1 H), 5.53 (s, 2 H), 4.80 (br s, 2 H), 4.33 (br s, 2 H), 3.96 (s, 3 H), 2.63 (br d, 3 H), 1.42 (br d, 9 H). LCMS ES m/z 440 [M–$^t$Bu]$^+$.

Step 2:
The procedure described in step 2 for Example 1 was used to prepare compound 356, where LiOH was used instead of NaOH (123 mg, quantitative yield). LCMS ES m/z 482 [M+H]$^+$.

Step 3:
The procedure described in step 3 for Example 1 was used to prepare compound 357 (36 mg, 47% yield). $^1$H NMR (400 MHz, CD$_3$OD) δ 7.70 (dd, 1 H), 7.63 (m, 1 H), 7.45 (m, 3 H), 7.32 (m, 2 H), 7.22 (d, 1 H), 7.02 (ddd, 1 H), 5.55 (s, 2 H), 4.08 (s, 2 H), 2.56 (s, 3 H). LCMS ES m/z 383 [M+H]$^+$.

Step 4:
To a suspension of compound 357 (36 mg, 0.09 mmol) in DMF (6 mL) was added DIPEA (84 μL, 0.48 mmol) followed by HATU (72 mg, 0.19 mmol). The resulting solution was stirred at room temperature for 30 minutes. LCMS analysis indicated that a mixture of the desired product and a dimer was formed (ratio 2:1). After being concentrated in vacuo, the residue was purified by reverse phase prep-HPLC (water/ MeCN gradient, 30 min run), to yield Example 7 as a brown solid (14 mg, 41% yield). $^1$H NMR (400 MHz, CD$_3$OD) δ 7.56 (m, 2 H), 7.37-7.45 (m, 5 H), 7.15 (d, 1 H), 7.10 (ddd, 1 H), 5.53 (d, 1 H), 5.24 (d, 1 H), 4.47 (d, 1 H), 4.38 (d, 1 H), 3.10 (s, 3 H). LCMS ES m/z 364 [M+H]$^+$.

Preparation of 8-amino-3-fluoro-5,17-dimethyl-16, 17-dihydro-7,11-(metheno)dibenzo[g,l]-[1,4,10]- oxadiazacyclotetradecin-18(5H)-one (Example 8)

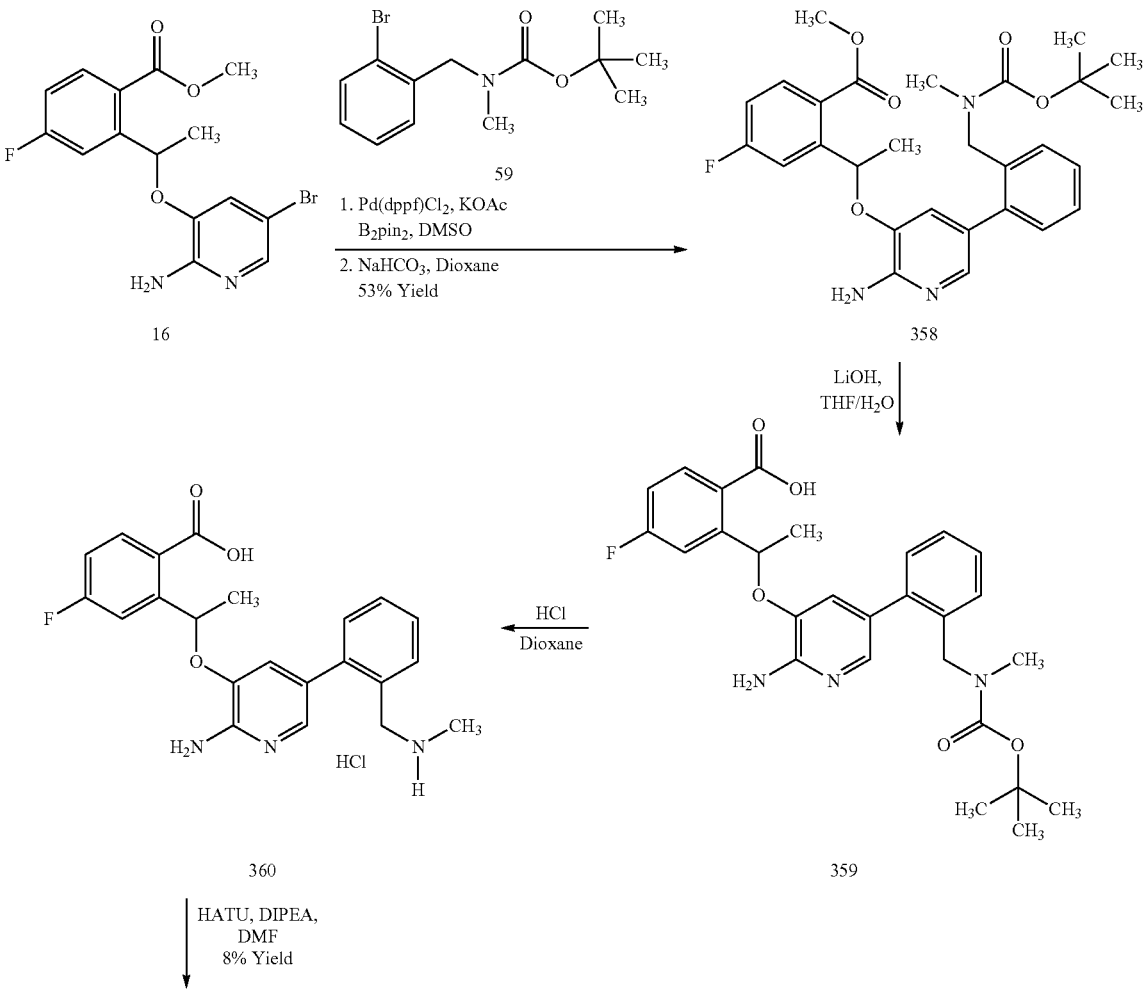

Example 8

Step 1:
The procedure described in step 1 for Example 7 was used to prepare compound 358 (820 mg, 53% yield). $^1$H NMR (400 MHz, CDCl$_3$) δ 8.01 (dd, 1 H), 7.54 (br s, 1 H), 7.34-7.18 (m, 4 H), 7.07 (dd, 1 H), 6.99 (br s, 1 H), 6.62-6.49 (m, 1 H), 6.44-6.32 (m, 1 H), 4.86 (br s, 2 H), 4.11-4.02 (m, 2 H), 3.86 (br s, 3 H), 2.60-2.45 (m, 3 H), 1.67 (d, 3 H), 1.55-1.31 (m, 9 H). LCMS ES m/z 510 [M+H]$^+$.

Step 2:
The procedure described in step 2 for Example 1 was used to prepare compound 359, where LiOH was used instead of NaOH (629 mg, quantitative yield). LCMS ES m/z 496 [M+H]$^+$.

Step 3:
The procedure described in step 3 for Example 1 was used to prepare compound 360 (810 mg, quantitative yield). LCMS ES m/z 396 [M+H]$^+$.

Step 4:
The procedure described in step 4 for Example 7 was used to prepare Example 8 (49 mg, 8% yield). $^1$H NMR (400 MHz, CDCl$_3$) δ 7.53 (d, 1 H, J=2.0 Hz), 7.48-7.32 (m, 4 H), 7.28 (dd, 1 H, J=10.0, 2.8 Hz), 7.17-7.13 (m, 2 H), 6.94 (td, 1 H, J=8.0, 2.4 Hz), 5.83 (qd, 1 H, J=6.0, 2.0 Hz), 4.75 (br s, 2 H), 4.50 (d, 1 H, J=13.2 Hz), 4.16 (d, 1 H, J=13.6 Hz), 3.12 (s, 3 H), 1.78 (d, 3 H, J=6.4 Hz). LCMS ES m/z 378 [M+H]$^+$.

Preparation of 7-amino-16-ethyl-12-fluoro-1,3,10-trimethyl-16,17-dihydro-1H-8,4-(metheno)pyrazolo[4,3-h][2,5,11]benzoxadiazacyclotetradecin-15(10H)-one (Example 9 and Example 10)

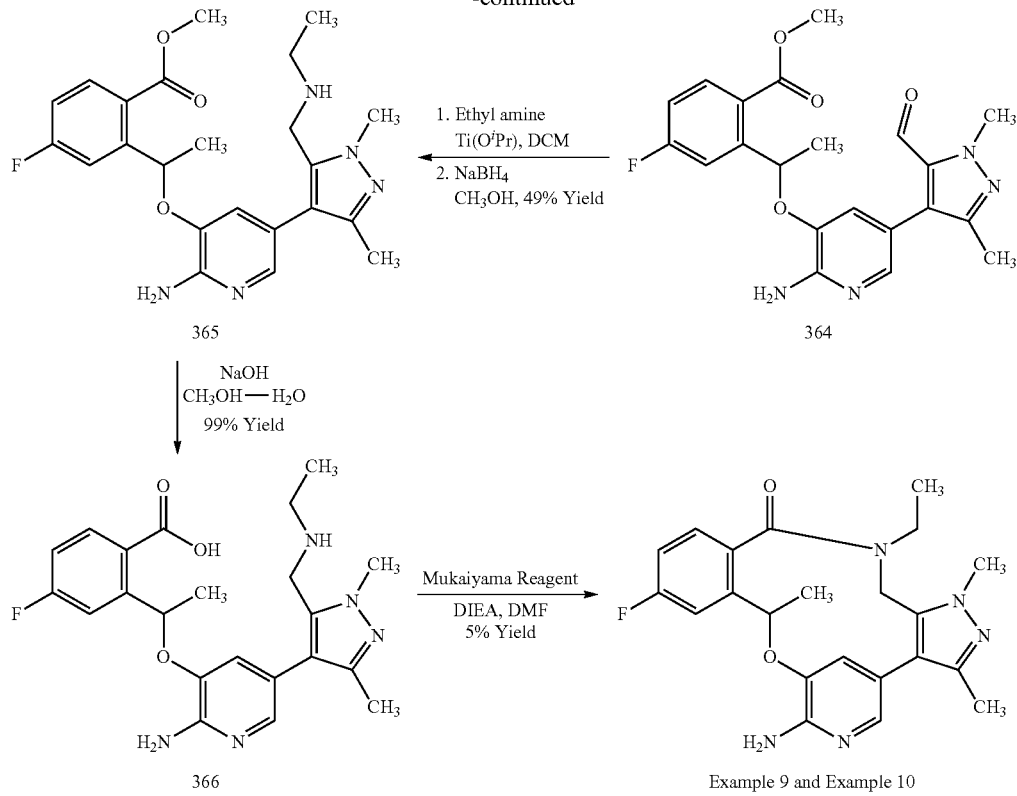

Example 9 and Example 10

Step 1:
To a solution of compound 361 (1.0 g, 7.9 mmol) in DMF (53 mL) was added NBS (1.4 g, 7.9 mmol). The solution was stirred at room temperature overnight then concentrated. To the solid was added 1 N $Na_2CO_3$ (10 mL) and the mixture was concentrated to remove water. The solid was slurried in DCM/MeOH and filtered. The mother liquor was concentrated and purified by flash chromatography over silica gel, which was eluted with DCM/7 N $NH_3$ in MeOH (0-10%) to give compound 362 (749 mg, 46% yield). $^1$H NMR (400 MHz, DMSO-$d_6$) δ 5.31 (t, J=5.4 Hz, 1 H), 4.43 (d, J=5.3 Hz, 2 H), 3.77 (s, 3 H), 2.08 (s, 3 H).

Step 2:
In a sealed tube, a mixture of compound 16 (500 mg, 1.35 mmol), compound 362 (555 mg, 2.03 mmol), diboron pinacol ester (1.38 g, 5.42 mmol) and cesium fluoride (1.03 g, 6.77 mmol) in MeOH (9.0 mL) and water (0.90 mL) was heated at 60° C. and bubbled with nitrogen. A solution of $Pd(OAc)_2$ (30 mg, 0.14 mmol) and di(1-adamantyl)-n-butylphosphine (100 mg, 0.72 mmol) in toluene (0.5 mL) was added and the mixture was heated at 100° C. After ~6 hours, the mixture was cooled to room temperature and diluted with EtOAc, washed with water and brine, dried over $MgSO_4$, filtered and concentrated. The residue was purified by flash chromatography over silica gel, which was eluted with DCM/MeOH (0-9%) and gave compound 363 as a yellow gum (433 mg, 77% yield). LCMS ES m/z 415 [M+H]$^+$.

Step 3:
To a solution of compound 363 (560 mg, 1.35 mmol) in DCE (13.5 mL) was added $MnO_2$ (1.2 g, 10.0 mmol). The reaction was heated at 50° C. overnight. The mixture was filtered and the mother liquor was concentrated and purified by flash chromatography over silica gel, which was eluted with heptanes/EtOAc (0-75%) and gave compound 364 (226 mg, 41% yield over 2 steps). $^1$H NMR (400 MHz, DMSO-$d_6$) δ 9.40 (s, 1 H), 7.94 (dd, J=5.9, 8.7 Hz, 1 H), 7.55 (dd, J=2.6, 10.4 Hz, 1 H), 7.50 (d, J=1.8 Hz, 1 H), 7.26 (dt, J=2.8, 8.4 Hz, 1 H), 6.71 (d, J=1.8 Hz, 1 H), 6.25 (q, J=6.1 Hz, 1 H), 6.16 (s, 2 H), 4.00 (s, 3 H), 3.84 (s, 3 H), 1.92 (s, 3 H), 1.62 (d, J=6.3 Hz, 3 H). LCMS ES m/z 413 [M+H]$^+$.

Step 4:
A solution of the compound 364 (226 mg, 0.548 mmol) in DCM (5.5 mL) was added ethyl amine (2 M in THF, 548 μL, 1.10 mmol) followed by $Ti(O^iPr)_4$ (642 μL, 2.19 mmol). After 1 hour, MeOH (2.0 mL) and $NaBH_4$ (104 mg, 2.74 mmol) were added (gas evolved). The reaction was quenched with water, and white solids formed. The mixture was filtered through celite and the mother liquor was diluted with EtOAc, washed with saturated $NH_4Cl$ and brine, dried over $MgSO_4$, filtered and concentrated. The residue was purified by flash chromatography over silica gel, which was eluted with heptanes/EtOAc (0-100%) followed by MeOH/DCM (0-10%) and gave compound 365 (119 mg, 49% yield). $^1$H NMR (400 MHz, DMSO-$d_6$) δ 7.96 (dd, J=6.0, 8.8 Hz, 1 H), 7.52 (dd, J=2.5, 10.3 Hz, 1 H), 7.42 (d, J=1.8 Hz, 1 H), 7.25 (dt, J=2.8, 8.4 Hz, 1 H), 6.58 (d, J=1.5 Hz, 1 H), 6.22 (q, J=6.0 Hz, 1 H), 5.86 (s, 2 H), 3.86 (s, 3 H), 3.72 (s, 3 H), 3.48-3.35 (m, 2 H), 2.32 (q, J=7.1 Hz, 2 H), 1.83 (s, 3 H), 1.79 (br s, 1 H), 1.61 (d, J=6.3 Hz, 3 H), 0.88 (t, J=7.1 Hz, 3 H). LCMS ES m/z 442 [M+H]$^+$.

Step 5:
To a solution compound 365 (115 mg, 0.26 mmol) in MeOH (520 μL) was added 15% NaOH (68 μL, 0.26 mmol). The reaction was heated at 50° C. Once complete by LCMS, the reaction was concentrated to afford the sodium salt of compound 366 (116 mg, 99% yield).

Step 6:

To a solution of sodium salt of compound 366 (90 mg, 0.20 mmol) in DMF (13 mL) was added DIEA (70 μL, 0.40 mmol) followed by 2-chloro-1-methylpyridinium iodide (57 mg, 0.22 mmol). After 30 min the reaction was concentrated and purified by flash chromatography over silica gel, which was eluted with DCM/MeOH (0-10%) followed by chiral separation by SFC to afford both enantiomers of the title compound. The analytical chiral separation by SFC was performed using a Regis Whelk-01 (S,S) column (4.6 mm×100 mm column, 5 micron particle size), which was eluted with 30% MeOH in $CO_2$ held at 25° C. at 140 bar. A flow rate of 5 mL/min gave $Rt_{(Peak}$ 1)=1.28 minutes and $Rt_{(Peak}$ 2)=1.78 minutes.

Example 9 (Peak 1): 3.7 mg, >98% ee, 4.5% yield. $^1$H NMR (DMSO-$d_6$, 400 MHz) δ 7.59 (dd, J=2.5, 10.4 Hz, 1 H), 7.37 (s, 1 H), 7.34 (dd, J=5.6, 8.4 Hz, 1 H), 7.16 (dt, J=2.5, 8.4 Hz, 1 H), 6.83 (s, 1 H), 5.80 (s, 2 H), 5.60 (d, J=6.4 Hz, 1 H), 4.68 (d, J=15.3 Hz, 1 H), 4.07 (d, J=15.5 Hz, 1 H), 3.87 (s, 3 H), 3.37 (d, J=6.9 Hz, 1 H), 2.19 (s, 3 H), 1.66 (d, J=6.4 Hz, 3 H), 1.02 (t, J=7.0 Hz, 3 H). LCMS ES m/z 410 [M+H]$^+$.

Example 10 (Peak 2): 4.0 mg, 90% ee, 4.9% yield. $^1$H NMR (DMSO-$d_6$, 400 MHz) δ 7.59 (dd, J=2.5, 10.2 Hz, 1 H), 7.37 (s, 1 H), 7.34 (dd, J=5.6, 8.4 Hz, 1 H), 7.16 (d, J=2.5 Hz, 1 H), 6.83 (d, J=1.3 Hz, 1 H), 5.80 (s, 2 H), 5.60 (d, J=5.6 Hz, 1 H), 4.68 (d, J=15.3 Hz, 1 H), 4.07 (d, J=15.5 Hz, 1 H), 3.87 (s, 3 H), 2.19 (s, 3 H), 1.66 (d, J=6.1 Hz, 3 H), 1.02 (t, J=7.0 Hz, 3 H). LCMS m/z 410 [M+H]$^+$.

Synthesis of 7-amino-16-cyclopropyl-12-fluoro-1,3,10-trimethyl-16,17-dihydro-1H-8,4-(metheno)pyrazolo[4,3-h][2,5,11]benzoxadiazacyclotetradecin-15(10H)-one (Example 11 and Example 12)

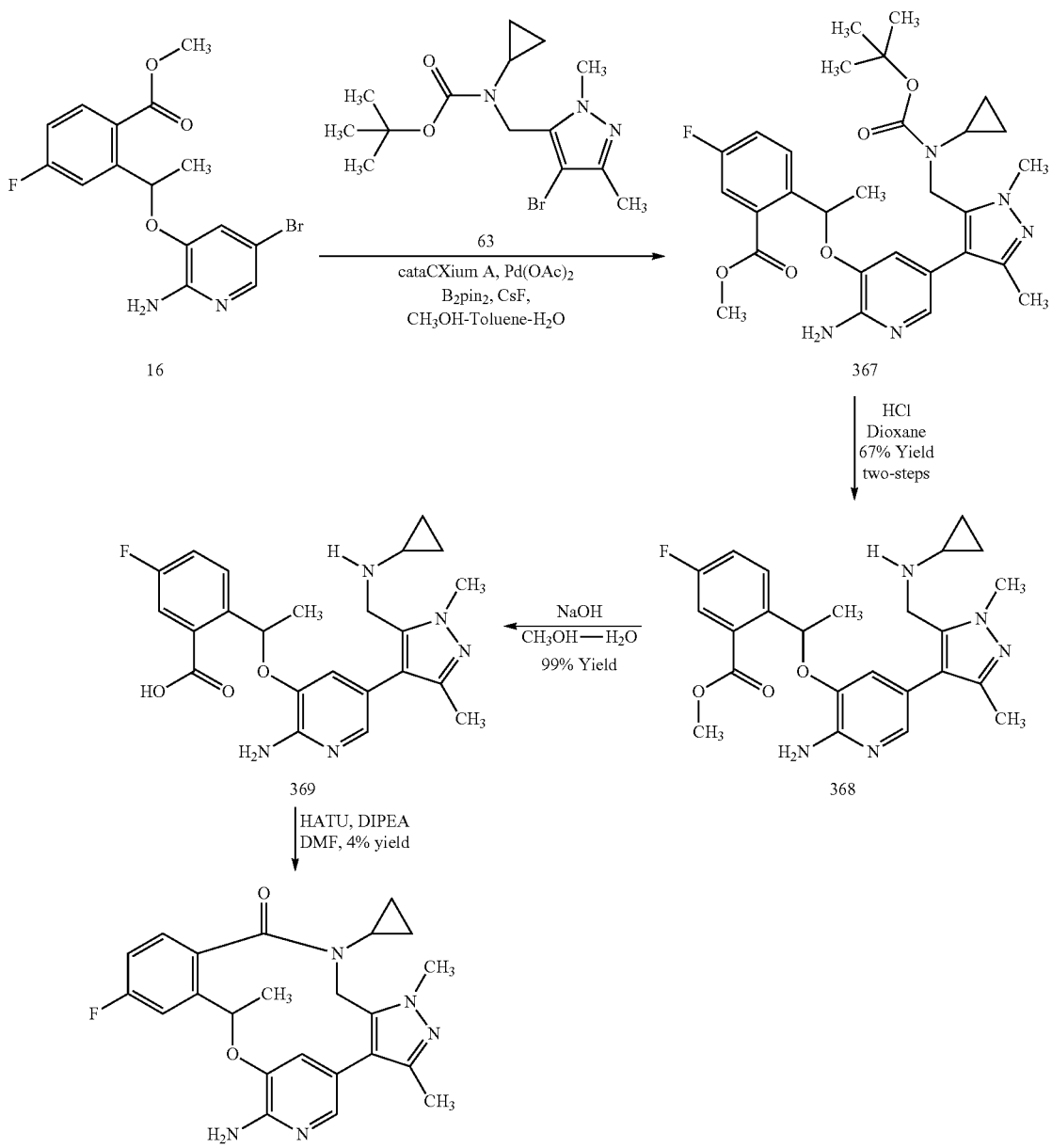

Example 11 and Example 12

Step 1:

The procedure described in step 2 for Example 9 and 10 was used to prepare compound 367 (191 mg). $^1$H NMR (DMSO-$d_6$, 400 MHz) δ 7.89 (dd, J=5.8, 8.8 Hz, 1 H), 7.49 (dd, J=2.4, 10.4 Hz, 1 H), 7.32 (s, 1 H), 7.20 (dt, J=2.4, 8.5 Hz, 1 H), 6.49 (s, 1 H), 6.22 (q, J=6.0 Hz, 1 H), 5.89 (s, 2 H), 4.34 (d, J=15.9 Hz, 1 H), 4.07 (d, J=15.6 Hz, 1 H), 3.85 (s, 3 H), 3.66 (s, 3 H), 1.87 (s, 3 H), 1.69 (br. s., 1 H), 1.61 (d, J=6.3 Hz, 3 H), 1.35 (s, 9 H), 0.09-0.15 (m, 4 H). LCMS ES m/z 554 [M+H]$^+$.

Step 2:

To a solution of compound 367 (191 mg) in DCM (1.7 mL) was added HCl (4 N in dioxane, 1.7 mL). Diluted with EtOAc washed with saturated NaHCO$_3$ (2×) and brine, dried (MgSO$_4$), filtered, and concentrated. Purified by flash chromatography eluting with heptanes/EtOAc (50-100%) then DCM/MeOH (0-10%) to afford compound 368 (104 mg, 67% yield over 2 steps). $^1$H NMR (DMSO-$d_6$, 400 MHz) δ 7.95 (dd, J=5.8, 8.8 Hz, 1 H), 7.52 (dd, J=2.6, 10.2 Hz, 1 H), 7.44 (d, J=1.0 Hz, 1 H), 7.24 (dt, J=2.8, 8.3 Hz, 1 H), 6.57 (s, 1 H), 6.22 (q, J=6.1 Hz, 1 H), 5.86 (s, 2 H), 3.85 (s, 3 H), 3.69 (s, 3 H), 3.48 (s, 2 H), 2.40 (br. s., 1 H), 1.82 (s, 4 H), 1.60 (d, J=6.3 Hz, 3 H), 0.24-0.15 (m, 2 H), 0.11-0.04 (m, 2 H). LCMS ES m/z 454 [M+H]$^+$.

Step 3:

The procedure described in step 5 for Example 9 and 10 was used to prepare compound 369 (105 mg of the sodium salt).

Step 4:

The procedure described in step 6 for Example 9 and 10 was used to prepare Examples 11 and 12. The analytical chiral separation by SFC was performed using a Regis Whelk-01 (S,S) 4.6 mm×100 mm column (5 micron particle size) which was eluted with 30% MeOH in CO$_2$ held at 35° C. at 120 bar. The flow rate of 5 mL/min gave Rt$_{(Peak\ 1)}$=1.69 minutes and Rt$_{(Peak\ 2)}$=2.73 minutes.

Example 11 (Peak 2): 1.8 mg; 85% ee, 2% yield. $^1$H NMR (DMSO-$d_6$, 400 MHz) δ 7.57 (dd, J=2.5, 10.4 Hz, 1 H), 7.37-7.32 (m, 2 H), 7.13 (dt, J=2.8, 8.4 Hz, 1 H), 6.74 (s, 1 H), 5.80-5.75 (m, 2 H), 5.70-5.64 (m, 1 H), 4.64 (d, J=15.3 Hz, 1 H), 4.09 (d, J=15.0 Hz, 1 H), 3.91 (s, 3 H), 2.44-2.39 (m, 1 H), 2.19 (s, 3 H), 1.65 (d, J=6.1 Hz, 3 H), 1.10 (br. s, 1 H), 0.97-0.91 (m, 1 H), 0.86-0.77 (m, 2 H). LCMS ES m/z 422 [M+H]$^+$.

Example 12 (Peak 1): 2.2 mg; 85% ee, 2% yield. $^1$H NMR (DMSO-$d_6$, 400 MHz) δ 7.57 (d, J=9.7 Hz, 1 H), 7.37-7.32 (m, 2 H), 7.13 (t, J=8.4 Hz, 1 H), 6.74 (s, 1 H), 5.77 (s, 2 H), 5.70-5.64 (m, 1 H), 4.64 (d, J=15.3 Hz, 1 H), 4.09 (d, J=15.5 Hz, 1 H), 3.91 (s, 3 H), 2.44-2.39 (m, 1 H), 2.19 (s, 3 H), 1.65 (d, J=5.8 Hz, 3 H), 1.13-1.06 (m, 1 H), 0.98-0.90 (m, J=6.9 Hz, 1 H), 0.82 (br s, 2 H). LCMS ES m/z 422 [M+H]$^+$.

Preparation of 7-amino-12-fluoro-1,3,10,16-tetramethyl-16,17-dihydro-1H-8,4-(metheno)pyrazolo[4,3-h][2,5,11]benzoxadiazacyclotetradecin-15(10 H)-one
(Example 13 and Example 14)

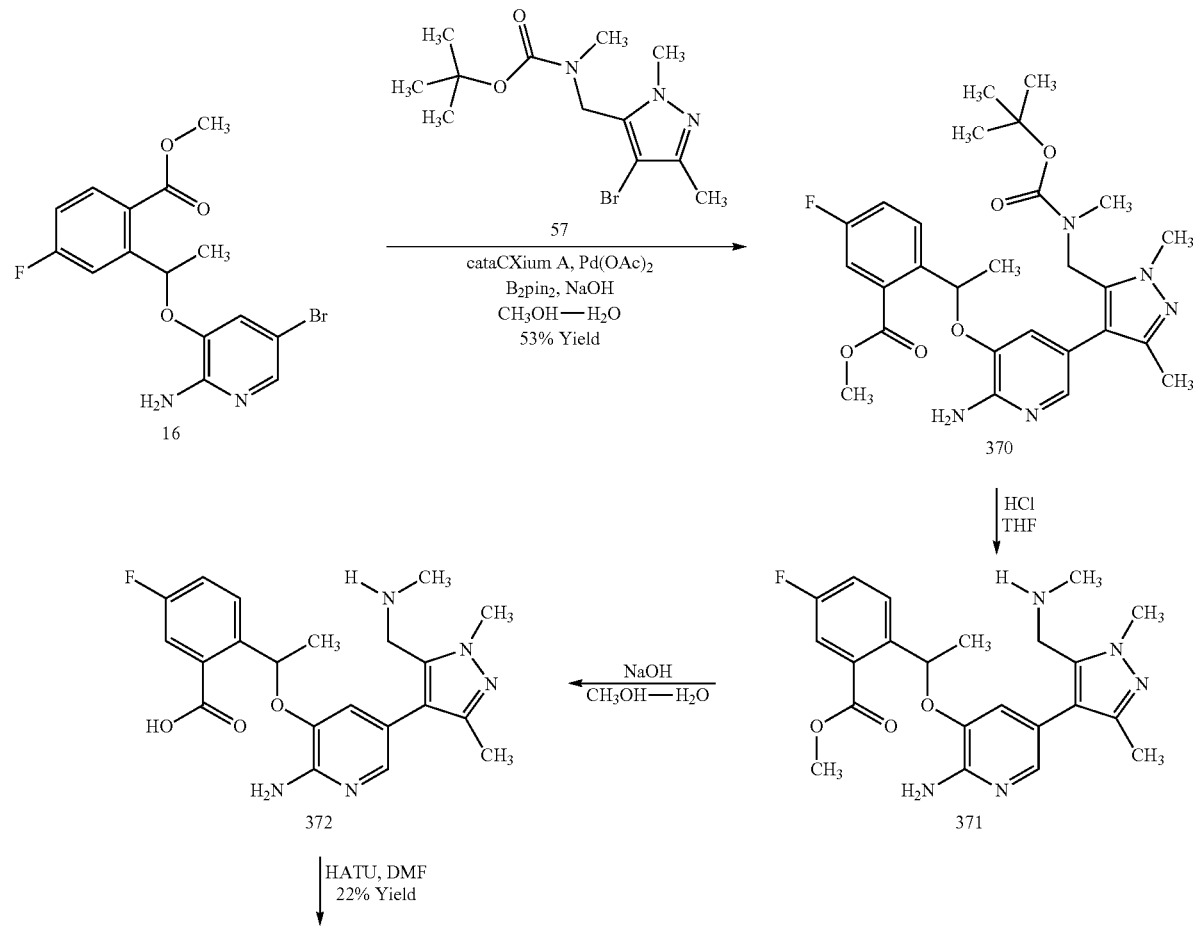

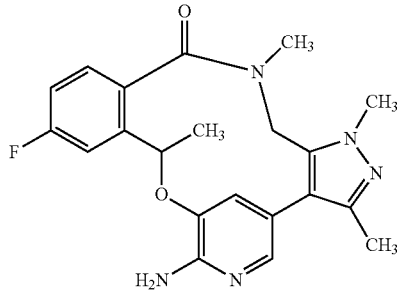

Examples 13 and Example 14

Step 1:

To a solution of compound 57 (689 mg, 2.2 mmol) and compound 16 (400 mg, 1.1 mmol) and bis pinacol ester (825 mg, 3.25 mmol) in MeOH (11.6 mL) was added 1 N NaOH in water (2.2 mL, 2.2 mmol). The reaction mixture was purged with nitrogen. Next, Pd(OAc)$_2$ (30.3 mg, 0.14 mmol) and di(1-adamantyl)-n-butylphosphine (4 mg, 0.14 mmol) were sequentially added and the reaction mixture was purged with nitrogen. The reaction mixture was heated at 80° C. in an oil bath over night, and cooled to room temperature. The reaction mixture was filtered through a celite pad and washed with MeOH. The resulting solution was concentrated and purified via reversed phase chromatography and gave compound 370 as an oil (300 mg, 53% yield). LCMS m/z 528 [M+H]$^+$.

Step 2:

To compound 370 (50 mg, 0.09 mmol) in THF (3 mL) was added 0.5 mL of 38% HCl at room temperature. The reaction mixture formed two layers. The reaction mixture was heated in microwave at 60° C. for 30 minutes which gave compound 371.

Step 3:

Compound 371 was cooled to room temperature and to the reaction mixture was added 50% NaOH (approximately 1.0 mL) until pH ~12, and MeOH (3 mL). After heating at 60° C. for 30 min in an oil bath, the reaction was concentrated and lyophilized overnight and gave compound 372. The assumed theoretical yield was 39 mg.

Step 4:

To a reaction mixture containing compound 372 (39 mg, 0.09 mmol) in anhydrous DMF (3 mL) at pH ~10 was added HATU (72 mg, 0.18 mmol) and stirred at room temperature. After 4 hours, LCMS of the reaction mixture showed completed conversion to the desired product. The reaction mixture was diluted with MeOH and filtered through a celite pad and concentrated. After reversed phase purification using ammonium acetate as additive, the desired product was obtained as a solid (8 mg 22% yield). $^1$H NMR (600 MHz, DMSO-d$_6$) δ 7.59-7.63 (m, 1 H), 7.36-7.41 (m, 2 H), 7.17 (d, J=2.5 Hz, 1 H), 6.75 (s, 1 H), 5.81 (s, 2 H), 5.50-5.64 (m, 1 H), 4.61 (d, J=14.9 Hz, 1 H), 4.08 (d, J=15.2 Hz, 1 H), 3.87 (s, 3 H), 2.98 (s, 3 H), 2.20 (s, 3 H), 1.65 (d, J=6.4 Hz, 3 H). The analytical chiral separation by SFC was performed using a Chiralcel OD-3 (4.6 mm×100 mm column, 3 micron particle size) which was eluted with 30% MeOH in CO$_2$ held at 25° C. at 120 bar. The flow rate of 5 mL/min gave Rt$_{(Peak\ 1)}$=0.75 minutes and Rt$_{(Peak\ 2)}$=1.3 minutes.

Example 13 (Peak 1): $^1$H NMR (400 MHz, DMSO-d$_6$) δ 7.62 (dd, J=2.5, 10.3 Hz, 1 H), 7.33-7.43 (m, 2 H), 7.15-7.23 (m, 1 H), 6.76 (d, J=1.5 Hz, 1 H), 5.81 (s, 2 H), 5.60 (br s, 1 H), 4.62 (d, J=15.1 Hz, 1 H), 4.08 (d, J=15.1 Hz, 1 H), 3.88 (s, 3 H), 2.99 (s, 3 H), 2.21 (s, 3 H), 1.65 (d, J=6.0 Hz, 3 H).

Example 14 (Peak 2): $^1$H NMR (400 MHz, DMSO-d$_6$) δ 7.57-7.65 (m, 1 H), 7.33-7.44 (m, 2H), 7.12-7.23 (m, 1 H), 6.76 (s, 1 H), 5.80 (s, 2 H), 5.61 (br. s, 1 H), 4.62 (d, J=15.4 Hz, 1 H), 4.09 (d, J=15.1 Hz, 1 H), 3.88 (s, 3 H), 2.99 (s, 3 H), 2.21 (s, 3 H), 1.66 (d, J=6.0 Hz, 3 H).

Preparation of 7-amino-3-cyclopropyl-12-fluoro-2,10,16-trimethyl-16,17-dihydro-2H-8,4-(metheno)pyrazolo[4,3-h][2,5,11]benzoxadiazacyclotetradecin-15(10 H)-one (Example 15 and Example 16)

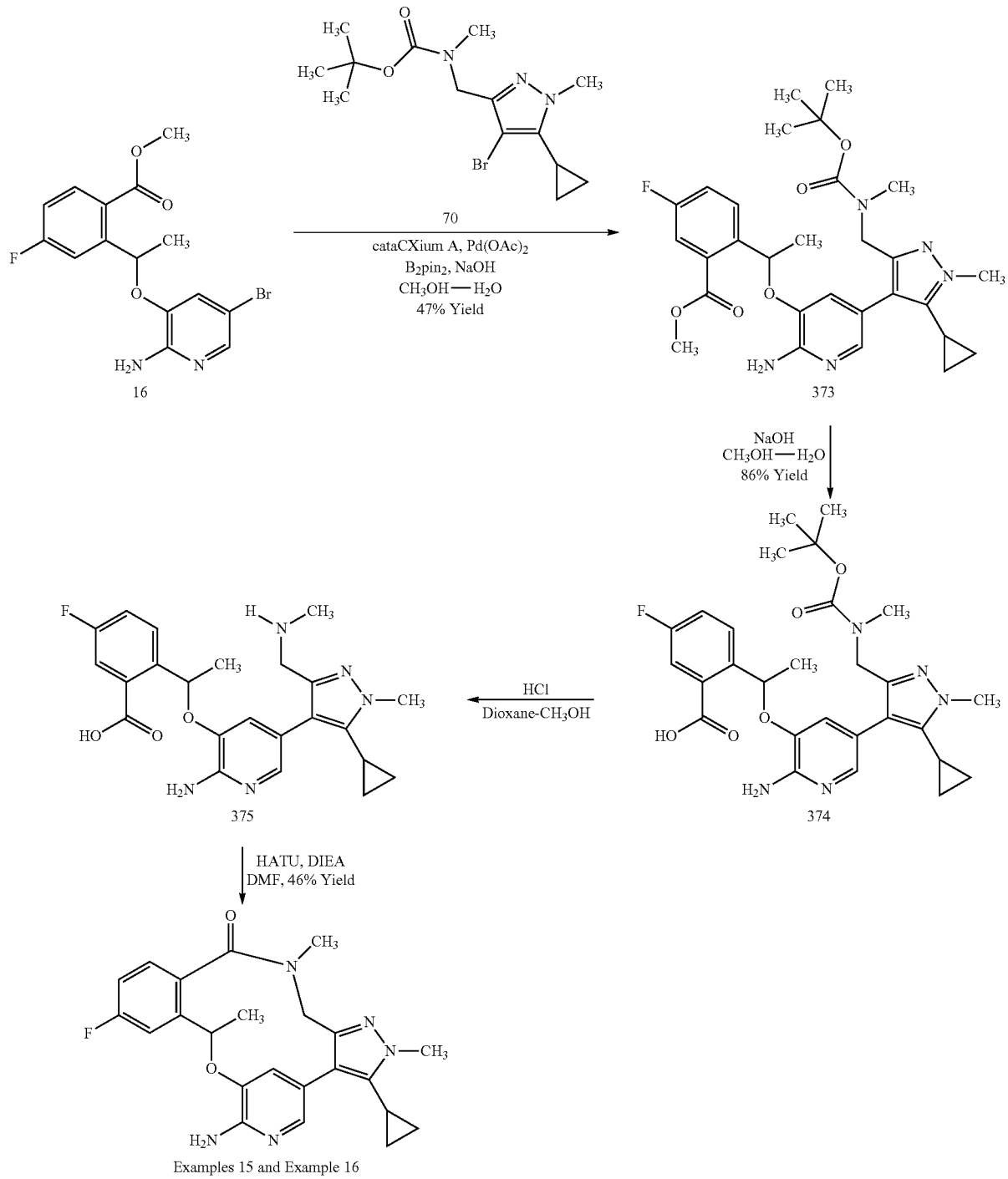

Examples 15 and Example 16

Step 1:

The procedure described in step 1 for Example 13 and 14 was used to prepare compound 373 (380 mg, 43% yield). LCMS m/z 554 [M+H]+. Step 2:

A mixture of compound 373 (380 mg, 0.557 mmol) and NaOH (0.55 g, 13.74 mmol) in methanol (10 mL) and water (10 mL) was stirred at 40° C. for 3 hours. None of the compound 374 was detected by LCMS. The reaction mixture was concentrated under reduced pressure and the resultant residue was dissolved in water (20 mL). The aqueous layer was extracted with MTBE (20 mL). The organic layer was discarded and the aqueous layer was acidified with 6 N HCl to pH ~5. The mixture was saturated with solid NaCl and extracted with EtOAc (30 mL×5). The combined EtOAc layers were dried over $Na_2SO_4$ and concentrated in vacuo and gave compound 374 as a yellow solid (320 mg, 86% yield). LCMS m/z 540 [M+H]+.

Step 3:

To a solution of compound 374 (320 mg, 0.515 mmol) in methanol (5 mL) was added drop-wise ~4 M HCl in dioxane (10 mL). The reaction mixture was stirred at 40° C. for 3 hours. None of compound 147 was detected by LCMS. The reaction mixture was concentrated under reduced pressure and the resultant residue was dissolved in toluene and concentrated. This was repeated two times and gave compound 375. LCMS m/z 440 [M+H]+.

Step 4:

To a solution of HATU (338 mg, 0.89 mmol) in DMF (70 mL) was added drop-wise a solution of compound 375 (0.515 mmol) and DIPEA (1.2 g, 9.5 mmol) in DMF (20 mL) at 0° C. After addition, the resulting mixture was stirred at 0° C. for 1 hour. None of the compound 375 was detected by LCMS. The mixture was poured into ice water (50 mL) and the aqueous layer was extracted with EtOAc (40 mL×5). The combined EtOAc layers were washed with brine (20 mL×5), dried over $Na_2SO_4$ and concentrated under reduced pressure. The crude product was purified by flash chromatography over silica gel which was eluted with EtOAc and gave pure a mixture of Example 15 and Example 16 as an off-white solid (100 mg, 46% yield). The analytical chiral separation was performed by SFC on a Chiralpak AS-H (150×4.6 mm I.D., 5 micron particle size), which was eluted with 5-40% ethanol (0.05% DEA) in $CO_2$. The flow rate of 3 mL/min gave $Rt_{(Peak}$ 1)=3.08 minutes and $Rt_{(Peak}$ 2)=3.47 minutes. The racemic mixture was purified by preparative SFC and gave peak 1 as a white solid (27 mg) and as a white solid peak 2 (22 mg).

Example 16 (Peak 1): 98% ee. $^1$H NMR (400 MHz, Methanol-$d_4$) δ 7.42-7.39 (m, 2 H), 7.29 (dd, 1 H), 7.00 (dd, 1 H), 6.77 (s, 1 H), 5.63-5.58 (m, 1 H), 4.22 (q, 2 H), 3.84 (s, 3 H), 2.99 (s, 3 H), 1.78-1.72 (m, 1 H), 1.68-1.67 (d, 3 H), 0.98-0.94 (m, 1 H), 0.86-0.82 (m, 1 H), 0.46-0.42 (m, 1 H), 0.28-0.24 (m, 1 H). LCMS m/z 422 [M+H]+.

Example 15 (Peak 2): 100% ee. $^1$H NMR (400 MHz, Methanol-$d_4$) δ 7.42-7.39 (m, 2 H), 7.29 (dd, 1 H), 7.00 (dd, 1 H), 6.77 (s, 1 H), 5.63-5.58 (m, 1 H), 4.22 (q, 2 H), 3.84 (s, 3 H), 2.99 (s, 3 H), 1.78-1.72 (m, 1 H), 1.68-1.67 (d, 3 H), 0.98-0.94 (m, 1 H), 0.86-0.82 (m, 1 H), 0.46-0.42 (m, 1 H), 0.28-0.24 (m, 1 H). LCMS m/z 422 [M+H]+.

Preparation of 7-amino-3-cyclopropyl-12-fluoro-1, 10,16-trimethyl-16,17-dihydro-1H-8,4-(metheno) pyrazolo[4,3-h][2,5,11]benzoxadiazacyclotetradecin-15(10 H)-one (Example 17 and Example 18)

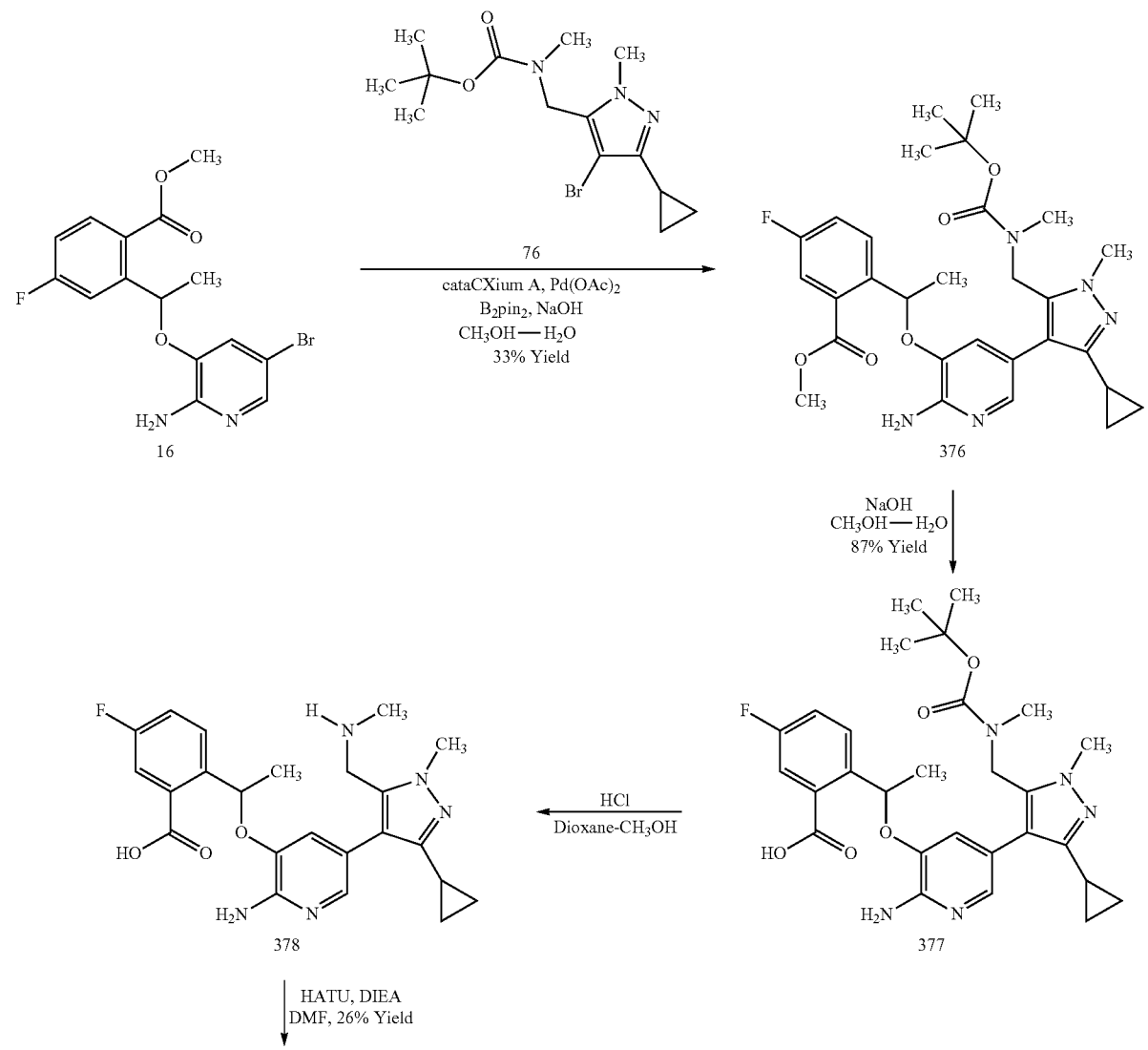

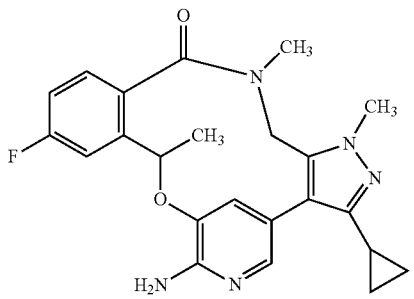

Examples 17 and Example 18

Step 1:
The procedure described in step 1 for Example 13 and 14 was used to prepare compound 376 (495 mg, 33% yield). LCMS m/z 554 [M+H]$^+$.

Step 2:
The procedure described in step 3 for Example 13 and 14 was used to prepare compound 377 (420 mg, 87% yield). LCMS m/z 540 [M+H]$^+$.

Step 3:
The procedure described in step 2 for Example 13 and 14 was used to prepare compound 378. LCMS m/z 439 [M+H]$^+$.

Step 4:
To a solution of HATU (520 mg, 1.4 mmol) in DMF (100 mL) was added drop-wise a solution of compound 378 (0.91 mmol) and DIPEA (1.88 g, 14.6 mmol) in DMF (20 mL) at 0° C. The resultant mixture was stirred at 0° C. for 1 hour. None of compound 378 was detected by LCMS. The mixture was poured into ice water (50 mL) and the aqueous layer was extracted with EtOAc (40 mL×5). The combined EtOAc layers were washed with brine (20 mL×5), dried over Na$_2$SO$_4$ and concentrated in vacuo. The crude product was purified by flash chromatography over silica gel, which was eluted with EtOAc and gave a mixture of Example 17 and Example 18 as a dark solid (100 mg, 26% yield). The analytical chiral separation was performed by SFC on a Chiralcel (50×4.6 mm I.D., 3 micron particle size), which was eluted with 5-40% methanol (0.05% DEA) in CO$_2$. The flow rate of 4 mL/min gave Rt$_{(Peak\ 1)}$=1.47 min and Rt$_{(Peak\ 2)}$=1.74 min. The racemic mixture was separated by preparative SFC and gave peak 1 as a white solid (30 mg) and peak 2 as a white solid (39 mg).

Example 17 (Peak 1): 93.7% ee. $^1$H NMR (400 MHz, CDCl$_3$) δ 7.76-7.75 (m, 1 H), 7.25 (dd, 1H), 7.10 (dd, 1 H), 693-6.90 (m, 1 H), 6.80 (m, 1 H), 5.70-5.68 (s, 1 H), 4.54 (s, 2 H), 4.40 (d, 1 H), 4.22 (d, 1 H), 3.85 (s, 3 H), 3.06 (s, 3 H), 1.85 (m, 1 H), 1.70 (d, 3 H), 1.02-1.01 (m, 1 H), 0.95-0.93 (m, 1 H), 0.81-0.79 (m, 1 H), 0.63 (m, 1 H). LCMS m/z 422 [M+H]$^+$.

Example 18 (Peak 2): 94.6% ee. $^1$H NMR (400 MHz, CDCl$_3$) δ 7.75 (s, 1 H), 7.22 (dd, 1 H), 7.18 (dd, 1 H), 693-6.90 (m, 1 H), 6.81 (m, 1 H), 5.70-5.68 (s, 1 H), 4.67 (s, 2 H), 4.32 (d, 1H), 4.26 (d, 1 H), 3.85 (s, 3 H), 3.06 (s, 3 H), 1.85 (m, 1 H), 1.70 (d, 3 H), 1.02-1.01 (m, 1 H), 0.95-0.93 (m, 1 H), 0.81-0.79 (m, 1 H), 0.63 (m, 1 H). LCMS m/z 422 [M+H]$^+$.

Preparation of 7-amino-12-fluoro-3-methoxy-2,10,16-trimethyl-16,17-dihydro-2H-8,4-(metheno)pyrazolo[4,3-h][2,5,11]benzoxadiazacyclotetradecin-15(10 H)-one (Example 19 and Example 20)

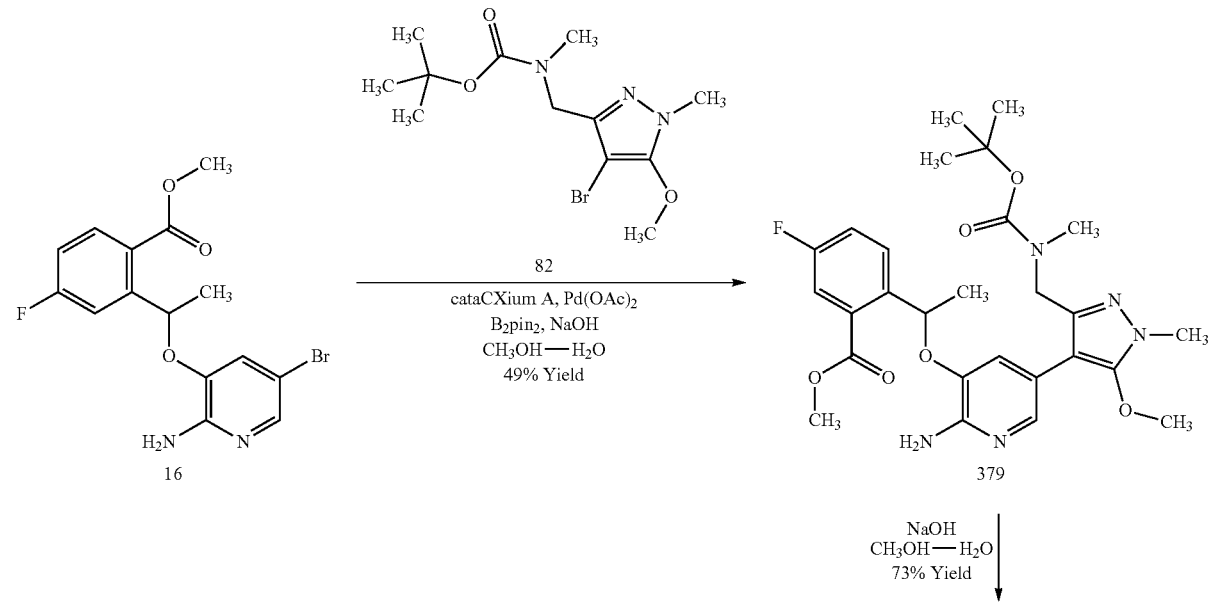

-continued

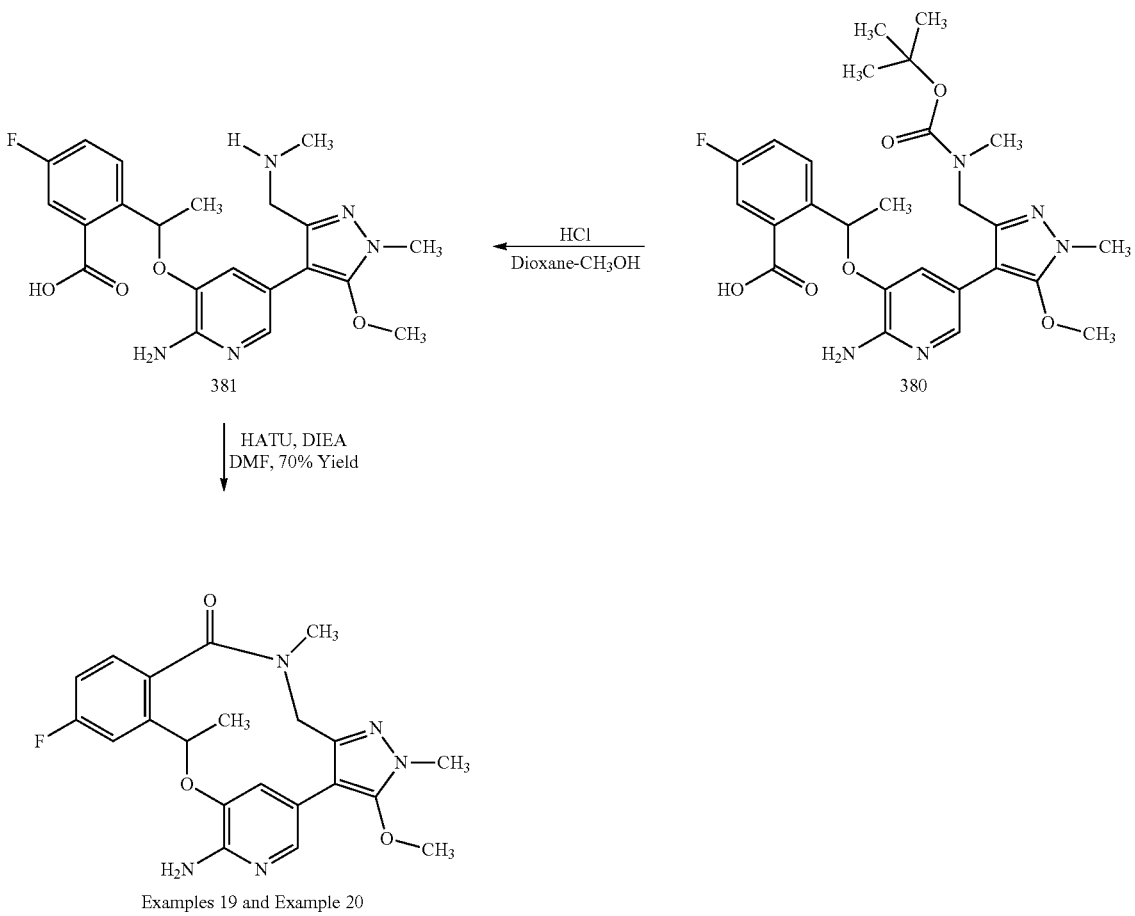

Examples 19 and Example 20

Step 1:
The procedure described in step 1 for Example 13 and 14 was used to prepare compound 379 (1.0 g, 49% yield). LCMS m/z 544 [M+H]$^+$.

Step 2:
The procedure described in step 3 for Example 13 and 14 was used to prepare compound 380 (700 mg, 73% yield). LCMS m/z 540 [M+H]$^+$.

Step 3:
The procedure described in step 3 for Example 15 and 16 was used to prepare compound 381. LCMS m/z 430 [M+H]$^+$.

Step 4:
To a solution of HATU (710 mg, 1.85 mmol) in DMF (30 mL) was added drop-wise a solution of compound 381 (1.32 mmol) and DIPEA (2.7 g, 21.1 mmol) in DMF (30 mL) and THF (6 mL) at 0° C. After addition, the resulting mixture was stirred at the same temperature for 1 hour. LCMS showed the reaction was complete. The mixture was poured into ice water (100 mL), and the aqueous layer was extracted with EtOAc (60 mL×5). The combined EtOAc layers were washed with brine (50 mL×5), dried over Na$_2$SO$_4$ and concentrated in vacuo to give a residue, which was purified by column chromatography over silica gel, which was eluted with DCM/MeOH=15:1 (Rf=0.3) and gave a mixture of Example 19 and Example 20 as a yellow solid (390 mg, 70% yield). The analytical chiral separation was performed by SFC on a Chiralpak AD-3 (150×4.6 mm I.D., 3 micron particle size), which was eluted with 5-40% methanol (0.05% DEA) in CO$_2$. Rt$_{(Peak\ 1)}$=4.85 minutes and Rt$_{(Peak\ 2)}$=5.79 minutes. The racemic mixture was separated by preparative SFC to give Peak 1 as a white solid (130 mg) and peak 2 as a white solid (128 mg).

Example 19 (Peak 1): 100% ee. $^1$H NMR (400 MHz, Methanol-d$_4$) δ 7.41-7.38 (m, 2 H), 7.30 (dd, 1 H), 7.00 (dd, 1 H), 6.80 (s, 1 H), 5.64-5.60 (m, 1 H), 4.26 (d, 1 H), 4.12 (d, 1 H), 3.73 (s, 3H), 3.56 (s, 3 H), 3.02 (s, 3 H), 1.68 (d, 3 H). LCMS m/z 412 [M+H]$^+$.

Example 20 (Peak 2): 98.2% ee. $^1$H NMR (400 MHz, Methanol-d$_4$) δ 7.41-7.38 (m, 2 H), 7.30 (dd, 1 H), 7.00 (dd, 1 H), 6.80 (s, 1 H), 5.64-5.60 (m, 1 H), 4.26 (d, 1 H), 4.12 (d, 1 H), 3.73 (s, 3 H), 3.61 (s, 3 H), 3.02 (s, 3 H), 1.68 (d, 3 H). LCMS m/z 412 [M+H]$^+$.

Preparation of 7-amino-12-fluoro-3-methoxy-1,10,16-trimethyl-16,17-dihydro-1H-8,4-(metheno)pyrazolo[4,3-h][2,5,11]benzoxadiazacyclotetradecin-15(10 H)-one (Example 21 and Example 22)

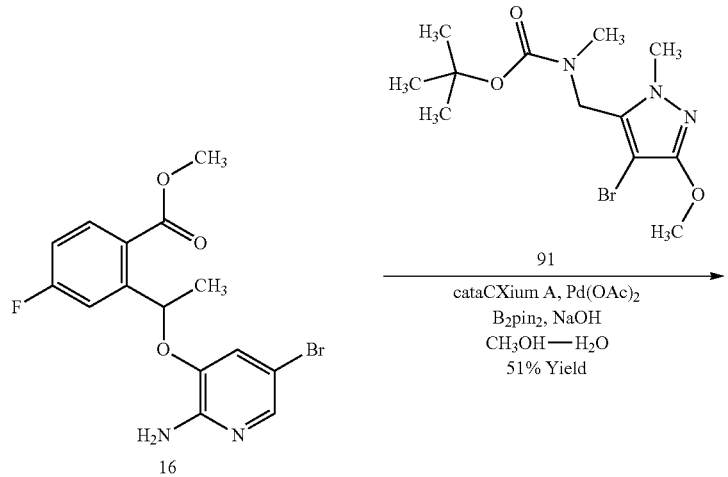

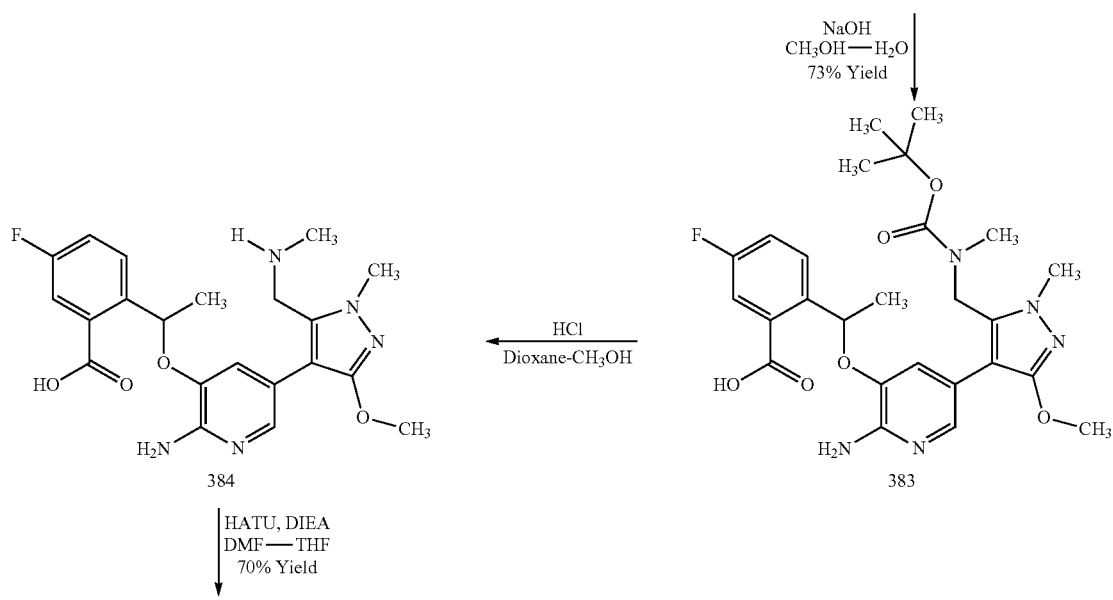

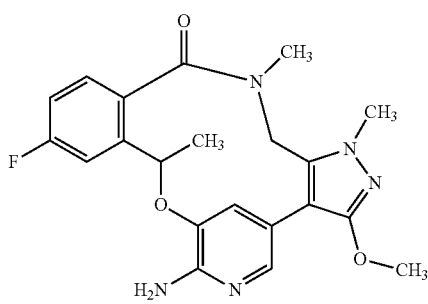

Examples 21 and Example 22

Step 1:
The procedure described in step 1 for Example 13 and 14 was used to prepare compound 382 as a brown oil (300 mg, 51% yield). LCMS m/z 544 [M+H]$^+$.

Step 2:
The procedure described in step 3 for Example 13 and 14 was used to prepare compound 383 as a yellow solid (320 mg, 73% yield). LCMS m/z 529 [M+H]$^+$.

Step 3:
The procedure described in step 2 for Example 15 and 16 was used to prepare compound 384. LCMS m/z 430 [M+H]+.

Step 4:

To a solution of HATU (280 mg, 0.74 mmol) in DMF (25 mL) was added drop-wise a solution of compound 384 (0.53 mmol) and DIPEA (1.09 g, 8.48 mmol) in DMF (25 mL) and THF (5 mL) at 0° C. The mixture was stirred at same temperature for 1 hour. LCMS showed the reaction was complete. The mixture was poured into ice water (100 mL) and the aqueous later was extracted with EtOAc (60 mL×5). The combined EtOAc layers were washed with brine (50 mL×5), dried over $Na_2SO_4$, filtered and concentrated in vacuo to give a residue, which was purified via Biotage (DCM/MeOH=15:1, Rf=0.3) to give a mixture of Example 21 and Example 22 as a yellow solid (170 mg, 78%). The analytical chiral separation was performed by SFC on a Chiralcel OD-3 (50×4.6 mm I.D., 3 micron particle size), which was eluted with 5-40% methanol (0.05% DEA) in $CO_2$. $Rt_{(Peak}$ 1)=1.44 minutes and $Rt_{(Peak}$ 2)=1.59 minutes. The racemic mixture was separated by preparative SFC and gave Peak 1 as a white solid (62 mg) and Peak 2 as a white solid (72 mg).

Example 21 (Peak 1): 96.6% ee. $^1$H NMR (400 MHz, Methanol-$d_4$) δ 7.62 (d, 1 H), 7.50 (dd, 1H), 7.43 (dd, 1 H), 7.16-7.11 (m, 1 H), 6.90 (d, 1 H), 5.64-5.60 (m, 1 H), 4.84 (d, 1 H), 4.37 (d, 1 H), 3.92 (d, 6 H), 3.17 (s, 3 H), 1.78 (d, 3 H). LCMS m/z 412 [M+H]$^+$.

Example 22 (Peak 2): 96.9% ee. $^1$H NMR (400 MHz, Methanol-$d_4$) δ 7.61 (d, 1 H), 7.50 (dd, 1H), 7.42 (dd, 1 H), 7.15-7.10 (m, 1 H), 6.90 (d, 1 H), 5.68-5.64 (m, 1 H), 4.82 (d, 1 H), 4.36 (d, 1 H), 3.90 (d, 6 H), 3.15 (s, 3 H), 1.78 (d, 3 H). LCMS m/z 412 [M+H]$^+$.

Preparation of 7-amino-10-ethyl-12-fluoro-3-methoxy-1,16-dimethyl-16,17-dihydro-1H-8,4-(metheno)pyrazolo[4,3-h][2,5,11]benzoxadiazacyclotetradecin-15(10 H)-one (Example 23 and Example 24)

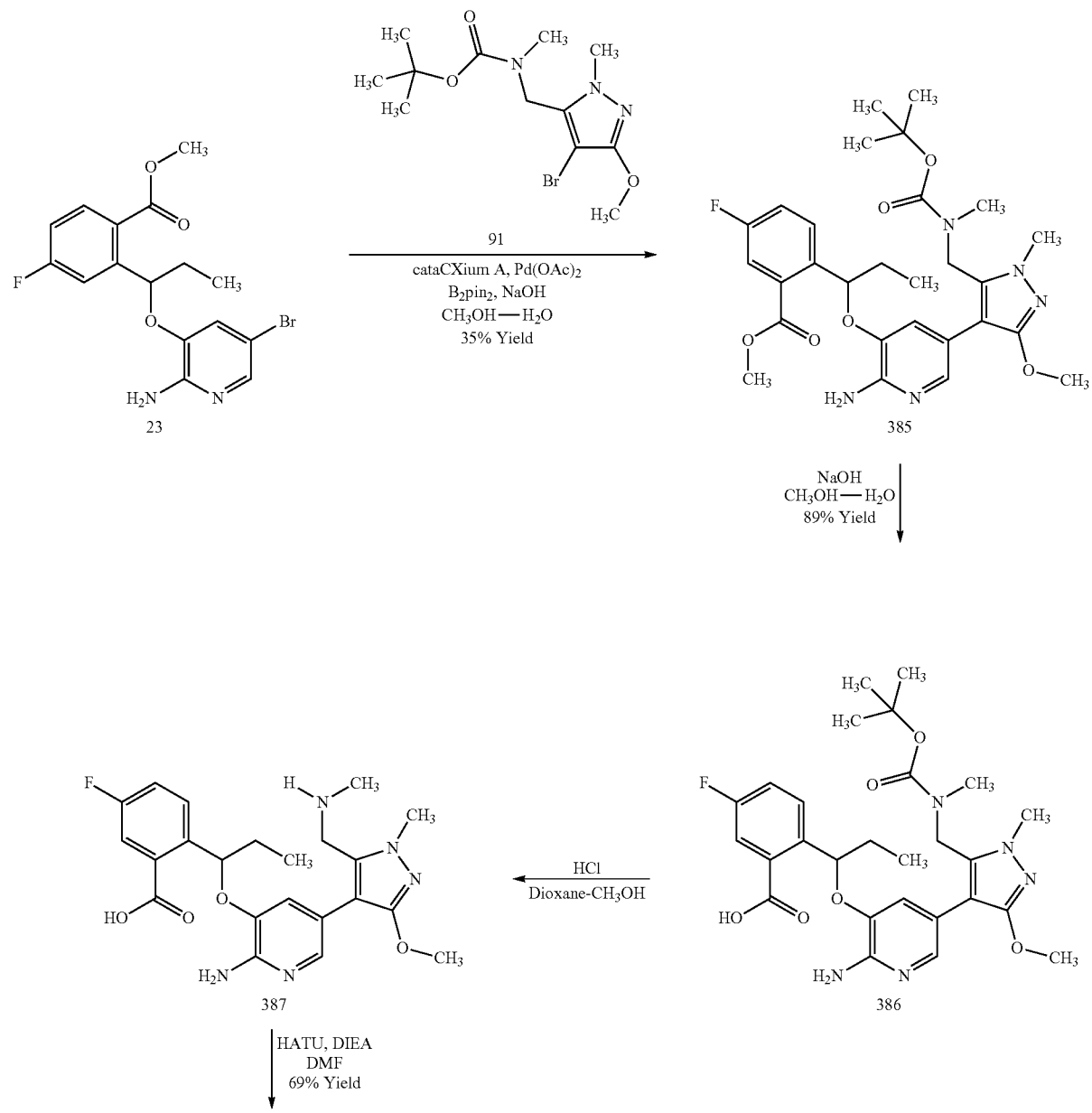

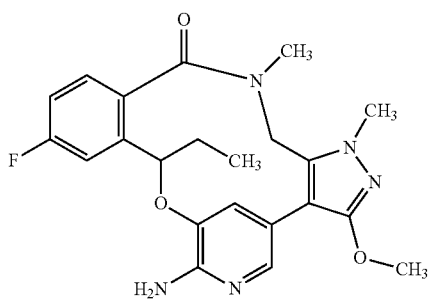

Examples 23 and Example 24

Step 1:
The procedure described in step 1 for Example 13 and 14 was used to prepare compound 385 as a brown solid (470 mg, 35% yield).

Step 2:
The procedure described in step 3 for Example 13 and 14 was used to prepare compound 386 as a pale yellow solid (410 mg, 89% yield).

Step 3:
The procedure described in step 2 for Example 15 and 16 was used to prepare compound 387 as a pale yellow solid (410 mg, quantitative).

Step 4:
To a solution of HATU (399 mg, 1.05 mmol) in DMF (80 mL) was added drop-wise a solution of compound 387 (0.75 mmol) and DIPEA (1.4 g, 11.3 mmol) in DMF (20 mL) at 0° C. After addition, the resulting mixture was stirred at same temperature for 1 hour. LCMS showed the reaction was complete. The mixture was poured into ice water (100 mL). The aqueous layer was extracted with EtOAc (50 mL×2). The combined EtOAc layers were washed with $H_2O$ (40 mL×2), brine (40 mL), dried over $Na_2SO_4$ and concentrated in vacuo to give a residue, which was purified via Biotage ($CH_2Cl_2$/MeOH from 15:1 to 10:1) to give Example 23 and Example 24 as an off-white solid (220 mg, 69% yield). The analytical chiral separation was performed by SFC on a Chiralcel AD-H (250×4.6 mm I.D., 5 micron particle size), which was eluted with 5-40% ethanol (0.05% DEA) in $CO_2$. A flow rate of 2.3 ml/min gave $Rt_{(Peak\ 1)}$=7.6 minutes and $Rt_{(Peak\ 2)}$=8.7 minutes. The racemic mixture was separated by preparative SFC to give Peak 1 as an off-white solid (65 mg) and peak 2 as an off-white solid (79 mg).

Example 23 (Peak 1): 99.0% ee. $^1$H NMR (400 MHz, $CDCl_3$) δ 7.82 (s, 1 H), 7.28 (m, 1 H), 7.19-7.17 (m, 1 H), 7.01-6.98 (m, 1 H), 6.90 (s, 1 H), 5.41-5.38 (m, 1 H), 4.76 (m, 2 H), 4.44 (d, 1 H), 4.28 (d, 1 H), 3.93 (s, 3 H), 3.72 (s, 3 H), 3.13 (s, 3 H), 2.26-2.16 (m, 1 H), 2.04-1.97 (m, 1 H), 1.05 (t, 3 H). LCMS m/z 426 [M+H]$^+$.

Example 24 (Peak 2): 94.4% ee. $^1$H NMR (400 MHz, $CDCl_3$) δ 7.79 (s, 1 H), 7.27 (m, 1 H), 7.17-7.15 (m, 1 H), 6.94-6.90 (m, 1 H), 6.72 (s, 1 H), 5.35-5.32 (m, 1 H), 4.63 (s, 2 H), 4.38 (d, 1 H), 4.21 (d, 1 H), 3.87 (s, 3 H), 3.66 (s, 3 H), 3.08 (s, 3 H), 2.21-2.09 (m, 1 H), 1.97-1.92 (m, 1 H), 1.02 (t, 3 H). LCMS m/z 426 [M+H]$^+$.

Preparation of 7-amino-10-cyclopropyl-12-fluoro-3-methoxy-1,16-dimethyl-16,17-dihydro-1H-8,4-(metheno)pyrazolo[4,3-h][2,5,11]benzoxadiazacyclotetradecin-15(10 H)-one (Example 25 and Example 26)

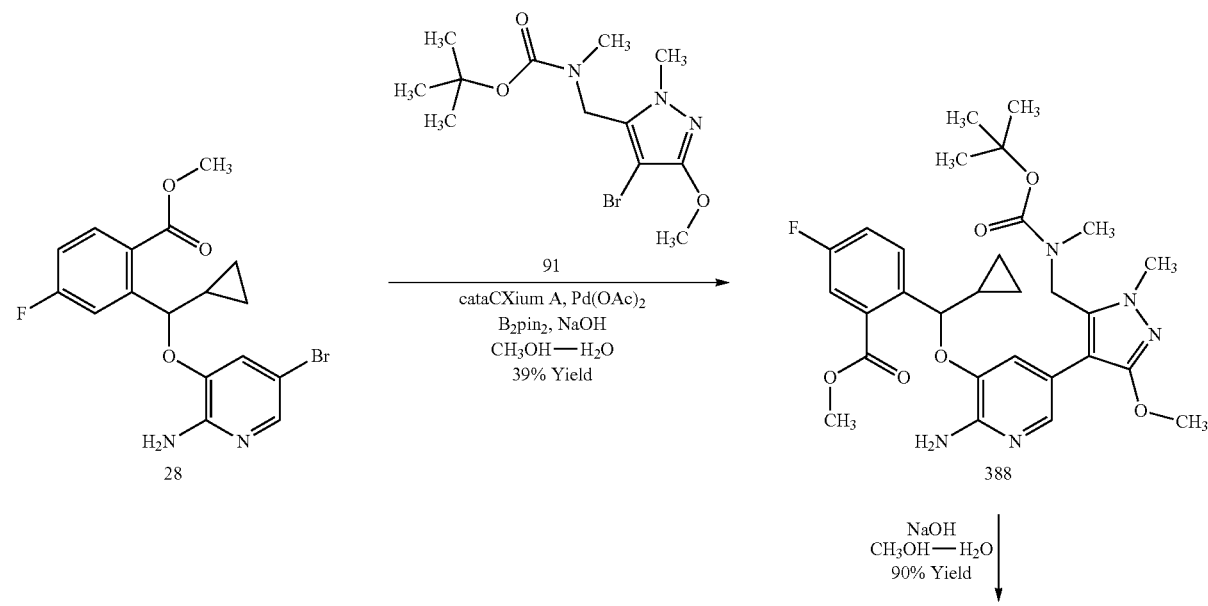

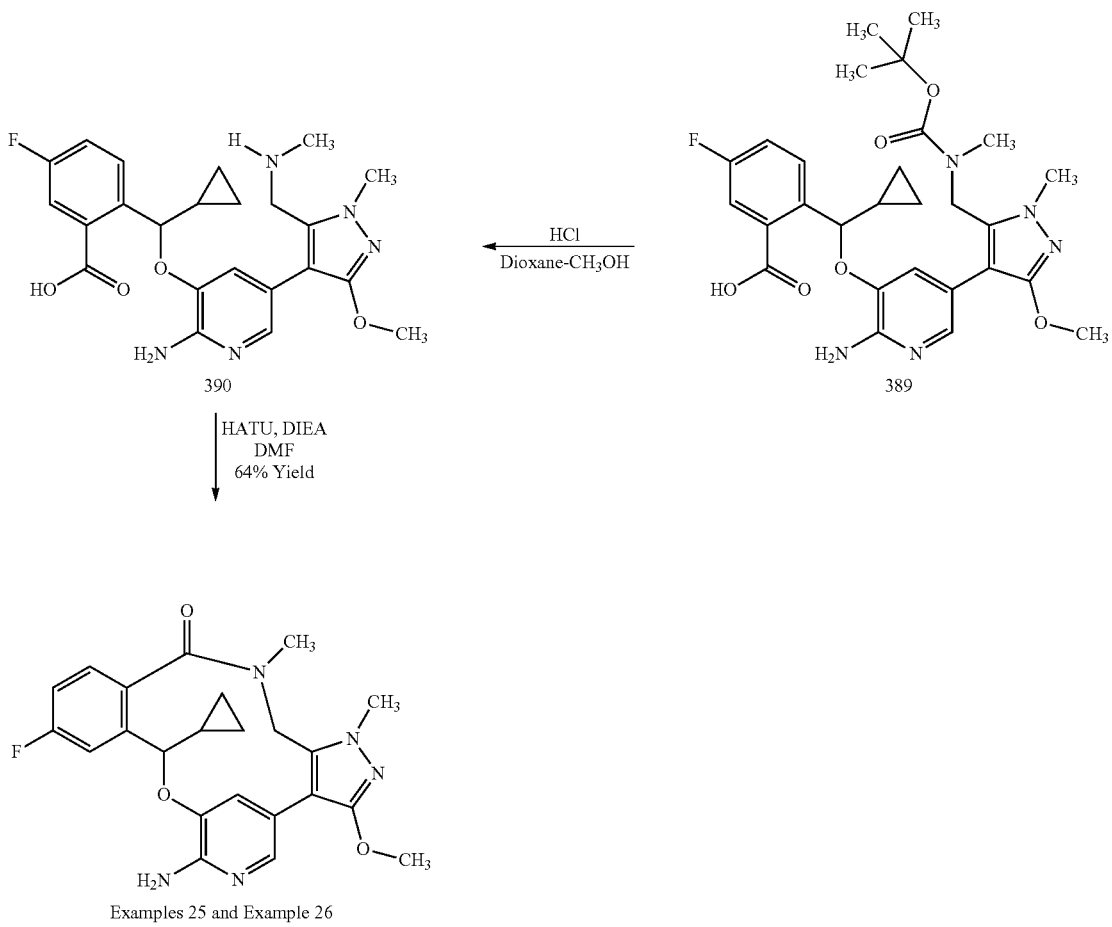

Examples 25 and Example 26

Step 1:
The procedure described in step 1 for Example 13 and 14 was used to prepare compound 388 as a pale brown solid (550 mg, 39% yield).

Step 2:
The procedure described in step 2 for Example 13 and 14 was used to prepare compound 389 as a pale yellow solid (482 mg, 90% yield).

Step 3:
The procedure described in step 3 for Example 13 and 14 was used to prepare compound 390 as a pale yellow solid (480 mg, quantitative).

Step 4:
To a solution of HATU (456 mg, 1.2 mmol) in DMF (80 mL) was added drop-wise a solution of compound 390 (0.86 mmol) and DIPEA (1.6 g, 12.4 mmol) in DMF (20 mL) at 0° C. After addition, the resulting mixture was stirred at same temperature for 1 hour. LCMS showed the reaction was complete. The mixture was poured into ice water (100 mL). The mixture was extracted with EtOAc (60 mL×2). The combined EtOAc layers were washed with $H_2O$ (50 mL×2), brine (50 mL), dried over $Na_2SO_4$ and concentrated in vacuo to give a residue, which was purified via Biotage ($CH_2Cl_2$/MeOH from 15:1 to 10:1) to give a mixture of Example 25 and Example 26 as an off-white solid (240 mg, 64% yield). The analytical chiral separation was performed by SFC on a Chiralcel AD-H (250×4.6 mm I.D., 5 micron particle size), which was eluted with 5-40% ethanol (0.05% DEA) in $CO_2$. A flow rate of 2.3 mL/min gave $Rt_{(Peak\ 1)}$=8.1 minutes and $Rt_{(Peak\ 2)}$=9.1 minutes. The racemic mixture was separated by preparative SFC to give Peak 1 as an off-white solid (75 mg) and Peak 2 as an off-white solid (76 mg).

Example 25 (Peak 1): 100% ee. $^1$H NMR (400 MHz, $CDCl_3$) δ 7.75 (s, 1 H), 7.35-7.32 (m, 1H), 7.16-7.12 (m, 1 H), 6.95-6.92 (m, 1 H), 6.60 (s, 1 H), 4.65-4.61 (m, 3 H), 4.35 (d, 1 H), 4.20 (d, 1 H), 3.86 (s, 3 H), 3.73 (s, 3 H), 3.06 (s, 3 H), 1.41-1.36 (m, 1 H), 0.85-0.82 (m, 2 H), 0.60-0.52 (m, 2 H). LCMS m/z 438 [M+H]$^+$ Example 26 (Peak 2): 94.8% ee. $^1$H NMR (400 MHz, $CDC_3$) δ 7.76 (s, 1 H), 7.34-7.32 (m, 1H), 7.15-7.12 (m, 1 H), 6.96-6.93 (m, 1 H), 6.61 (s, 1 H), 4.64-4.62 (m, 3 H), 4.34 (d, 1 H), 4.20 (d, 1 H), 3.85 (s, 3 H), 3.71 (s, 3 H), 3.04 (s, 3 H), 1.42-1.37 (m, 1 H), 0.84-0.81 (m, 2 H), 0.61-0.53 (m, 2 H). LCMS m/z 438 [M+H]$^+$.

Preparation of (10R)-7-amino-3-ethyl-12-fluoro-10, 16-dimethyl-16,17-dihydro-3H-8,4-(metheno)pyrazolo[3,4-h][2,5,11]benzoxadiazacyclotetradecin-15 (10 H)-one (Example 27)

H), 7.45 (s, 1 H), 7.39 (s, 1 H), 7.18-7.15 (m, 1 H), 6.94 (d, 1 H), 6.38 (s, 1 H), 6.33 (d, 1 H), 4.93 (s, 2H), 3.84 (d, 2 H), 3.71 (d, 3 H), 3.69-3.67 (m, 2 H), 2.34 (s, 3 H), 1.62 (d, 3 H), 1.36 (s, 9 H), 1.07 (t, 3 H).

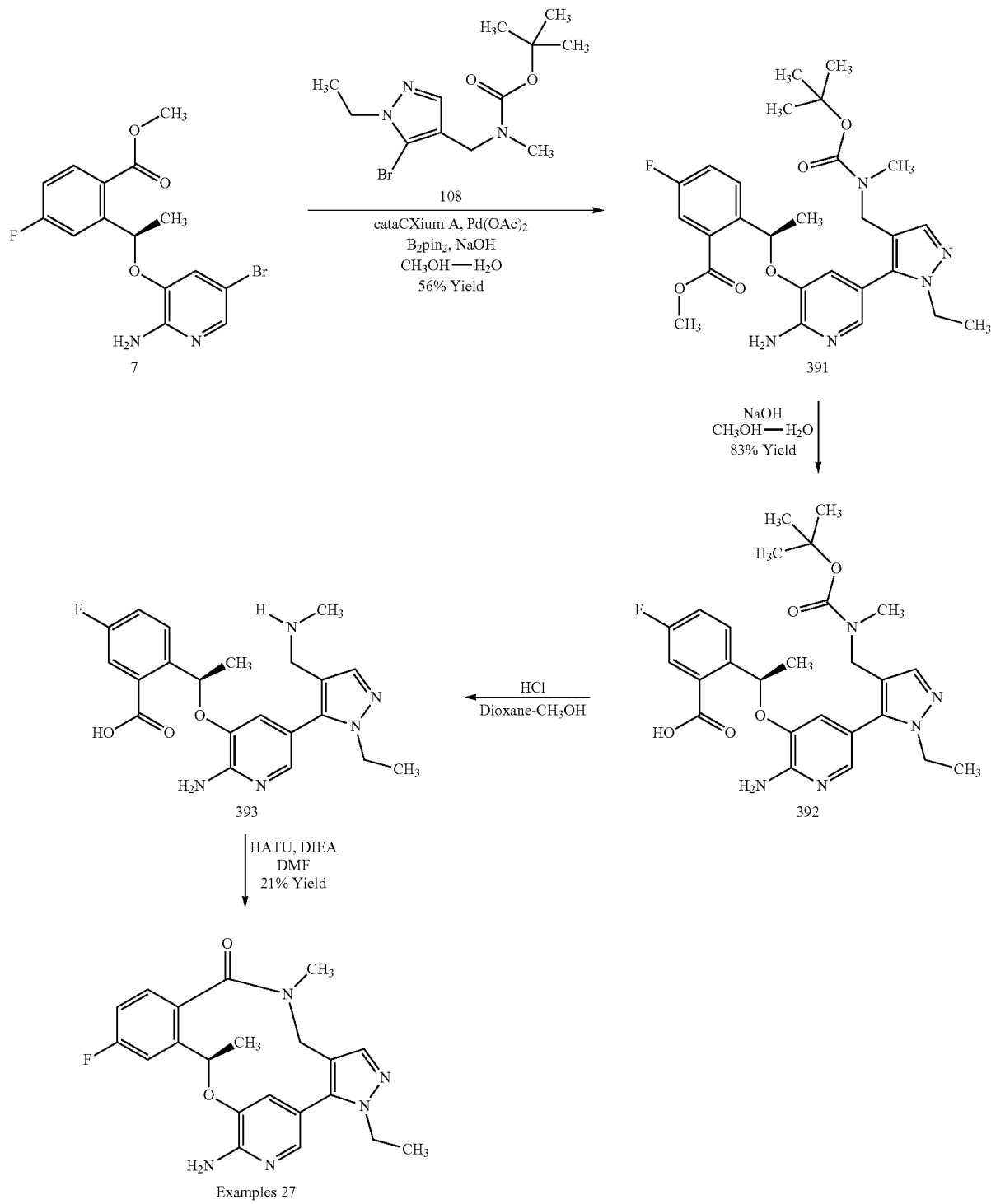

Step 1:

The procedure described in step 1 for Example 13 and 14 was used to prepare compound 391 as a brown solid (400 mg, 56% yield). $^1$H NMR (400 MHz, CDCl$_3$) δ 7.99-7.95 (m, 1

Step 2:

The procedure described in step 2 for Example 13 and 14 was used to prepare compound 392 as a yellow solid (320 mg, 83% yield). LCMS m/z 514 [M+H]$^+$.

Step 3:

The procedure described in step 3 for Example 13 and 14 was used to prepare compound 393 as a pale yellow solid (320 mg, quantitative).

Step 4:

To a solution of HATU (684 mg, 1.8 mmol) in DMF (60 mL) was added drop-wise a solution of compound 393 (0.62 mmol) and DIPEA (2.5 g, 19.2 mmol) in DMF (20 mL) at 0° C. After the addition, the resulting mixture was stirred at room temperature for 1 hour. LCMS showed the reaction was complete. The mixture was poured into ice water (50 mL). The aqueous layer was extracted with EtOAc (40 mL×5). The combined EtOAc layers were washed with brine (20 mL×5), dried over $Na_2SO_4$ and concentrated in vacuo to give a residue. The residue was purified by column chromatography over silica gel, which was eluted with petroleum ether/EtOAc (2:1-1:2), and gave Example 27 as a pink solid (52 mg, 21% yield). $^1$H NMR (400 MHz, $CDCl_3$) δ 7.52 (s, 1 H), 7.48 (d, 1 H), 7.21 (s, 1 H), 7.19 (s, 1 H), 7.10 (d, 1 H), 6.85 (m, 1 H), 5.79 (s, 1H), 4.94 (s, 2 H), 4.19-4.16 (m, 2 H), 4.11 (m, 2 H), 3.05 (s, 3 H), 1.72 (d, 3 H), 1.39 (t, 3 H). LCMS m/z 396 $[M+H]^+$. Analysis by chiral chromatography using Chiralcel OD-3 (150×4.6 mm I.D., 3 micron particle size) and eluting with methanol (5% to 40% with 0.05% DEA) in $CO_2$ at a flow rate of 2.5 mL/min gave a retention time of 6.23 minutes (100% ee).

Preparation of 7-amino-12-fluoro-1,3,10,16-tetramethyl-16,17-dihydro-1H-8,4-(azeno)-pyrazolo[4,3-h][2,5,11]benzoxadiazacyclotetradecin-15(10 H)-one
(Example 28 and Example 29)

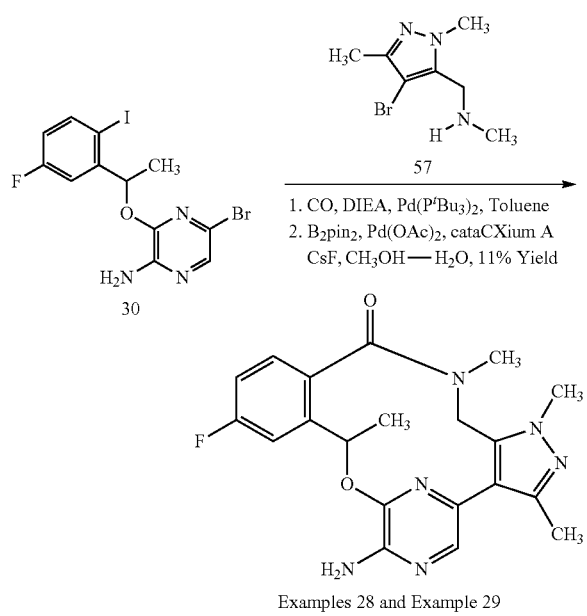

Examples 28 and Example 29

To a solution of compound 30 (266 mg, 0.607 mmol), compound 57 (166 mg, 0.759) and DIEA (211 μL, 1.21 mmol) in toluene (60 mL) was added Pd(P$^t$Bu$_3$)$_2$ (32 mg, 0.61 mmol). The reaction mixture was heated at 100° C. under 4 bar CO overnight then concentrated. The residue was taken-up in MeOH (12 mL) and water (1.3 mL) and added to a vial containing diboron pinacol ester (771 mg, 3.04 mmol) and CsF (461 mg, 3.04 mmol). The vial was sealed and the reaction mixture was bubbled with nitrogen before adding a solution of Pd(OAc)$_2$ (14 mg, 0.61 mmol) and di(1-adamantyl)-n-butylphosphine (45 mg, 0.12 mmol) in toluene (0.5 mL).

After heating for 30 min at 60° C., the temperature was increased to 90° C. for 6 hours. The reaction was allowed to stand at room temperature overnight then additional Pd(OAc)$_2$ (14 mg, 0.61 mmol) and di(1-adamantyl)-n-butylphosphine (45 mg, 0.12 mmol) in toluene (0.5 mL) were added. After heating for 2 hours at 100° C., the reaction mixture was cooled to room temperature and filtered. The mother liquor was diluted with EtOAc, washed with water (2×) and brine, dried (MgSO$_4$), filtered and concentrated. The crude product was purified by flash chromatography eluting with DCM/MeOH (0-8%) followed by a second column eluting with heptanes/EtOAc (50-100%) then DCM/MeOH (0-6%), and finally chiral separation by SFC to afford both enantiomers of the title compound. The chiral separation was performed by SFC on a Chiralcel OD-H (4.6 mm×250 mm, 5 micron particle size) column which was eluted with 25% MeOH in CO$_2$ held at 25° C. at 140 bar. A flow rate of 3.0 mL/min gave Peak 1 Rt$_{(Peak\ 1)}$=4.23 min ($[α]_d^{20}$=−77.1° (C=0.23, MeOH), and Peak 2 Rt$_{(Peak\ 2)}$=5.60 min ($[α]_d$20=+78.60 (C=0.24, MeOH).

Example 28 (Peak 1): 14 mg, >99% ee, 6% yield. $^1$H NMR (400 MHz, DMSO-d$_6$) δ 7.51 (s, 1H), 7.51-7.46 (m, 1 H), 7.36 (dd, J=5.8, 8.3 Hz, 1 H), 7.17 (dt, J=2.5, 8.6 Hz, 1 H), 6.29 (s, 2H), 5.95-5.84 (m, 1 H), 4.47 (d, J=14.7 Hz, 1 H), 4.27 (d, J=14.4 Hz, 1 H), 3.87 (s, 3 H), 2.87 (s, 3 H), 2.26 (s, 3 H), 1.62 (d, J=6.6 Hz, 3 H). LCMS ES m/z 397 $[M+H]^+$.

Example 29 (Peak 2): 13 mg, 99% ee, 5% yield. $^1$H NMR (400 MHz, DMSO-d$_6$) δ 7.51 (s, 1 H), 7.49 (dd, J=2.7, 10.2 Hz, 1 H), 7.36 (dd, J=5.7, 8.5 Hz, 1 H), 7.17 (dt, J=2.5, 8.5 Hz, 1 H), 6.29 (s, 2 H), 5.95-5.82 (m, 1 H), 4.47 (d, J=14.7 Hz, 1 H), 4.27 (d, J=14.4 Hz, 1 H), 3.87 (s, 3 H), 2.87 (s, 3 H), 2.26 (s, 3 H), 1.62 (d, J=6.6 Hz, 3 H). LCMS ES m/z 397 $[M+H]^+$.

Preparation of 8-amino-13-fluoro-4-methoxy-11,17-dimethyl-17,18-dihydro-9,5-(azeno)pyrido[3,4-h][2,5,11]benzoxadiazacyclotetradecin-16(11 H)-one
(Example 30 and Example 31)

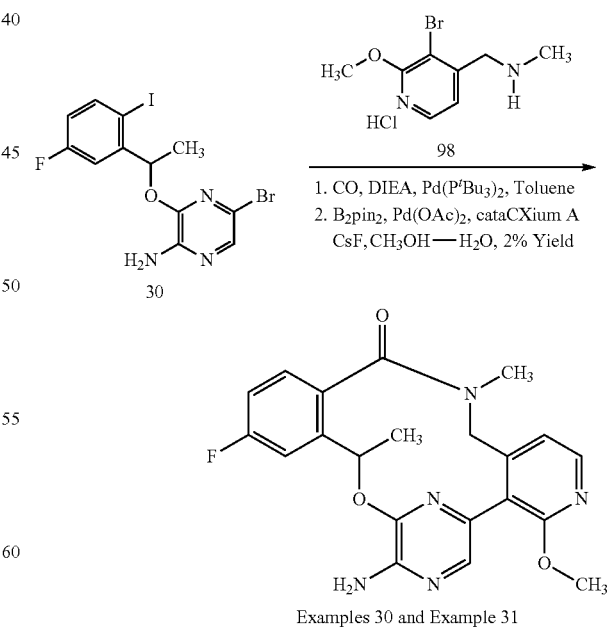

Examples 30 and Example 31

The procedure described for Example 28 was used to prepare Example 30 and Example 31. The analytical chiral separation was performed by SFC on a Chiralcel OD-H (4.6×250 mm, 5 micron particle size), which was eluted with 25% methanol in $CO_2$ at 140 bar. A flow rate of 3.0 mL/min gave $Rt_{(Peak\ 1)}$=4.4 minutes and $Rt_{(Peak\ 2)}$=5.3 minutes.

Example 30 (Peak 1): 4 mg; >98% ee, 1% yield. $^1$H NMR (400 MHz, DMSO-d$_6$) δ 8.14 (d, J=5.3 Hz, 1 H), 7.66 (s, 1 H), 7.63 (dd, J=2.5, 10.3 Hz, 1 H), 7.28 (dd, J=5.8, 8.6 Hz, 1 H), 7.22 (d, J=5.3 Hz, 1 H), 7.11 (dt, J=2.6, 8.5 Hz, 1 H), 6.52 (s, 2 H), 6.08-5.98 (m, 1 H), 4.20 (d, J=12.4 Hz, 1 H), 4.16 (d, J=12.1 Hz, 1 H), 3.82 (s, 3 H), 2.89 (s, 3 H), 1.65 (d, J=6.5 Hz, 3 H). LCMS ES m/z 410 [M+H]$^+$.

Example 31 (Peak 2): 3 mg, ~80% ee, 1% yield. $^1$H NMR (400 MHz, DMSO-d$_6$) δ 8.14 (d, J=5.0 Hz, 1 H), 7.65 (s, 1 H), 7.62 (dd, J=2.6, 10.2 Hz, 1 H), 7.28 (dd, J=5.7, 8.4 Hz, 1 H), 7.22 (d, J=5.0 Hz, 1 H), 7.15-7.06 (m, 1 H), 6.51 (s, 2 H), 6.07-5.97 (m, 1 H), 4.20 (d, J=12.3 Hz, 1 H), 4.16 (d, J=12.4 Hz, 1 H), 3.82 (s, 3 H), 2.88 (s, 3 H), 1.65 (d, J=6.5 Hz, 3 H). LCMS ES m/z 410 [M+H]$^+$.

Synthesis of 7-amino-12-fluoro-2,10,16-trimethyl-15-oxo-10,15,16,17-tetrahydro-2H-8,4-(azeno)pyrazolo[4,3-h][2,5,11]benzoxadiazacyclotetradecine-3-carbonitrile (Example 32 and Example 33)

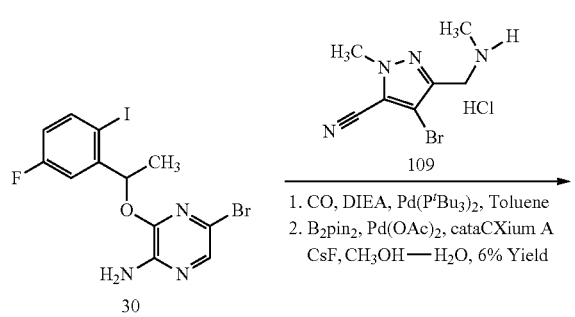

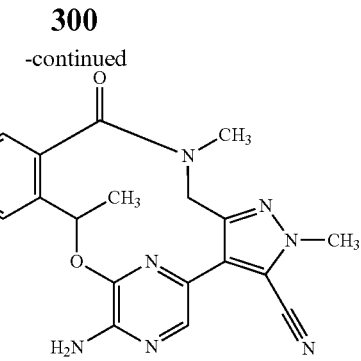

Examples 32 and Example 33

The procedure described for Example 28 and 29 was used to prepare Example 32 and Example 33. The analytical chiral separation was performed by SFC on a Regis Whelk-01 (R, R) (4.6×250 mm, 5 micron particle size), which was eluted with 20% methanol in $CO_2$ at 140 bar. A flow rate of 3.0 mL/min gave $Rt_{(Peak\ 1)}$=4.5 minutes and $Rt_{(Peak\ 2)}$=6.6 minutes.

Example 32 (Peak 1): 8 mg; >99% ee, 3% yield. $^1$H NMR (400 MHz, DMSO-d$_6$) δ 7.77 (s, 1 H), 7.47 (dd, J=2.8, 10.1 Hz, 1 H), 7.41 (dd, J=5.7, 8.4 Hz, 1 H), 7.16 (dt, J=2.8, 8.6 Hz, 1 H), 6.72 (s, 2 H), 5.97-5.81 (m, 1 H), 4.30 (AB q, J=13.9 Hz, 1 H), 4.03 (s, 3 H), 2.89 (s, 3 H), 1.64 (d, J=6.5 Hz, 3 H). LCMS m/z 408 [M+H]$^+$.

Example 33 (Peak 2): 10 mg, 96% ee, 3% yield. $^1$H NMR (400 MHz, DMSO-d$_6$) δ 7.77 (1 H, s), 7.47 (1 H, dd, J=10.0, 2.7 Hz), 7.41 (1 H, dd, J=8.3, 5.8 Hz), 7.16 (1 H, td, J=8.5, 2.7 Hz), 6.74 (2 H, s), 5.84-5.98 (1 H, m), 4.31 (2 H, AB q, J=13.7 Hz), 4.03 (4 H, s), 2.89 (3 H, s), 1.64 (3 H, d, J=6.6 Hz). LCMS m/z 408 [M+H]$^+$.

Preparation of (11R)-8-amino-13-fluoro-4-methoxy-11,17-dimethyl-17,18-dihydro-9,5-(metheno)pyrido[3,4-h][2,5,11]benzoxadiazacyclotetradecin-16(11H)-one (Example 34)

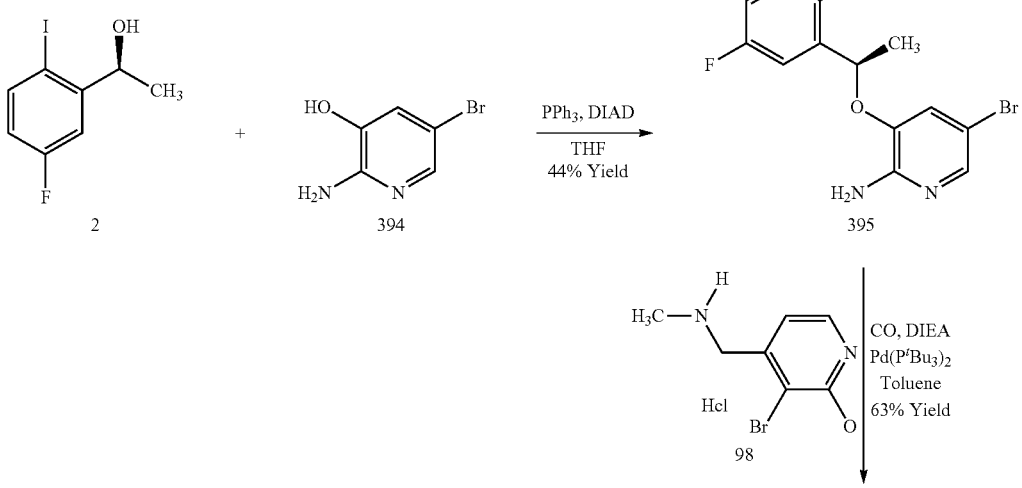

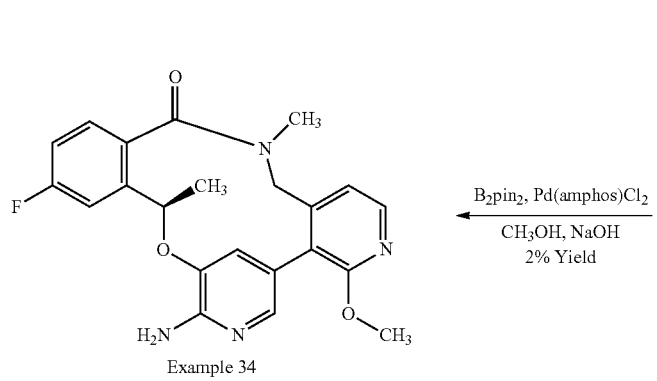

Example 34

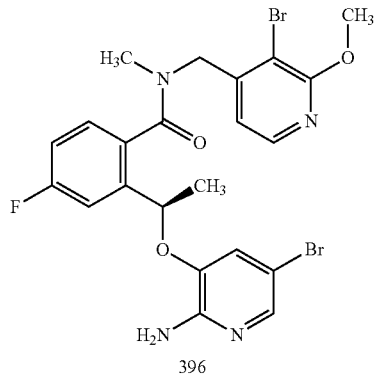

396

Step 1:

To a solution of both compound 2 (338 mg, 1.27 mmol), compound 394 (200 mg, 1.06 mmol) and triphenylphosphine (333 mg, 1.27 mmol) in THF (11 mL) was added DIAD (260 μL, 1.27 mmol). The solution was dark brown. After 30 minutes at room temperature, LCMS showed mostly product. The solvent was removed under reduced pressure and the crude product was purified by column chromatography over silica gel, which was eluted with 0-13% EtOAc-DCM, which gave compound 395 as a yellow gum (205 mg, 44% yield. ¹H NMR (400 MHz, DMSO-d₆) δ 7.89 (dd, J=5.7, 8.7 Hz, 1 H), 7.54 (d, J=2.0 Hz, 1 H), 7.42 (dd, J=3.0, 10.1 Hz, 1 H), 6.99 (dt, J=3.0, 8.6 Hz, 1 H), 6.75 (d, J=2.0 Hz, 1 H), 6.18 (s, 2 H), 5.45 (q, J=6.1 Hz, 1 H), 1.54 (d, J=6.3 Hz, 3 H). LCMS ES m/z 437/439.

Step 2:

A mixture of compound 395 (200 mg, 0.46 mmol), compound 98 (135 mg, 0.50 mmol), DIEA (0.32 mL, 1.8 mmol) and Pd(Pt-Bu₃)₂ (24 mg, 0.05 mmol) in toluene (42 mL) was heated at 85° C. in an atmosphere of carbon monoxide at 4 bar. After 18 hours, the reaction mixture was concentrated and purified by column chromatography over silica, which was eluted with 0-100% EtOAc-heptane and gave compound 396 (165 mg, 63% yield). LCMS ES m/z 566/568/571.

Step 3:

A mixture of compound 396 (165 mg, 0.29 mol), diboron pinacol ester (368 mg, 1.45 mmol), sodium hydroxide (58 mg, 1.45 mmol) and Pd(amphos)Cl₂ (20 mg, 0.03 mmol) in methanol (10 mL) was degassed and purged with nitrogen. The mixture was heated at 100° C. for 18 hours and cooled to room temperature. The crude reaction mixture was diluted with EtOAc and sequentially washed with water and brine. The organic layer was dried over MgSO₄, filtered, and concentrated under reduced pressure. The crude product was purified by column chromatography over silica gel, which was eluted with 0-100% EtOAc-heptane followed by purification by reversed phase chromatography which gave Example 34 (3 mg, 2% yield). ¹H NMR (400 MHz, DMSO-d₆) δ 8.14 (d, J=5.0 Hz, 1 H), 7.72 (dd, J=2.5, 10.3 Hz, 1 H), 7.44 (d, J=1.8 Hz, 1 H), 7.29 (dd, J=5.7, 8.4 Hz, 1 H), 7.22 (d, J=5.3 Hz, 1 H), 7.09 (dt, J=2.5, 8.4 Hz, 1 H), 6.96 (s, 1 H), 5.95 (s, 2 H), 5.73-5.61 (m, J=6.0 Hz, 1 H), 4.26 (d, J=12.8 Hz, 1 H), 4.04 (d, J=12.8 Hz, 1 H), 3.81 (s, 3 H), 2.99 (s, 3 H), 1.68 (d, J=6.0 Hz, 3 H). LCMS m/z 409 [M+H]⁺.

Preparation of (5R)-3-fluoro-5,17-dimethyl-13-(methylsulfonyl)-5,16,17,18-tetrahydro-7,11-(metheno)dibenzo[g,l][1,4,10]oxadiazacyclotetradecin-8-amine (Example 35)

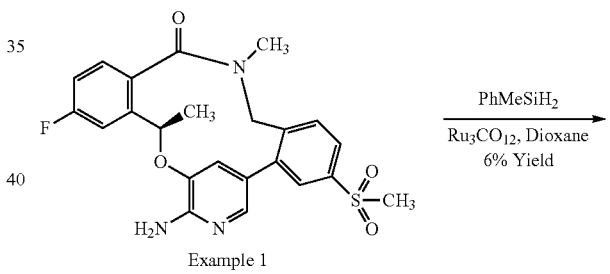

Example 1

Example 35

To a stirred solution of Example 1 (18.2 mg, 0.04 mmol) in dry dioxane (4 mL) was added Ru₃CO₁₂ (4.0 mg, 0.006 mmol) followed by PhMeSiH₂ (200 μL, 1.6 mmol). The reaction was stirred overnight at 90° C. for 18 hours. After 18 hours the reaction was concentrated to 1 mL and purified by reversed phase preparative chromatography and gave Example 35 (1 mg, 6% yield). ¹H NMR (600 MHz, DMSO-d₆) δ 9.51 (m, 1 H), 7.87 (d, J=2 Hz, 1 H), 7.76 (dd, J=8.0, 2.0 Hz, 1 H), 7.56 (m, 1 H), 7.36 (m, 2 H), 7.19 (dd, J=8.3, 6.0 Hz, 1 H), 6.97 (dt, J=8.3, 2.8 Hz, 1 H), 6.08 (br s, 2 H), 6.00 (q, J=6.4 Hz, 1 H), 4.33 (d, J=10.2 Hz, 2 H), 3.17 (s, 2 H), 2.80 (d, J=10.2 Hz, 1 H), 2.53 (s, 3 H), 2.35 (s, 3 H), 1.65 (d, J=6.4 Hz, 3 H). LCMS m/z 442 [M+H]+.

Preparation of (10R)-7-amino-12-fluoro-2,10,16-trimethyl-10,15,16,17-tetrahydro-2H-4,8-(metheno) pyrazolo[4,3-h][2,5,11]benzoxadiazacyclotetradecine-3-carbonitrile (Example 36)

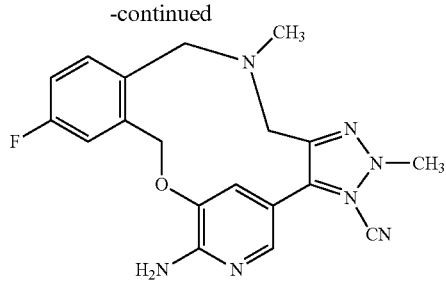

Example 36

The procedure described for Example 2 was used to prepare compound Example 36 (3 mg, 8%). 1H NMR (600 MHz, DMSO-d6) δ 9.64 (m, 1 H), 7.61 (m, 1 H), 7.42 (m, 1 H), 7.24 (m, 1 H), 6.98 (m, 2 H), 6.09 (br s, 2 H), 5.88 (q, J=6.4 Hz, 1 H), 4.33 (d, J=15.5 Hz, 2 H), 3.26 (d, J=15.5 Hz, 2 H), 3.16 (d, J=13.8 Hz, 2 H), 2.94 (d, J=13.8 Hz, 2 H), 3.34 (s, 3 H), 1.65 (d, J=6.4 Hz 3 H). LCMS m/z 393 [M+H]+.

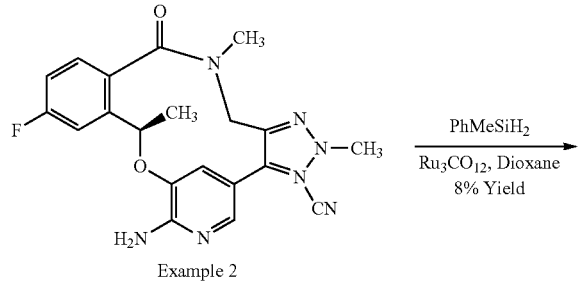

Example 2

Synthesis of 12-fluoro-3-methyl-3,16,17,18-tetrahydro-10H-8,4-(metheno)pyrazolo[4,3-e][1,12,9]benzodioxazacyclopentadecin-7-amine (Example 37)

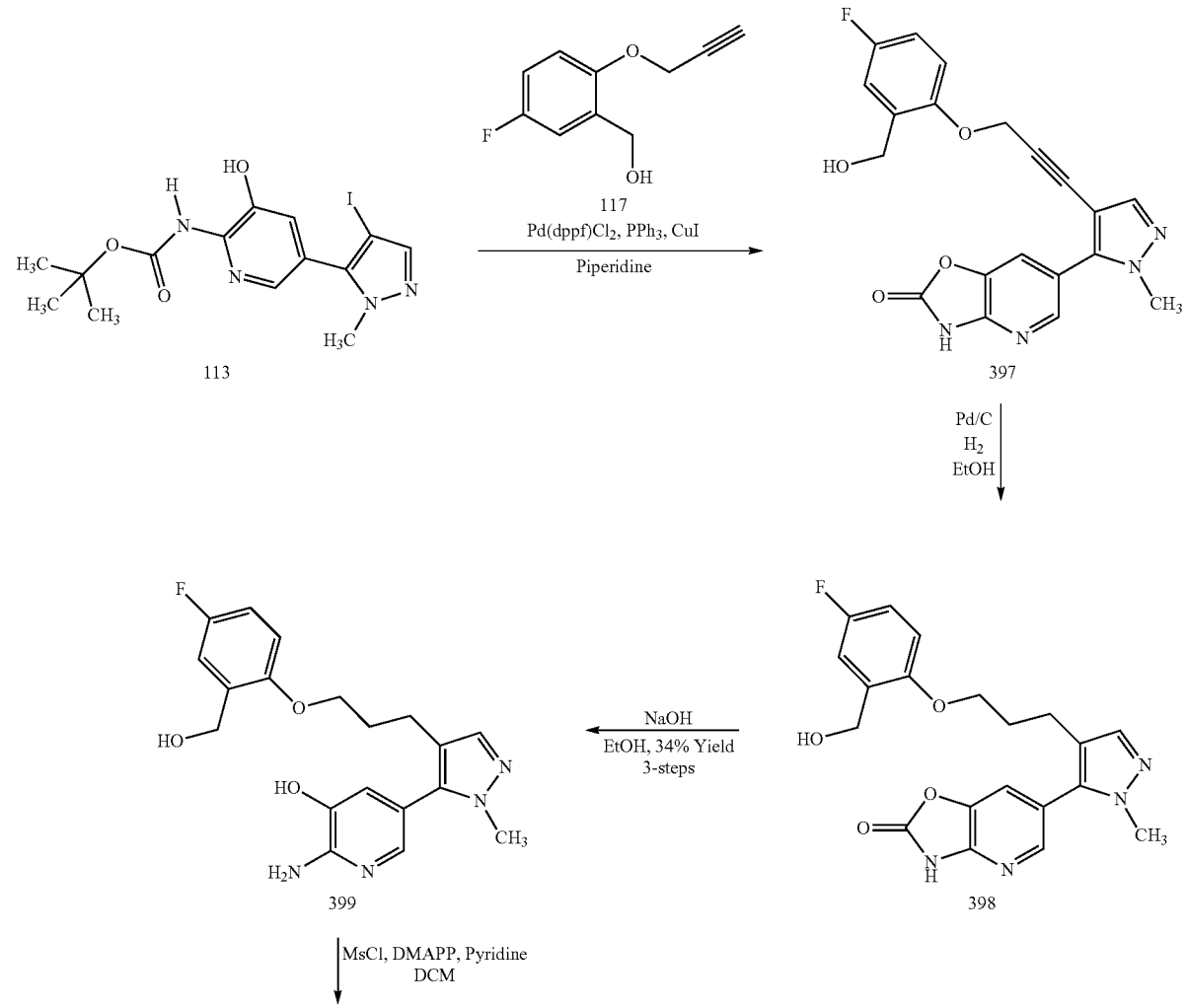

-continued

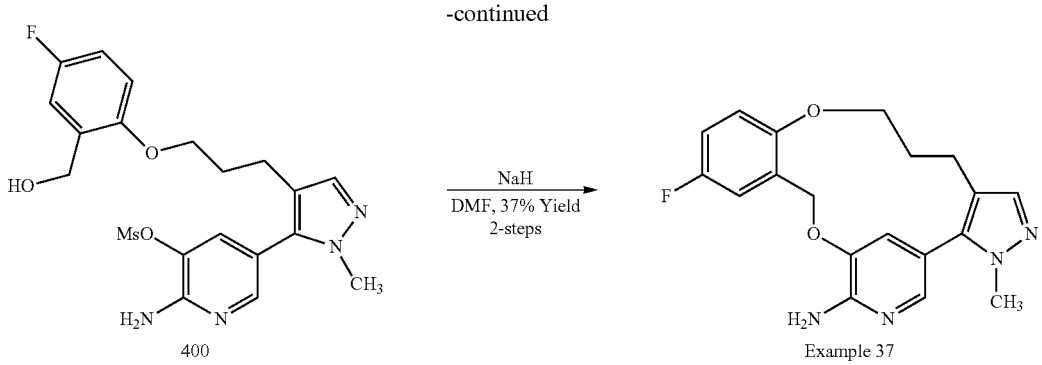

Step 1:
A mixture of compound 174 (270 mg, 0.65 mmol), compound 117 (176 mg, 0.974 mmol), cuprous iodide (6 mg, 0.032 mmol), triphenylphosphine (17 mg, 0.065 mmol) and PdCl$_2$(PPh$_3$)$_2$ (23 mg, 0.032 mmol) in neat piperidine (4.3 mL) was bubbled with nitrogen then heated at 80° C. After 5 hours, the reaction mixture was diluted with EtOAc, washed with saturated NH$_4$Cl (2×) and brine, dried (MgSO$_4$), filtered and concentrated. The material was purified by flash chromatography over silica gel, which was eluted with DCM/MeOH (0-5%) to give compound 397.

Step 2:
To a solution of compound 397 (0.65 mmol) in EtOH (50 mL) was added Pd(OH)$_2$ (50 mg). The mixture was heated at 50° C. at 3-4 bar of hydrogen for 18 hrs. The reaction mixture was filtered through celite and the mother liquor was concentrated to give compound 398.

Step 3:
Compound 398 was dissolved in EtOH (5 mL) then 15% NaOH (5 mL) was added and the solution was heated at 85° C. overnight. The reaction was neutralized with 1 N HCl and extracted with EtOAc (3×). Saturated NaHCO$_3$ was added to the aqueous layer which was extracted with EtOAc (2×). The combined organic layers were dried (MgSO$_4$), filtered and concentrated. The residue was purified by flash chromatography over silica gel, which was eluted with DCM/MeOH (0-10%) to give compound 399 (82 mg, 34% yield over 3 steps). $^1$H NMR (400 MHz, DMSO-d$_6$) δ 1.85 (q, J=6.9 Hz, 2 H), 2.42-2.49 (m, 2 H), 3.64 (s, 3 H), 3.87 (t, J=6.2 Hz, 2 H), 4.43 (br s, 2 H), 5.11 (br. s, 1 H), 5.75 (s, 2 H), 6.80 (d, J=1.5 Hz, 1 H), 6.83 (dd, J=9.1, 4.5 Hz, 1 H), 6.89-7.00 (m, 1 H), 7.12 (dd, J=9.6, 3.0 Hz, 1 H), 7.33 (s, 1 H), 7.41 (s, 1 H), 9.72 (br s, 1 H). LCMS m/z 373 [M+H]$^+$.

Step 4:
To a cooled (0° C.) solution of compound 399 (80 mg, 0.22 mmol), DMAP (1.3 mg, 0.011 mmol), and pyridine (200 μL, 2.5 mmol) in DCM (1.4 mL) was added a solution of MsCl (17 μL, 0.22 mmol) in DCM (0.5 mL). After 1 hour the reaction was diluted with EtOAc, washed with saturated NH$_4$Cl (2×) and brine, dried (MgSO$_4$), filtered and concentrated to give compound 400 (96 mg).

Step 5:
To a solution of compound 400 (96 mg, 0.21 mmol) in DMF (4.1 mL) was added NaH (60% dispersion on mineral oil, 9.1 mg, 0.23 mmol). The reaction mixture was heated at 50° C. for 30 minutes then diluted with EtOAc, washed with water and brine, dried (MgSO$_4$), filtered and concentrated. The residue was purified by flash chromatography over silica gel, which was eluted with DCM/MeOH (0-10%) to give Example 37 (27 mg, 37% yield over 2 steps). $^1$H NMR (400 MHz, DMSO-d$_6$) δ 2.04-2.20 (m, 2 H), 2.65 (t, J=6.8 Hz, 2 H), 3.78 (s, 3 H), 3.97-4.14 (m, 2 H), 5.22 (s, 2 H), 5.68 (br s, 2 H), 6.99-7.16 (m, 2 H), 7.25-7.36 (m, 2 H), 7.38 (s, 1 H), 7.65 (d, J=1.5 Hz, 1 H). LCMS 355 [M+H]$^+$.

Preparation of 12-fluoro-3-methyl-1,16,17,18-tetrahydro-10H-8,4-(metheno)pyrazolo[3,4-e][1,12,9]benzodioxazacyclopentadecin-7-amine (Example 38)

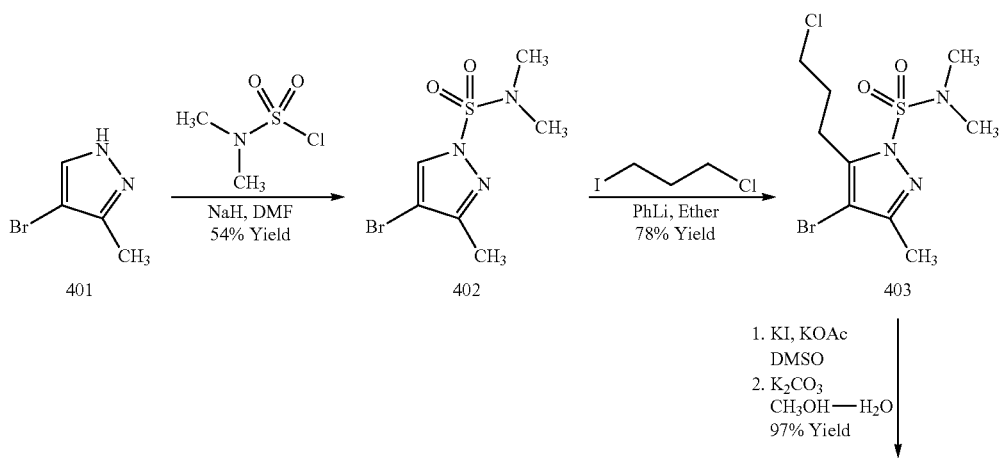

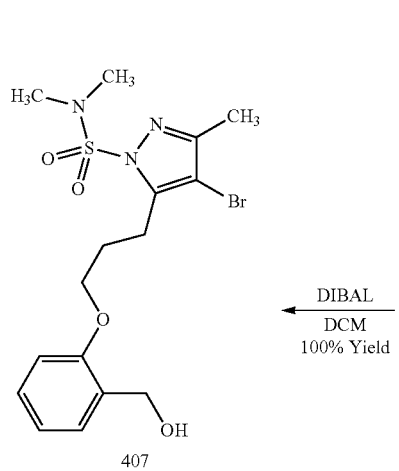
407

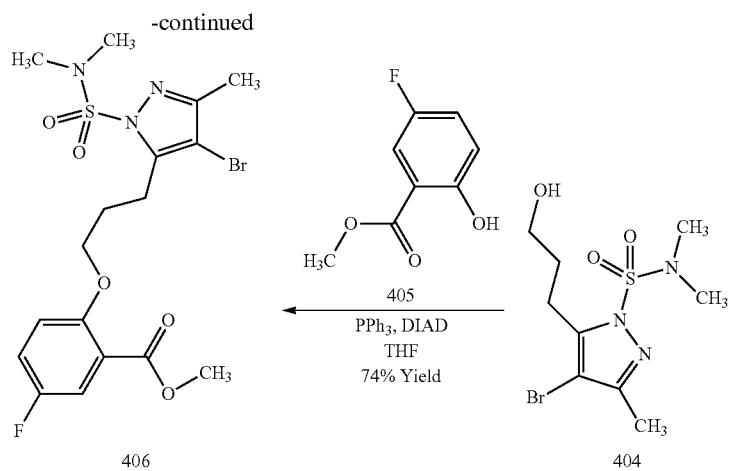
406        405        404

-continued

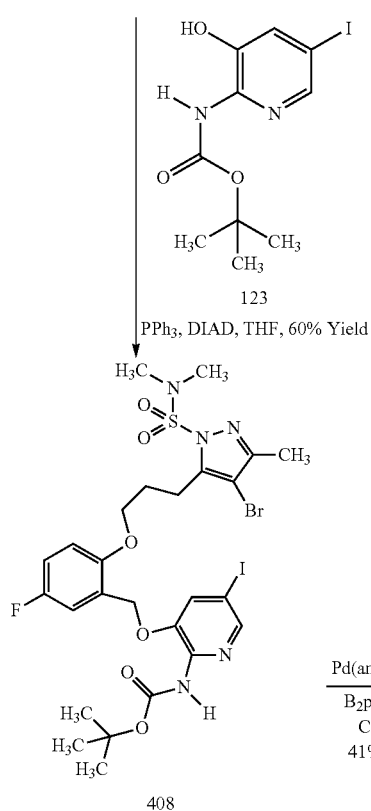
123
PPh₃, DIAD, THF, 60% Yield

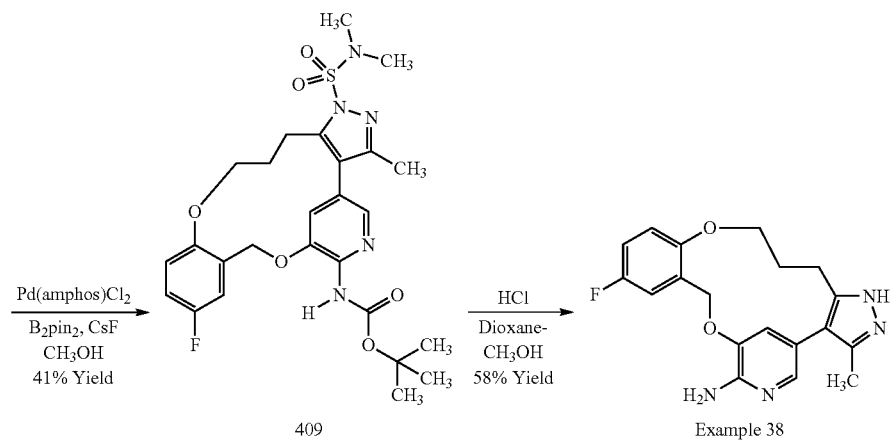
408        409        Example 38

Step 1:

To a cooled (0° C.) solution of compound 401 (2.50 g, 15.5 mmol) in DMF (40 mL) was added NaH (60% dispersion on mineral oil, 745 mg, 18.6 mmol). After 30 min a solution of N,N-dimethylsulfamoyl chloride (1.67 mL, 15.5 mmol) in DMF (5 mL) was added. The reaction mixture was gradually warmed to room temperature and stirred for 5 hours. The reaction was quenched with saturated NH₄Cl and diluted with EtOAc. The organic layer was sequentially washed with water, brine, dried over MgSO₄, filtered and concentrated under reduced pressure. The crude product was purified by flash chromatography over silica gel which was eluted with heptanes/EtOAc (0-30%) and gave compound 402 as a white waxy solid (2.3 g, 54% yield). ¹H NMR (400 MHz, DMSO-d₆) δ 8.47 (s, 1 H), 2.85 (s, 6 H), 2.23 (s, 3 H).

Step 2:

To a cooled (−78° C.) solution of compound 402 (2.3 g, 8.4 mmol) in Et₂O (25.5 mL) was added drop-wise phenyl lithium (1.8 M in dibutyl ether, 5.2 mL, 9.3 mmol) keeping the internal temperature less than −65° C. A white precipitate formed and the mixture became thick. The mixture was warmed to 0° C. and stirred for 30 minutes, and cooled back down to −78° C. and a solution of 1-chloro-3-iodopropane (2.7 mL, 25.3 mmol) in THF (5.0 mL) was added. The reaction was warmed to room temperature and stirred overnight. The solution was diluted with EtOAc, washed sequentially with saturated NH₄Cl and brine, dried over MgSO₄, filtered and concentrated under reduced pressure. The crude product was purified by flash chromatography over silica gel which was eluted with heptanes/EtOAc (0-20%) and gave compound 403 as a clear gum (2.3 g, 78% yield). ¹H NMR (400

MHz, DMSO-d$_6$) δ 3.67 (t, J=6.3 Hz, 2 H), 3.03-2.97 (m, 2 H), 2.95 (s, 6 H), 2.20 (s, 3 H), 2.07-1.93 (m, 2 H).

Step 3:

A mixture of compound 403 (1.82 g, 5.28 mmol), potassium iodide (544 mg, 3.27 mmol), and potassium acetate (1.04 g, 10.6 mmol) in DMSO (13.2 mL) was heated at 80° C. overnight. The reaction mixture was diluted with EtOAc, washed with water (2x) and brine, then concentrated to obtain a gum. The residue was dissolved in methanol (26 mL) then water (870 μL) and K$_2$CO$_3$ (737 mg, 5.33 mmol) were added. After 30 minutes the reaction was diluted with EtOAc, washed with water and brine, dried (MgSO$_4$), filtered and concentrated to give compound 404 as a faint yellowish-orange gum (1.67 g, 97% yield). $^1$H NMR (400 MHz, DMSO-d$_6$) δ 4.57 (t, J=5.3 Hz, 1 H), 3.47-3.37 (m, 2 H), 2.94 (s, 6 H), 2.89-2.82 (m, 2 H), 2.19 (s, 3 H), 1.77-1.58 (m, 2 H).

Step 4:

To a solution of the compound 404 (1.1 g, 3.37 mmol), compound 405 (602 mg, 3.54 mmol), and triphenylphosphine (1.11 g, 4.22 mmol) in THF (16.9 mL) was added DIAD (859 μL, 4.22 mmol) drop-wise, very slowly over 1.5 hours. After stirring at room temperature overnight the reaction was concentrated and purified by flash chromatography eluting with heptanes/EtOAc (0-30%) to give compound 406 as a clear gum (1.2 g, 74% yield). $^1$H NMR (400 MHz, DMSO-d$_6$) δ 1.91-2.05 (m, 2 H), 2.19 (s, 3 H), 2.95 (s, 6 H), 3.04 (dd, J=8.6, 6.8 Hz, 2 H), 3.81 (s, 3 H), 4.04 (t, J=5.8 Hz, 2 H), 7.15 (dd, J=9.2, 4.4 Hz, 1 H), 7.38 (m, 1 H), 7.44 (dd, J=8.8, 3.3 Hz, 1 H).

Step 5:

To a cooled (−78° C.) solution of the compound 406 (1.2 g, 2.51 mmol) in DCM (12.5 mL) was added DiBAL (1 M in hexanes, 6.27 mL, 6.27 mmol) drop-wise. Once the addition was complete the reaction was quenched with methanol at −78° C. The ice bath was removed, saturated sodium potassium tartrate (5 mL) was added, and the flask was filled with EtOAc. Once a clear solution formed, the biphasic mixture was washed with water and brined, dried (MgSO$_4$), filtered and concentrated to give compound 407 as a clear gum (1.2 g, 100% yield). $^1$H NMR (400 MHz, DMSO-d$_6$) δ 0.95-2.05 (m, 2 H), 2.14-2.23 (m, 3 H), 2.87-2.99 (m, 6 H), 2.98-3.09 (m, 2 H), 3.91-4.01 (m, 2 H), 4.50 (d, J=5.8 Hz, 2 H), 5.15 (t, J=5.7 Hz, 1 H), 6.83-6.92 (m, 1 H), 6.92-7.03 (m, 1 H), 7.14 (dd, J=9.6, 3.3 Hz, 1 H).

Step 6:

To a solution of compound 407 (660 mg, 1.47), compound 123 (493 mg, 1.47 mmol) and triphenyphosphine (481 mg, 1.83 mmol) in THF (9.8 mL) was added DIAD drop-wise over 1 hour. After stirring at room temperature for 1 hour, the solution was concentrated and purified by flash chromatography eluting with heptanes/EtOAc (0-40%) to yield compound 408 (660 mg, 60% yield). $^1$H NMR (400 MHz, DMSO-d$_6$) δ 1.40 (s, 9 H), 1.98-2.10 (m, 2 H), 2.19 (s, 3 H), 2.96 (s, 6 H), 3.02-3.12 (m, 2 H), 4.07 (t, J=5.5 Hz, 2 H), 5.12 (s, 2 H), 6.98-7.06 (m, 1 H), 7.13 (td, J=8.7, 3.3 Hz, 1 H), 7.36 (dd, J=9.2, 3.2 Hz, 1 H), 7.78 (d, J=1.8 Hz, 1 H), 8.16 (d, J=1.8 Hz, 1 H), 9.01 (s, 1 H).

Step 7:

A warm (60° C.) solution of compound 408 (569 mg, 0.740 mmol), diboron pinacol ester (752 mg, 2.96 mmol), and 1 N cesium fluoride (3.7 mL) in MeOH (37 mL) was bubbled with nitrogen. A solution of bis(di-tert-butyl(4-dimethylaminophenyl)phosphine)-dichloropalladium (11) (79 mg, 0.11 mmol) in toluene (0.5 mL) was added. The mixture was heated at 60° C. for 30 minutes then diluted with EtOAc, washed with brine (2x), dried (MgSO$_4$), filtered, concentrated and purified by flash chromatography eluting with DCM/MeOH (0-6%). The fractions containing the desired product were concentrated and the resultant solids was slurring in 25% EtOAc/heptanes. The solids were collected by vacuum filtration to yield compound 409 as a cream solid (170 mg, 41% yield). $^1$H NMR (400 MHz, DMSO-d$_6$) δ 1.46 (s, 9 H), 2.31 (s, 5 H), 2.91-3.06 (m, 8 H), 4.19 (br s, 2 H), 5.29 (br s, 2 H), 7.04-7.23 (m, 2 H), 7.39 (dd, J=8.9, 2.9 Hz, 1 H), 7.69 (d, J=1.5 Hz, 1 H), 7.94 (d, J=1.5 Hz, 1 H), 8.85 (s, 1 H).

Step 8:

To a solution of compound 409 (170 mg, 0.303 mmol) in dioxane (3.0 ml) was added HCl (4 N in dioxane, 1.52 mL, 6.06 mmol). Methanol (0.5 mL) was added and the solution was heated at 40° C. After 4 hour, the reaction mixture was diluted with EtOAc, washed with saturated sodium bicarbonate and brine, dried (MgSO$_4$), filtered, concentrated. The residue was slurried in DCM and the solids were collected by vacuum filtration to give Example 38 as a white solid (62 mg, 58% yield). $^1$H NMR (400 MHz, DMSO-d$_6$) δ 2.19 (s, 5 H), 2.71-2.98 (m, 2 H), 4.04 (br s, 2 H), 5.18 (br s, 2 H), 5.56 (s, 2 H), 6.99-7.16 (m, 2 H), 7.19-7.35 (m, 2 H), 7.48 (s, 1 H), 12.32 (br s, 1 H). LCMS m/z 355 [M+H]$^+$.

Preparation of 7-amino-12-fluoro-2,16,17,18-tetrahydro-10H-8,4-(metheno)pyrazolo[3,4-e][1,12,9]benzodioxazacyclopentadecine-3-carbonitrile (Example 39)

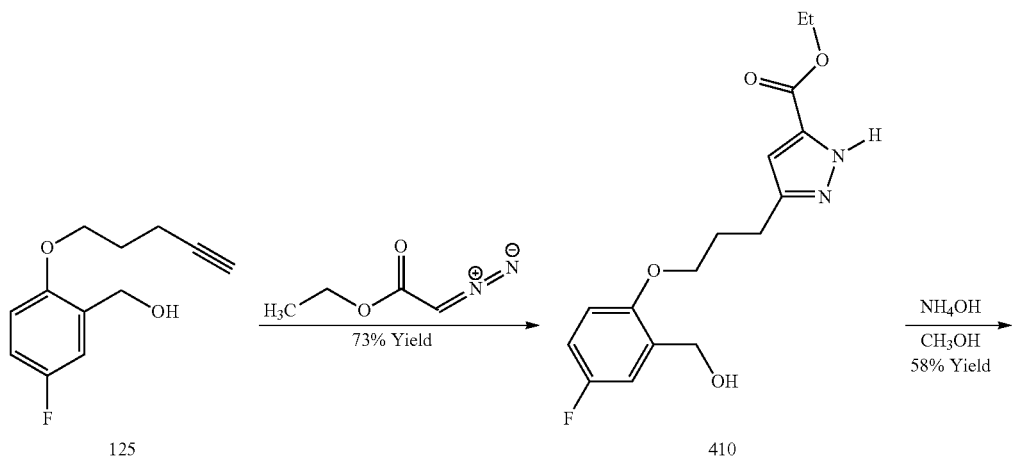

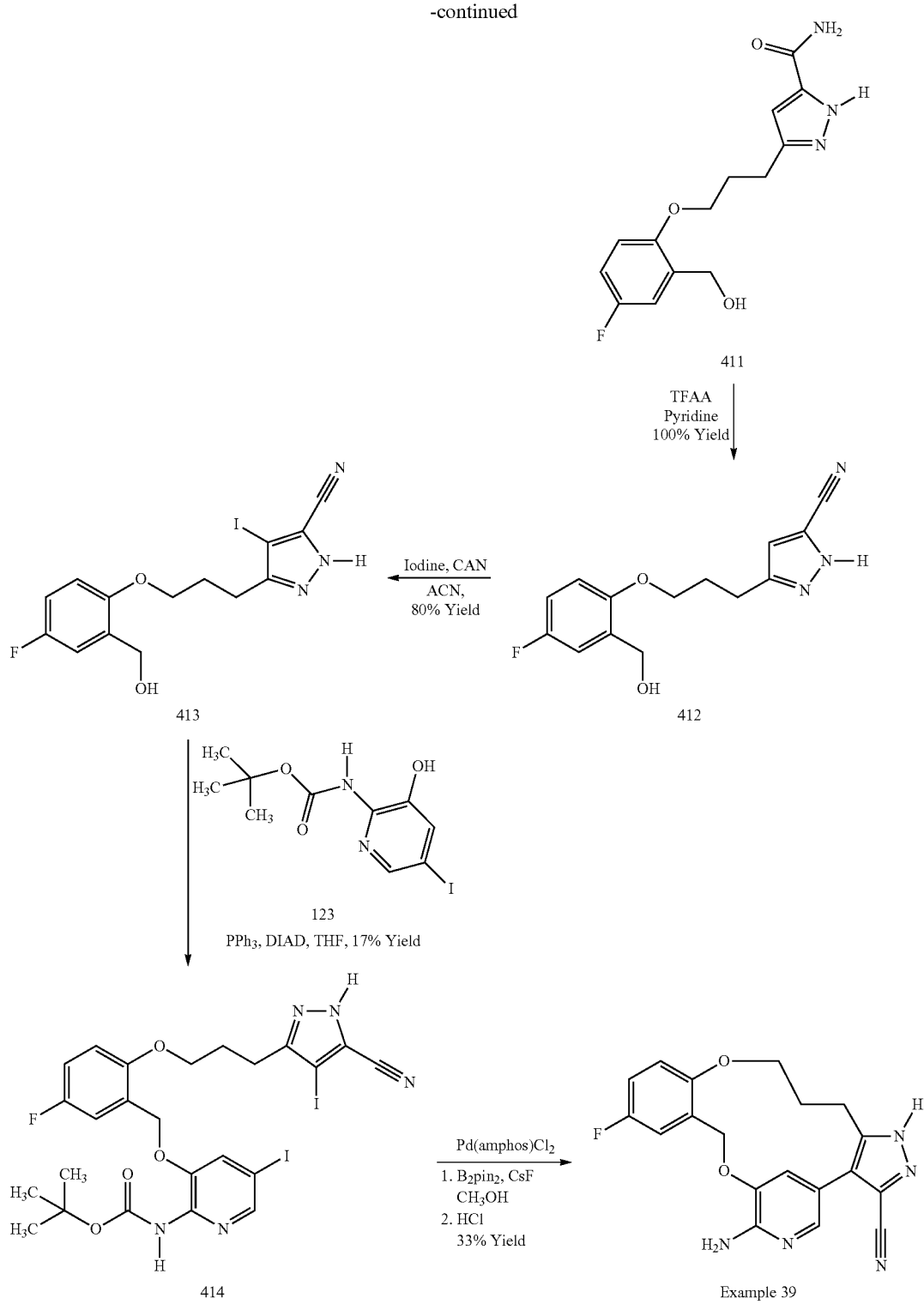

Step 1:

Ethyl diazoacetate (2.44 mL, 23.5 mmol) and compound 125 (4.45 g, 21.4 mmol) were heated at 100° C. in a sealed tube for 2 days. The crude product was purified by flash chromatography eluting with heptanes/EtOAc (0-75%) to give compound 410 as the major regioisomeric pyrazole (5.0 g, 4:1 mixture of regioisomers, 73% yield).

Step 2:

In a sealed tube a solution of compound 410 (5.0 g, 16 mmol) in MeOH (31 mL) was heated at 60° C. for 1 hour. Ammonium hydroxide was added and the solution was heated at 60° C. overnight. The reaction mixture was cooled to 0° C. and the solids were collected by vacuum filtration to give a single regioisomer of compound 411 (2.7 g, 58% yield).

Step 3:

To a cooled (0° C.) mixture of compound 411 (1.50 g, 5.11 mmol) in pyridine (26 mL) was added TFAA (2.87 mL, 20.5 mmol) drop-wise. After 1 hour at 0° C. the solution was diluted with EtOAc, washed with saturated NaHCO$_3$ (2×), brine, 1 N HCl (2×), brine, dried (Na$_2$SO$_4$), filtered and concentrated. The residue was dissolved in 20% MeOH/DCM and passed through an SCX cartridge and the mother liquor was concentrated to give compound 412 (1.4 g, 100% yield). $^1$H NMR (400 MHz, DMSO-d$_6$) δ 13.71 (br s, 1 H), 7.14 (dd, J=3.1, 9.4 Hz, 1 H), 7.03-6.94 (m, 1 H), 6.94-6.88 (m, 1 H), 6.76 (s, 1 H), 4.48 (s, 2 H), 3.96 (t, J=6.0 Hz, 2 H), 2.82 (t, J=7.7 Hz, 2 H), 2.12-1.96 (m, 2 H).

Step 4:

To a solution of compound 412 (1.4 g, 5.1 mmol) and cerium ammonium nitrate (1.95 g, 3.56 mmol) in ACN (45 mL) was added a solution of iodine (904 mg, 3.56 mmol) in ACN (5 mL). The reaction was heated at 60° C. and stirred for 2 hours. The reaction mixture was diluted with EtOAc, washed with saturated Na$_2$S$_2$O$_3$ (2×) and brine, dried (Na$_2$SO$_4$), filtered and concentrated. The crude product was purified by flash chromatography eluting with heptanes/EtOAc (0-50%) to give compound 413 (1.2 g, 80% pure) which contains 20% of the aldehyde. $^1$H NMR (400 MHz, DMSO-d$_6$) δ 7.15 (dd, J=3.1, 9.4 Hz, 1 H), 7.02-6.94 (m, 1 H), 6.91-6.87 (m, 1 H), 4.50 (s, 2 H), 3.94 (t, J=5.9 Hz, 2 H), 2.81 (t, J=7.6 Hz, 2 H), 2.08-1.99 (m, 2 H).

Step 5:

To a solution of compound 413 (500 mg, 80% pure, 1.0 mmol), compound 123 (340 mg, 1.0 mmol) and triphenylphosphine (327 mg, 1.25 mmol) in THF (6.7 mL) was added DIAD (254 μL, 1.25 mmol) drop-wise over 1 hour. Once the reaction was complete by LCMS, the solution was concentrated and purified by flash chromatography eluting with heptanes/EtOAc (0-50%). The fractions containing the desired product were concentrated and the solids were triturated with Et$_2$O to give compound 414 (125 mg, 17% yield). $^1$H NMR (400 MHz, DMSO-d$_6$) δ 1.40 (s, 9H), 1.99-2.15 (m, 2 H), 2.85 (t, J=7.4 Hz, 2 H), 4.02 (t, J=5.7 Hz, 2 H), 5.12 (s, 2 H), 7.02 (dd, J=9.2, 4.4 Hz, 1 H), 7.13 (td, J=8.8, 3.2 Hz, 1 H), 7.35 (dd, J=9.2, 3.2 Hz, 1 H), 7.80 (d, J=1.5 Hz, 1 H), 8.15 (d, J=1.5 Hz, 1 H), 9.00 (s, 1 H), 14.14 (br s, 1 H).

Step 6:

In a sealed vial a mixture of compound 414 (120 mg, 0.17 mmol), diboron pinacol ester (212 mg, 0.84 mmol), and cesium fluoride (127 mg, 0.835 mmol) in MeOH (8.4 mL) and water (0.80 mL) was bubbled with nitrogen. A solution of bis(di-tert-butyl(4-dimethylaminophenyl)phosphine)dichloropalladium (11) (18 mg, 0.025 mmol) in toluene (0.5 mL) was added. The mixture was heated at 60° C. for 1 hour then diluted with EtOAc, washed with brine (2×), dried (Na$_2$SO$_4$), filtered, concentrated. The residue was dissolved in DCM (1 mL) and HCl was added (4 N in dioxane, 1 mL, 4.2 mmol). After stirring at room temperature overnight, the reaction was concentrated and purified by flash chromatography eluting with DCM/7 N NH$_3$ MeOH (0-6%). The fractions containing the desired product were concentrated and the resultant solids were triturated with Et$_2$O to give Example 39 (20 mg, 33% yield). $^1$H NMR (400 MHz, DMSO-d$_6$) δ 2.23 (br s, 2 H), 3.03 (br s, 2 H), 3.55-4.55 (m, 2 H), 5.21 (br s, 2 H), 5.90 (s, 2 H), 7.04-7.16 (m, 2 H), 7.30 (dd, J=8.9, 2.4 Hz, 1 H), 7.38 (d, J=2.0 Hz, 1 H), 7.75 (d, J=1.8 Hz, 1 H), 13.88 (br s, 1 H). LCMS m/z 366 [M+H]$^+$.

Preparation of 7-amino-12-fluoro-16,17-dihydro-1H, 10H-8,4-(metheno)pyrazolo-[3,4-d][1,11,8]benzodioxazacyclotetradecine-3-carbonitrile (Example 40)

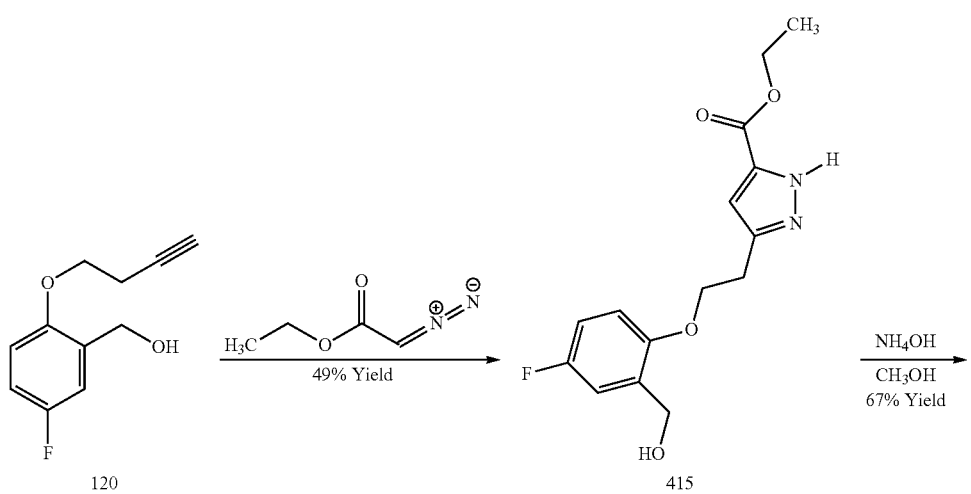

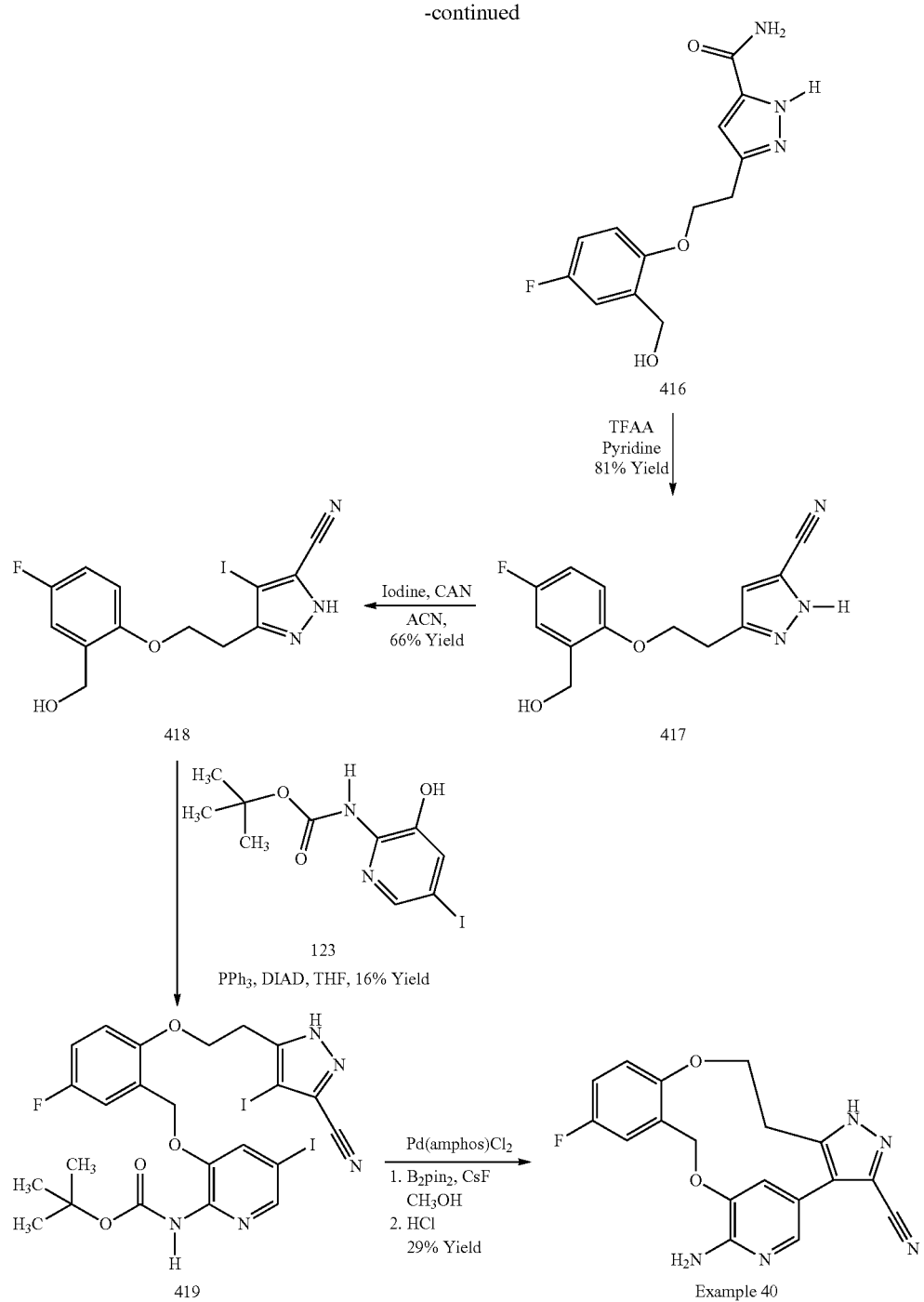

Step 1:

The procedure described in step 1 for Example 39 was used to prepare compound 415 (1.6 g, 49% yield). $^1$H NMR (400 MHz, DMSO-$d_6$) δ 1.28 (t, J=7.0 Hz, 3 H), 3.07 (br. s, 2 H), 4.13-4.22 (m, 2 H), 4.25 (d, J=6.6 Hz, 2 H), 4.40 (s, 2 H), 4.95-5.34 (m, 1 H), 6.63 (br. s, 1 H), 6.89-7.06 (m, 2 H), 7.13 (dd, J=9.4, 2.6 Hz, 1 H), 13.29 (br s, 1 H).

Step 2:

The procedure described in step 2 for Example 39 was used to prepare Compound 416 (930 mg, 67% yield). $^1$H NMR (400 MHz, DMSO-$d_6$) δ 12.97 (br s, 1 H), 7.38 (br s, 1 H), 7.18-7.05 (m, 2 H), 7.02-6.90 (m, 2 H), 6.49 (s, 1 H), 5.19 (t, J=5.4 Hz, 1 H), 4.41 (d, J=5.0 Hz, 2 H), 4.18 (t, J=6.4 Hz, 2 H), 3.06 (t, J=5.9 Hz, 2 H).

Step 3:

The procedure described in step 3 for Example 39 was used to prepare Compound 417 (700 mg, 81% yield). $^1$H NMR (400 MHz, DMSO-$d_6$) δ 3.10 (t, J=6.2 Hz, 2 H), 4.19 (t, J=6.3 Hz, 2H), 4.37 (s, 2 H), 6.82 (s, 1 H), 6.91-7.05 (m, 2 H), 7.13 (dd, J=9.6, 3.0 Hz, 1 H), 13.77 (br s, 1H).

Step 4:

The procedure described in step 4 for Example 39 was used to prepare Compound 418 (630 mg, 66% yield). $^1$H NMR (400 MHz, DMSO-$d_6$) δ 3.10 (t, J=6.2 Hz, 2 H), 4.20 (t, J=6.2 Hz, 2H), 4.34 (s, 2 H), 6.91-7.05 (m, 2 H), 7.13 (dd, J=9.4, 3.2 Hz, 1 H).

Step 5:

The procedure described in step 5 for Example 39 was used to prepare Compound 419 (180 mg, 16% yield). $^1$H NMR (400 MHz, DMSO-$d_6$) δ 1.41 (s, 9 H) 3.16 (t, J=6.2 Hz, 2 H) 4.25 (t, J=6.3 Hz, 2 H) 5.00 (s, 2 H) 6.96-7.19 (m, 2 H) 7.33 (dd, J=9.3, 3.0 Hz, 1 H) 7.74 (d, J=1.8 Hz, 1 H) 8.17 (d, J=1.8 Hz, 1 H) 9.03 (s, 1 H) 14.23 (br s, 1 H).

Step 6:

The procedure described in step 6 for Example 39 was used to prepare Example 40 (25 mg, 29% yield). $^1$H NMR (400 MHz, DMSO-$d_6$) δ 3.06-3.17 (m, 2 H), 4.51 (br s, 2 H), 5.19 (br s, 2H), 5.54 (br s, 2 H), 7.02-7.19 (m, 2 H), 7.37 (dd, J=9.1, 3.0 Hz, 1 H), 7.67 (d, J=1.8 Hz, 1H), 7.86 (d, J=1.8 Hz, 1 H), 13.46 (s, 1 H). LCMS ES m/z 352 [M+H]$^+$.

Preparation of (10R)-7-amino-12-fluoro-10,16-dimethyl-3-propyl-16,17-dihydro-3H-8,4-(metheno)[1,2,3]triazolo[4,5-h][2,5,11]benzoxadiazacyclotetradecin-15(10H)-one (Example 41)

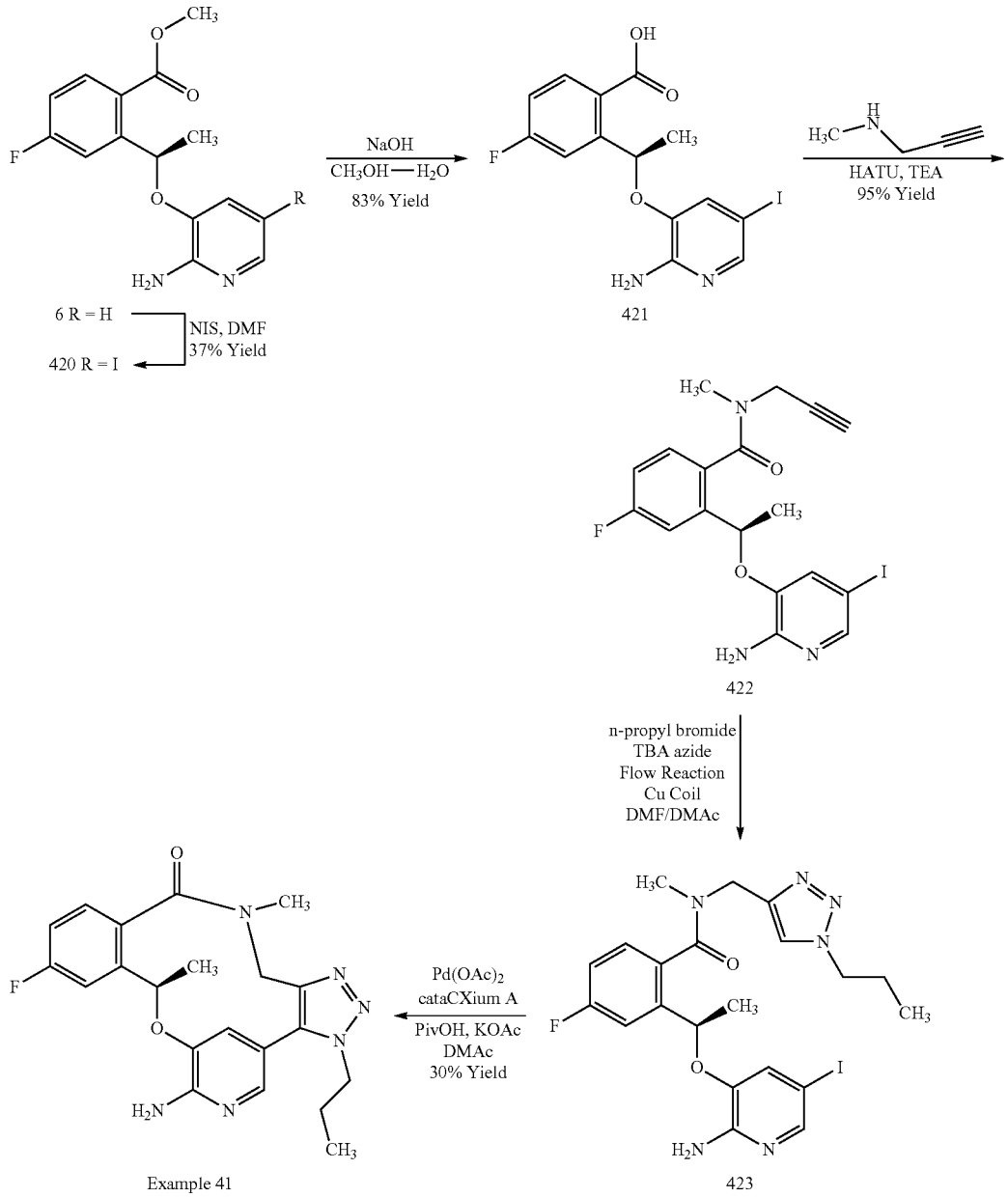

Step 1:

Compound 6 (7.6 g, 26.2 mmol) was dissolved in DMF (76 mL) to give a brown solution which was cooled to −5° C. under a nitrogen atmosphere. N-iodosuccinimide (5.9 g, 26.2 mmol) was added in portions (7 portions) with no noticeable exotherm detected. After warming to room temperature, a TLC (50% EtOAc/heptane) showed compound 6 was present. The reaction mixture was re-cooled to 0° C. and more NIS (5.6 g, 24.9 mmol) was added over 2.5 h. The reaction was quenched with 10% aqueous sodium thiosulphate (50 mL)

and saturated sodium bicarbonate (30 mL). The brown mixture was evaporated to a residue (ca. 60 mL) which was partitioned between EtOAc (200 mL) and 10% aqueous sodium thiosulphate (200 mL). After separation, the organic was washed with saturated aqueous sodium bicarbonate (100 mL) and then brine (100 mL). The aqueous layer was back extracted with EtOAc (50 mL). The combined EtOAc layers were dried over MgSO$_4$, filtered and evaporated to give a brown oily residue (ca. 7 g). The crude product was absorbed onto silica and purified by column chromatography (eluent: 20 to 40% EtOAc/heptane) and gave compound 420 as a brown solid (4.0 g, 37% yield). $^1$H NMR (400 MHz, DMSO-d$_6$) δ 7.88 (1 H, m), 7.57 (2 H, m), 7.21 (1 H, t), 6.91 (1 H, s), 6.13 (1 H, m), 6.10 (2 H, s), 3.85 (3 H, s), 1.51 (3 H, d). LCMS ES m/z 417 [M+H]$^+$.

Step 2:

To a solution of compound 420 (400 mg, 0.961 mmol) in MeOH, was added 2 M NaOH (1.0 mL, 2.0 mmol). The mixture was stirred at room temperature. After 6 hours, the reaction was only ~20% complete by LCMS. Additional 4 M NaOH (1.0 mL, 4.0 mmol) was added. The mixture was stirred at room temperature. After 11 h, the reaction was complete. About 70% of the solvent was removed under reduced pressure and the residue was adjusted to pH=~7 with 2 N HCl. The precipitate was collected through filtration and rinsed with MeOH/water to afford compound 421 as a solid (321 mg, 83% yield). $^1$H NMR (400 MHz, DMSO-d$_6$) δ 1.56 (d, J=6.3 Hz, 3 H), 6.19 (br s, 2 H), 6.33 (q, J=6.4 Hz, 1 H), 6.93 (d, J=1.5 Hz, 1 H), 7.23 (td, J=8.5, 2.8 Hz, 1 H), 7.54 (dd, J=10.4, 2.5 Hz, 1 H), 7.61 (d, J=1.8 Hz, 1 H), 7.97 (dd, J=8.7, 5.9 Hz, 1 H), 13.42 (br s, 1 H). LCMS APCI m/z 403 [M+H]$^+$.

Step 2:

To a solution of compound 421 (300 mg, 0.746 mmol), the N-methyl propargyl amine (57 mg, 0.82 mmol), DIEA (289 mg, 2.24 mmol) in DMF (3 mL) was added HATU (340 mg, 0.895). The resulting mixture was stirred at room temperature. After 1.5 h, the reaction was only ~15% complete. The reaction mixture was heated up to 55° C. After 1 h, the reaction was complete. The solvent was removed under reduced pressure. The residue was diluted with EtOAc and washed with water, saturated NaHCO$_3$ and brine. The organic layer was filtered, concentrated and purified by flash chromatography over silica gel, which was eluted with 3% to 50% EtOAc/heptane, and gave compound 422 as a light brown gum (323 mg, 95% yield). $^1$H NMR (400 MHz, DMSO-d$_6$) δ 1.54 (d, J=6.3 Hz, 3 H), 2.85 (s, 3 H), 3.07 (s, 1 H), 4.33-4.40 (m, 2H), 5.35-5.50 (m, 1 H), 6.12 (s, 1 H), 7.17-7.28 (m, 1 H), 7.30-7.37 (m, 1 H), 7.50 (d, J=8.1 Hz, 1 H), 7.62 (d, J=1.8 Hz, 1 H). LCMS APCI m/z 454 [M+H]$^+$.

Step 3:

To a stirred solution of 1-bromopropane (0.4 mmol) in DMAc (200 μL) was added tetrabutylammonium azide (0.4 mmol) drop-wise (200 μL/min) as a solution in DMF (400 μL). To this solution was then added compound 422 (91 mg, 0.2 mmol) drop-wise (200 μL/min) as a solution in DMAc (200 μL). After 30 seconds the reaction segment (800 μL) was injected into a flow reactor device and passed through a coil of copper tubing for 3 minutes at 150° C. The reaction segment was then cooled and collected by a UV (280 nm) triggered fraction collector. LCMS analysis of this segment showed the presence of the desired mass ion for compound 423. LCMS m/z 539 [M+H]$^+$. The solvent was removed under a purge of N$_2$ at 50° C. and used crude in the subsequent step.

Step 4:

To compound 423 (108 mg, 0.2 mmol) was added dry, degassed DMAc (3 mL), Pd(OAc)$_2$ (0.0021 mmol), cataCXium® A (0.0042 mmol), Pivalic Acid (0.0067 mmol) and KOAc (0.167 mmol) under controlled glove box conditions (<50 ppm O$_2$, <50 ppm H$_2$O). The reaction mixture was stirred at 110° C. for 18 hours. After cooling to room temperature, the reaction mixture was diluted with water and EtOAc. The organic layer was collected and washed with saturated NaHCO$_3$ and water. The organic layer was filtered and the filtrate was concentrated under reduced pressure. The crude product was purified by column chromatography over silica gel, which was eluted with 30-90% EtOAc-heptane and gave unpure product. The sample was re-purified by reverse phase chromatography which gave Example 41 as a white solid (16 mg, 30% Yield). $^1$H NMR (400 MHz, DMSO-d$_6$) δ 7.55-7.72 (m, 2 H), 7.44 (dd, J=5.7, 8.5 Hz, 1H), 7.16 (dt, J=2.8, 8.5 Hz, 1 H), 6.77 (s, 1 H), 6.33 (s, 2 H), 5.65 (q, J=7.2, 3.6 Hz, 1 H), 4.51 (d, J=14.4 Hz, 1 H), 4.29-4.43 (m, 2 H), 4.15 (d, J=14.7 Hz, 1 H), 2.99 (s, 3 H), 1.73-1.83 (m, 2 H), 1.67 (d, J=6.1 Hz, 3 H), 0.78 (t, J=7.3 Hz, 3 H). LCMS APCI m/z 412 [M+H]$^+$.

Preparation of 12-fluoro-1-methyl-1,4,5,6,7,8-hexahydro-14H-16,20-(metheno) pyrazolo[4,3-g][1,14,11]benzodioxazacycloheptadecin-17-amine (Example 42)

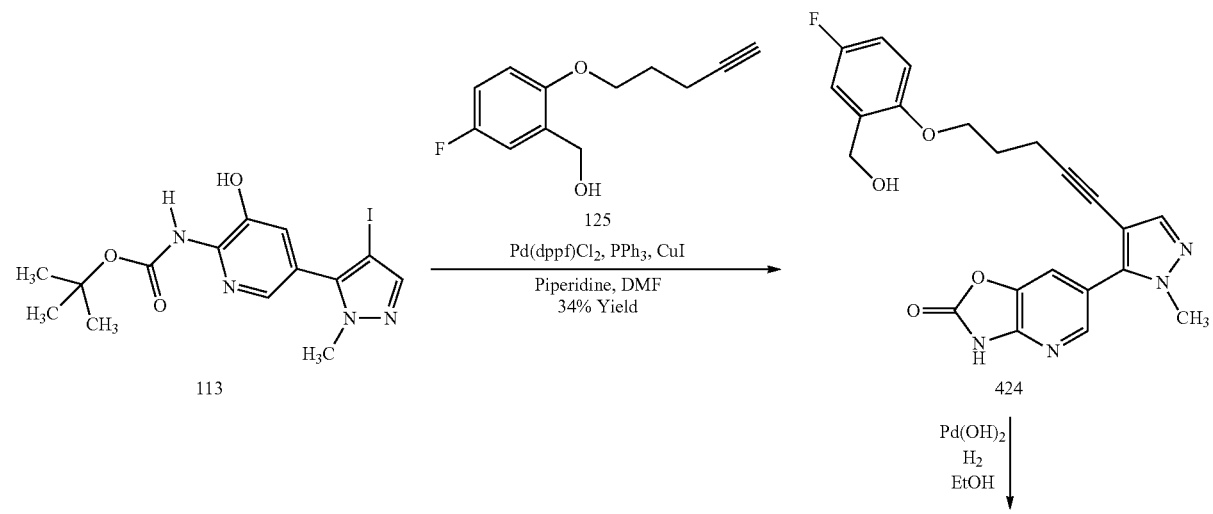

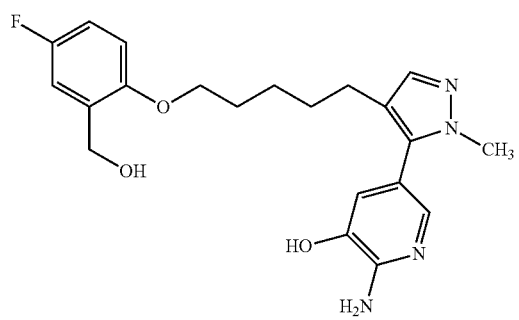

426

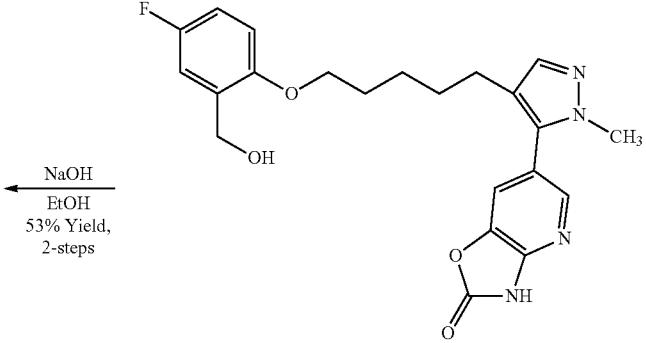

425

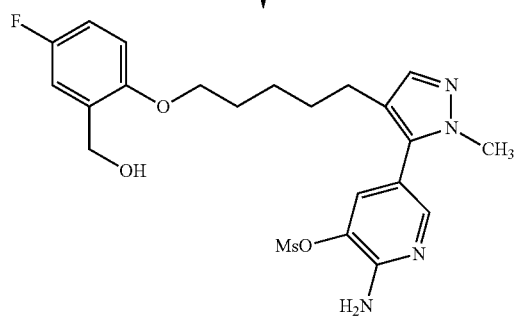

427

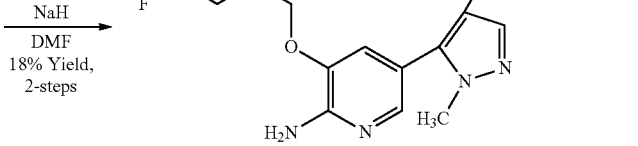

Example 42

Step 1:

A mixture of compound 113 (300 mg, 0.72 mmol), compound 125 (300 mg, 1.4 mmol), cuprous iodide (6.9 mg, 0.036 mmol), triphenyl phosphine (9.4 mg, 0.036 mmol) and PdCl$_2$(PPh$_3$)$_2$ (50.5 mg, 0.072 mmol) in a mixture of DMF (4.81 mL) and piperidine (4.81 mL) was bubbled with nitrogen, and then heated in an oil bath to 90° C. After 4 hours, the reaction was allowed to cool, and diluted with ethyl acetate. The solution was washed with saturated aqueous NH$_4$Cl (3×), brine, and the organics dried over MgSO$_4$. The solution was filtered, concentrated, and the residue subjected to column chromatography over silica gel (50-100% EA/heptane) to afford compound 424 (102 mg, 34%) as a white solid. $^1$H NMR (400 MHz, DMSO-d$_6$) δ 12.69 (br. s., 1 H), 8.22 (d, J=1.77 Hz, 1 H), 7.88 (d, J=1.77 Hz, 1 H), 7.64 (s, 1H), 7.12 (dd, J=9.35, 3.28 Hz, 1 H), 6.90-6.99 (m, 1 H), 6.82, (dd, J=8.84, 4.55 Hz, 1 H), 5.12 (br. s., 1 H), 4.45 (br. s., 2 H), 3.96 (t, J=6.06 Hz, 2 H), 3.80 (s, 3 H), 1.88 (quin, J=6.51 Hz, 2 H). LCMS m/z 423 [M+H]$^+$.

Step 2:

Compound 424 (100 mg, 0.237 mmol) was dissolved in ethanol (0.5 mL), and palladium hydroxide 25 mg, 20% on carbon) added. The mixture was flushed with nitrogen, followed by being pressurized under 3-4 bar of hydrogen. The reaction was agitated, and heated to 60° C. for 12 hours. The reaction vessel was allowed to cool, and LCMS indicated that the major product was the desired accompanied by minor amounts of the ethyl carbamate. The reaction was filtered through a celite cartridge to remove the catalyst, and washed with methanol. The filtrate was concentrated, and to the residue (compound 425) added 2N aqueous NaOH (2 mL), and methanol (0.8 mL). The reaction was heated to 90° C. for 4 hours, allowed to cool, and stirred for a further 48 hours. The mixture was diluted with EtOAc, and washed with saturated aqueous NH$_4$Cl. The aqueous was adjusted to pH 6 using 4N HCl, and further extracted with EtOAc. The organics were dried over MgSO$_4$, concentrated, and purified by column chromatography over silica gel (0-10% MeOH/DCM) to afford compound 426 (5 mg, 53%) as a colorless solid. $^1$H NMR (400 MHz, DMSO-d$_6$) δ 9.72 (br. s., 1 H), 7.40 (d, J=1.76 Hz, 1 H), 7.31 (s, 1 H), 7.12 (dd, J=9.57, 3.27 Hz, 1 H), 6.93-7.02 (m, 1 H), 6.83-6.92 (m, 1 H), 6.79 (d, J=1.76 Hz, 1 H), 5.75 (s, 2 H), 5.13 (br. s., 1 H), 4.45 (s, 2 H), 3.88 (t, J=6.42 Hz, 2 H), 3.63 (s, 3 H), 2.31 (t, J=7.55 Hz, 2 H), 1.56-1.69 (m, 2 H), 1.41-1.56 (m, 2 H), 1.27-1.41 (m, 2 H). LCMS m/z 401 [M+H]$^+$.

Step 3:

To a cooled 0° C. solution of compound 426 in DCM (500 μL) was added TEA (20.9 μL, 0.15 mmol), and a catalytic amount of DMAP (0.6 mg), followed by a solution of MsCl (9.7 μl, 0.125 mmol) in DCM (250 μL). The reaction was allowed to slowly warm to room temperature, and after one hour, LCMS indicated that the desired product was the major component formed. The reaction was diluted with DCM, and washed with water. The organics were dried (MgSO$_4$), filtered and concentrated. After being dried overnight under high vacuum, compound 427 (53 mg, 89%), was isolated as a light foamy solid, which was used without purification in the cyclization step. LCMS m/z 479 [M+H]$^+$.

Step 4:

To a solution of the compound 427 (50 mg, 0.1 mmol) in DMF (2.08 mL) was added NaH (5.6 mg, 0.15 mmol, 60% dispersion). The reaction was heated to 50° C. for 3 hours. A further portion of NaH (5 mg) was added, and the reaction heated for a further hour. The reaction was diluted with EtOAc, washed with saturated aqueous NH$_4$Cl/water mixture, brine, dried (MgSO$_4$), filtered and concentrated. The residue was purified by column chromatography over silica gel (0-10% MeOH/DCM) to afford Example 42 (6 mg, 20%) as a yellow cream solid. $^1$H NMR (400 MHz, DMSO-d$_6$) δ 7.55 (s, 1 H), 7.23-7.30 (m, 2 H), 7.02-7.10 (m, 1 H), 6.95-7.02 (m, 1 H), 6.86 (s, 1 H), 5.77 (br. s., 2 H), 5.26 (s, 2 H), 4.01 (t, J=5.41 Hz, 2 H), 3.65 (s, 3 H), 2.30 (t, J=6.29 Hz, 2 H), 1.68 (m, J=5.29 Hz, 2 H) 1.41-1.58 (m, 4 H). LCMS APCI m/z 383 [M+H]$^+$.

Preparation of 12-fluoro-3-methyl-16,17,18,19-tetrahydro-3H,10H-8,4-(metheno)-pyrazolo[4,3-f][1,13,10]benzodioxazacyclohexadecin-7-amine (Example 43)

Step 1:

A mixture of compound 113 (400 mg, 0.96 mmol), compound 120 (233 mg, 1.2 mmol), cuprous iodide (9.1 mg, 0.048 mmol), triphenyl phosphine (25.2 mg, 0.096 mmol) and PdCl$_2$ (PPh$_3$)$_2$ (33.7 mg, 0.048 mmol) in piperidine (6.4 mL) was bubbled with nitrogen, and then heated in an oil bath to 90° C. After 4 hours, the reaction was allowed to cool, and diluted with EtOAc. The solution was washed with saturated aqueous NH$_4$Cl (3×), brine, and the organics dried over MgSO$_4$. The solution was filtered, concentrated, and the residue subjected to column chromatography over silica gel (0-10% MeOH/DCM) to afford compound 428 as a gummy solid contaminated with excess piperidine. This material was used without further purification in the following step. $^1$H NMR (400 MHz, DMSO-d$_6$) δ 9.22 (s, 1H), 8.06 (d, J=2.01

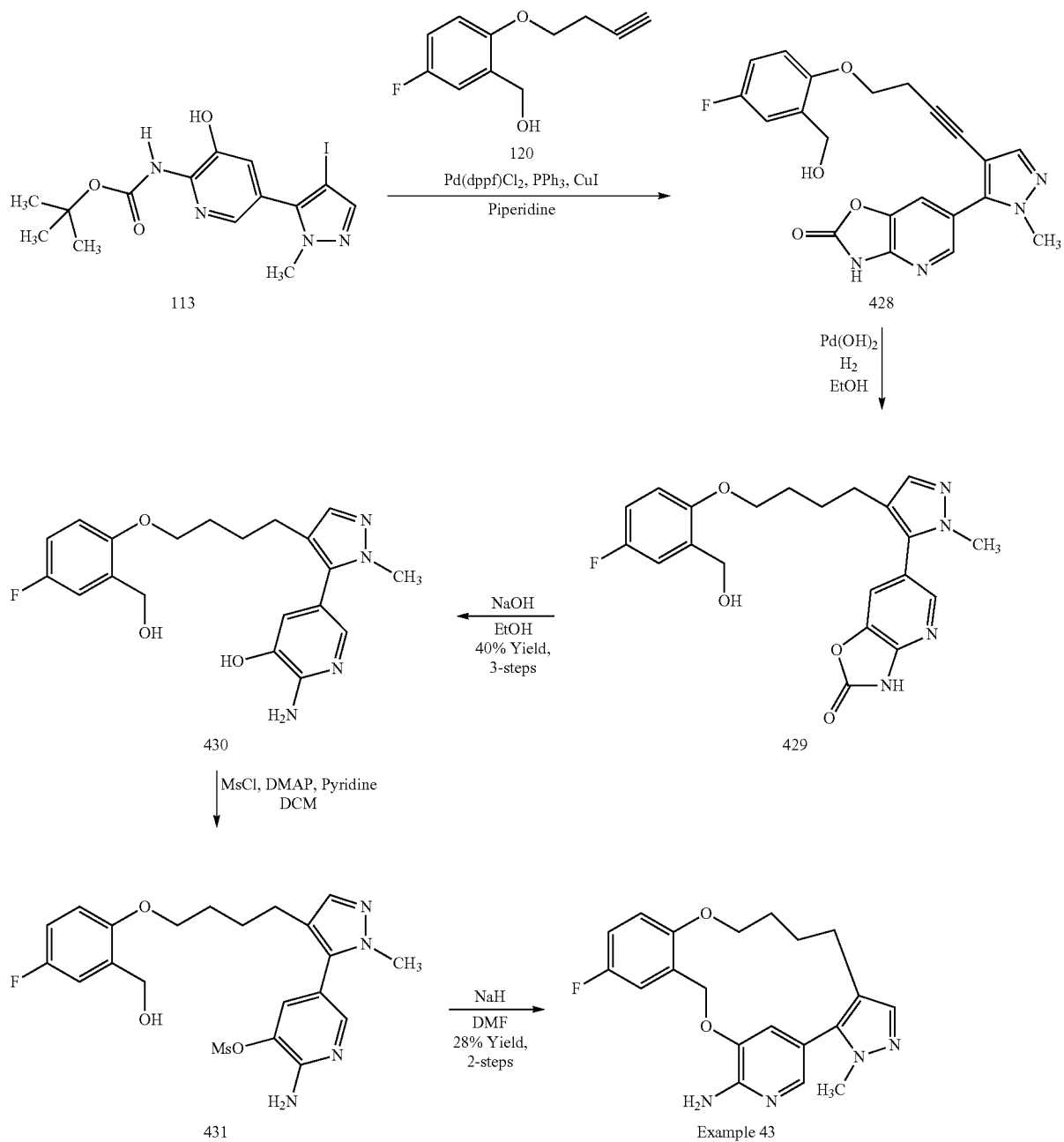

Hz, 1 H), 7.64 (s, 1 H) 7.45 (d, J=1.76 Hz, 1 H), 7.13 (dd, J=9.32, 2.77 Hz, 1 H), 6.92-7.01 (m, 2 H), 5.13 (br. s., 1 H), 4.48 (d, J=2.27 Hz, 2 H), 4.06 (t, J=6.67 Hz, 2 H), 3.82 (s, 3 H), 2.78 (t, J=6.55 Hz, 2H). LCMS m/z 409 [M+H].

Step 2:

Compound 428 (400 mg, 0.979 mmol) was dissolved in ethanol (9.8 mL), and palladium hydroxide (40 mg, 20% on carbon) added. The mixture was flushed with nitrogen, followed by being pressurized under 3-4 bar of hydrogen. The reaction was agitated, and heated to 50° C. for 18 hours. The reaction vessel was allowed to cool, and LCMS indicated that the major product was the desired accompanied by minor amounts of the ethyl carbamate. The reaction was filtered through a celite cartridge to remove the catalyst, and washed with methanol. The filtrate was concentrated, dissolved in ethanol (10 mL), and 15% aqueous NaOH (7.83 mL) was added. The reaction was heated to 85° C. for 12 hours, and allowed to cool. The mixture was neutralized with 1N aqueous HCl, and extracted with EtOAc. The organics were dried over MgSO$_4$, concentrated, and purified by column chromatography over silica gel (0-10% MeOH/DCM) to afford compound 430 (151 mg, 40%) as a colorless solid. $^1$H NMR (400 MHz, DMSO-d$_6$) δ 9.72 (br. s., 1 H), 7.41 (d, J=1.76 Hz, 1 H), 7.33 (s, 1 H), 7.12 (dd, J=9.44, 3.15 Hz, 1 H), 6.91-7.02 (m, 1 H), 6.85 (dd, J=8.81, 4.53 Hz, 1 H), 6.79 (d, J=2.01 Hz, 1 H), 5.75 (s, 2 H), 5.13 (br. s., 1 H), 4.45 (s, 2 H), 3.87 (t, J=6.04 Hz, 2 H), 3.64 (s, 3 H), 2.35 (t, J=7.30 Hz, 2 H), 1.47-1.74 (m, 4 H). LCMS m/z 387 [M+H]$^+$.

Step 3:

To a cooled 0° C. solution of compound 430 (150 mg, 0.388 mmol) in DCM (2 mL) was added TEA (65 μL, 0.47 mmol), and a catalytic amount of DMAP (2-3 mg), followed by a solution of MsCl (30 μL, 0.39 mmol) in DCM (0.5 mL). The reaction was allowed to slowly warm to room temperature. After 2 hours, pyridine (2 mL), and MsCl (15 μL, 0.2 mmol) were added to the reaction, which was allowed to stir for a further hour. The reaction was diluted with EtOAc, and washed with saturated aqueous NH$_4$Cl and brine. The organics were dried (MgSO$_4$), filtered and concentrated. After being dried overnight under high vacuum, compound 431 (156 mg, 86%), was isolated as an orange gum, which was used without purification in the cyclization step.

Step 4:

To a solution of the compound 431 (156 mg, 0.34 mmol) in DMF (2.08 mL) was added NaH (13.4 mg, 0.34 mmol, 60% dispersion). The reaction was heated to 50° C. for 2 hours. The reaction was diluted with EtOAc, washed with saturated aqueous NH$_4$Cl/water mixture, brine, dried (MgSO$_4$), filtered and concentrated. The residue was purified by column chromatography over silica gel (0-8% MeOH/DCM) to afford Example 43 (40 mg, 32%) as a yellow cream solid. $^1$H NMR (400 MHz, 80° C., DMSO-d$_6$) δ 7.50-7.57 (m, 2 H), 7.29-7.33 (m, 2 H), 7.01-7.09 (m, 1 H), 6.92-7.00 (m, 1 H), 5.77 (br. s., 2 H), 5.28 (s, 2 H), 4.02 (t, J=5.54 Hz, 2 H), 3.69 (s, 3 H), 2.18-2.34 (m, 2 H), 1.71-1.89 (m, 4 H). LCMS APCI m/z 369 [M+H]$^+$.

Preparation of 7-amino-12-fluoro-N,N,3-trimethyl-17,18-dihydro-10H-8,4-(metheno)-pyrazolo[3,4-e][1,12,9]benzodioxazacyclopentadecine-1 (16 H)-sulfonamide (Example 44)

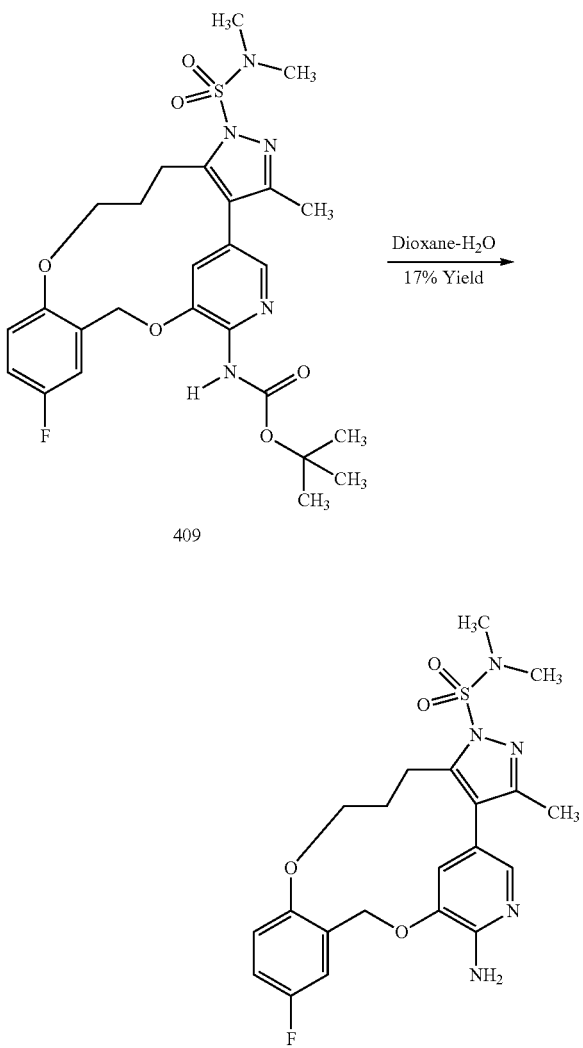

Compound 409 (30 mg, 0.053 mmol) was dissolved in dioxane/water (500 μL/50 μL), and heated to 100° C. for 14 hours. The reaction was concentrated, and purified by column chromatography over silica gel (0-60% EtOAc/DCM), followed by reverse phase HPLC to afford Example 44 (13 mmol, 17%—determined by ELSD analysis of DMSO solution), which was submitted directly for screening. $^1$H NMR (600 MHz, DMSO-d$_6$) δ 7.51 (d, J=1.65 Hz, 1 H), 7.37 (dd, J=8.78, 2.74 Hz, 1 H), 7.33 (d, J=1.65 Hz, 1 H), 7.07-7.17 (m, 2 H), 5.85 (s, 2 H), 5.22 (s, 2 H), 4.18 (m, J=4.94 Hz, 2 H), 2.96 (s, 6 H), 2.88 (br. s., 2 H), 2.30 (s, 2 H), 2.24 (s, 3H). LCMS ES m/z 462 [M+H]$^+$.

Preparation of 8-amino-13-fluoro-4-methoxy-11,17-dimethyl-17,18-dihydro-9,5-(metheno)pyrido[3,4-h][2,5,11]benzoxadiazacyclotetradecin-16(11H)-one (Example 45)

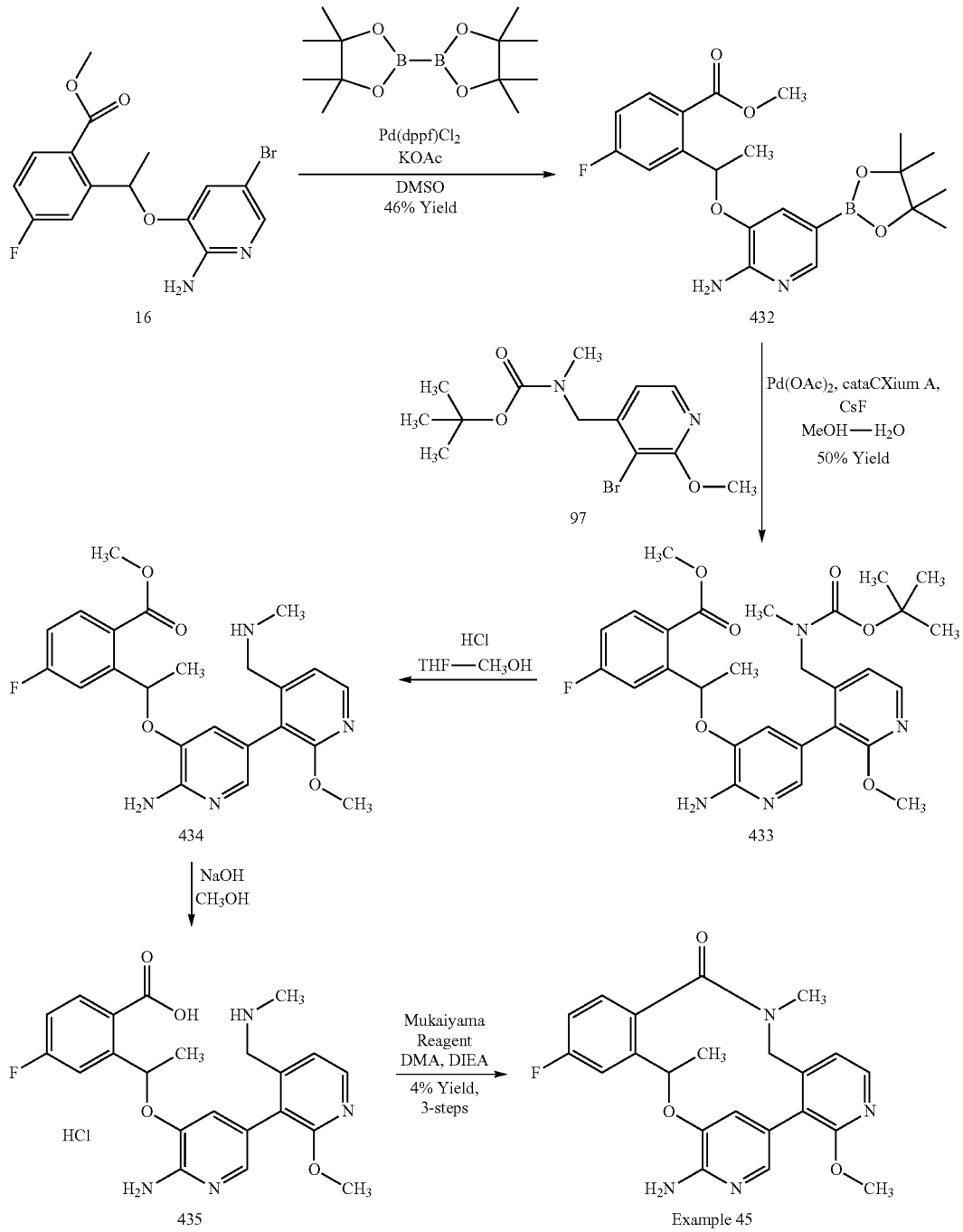

Step 1:

A mixture of bromo starting material compound 16 (1.364 g, 3.70 mmol), bis(pinacolato)diboron (1.44 g, 5.54 mmol), KOAc (1.27 g, 12.9 mmol), Pd(dppf)Cl₂ (272 mg, 0.333 mmol) and anhydrous DMSO (17 mL) was stirred at room temperature for 10 minutes to obtain a dark orange suspension. The mixture was then heated to 80° C. for 5 hours. EtOAc was added to the mixture followed by Si-Thiol. The suspension was allowed to cool to room temperature with stirring. After 30 minutes, the mixture was filtered and the solids were washed with EtOAc. The filtrate (clear dark orange) was further diluted with EtOAc and washed with water (2×) and then brine. The aqueous layers were back extracted with EtOAc (2×). The organic layers were combined and washed with 1M HCl. The aqueous layers were collected and then cooled to 0° C. and neutralized with 10 M NaOH (aq) to pH=7. The suspension was then extracted with EtOAc and the organic layers were combined and washed with brine. The organic layer was then dried (Na₂SO₄), filtered, and concentrated to give 1.42 g of crude material as a brown solid. The material was dissolved in a minimal amount of EtOAc and then heptane was added. A precipitate formed. The mixture was allowed to sit for 1 hour, and then filtered and washed with heptane to provide compound 432 (702.2 mg, 46%) as a light-brown solid. $^1$H NMR (600 MHz, DMSO-$d_6$) δ 7.94 (dd, J=8.80, 5.87 Hz, 1 H), 7.74 (s, 1 H), 7.68 (dd, J=10.56, 2.35 Hz, 1 H), 7.25 (td, J=8.36, 2.64 Hz, 1 H), 6.87 (s, 1 H), 6.36 (s, 2 H), 6.26 (q, J=6.46 Hz, 1 H), 3.91 (s, 3 H), 1.57 (d, J=5.87 Hz, 3 H), 1.21 (d, J=5.87 Hz, 12 H).

Step 2:

To a microwave vial was added compound 97 (100 mg, 0.3 mmol), compound 432 (189 mg, 0.45 mmol). cesium fluoride (138 mg, 0.91 mmol), cataCXium A (12.9 mg, 0.036 mmol), palladium acetate (8.1 mg, 0.036 mmol), methanol (3 mL) and water (0.3 mL). The reaction mixture was degassed, and the vial sealed, and heated to 80° C. for 2 hours. The mixture was diluted with EtOAc, washed with water and brine, dried (MgSO$_4$), filtered and concentrated. The residue was purified by column chromatography over silica gel (20-50% EtOAc/Heptane, then 5-10% MeOH/EtOAc) to afford compound 433 (82 mg, 50%) as a brown gum. $^1$H NMR (400 MHz, CDCl$_3$) δ 7.96-8.10 (m, 2 H), 7.46 (d, J=13.64 Hz, 1 H), 7.27-7.35 (m, 1 H), 7.00 (t, J=7.33 Hz, 1 H), 6.75 (d, J=5.31 Hz, 1 H), 6.51 (br. s., 1 H), 6.30-6.37 (m, 1 H), 4.96 (br. s., 2H), 3.87 (s, 3 H), 3.66-3.77 (m, 3 H), 2.53-2.68 (m, 3 H), 1.63-1.69 (m, 3 H), 1.41 (br. s., 9H). LCMS m/z 541 [M+H]$^+$.

Step 3:

Compound 433 (82 mg, 0.15 mmol) was dissolved in THF (1 mL) and MeOH (0.3 mL), before 38% HCl (0.1 mL) was added. The reaction was heated using an oil bath at 50° C. for 4 hours. The reaction was allowed to cool to room temperature, and 50% aqueous NaOH was added until the pH reached 12 (~0.2 mL). 0.3 mL of MeOH was added, and the reaction heated at 50° C. for 1 hour. The reaction was concentrated, and subjected to lyophilization. The solid was filtered, and washed with EtOAc, followed by MeOH/CH$_2$Cl$_2$, and the filtrates concentrated to give compound 435 (126 mg) as a white solid, which was used in the following step without further purification.

Step 4:

Compound 435 (65 mg, 0.15 mmol) was dissolved in DMA (15 mL), and the solution was cooled to 0° C. DIEA (53 µL, 0.3 mmol) was added, followed by CMPI (43.1 mg, 0.17 mmol), and the mixture was stirred at 0° C. for 30 minutes. The reaction mixture was diluted with water, and subjected to lyophilization. The solid was washed with EtOAc and MeOH/CH$_2$Cl$_2$, the filtrates concentrated, and purified by reverse phase HPLC to afford Example 45 (2.38 mg, 4%) as an off-white solid. $^1$H NMR (400 MHz, Acetone-$d_6$) δ 8.03-8.15 (m, 1 H), 7.59 (dd, J=10.11, 2.53 Hz, 1 H), 7.53 (d, J=2.02 Hz, 1 H), 7.31 (dd, J=8.46, 5.68 Hz, 1 H), 7.19 (s, 1 H), 6.96-7.06 (m, 2 H), 5.76-5.85 (m, 1 H), 5.47 (s, 1 H), 4.28 (s, 2 H), 3.79-3.87 (m, 3 H), 3.06 (s, 3H), 1.69-1.74 (m, 3 H). LCMS APCI m/z 409 [M+H]$^+$.

Preparation of 7-amino-12-fluoro-2,16-dimethyl-15-oxo-10,15,16,17-tetrahydro-2H-8,4-(azeno)pyrazolo[4,3-h][2,5,11]benzoxadiazacyclotetradecine-3-carbonitrile (Example 46)

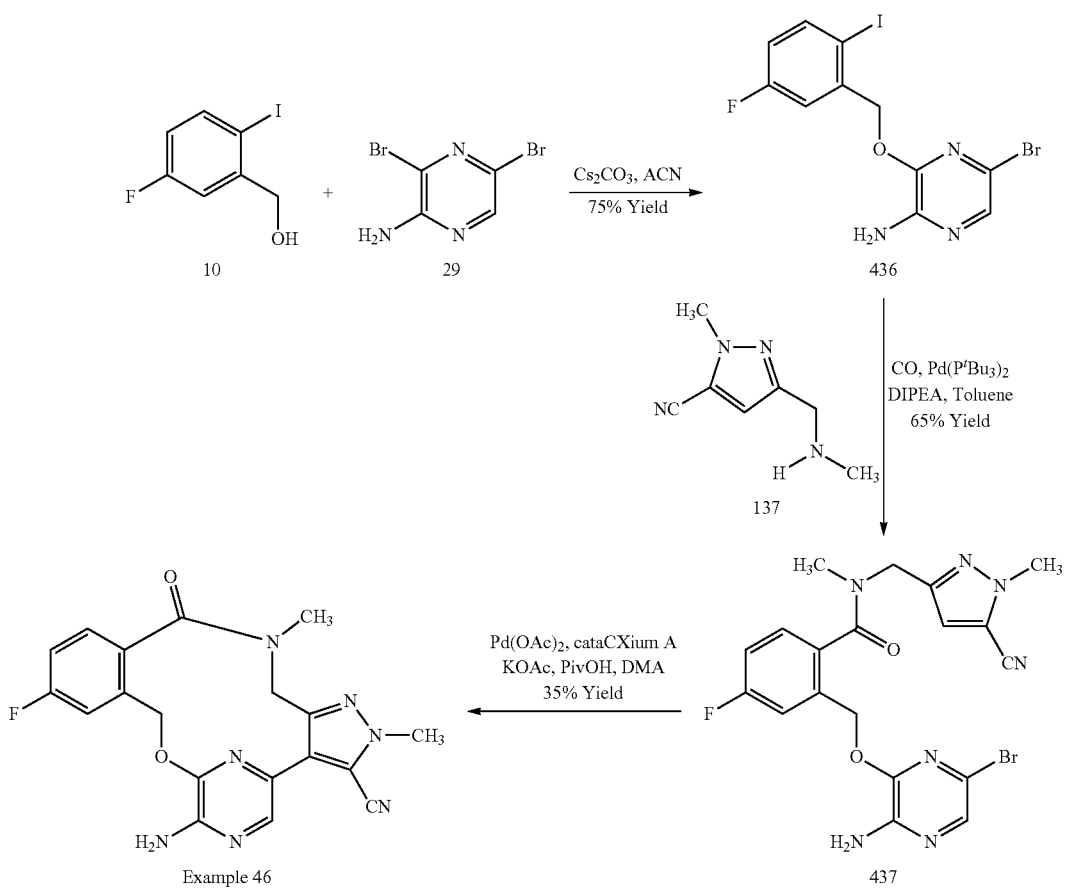

Compound 10 (1.89 g, 7.5 mmol), compound 29 (2.28 g, 9 mmol), and cesium carbonate (6.11 g, 18.7 mmol) were combined in acetonitrile (75 mL), and heated at 80° C. for 18 hours. The crude suspension was added to brine (400 mL) and the resulting rust colored solids were collected by filtration and rinsed with water. The partially dried solids were recrystallized from hot acetonitrile (~200 mL) to afford compound 436 (2.37 g, 75%) as an orange solid. $^1$H NMR (400 MHz, DMSO-$d_6$) δ 7.92 (dd, 1 H), 7.58-7.69 (m, 2 H), 7.05 (td, J=8.65, 3.24 Hz, 1 H), 6.69 (s, 2 H), 5.27 (s, 2 H). LCMS m/z 423/425 [M+H]$^+$.

Step 2:

Compound 436 (450 mg, 1.06 mmol), compound 137 (155 mg, 0.30 mmol), DIEA (0.578 mL, 3.32 mmol) and Pd(P$^t$Bu$_3$)$_2$ (43.3 mg, 0.083 mmol) were dissolved in toluene (40 mL) in a stainless steel bomb, and heated to 85° C. under 4 bar CO pressure for 15 hours. The mixture was concentrated and purified by column chromatography over silica gel (25-100% EtOAc/heptane) to afford compound 437 (255 mg, 65%) as a yellow solid. $^1$H NMR (400 MHz, 80° C., DMSO-$d_6$) δ ppm 7.64 (s, 1 H), 7.51 (dd, J=10.20, 2.64 Hz, 1 H), 7.40 (dd, J=8.31, 5.79 Hz, 1 H), 7.15-7.32 (m, 1 H), 6.94 (s, 1 H), 6.23 (br. s., 2 H), 5.34 (s, 2 H), 4.13-4.83 (m, 2 H), 3.95 (s, 3 H), 2.87 (br. s., 3 H). LCMS m/z 474/476 [M+H]$^+$.

Step 3:

Compound 437 (125 mg, 0.264 mmol), cataCXium A (29.2 mg, 0.079 mmol), palladium acetate (9 mg, 0.04 mmol), KOAc (130 mg, 1.32 mmol), and pivalic acid (8.1 mg, 0.079 mmol) were dissolved in DMA (5.29 mL) in a microwave vial. The vial was flushed with nitrogen, and heated in the microwave at 150° C. for 1 hour. The mixture was diluted with water, and the solids removed by filtration. The aqueous was extracted with EtOAc, washed with brine. The solids were combined with the organics, and dried over MgSO$_4$. The organics were filtered, and concentrated. The residue was purified by column chromatography over silica gel (25-100% 3:1 DCM in heptanes/5% MeOH in EtOAc). Trituration of the product containing fractions with MTBE afforded Example 46 (36 mg, 35%) as a colorless solid as a mixture of atropisomers. $^1$H NMR (400 MHz, DMSO-$d_6$) δ 7.80 (s, 1 H), 7.35-7.53 (m, 2 H), 7.19 (td, J=8.50, 2.64 Hz, 1 H), 6.75 (s, 2 H), 5.57 (dd, J=12.46, 1.64 Hz, 1 H), 5.10 (d, J=12.59 Hz, 1 H), 4.23-4.50 (m, 2 H), 4.04 (s, 3 H), 2.88 (s, 3 H). LCMS APCI m/z 394 [M+H]$^+$.

The analytical chiral separation by SFC was performed using a Chiralpak OD-H (4.6 mm×250 mm column, 5 micron particle size), which was eluted with 30% MeOH in CO$_2$ held at 35° C. at 140 bar. A flow rate of 3 mL/minutes gave Rt$_{(Peak\ 1)}$=4.85 minutes and Rt$_{(Peak\ 2)}$=5.79 minutes.

Example 46 (Atropisomer peak 1): 99% ee. $^1$H NMR (400 MHz, DMSO-$d_6$) δ 7.79 (s, 1 H), 7.37-7.56 (m, 2 H), 7.19 (td, J=8.46, 2.78 Hz, 1 H), 6.77 (s, 2 H), 5.57 (dd, J=12.51, 1.64 Hz, 1H), 5.10 (d, J=12.38 Hz, 1 H), 4.25-4.41 (m, 2 H), 4.04 (s, 3 H), 2.88 (s, 3 H).

Example 46 (Atropisomer peak 2): 96% ee. $^1$H NMR (400 MHz, DMSO-$d_6$) δ ppm 7.79 (s, 1 H), 7.37-7.53 (m, 2 H), 7.19 (td, J=8.53, 2.65 Hz, 1 H), 6.77 (s, 2 H), 5.57 (dd, J=12.38, 1.52 Hz, 1 H), 5.10 (d, J=12.63 Hz, 1 H), 4.24-4.47 (m, 2 H), 4.04 (s, 3 H), 2.88 (s, 3 H).

Preparation of (10R)-7-amino-3-ethyl-12-fluoro-10,16-dimethyl-16,17-dihydro-8,4-(azeno)[1,2]oxazolo[4,5-h][2,5,11]benzoxadiazacyclotetradecin-15(10H)-one (Example 47)

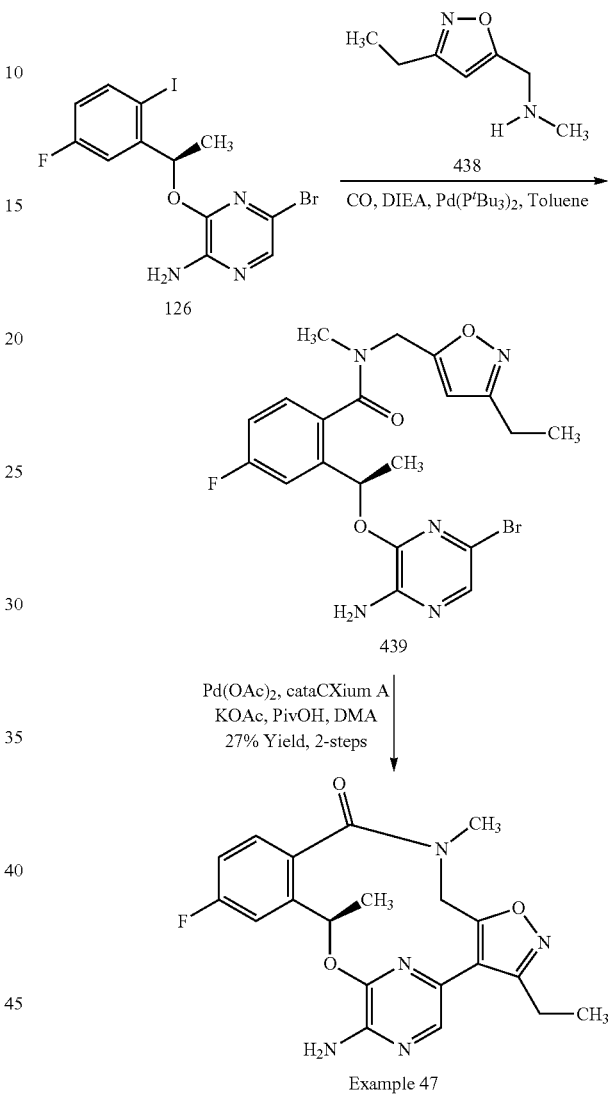

Step 1:

Compound 126 (286 mg, 0.653 mmol), compound 438 (115 mg, 0.653 mmol), DIEA (0.455 mL, 2.61 mmol), Pd(P$^t$Bu$_3$)$_2$ (33.9 mg, 0.05 mmol) were dissolved in toluene (20 mL) in a stainless steel vessel. The reactor was pressurized to 4 bar of CO, and heated to 85° C. for 14 hours. The reaction mixture was diluted with EtOAc, washed with water, saturated aqueous NH$_4$Cl, and brine. The organics were dried (MgSO$_4$), and concentrated. The residue of compound 439 was used in the next step without further purification.

Step 2:

Compound 439 (312 mg, 0.653 mmol), KOAc (320 mg, 3.26 mmol), pivalic acid (16.8 mg, 0.163 mmol) were combined in DMF (4.35 mL) and the solution purged with nitrogen. Pd(OAc)$_2$ (14.6 mg, 0.065 mmol) and cataCXium A (48.4 mg, 0.131 mmol) were then added, and the reaction heated to 150° C. for 45 minutes in the microwave. The reaction was diluted with EtOAc, washed with water and brine, dried (MgSO$_4$), filtered and concentrated. Purification by reverse phase HPLC afforded Example 47 (71 mg, 27%) as a colorless solid. $^1$H NMR (400 MHz, CDCl$_3$) δ 7.31-7.25 (m, 3 H), 7.08 (dt, J=2.6, 8.2 Hz, 1 H), 6.30-6.22 (m, 1 H), 4.57 (d, J=13.6 Hz, 1H), 4.41 (d, J=13.4 Hz, 1 H), 3.12 (s, 3 H), 3.01-2.77 (m, 2 H), 1.84 (d, J=6.6 Hz, 3 H), 1.39 (t, J=7.6 Hz, 3 H). LCMS APCI m/z 398 [M+H]$^+$.

Preparation of (10R)-7-amino-3-ethyl-12-fluoro-10, 16-dimethyl-16,17-dihydro-8,4-(azeno)[1,2]oxazolo [4,3-h][2,5,11]benzoxadiazacyclotetradecin-15(10 H)-one (Example 48)

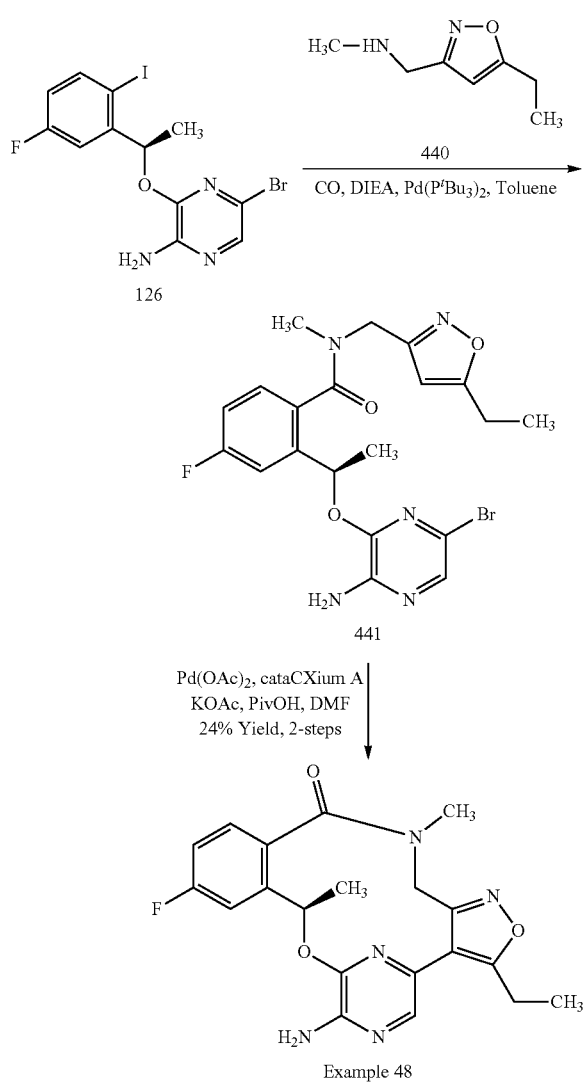

Example 48

Step 1:
Compound 126 (285 mg, 0.650 mmol), compound 440 (115 mg, 0.650 mmol), DIEA (0.453 ml, 2.61 mmol), Pd (P$^t$Bu$_3$)$_2$ (33.9 mg, 0.05 mmol) were dissolved in toluene (20 mL) in a stainless steel vessel. The reactor was pressurized to 4 bar of CO, and heated to 85° C. for 14 hours. The reaction mixture was diluted with EtOAc, washed with water, saturated aqueous NH$_4$Cl, and brine. The organics were dried (MgSO$_4$), and concentrated. The residue of compound 441 was used in the next step without further purification.

Step 2:
Compound 441 (311 mg, 0.650 mmol), KOAc (320 mg, 3.26 mmol), pivalic acid (16.8 mg, 0.163 mmol) were combined in DMF (5 mL) and the solution purged with nitrogen. Pd(OAc)$_2$ (14.6 mg, 0.065 mmol) and cataCXium A (48.6 mg, 0.131 mmol) were then added, and the reaction heated to 150° C. for 45 minutes in the microwave. The reaction was diluted with EtOAc, washed with water and brine, dried (MgSO$_4$), filtered and concentrated. Purification by reverse phase HPLC afforded Example 48 (62 mg, 24%) as a colorless solid. $^1$H NMR (400 MHz, CDCl$_3$) δ 7.66 (s, 1 H), 7.31-7.27 (m, 1 H), 7.21 (dd, J=5.5, 8.4 Hz, 1 H), 7.01 (dt, J=2.6, 8.3 Hz, 1 H), 6.16-6.03 (m, 1 H), 5.01 (br. s., 2 H), 4.67 (d, J=14.1 Hz, 1 H), 4.33 (d, J=14.1 Hz, 1 H), 3.11 (s, 3 H), 2.95-2.75 (m, 2 H), 1.76 (d, J=6.6 Hz, 3 H), 1.34 (t, J=7.5 Hz, 3H). LCMS APCI m/z 398 [M+H]$^+$.

Preparation of (10R)-7-amino-3-ethyl-12-fluoro-10, 16-dimethyl-16,17-dihydro-3H-8,4(azeno)pyrazolo [3,4-h][2,5,11]benzoxadiazacyclotetradecin-15(10 H)-one (Example 49)

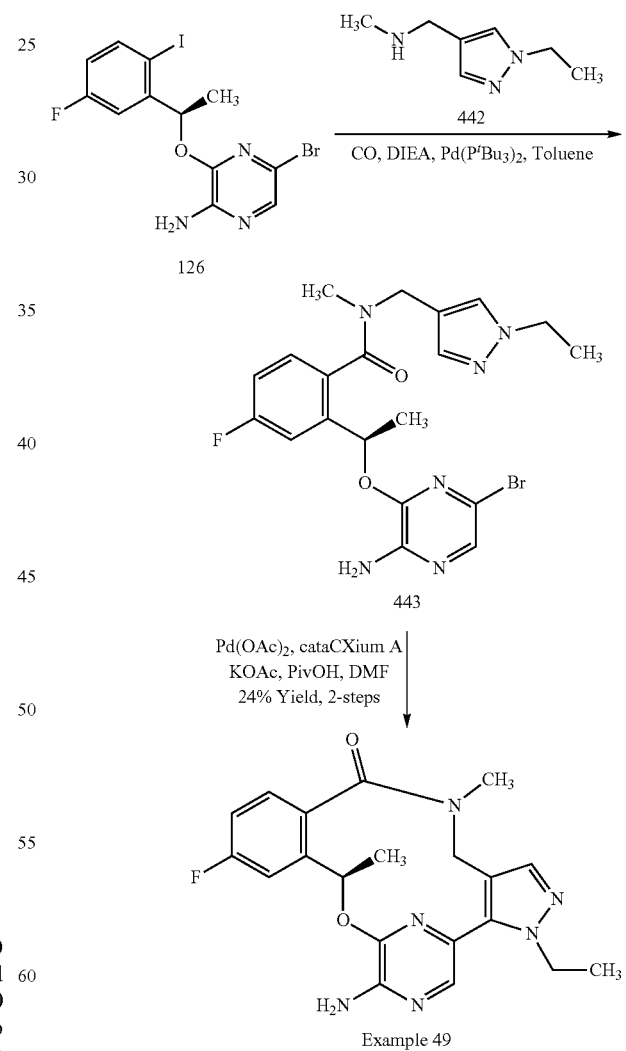

Example 49

Step 1:
Compound 126 (314 mg, 0.718 mmol), compound 442 (100 mg, 0.718 mmol), DIEA (0.5 mL, 2.87 mmol), Pd (P'Bu₃)₂ (37.5 mg, 0.072 mmol) were dissolved in toluene (20 mL) in a stainless steel vessel. The reactor was pressurized to 4 bar of CO, and heated to 85° C. for 14 hours. The reaction mixture was diluted with EtOAc, washed with water, saturated aqueous NH₄Cl, and brine. The organics were dried (MgSO₄), and concentrated. The residue of compound 443 was used in the next step without further purification. LCMS m/z 477/479 [M+H]⁺.

Step 2:

Compound 443 (258 mg, 0.540 mmol), KOAc (265 mg, 2.7 mmol), pivalic acid (13.9 mg, 0.135 mmol) were combined in DMF (4 mL) and the solution purged with nitrogen. Pd(OAc)₂ (12.1 mg, 0.054 mmol) and cataCXium A (39.9 mg, 0.108 mmol) were then added, and the reaction heated to 150° C. for 30 minutes in the microwave. The reaction was diluted with EtOAc, washed with water and brine, dried (MgSO₄), filtered and concentrated. Purification by reverse phase HPLC afforded Example 49 (52 mg, 24%) as a colorless solid. ¹H NMR (400 MHz, DMSO-d₆) δ 7.67 (s, 1 H), 7.60 (s, 1 H), 7.54 (dd, J=2.6, 10.1 Hz, 1 H), 7.31 (dd, J=5.7, 8.4 Hz, 1 H), 7.12 (dt, J=2.6, 8.5 Hz, 1 H), 6.75 (s, 2 H), 6.09-5.96 (m, 1 H), 4.20-4.13 (m, 2 H), 4.13-4.04 (m, 2 H), 2.90 (s, 3 H), 1.64 (d, J=6.6 Hz, 3 H), 1.33 (t, J=7.2 Hz, 3 H). LCMS APCI m/z 397 [M+H]⁺.

Preparation of (5R)-8-amino-3-fluoro-5,19-dimethyl-18,19-dihydro-7,11-(metheno)pyrido-[2',1':2,3]imidazo[4,5-h][2,5,11]benzoxadiazacyclotetradecin-20(5H)-one (Example 50)

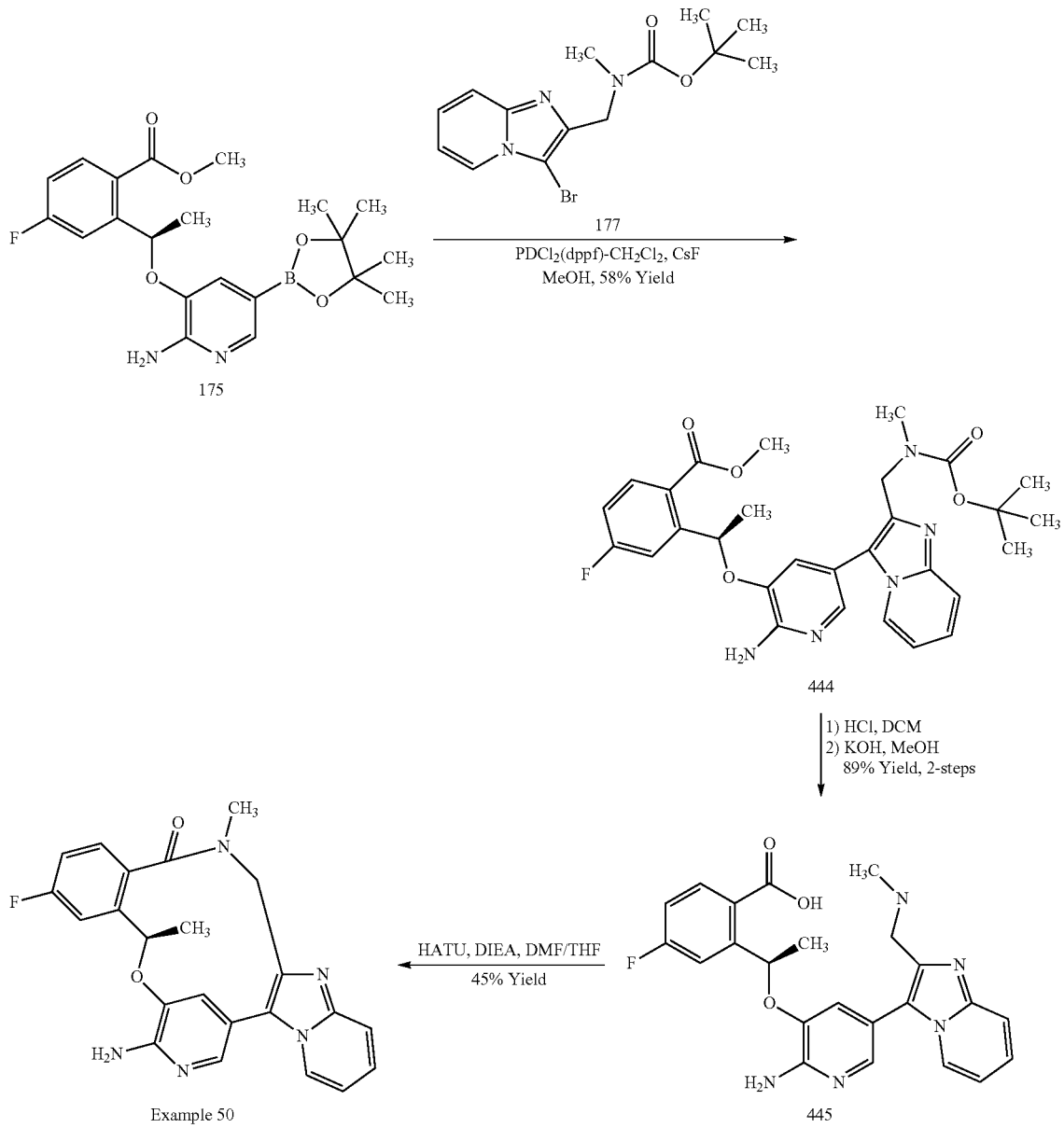

Step 1:

A mixture of compound 175 (355 mg, 0.852 mmol), compound 177 (348 mg, 1.02 mmol) and CsF (388 mg, 2.56 mmol). in MeOH (10 mL) was purged with nitrogen prior to the addition of PdCl$_2$(dppf).CH$_2$Cl$_2$ (35.1 mg, 0.043 mmol). The reaction was heated at 120° C. in the microwave for 1 hour, and then partitioned between EtOAc and brine. The aqueous layer was extracted with EtOAc. The combined organics were washed with brine, dried (MgSO$_4$) and reduced to minimum volume. The residue was purified by column chromatography over silica gel (0-10% MeOH:10% aqueous NH$_4$OH/DCM:EtOAc, 1:1) to afford compound 444 (272 mg, 58%) of the product as a pale orange foam. LCMS m/z 550 [M+H]$^+$.

Step 2:

To a solution of compound 444 (440 mg, 0.801 mmol) in DCM (4 mL) was added HCl (4 mL, 4M in dioxane, 20 mmol). The mixture quickly became cloudy and formed a suspension. The reaction mixture was stirred at room temperature for 4 hours, and then stripped to dryness. The residue azeotroped with MTBE, and dried in a vacuum oven at ~50° C. for 1 hour to give a pale orange solid. The solid was dissolved in MeOH (8 mL) and solid KOH (378 mg, 6.74 mmol) was added. The resulting suspension was stirred at 50° C. overnight. The pH of the resulting suspension was adjusted to 5-6 by drop-wise addition of 6N HCl. The reaction was filtered, and the filtrate concentrated in vacuo. The residue was azeotroped with toluene to afford a brown solid, which was dried in the vacuum over at 50° C. for 1 hour to afford compound 445 (401 mg, 89%), which was used without purification.

Step 3:

To a solution of HATU (439 mg, 1.12 mmol) in DMF/THF (20 mL/4 mL) at 0° C. was added in a dropwise manner a solution of compound 445 (348 mg, 0.8 mmol) and DIEA (0.7 mL, 4 mmol) in DMF/THF (20 mL/4 mL). The addition took 35 minutes. After addition, the resulting mixture was stirred at 0° C. for 20 minutes. The mixture was poured into aqueous NaHCO$_3$ (400 mL). The mixture was filtered, and filtrate was extracted with EtOAc (3x). The combined EtOAc layers were washed with water, (2x), brine (1x), dried over MgSO$_4$ and concentrated in vacuo to give a residue, which was purified by column chromatography over silica gel (0-10% Methanol/DCM:EtOAc 1:1). The desired fractions were concentrated in vacuo to give a residue, which was triturated with MTBE to afford Example 50 (164 mg, 45%) as an off-white solid. $^1$H NMR (400 MHz, DMSO-d$_6$) δ 8.52 (d, 1 H), 7.79 (d, J=1.52 Hz, 1 H), 7.59-7.70 (m, 2 H), 7.46 (dd, J=8.59, 5.81 Hz, 1 H), 7.28 (ddd, J=9.03, 6.76, 1.14 Hz, 1 H), 7.17 (td, J=8.46, 2.78 Hz, 1 H), 6.94 (td, J=6.82, 1.01 Hz, 1 H), 6.89 (d, J=1.52 Hz, 1 H), 6.18 (s, 2 H), 5.62-5.82 (m, 1H), 4.47 (d, J=13.89 Hz, 1 H), 4.31 (d, J=13.89 Hz, 1 H), 3.06 (s, 3 H), 1.69 (d, J=6.32 Hz, 3H). LCMS APCI m/z 418 [M+H]$^+$.

Preparation of (10R)-7-amino-12-fluoro-3-methoxy-10,16-dimethyl-16,17-dihydro-8,4-(azeno)[1,2]thiazolo[4,3-h][2,5,11]benzoxadiazacyclotetradecin-15 (10 H)-one (Example 51)

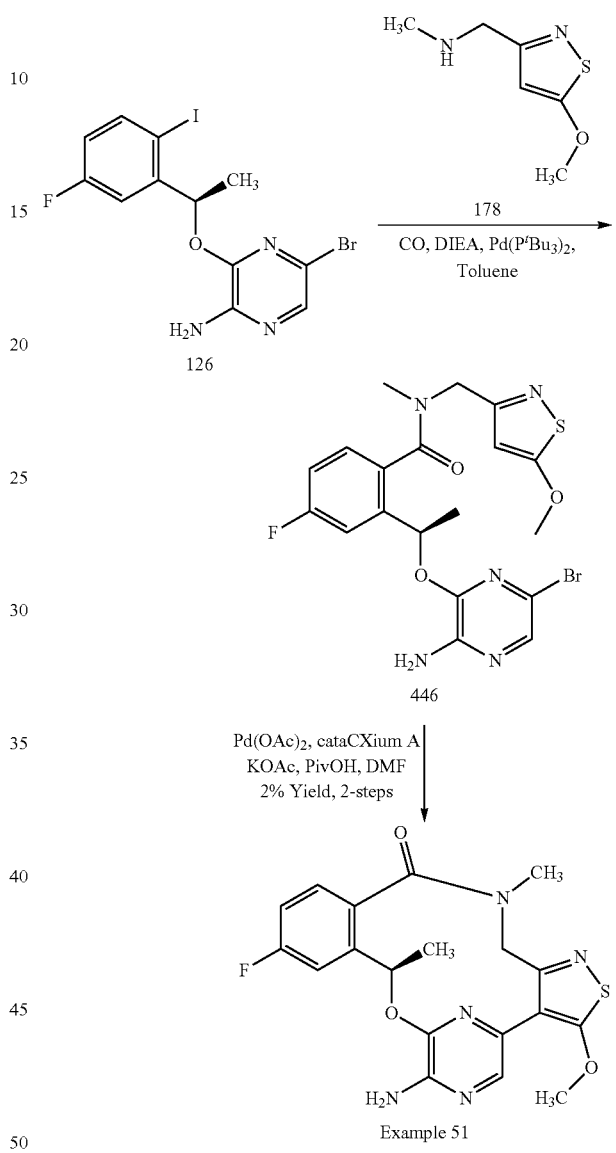

Example 51

Step 1:
Compound 126 (442 mg, 1.01 mmol), compound 178 (197 mg, 1.01 mmol), DIPEA (0.704 mL, 4.04 mmol), Pd (P$^t$Bu$_3$)$_2$ (52.7 mg, 0.101 mmol) were dissolved in toluene (20 mL) in a stainless steel vessel. The reactor was pressurized to 4 bar of CO, and heated to 85° C. for 14 hours. The reaction mixture was diluted with EtOAc, washed with water, saturated aqueous NH$_4$Cl, and brine. The organics were dried (MgSO$_4$), and concentrated. The residue of compound 446 was used in the next step without further purification. LCMS APCI m/z 497 [M+H]$^+$.
Step 2:
Compound 446 (440 mg, 0.886 mmol), KOAc (435 mg, 4.43 mmol), pivalic acid (22.9 mg, 0.222 mmol) were combined in DMF (9 mL) and the solution purged with nitrogen.

Pd(OAc)$_2$ (20 mg, 0.089 mmol) and cataCXium A (65.4 mg, 0.177 mmol) were then added, and the reaction heated to 120° C. for 60 minutes in the microwave. The reaction was diluted with EtOAc, washed with water and brine, dried (MgSO$_4$), filtered and concentrated. Purification by reverse phase HPLC afforded Example 51 (5.2 mg, 2%) as a colorless solid. $^1$H NMR (400 MHz, DMSO-d$_6$) δ 7.71 (s, 1 H), 7.51 (dd, J=2.5, 10.1 Hz, 1 H), 7.38 (dd, J=5.8, 8.6 Hz, 1 H), 7.14 (dt, J=2.5, 8.6 Hz, 1 H), 6.50 (s, 2 H), 5.99-5.85 (m, 1 H), 4.36 (d, J=12.8 Hz, 1 H), 4.18 (d, J=12.8 Hz, 1 H), 4.08 (s, 3 H), 2.94 (s, 3 H), 1.63 (d, J=6.5 Hz, 3 H). LCMS APCI m/z 416 [M+H]$^+$.

Preparation of 7-amino-14-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Example 52 and 53)

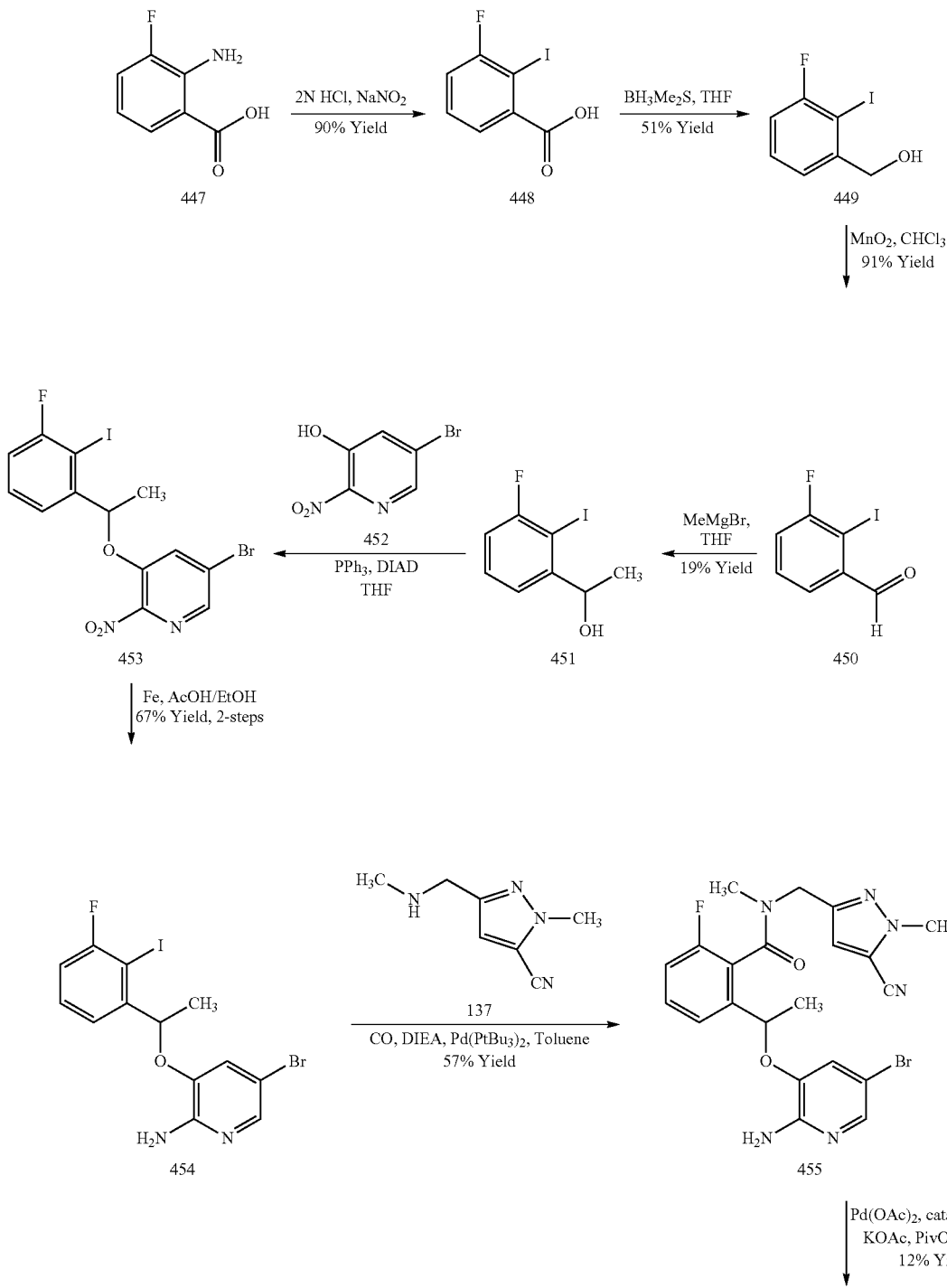

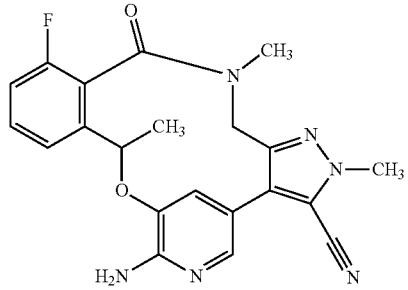

Examples 52/53

Step 1:

To a cooled (0° C.) solution of compound 447 (2.5 g, 166 mmol) in 2N aqueous HCl (32 mL) was added a solution of NaNO₂ (1.14 g, 16.1 mmol) in water 16 mL, maintaining the internal temperature at 0-5° C. After the addition was complete, the mixture was stirred at 0° C. for 1.5 hours This solution was then added dropwise (maintaining the internal T<10° C.), to a mixture of KI (5.35 g, 32.2 mmol) and CuI (1.54 g, 8.06 mmol) in water (16 mL). The ice bath was removed and the reaction was stirred overnight. The mixture was filtered, and the resulting solids were slurried in MTBE and heated to 40° C. for 1 hour. The solids were filtered again, then and the filtrates concentrated to give compound 448 (3.86 g, 90%) as an orange solid. ¹H NMR (400 MHz, DMSO-d₆) δ 13.51 (br. s., 1 H), 7.53-7.44 (m, 2 H), 7.43-7.32 (m, 1 H).

Step 2:

To a cooled (0° C.) solution of the compound 448 (3.8 g, 14 mmol) in THF (30 mL) was added BH₃·Me₂S (28.6 mL. 1M in THF, 28.6 mmol). The ice bath was removed and the solution was heated to 60° C. for three hours. The reaction was cooled to room temperature, and quenched with saturated aqueous NH₄Cl. The reaction was extracted with EtOAc (2×), and the combined organics washed with brine, dried (MgSO₄), filtered and concentrated. The residue was purified by column chromatography over silica gel (0-50% EtOAc/heptanes) to afford compound 449 (1.82 g, 51%) as a white solid. ¹H NMR (400 MHz, DMSO-d₆) δ 7.42 (dt, J=5.9, 7.9 Hz, 1 H), 7.31 (d, J=7.6 Hz, 1 H), 7.14 (t, J=8.1 Hz, 1 H), 5.53 (t, J=5.7 Hz, 1 H), 4.45 (d, J=5.0 Hz, 2H).

Step 3:

To a solution of the compound 449 (1.82 g, 7.22 mmol) in CHCl₃ (40 mL) was added activated MnO₂ (3.77 g, 43.3 mmol). The mixture was heated to 50° C. overnight, filtered through a glass filter, and concentrated to afford compound 450 (1.65 g, 91%) as a yellow solid, which was used without further purification. ¹H NMR (400 MHz, DMSO-d₆) δ 10.00 (s, 1 H), 7.66-7.61 (m, 1 H), 7.61-7.56 (m, 2 H).

Step 4:

To a cooled (−78° C.) solution of compound 450 (1.65 g, 6.6 mmol) in THF (33 mL) was added MeMgBr (6.6 mL, 3 M in diethyl ether, 19.8 mmol). The reaction was stirred for 2 hours, quenched with saturated aqueous NH₄Cl, and then extracted with EtOAc (2×). The organics were dried over MgSO₄, filtered and concentrated to an orange brown gum. This residue was purified by column chromatography over silica gel (0-25% EtOAc/heptane) to afford compound 451 (330 mg, 19%) as a white solid. ¹H NMR (400 MHz, DMSO-d₆) δ 7.45-7.34 (m, 2 H), 7.13 (dt, J=1.8, 7.9 Hz, 1 H), 5.49 (d, J=4.3 Hz, 1 H), 4.90-4.81 (m, 1 H), 1.27 (d, J=6.3 Hz, 3 H).

Step 5:

To a solution of compound 452 (302 mg, 1.38 mmol) and compound 451 (333 mg, 1.25 mmol) in THF (6 mL)was added a solution of PPh₃ (410 mg, 1.56 mmol) and DIAD (330 mg, 1.56 mmol) in THF (6 mL). The reaction was stirred at room temperature for 12 hours, concentrated and purified by column chromatography over silica gel (0-25% EtOAc/heptane) to afford compound 453 (379 mg, 69%) as a colorless solid. The material contained 10-15% of reduced DIAD, but was used without further purification in the next step. ¹H NMR (400 MHz, DMSO-d₆) δ 8.29 (d, J=1.8 Hz, 1 H), 7.87 (d, J=1.8 Hz, 1 H), 7.48 (dt, J=5.9, 8.0 Hz, 1 H), 7.30-7.23 (m, 2 H), 5.92 (q, J=6.3 Hz, 1 H), 1.61 (d, J=6.3 Hz, 3 H).

Step 6:

A mixture of compound 453 (379 mg, 0.811 mmol) and iron (453 mg, 8.11 mmol) in AcOH/EtOH (5.4 mL/5.4 mL) was heated to 80° C. The reaction was complete after 1.5 hours. Water was added, and the reaction neutralized with solid Na₂CO₃. The reaction was extracted with EtOAc (2×), dried (MgSO₄), filtered and concentrated. The residue was purified by column chromatography over silica gel (0-50% EtOAc/heptane) to afford compound 454 (235 mg, 67%) as a white solid. ¹H NMR (400 MHz, DMSO-d₆) δ 7.52 (d, J=2.0 Hz, 1 H), 7.47-7.37 (m, 1 H), 7.32 (dd, J=1.5, 7.8 Hz, 1 H), 7.20 (dt, J=1.5, 8.1 Hz, 1 H), 6.68 (d, J=2.0 Hz, 1 H), 6.14 (s, 2H), 5.54 (q, J=6.4 Hz, 1 H), 1.56 (d, J=6.3 Hz, 3 H). LCMS m/z 436/438 [M+H]⁺.

Step 7:

Compound 454 (230 mg, 0.526 mmol), compound 137 (103 mg, 0.552 mmol), DIEA (0.366 mL, 2.1 mmol), Pd(PʳBu₃)₂ (27.6 mg, 0.053 mmol) were dissolved in toluene (20 mL) in a stainless steel vessel. The reactor was pressurized to 4 bar of CO, and heated to 85° C. for 14 hours. The reaction mixture was shown not to be complete, and Pd(PʳBu₃)₂ (27.6 mg, 0.053 mmol) was again added, and the reaction heated at 85° C. under 4 bar of CO for a further 4 hours. The reaction was diluted with EtOAc, washed with water, saturated aqueous NH₄Cl, and brine. The organics were dried (MgSO₄), and concentrated. The residue was purified by column chromatography over silica gel (0-75% EtOAc/heptane, then 0-10% MeOH/DCM) to afford compound 455 (198 mg, 57%) as a yellow solid.

Step 8:

Compound 455 (198 mg, 0.406 mmol), KOAc (199 mg, 2.03 mmol), pivalic acid (10.5 mg, 0.102 mmol) were combined in t-amylalcohol (6.44 mL) and water (7.3 μL). The solution purged with nitrogen. Pd(OAc)₂ (5.6 mg, 0.025 mmol) and cataCXium A (18.9 mg, 0.0510 mmol) were then added, and the reaction heated to 150° C. for 60 minutes in the microwave. The reaction was diluted with EtOAc, washed with water and brine, dried (MgSO₄), filtered and concentrated. The residue was purified by column chromatography over silica gel (0-10% MeOH/DCM) to afford Examples 52 and 53 as a mixture of enantiomers (20 mg, 12%), which were subjected to chiral separation by SFC to afford both enantiomers of the title compound. The analytical chiral separation by SFC was performed using a Regis Whelk-01 (R,R) column (4.6 mm×250 mm column, 5 micron particle size), which was eluted with 20% MeOH in CO$_2$ held at 25° C. at 140 bar. A flow rate of 3 mL/min gave Rt$_{(Peak\ 1)}$=1.28 minutes and Rt$_{(Peak\ 2)}$=1.78 minutes.

Example 52 (Peak 1): 5.56 mg, >99% ee, 8.3% yield. $^1$H NMR (400 MHz, DMSO-d$_6$) δ 7.66-7.46 (m, 3 H), 7.22 (t, J=8.6 Hz, 1 H), 6.90 (s, 1 H), 6.18 (s, 2 H), 5.55 (q, J=5.9 Hz, 1 H), 4.36 (d, J=14.1 Hz, 1 H), 4.24-4.16 (m, 1 H), 4.04 (s, 3 H), 3.02 (s, 3 H), 1.67 (d, J=6.0 Hz, 3 H). LCMS ES m/z 407 [M+H]$^+$.

Example 53 (Peak 2): 5.06 mg, 90% ee, 7.6% yield. $^1$H NMR (400 MHz, DMSO-d$_6$) δ 7.62-7.55 (m, 2 H), 7.54-7.47 (m, 1 H), 7.22 (t, J=8.8 Hz, 1 H), 6.90 (s, 1 H), 6.18 (s, 2 H), 5.55 (q, J=6.1 Hz, 1 H), 4.36 (d, J=14.1 Hz, 1 H), 4.24-4.15 (m, 1 H), 4.04 (s, 2 H), 3.02 (s, 2 H), 1.67 (d, J=6.3 Hz, 2 H). LCMS ES m/z 407 [M+H]$^+$.

Preparation of (10R)-7-amino-16-cyclopropyl-12-fluoro-2,10-dimethyl-15-oxo-10,15,16,17-tetrahydro-2H-8,4-(azeno)pyrazolo[4,3-h][2,5,11]benzoxadiazacyclotetradecine-3-carbonitrile (Example 54)

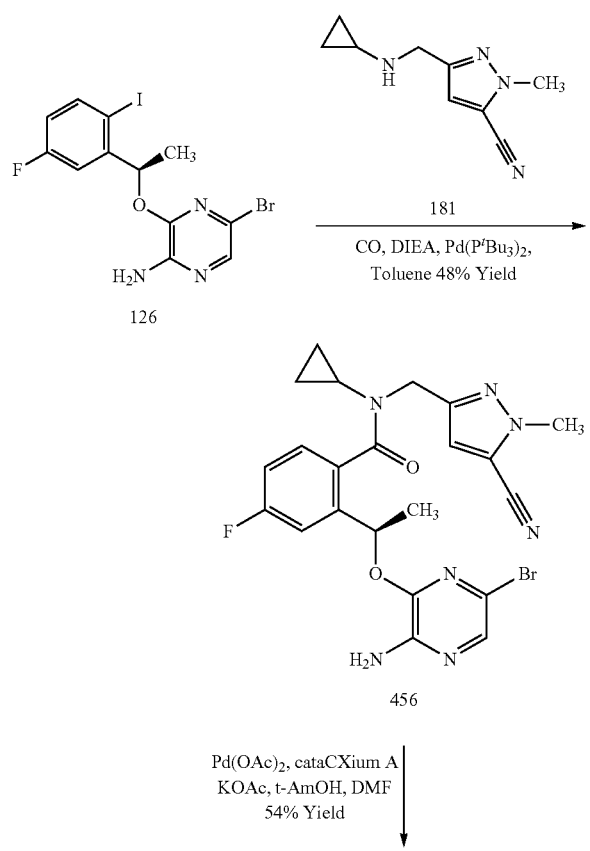

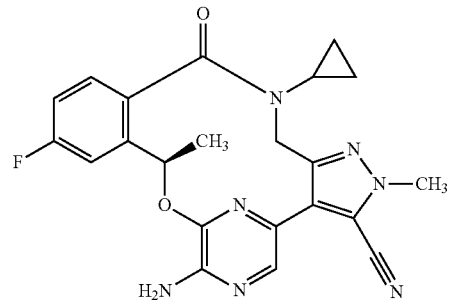

Example 54

Step 1:

Compound 126 (300 mg, 0.685 mmol), compound 181 (146 mg, 0.685 mmol), DIEA (0.597 mL, 3.42 mmol), Pd(P$^t$Bu$_3$)$_2$ (36 mg, 0.069 mmol) were dissolved in toluene (20 mL) in a stainless steel vessel. The reactor was pressurized to 4 bar of CO, and heated to 85° C. for 14 hours. The reaction mixture was concentrated, and subjected to column chromatography over silica gel (0-75% EtOAc/heptane) to afford compound 456 (168 mg, 48%) as a cream solid. $^1$H NMR (400 MHz, 80° C., DMSO-d$_6$) δ 7.63-7.50 (m, 2 H), 7.47-7.36 (m, 1 H), 7.14 (dt, J=2.8, 8.6 Hz, 1 H), 7.01 (s, 1 H), 6.41 (br. s., 2 H), 6.17 (d, J=5.5 Hz, 1 H), 4.74-4.48 (m, 2 H), 3.97 (s, 3 H), 2.83 (br. s., 1 H), 1.59 (d, J=6.5 Hz, 3 H), 0.57 (br. s., 4 H).

Step 2:

A mixture of compound 456 (165 mg), pivalic acid (9.9 mg, 0.096 mmol) and KOAc (158 mg, 1.6 mmol) in t-AmOH (8.68 mL) with 1 drop of water added was purged with nitrogen for 10 minutes. CataCXium A (35.5 mg, 0.096 mmol) and Pd(OAc)$_2$ (10.8 mg, 0.048 mmol) were added, and the vial heated to 140° C. for 1 hour in the microwave. The reaction was concentrated, and purified by column chromatography over silica gel (0-100% EtOAc/heptane). Fractions containing the desired product were slurried in water, filtered and dried in the vacuum oven to afford Example 54 (75 mg, 54%) as a cream solid. $^1$H NMR (400 MHz, DMSO-d$_6$) δ 7.74 (s, 1 H), 7.47 (dd, J=2.5, 10.1 Hz, 1 H), 7.31 (dd, J=5.8, 8.6 Hz, 1 H), 7.12 (dt, J=2.6, 8.5 Hz, 1 H), 6.71 (s, 2 H), 6.16-6.05 (m, 1 H), 4.33-4.26 (m, 1 H), 4.22-4.15 (m, 1 H), 4.02 (s, 3 H), 2.16-2.06 (m, 1 H), 1.66 (d, J=6.5 Hz, 3 H), 1.11-1.00 (m, 1 H), 0.97-0.84 (m, 1 H), 0.81-0.71 (m, 1 H), 0.70-0.61 (m, 1 H). LCMS APCI m/z 434 [M+H]$^+$.

Preparation of (10R)-7-amino-16-cyclopropyl-12-fluoro-2,10-dimethyl-15-oxo-10,15,16,17-tetrahydro-2H-8,4-(metheno)pyrazolo[4,3-h][2,5,11]benzoxadiazacyclotetradecine-3-carbonitrile (Example 55)

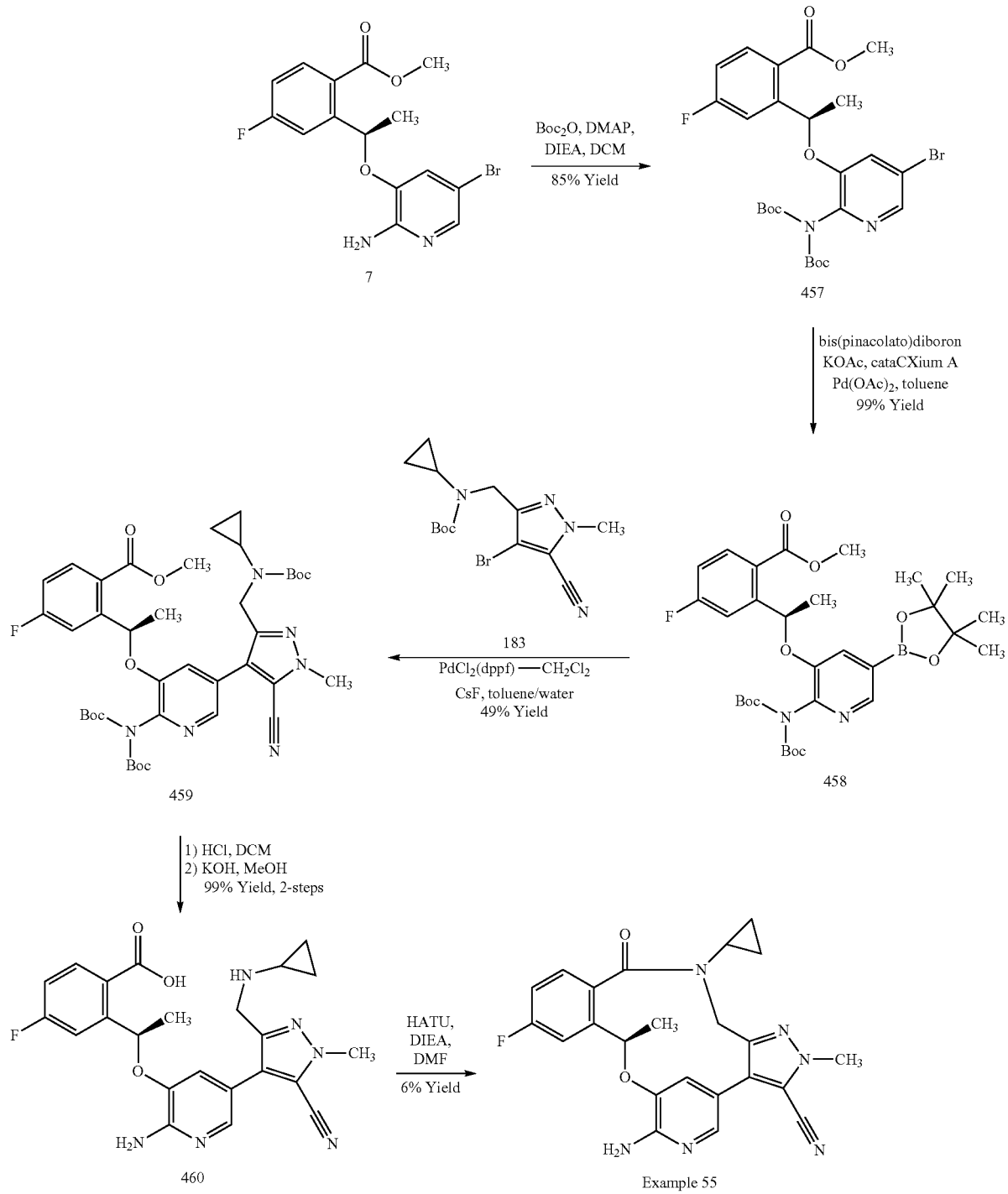

Step 1:

To a solution of compound 7 (30 g, 81.3 mmol) in DCM (325 mL) was added DIEA (42.5 mL, 244 mmol), DMAP (1.99 g, 16.3 mmol) and (Boc)₂O (53.2 g, 244 mmol). The reaction was stirred overnight, and then concentrated. Purification by column chromatography over silica gel (0-25% EtOAc/heptane) afforded compound 457 (39.3 g, 85%) as a viscous gum. $^1$H NMR (400 MHz, 30° C., DMSO-d$_6$) δ 8.16 (d, J=2.0 Hz, 1 H), 8.00 (dd, J=5.9, 8.7 Hz, 1 H), 7.53 (d, J=2.0 Hz, 1 H), 7.35-7.25 (m, 2 H), 6.38-6.26 (m, 1 H), 3.91 (s, 3 H), 1.55 (d, J=6.3 Hz, 3 H), 1.38 (s, 18 H). LCMS APCI m/z 469 [M−Boc]⁺.

Step 2:

A mixture of the compound 457 (22 g, 39 mmol), bis(pinacolato)diboron (10.8 g, 42.5 mmol) and KOAc (11.4 g, 116 mmol) in toluene (260 mL) was bubbled with nitrogen for 30 min before addition of cataCXium A (1.43 g, 3.86 mmol) and Pd(OAc)$_2$ (434 mg, 1.93 mmol). The reaction was heated to 100° C. using an oil bath for 16 hours. The reaction was allowed to cool, and diluted with EtOAc. The organics were washed with water (2×) and brine, dried (MgSO$_4$), filtered and concentrated. Purification by column chromatography over silica gel (0-10% MeOH/DCM) afforded compound 458 (24.9 g, 99%) as a yellow viscous gum. $^1$H NMR (400 MHz, DMSO-d$_6$) δ 8.17 (d, J=1.3 Hz, 1 H), 8.01 (dd, J=6.0, 8.8 Hz, 1 H), 7.92 (s, 1 H), 7.37 (s, 1 H), 7.36-7.25 (m, 2 H), 6.38 (q, J=6.0 Hz, 1 H), 3.92 (s, 3 H), 1.54 (d, J=6.3 Hz, 3 H), 1.37 (s, 18 H), 1.27 (d, J=5.5 Hz, 12 H).

Step 3:

A mixture of compound 458 (684 mg, 0.887 mmol), compound 183 (315 mg, 0.887 mmol), and cesium fluoride (404 mg, 2.66 mmol) in toluene/water (6 mL/0.2 mL) were flushed with nitrogen. PdCl$_2$(dppf).CH$_2$Cl$_2$ (73 mg, 0.089 mmol) was added, and the mixture heated to reflux for 16 hours. The reaction was cooled, diluted with EtOAc, washed with water and brine, dried (MgSO$_4$) and concentrated. Purification of the residue by column chromatography over silica gel (0-50% EtOAc/heptane) afforded compound 459 (332 mg, 49%) as a glassy solid. $^1$H NMR (400 MHz, DMSO-d$_6$) δ 8.11 (d, J=2.0 Hz, 1 H), 7.98 (dd, J=5.8, 8.8 Hz, 1 H), 7.36 (dd, J=2.8, 10.3 Hz, 1 H), 7.27-7.19 (m, 2 H), 6.35 (q, J=6.0 Hz, 1 H), 4.36-4.26 (m, 1 H), 4.18-4.10 (m, 1 H), 4.01 (s, 3 H), 3.90 (s, 3 H), 2.43-2.33 (m, 1 H), 1.61 (d, J=6.3 Hz, 3 H), 1.43 (s, 18 H), 1.30 (s, 9 H), 0.61-0.35 (m, 4 H).

Step 4:

To a cooled (0° C.) solution of the compound 459 (330 mg, 0.431 mmol) in DCM (2.16 mL) was added HCl (2.16 mL, 4M in dioxane, 8.63 mmol). The reaction was stirred at room temperature for 2 hours then concentrated. The residue was dissolved in MeOH (2 mL), and KOH (0.242 g, 4.31 mmol) added. The reaction was heated at 50° C. for 48 hours. After being cooled to 0° C., the reaction was neutralized with concentrated HCl. The solids were filtered, and the filtrate concentrated and dried in the vacuum oven. This residue was dissolved in methanol, filtered again, concentrated and dried to afford compound 460 (272 mg, 99%), which was used without further purification. LCMS APCI m/z 451 [M+H]$^+$.

Step 5:

To a cooled (0° C.) solution of HATU (186 mg, 0.474 mmol) in DMF (8.5 mL) was added in a dropwise fashion a solution of compound 460 (200 mg, 0.431 mmol) and DIEA (375 μL, 2.16 mmol) in DMF (8.5 mL). On completion of addition, the reaction was allowed to warm to room temperature, and stirred for 14 hours. The reaction was then concentrated, and the residue dissolved in EtOAc. The organics were washed with saturated aqueous Na$_2$CO$_3$ (2×) and brine, dried (MgSO$_4$), filtered and concentrated. The reaction was purified by column chromatography over silica gel (25-100% EtOAc/heptane). Fractions containing the desired product were concentrated, and slurried in water. The solids were filtered, and dried in the vacuum oven overnight to afford Example 55 (11 mg, 6%) as a cream solid. $^1$H NMR (400 MHz, DMSO-d$_6$) δ 7.60 (dd, J=2.6, 10.2 Hz, 1 H), 7.56 (d, J=1.8 Hz, 1 H), 7.39 (dd, J=5.8, 8.6 Hz, 1 H), 7.15 (dt, J=2.5, 8.4 Hz, 1 H), 6.74 (d, J=1.3 Hz, 1 H), 6.17 (s, 2 H), 5.86-5.70 (m, 1 H), 4.47 (d, J=14.4 Hz, 1 H), 4.06-3.98 (m, 4 H), 2.40-2.23 (m, 1 H), 1.69 (d, J=6.3 Hz, 3 H), 1.19-1.08 (m, 1 H), 0.99-0.87 (m, 1 H), 0.79 (td, J=7.2, 14.5 Hz, 1 H), 0.75-0.64 (m, 1 H). LCMS APCI m/z 433 [M+H]$^+$.

Preparation of (10R)-7-amino-12-fluoro-2,10,16-trimethyl-16,17-dihydro-2H-8,4-(azeno)pyrazolo[4,3-h][2,5,11]benzoxadiazacyclotetradecin-15(10H)-one (Example 56)

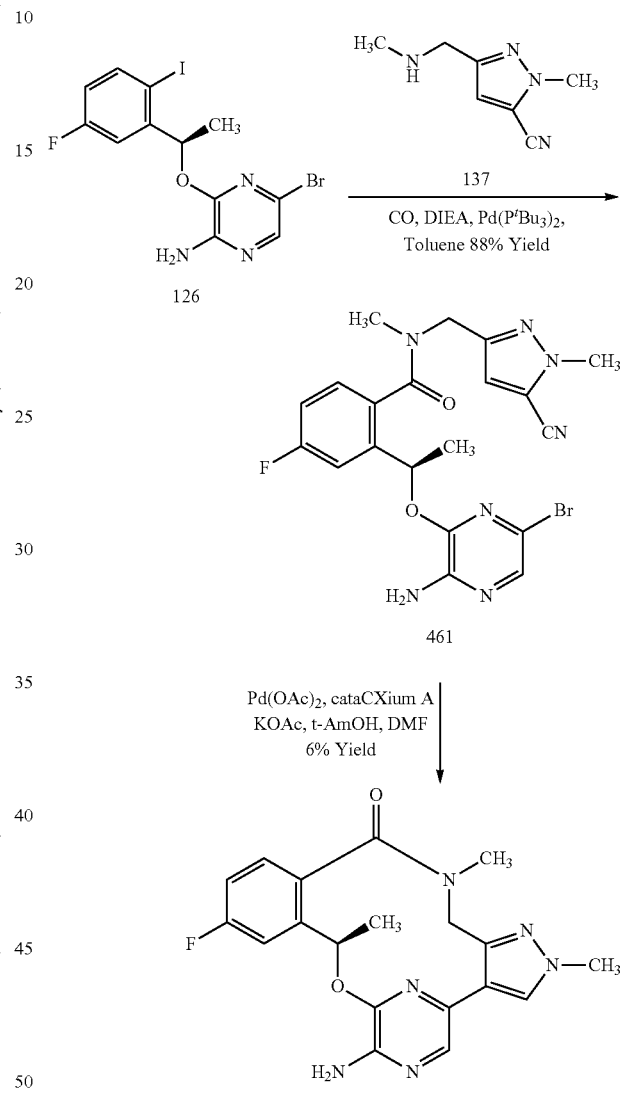

Example 56

Step 1:

A mixture of compound 126 (8.5 g, 19 mmol), compound 137 (3.69 g, 19.8 mmol), DIEA (13.5 mL, 77.6 mmol) and Pd(P$^t$Bu$_3$)$_2$ (1.01 g, 1.94 mmol) in toluene (320 mL) was heated to 85° C. under 4 bar of CO pressure for 4 hours. The reaction was cooled, concentrated, and purified by column chromatography over silica gel (0-60% EtOAc/heptane) to afford compound 461 (8.25 g, 88%) as a white solid. LCMS APCI m/z 488/490 [M+H]$^+$.

Step 2:

Compound 461 (10.23 g, 20.95 mmol), KOAc (10.3 g, 105 mmol), cataCXium A (968 mg, 2.62 mmol), and Pd(OAc)$_2$ (294 mg, 1.31 mmol) were combined with t-amylalcohol (300 mL) in a 500 mL stainless steel vessel. The reaction was sealed, and heated to 120° C. for 16 hours. The reaction was allowed to cool, and the vessel opened. The mixture was diluted with EtOAc, washed with water, dried ($Na_2SO_4$), and the solvent evaporated. The residue was purified by column chromatography over silica gel (1-6% MeOH/EtOAc) to afford Example 56 (415 mg, 6%) as a yellow solid. $^1$H NMR (400 MHz, $CDCl_3$) δ 7.60 (s, 1 H), 7.55 (s, 1 H), 7.18-7.30 (m, 2H), 6.97 (td, J=8.27, 2.65 Hz, 1 H), 6.07 (dd, J=6.57, 1.77 Hz, 1 H), 4.95 (s, 2 H), 4.60 (d, J=13.39 Hz, 1 H), 4.20 (d, J=13.14 Hz, 1 H), 3.91 (s, 3 H), 3.04 (s, 3 H), 1.38 (d, J=12.38 Hz, 3H). LCMS APCI m/z 383 [M+H]$^+$.

Preparation of (5R)-8-amino-3-fluoro-5,14,19-trimethyl-18,19-dihydro-7,11-(metheno)-pyrimido[2',1': 2,3]imidazo[4,5-h][2,5,11]benzoxadiazacyclotetradecin-20(5H)-one (Example 57)

Step 2:
Compound 463 (280 mg, 0.37 mmol) was dissolved in DCM (2 mL), and HCl (2 mL, 4M in dioxane, 7.32 mmol) was added. The reaction was stirred for 38 hours at room temperature. The reaction was then concentrated, the residue dissolved in methanol (2 mL), and KOH (0.205 g, 3.66 mmol) added. The reaction was heated to 60° C. for 6 hours, cooled and neutralized with concentrated HCl. The solids were filtered, and the filtrate concentrated, and dried overnight in the vacuum oven to afford compound 307 as an orange-brown solid, which was used without further purification.

Step 3:
To a cooled (0° C.) solution of HATU (158 mg, 0.403 mmol) in DMF (7.3 mL) was added a solution of compound

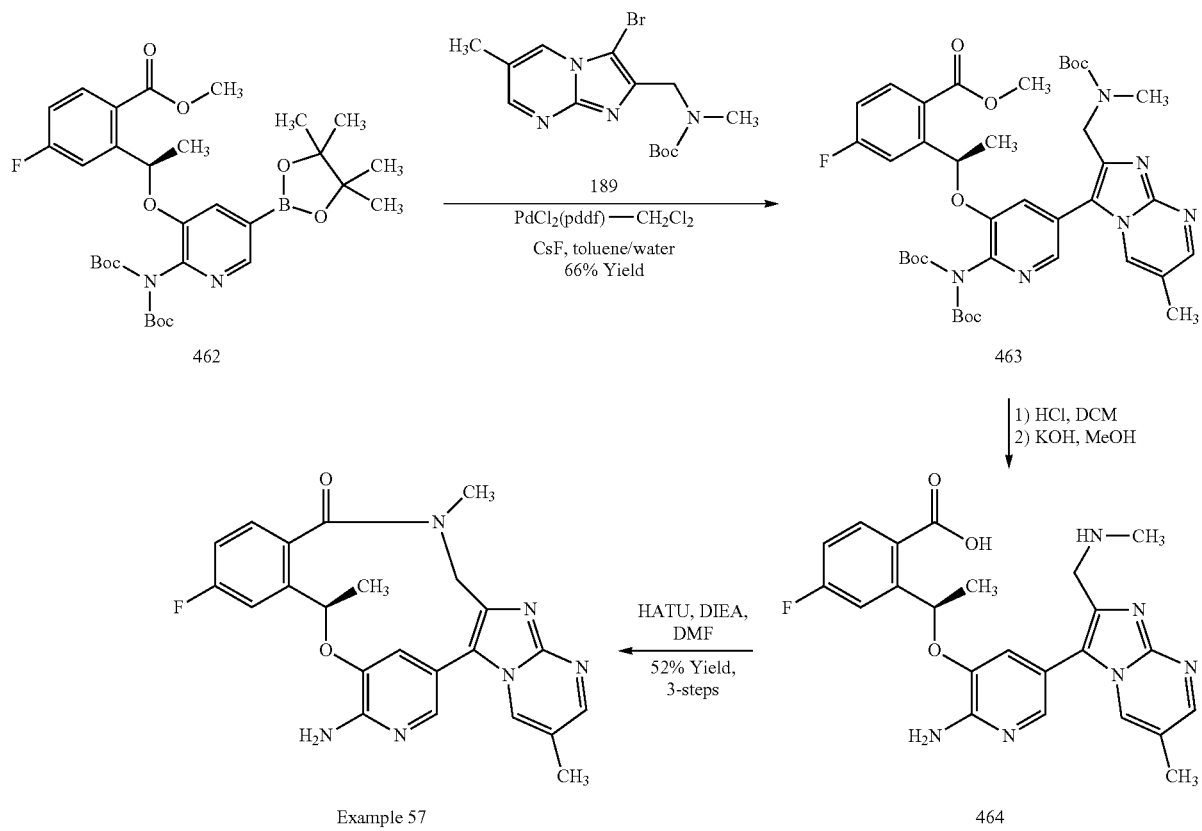

Step 1:
Compound 462 (489 mg, 0.56 mmol), compound 189 (197 mg, 0.56 mmol), cesium fluoride (253 mg, 1.66 mmol) were combined in toluene/water (3.7 mL/370 µL), and nitrogen was flushed through the mixture. $PdCl_2(dppf).CH_2Cl_2$ (45.7 mg, 0.056 mmol) was added, and the reaction mixture refluxed for 14 hours. The reaction was allowed to cool, diluted with EtOAc, washed with water (2×) and brine, dried ($MgSO_4$) filtered and concentrated. Purification by column chromatography over silica gel (0-100% EtOAc/heptane) afforded compound 463 (280 mg, 66%) as a viscous gum. $^1$H NMR (400 MHz, DMSO-$d_6$) δ 8.46 (s, 1H), 8.20 (s, 2H), 7.97 (dd, J=6.2, 8.7 Hz, 1H), 7.44-7.33 (m, 2H), 7.28-7.21 (m, 1H), 6.41-6.30 (m, 1H), 4.45-4.25 (m, 1H), 3.82 (s, 3H), 2.74 (s, 3H), 2.28 (s, 3H), 1.61 (d, J=6.3 Hz, 3H), 1.47 (s, 18H), 1.30 (br. s., 9H).

464 (165 mg, 0.366 mmol) and DIEA (0.319 mL, 1.83 mmol in DMF (7.3 mL). The reaction was allowed to warm to room temperature, and stirred for 14 hours. The mixture was diluted with EtOAc, washed with saturated aqueous $NH_4Cl$ (3×), saturated aqueous $Na_2CO_3$ (3×), brine, dried ($MgSO_4$), filtered and concentrated. The residue was purified by column chromatography over silica gel (25-100% EtOAc/heptane then 0-10% MeOH/DCM) to afford Example 57 (83 mg, 52%) as a yellow solid. $^1$H NMR (400 MHz, DMSO-$d_6$) δ 8.79 (dd, J=1.2, 2.1 Hz, 1H), 8.45 (d, J=2.2 Hz, 1H), 7.82 (d, J=1.7 Hz, 1H), 7.66 (dd, J=2.6, 10.3 Hz, 1H), 7.47 (dd, J=5.8, 8.5 Hz, 1H), 7.17 (dt, J=2.7, 8.4 Hz, 1H), 6.88 (d, J=1.6 Hz, 1H), 6.22 (s, 2H), 5.73-5.63 (m, 1H), 4.50 (d, J=13.9 Hz, 1H), 4.31 (d, J=13.8 Hz, 1H), 3.06 (s, 3H), 2.31 (s, 3H), 1.69 (d, J=6.2 Hz, 3H). LCMS APCI m/z 433 [M+H]$^+$.

Preparation of (10R)-7-amino-11-chloro-12-fluoro-1-(2-hydroxyethyl)-3,10,16-trimethyl-16,17-dihydro-1H-8,4-(azeno)pyrazolo[4,3-h][2,5,11]benzoxadiaza-cyclotetradecin-15(10H)-one/(10S)-7-amino-11-chloro-12-fluoro-1-(2-hydroxyethyl)-3,10,16-trimethyl-16,17-dihydro-1H-8,4-(azeno)pyrazolo[4,3-h][2,5,11]benzoxadiazacyclotetradecin-15(10H)-one (Example 58 and 59)
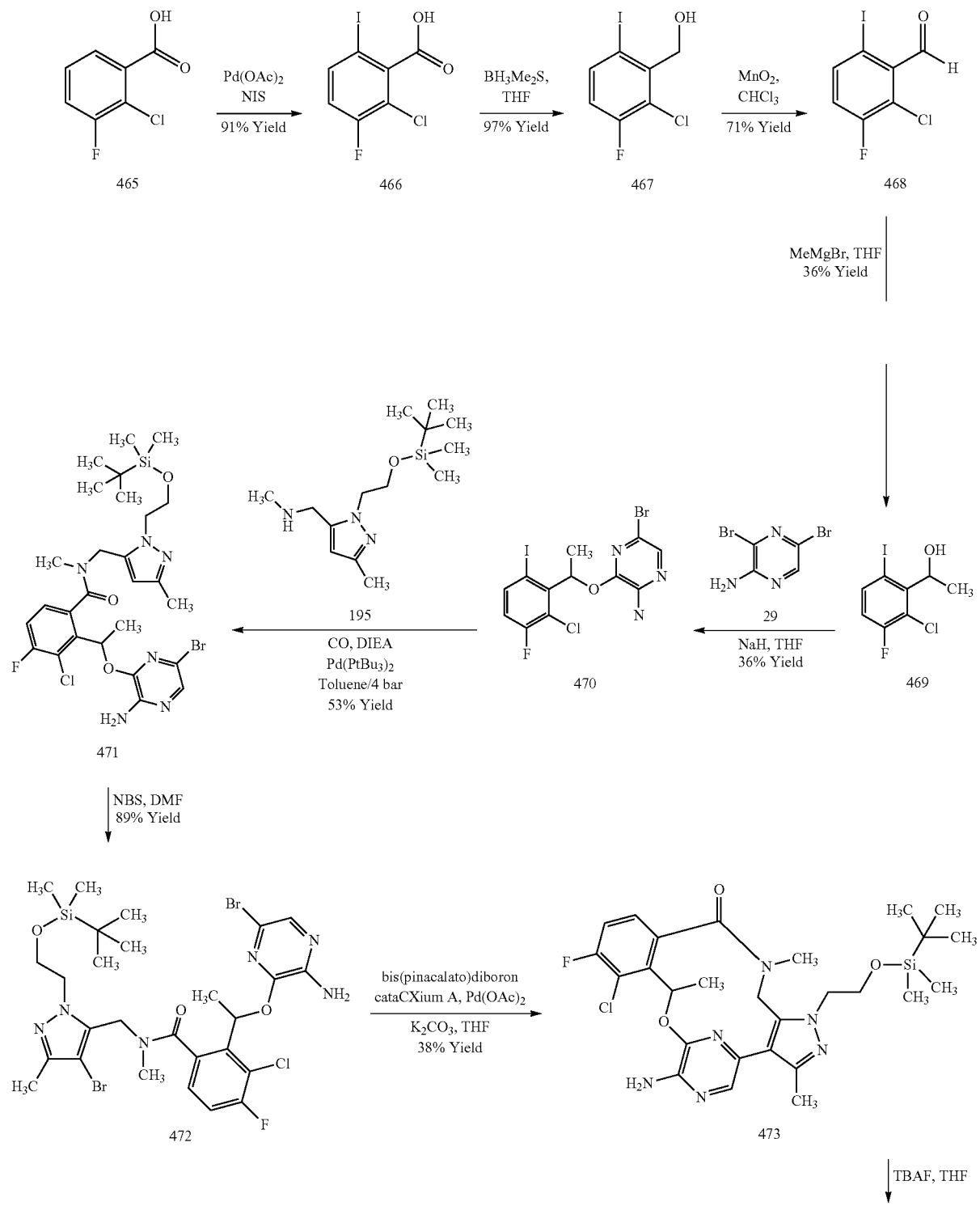

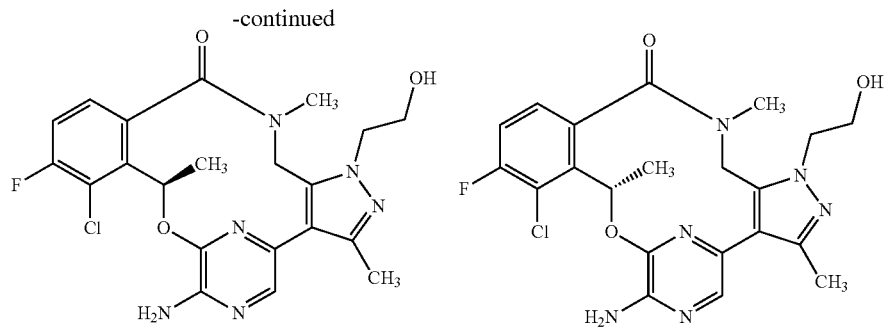

Example 58/59

Step 1:

Pd(OAc)₂ (642 mg, 2.86 mmol) was added to a degassed solution of compound 465 (4.99 g, 28.61 mmol) and NIS (7.08 g, 31.5 mmol) in DMF (143 mL). The resulting solution was stirred at 100° C. for 24 hours. The reaction was filtered, diluted with EtOAc, and the combined organics washed with water (3×), brine (2×) and dried (Na₂SO₄). The solution was filtered, concentrated, and the residue purified by column chromatography over silica gel (0-100% EtOAc/heptane) to afford compound 466 (7.9 g, 91%) as a white solid. ¹H NMR (400 MHz, CDCl₃) δ 7.74 (dd, J=4.58, 8.74 Hz, 1H), 7.00 (t, J=8.56 Hz, 1H).

Step 2:

To a solution of compound 466 (7.26 g, 24.16 mmol) in dry THF (100 mL) was added a solution of BH₃.SMe₂ (5.32 mL, 10 M in THF, 53.2 mmol) in a dropwise fashion at 0° C. under nitrogen.

After the addition was complete, the mixture was stirred at 0° C. for 30 minutes, and then refluxed overnight. The mixture was quenched with saturated aqueous NH₄Cl solution, and the reaction diluted with water and extracted with EtOAc. The combined organic layers were washed with brine, dried (Na₂SO₄) and concentrated. The reaction was purified by column chromatography over silica gel (0-30% EtOAc/heptane) to afford compound 467 (6.7 g, 97%) as a white solid. ¹H NMR (400 MHz, CDCl₃) δ 7.76 (dd, J=5.07, 8.74 Hz, 1H), 6.90 (t, J=8.50 Hz, 1H), 5.00 (d, J=6.97 Hz, 2H), 2.11 (t, J=7.03 Hz, 1H).

Step 3:

To a solution of compound 467 (6.67 g, 23.35 mmol) in CHCl₃ (60 mL) was added activated MnO₂ (135 g, 140 mmol), and the reaction was refluxed (70° C.) for 18 hours. The reaction was not complete, and a further portion of MnO₂ (9 g) and CHCl₃ (5 mL) was added. The reaction was refluxed for a further 12 hours. The reaction was cooled, filtered, and the solids washed with DCM. The organics were dried (Na₂SO₄), filtered and concentrated to afford a yellow solid. This was purified by column chromatography over silica gel (0-20% EtOAc/heptane) to afford compound 468 (4.73 g, 71%) as a yellow solid. ¹H NMR (400 MHz, CDCl₃) δ 10.13 (s, 1H), 7.91 (dd, J=4.77, 8.68 Hz, 1H), 7.07 (t, J=8.44 Hz, 1H).

Step 4:

To a solution of the compound 468 (4.72 g, 16.59 mmol) in dry THF (70 mL) was added MeMgBr (6.08 mL, 3M in diethyl ether, 18.3 mmol) at 0° C. under nitrogen. The reaction was stirred at 0° C. for 10 minutes, and allowed to warm to room temperature. The reaction was quenched with saturated aqueous NH₄Cl, and extracted with EtOAc. The combined organics were washed with brine, dried (Na₂SO₄), filtered and concentrated. The residue was purified by column chromatography over silica gel (0-30% EtOAc/heptane) to afford compound 469 (4.8 g, 96%) as a white solid. ¹H NMR (400 MHz, CDCl₃) δ 7.76 (dd, J=5.26, 8.68 Hz, 1H), 6.81 (t, J=8.50 Hz, 1H), 5.39 (dd, J=6.97, 8.93 Hz, 1H), 2.85 (s, 1H), 1.62 (d, J=6.85 Hz, 3H).

Step 5:

To a solution of the alcohol 469 (4.76 g, 15.85 mmol) in THF (16 mL) was added NaH (697 mg, 17.4 mmol, 60% dispersion). The reaction was stirred for 30 minutes, and then the pyrazine 29 (3.81 g, 15.1 mmol) was added as a solid. The reaction was stirred at 55° C. for 4 hours. The reaction was allowed to cool, diluted with water, and extracted with EtOAc. The organic extracts were dried (Na₂SO₄), filtered and concentrated. Trituration with diethyl ether afforded compound 470 (2.8 g, 37%) as a white solid. The mother liquors were combined, concentrated, and purified by column chromatography over silica gel (0-20% EtOAc/heptane). Trituration of the product containing fractions with diethyl ether afforded a second crop of compound 470 (2.7 g, 36%) as a white solid. ¹H NMR (400 MHz, CDCl₃) δ 7.71-7.86 (m, 1H), 7.61 (s, 1H), 6.82 (t, J=8.72 Hz, 1H), 6.47-6.60 (m, J=6.10 Hz, 1H), 4.91 (br. s., 2H), 1.80 (d, J=6.82 Hz, 3H).

Step 6:

Compound 470 (2.97 g, 6.29 mmol), the pyrazole 195 (1.87 g, 6.61 mmol), DIEA (4.39 mL, 25.2 mmol), and Pd(P$^t$Bu₃)₂ (161 mg, 0.315 mmol) were combined in toluene (63 mL) in a stainless steel vessel. The reaction was heated to 85° C. under 4 bar CO pressure for 16 hours. The vessel was then allowed to cool, and the reaction filtered. The filtrate was concentrated, and the residue subjected to column chromatography over silica gel (0-100% EtOAc/heptane) to afford compound 471 (2.2 g, 53%) as a viscous gum. LCMS APCI m/z 655/660 [M+H]⁺.

Step 7:

To an ice-cooled solution of compound 471 (500 mg, 0.762 mmol) in DMF (15 mL) was added NBS (137 mg, 0.762 mmol). After 10 minutes, the reaction was diluted with EtOAc and saturated aqueous NaHCO₃. The organic was separated, washed with water, dried (Na₂SO₄), filtered and concentrated. The residue was purified by column chromatography over silica gel (0-100% EtOAc/heptane) to afford compound 472 (498 mg, 89%) as a light yellow solid. LCMS APCI m/z 737/740 [M+H]⁺.

Step 8:

To a solution of compound 472 (400 mg, 0.544 mmol), bis(pinacalato)diboron (414 mg, 1.63 mmol) in THF (5.5 mL) was added anhydrous K₂CO₃ (376 mg, 2.72 mmol). The system was flushed with nitrogen, and cataCXium A (50.3 mg, 0.136 mmol) was then added followed by Pd(OAc)₂ (15.3 mg, 0.068 mmol). The reaction was purged again, and stirred at 80° C. for 7 hours. The reaction was 50% complete, and an additional portion of Pd(OAc)₂ (15.3 mg, 0.068 mmol) was added followed by purging with nitrogen. The reaction was heated at 80° C. for another 5 hours. After cooling, the reaction was filtered, concentrated, and the residue subjected to column chromatography over silica gel (0-100% EtOAc/heptane) to afford compound 473 (120 mg, 38%, 80% pure) as a yellow gum. This material was used directly in the next step. LCMS APCI m/z 575/578 [M+H]⁺.

Step 9:

To a solution of compound 473 (120 mg, 0.209 mmol) in THF (5 mL) was added TBAF (0.209 mL, 1M in THF, 0.209 mmol). The reaction was stirred for 2 hours and concentrated. The residue was diluted with DCM, washed with water, dried (Na₂SO₄), and concentrated to afford 155 mg of 80% pure material as a mixture, which was followed by chiral separation by SFC to afford both enantiomers of the title compound. The analytical chiral separation by SFC was performed using a Regis Whelk-01 (R, R) column (4.6 mm×100 mm column, 5 micron particle size), which was eluted with 40% MeOH in CO₂ held at 25° C. at 140 bar. A flow rate of 3 mL/min gave Rt$_{(Peak\ 1)}$=2.62 minutes and Rt$_{(Peak\ 2)}$=3.61 minutes.

Example 58 (Peak 1): 13.7 mg, >99% ee (−), 13% yield. ¹H NMR (400 MHz, DMSO-d₆) δ 7.58 (s, 1H), 7.35-7.48 (m, 2H), 6.20 (s, 2H), 6.08-6.16 (m, J=7.00 Hz, 1H), 4.78-4.89 (m, 1H), 4.60 (d, J=14.43 Hz, 1H), 4.14-4.40 (m, 3H), 3.74-3.81 (m, 1H), 3.65-3.73 (m, 1H), 2.85 (s, 3H), 2.30 (s, 3H), 1.81 (d, J=6.97 Hz, 3H). LCMS APCI m/z 461/464 [M+H]⁺.

Example 59 (Peak 2): 13.9 mg, 97% ee (+), 13% yield. ¹H NMR (400 MHz, DMSO-d₆) δ 7.57 (s, 1H), 7.35-7.49 (m, 2H), 6.20 (s, 2H), 6.12 (q, J=6.72 Hz, 1H), 4.78-4.91 (m, 1H), 4.60 (d, J=14.43 Hz, 1H), 4.15-4.38 (m, 3H), 3.73-3.82 (m, 1H), 3.71 (dd, J=4.03, 7.46 Hz, 1H), 2.84 (s, 3H), 2.30 (s, 3H), 1.81 (d, J=6.85 Hz, 3H). LCMS APCI m/z 461/464 [M+H]⁺.

Preparation of (10R)-7-amino-12-fluoro-2,10,16-trimethyl-15-oxo-10,15,16,17-tetrahydro-2H-8,4-(metheno)pyrazolo[4,3-h][2,5,6,11]benzoxatriazacyclotetradecine-3-carbonitrile (Example 60)

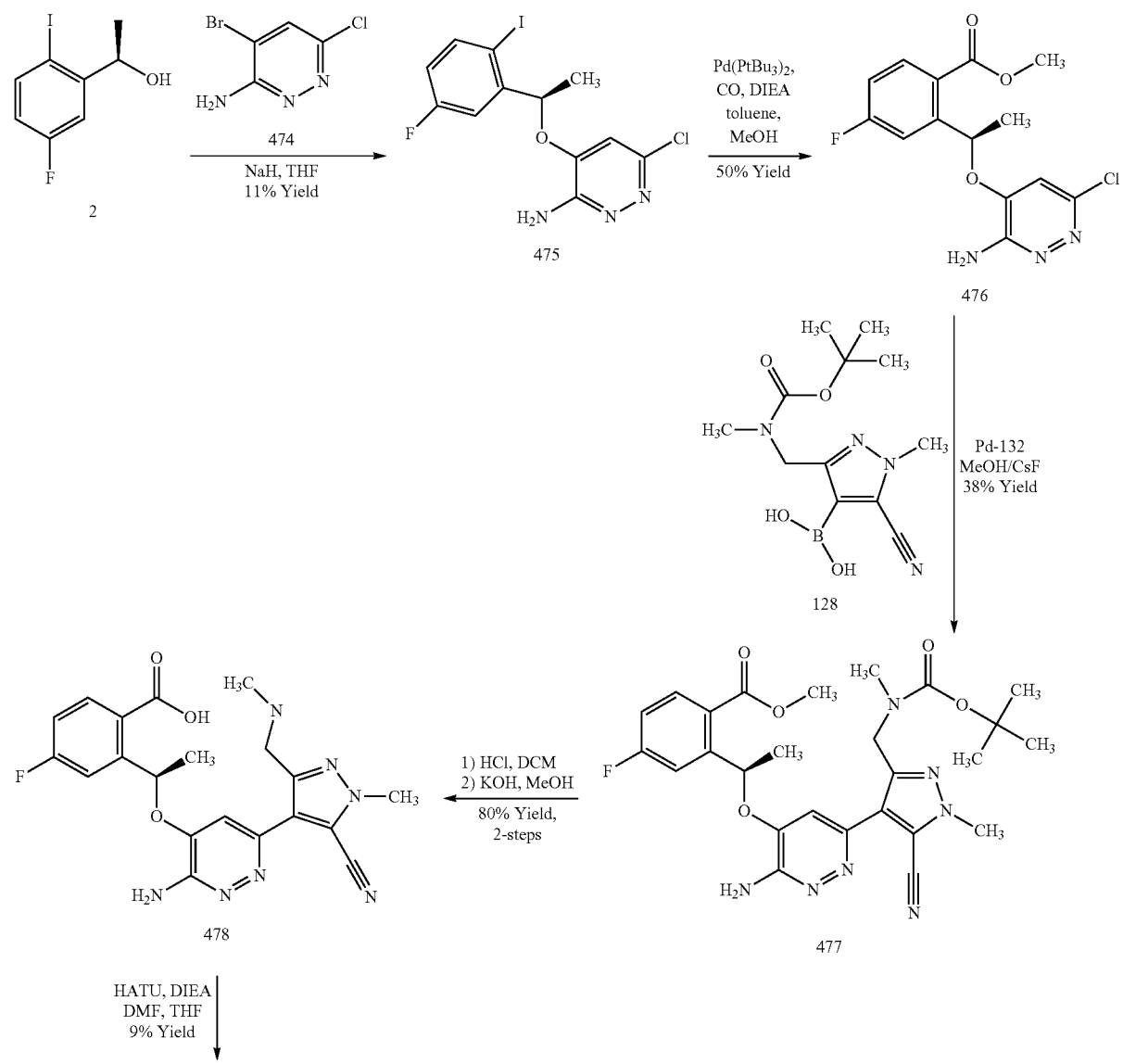

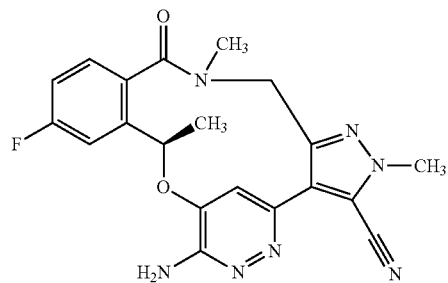

Example 60

Step 1:

To a solution of compound 2 (2.55 g, 9.6 mmol) in THF (50 mL) at 0° C. was added NaH (384 mg, 9.6 mmol, 60% dispersion). After being stirred at 0° C. for 30 minutes and being allowed to warm to room temperature, the pyridazine 474 (2 g, 9.6 mmol) was added. The dark brown mixture was then stirred at 75° C. for 18 hours. The reaction mixture was concentrated, and the residue taken up in DCM. The organics were filtered, concentrated, and the residue purified by two column chromatographies over silica gel (10-100% EtOAc/heptanes, followed by 10-75% EtOAc/heptanes) to afford compound 475 (451 mg, 11%) as a white solid. $^1$H NMR (400 MHz, DMSO-$d_6$) δ 7.92 (dd, 1 H) 7.44 (dd, J=10.11, 3.03 Hz, 1 H) 7.02 (td, J=8.46, 3.03 Hz, 1 H) 6.62 (s, 2 H) 6.52 (s, 1 H) 5.40-5.72 (m, 1 H) 1.57 (d, J=6.32 Hz, 3 H).

Step 2:

To a solution of compound 475 (756 mg, 1.92 mmol) and DIEA (1.27 mL, 7.3 mmol) in toluene (18 mL) and methanol (4 mL) in a stainless steel vessel was added Pd(P$^t$Bu$_3$)$_2$ (47 mg, 0.09 mmol). The reaction was heated to 85° C. under 4 bar CO pressure for 16 hours. The residue was concentrated, and subjected to column chromatography over silica gel (10-75% EtOAc/heptane). The product containing fractions were triturated with MTBE, and filtered. The solids were washed with warm MTBE. Evaporation of the filtrate afforded compound 476 (314 mg, 50%) as a brown solid. $^1$H NMR (400 MHz, DMSO-$d_6$) δ 7.97 (dd, 1 H) 7.59 (dd, J=10.36, 2.78 Hz, 1 H) 7.30 (td, J=8.46, 2.78 Hz, 1 H) 6.69 (s, 1 H) 6.63 (s, 2 H) 6.35 (q, J=5.98 Hz, 1 H) 3.90 (s, 3 H) 1.62 (d, J=6.32 Hz, 3 H).

Step 3:

To the methanolic solution of compound 476 (9 mL, 1.3 mmol) was added the compound 128 (204 mg, 0.626 mmol) and CsF (400 mg, 2.6 mmol). The mixture was then degassed, and Pd-132 (22 mg, 0.031 mmol) added. The mixture was heated at 120° C. in the microwave for 30 minutes. LCMS indicates consumption of the boronic acid, but the reaction was not completed. Additional quantities of the boronic acid solution (2 mL, 0.288 mmol), cesium fluoride (400 mg, 2.6 mmol) and Pd-132 (22 mg, 0.031 mmol) were added and the reaction heated to 120° C. in the microwave for a further 30 minutes. The reaction was partitioned between EtOAc/brine, and the aqueous layer was extracted with EtOAc. The combined organics were washed with brine, dried (MgSO$_4$), and concentrated. The residue was purified by column chromatography over silica gel (10-100% EA/heptane followed by 5% MeOH/EtOAc) to afford compound 477 (128 mg, 38%) as a foam-like solid after trituration with MTBE. $^1$H NMR (400 MHz, 80° C., DMSO-$d_6$) δ 7.97 (dd, J=8.69, 5.92 Hz, 1 H) 7.53 (dd, J=10.32, 2.77 Hz, 1 H) 7.23 (td, 1 H) 6.75 (s, 1 H) 6.39-6.54 (m, 1 H) 6.30 (s, 2 H) 4.48-4.62 (m, 1 H) 4.36 (d, J=15.86 Hz, 1 H) 3.98 (s, 3 H) 3.90 (s, 3 H) 2.73 (s, 3 H) 1.69 (d, J=6.29 Hz, 3 H) 1.26 (s, 9 H).

Step 4:

To a solution of compound 477 (155 mg, 0.287 mmol) in DCM (1.5 mL) was added HCl (1.5 mL, 4M in dioxane, 6 mmol). The reaction mixture was stirred for 1 hour, and concentrated. The residue was azeotroped with MTBE, concentrated, and dried at 50° C. in the vacuum oven for 1 hour. The residue was dissolved in MeOH (3 mL), and KOH (136 mg, 2.41 mmol) added. The reaction was heated to 50° C. for 8 hours. The suspension was allowed to cool, and neutralized with 6N HCl. The solids were removed by filtration, and the filtrate concentrated. The residue was azeotroped with toluene, concentrated and dried at 50° C. in the vacuum oven to afford compound 478 (122 mg, 70-80% purity by LCMS) as a brown solid, which was used directly in the next step.

Step 5:

To a solution of HATU (158 mg, 0.402 mmol) in DMF (7 mL) at 0° C. was added dropwise a solution of compound 478 (122 mg, 0.287 mmol) and DIEA (0.3 mL, 1 mmol) in DMF/THF (7 mL/1.4 mL). The addition took 50 minutes. After addition, the resulting mixture was stirred at 0° C. for 10 minutes. The mixture was then poured into saturated aqueous NaHCO3 (400 mL), and filtered. The filtrate was extracted with EtOAc (3×), and the organics washed with water (2×), and brine. The combined organics were dried (MgSO$_4$), filtered and concentrated. The residue was purified by column chromatography over silica gel (0-10% MeOH/DCM:EtOAc 1:1) to afford Example 60 (10 mg, 9%) as a white solid. $^1$H NMR (400 MHz, DMSO-$d_6$) δ 7.46-7.68 (m, 2 H) 7.15-7.31 (m, 1 H) 6.71 (s, 1 H) 6.49 (br. s., 2 H) 5.61-5.88 (m, 1 H) 4.50 (d, J=14.43 Hz, 1H) 4.29 (d, J=14.55 Hz, 1 H) 4.07 (s, 3 H) 3.00 (s, 3 H) 1.71 (d, J=5.75 Hz, 3 H). LCMS APCI m/z 408 [M+H]$^+$.

Preparation of 7-amino-12-fluoro-2,10,16-trimethyl-15-oxo-2,9,10,15,16,17-hexahydro-8,4-(metheno)pyrazolo[3,4-d][2,8]benzodiazacyclotetradecine-3-carbonitrile/7-amino-12-fluoro-2,10,16-trimethyl-15-oxo-2,9,10,15,16,17-hexahydro-8,4-(metheno)pyrazolo[3,4-d][2,8]benzodiazacyclotetradecine-3-carboxamide (Example 61 and 62)

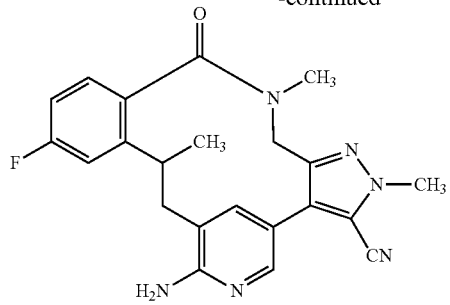

Example 61
Example 63/64

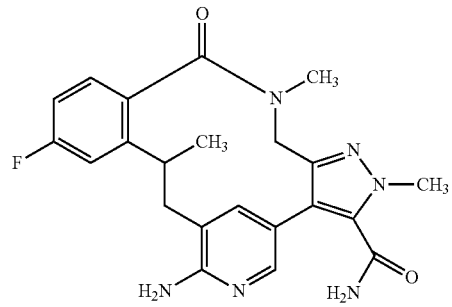

Example 62

Step 1:

Triethylamine (13 mL, 9.44 g, 93.3 mmol), potassium isopropenyltrifluoroborate (18.0 g, 121.6 mmol) and PdCl$_2$(dppf).CH$_2$Cl$_2$ (1.38 g, 1.70 mmol) were added to a solution of compound 479 (21.8 g, 93.6 mmol) in n-propanol (640 mL) and the mixture was heated at reflux for 17 hours. TLC analysis (10% 2-butanone in heptane) showed starting material remaining and PdCl$_2$(dppf).CH$_2$Cl$_2$ (0.69 g, 0.84 mmol) was added and heating continued for a further 4 hours. After cooling to room temperature the mixture was concentrated to ~100 mL in vacuo and diluted with EtOAc (400 mL) before being washed with 1M HCl (250 mL) and brine (250 mL). The combined aqueous washings were extracted with EtOAc (100 mL) and this was washed with brine (75 mL). The combined organic layers were dried (MgSO$_4$) and concentrated in vacuo to give a dark brown oil. Purification by column chromatography (1500 mL silica, 4% EtOAc in heptane) gave the desired product (8.63 g, 47%) as a colorless liquid, contaminated with methyl 4-fluorobenzoate (<10%), and a mixture of the desired product and starting material (5.05 g) also contaminated with methyl 4-fluorobenzoate. Further purification by column chromatography (500 mL silica, 4% EtOAc in heptane) gave a further 1.60 g (9%) of the desired product contaminated with methyl 4-fluorobenzoate (<10%). The product was further purified by Kugelrohr distillation, discarding the forerun (70° C., 4 mmHg), and then increasing the temperature to 95° C. to collect the compound 480 (95% recovery) containing <5% methyl 4-fluorobenzoate. $^1$H NMR (400 MHz, CDCl$_3$) δ 7.84 (dd, J=8.7, 5.9 Hz, 1H) 6.99 (ddd, J=8.6, 8.0, 2.6 Hz, 1H) 6.93 (dd, J=9.4, 2.6 Hz, 1H) 5.12 (p, J=1.6 Hz, 1H) 4.85 (dq, J=1.8, 0.9 Hz, 1H) 3.85 (s, 3H) 2.07 (t, J=1.2 Hz, 3H). LCMS m/z 195 [M+H]$^+$.

Step 2:

[Ir(1,5-cod)Cl]$_2$ (751 mg 1.11 mmol) and DPPB (944 mg 2.21 mmol) were stirred in THF (100 mL) under nitrogen at room temperature for 5 minutes to give a clear yellow solution. Compound 480 (8.6 g, 44.28 mmol) in THF (10 mL) was added, and the solution stirred for 10 minute. Pinacolborane (7.95 mL, 53.1 mmol) in THF (20 mL) was added in a dropwise fashion, and the cloudy yellow solution stirred for 48 hours. The reaction was concentrated, and purified by column chromatography on silica gel (0-100% DCM/heptane) to give compound 481 as a colorless oil (7.2 g, 51%). $^1$H NMR (400 MHz, CDCl$_3$) δ 7.76 (dd, J=8.68, 6.11 Hz, 1H) 7.10 (dd, J=10.70, 2.63 Hz, 1H) 6.87 (dt, J=1.00 Hz, 1H) 3.84-3.99 (m, 4H) 1.29 (d, J=1.00 Hz, 3H), 1.13 (d, J=1.00 Hz, 14H). LCMS APCI m/z 323 [M+H]$^+$.

Step 3:

To compound 481 (5.7 g, 17.69 mmol) and 2-amino-3-bromopyridine (6.12 g, 35.40 mmol) in toluene (300 mL) and water (60 mL) was added Pd(OAc)$_2$ (248 mg, 1.11 mmol) and cataCXium A (793 mg, 2.21 mmol) followed by CsF (6.72 g, 44.20 mmol). The biphasic reaction mixture was stirred at 120° C. for 48 hrs. LCMS indicated only 20% conversion to the desired product. The reaction was cooled, and the organic layer extracted. The aqueous was further extracted with DCM, and the combined organics dried (Na$_2$SO$_4$), filtered and concentrated. The residue was purified by column chromatography over silica gel (0-75% DCM/heptanes) to give compound 482 as a brown oil (401 mg, 8%). $^1$H NMR (400 MHz, CDCl$_3$) δ 7.98 (dd, J=5.01, 1.71 Hz, 1H) 7.91 (dd, J=8.80, 6.11 Hz, 1H) 7.15-7.23 (m, 2H) 6.97 (ddd, J=8.68, 7.70, 2.57 Hz, 1H) 6.58 (dd, J=7.21, 5.01 Hz, 1H) 5.21 (brs., 2H) 4.04-4.17 (m, 1H) 3.90 (s, 3H) 3.01 (dd, J=13.88, 4.34 Hz, 1H) 2.33 (dd, J=13.88, 11.07 Hz, 1H) 1.16 (d, J=6.85 Hz, 3H). LCMS APCI m/z 323 [M+H]$^+$. LCMS APCI m/z 289 [M+H]$^+$.

Step 4:

Compound 482 (720 mg, 2.50 mmol) was stirred in DMF (20 mL) under nitrogen at room temperature. NBS (494 mg, 2.75 mmol) was added, and the reaction stirred for 14 hours. The reaction was concentrated, and partitioned between EtOAc and saturated aqueous NaHCO$_3$ solution. The organics were dried (Na$_2$SO$_4$), filtered, and concentrated. The residue was purified by column chromatography over silica gel (0-75% EtOAc/heptane) to give compound 483 as a brown oil (558 mg, 61%). $^1$H NMR (400 MHz, CDCl$_3$) δ 8.01 (d, J=2.32 Hz, 1H) 7.93 (dd, J=8.80, 6.11 Hz, 1H) 7.33 (d, J=2.32 Hz, 1H) 7.17 (dd, J=10.39, 2.57 Hz, 1H) 6.98 (ddd, J=8.68, 7.70, 2.57 Hz, 1H) 5.34 (brs., 2H) 4.08 (m, J=1.50 Hz, 1H) 3.91 (s, 3H) 3.00 (dd, J=13.94, 4.16 Hz, 1H) 2.27 (dd, J=13.82, 11.37 Hz, 1H) 1.17 (d, J=6.85 Hz, 3H). LCMS APCI m/z 366/368 [M+H]$^+$.

Step 5:

Compound 483 (478 mg, 1.30 mmol), compound 47 (857 mg, 2.60 mmol), bis(pinacalato)diboron (1 g, 3.91 mmol) cesium fluoride (989 mg, 6.51 mmol) and Pd(P$^t$Bu$_3$)$_2$ (33.9 mg, 0.065 mmol) were combined in THF/water (70 mL/7 mL) and the mixture degassed with nitrogen. The reaction was heated at 100° C. for 14 hours. The reaction was concentrated, and the residue dissolved in EtOAc. The organics were washed with water, dried (Na$_2$SO$_4$), and concentrated to give a yellow oil. The residue was purified by column chromatography over silica gel (0-100% EtOAc/heptane) to afford compound 484 as a golden oil (495 mg, 71%). LCMS APCI m/z 537 [M+H]$^+$.

Step 6:
Compound 484 (495 mg, 0.922 mmol) and sodium hydroxide (192 mg, 4.80 mmol) were stirred in water (4.0 mL) and methanol (20 mL) for 10 hours at 40° C. The reaction was concentrated and acidified to pH-5 with 1M AcOH. The reaction was extracted in EtOAc, dried ($Na_2SO_4$), and concentrated to give compound 485 as a brown solid (430 mg 90%— observe ca. 10-15% of amide resulting from cyano hydrolysis). LCMS APCI m/z 523 $[M+H]^+$.

Step 7:
Compound 485 (430 mg, 0.823 mmol) was stirred in 4M HCl in dioxane (2.06 mL) and DCM (10 mL) at room temperature for 2 hours. The brown solution was concentrated and azeotroped with toluene to give compound 486 as a brown solid which was used directly in the next step. LCMS APCI m/z 423 $[M+H]^+$.

Step 8:
A solution of compound 486 (assumed 0.823 mmol) as the HCl salt and DIEA (2.30 mL, 13.20 mmol) in DMF (10 mL) was added dropwise to a solution of HATU (438 mg, 1.15 mmol) in DMF (15 mL) at 0° C. over 1 hour using a syringe pump. After the addition, the clear yellow solution was allowed to warm to room temperature, and stirred for 14 hours. The reaction was concentrated, and water added. The mixture was extracted into EtOAc (3×), and the combined organics washed with 1M aqueous $Na_2CO_3$ (5×), 10% aqueous $NH_4OH$, water and brine, dried ($Na_2SO_4$) and evaporated to give brown foam. Purification by reverse HPLC gave Example 61 (81 mg, 24%) as a cream solid, and Example 62 (15 mg, 4%) resulting from amide hydrolysis, also as a cream solid.

Example 61 (81 mg, 24%) $^1$H NMR (400 MHz, $CDCl_3$) δ 7.95 (brs, 1H) 7.39 (dt, J=1.00 Hz, 1H) 7.28 (dd, J=1.00 Hz, 1H) 7.12 (s, 1H) 7.02 (dt, J=1.00 Hz, 1H) 6.11 (b s, 2H) 4.42 (d, J=14.31 Hz, 1H) 4.24 (d, J=1.00 Hz, 1H) 4.0 (s, 3H) 3.61 (bs, 1H) 2.97 (s, 3H) 2.89-2.96 (m, 1H) 2.64 (bd, J=1.00 Hz, 1H) 1.35 (d, J=6.48 Hz, 3H). LCMS APCI m/z 405 $[M+H]^+$.

Example 62 (15 mg, 4%) $^1$H NMR (400 MHz, $CDCl_3$) δ 7.56-7.90 (m, 3H) 7.24-7.40 (m, 2H) 7.08 (s, 1H) 6.94-7.04 (m, 1H) 5.81 (bs, 2H) 4.29 (d, J=13.82 Hz, 1H) 4.11 (d, J=13.82 Hz, 1H) 3.89 (s, 3H) 3.61 (bs, 1H) 2.87-3.07 (m, 4H) 2.56-2.75 (m, 2H) 1.35 (d, J=6.36 Hz, 3H). LCMS APCI m/z 423 $[M+H]^+$.

68 mg of Example 61 was subjected to chiral separation by SFC to afford both enantiomers of the title compound. The analytical chiral separation by SFC was performed using a Regis Whelk-01 (R, R) column (4.6 mm×100 mm column, 5 micron particle size), which was eluted with 30% MeOH in $CO_2$ held at 140 bar. A flow rate of 3 mL/min gave $Rt_{(Peak\ 1)}$=3.46 minutes and $Rt_{(Peak\ 2)}$=4.76 minutes.

Example 63 (Peak 1): 25.0 mg, >99% ee (−). $^1$H NMR (400 MHz, $CDCl_3$) δ 7.95 (brs, 1H) 7.39 (dt, J=1.00 Hz, 1H) 7.28 (dd, J=1.00 Hz, 1H) 7.12 (s, 1H) 7.02 (dt, J=1.00 Hz, 1H) 6.11 (b s, 2H) 4.42 (d, J=14.31 Hz, 1H) 4.24 (d, J=1.00 Hz, 1H) 4.0 (s, 3H) 3.61 (bs, 1H) 2.97 (s, 3H) 2.89-2.96 (m, 1H) 2.64 (bd, J=1.00 Hz, 1H) 1.35 (d, J=6.48 Hz, 3H). LCMS APCI m/z 405 $[M+H]^+$.

Example 64 (Peak 2): 24.8 mg, 98% ee (+). $^1$H NMR (400 MHz, $CDCl_3$) δ 7.95 (brs, 1H) 7.39 (dt, J=1.00 Hz, 1H) 7.28 (dd, J=1.00 Hz, 1H) 7.12 (s, 1H) 7.02 (dt, J=1.00 Hz, 1H) 6.11 (b s, 2H) 4.42 (d, J=14.31 Hz, 1H) 4.24 (d, J=1.00 Hz, 1H) 4.0 (s, 3H) 3.61 (bs, 1H) 2.97 (s, 3H) 2.89-2.96 (m, 1H) 2.64 (bd, J=1.00 Hz, 1H) 1.35 (d, J=6.48 Hz, 3H). LCMS APCI m/z 405 $[M+H]^+$.

Preparation of 7-amino-3-methoxy-1,10,16-trimethyl-16,17-dihydro-1H-8,4-(metheno)-pyrazolo[4,3-g]pyrido[2,3-l][1,4,10]oxadiazacyclotetradecin-15(10H)-one (Example 65 and 66)

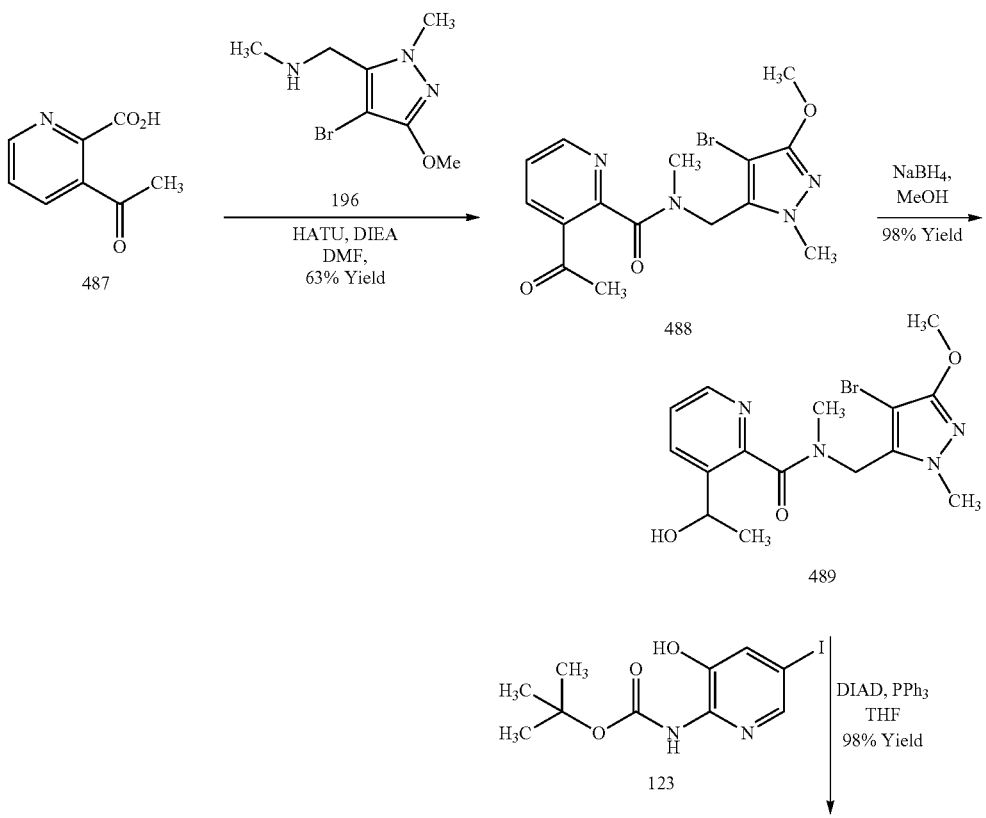

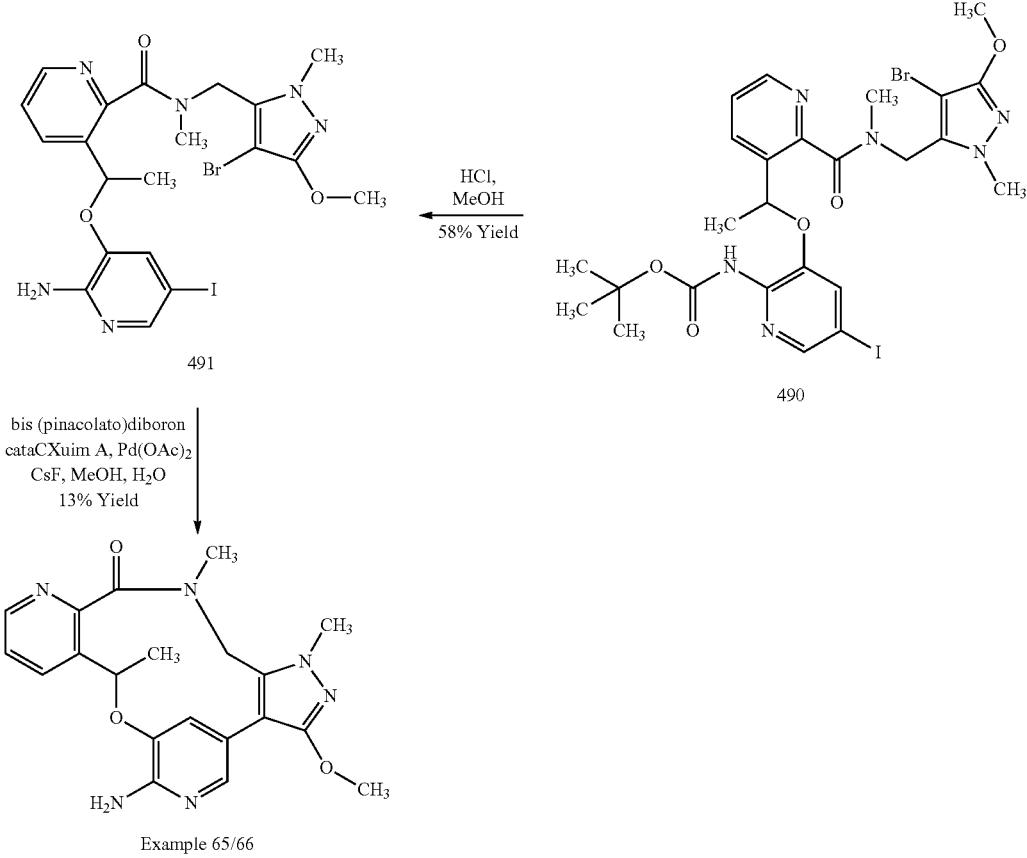

Example 65/66

Step 1:

A suspension of compound 487 (965 mg, 5.84 mmol) and compound 196 (580 mg, 5.84 mmol) in DMF (40 mL) was stirred under nitrogen. DIEA (3.05 mL, 17.5 mmol) was added, and the suspension turned into a thick gel. HATU (2890 mg, 7.60 mmol) was added, and the reaction was stirred for 14 hours. During this time, the solid slowly dissolved to give a clear brown solution. The reaction was concentrated, and the residue dissolved in EtOAc. The organic extract was washed with saturated aqueous $NaHCO_3$, and dried ($Na_2SO_4$). The organics were filtered, concentrated, and the residue purified by column chromatography over silica gel (0-4% MeOH/DCM) to give compound 488 as a cream solid (1400 mg, 63%). $^1$H NMR (400 MHz, $CDCl_3$) δ 8.70 (dd, J=4.93, 1.39 Hz, 1H) 8.11 (dd, J=8.08, 1.52 Hz, 1H) 7.43 (dd, J=7.83, 4.80 Hz, 1H) 4.87 (m, 2H) 4.80-3.95 (s, 3H) 3.90 (s, 3H) 2.72 (s, 3H) 2.59 (s, 3H). LCMS APCI m/z 381/383 $[M+H]^+$.

Step 2

A suspension of compound 488 (1324 mg, 3.473 mmol) in MeOH (60 mL) was stirred at room temperature under nitrogen. $NaBH_4$ (144 mg, 3.82 mmol) was added leading to a vigorous gas evolution and a clear colorless solution. The reaction was stirred for a further 2 hours, concentrated and the residue dissolved in DCM. The organic was washed with water, dried ($Na_2SO_4$), and concentrated to give compound 489 as a white solid (1300 mg, 98%). LCMS APCI m/z 382/385 $[M+H]^+$.

Step 3

To compound 489 (650 mg, 1.70 mmol) and compound 123 (570 mg, 1.70 mmol) in THF (40 mL) under nitrogen at room temperature was added triphenylphosphine (489 mg, 1.87 mmol) followed by dropwise addition of a solution of DIAD (0.37 ml, 1.87 mmol) in THF (4 mL) to give a yellow solution. The reaction was then stirred for 14 hours, concentrated and purified by column chromatography over silica gel (50% DCM/EtOAc) to give compound 490 as a white solid (1800 mg, 151%). NMR ($CDCl_3$) indicated that the solid is approximately a 1:2 mixture of required product and PPh3=O. Thus 1800 mg of the mixture is equivalent to 1008 mg of product, yield 85%. $^1$H NMR (400 MHz, $CDCl_3$) δ 8.55 (dd, J=4.71, 1.53 Hz, 1H) 8.18 (d, J=1.83 Hz, 1H) 7.86 (dd, J=7.95, 1.47 Hz, 1H) 7.37 (dd, J=8.07, 4.77 Hz, 1H) 7.34 (d, J=1.71 Hz, 1H) 5.63 (q, J=6.40 Hz, 1H) 4.80-5.02 (m, 2H) 3.97 (s, 3H) 3.87 (s, 3H) 2.86 (s, 3H) 1.74 (d, J=6.36 Hz, 3H) 1.57 (s, 9H). LCMS APCI m/z 700/703 $[M+H]^+$.

Step 4

To a solution of compound 490 (1800 mg, theory 1.40 mmol) in MeOH (30 mL) was added 4M HCl in dioxane (3.6 mL) giving a solution, which was stirred at room temperature for 15 hours. The reaction was concentrated to give a sticky cream solid. This was slurried in DCM, and washed with saturated aqueous $NaHCO_3$ to form the free base. The organics were dried ($Na_2SO_4$), concentrated, and purified by column chromatography over silica gel (0-100% EtOAc/DCM) to afford compound 491 as a cream foam (500 mg, 58%). $^1$H NMR (400 MHz, $CDCl_3$) δ 8.53 (dd, J=4.77, 1.59 Hz, 1H) 7.86 (dd, J=8.07, 1.47 Hz, 1H) 7.81 (d, J=1.71 Hz, 1H) 7.37 (dd, J=7.95, 4.77 Hz, 1H) 7.05 (d, J=1.59 Hz, 1H) 5.56 (q, J=6.40 Hz, 1H) 4.80-5.00 (m, 2H) 4.76 (bs, 1H) 3.97 (s, 3H) 3.84-3.90 (m, 3H) 2.84 (s, 3H) 1.71 (d, J=6.36 Hz, 3H). LCMS APCI m/z 601/602 [M+H]+.

Step 5

Compound 491 (500 mg, 0.832 mmol), bis(pinacolato) diboron (1070 mg, 4.16 mmol), cataCXium A (60 mg, 0.166 mmol), cesium fluoride (638 mg, 4.16 mmol) and palladium acetate (19 mg, 0.830 mmol) in water (20 mL) methanol (200 mL) were heated at 100° C. overnight. The reaction was concentrated, and partitioned between water and EtOAc. The organics were dried (Na$_2$SO$_4$), concentrated to a yellow oil, which was purified by preparative reverse phase HPLC to give Example 65 and Example 66 as a white powder (43 mg, 13%). $^1$H NMR (400 MHz, CDCl$_3$) δ 8.48 (dd, J=4.67, 1.39 Hz, 1H) 8.15 (dd, J=8.08, 1.26 Hz, 1H) 7.43-7.54 (m, 2H) 6.75 (d, J=1.26 Hz, 1H) 5.73 (s, 2H) 5.56 (d, J=6.32 Hz, 1H) 4.59 (d, J=15.66 Hz, 1H) 4.01 (d, J=15.41 Hz, 1H) 3.83 (d, J=7.58 Hz, 5H) 3.0 (s, 3H) 1.69 (d, J=6.32 Hz, 3H). LCMS APCI m/z 395 [M+H]+.

A sample of 43 mg was subjected to chiral separation by SFC to afford both enantiomers of the title compound. The analytical chiral separation by SFC was performed using a Regis Whelk-01 (R, R) column (4.6 mm×100 mm column, 5 micron particle size), which was eluted with 30% MeOH in CO$_2$ held at 140 bar. A flow rate of 3 mL/min gave Rt$_{(Peak\ 1)}$=5.77 minutes and Rt$_{(Peak\ 2)}$=7.01 minutes.

Example 65 (Peak 1): 12 mg, 99% ee (−). $^1$H NMR (400 MHz, CDCl$_3$) δ 8.48 (dd, J=4.67, 1.39 Hz, 1H) 8.15 (dd, J=8.08, 1.26 Hz, 1H) 7.43-7.54 (m, 2H) 6.75 (d, J=1.26 Hz, 1H) 5.73 (s, 2H) 5.56 (d, J=6.32 Hz, 1H) 4.59 (d, J=15.66 Hz, 1H) 4.01 (d, J=15.41 Hz, 1H) 3.83 (d, J=7.58 Hz, 5H) 3.0 (s, 3H) 1.69 (d, J=6.32 Hz, 3H). LCMS APCI m/z 395 [M+H]+.

Example 66 (Peak 2): 15 mg, 97% ee (+). $^1$H NMR (400 MHz, CDCl$_3$) δ 8.48 (dd, J=4.67, 1.39 Hz, 1H) 8.15 (dd, J=8.08, 1.26 Hz, 1H) 7.43-7.54 (m, 2H) 6.75 (d, J=1.26 Hz, 1H) 5.73 (s, 2H) 5.56 (d, J=6.32 Hz, 1H) 4.59 (d, J=15.66 Hz, 1H) 4.01 (d, J=15.41 Hz, 1H) 3.83 (d, J=7.58 Hz, 5H) 3.0 (s, 3H) 1.69 (d, J=6.32 Hz, 3H). LCMS APCI m/z 395 [M+H]+.

Preparation of 7-amino-3-tert-butyl-1,10,16-trimethyl-16,17-dihydro-1H-8,4-(metheno)pyrazolo[4,3-g]pyrido[2,3-l][1,4,10]oxadiazacyclotetradecin-15 (10H)-one (Example 67, 68 and 69)

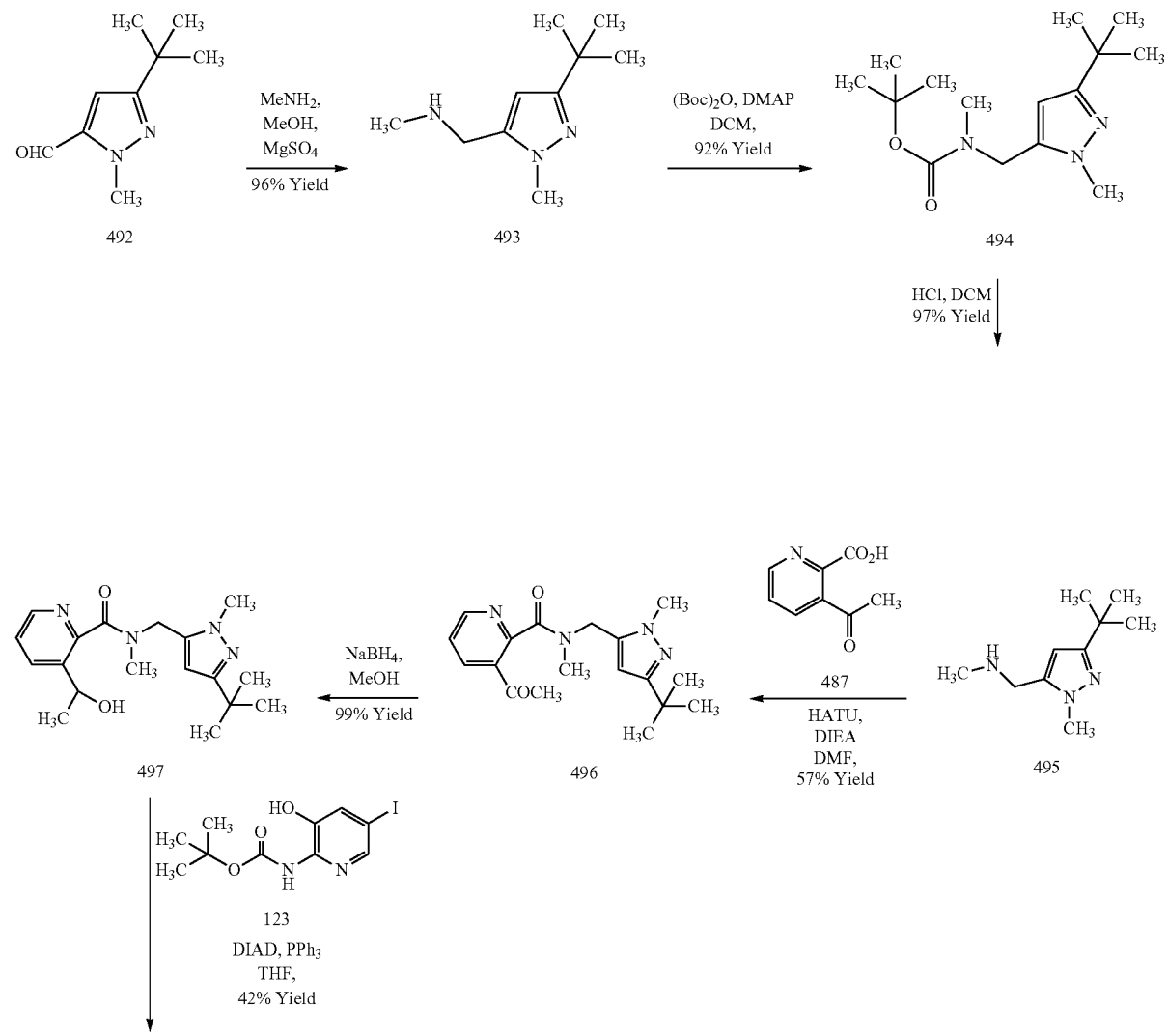

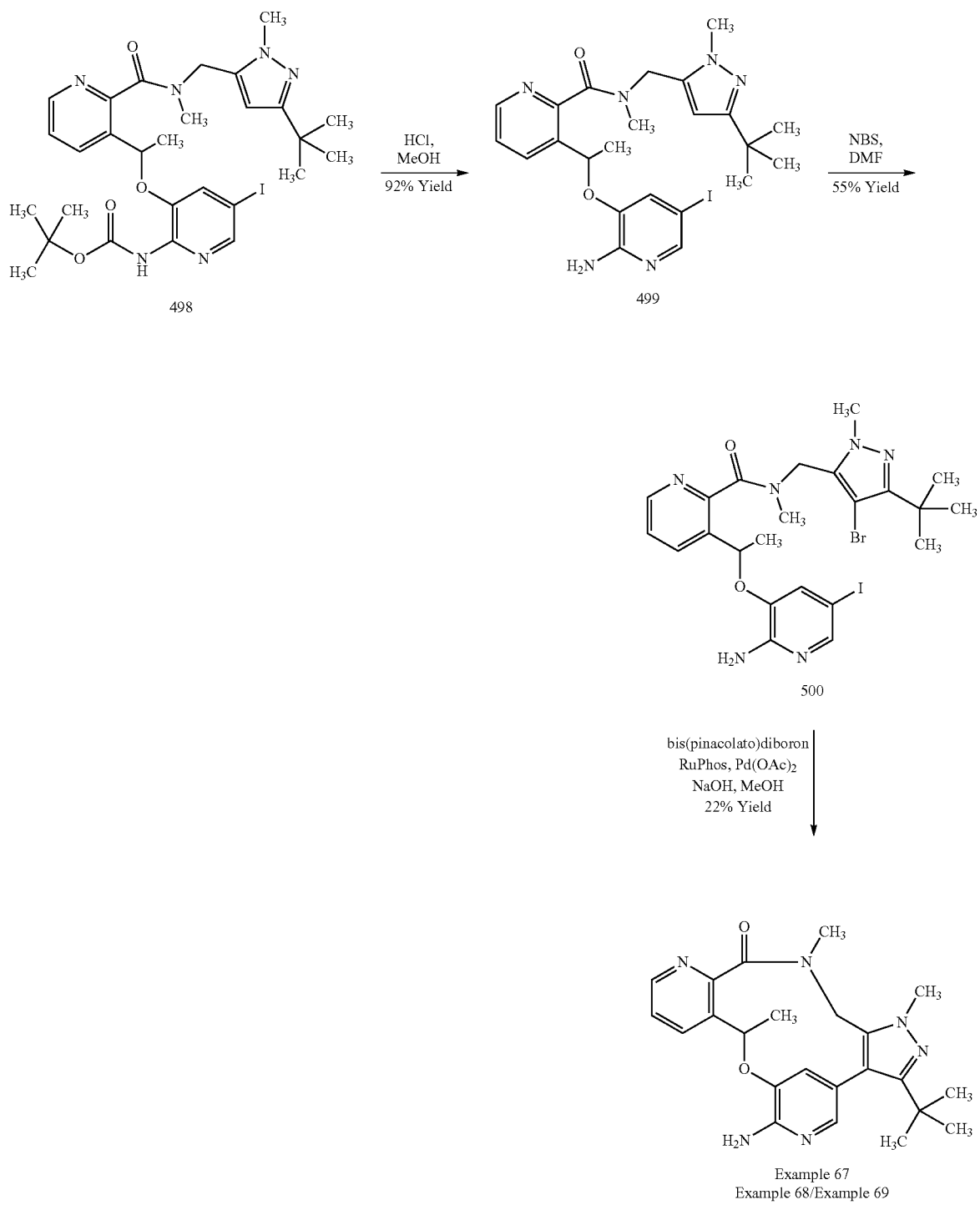

Example 67
Example 68/Example 69

Step 1:

Compound 492 (2000 mg, 12.03 mmol) in MeOH (50 mL) was stirred under nitrogen with 33% methylamine in EtOH (1.80 mL. 5.09 mmol). Anhydrous MgSO₄ (3000 mg) was added, and the reaction stirred for a further 1.5 hours. The reaction flask was cooled in an ice-bath and NaBH₄ (546 mg, 14.40 mmol) added. The reaction was stirred for 14 hours, concentrated and partitioned between water and DCM. The organic was separated, and the aqueous further extracted with DCM (2×). The combined organics were dried (Na₂SO₄), and concentrated to give compound 493 as a colorless oil (2100 mg, 96%). LCMS APCI m/z 182 [M+H]⁺.

Step 2:
To a solution of compound 493 (2100 mg, 11.58 mmol) in dichloromethane (60 mL) was added DMAP (283 mg, 2.32 mmol), followed by (Boc)$_2$O (4040 mg, 18.50 mmol) to give a yellow solution. The reaction was stirred at room temperature for 2 hours, and then the solvent was removed under reduced pressure to give a yellow oil. The reaction was purified by column chromatography over silica gel (0-100% EtOAc/heptane) to give compound 494 as a colorless oil (3000 mg, 92%). $^1$H NMR (400 MHz, CDCl$_3$) δ 5.97 (s, 1H) 4.40 (s, 2H) 3.77 (s, 3H) 2.77 (s, 3H) 1.46 (s, 9H), 1.27 (s, 9H). LCMS APCI m/z 282 [M+H]$^+$.

Step 3:
To a solution of compound 494 (3800 mg, 13.50 mmol) in DCM (50 mL) was added 4M HCl in dioxane (34 mL, 135 mmol), and the reaction stirred for 2 hours. At this time, the reaction had turned cloudy, and MeOH was added to give a clear yellow solution, which was stirred for a further 2 hours. The reaction was concentrated to give a cream solid, which was slurried in heptanes, filtered and dried to give compound 495 as a solid (3318 mg, 97%). $^1$H NMR (400 MHz, DMSO-d$_6$) δ 9.32-9.49 (m, 1H) 6.29-6.39 (m, 1H) 4.15 (t, 2H) 3.79-3.83 (m, 3H) 2.54 (t, 3H) 1.17-1.23 (m, 9H). LCMS APCI m/z 182 [M+H]$^+$.

Step 4:
To a suspension of compound 495 (965 mg, 5.84 mmol) and compound 487 (1490 mg, 5.84 mmol) in DMF (40 mL) under nitrogen was added DIEA (3.05 mL, 17.5 mmol) to give a clear brown solution. HATU (2890 mg, 7.60 mmol) was added, and the reaction stirred for 16 hours. The reaction was concentrated and the residue dissolved in EtOAc. The organics were washed with saturated aqueous NaHCO$_3$, dried (Na$_2$SO$_4$), and concentrated to afford a residue, which was purified by column chromatography over silica gel (0-4% MeOH/DCM) to give compound 496 as a brown solid (1100 mg, 57%). $^1$H NMR (400 MHz, CDCl$_3$) δ 8.71 (dd, J=4.83, 1.53 Hz, 1H) 8.11 (dd, J=7.95, 1.59 Hz, 1H) 7.44 (dd, J=7.89, 4.83 Hz, 1H) 6.17 (s, 1H) 4.81 (s, 2H) 3.93 (s, 3H) 2.75 (s, 3H) 2.61 (s, 3H) 1.32 (s, 9H). LCMS APCI m/z 329 [M+H]$^+$.

Step 5:
To a stirred solution of compound 496 (1100 mg, 3.349 mmol) in MeOH (20 mL) under nitrogen was added sodium borohydride (152 mg, 4.02 mmol) in a portionwise manner. A vigorous gas evolution was observed, and the reaction rapidly turned to a yellow solution. The reaction was stirred for one hour, concentrated and the residue dissolved in DCM. The organic solution was washed with water, dried (Na$_2$SO$_4$), and concentrated to give compound 497 (1100 mg, 99%). $^1$H NMR (400 MHz, CDCl$_3$) 8.52 (dd, J=4.71, 1.65 Hz, 1H) 7.90 (dd, J=7.83, 1.47 Hz, 1H) 7.37 (m, J=7.90, 4.70 Hz, 1H) 4.88-4.99 (m, 1H) 4.82 (q, J=1.00 Hz, 2H) 3.92 (s, 3H) 2.86 (s, 3H) 1.55 (d, J=6.60 Hz, 3H) 1.30 (s, 9H). LCMS APCI m/z 331 [M+H]$^+$.

Step 6:
To a solution of compound 497 (1100 mg, 3.329 mmol) and compound 123 (1120 mg, 3.33 mmol) in THF (40 mL) under nitrogen at room temperature was added triphenylphosphine (960 mg, 3.66 mmol) followed by dropwise addition of a solution of DIAD (0.72 mL. 3.66 mmol) in THF (5 mL) to give a yellow solution. The reaction was stirred at room temperature for 20 hours, concentrated, and purified by column chromatography over silica gel (50:50 DCM/EtOAc) to give compound 498 as a yellow solid (900 mg, 42%). $^1$H NMR (400 MHz, CDCl$_3$) δ 8.55 (dd, J=4.65, 1.47 Hz, 1H) 8.18 (d, J=1.83 Hz, 1H) 7.85 (dd, J=8.01, 1.41 Hz, 1H) 7.37 (dd, J=7.95, 4.77 Hz, 1H) 7.27-7.33 (m, 3H) 6.14 (s, 1H) 5.62 (q, J=6.50 Hz, 1H) 4.67-5.01 (m, 2H) 3.92 (s, 3H) 2.82-2.89 (m, 3H) 1.75 (d, J=6.36 Hz, 3H) 1.57 (s, 9H) 1.29 (s, 9H). LCMS APCI m/z 649 [M+H]$^+$.

Step 7:
To a stirred solution of compound 498 (900 mg, 1.39 mmol) in MeOH (30 mL) was added 4M HCl in dioxane (3.6 mL) to give a yellow solution, which was stirred at room temperature for 16 hours. The reaction was concentrated to give an oil, which was partitioned between DCM and saturated aqueous NaHCO$_3$. The organic was separated, and the aqueous further extracted with DCM (3×). The combined organics were dried (Na$_2$SO$_4$), and concentrated to give compound 499 as a golden foam (700 mg, 92%). $^1$H NMR (400 MHz, CDCl$_3$) δ 8.54 (dd, J=4.71, 1.53 Hz, 1H) 7.85 (dd, J=8.07, 1.47 Hz, 1H) 7.80 (d, J=1.59 Hz, 1H) 7.64-7.72 (m, 2H) 7.03 (d, J=1.59 Hz, 1H) 6.14 (s, 1H) 5.55 (q, J=6.40 Hz, 1H) 4.94 (d, J=15.16 Hz, 1H) 4.69-4.82 (m, 3H) 3.92 (s, 3H) 2.85 (s, 3H) 1.71 (d, J=6.36 Hz, 3H) 1.29 (s, 9H). LCMS APCI m/z 549 [M+H]$^+$.

Step 8:
Compound 499 (650 mg, 1.18 mmol) and NBS (234 mg, 1.30 mmol) in DMF (20 mL) were stirred under nitrogen for 1 hour. The reaction was concentrated, and partitioned between EtOAc and saturated aqueous NaHCO$_3$. The organics were dried (Na$_2$SO$_4$), concentrated to give a brown oil, which was purified by column chromatography over silica gel (0-4% MeOH/DCM) to give compound 500 as a brown foam (411 mg, 55%—LCMS indicates dibromo impurity is present). LCMS APCI m/z 581/583. [M+H]$^+$.

Step 9:
Compound 500 (370 mg, 0.590 mmol), bis(pinacolato)diboron (454 mg, 1.77 mmol), RuPhos (36 mg, 0.074 mmol) and palladium acetate (8.3 mg, 0.037 mmol) in 1M NaOH (3 mL) and methanol (35 mL) were heated at 100° C. for 14 hours. The reaction was concentrated, and partitioned between water and EtOAc. The organics were dried (Na$_2$SO$_4$), and concentrated to give a yellow oil, which was purified by preparative HPLC to give Example 67 as a white solid (55 mg, 22%). $^1$H NMR (400 MHz, DMSO-d$_6$) δ 8.38 (dd, J=4.66, 1.64 Hz, 1H) 8.21 (dd, J=8.06, 1.51 Hz, 1H) 7.40 (dd, J=8.06, 4.53 Hz, 1H) 7.33 (d, J=2.01 Hz, 1H) 6.85 (d, J=1.76 Hz, 1H) 5.72 (q, J=6.30 Hz, H) 5.49 (s, 2H) 4.43 (d, J=15.36 Hz, 1H) 3.97 (d, J=15.11 Hz, 1H) 3.91 (s, 3H) 2.98 (s, 3H) 1.73 (d, J=1.00 Hz, 3H) 1.23 (s, 9H). LCMS APCI m/z 421 [M+H]$^+$.

50 mg of Example 67 was subjected to chiral separation by SFC to afford both enantiomers of the title compound. The analytical chiral separation by SFC was performed using a Regis Whelk-01 (R, R) column (4.6 mm×100 mm column, 5 micron particle size), which was eluted with 30% MeOH in CO$_2$ held at 140 bar. A flow rate of 3 mL/min gave Rt$_{(Peak\ 1)}$=4.87 minutes and Rt$_{(Peak\ 2)}$=6.99 minutes. Each peak rapidly equilibrated to a 90:10 mixture of atropisomers.

Example 68 (Peak 1): 12 mg, 95% ee (−). $^1$H NMR (400 MHz, DMSO-d$_6$) δ 8.38 (dd, J=4.66, 1.64 Hz, 1H) 8.21 (dd, J=8.06, 1.51 Hz, 1H) 7.40 (dd, J=8.06, 4.53 Hz, 1H) 7.33 (d, J=2.01 Hz, 1H) 6.85 (d, J=1.76 Hz, 1H) 5.72 (q, J=6.30 Hz, H) 5.49 (s, 2H) 4.43 (d, J=15.36 Hz, 1H) 3.97 (d, J=15.11 Hz, 1H) 3.91 (s, 3H) 2.98 (s, 3H) 1.73 (d, J=1.00 Hz, 3H) 1.23 (s, 9H). LCMS APCI m/z 421 [M+H]$^+$.

Example 69 (Peak 2): 13 mg, 95% ee (+). $^1$H NMR (400 MHz, DMSO-$d_6$) δ 8.38 (dd, J=4.66, 1.64 Hz, 1H) 8.21 (dd, J=8.06, 1.51 Hz, 1H) 7.40 (dd, J=8.06, 4.53 Hz, 1H) 7.33 (d, J=2.01 Hz, 1H) 6.85 (d, J=1.76 Hz, 1H) 5.72 (q, J=6.30 Hz, H) 5.49 (s, 2H) 4.43 (d, J=15.36 Hz, 1H) 3.97 (d, J=15.11 Hz, 1H) 3.91 (s, 3H) 2.98 (s, 3H) 1.73 (d, J=1.00 Hz, 3H) 1.23 (s, 9H). LCMS APCI m/z 421 [M+H]$^+$.

Preparation of (10R)-7-amino-2,10,16-trimethyl-15-oxo-10,15,16,17-tetrahydro-2H-8,4-(azeno)pyrazolo[4,3-h][2,5,11]benzoxadiazacyclotetradecine-3-carbonitrile (Example 70)

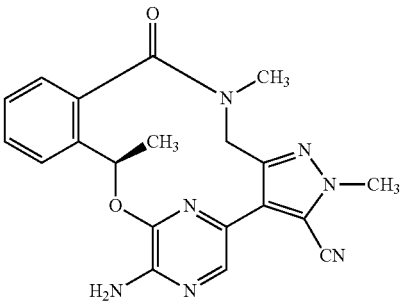

Example 70

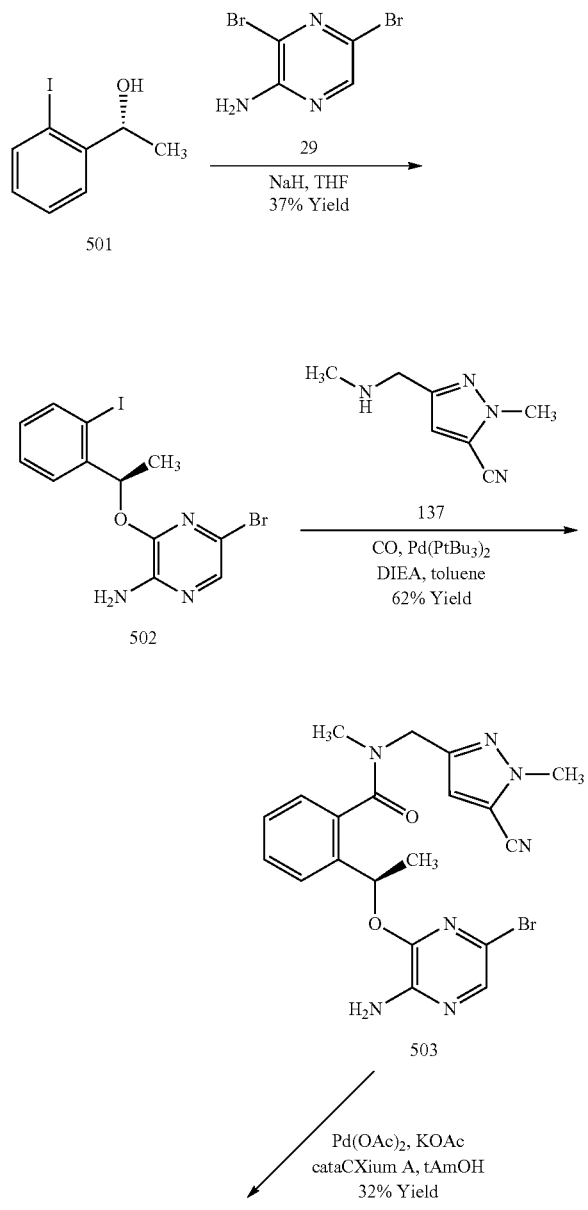

To an ice-cooled solution of compound 501 (1593 mg, 6.422 mmol) in THF (30 mL) under nitrogen was added NaH (282 mg, 7.06 mmol, 60% dispersion) leading to a white suspension with very slow gas evolution. The suspension was stirred for 30 minutes, and then a solution of compound 29 (1620 mg, 6.42 mmol) in THF (8 mL) was added in a dropwise fashion. The bright orange solution was heated to 50° C. for 48 hours. The reaction was concentrated, and partitioned between EtOAc and brine. The insolubles were filtered, and the organic separated, and the aqueous further extracted with EtOAc. The combined organics were dried (Na$_2$SO$_4$), concentrated, and the residue purified by column chromatography over silica gel (DCM to give compound 502, (R)-5-bromo-3-(1-(2-iodophenyl)ethoxy)pyrazin-2-amine, as a pale yellow oil (1000 mg, 37%). LCMS APCI m/z 419/421 [M+H]$^+$.

Step 2:

A mixture of compound 502 (1000 mg, 2.381 mmol), compound 137 (692 mg, 3.10 mmol), DIEA (1.66 mL 9.52 mmol) and Pd (P$^t$Bu$_3$)$_2$ (124 mg, 0.238 mmol) in toluene (25 mL) was stirred at 85° C. under 4 bar CO for 2 hours. The reaction was concentrated to give a red oil, which was purified by column chromatography over silica gel (0-25% EtOAc/heptane) to give compound 503, (R)-2-(1-(3-amino-6-bromopyrazin-2-yloxy)ethyl)-N-((5-cyano-1-methyl-1H-pyrazol-3-yl)methyl)-N-methylbenzamide, as a pale yellow oil (689 mg, 62%). $^1$H NMR (400 MHz, DMSO) δ 7.67 (d, J=1.00 Hz, 1H) 7.55 (s, 1H) 7.43 (dt, J=1.00 Hz, 1H) 7.35 (m, 1H) 7.21-7.29 (m, 1H) 6.92-7.09 (m, 1H) 6.28 (bs, 2H) 6.10 (q, J=1.00 Hz, 1H) 4.70 (bs, 2H) 3.97 (s, 3H) 2.86 (bs, 3H) 1.61 (d, J=6.55 Hz, 3H). LCMS APCI m/z 470/472 [M+H]$^+$.

Step 3:

Compound 503 (689 mg, 1.46 mmol), KOAc (733 mg, 7.47 mmol) and cataCXium A (163 mg, 0.440 mmol) were combined in tert-amylalcohol (30 ml) and nitrogen bubbled through the solution prior to Pd(OAc)$_2$ (49 mg, 0.220 mmol) being added. The reaction was heated to 120° C. for 3 hours in the microwave. The reaction was concentrated, and partitioned between water and EtOAc. The insolubles were filtered, and the organics dried (Na$_2$SO$_4$) to give the crude product as a yellow oil, which was purified by preparative HPLC to give the macrocycle as a yellow foam. This was slurried in water for 30 minutes then filtered, further washed with water, and dried under vacuum overnight to give Example 70 (185 mg, 32%) as a yellow powder. $^1$H NMR (400 MHz, DMSO-$d_6$) δ 7.75 (s, 1H) 7.65 (d, J=7.83 Hz, 1H) 7.39-7.46 (m, 1H) 7.28-7.34 (m, 2H) 6.73 (bs, 2H) 5.91 (q, J=6.50 Hz, 1H) 4.38 (d, J=1.00 Hz, 1H) 4.28 (d, J=1.00 Hz, 1H) 4.03 (s, 3H) 2.90 (s, 3H) 1.65 (d, J=6.60 Hz, 3H). LCMS APCI m/z 390 [M+H]$^+$.

Preparation of (10R)-7-amino-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Example 71)

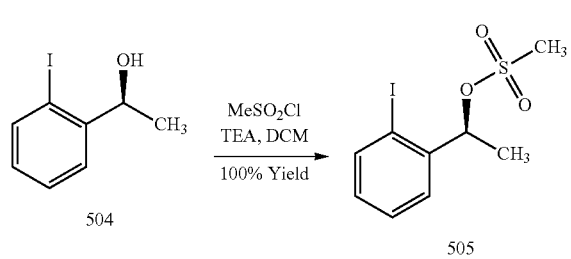

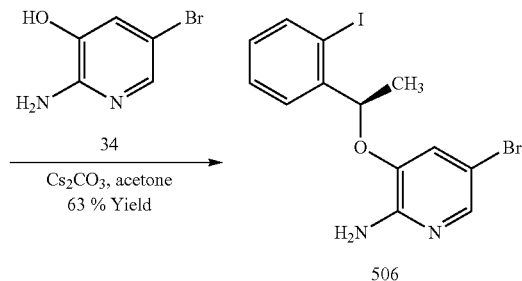

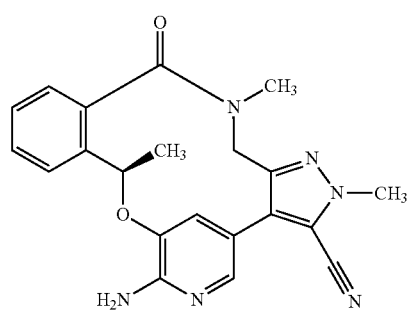

Step 1:

To a cooled solution of compound 504 (1283 mg, 5.172 mmol) and triethylamine (1.44 mL, 10.30 mmol) in DCM (15 mL) under nitrogen was slowly added in a dropwise fashion methanesulfonyl chloride (0.60 mL, 7.76 mmol) to give a cream suspension. The reaction was allowed to warm to room temperature and stirred for 15 hours. The reaction was washed with 1M aqueous HCl and saturated aqueous NaHCO$_3$. The organics were dried (Na$_2$SO$_4$), and concentrated to give compound 505 as an orange oil (1704 mg, 100%), which was used directly in the next step without further purification.

Step 2:

Compound 34 (815 mg, 4.31 mmol) and compound 505 (1687 mg, 5.172 mmol) were stirred at 50° C. in acetone (50 mL) with cesium carbonate (2810 mg, 8.62 mmol) for 6 hours. The reaction was filtered, and the solids rinsed with acetone. The filtrate was concentrated to give a dark residue, which was purified by column chromatography over silica gel (0-25% EtOAc/heptanes) to give compound 506 as a orange oil (1144 mg, 63%). LCMS APCI m/z 418/420 [M+H]$^+$.

Step 3:

A mixture of compound 506 (1144 mg, 1.60 mmol), compound 109 (447 mg, 1.68 mmol), DIEA (1.14 mL, 6.55 mmol) and Pd(P$^t$Bu$_3$)$_2$ (86 mg, 0.164 mmol) in toluene (20 mL) was heated to 85° C. under an atmosphere of 4 bar CO for 14 hours. The reaction was concentrated to give a red oil, which was purified by column chromatography over silica gel (0-100% EtOAc/heptane) to give compound 507 as a yellow solid (770 mg, 86%). $^1$HNMR (CDCl$_3$) indicates the presence of rotamers. LCMS APCI m/z 548/550 [M+H]$^+$.

Step 4:

Compound 507 (770 mg, 1.40 mmol), bis(pinacolato)diboron (1800 mg, 7.02 mmol), cataCXium A (101 mg, 0.281 mmol), cesium fluoride (1070 mg 7.02 mmol) and palladium acetate (32 mg, 0.14 mmol) in water (10 mL) methanol (100 mL) were heated at 100° C. overnight. The reaction was then concentrated, and partitioned between water and EtOAc. The organics were dried (Na$_2$SO$_4$), and concentrated to give a yellow oil, which was subjected to column chromatography over silica gel (0-5% MeOH/DCM) and reverse phase preparative HPLC. The material obtained was slurried in heptane, filtered, and dried under vacuum to give Example 71 (43 mg, 13%) as a white powder. $^1$H NMR (400 MHz, DMSO-d$_6$) δ 7.72 (d, J=7.81 Hz, 1H) 7.57 (d, J=2.01 Hz, 1H) 7.44 (dt, J=1.00 Hz, 1H) 7.29-7.39 (m, 2H) 6.83 (d, J=1.76 Hz, 1H) 6.11 (bs, 2H) 5.59 (q, J=6.30 Hz, 1H) 4.45 (d, J=14.35 Hz, 1H) 4.24 (d, J=14.10 Hz, 1H) 4.03 (s, 3H) 3.00 (s, 3H) 1.69 (d, J=6.29 Hz, 3H). LCMS APCI m/z 389 [M+H]$^+$.

377

Preparation of (10R)-7-amino-12-fluoro-10,16-dimethyl-15-oxo-10,15,16,17-tetrahydro-8,4-(azeno)[1,2]oxazolo[4,5-h][2,5,11]benzoxadiazacyclotetradecine-3-carboxamide (Example 72)

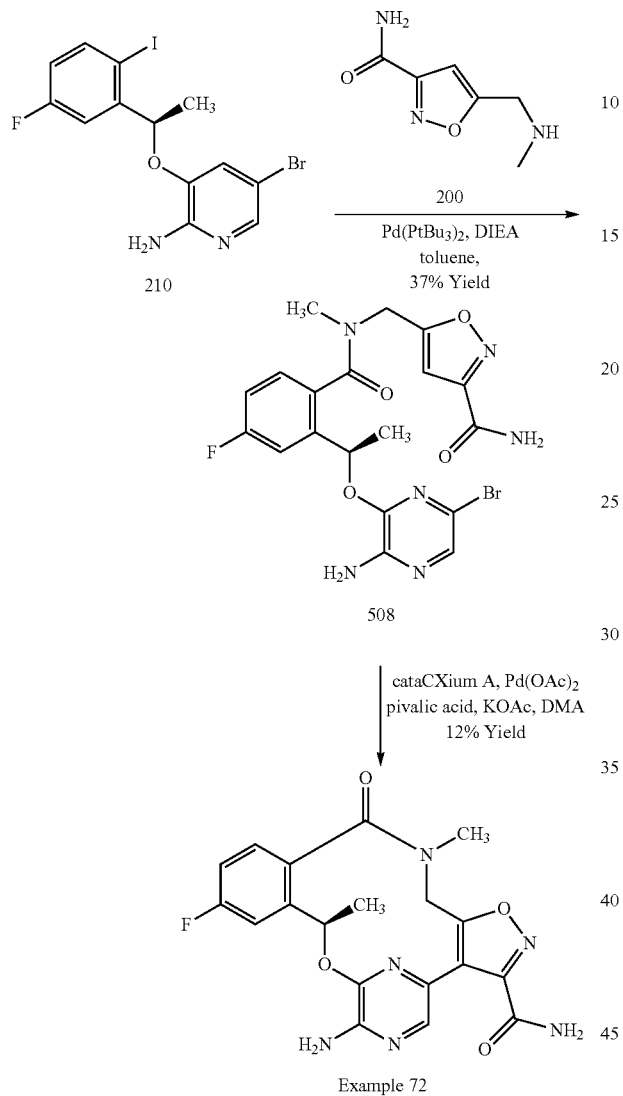

Example 72

Step 1:

To compound 210 (150 mg, 0.342 mmol) in toluene (10 mL) was added compound 200 (55.7 mg, 0.359 mmol), DIEA (0.238 mL, 1.37 mmol), and Pd(P$^t$Bu$_3$)$_2$ (17.7 mg, 0.034 mmol). The mixture was heated in a sealed vessel at 85° C. under 4 bar CO for 16 hours. The reaction was concentrated and purified by column chromatography over silica gel (0-40% EtOAc/heptane—two columns) to give compound 508 (62 mg, 37%) as a yellow gum. LCMS APCI m/z 493 [M+H]$^+$.

Step 2:

To compound 508 (62.0 mg, 0.13 mmol) in DMA (2.5 mL) was added KOAc (61.8 mg, 0.63 mmol), pivalic acid (3.9 mg, 0.038 mmol.), cataCXium A (14.0 mg, 0.038 mmol) and Pd(OAc)$_2$ (4.3 mg, 0.019 mmol). The mixture was flushed with nitrogen, and was then heated in a microwave at 120° C. for 1 hour. Water was added to the reaction, which was extracted with EtOAc (3×), dried (Na$_2$SO$_4$), concentrated, and purified by reverse phase HPLC to give Example 72 (6.48 mg, 12%) as a white solid. $^1$H NMR (400 MHz, DMSO-d$_6$) δ 8.36 (s, 1 H) 8.03 (s, 1 H) 7.73 (s, 1 H) 7.52 (dd, J=10.03, 2.57 Hz, 1 H) 7.41 (dd, J=8.50, 5.69 Hz, 1 H) 7.20 (td, J=8.53, 2.63 Hz, 1 H) 6.67 (s, 2 H) 5.89 (dd, J=6.54, 1.77 Hz, 1 H) 4.44-4.57 (m, 2 H) 2.96 (s, 3H) 1.65 (d, J=6.48 Hz, 3 H). LCMS APCI m/z 413 [M+H]$^+$.

378

Preparation of (10R)-7-amino-12-fluoro-10,16-dimethyl-15-oxo-10,15,16,17-tetrahydro-8,4-(azeno)[1,2]oxazolo[4,5-h][2,5,11]benzoxadiazacyclotetradecine-3-carbonitrile (Example 73)

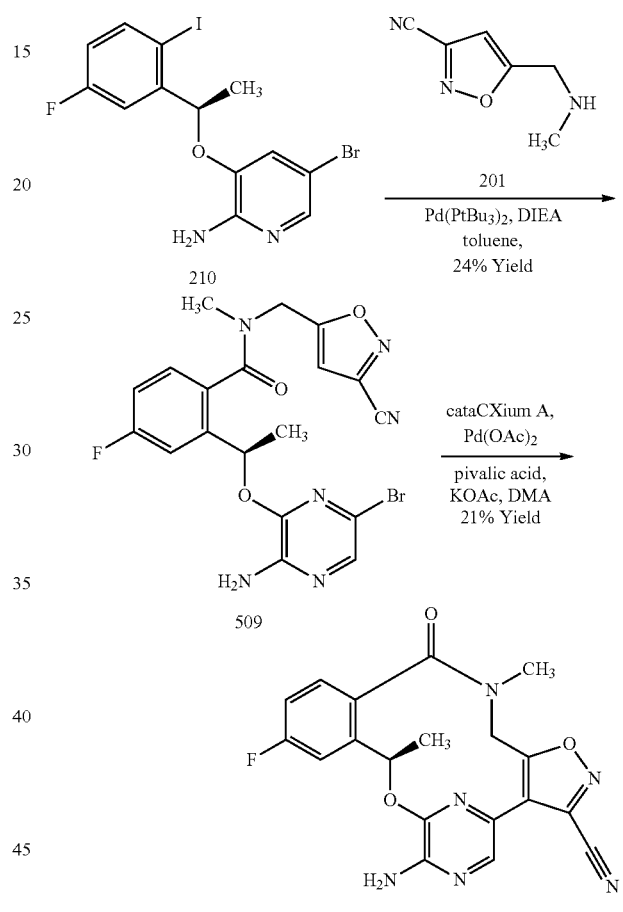

Example 73

Step 1:

To a solution of compound 210 (800 mg, 1.83 mmol) in toluene (50 mL) was added compound 360 (686 mg, 2.73 mmol), DIEA (1.27 mL, 7.30 mmol), and Pd(P$^t$Bu$_3$)$_2$ (95.4 mg, 0.183 mmol). The mixture was heated in a sealed vessel at 85° C. under 4 bar CO for 16 hours. The reaction was concentrated, and purified by column chromatography over silica gel (0-40% EtOAc/heptane) to give compound 509 (212 mg, 24%) as a yellowish solid. LCMS APCI m/z 476 [M+H]$^+$.

Step 2:

To a solution of compound 509 (188 mg, 0.395 mmol) in DMA (7.92 mL) was added KOAc (194 mg, 1.98 mmol), pivalic acid (12.3 mg, 0.119 mmol.), cataCXium A (44.0 mg, 0.30 mmol) and Pd(OAc)$_2$ (13.2 mg, 0.059 mmol). After being flushed with nitrogen, the mixture was heated in a microwave at 120° C. for 1 hour. Water was added, and the reaction extracted with EtOAc (3×). The combined organics were dried (Na2SO4), concentrated and purified by reverse phase HPLC to give Example 73 (32.12 mg, 21%) as a white solid. $^1$H NMR (400 MHz, DMSO-d$_6$) δ 7.89 (s, 1 H) 7.48 (dd, J=10.03, 2.57 Hz, 1 H) 7.43 (dd, J=8.50, 5.69 Hz, 1 H) 7.18-7.25 (m, 1 H) 6.93 (bs., 2 H) 5.85 (dd, J=6.60, 1.59 Hz, 1 H) 4.54-4.69 (m, 2 H) 2.94 (s, 3 H) 1.65 (d, J=6.48 Hz, 3 H). LCMS ES m/z 395 [M+H]$^+$.

Preparation of (9R)-6-amino-11-fluoro-9,15-dimethyl-14-oxo-9,14,15,15a,16,17-hexahydro-7,3-(azeno)-8-oxa-1,5,15,17a-tetraazabenzo[11,12]cyclotetradeca[1,2,3-cd]pentalene-2-carbonitrile (Example 74 and 75)

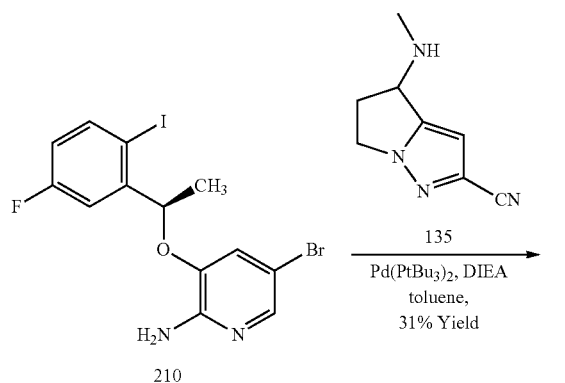

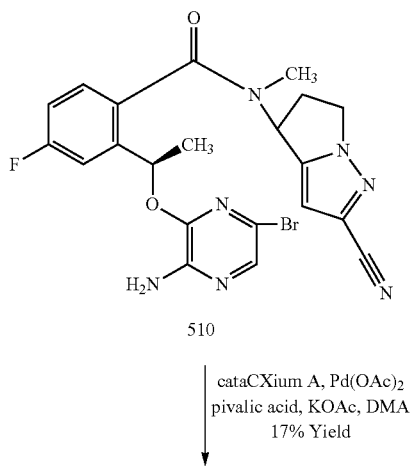

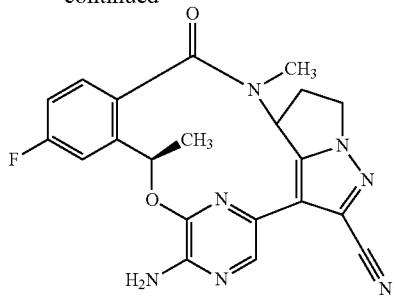

Example 74/75

Step 1:
To compound 210 (250 mg, 0.571 mmol) in toluene (20 mL) was added compound 135 (140 mg, 0.685 mmol), DIEA (0.398 mL, 2.28 mmol), and Pd(P$^t$Bu$_3$)$_2$ (29.7 mg, 0.057 mmol). The mixture was heated in a sealed vessel at 85° C. under 4 bar CO pressure for 16 hours. It was concentrated and purified by column chromatography over silica gel (0-70% EtOAc/heptane) to give compound 510 (88 mg, 31%) as a colorless gum. LCMS ES m/z 500 [M+H]$^+$.

Step 2:
To a solution of compound 510 (88 mg, 0.18 mmol) in t-amyl alcohol (6 ml) was added KOAc (86.4 mg, 0.88 mmol), cataCXium A (8.10 mg, 0.022 mmol) and Pd(OAc)$_2$ (8.1 mg, 0.022 mmol). After being flushed with nitrogen, the mixture was heated in a microwave at 140° C. for 1 hour. The reaction was filtered and was subjected to chiral separation by SFC to afford both Example 74 and Example 75. The chiral separation by SFC was performed using a Chiralcel OD-H column (21.2 mm×250 mm column, 5 micron particle size), which was eluted with 34% MeOH in CO$_2$ held at 100 bar. A flow rate of 62 mL/min gave Rt$_{(Peak\ 1)}$=3.11 minutes and Rt$_{(Peak\ 2)}$=4.80 minutes.

Example 74 (Peak 1): 4.97 mg, >99% ee. $^1$H NMR (400 MHz, CDCl$_3$) δ 8.44 (s, 1 H) 7.42 (dd, J=9.60, 2.53 Hz, 1 H) 7.21-7.25 (m, 1 H) 7.06 (td, J=8.21, 2.53 Hz, 1 H) 6.83 (t, J=8.72 Hz, 1 H) 6.59-6.67 (m, 1 H) 5.02 (s, 2 H) 4.39-4.48 (m, 1 H) 4.25 (td, J=10.80, 7.20 Hz, 1 H) 3.06-3.21 (m, 1 H) 2.55-2.68 (m, 1 H) 2.43 (s, 3 H) 1.69 (d, J=6.57 Hz, 3 H). LCMS ES m/z 420 [M+H]$^+$.

Example 75 (Peak 2): 7.44 mg, >99% ee. $^1$H NMR (400 MHz, CDCl$_3$) δ 8.31 (s, 1 H) 7.33 (dd, J=9.60, 2.27 Hz, 1 H) 7.17 (dd, J=8.46, 5.43 Hz, 1 H) 7.03 (td, J=8.21, 2.27 Hz, 1 H) 5.80 (d, J=5.56 Hz, 1 H) 5.35 (d, J=8.84 Hz, 1 H) 5.07 (s, 2 H) 4.44-4.56 (m, 1 H) 4.23 (t, J=10.61 Hz, 1 H) 3.08 (dd, J=14.02, 9.47 Hz, 1 H) 2.94 (s, 3 H) 2.69 (dd, J=14.15, 7.58 Hz, 1 H) 1.72 (d, J=6.57 Hz, 3 H). LCMS ES m/z 420 [M+H]$^+$.

Preparation of 7-amino-12-fluoro-2,9,16-trimethyl-15-oxo-2,15,16,17-tetrahydro-9H-8,4-(metheno)pyrazolo[4,3-h][1,5,11]benzoxadiazacyclotetradecine-3-carbonitrile (Example 76 and 77)

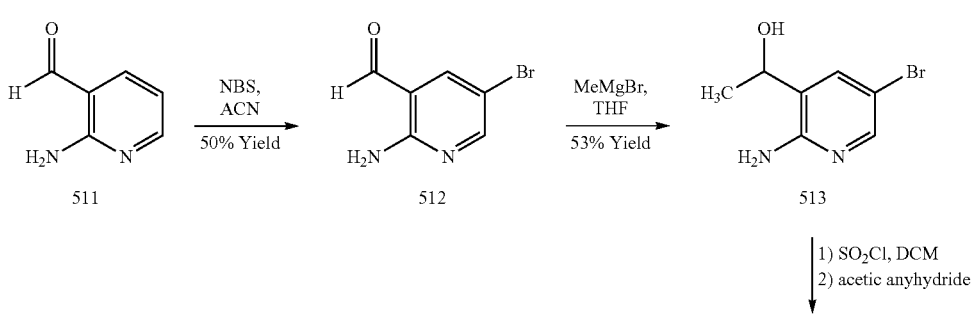

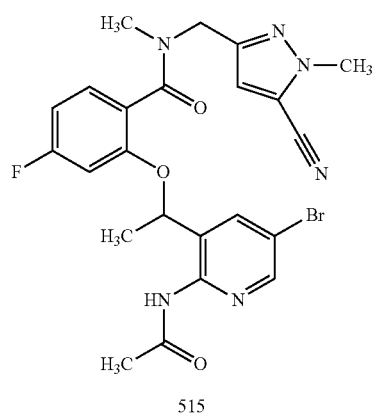

515

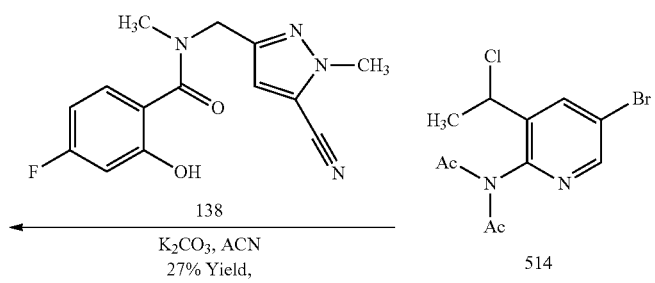

138 → K₂CO₃, ACN
27% Yield,
3-steps

514

1) KOAc, tAmOH, Pd(OAc)₂
   cataCXium A
2) HCl, MeOH
   22% Yield, 2-steps

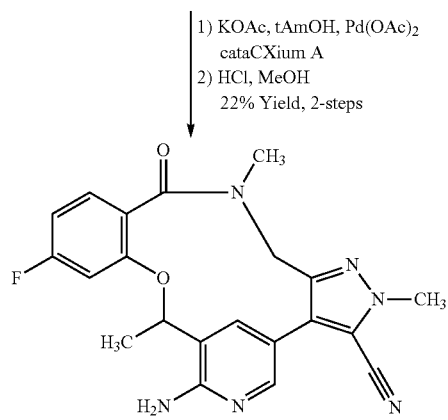

Example 76/77

Step 1:

A mixture of compound 511 (1.0 g, 8.2 mmol) and NBS (1.5 g, 8.6 mmol) in acetonitrile (16 mL) was heated to reflux for 1 hour. The reaction was reduced to half the volume and the solids were collected by filtration to give compound 512, 2-amino-5-bromopyridine-3-carbaldehyde (820 mg, 50%). ¹H NMR (400 MHz, DMSO-$d_6$) δ 9.83 (s, 1 H) 8.31 (d, J=2.5 Hz, 1 H) 8.24 (d, J=2.5 Hz, 1 H) 7.68 (d, J=2.0 Hz, 2 H).

Step 2:

To a cooled (−50° C.) mixture of compound 512 (1.1 g, 5.4 mmol) in THF (36 mL) was added dropwise MeMgBr (3 M in Et₂O, 18 mL, 54 mmol) keeping T<−40° C. The reaction was stirred at 50° C. for 1 hour then 0° C. for 1 hour before quenching with saturated aqueous ammonium chloride. The aqueous was extracted with Et₂O (3×), and the combined organics dried over MgSO₄, filtered and concentrated. The residue was purified by column chromatography over silica gel eluting with DCM/MeOH (0-5%) to give compound 513, 1-(2-amino-5-bromopyridin-3-yl)ethanol (630 mg, 53%). ¹H NMR (400 MHz, DMSO-$d_6$) δ 7.87 (d, J=2.5 Hz, 1 H) 7.52 (d, J=2.3 Hz, 1 H) 5.95 (s, 2 H) 5.33 (d, J=4.3 Hz, 1 H) 4.75-4.63 (m, 1 H) 1.27 (d, J=6.5 Hz, 3 H).

Step 3:

To a cooled (−0° C.) solution of compound 513 (260 mg, 1.2 mmol) in dichloromethane (12 mL) was added thionyl chloride (180 μL, 2.4 mmol). The ice bath was removed, and after stirring for ~4 hours, the solution was concentrated using high vacuum. The residue was dissolved in acetic anhydride and heated to 100° C. overnight. The solution was concentrated and azeotroped with toluene (2×) to give compound 514, N-acetyl-N-[5-bromo-3-(1-chloroethyl)pyridin-2-yl]acetamide which was used directly in the next step.

Step 4:

A mixture of compound 514 (~1.2 mmol), compound 138 (350 mg, 1.2 mmol), and potassium carbonate (830 mg, 6.0 mmol) in acetonitrile (8.0 mL) was heated to 60° C. After ~5 hours, the reaction mixture was cooled and diluted with EtOAc, washed with water and brine, dried over MgSO₄, filtered and concentrated. The crude material was purified by column chromatography over silica gel eluting with heptane/ethyl acetate (0-100%) to afford compound 515, 2-{1-[2-(acetylamino)-5-bromopyridin-3-yl]ethoxy}-N-[(5-cyano-1-methyl-1H-pyrazol-3-yl)methyl]-4-fluoro-N-methylbenzamide (170 mg, 27% over 3 steps). ¹H NMR (400 MHz, 80° C., DMSO-$d_6$) δ 10.00 (br. s., 1 H) 8.47 (d, J=2.5 Hz, 1 H) 7.90 (br. s., 1 H) 7.25 (dd, J=6.8, 8.3 Hz, 1 H) 7.07-6.84 (m, 2 H) 6.83-6.69 (m, 1 H) 5.56 (q, J=6.3 Hz, 1 H) 4.84-4.55 (m, 1 H) 4.31 (br. s., 1 H) 3.98 (br. s., 3 H) 2.79 (br. s., 3 H) 2.14 (s, 3 H) 1.50 (d, J=6.3 Hz, 3 H). LCMS APCI m/z 529/531 [M+H]⁺.

Step 5:

Into a microwave vial was charged compound 515 (120 mg, 0.23 mmol), KOAc (110 mg, 1.10 mmol) and ᵗAmOH (2.3 mL). The mixture was bubbled with nitrogen then palladium (II) acetate (5.2 mg, 0.023 mmol) and cataCXium A (17 mg, 0.045 mmol) were added. The vial was sealed and the reaction was irradiated in the microwave for 30 min at 150° C. The reaction was diluted with EtOAc, washed with water and brine, dried over MgSO$_4$, filtered and concentrated. The residue was purified by column chromatography over silica gel eluting with DCM/MeOH (0-10%) to give the protected intermediate. The residue was dissolved in MeOH (1.0 mL) then HCl (4 N in dioxane, 1.0 mL) was added and the solution was heated to 50° C. overnight. The reaction was diluted with EtOAc, washed with saturated aqueous NaHCO$_3$ (2×) and brine, dried over MgSO$_4$, filtered and concentrated. The residue was purified by flash chromatography eluting with DCM/MeOH (0-6%) to give a mixture of Example 76 and Example 77. The chiral separation by SFC was performed using a Regis Whelk-01 (R, R) column (4.6 mm×100 mm column, 5 micron particle size), which was eluted with 30% MeOH in CO$_2$ held at 140 bar. A flow rate of 3 mL/min gave Rt$_{(Peak\ 1)}$=2.68 minutes and Rt$_{(Peak\ 2)}$=4.65 minutes.

Example 76 (Peak 1): 10 mg (11%), >99% ee. $^1$H NMR (400 MHz, DMSO-d$_6$) δ 7.93 (d, J=2.5 Hz, 1 H) 7.45 (d, J=2.3 Hz, 1 H) 7.33 (dd, J=6.9, 8.4 Hz, 1 H) 7.21 (dd, J=2.3, 11.3 Hz, 1 H) 6.85 (dt, J=2.0, 8.3 Hz, 1 H) 6.26 (s, 2 H) 5.88 (q, J=6.5 Hz, 1 H) 4.30 (d, J=14.4 Hz, 1 H) 4.13 (d, J=14.4 Hz, 1 H) 4.04 (s, 3 H) 2.95 (s, 3 H) 1.48 (d, J=6.0 Hz, 3 H). LCMS APCI m/z 407 [M+H]$^+$.

Example 77 (Peak 2): 11 mg (11%), ~98% ee. $^1$H NMR (400 MHz, DMSO-d$_6$) δ 7.93 (d, J=2.3 Hz, 1 H) 7.45 (d, J=2.3 Hz, 1 H) 7.33 (dd, J=6.9, 8.4 Hz, 1 H) 7.21 (dd, J=2.3, 11.3 Hz, 1 H) 6.85 (dt, J=2.3, 8.3 Hz, 1 H) 6.26 (s, 2 H) 5.88 (q, J=6.0 Hz, 1 H) 4.30 (d, J=14.4 Hz, 1 H) 4.13 (d, J=14.4 Hz, 1 H) 4.04 (s, 3 H) 2.95 (s, 3 H) 1.48 (d, J=6.0 Hz, 3 H). LCMS APCI m/z 407 [M+H]$^+$.

Preparation of 7-amino-12-fluoro-2,16,17-trimethyl-15-oxo-10,15,16,17-tetrahydro-2H-8,4-(azeno)pyrazolo[4,3-h][2,5,11]benzoxadiazacyclotetradecine-3-carbonitrile (Example 78, 79 and 80)

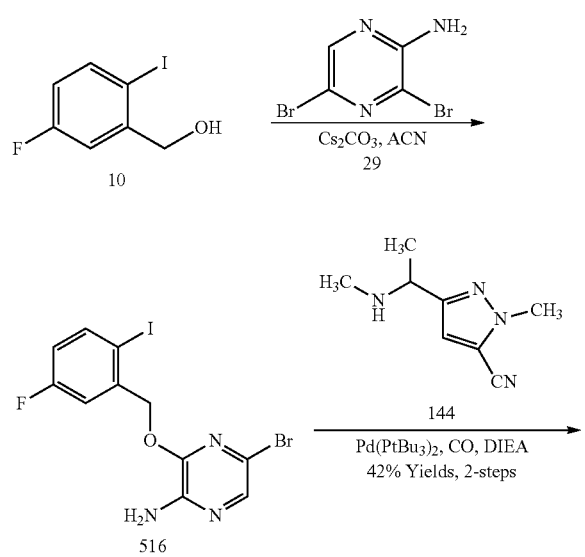

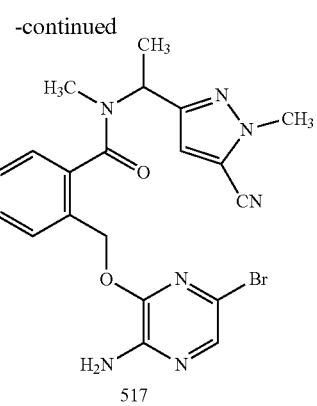

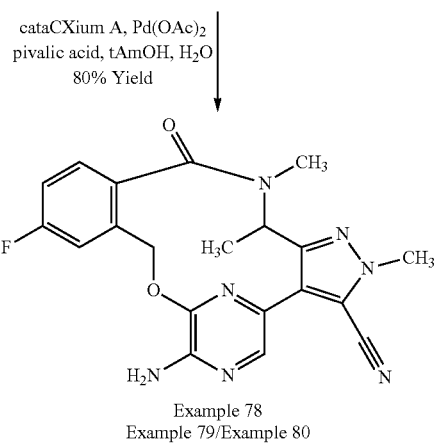

Example 78
Example 79/Example 80

Step 1:
A mixture of compound 10 [1.89 g, ~7.5 mmol, (containing ~25% (5-fluoro-2-bromo-phenyl)methanol)], compound 29 (2.28 g, 9 mmol) and cesium carbonate (6.11 g, 18.7 mmol) in acetonitrile (7 mL) was heated at 80° C. for 18 hours. The crude suspension was added to brine (~400 mL) and the resulting rust colored solids were collected by filtration and rinsed with water. The partially dried solids were taken up in hot acetonitrile (~200 mL) and filtered to remove fine dark insolubles which were subsequently discarded. The filtrate was allowed to stand at room temperature overnight. Some crystals were evident in the flask after standing overnight. The supernatant was removed and concentrated to dryness to give compound 516 as a reddish solid (2.822 g), which was carried forward without further purification. $^1$H NMR (400 MHz, DMSO-d$_6$) δ 7.92 (dd, 1 H) 7.58-7.69 (m, 2 H) 7.05 (td, J=8.65, 3.24 Hz, 1 H) 6.69 (s, 2 H) 5.27 (s, 2H).

Step 2:
A mixture of compound 516 (616 mg, ~1.45 mmol), compound 144 (228 mg, 1.14 mmol), DIEA (0.792 mL, 4.54 mmol) and Pd(P$^t$Bu$_3$)$_2$ (59 mg, 0.114 mmol) in toluene was heated to 85° C. under 4 bar CO overnight. The mixture was concentrated and purified by flash chromatography using a gradient of 25-100% EtOAc/heptane as eluent. The desired fractions were concentrated to dryness to give compound 517 (233 mg, 42%) as a foamy solid. $^1$H NMR (400 MHz, 80° C., DMSO-d$_6$) δ 7.64 (s, 1 H), 7.51 (dd, J=10.20, 2.64 Hz, 1 H), 7.35-7.46 (m, 1H), 7.24 (td, J=8.62, 2.39 Hz, 1 H), 6.99 (s, 1 H), 6.25 (br. s., 2 H), 5.86 (s, 1 H), 5.35 (s, 2 H), 3.94 (s, 3 H), 2.65 (br. s., 3 H), 1.49 (d, J=7.05 Hz, 3 H).

Step 3:
To a solution of compound 517 (179 mg, 0.367 mmol) in t-amyl alcohol (10 mL) was added cataCXium A (40 mg, 0.1 mmol), pivalic acid (11 mg, 0.11 mmol), potassium acetate (180 mg, 1.8 mmol), and water (40 mL). The resulting suspension was sparged with a Nitrogen bubbler for ~5 minutes. Palladium Acetate (12 mg, 0.055 mmol) was then added. The mixture was crimp sealed and heated at 140° C. with microwave irradiation for 1 hour. LCMS indicated desired product as major peak. The mixture was reduced to minimum volume. The residue was suspended in DCM, filtered and the filtrate concentrated, and purified by column chromatography over silica gel using a gradient of 25-100% (EtOAc containing 10% MeOH)/heptanes) as eluent. The desired fractions were reduced to minimum volume to give Example 78 (120 mg, 0.294 mmol, 80%) as a pale yellow solid. $^1$H NMR (400 MHz, DMSO-d$_6$) δ 7.75 (s, 1 H) 7.40-7.60 (m, 2 H) 7.18 (td, J=8.44, 3.02 Hz, 1 H) 6.75 (s, 2 H) 5.60 (dd, J=12.46, 1.64 Hz, 1 H) 5.07 (d, J=12.09 Hz, 1 H) 4.59-4.77 (m, 1 H) 4.04 (s, 3 H) 2.83 (s, 3 H) 1.61 (d, J=6.80 Hz, 3 H).

The chiral separation by SFC was performed using a Chiralcel OJ-H column (4.6 mm×250 mm column, 5 micron particle size), which was eluted with 30% MeOH in CO$_2$ held at 140 bar. A flow rate of 3 mL/min gave Rt$_{(Peak\ 1)}$=3.67 minutes and Rt$_{(Peak\ 2)}$=4.97 minutes.

Example 79 (Peak 1): 44.9 mg >99% ee (−). $^1$H NMR (600 MHz, DMSO-d$_6$) δ 7.72 (s, 1 H) 7.41-7.58 (m, 2 H) 7.18 (td, J=8.52, 2.54 Hz, 1 H) 6.78 (s, 2 H) 5.55 (d, J=12.46 Hz, 1 H) 5.08 (d, J=12.46 Hz, 1 H) 4.64 (q, J=6.87 Hz, 1 H) 4.02 (s, 3 H) 2.81 (s, 3 H) 1.59 (d, J=6.87 Hz, 3H). LCMS APCI m/z 407 [M+H]$^+$.

Example 80 (Peak 2): 45.2 mg >99% ee (+). $^1$H NMR (600 MHz, DMSO-d$_6$) δ 7.72 (s, 1 H) 7.42-7.58 (m, 2 H) 7.17 (td, J=8.52, 2.54 Hz, 1 H) 6.78 (s, 2 H) 5.55 (d, J=12.46 Hz, 1 H) 5.08 (d, J=12.46 Hz, 1 H) 4.64 (q, J=7.04 Hz, 1 H) 4.02 (s, 3 H) 2.81 (s, 3 H) 1.59 (d, J=6.87 Hz, 3 H). LCMS APCI m/z 407 [M+H]$^+$.

Preparation of (10R)-7-amino-3-ethyl-12-fluoro-10, 16-dimethyl-16,17-dihydro-8,4-(metheno)[1,2]oxazolo[4,5-h][2,5,11]benzoxadiazacyclotetradecin-15 (10 H)-one (Example 81)

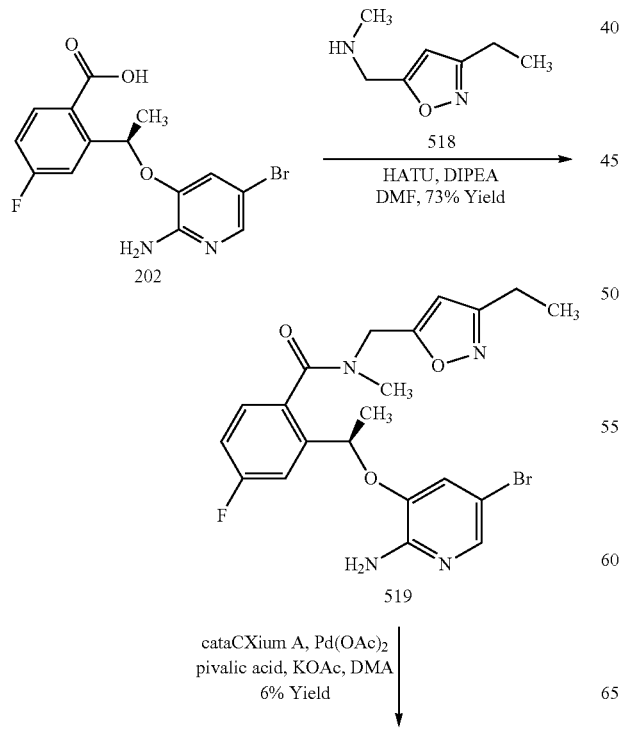

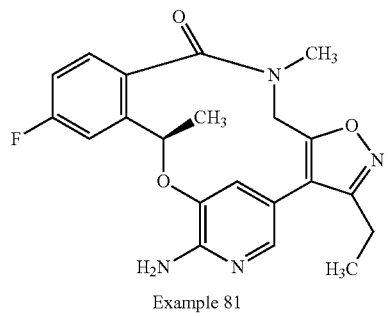

Example 81

Step 1:

Into a solution of compound 518 (41 mg, 0.3 mmol), compound 202 (70 mg, 0.2 mmol), DIPEA (76 mg, 3.0 equiv) in DMF (0.8 mL, 0.25 M) was added HATU (90 mg, 1.2 equiv). The resulting mixture was stirred at room temperature for 1 hour. The solvent was removed under reduced pressure. The residue was diluted with EtOAc and washed with water, saturated aqueous NaHCO$_3$ solution and brine. Concentration and purification by reverse phase preparative HPLC provided compound 519 (69 mg, 73%) as white solid. LCMS APCI m/z 477 [M+H]$^+$.

Step 2:

To a solution of the compound 519 (63 mg, 0.13 mmol) and pivalic acid (6 mg, 0.4 equiv) in DMA (2.6 mL) was added KOAc solid (65 mg, 5 equiv), followed by Pd(OAc)$_2$ (6 mg, 0.20 equiv) and cataCXium A (20 mg, 0.4 equiv) under argon. The reaction was heated in the microwave at 160° C. for 65 minutes and purified by reverse phase HPLC to afford Example 81 (3.3 mg, 6%) as a white solid. $^1$H NMR (400 MHz, DMSO-d$_6$) δ 7.63 (dd, J=2.5, 10.4 Hz, 1H) 7.53 (d, J=1.5 Hz, 1H) 7.42 (dd, J=5.8, 8.6 Hz, 1H) 7.18 (dt, J=2.7, 8.4 Hz, 1H) 6.69 (s, 1H) 6.07 (s, 2H) 5.57-5.67 (m, 1H) 4.57 (d, J=15.2 Hz, 1H) 4.28 (d, J=14.9 Hz, 1H) 3.02 (s, 3H) 2.69-2.85 (m, 2H) 1.66 (d, J=6.3 Hz, 3H) 1.18 (t, J=7.5 Hz, 3H). LCMS APCI m/z 397 [M+H]$^+$.

Preparation of (10R)-7-amino-3-ethyl-12-fluoro-10, 16-dimethyl-16,17-dihydro-8,4-(metheno)[1,2]oxazolo[4,3-h][2,5,11]benzoxadiazacyclotetradecin-15 (10H)-one (Example 82)

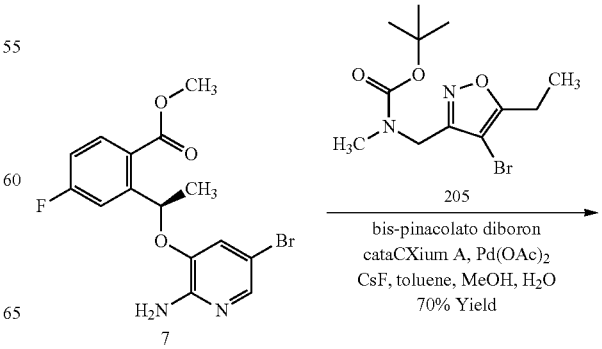

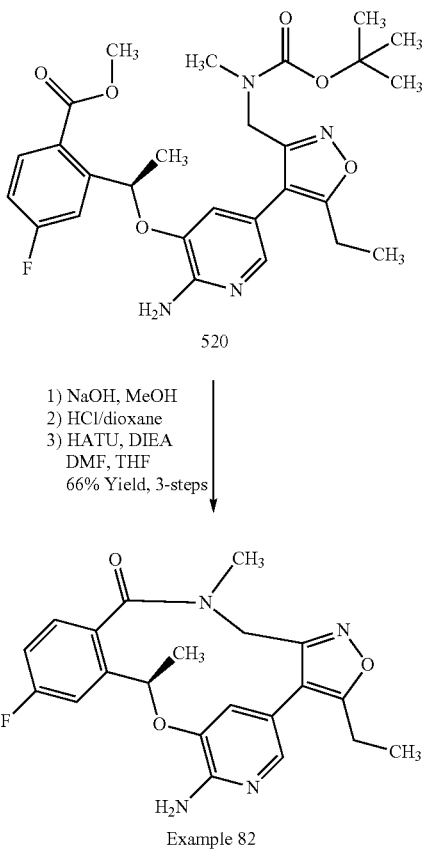

Example 82

Step 1:
Palladium (II) acetate (82.4 mg, 0.367 mmol) and cataCXium A (271 mg, 0.733 mmol) were mixed together in toluene (3.0 mL, de-gassed) and the resulting solution was added via pipette to a stirred solution of compound 7 (1.35 g, 3.67 mmol), bis-pinacolato diboron (1.86 g, 7.33 mmol) and CsF (2.23 g, 14.7 mmol) in MeOH/H$_2$O (4:1, 25.5 mL, de-gassed) at 50° C. After 5 minutes, a solution of compound 205 (900 mg, 2.82 mmol) in MeOH (5.8 mL, de-gassed) was added. The resulting mixture was stirred at 80° C. After stirring for 1.5 hours, the reaction was judged to be complete by LCMS analysis. After being cooled to room temperature, the mixture was diluted with EtOAc, washed with water, brine, dried over Na$_2$SO$_4$ and concentrated in vacuo to give a residue, which was purified by column chromatography over silica gel (0-5% MeOH/DCM) to afford compound 520 (1.045 g, 70%). $^1$H NMR (400 MHz, DMSO-d$_6$) δ 7.88-7.99 (m, 1 H) 7.50 (dd, J=10.48, 2.65 Hz, 1 H) 7.39 (d, J=1.77 Hz, 1 H) 7.24 (td, J=8.46, 2.53 Hz, 1 H) 6.54 (br. s., 1 H) 6.22 (br. s., 1 H) 6.08 (br. s., 2 H) 3.85 (s, 3 H) 2.64 (s, 3 H) 2.43-2.48 (m, 2 H) 1.62 (d, J=6.32 Hz, 3 H) 1.31 (br. s., 3 H) 1.12-1.28 (m, 6 H) 1.00 (t, J=7.58 Hz, 3 H). LCMS APCI m/z 529 [M+H]$^+$.

Step 2:
NaOH (1.84 g, 46.1 mmol) in 1 mL water was added to a solution of compound 520 (995 mg, 1.8 mmol) in MeOH (30 mL) and water (3 mL). The reaction mixture was stirred at room temperature. After stirring for 2.5 hours, the reaction was completed, and 4M HCl in dioxane (15 mL) was added slowly. The mixture was stirred at room temperature for 20 hours. The reaction mixture was concentrated under reduced pressure to give crude the deprotected product, which was carried directly to the cyclization step without further purification. To a solution of HATU (1.0 g, 2.56 mmol) in DMF (76 mL) was added dropwise a solution of the crude product and DIEA (5.1 mL, 29.3 mmol) in DMF (76 mL) and THF (7.6 mL) at 0° C. After addition, the resulting mixture was stirred at 0° C. for 1 hour. The mixture was poured into ice water (400 mL), and the aqueous layer was extracted with EtOAc. The combined EtOAc layers were washed with brine, dried over Na$_2$SO$_4$ and concentrated in vacuo to give a residue, which was purified by column chromatography over silica gel (0-10% MeOH/DCM). After purification, $^{19}$F NMR indicated the product was contaminated by PF6$^-$. The glue like product was dissolved in EtOAc and washed with 10% aqueous Na$_2$CO$_3$ (3×), and then dried over sodium sulfate and concentrated under reduced pressure to give Example 82 as a white solid (480 mg, 66%). $^1$H NMR (400 MHz, DMSO-d$_6$) δ 7.63 (dd, J=10.32, 2.77 Hz, 1 H) 7.47 (dd, J=8.56, 5.79 Hz, 1 H) 7.40 (d, J=1.76 Hz, 1 H) 7.17 (td, J=8.50, 2.64 Hz, 1 H) 6.78 (d, J=1.76 Hz, 1 H) 6.03 (s, 2H) 5.65 (dd, J=6.29, 1.76 Hz, 1 H) 4.47 (d, J=14.35 Hz, 1 H) 4.21 (d, J=14.35 Hz, 1 H) 3.01 (s, 3 H) 2.82-2.92 (m, 2 H) 1.67 (d, J=6.29 Hz, 3 H) 1.22 (t, J=7.55 Hz, 3 H). LCMS APCI m/z 397 [M+H]$^+$.

Preparation of (10S)-7-amino-12-fluoro-2,10,16-trimethyl-16,17-dihydro-2H-8,4-(azeno)pyrazolo[4,3-h][2,5,11]benzoxadiazacyclotetradecin-15(10H)-one (Example 83)

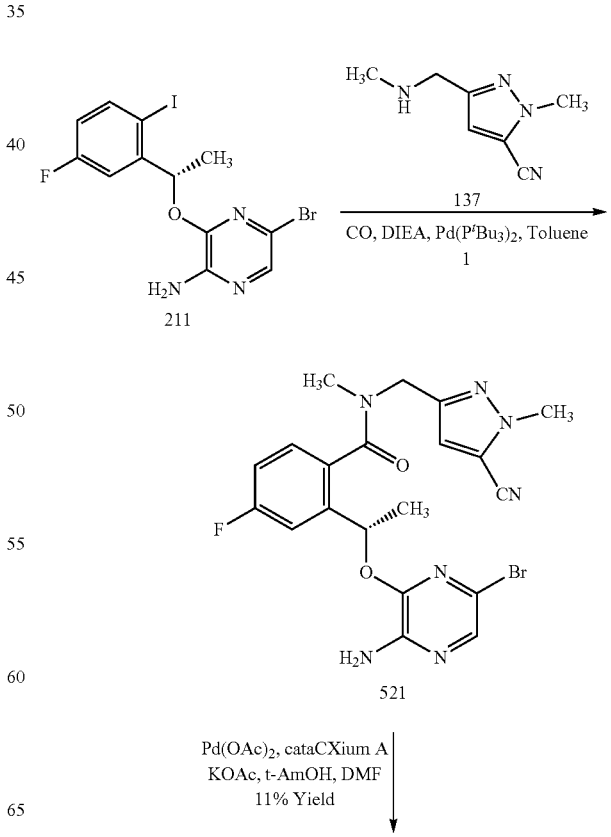

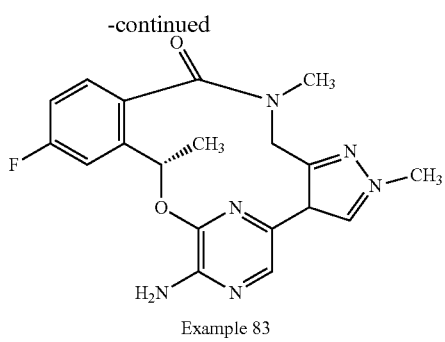
Example 83
Using the two step procedure of Example 56, Example 83 (41.4 mg, 11%) was prepared as a white solid. $^1$H NMR (600 MHz, DMSO-$d_6$) δ 8.02 (s, 1 H), 7.63 (s, 1 H) 7.44 (dd, J=10.09, 2.63 Hz, 1 H) 7.40 (dd, J=8.57, 5.53 Hz, 1 H) 7.15 (td, J=8.57, 2.76 Hz, 1 H) 6.25 (s, 2 H) 5.74-6.04 (m, 1 H) 4.33 (d, J=13.27 Hz, 1 H) 4.18 (d, J=13.27 Hz, 1 H) 3.83 (s, 3 H) 2.87 (s, 3 H) 1.62 (d, J=6.36 Hz, 3 H). LCMS APCI m/z 383 [M+H]$^+$.
Preparation of 7-amino-12-fluoro-10-(fluoromethyl)-2,16-dimethyl-15-oxo-10,15,16,17-tetrahydro-2H-8,4-(metheno)pyrazolo[4,3-h][2,5,11]benzoxadiazacyclotetradecine-3-carbonitrile (Example 84 and 85)
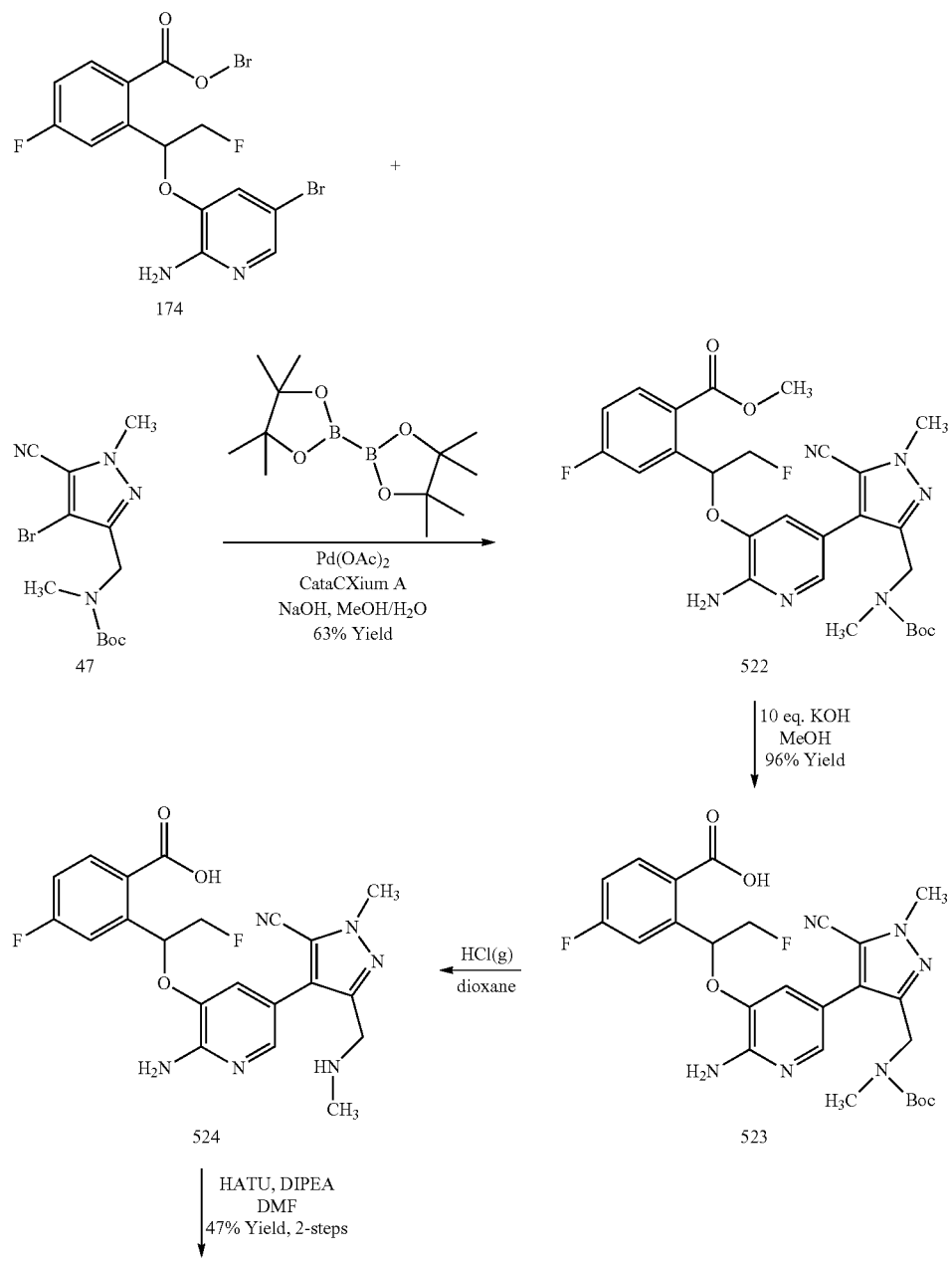

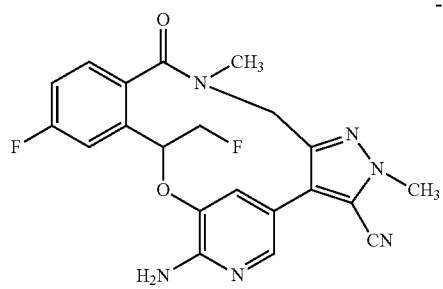

Example 84 and Example 85

Step 1:

To a solution of compound 174 (0.7 g, 1.81 mmol), compound 47 (1.22 g, 3.07 mmol) and bis-(pinacalato)diboron (1.38 g, 5.42 mmol) in dry methanol (280 mL) was added NaOH (145 mg, 3.62 mmol) in water (10 mL) under nitrogen gas at room temperature. After the mixture was degassed three times with nitrogen, cataCXium A (68 mg, 0.18 mmol) and Pd(OAc)$_2$ (21 mg, 0.09 mmol) was added. The resulting mixture was degassed with nitrogen three times, and was then refluxed for 16 hours. TLC (petroleum ether/EtOAc 1/1) showed the reaction mixture was completed. The reaction mixture was diluted with EtOAc (300 mL). The mixture was then washed with brine (2×), dried over Na$_2$SO$_4$ and concentrated in vacuo to give residue, which was purified via Biotage (petroleum ether/EtOAc=1:1, Rf=0.1) to give compound 522 (0.7 g, 62.8%) as a brown solid. LCMS m/z 579 [M+Na]$^+$ Step 2:

A mixture of compound 522 (0.5 g, 0.90 mmol) and KOH (0.5 g, 8.99 mmol) in methanol (20 mL) was heated to 50° C. for 24 hours. LC-MS showed that the reaction was completed. The reaction mixture was concentrated in vacuo to give a residue. The residue was acidified with 1N HCl to pH ~5. The mixture was extracted with EtOAc (3×). The combined EtOAc layers were washed with brine, dried over Na$_2$SO$_4$, and concentrated in vacuo to give the residue, which was purified by flash chromatography over silica gel (DCM/MeOH=25:1, Rf=0.3) to give compound 523 (320 mg, 95.5% of purity, 62%) as a yellow solid. LCMS m/z 543 [M+H]$^+$.

Step 3:

To a stirred solution of compound 523 (320 mg, 95% pure, 0.56 mmol) in DCM (10 mL) was added dropwise ~4M HCl (g) in dioxane (2 mL) at room temperature. After addition, the reaction mixture was stirred at room temperature for 3 hours. LC-MS indicated that the reaction was completed. The reaction mixture was concentrated in vacuo to give crude compound 524, which was used in the next step without further purification. LCMS m/z 443 [M+H]$^+$.

Step: 4

To a solution of HATU (155 mg, 0.4 mmol) in DMF (8 mL) was added dropwise a solution of compound 424 (~0.29 mmol) and DIEA (0.60 g, 4.64 mmol) in dry DMF (8 mL) and dry THF (1 mL) at 0° C. After addition, the resulting mixture was stirred at the same temperature for 1 hour. LC-MS showed the reaction was completed. The mixture was poured into ice-water (30 mL). The mixture was extracted with EtOAc (30 mL×5). The combined EtOAc layers were washed with brine (30 mL×5), dried over Na$_2$SO$_4$ and concentrated in vacuo to give residue, which was purified column chromatography over silica gel (DCM/MeOH=25:1, Rf=0.3) to give a mixture of Example 84 and Example 85 (80 mg, 52.6%) as a yellow solid. The chiral separation was performed by preparative SFC on a Chiralcel OJ-H (50×4.6 mm I.D., 3 micron particle size) column, which was eluted with 5-40% methanol (0.05% DEA) in 140 bar CO$_2$ with a flow rate of 4 mL/min. Rt$_{(Peak\ 1)}$=5.93 minutes and Rt$_{(Peak\ 2)}$=9.28 minutes, and gave Peak 1 as a white solid (33 mg, 27%) and Peak 2 as a white solid (30 mg, 20%).

Example 84 (Peak 1): 100% ee. $^1$H NMR (400 MHz, Methanol-d$_4$) δ 7.70 (bs, 1H), 7.54-7.48 (m, 2H), 7.22-7.18 (m, 1H), 6.98 (s, 1H), 5.91-5.90 (m, 1H), 5.16-4.98 (m, 1H), 4.88-4.84 (m, 1H), 4.57-4.53 (d, 1H), 4.49-4.48 (d, 1H), 4.03 (s, 3H), 3.15 (s, 3H). LCMS ES m/z 425 [M+H]$^+$.

Example 85 (Peak 2): 100% ee. $^1$H NMR (400 MHz, Methanol-d$_4$) δ 7.71 (bs, 1H), 7.54-7.48 (m, 2H), 7.232-7.18 (m, 1H), 6.99 (s, 1H), 5.92-5.56 (dd, 1H), 5.12-4.95 (m, 1H), 4.87-4.83 (m, 1H), 4.53-4.50 (d, 1H), 4.43-4.40 (d, 1H), 4.09 (s, 3H), 3.15 (s, 3H). LCMS ES m/z 425 [M+H]$^+$.

Preparation of 7-amino-12-fluoro-10-(fluoromethyl)-3-methoxy-1,16-dimethyl-16,17-dihydro-1H-8,4-(metheno)pyrazolo[4,3-h][2,5,11]benzoxadiazacyclotetradecin-15(10H)-one
(Example 86/Example 87)

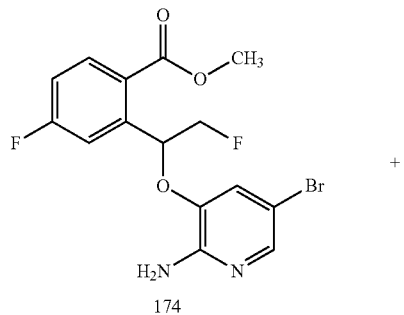

174

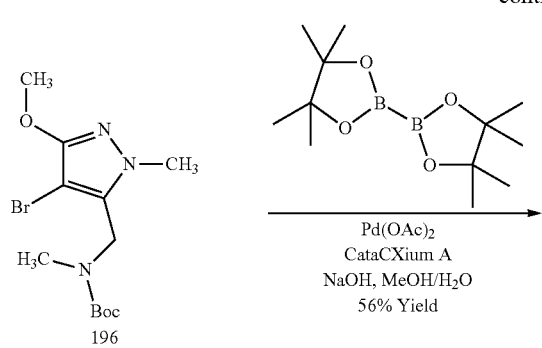

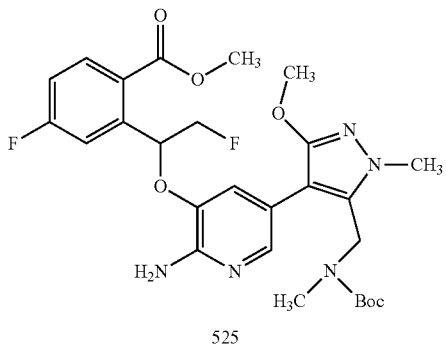

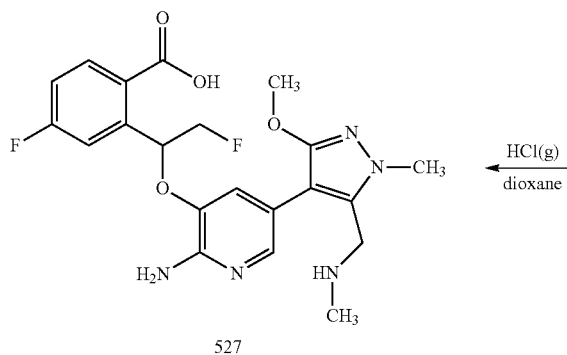

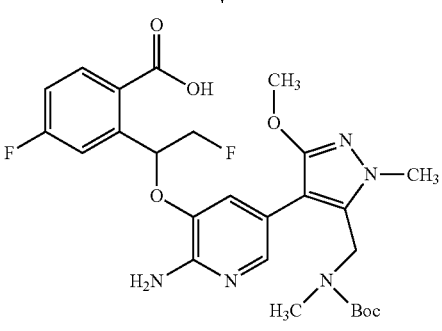

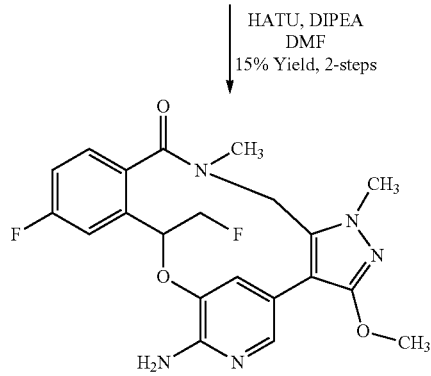

Example 86 and Example 87

Step 1:

To a solution of compound 174 (0.98 g, 2.5 mmol), compound 196 (1.01 g, 3.03 mmol) and bis(pinacalato)diboron (1.905 g, 7.5 mmol) in methanol (320 mL) was added NaOH (200 mg, 5 mmol) in water (11 mL) under nitrogen at room temperature. After the mixture was degassed three times with nitrogen, cataCXium A (116 mg, 0.325 mmol) and Pd(OAc)$_2$ (74 mg, 0.325 mmol) were added. The resulting mixture was degassed with nitrogen three times, and was refluxed for 16 hours. TLC (petroleum ether/EtOAc 1/1) showed the reaction was complete. The reaction mixture was diluted with EtOAc (300 mL). The combined EtOAc layers were washed with brine (100 mL×2), dried over Na$_2$SO$_4$ and concentrated in vacuo to give a residue, which was purified via column chromatography (silica gel, petroleum ether/EtOAc from 3/1 to 1/1) to give compound 525 (800 mg, 94% purity, 56%) as a brown solid. $^1$H NMR (400 MHz, CDCl$_3$): δ 8.07-8.03 (dd, 1H), 7.53 (s, 1H), 7.31-7.28 (dd, 1H), 7.03-6.99 (m, 1H), 6.55-6.54 (d, 1H), 6.53-6.42 (d, 1H), 6.43-6.37 (dd, 1H), 4.78 (s, 2H), 4.69-4.65 (m, 2H), 4.20-4.08 (m, 2H), 3.89-3.85 (t, 3H), 3.69 (s, 3H), 3.59 (s, 3H), 2.30 (s, 3H), 1.39 (s, 9H).

Step 2:

A mixture of compound 525 (800 mg, 1.42 mmol) and NaOH (1.14 g, 28.5 mmol) in methanol (30 mL) and water (10 mL) was stirred at room temperature for 18 hours. LC-MS showed the reaction was complete. MeOH was removed in vacuo to give a residue. The residue was acidified with 6N HCl to pH ~5. The mixture was saturated with solid NaCl and then extracted with EtOAc (30 mL×5). The combined EtOAc layers were dried over Na$_2$SO$_4$ and concentrated in vacuo to give compound 526 (700 mg, 89.7%) as a yellow solid. LCMS m/z 514 [M+H]$^+$.

Step 3:

To a solution of compound 526 (700 mg, 1.28 mmol) in dioxane (5 mL) was added dropwise ~4M HCl (g) in dioxane (10 mL) at room temperature. After addition, the reaction mixture was stirred at room temperature for 18 hours. TLC (EtOAc) showed the reaction was complete. The reaction mixture was concentrated in vacuo to give crude compound 527, which was used for next step without any further purification. LCMS m/z 448 [M+H]$^+$.

Step 4:

To a solution of HATU (813 mg, 2.14 mmol) in DMF (80 mL) was added dropwise the mixture of compound 527 (~636 mg, 1.13 mmol) and DIPEA (3.69 g, 28.6 mmol) in DMF (20 mL) at 0° C. After the addition, the resulting mixture was stirred at room temperature for 1 hour. LC-MS showed the reaction was complete. The mixture was poured into ice-water (50 mL). The mixture was extracted with EtOAc (40 mL×5). The combined EtOAc layers were washed with brine (20 mL×5), dried over $Na_2SO_4$ and concentrated in vacuo to give a residue. The residue was purified via column chromatography (silica gel, petroleum ether/EtOAc 30-70%) to give a mixture of Example 86 and Example 87 (0.2 g, 36.3%) as a pink solid. The chiral separation was performed by preparative SFC on a Chiralcel OD-3 (50×4.6 mm I.D., 3 micron particle size) column, which was eluted with 5-40% ethanol (0.05% DEA) in $CO_2$ with a flow rate of 4 mL/min. $Rt_{(Peak\ 1)}$=1.47 minutes and $Rt_{(Peak\ 2)}$=1.71 minutes, and gave Peak 1 as a pink solid (38 mg, 7%) and Peak 2 as a pink solid (42 mg, 8%).

Example 86 (Peak 1): 100% ee. $^1$H NMR (400 MHz, $CDCl_3$) δ 7.87-7.86 (d, 1H), 7.34-7.31 (dd, 1H), 7.28-7.25 (m, 1H), 7.09-7.04 (m, 1H), 6.81 (s, 1H), 5.78-5.73 (d, 1H), 4.91-4.78 (m, 4H), 4.45-4.41 (d, 1H), 4.33-4.30 (d, 1H), 3.94-3.91 (d, 3H), 3.74 (d, 3H), 3.16 (s, 3H). LCMS ES m/z 430 [M+H]$^+$.

Example 87 (Peak 2): 100% ee. $^1$H NMR (400 MHz, $CDCl_3$) δ 7.80 (s, 1H), 7.27-7.24 (dd, 1H), 7.22-7.19 (m, 1H), 7.03-7.0 (m, 1H), 6.76-6.75 (s, 1H), 5.71-5.67 (d, 1H), 4.85-4.72 (m, 4H), 4.38-4.35 (d, 1H), 4.27-4.23 (d, 1H), 3.89 (s, 3H), 3.81 (s, 3H), 3.09 (s, 3H). LCMS ES m/z 430 [M+H]$^+$.

Preparation of (10R)-7-amino-12-fluoro-10,16-dimethyl-15-oxo-10,15,16,17-tetrahydro-2H-8,4-(metheno)pyrazolo[4,3-h][2,5,11]benzoxadiazacyclotetradecine-3-carbonitrile (Example 88)

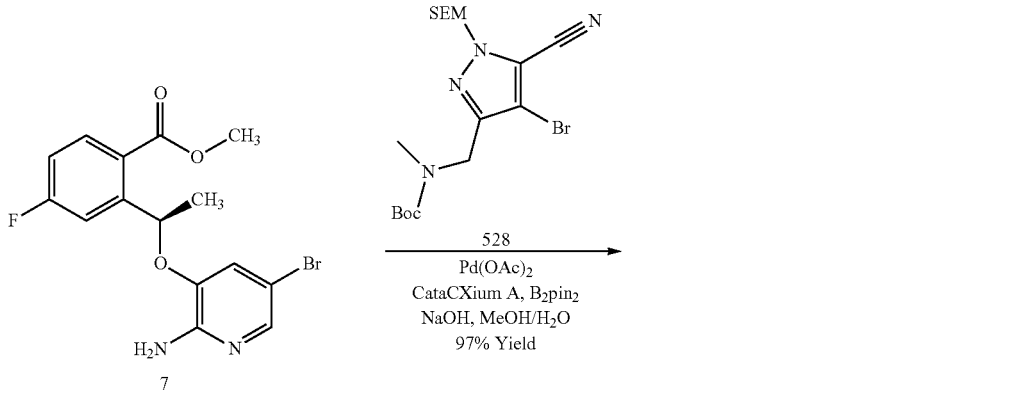

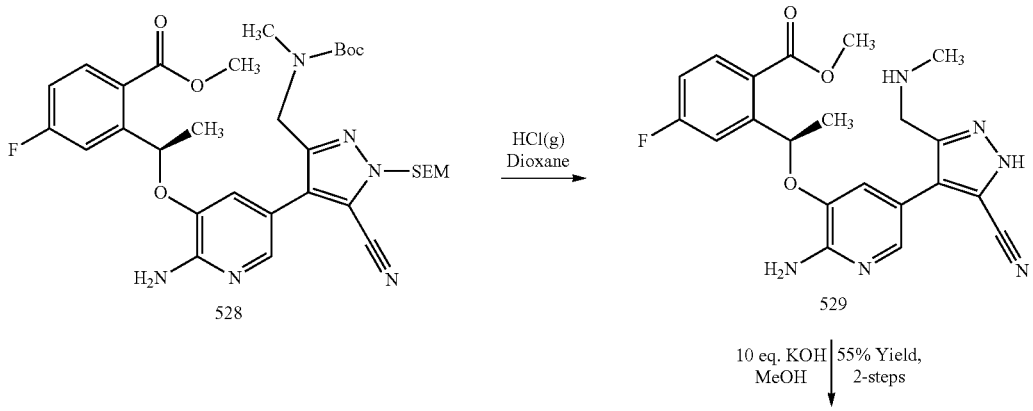

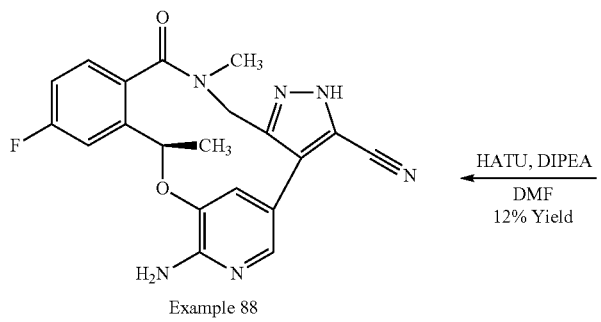

Example 88

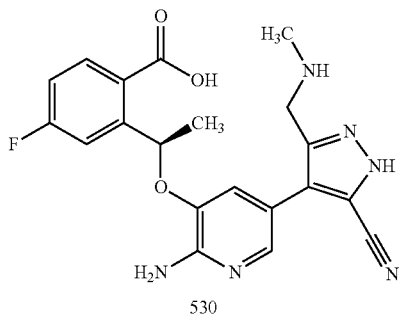

530

Step 1:

To a solution of compound 7 (600 mg, 1.62 mmol), compound 214 (1.08 g, 2.44 mmol) and bis-(pinacalato)diboron (1.23 g, 4.86 mmol) in methanol (120 mL) was added cataCXium A (80 mg, 0.2 mmol) and Pd(OAc)$_2$ (50 mg, 0.20 mmol). After the mixture was degassed three times with nitrogen, a solution of NaOH (130 mg, 3.2 mmol) in water (10 mL) was added under nitrogen at room temperature. The resulting mixture was degassed with nitrogen three times and was then refluxed for 16 hours. TLC (petroleum ether/EtOAc 3/1) showed the reaction was complete. The reaction mixture was diluted with EtOAc (100 mL×3). The combined EtOAc layers were washed with brine (50 mL×3), dried over Na$_2$SO$_4$ and concentrated in vacuo to give a residue, which was purified by column chromatography (silica gel, petroleum ether/EtOAc=1:1, Rf=0.3) to give compound 528 (650 mg, 96.8% of purify, 59%) as a yellow solid. LCMS m/z 655 [M+H]$^+$.

Step 2:

To a stirred solution of compound 529 (350 mg, 96.8% of purify, 0.55 mmol) in DCM (5 mL) was added dropwise ~4M HCl (g) in dioxane (5 mL) at room temperature. After addition, the reaction mixture was stirred at room temperature for 2 hours. LC-MS showed the reaction was complete. The reaction mixture was concentrated in vacuo to give crude compound 529, which was used for next step without any further purification. LCMS m/z 424 [M+H]$^+$ Step 3:

A mixture of compound 529 (~0.47 mmol) and KOH (0.65 g, 11.7 mmol) in methanol (15 mL) was stirred at 50° C. for 36 hours. LC-MS showed the reaction was complete. MeOH was removed in vacuo to give the residue, which was acidified with 1N aq. HCl to pH ~6. The mixture was extracted with EtOAc (20 mL×2). The aqueous layer was lyophilized to give crude product, which was diluted with DCM/MeOH (5:1, 20 mL) and filtered. The filtrate was concentrated to give compound 530 (140 mg, 75% of purity, 54.4%) as a brown solid. LCMS m/z 411 [M+H]$^+$.

Step 4:

To a solution of HATU (137 mg, 0.35 mmol) in DMF (20 mL) was added dropwise a solution of compound 530 (140 mg, 75% of purity, 0.25 mmol) and DIEA (516 mg, 4 mmol) in DMF (10 mL) at 0° C. After the addition, the resulting mixture was stirred at 0° C. for 1 hour. LC-MS showed the reaction was complete. The mixture was poured into water (50 mL). The mixture was extracted with EtOAc (50 mL×5). The combined EtOAc layers were washed with brine (40 mL×5), dried over Na$_2$SO$_4$ and concentrated in vacuo to give a residue. The residue was purified by column chromatography over silica gel (DCM/MeOH=25:1, Rf=0.3) to give crude material, which was further purified by preparative SFC (Chiralcel OD-3, 150×4.6 mm I.D., 3 μm. Retention Time 6.93 min Mobile phase: methanol (0.05% DEA) in CO$_2$ from 5% to 40% Flow rate: 3 mL/min) followed by preparative HPLC to afford Example 88 (12 mg, 12%) as a white solid. $^1$H NMR (400 MHz, Methanol-d4) δ 7.70 (s, 1H), 7.54-7.51 (dd, 1H), 7.46-7.42 (m, 1H), 7.15-7.11 (m, 1H), 6.91 (s, 1H), 5.76-5.73 (t, 1H), 4.54 (s, 2H), 3.15 (s, 3H), 1.81-1.80 (d, 3H). LCMS m/z 392 [M+H]$^+$.

Preparation of (10R)-7-amino-12-fluoro-10,16-dimethyl-15-oxo-10,15,16,17-tetrahydro-1H-8,4-(azeno)pyrazolo[4,3-h][2,5,11]benzoxadiazacyclotetradecine-3-carbonitrile (Example 89)

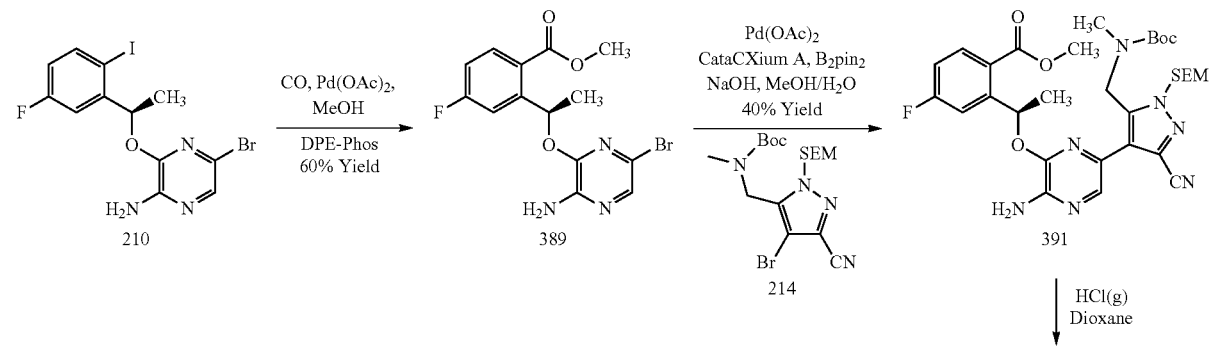

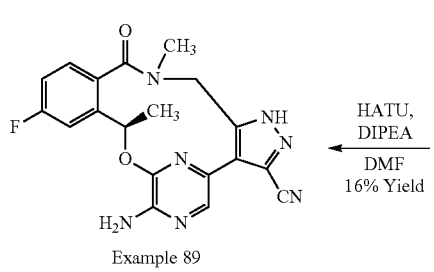 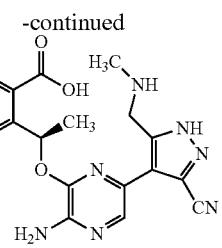 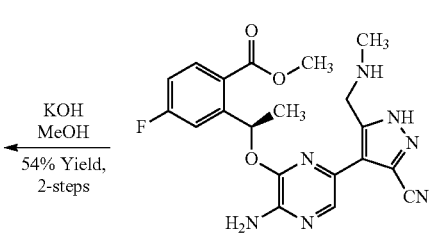

Step 1:

A mixture of compound 210 (1.5 g, 3.42 mmol), DIPEA (1.76 g, 13.68 mmol), DPE-Phos (0.3 g, 0.58 mmol) and Pd(OAc)$_2$ (77 mg, 0.34 mmol) in MeOH (50 mL) was stirred at 40° C. under 10 bar of CO pressure overnight. TLC (petroleum ether/EtOAc=3:1) showed the reaction was almost completed. The mixture was filtered, and the filtrate was concentrated. The residue was purified by column chromatography over silica gel (petroleum ether/EtOAc=3:1, Rf: 0.5) to give compound 531 (0.76 g, 60%) as a yellow solid.

Step 2:

To a solution of compound 531 (300 mg, 0.81 mmol), compound 214 (541 mg, 1.22 mmol) and bis-(pinacalato)-diboron (617 mg, 2.43 mmol) in methanol (60 mL) was added cataCXium A (40 mg, 0.1053 mmol) and Pd(OAc)$_2$ (25 mg, 0.1053 mmol). After the mixture was degassed for three times with nitrogen, a solution of NaOH (65 mg, 1.62 mmol) in water (12 mL) was added under nitrogen at room temperature. The resulting mixture was degassed with nitrogen three times, and was then refluxed for 16 hours. TLC (petroleum ether/EtOAc 3/1) showed the reaction was complete. The reaction mixture was diluted with EtOAc (50 mL×3). The combined EtOAc layers were washed with brine (20 mL×3), dried over Na$_2$SO$_4$ and concentrated in vacuo to give a residue, which was purified via column chromatography (silica gel, petroleum ether/EtOAc from 10/1 to 3/1) to give compound 532 (400 mg, 53% of purify, 40%) as a brown solid. LCMS m/z 655 [M+H]$^+$.

Step 3:

To a stirred solution of compound 532 (400 mg, 53% of purify, 0.32 mmol) in DCM (2 mL) was added dropwise ~4M HCl (g) in dioxane (10 mL) at room temperature. After addition, the reaction mixture was stirred at room temperature for 2 hours. LC-MS showed the reaction was complete. The reaction mixture was concentrated in vacuo to give crude compound 533, which was used for next step without any further purification. LCMS m/z 425 [M+H]$^+$.

Step 4:

A mixture of compound 533 (~300 mg) and KOH (0.395 g, 7.0 mmol) in methanol (15 mL) was stirred at 50° C. for 36 hours. LC-MS showed the reaction was complete. MeOH was removed in vacuo to give the residue, which was acidified with 1N aq. HCl to pH ~5. The mixture was saturated with solid NaCl and then extracted with EtOAc (30 mL×5). The combined EtOAc layers were dried over Na$_2$SO$_4$ and concentrated in vacuo to give compound 534 (180 mg, 39.8% of purity, 53.8%) as a brown solid. LCMS m/z 411 [M+H]$^+$.

Step 5:

To a solution of HATU (250 mg, 0.66 mmol) in DMF (25 mL) was added dropwise a solution of compound 534 (180 mg, 0.44 mmol) and DIEA (908 mg, 7.04 mmol) in DMF (10 mL) at 0° C. After the addition, the resulting mixture was stirred at room temperature for 1 hour. LC-MS showed the reaction was complete. The mixture was poured into ice-water (50 mL). The mixture was extracted with EtOAc (40 mL×5). The combined EtOAc layers were washed with brine (20 mL×5), dried over Na$_2$SO$_4$ and concentrated in vacuo to give a residue. The residue was purified via column chromatography (silica gel, petroleum ether/EtOAc 2:1-1:2) to give Example 89 (10.5 mg, 15.8%) as a white solid. $^1$H NMR (400 MHz, CDCl$_3$) δ 8.13 (s, 1H), 7.30-7.26 (dd, 1H), 7.23-7.20 (m, 1H), 7.01-7.00 (m, 1H), 6.19-6.14 (m, 1H), 5.07 (s, 2H), 4.75-4.72 (d, 1H), 4.28-4.25 (d, 1H), 3.04 (s, 3H), 1.17-1.15 (d, 3H). LCMS ES m/z 393 [M+H]$^+$.

Preparation of (10R)-7-amino-1-(2,2-difluoroethyl)-12-fluoro-10,16-dimethyl-15-oxo-10,15,16,17-tetrahydro-1H-8,4-(azeno)pyrazolo[4,3-h][2,5,11]benzoxadiazacyclotetradecine-3-carbonitrile (Example 90)

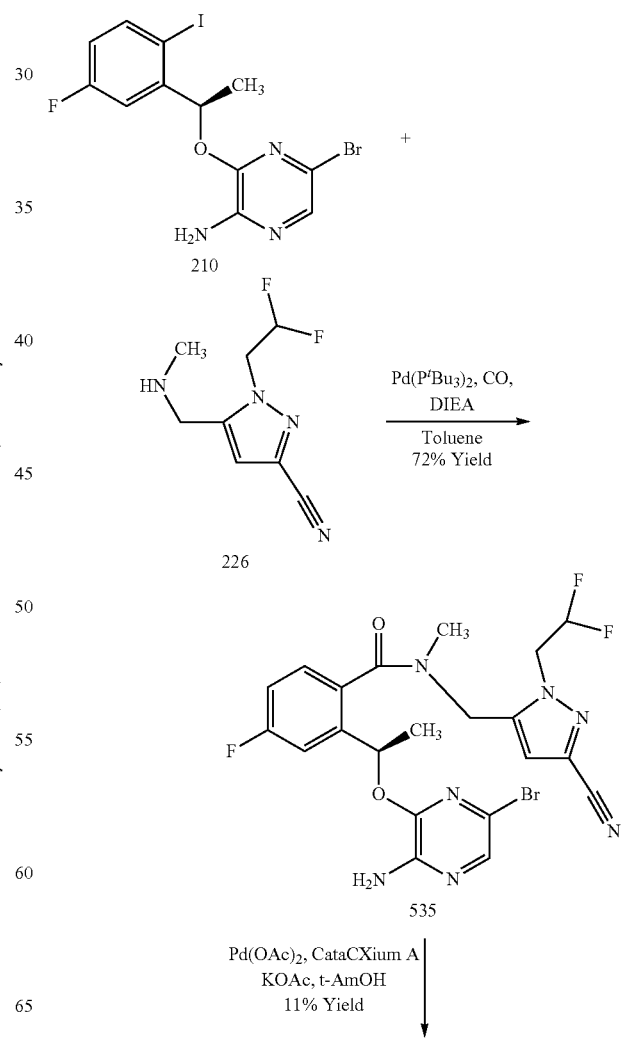

401
-continued

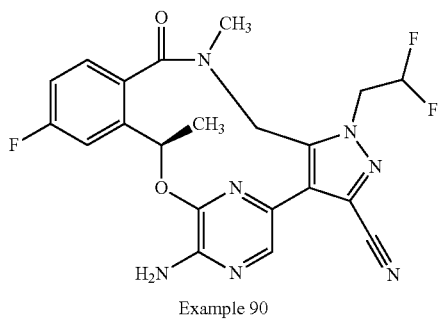

Example 90

Step 1:

Pd(P$^t$Bu$_3$)$_2$ (97 mg, 0.191 mmol) was added to a mixture of compound 226 (450 mg, 1.91 mmol), compound 210, (R)-5-bromo-3-(1-(5-fluoro-2-iodophenyl)ethoxy)-pyrazin-2-amine (838 mg, 1.91 mmol) and DIEA (1.23 g, 9.55 mmol) in de-gassed toluene (50 mL) and the mixture was stirred under a CO atmosphere (4 bar) at 80° C. for 18 hours. After cooling, the volatiles were removed and the residue purified by flash chromatography on silica gel (1:1EtOAc/heptane), giving compound 535 (750 mg, 72%) as a cream colored foam. $^1$H NMR (400 MHz, DMSO-d$_6$) δ 7.64-7.08 (m, 5H), 6.75 (s, 2H), 6.51 (tt, J=54.4, 3.5 Hz, 1H), 5.96 (d, J=6.6 Hz, 1H), 5.01-4.35 (m, 4H), 2.95 (d, J=44.5 Hz, 3H), 1.58 (d, J=6.4 Hz, 3H). LCMS m/z 538/540 [M+H]$^+$.

Step 2:

Pd(OAc)$_2$ (24.0 mg, 0.11 mmol) and cataCXium A (78.0 mg, 0.22 mmol) were added to a mixture of compound 535 (300 mg, 0.56 mmol), KOAc (274 mg, 2.8 mmol) and de-gassed t-amyl alcohol (12.0 mL) in a 20 mL microwave vial and stirred under microwave irradiation (130° C.) for 2.5 hours. After cooling, the volatiles were removed and the residue was purified by column chromatography (70% EtOAc in heptanes). Fractions containing the product (Rf=0.35) were evaporated (product not clean by TLC). The residue was re-purified by column chromatography (20% acetone in DCM). Fractions containing the product were evaporated (a close running impurity was still present by TLC). The residue was re-purified by column chromatography (70% TBME in heptanes). Fractions containing the product were evaporated and the residue was dissolved in MeOH (1.0 mL). Water (approx. 4 mL) was added slowly while stirring to precipitate the product. The solvent was carefully decanted from the resulting solids were dried under vacuum overnight to give Example 90 (28.0 mg, 11% yield) as a pale yellow powder. $^1$H NMR (400 MHz, DMSO-d$_6$) δ 7.86 (s, 1H), 7.48 (dd, J=10.0, 2.6 Hz, 1H), 7.32 (dd, J=8.5, 5.6 Hz, 1H), 7.23 (td, J=8.5, 2.6 Hz, 1H), 6.76 (s, 2H), 6.66-6.32 (m, 1H), 5.93-5.78 (m, 1H), 5.19-4.87 (m, 2H), 4.72 (d, J=14.9 Hz, 1H), 4.37 (d, J=14.9 Hz, 1H), 2.86 (s, 3H), 1.64 (d, J=6.6 Hz, 3H). LCMS ES m/z 458 [M+H]$^+$.

402

Preparation of (10R)-7-amino-2-(2,2-difluoroethyl)-12-fluoro-10,16-dimethyl-15-oxo-10,15,16,17-tetrahydro-2H-8,4-(azeno)pyrazolo[4,3-h][2,5,11]benzoxadiazacyclo-tetradecine-3-carbonitrile (Example 91)

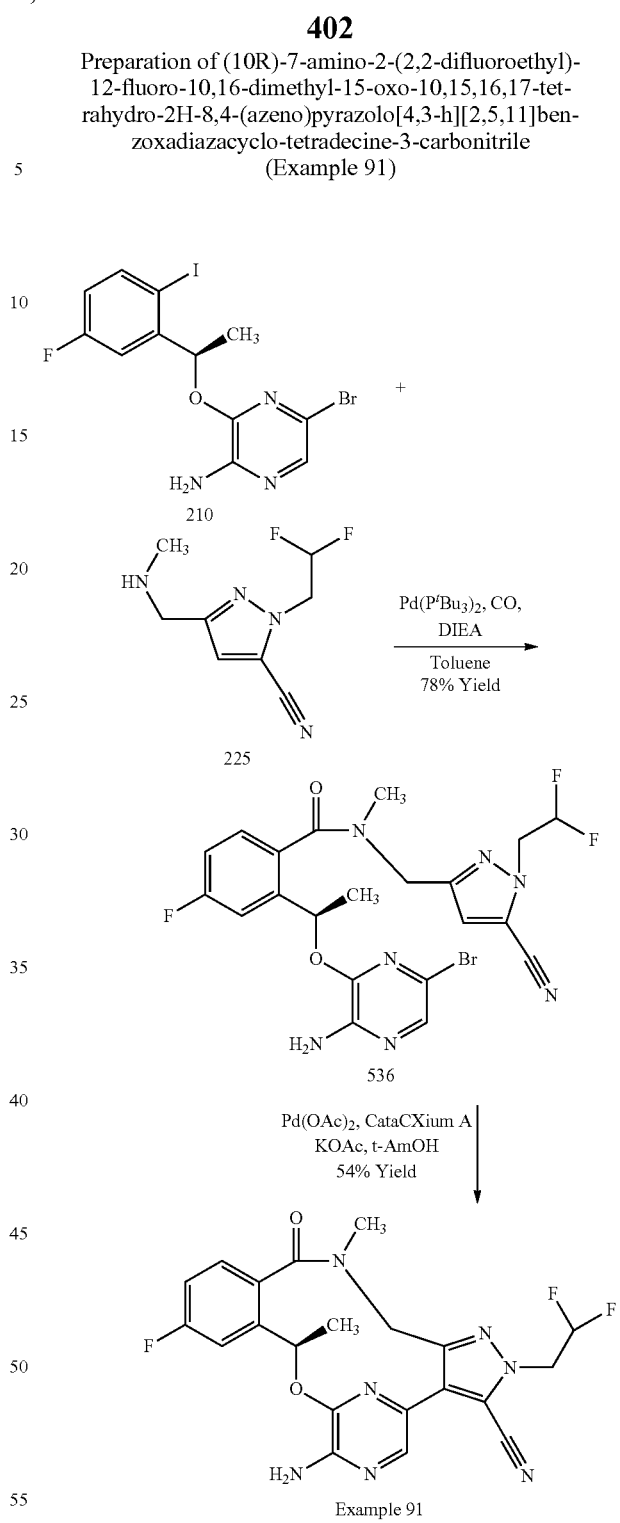

Step 1:

Pd(P$^t$Bu$^3$)$^2$ (32 mg, 0.064 mmol) was added to a mixture of compound 210, (R)-5-bromo-3-(1-(5-fluoro-2-iodophenyl)ethoxy)pyrazin-2-amine (280 mg, 0.64 mmol), compound 225 (150 mg, 0.64 mmol) and DIEA (413 mg, 3.2 mmol) in de-gassed toluene (20 mL). The mixture was then stirred under a CO atmosphere (4 bar) at 80° C. for 6 hours. The mixture was concentrated and the residue purified by column chromatography (40% to 75% EtOAc in heptanes), giving compound 536 (270 mg, 78%) as a pale yellow foam. $^1$H NMR (400 MHz, DMSO-d$_6$) δ 7.70-7.06 (m, 5H), 6.73 (s, 2H), 6.43 (tt, J=54.0, 3.0 Hz, 1H), 6.04 (d, J=6.5 Hz, 1H), 4.95-4.27 (m, 4H), 2.93 (m, 3H), 1.57 (d, J=6.5 Hz, 3H). LCMS m/z 538/540 [M+H]$^+$.

Step 2:

A mixture of compound 536 (108 mg, 0.20 mmol), Pd(OAc)$_2$ (6.60 mg, 0.03 mmol), cataCXium A (21.4 mg, 0.06 mmol), KOAc (98 mg, 1.0 mmol) in de-gassed t-amyl alcohol (7.0 mL) was stirred under microwave irradiation (120° C.) for 2 hours. After cooling, the mixture was concentrated, then purified by column chromatography (1:1 EtOAc/heptanes), giving the Example 91 (75 mg, 54%) as a cream powder. $^1$H NMR (400 MHz, DMSO-d$_6$) δ 7.78 (s, 1H), 7.48 (dd, J=10.1, 2.7 Hz, 1H), 7.42 (dd, J=8.5, 5.7 Hz, 1H), 7.17 (td, J=8.5, 2.7 Hz, 1H), 6.83 (s, 2H), 6.49 (tt, J=53.9, 2.8 Hz, 1H), 5.91 (qd, J=6.5, 1.8 Hz, 1H), 4.88 (td, J=15.8, 2.8 Hz, 2H), 4.35 (q, J=13.7 Hz, 2H), 2.88 (s, 3H), 1.64 (d, J=6.5 Hz, 3H). LCMS m/z 458 [M+H]$^+$.

Preparation of (10R)-7-amino-12-fluoro-10,16-dimethyl-15-oxo-2-(propan-2-yl)-10,15,16,17-tetrahydro-2H-8,4-(azeno)pyrazolo[4,3-h][2,5,11]benzoxadiazacyclotetradecine-3-carbonitrile (Example 92)

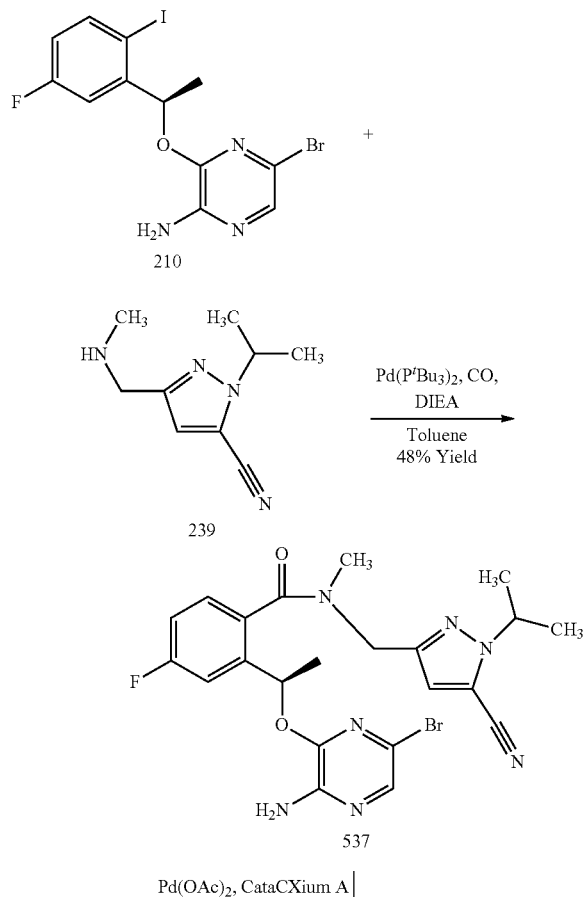

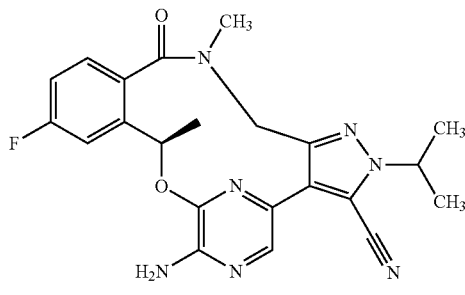

Example 92

Step 1:

The procedure described in step 1 for Example 91 was used to prepare compound 537 (200 mg, 48%) as a pale yellow foam. $^1$H NMR (400 MHz, DMSO-d$_6$) δ 7.69-6.98 (m, 5H), 6.74 (s, 2H), 6.17-5.90 (m, 1H), 4.95-4.22 (m, 3H), 2.93 (m, 3H), 1.57 (d, J=6.4 Hz, 3H), 1.42 (dd, J=8.3, 6.6 Hz, 6H). LCMS ES m/z 516/518 [M+H]$^+$.

Step 2:

The procedure described in step 2 for Example 91 was used to prepare Example 92 (70 mg, 41%) as a cream powder. $^1$H NMR (400 MHz, DMSO-d$_6$) δ 7.77 (s, 1H), 7.47 (dd, J=10.1, 2.6 Hz, 1H), 7.40 (dd, J=8.5, 5.7 Hz, 1H), 7.17 (td, J=8.5, 2.7 Hz, 1H), 6.75 (s, 2H), 5.90 (qd, J=6.4, 1.9 Hz, 1H), 4.77 (hept, J=6.7 Hz, 1H), 4.41-4.24 (m, 2H), 2.88 (s, 3H), 1.64 (d, J=6.5 Hz, 3H), 1.50 (dd, J=6.6, 1.1 Hz, 6H). LCMS ES m/z 436 [M+H]$^+$.

Preparation of (10R)-7-amino-12-fluoro-10,16-dimethyl-2-(oxetan-3-yl)-15-oxo-10,15,16,17-tetrahydro-2H-8,4-(azeno)pyrazolo[4,3-h][2,5,11]benzoxadiazacyclotetradecine-3-carbonitrile (Example 93)

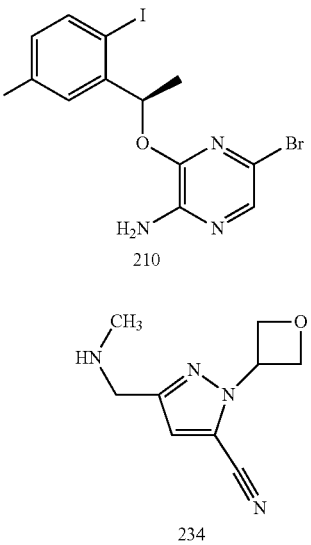

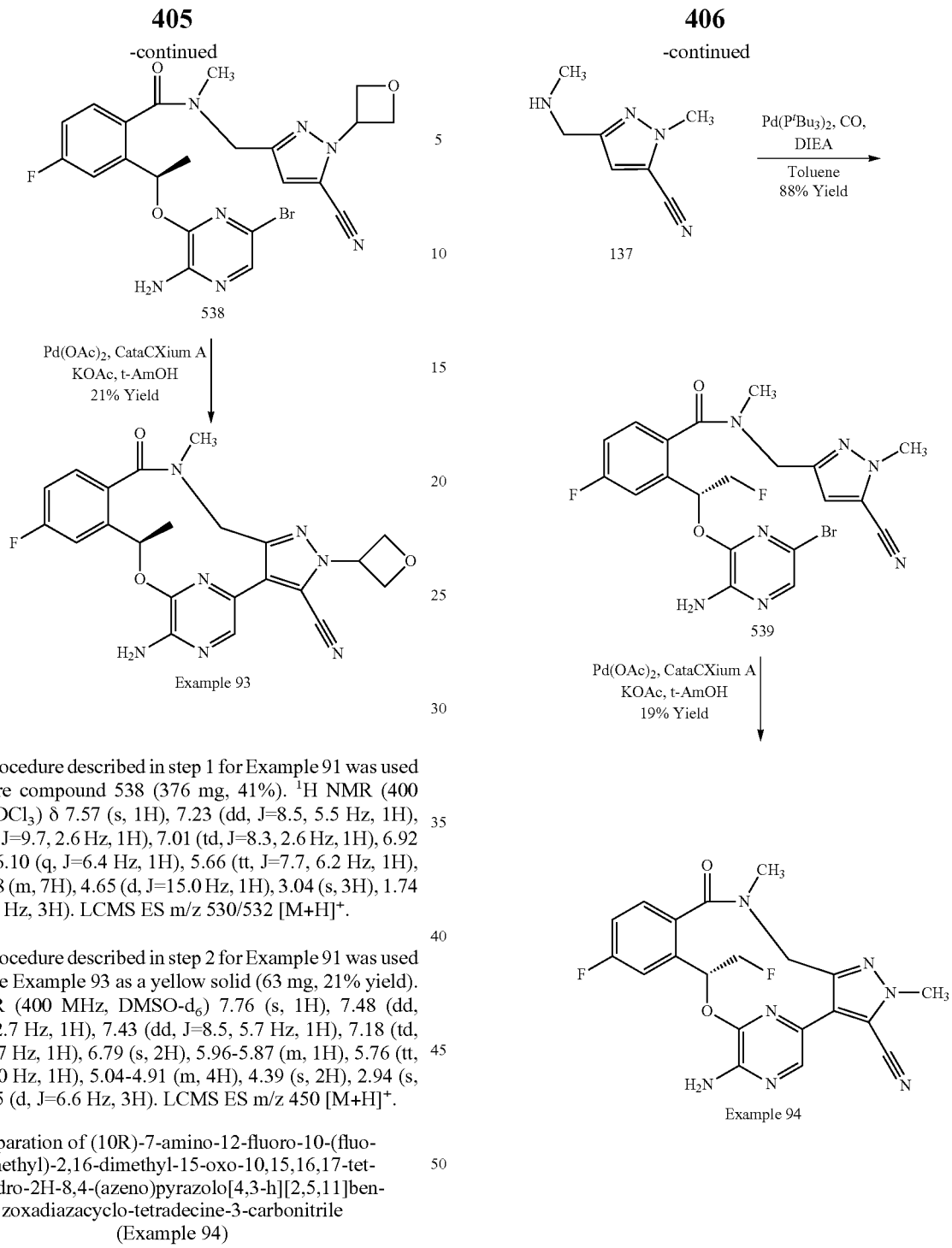

Step 1:

The procedure described in step 1 for Example 91 was used to prepare compound 538 (376 mg, 41%). ¹H NMR (400 MHz, CDCl₃) δ 7.57 (s, 1H), 7.23 (dd, J=8.5, 5.5 Hz, 1H), 7.15 (dd, J=9.7, 2.6 Hz, 1H), 7.01 (td, J=8.3, 2.6 Hz, 1H), 6.92 (s, 1H), 6.10 (q, J=6.4 Hz, 1H), 5.66 (tt, J=7.7, 6.2 Hz, 1H), 5.17-4.98 (m, 7H), 4.65 (d, J=15.0 Hz, 1H), 3.04 (s, 3H), 1.74 (d, J=6.5 Hz, 3H). LCMS ES m/z 530/532 [M+H]⁺.

Step 2:

The procedure described in step 2 for Example 91 was used to prepare Example 93 as a yellow solid (63 mg, 21% yield). ¹H NMR (400 MHz, DMSO-d₆) 7.76 (s, 1H), 7.48 (dd, J=10.1, 2.7 Hz, 1H), 7.43 (dd, J=8.5, 5.7 Hz, 1H), 7.18 (td, J=8.5, 2.7 Hz, 1H), 6.79 (s, 2H), 5.96-5.87 (m, 1H), 5.76 (tt, J=7.5, 6.0 Hz, 1H), 5.04-4.91 (m, 4H), 4.39 (s, 2H), 2.94 (s, 3H), 1.65 (d, J=6.6 Hz, 3H). LCMS ES m/z 450 [M+H]⁺.

Preparation of (10R)-7-amino-12-fluoro-10-(fluoromethyl)-2,16-dimethyl-15-oxo-10,15,16,17-tetrahydro-2H-8,4-(azeno)pyrazolo[4,3-h][2,5,11]benzoxadiazacyclo-tetradecine-3-carbonitrile (Example 94)

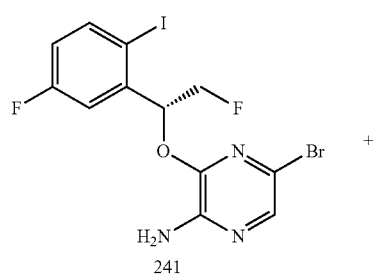

Step 1:

The procedure described in step 1 for Example 91 was used to prepare compound 539 (0.08 g, 88%) as a yellow solid.

Step 2:

The procedure described in step 2 for Example 91 was used to prepare Example 94 (16 mg, 19%) as a white solid (63 mg, 21% yield). ¹H NMR (400 MHz, Methanol-d₄) δ 7.94 (s, 1H), 7.50-7.43 (m, 2H), 7.21-7.17 (m, 1H), 6.17-6.11 (m, 1H), 5.06-5.01 (m, 1H), 4.74-4.71 (m, 1H), 4.56-4.53 (d, 1H), 4.40-4.37 (d, 1H), 4.14 (s, 3H), 3.05 (s, 3H). LCMS ES m/z 426 [M+H]⁺.

Preparation of 12-fluoro-1,14-dimethyl-1,4,5,6,7,8-hexahydro-14H-16,20-(metheno)-pyrazolo[4,3-g][1,14,11]benzodioxazacycloheptadecin-17-amine (Example 95) and (11R)-8-amino-13-fluoro-4,11,17-trimethyl-17,18-dihydro-9, 5:19,1-di(azeno)pyrimido[6,1-h][2,5,9,13]benzoxatriazacyclohexadecin-16(11H)-one (Example 96)

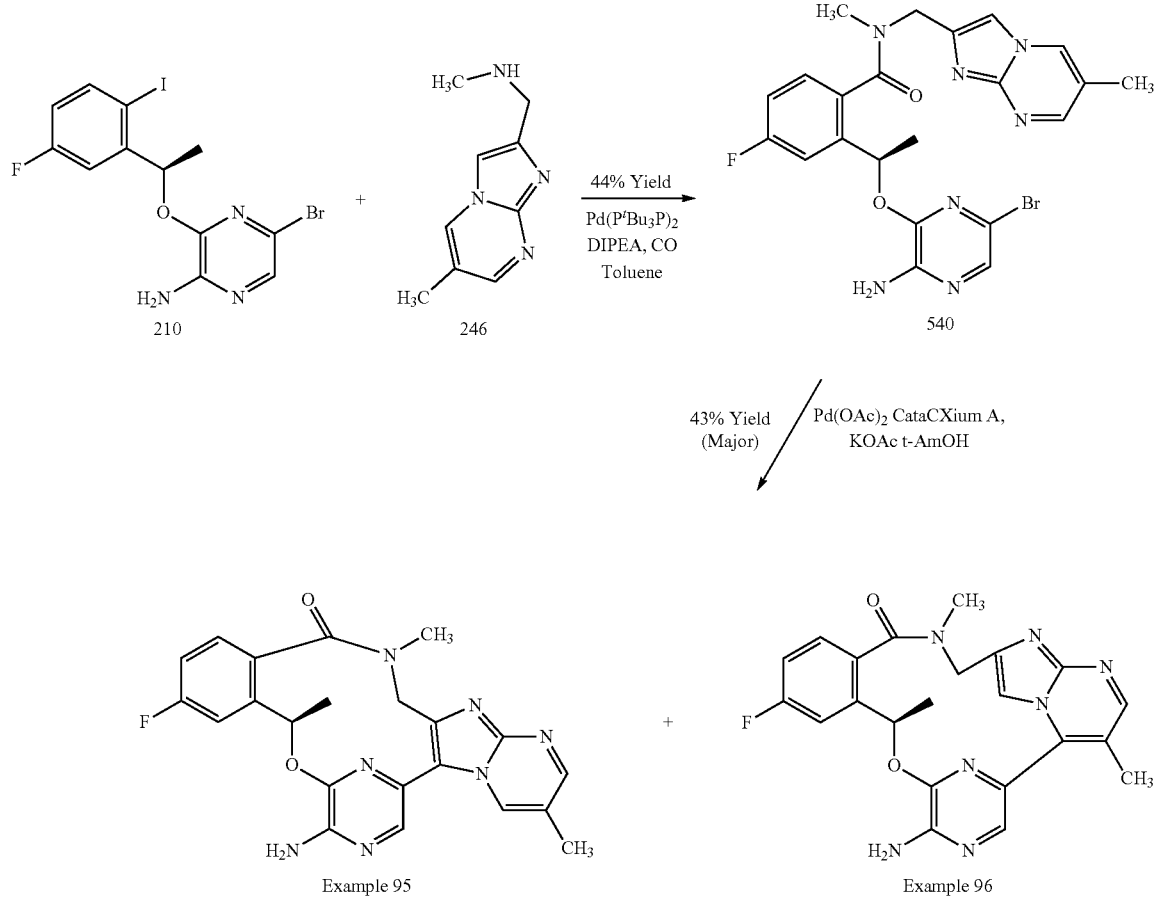

Step 1:

The procedure described in step 1 for Example 91 was used to prepare compound 540 (245 mg, 44%) as a pale yellow foam. $^1$H NMR (400 MHz, DMSO-d$_6$) δ 8.72 (dt, J=2.6, 1.3 Hz, 1H), 8.63 (s, 1H), 8.49-8.25 (m, 1H), 7.83 (s, 1H), 7.69 (s, 1H), 7.63-7.46 (m, 2H), 7.37 (dd, J=8.3, 5.8 Hz, 0H), 7.27-7.05 (m, 1H), 6.72 (d, J=7.1 Hz, 2H), 6.09 (t, J=6.5 Hz, 0H), 6.00 (d, J=16.3 Hz, 0H), 4.97-4.67 (m, 1H), 4.45 (t, J=18.3 Hz, 1H), 3.06 (s, 2H), 2.93 (s, 1H), 2.28 (d, J=7.4 Hz, 4H), 1.59 (dt, J=5.8, 2.4 Hz, 4H). LCMS ES m/z 511/513 [M+H]$^+$.

Step 2:

Compound 540 (230 mg, 0.45 mmol) and KOAc (219 mg, 2.23 mmol) were mixed in tert-amyl alcohol (15 mL). The mixture was degassed (bubbling nitrogen through for 30 minutes) then Pd(OAc)$_2$ (20 mg, 0.09 mmol) and cataCXium A (64 mg, 0.18 mmol) were added. The mixture was degassed again then heated in the microwave for 2 hours at 120° C. LC-MS of the crude mixture showed completion of the reaction. The mixture was filtered through a pad of celite and rinsed with EtOAc (50 mL). The filtrate was washed with water (100 mL), dried over MgSO$_4$, filtered and concentrated under vacuum. The oil obtained was purified by column chromatography (eluents EtOAc/MeOH from 100:0 to 90:10). The yellow glass obtained (pure macrocycle still containing EtOAc) was dissolved in MeOH (20 mL) and water was added (20 mL). The mixture was concentrated under vacuum then freeze-dried to give Example 95 as a pale yellow solid (82 mg, 43% yield, 97% purity by LC-MS). $^1$H NMR (400 MHz, DMSO-d$_6$) δ 8.84 (dd, J=2.5, 1.3 Hz, 1H), 8.45 (d, J=2.2 Hz, 1H), 7.92 (s, 1H), 7.54 (dd, J=10.1, 2.7 Hz, 1H), 7.42 (dd, J=8.5, 5.7 Hz, 1H), 7.17 (td, J=8.5, 2.7 Hz, 1H), 6.75 (s, 2H), 6.18-5.92 (m, 1H), 4.62-4.19 (m, 2H), 2.96 (s, 3H), 2.32 (d, J=1.1 Hz, 3H), 1.66 (d, J=6.5 Hz, 3H). LCMS ES m/z 434 [M+H]$^+$. Mixed fractions from the column were purified by reverse phase HPLC to give Example 96 (15 mg, 7% yield, 92% purity by LC-MS) as a mixture of two conformers by $^1$H NMR (about 1:1 mixture). $^1$H NMR (400 MHz, Methanol-d$_4$) δ 8.32 (d, J=8.4 Hz, 1H), 7.84 (s, 1H), 7.81-7.72 (m, 1H), 7.61 (dd, J=8.5, 5.7 Hz, 0.5H), 7.48 (dd, J=10.4, 2.7 Hz, 0.5H), 7.38 (dd, J=8.5, 5.5 Hz, 0.5H), 7.34 (s, 0.5H), 7.04 (td, J=8.3, 2.7 Hz, 1H), 6.86 (d, J=6.4 Hz, 0.5H), 6.14 (d, J=6.3 Hz, 0.5H), 5.24 (dd, J=15.9, 8.5 Hz, 1H), 4.08 (dd, J=38.3, 15.9 Hz, 1H), 2.97 (s, 1.5H), 2.93 (d, J=1.9 Hz, 1.5H), 2.39 (s, 1.5H), 2.32 (s, 1.5H), 1.63 (dd, J=9.0, 6.5 Hz, 1.5H), 1.40 (d, J=6.4 Hz, 1.5H). LCMS ES m/z 434 [M+H]$^+$.

Preparation of (5R)-8-amino-3-fluoro-5,17-dimethyl-18-oxo-5,16,17,18-tetrahydro-7,11-(azeno)dibenzo[g,l][1,4,10]oxadiazacyclotetradecine-12-carbonitrile (Example 97)

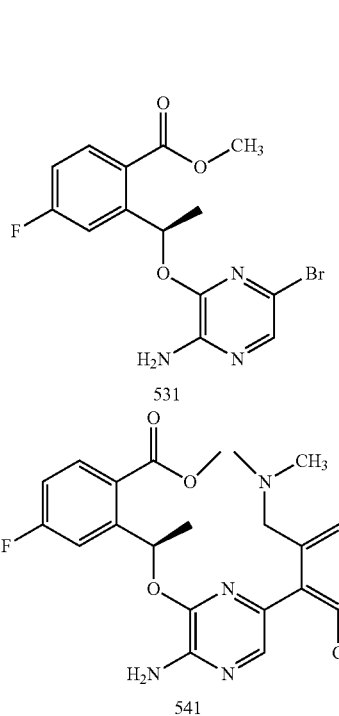
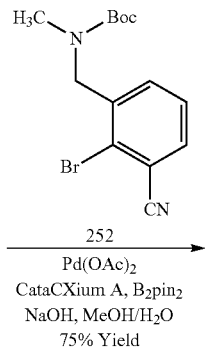
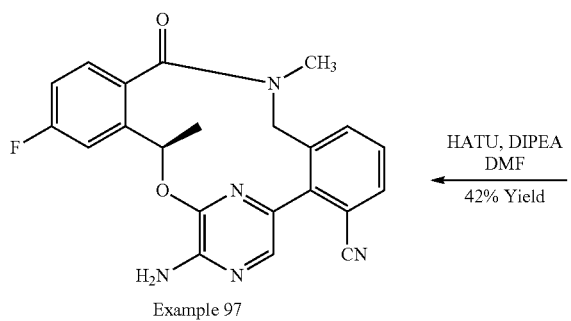
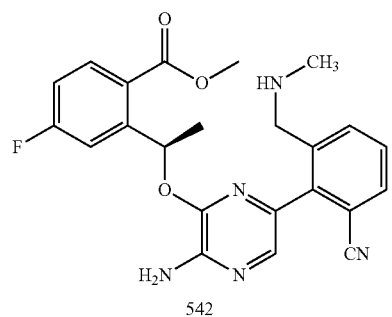
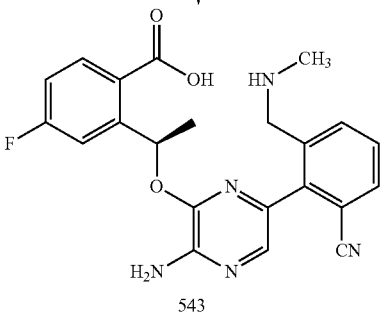

Step 1:

To a solution of compound 531 (300 mg, 0.81 mmol), compound 252 (393 mg, 1.21 mmol) and bis-(pinacalato) diboron (610 mg, 2.43 mmol) in methanol (60 mL) was added catacxium A (38 mg, 0.1053 mmol) and Pd(OAc)$_2$ (24 mg, 0.1053 mmol) was added. After the mixture was degassed for three times with nitrogen, a solution of NaOH (65 mg, 1.62 mmol) in water (12 mL) was added to the above mixture under nitrogen at room temperature. The resulting mixture was degassed with nitrogen three times and was then refluxed for 16 hours. TLC (petroleum ether/EtOAc 3/1) showed the reaction was complete. The reaction mixture was diluted with EtOAc (50 mL×3). The combined EtOAc layers were washed with brine (20 mL×2), dried over Na$_2$SO$_4$ and concentrated in vacuo to give a residue, which was purified via column chromatography (silica gel, petroleum ether/EtOAc from 10/1 to 5/1) to give compound 541 (400 mg, 80% of purity, 75%) as a brown solid. LCMS m/z 535 [M+H]$^+$.

Step 2:

To a stirred solution of compound 541 (400 mg, 80% of purity, 0.61 mmol) in DCM (2 mL) was added dropwise ~4M HCl (g) in dioxane (10 mL) at room temperature. After addition, the reaction mixture was stirred at room temperature for 2 hours. LC-MS showed the reaction mixture was complete. The reaction mixture was concentrated in vacuo to give crude compound 542, which was used for the next step without any further purification. LCMS m/z 435 [M+H]$^+$.

Step 3:

A mixture of compound 542 (~300 mg) and KOH (316 mg, 5.65 mmol) in methanol (20 mL) was stirred at room temperature for 36 hours. LC-MS showed the reaction was complete. The mixture was concentrated in vacuo. The residue was diluted with water, and adjusted to pH ~5 with 0.5N.HCl. The aqueous was extracted with EtOAc (30 mL×5). The combined EtOAc layers were dried over Na$_2$SO$_4$ and concentrated in vacuo to give compound 543 (0.2 g, 69%) as a yellow solid. LCMS m/z 422 [M+H]$^+$.

Step 4:

To a solution of HATU (271 mg, 0.69) in DMF (60 mL) was added dropwise the mixture solution of compound 543 (200 mg, 0.47 mmol) and DIPEA (980 mg, 7.6 mmol) in DMF (10 mL) at 0° C. After the addition, the resulting mixture was stirred at room temperature for 1 hour. LC-MS showed the reaction was complete. The mixture was poured into ice-water (20 mL). The mixture was extracted with EtOAc (40 mL×5). The combined EtOAc layers were washed with brine (20 mL×5), dried over Na$_2$SO$_4$, and concentrated in vacuo to give a residue. The residue was purified via column chromatography (silica gel, petroleum ether/EtOAc 5:1-1:1) to give Example 97 (80.8 mg, 42%) as a white solid. $^1$H NMR (400 MHz, CDCl$_3$) δ 7.81-7.78 (m, 2H), 7.67-7.65 (m, 1H), 7.50-7.47 (m, 1H), 7.29-7.27 (m, 1H), 7.18-7.17 (m, 1H), 6.98-6.94 (m, 1H), 6.34-6.29 (m, 1H), 5.10 (s, 2H), 4.65-4.62 (d, 1H), 4.15-4.12 (d, 1H), 2.94 (s, 3H), 1.79-1.78 (d, 3H). LCMS ES m/z 404 [M+H]$^+$.

Preparation of (5R)-8-amino-3-fluoro-5,19-dimethyl-20-oxo-5,18,19,20-tetrahydro-7,11-(azeno)pyrido[2',1':2,3]imidazo[4,5-h][2,5,11]benzoxadiazacyclotetradecine-14-carbonitrile (Example 98)

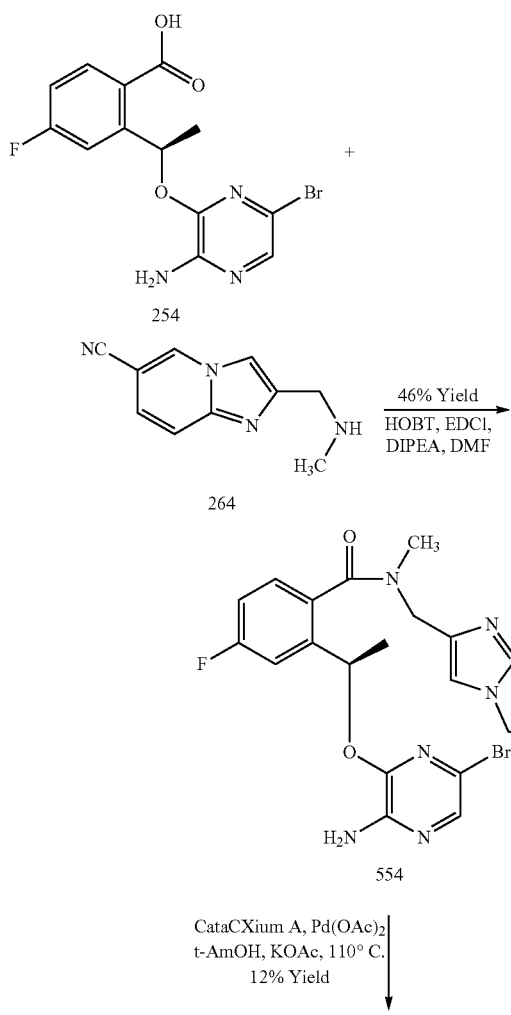

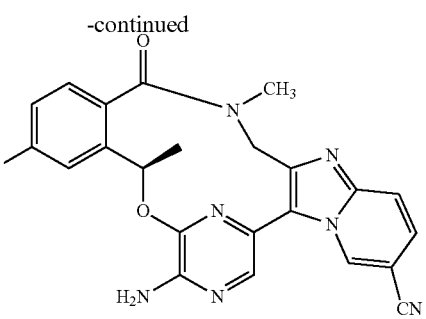

Example 98

Step 1:

To a mixture of compound 254 (0.217 g, 0.611 mmol), compound 264 (0.15 g, 0.673 mmol) in DMF (20 mL) was added EDCI (0.176 g, 0.916 mmol), HOBt (0.124 g, 0.916 mmol) and DIPEA (0.394 g, 3.055 mmol) at −35° C. The resulting mixture was stirred at −30° C. for 30 min and stirred at room temperature overnight. TLC (Petroleum ether/EtOAc=1:1) showed that most of compound 254 was consumed. The mixture was diluted with EtOAc (50 mL) and H$_2$O (10 mL). The organic layer was separated and the aqueous layer was extracted with EtOAc (20 mL×2). The organic layers were combined, washed with brine (10 mL×5), dried over Na$_2$SO$_4$, filtered and concentrated in vacuo to give the crude product, which was purified by prep. TLC to obtain compound 544 (150 mg, 46%) as a white solid.

Step 2:

The reaction was run on three 50 mg batches under identical conditions. To a mixture of compound 544 (0.05 g, 0.095 mmol), cataCXium (4.25 mg, 0.0118 mmol), t-AmOH (1.94 mg, 0.019 mmol) and KOAc (46.55 mg, 0.475 mmol) in freshly distilled DMAc (8 mL) was added Pd(OAc)$_2$ (2.66 mg, 0.0118 mmol) at room temperature under a nitrogen atmosphere. The resulting mixture was sealed and heated at 110° C. for 12 h. LC-MS showed the reaction was complete. The mixture was diluted with EtOAc (25 mL) and then washed with brine (5 mL×4). The organic layer was separated and dried over Na$_2$SO$_4$, filtered and concentrated in vacuo to give the crude product, which was purified by prep. TLC and then re-purified by reverse phase preparative. HPLC to obtain Example 98 (15.4 mg, 12%) as a yellow solid. $^1$H NMR (400 MHz, Methanol d$_4$+D$_2$O): δ 9.38-9.37 (m, 1H), 7.98-7.91 (m, 2H), 7.85-7.80 (m, 1H), 7.55-7.45 (m, 2H), 7.25-7.15 (m, 1H), 6.25-6.15 (m, 1H), 4.80-4.75 (m, 2H), 4.60-4.52 (m, 1H), 3.15 (s, 3H), 1.84-1.82 (dd, 3H). LCMS m/z 444 [M+1]$^+$.

Preparation of (10R)-7-amino-12-fluoro-10,16-dimethyl-15-oxo-10,15,16,17-tetrahydro-8,4-(azeno)[1,2]oxazolo[4,3-h][2,5,11]benzoxadiazacyclotetradecine-3-carbonitrile (Example 99)

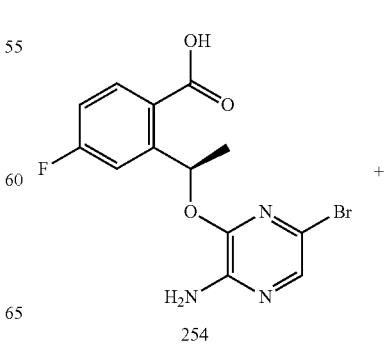

-continued

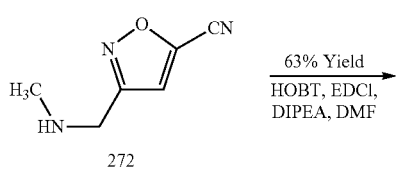

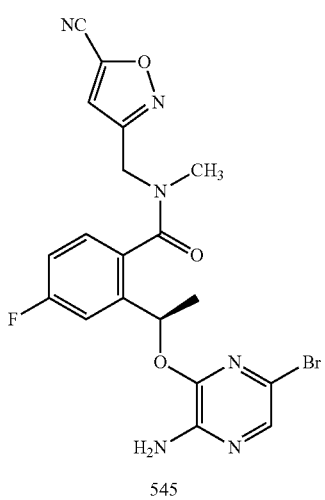

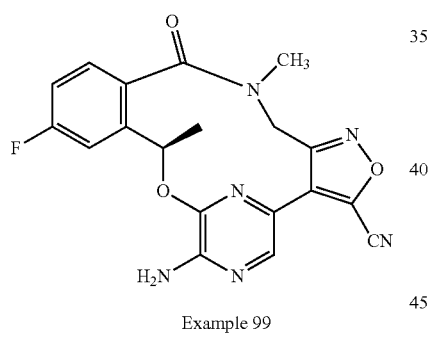

Example 99

Step 1:
To a stirred solution of compound 254 (250 mg, 0.7 mmol), compound 272 (145 mg, 0.7 mmol) and DIPEA (271 mg, 2.1 mmol) in DMF (15 mL) was added HOBt (143 mg, 1.05 mmol) and EDCI (135 mg, 1.05 mmol) at −35° C. under N2. After the addition, the mixture was stirred at room temperature for 24 hours. TLC (petroleum ether/EtOAc=1:1) indicated the reaction was complete. The mixture was poured into ice-water (20 mL), extracted with EtOAc (20 mL×5), the combined organic layers were washed with brine (20 mL×5), dried over $Na_2SO_4$, concentrated to give a residue, which was purified by column chromatography (silica. gel. Rf=0.3, petroleum ether/EtOAc=2:1-1:1) to give compound 545 (210 mg, 63%) as light yellow oil. $^1$H NMR (400 MHz, $CDC_3$) δ 7.60 (s, 1H), 7.22-7.21 (m, 2H), 7.18 (s, 1H), 7.04-7.02 (m, 1H), 6.12 (m, 1H), 5.02-4.98 (d, 1H), 4.89 (s, 2H), 4.77-4.74 (d, 2H), 3.04 (s, 3H), 1.74-1.72 (d, 3H).

Step 2:
A mixture of compound 545 (200 mg, 0.42 mmol), KOAc (0.21 g, 2.15 mmol), cataCXium A (18 mg, 0.0504 mmol) and $Pd(OAc)_2$ (5.6 mg, 0.025 mmol) in t-AmOH (20 mL) was stirred at 120° C. for 18 hours. LC-MS indicted ~30% of desire compound. The mixture was poured into ice-water (20 mL), extracted with EtOAc (30 mL×5), the combined organic layers were washed with brine (5 mL), dried over $Na_2SO_4$, and concentrated to give a residue, which was purified by reverse phase preparative HPLC to give Example 99 (14.1 mg, 9%) as a white solid. $^1$H NMR (400 MHz, $CDCl_3$) 8.12 (S, 1H), 7.29-7.28 (d, 1H), 7.23-7.22 (d, 1H), 7.05-7.00 (m, 1H), 6.08-6.05 (s, 1H), 5.24 (s, 2H), 4.7-4.45 (dd, 2H), 3.08 (s, 3H), 1.78-1.76 (d, 3H). LCMS m/z 395 [M+H]$^+$.

Preparation of (10R)-7-amino-12-fluoro-10,16-dimethyl-15-oxo-10,15,16,17-tetrahydro-8,4-(metheno)[1,2]oxazolo[4,3-h][2,5,11]benzoxadiazacyclotetradecine-3-carbonitrile (Example 100)

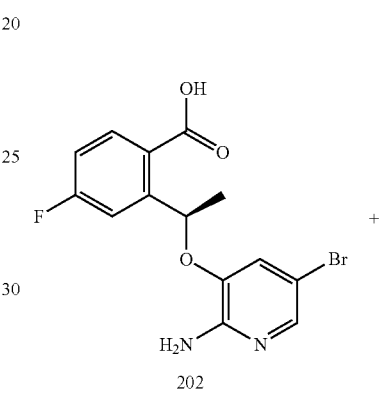

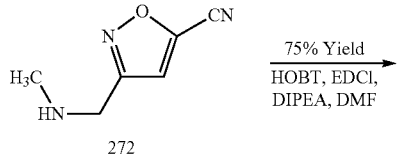

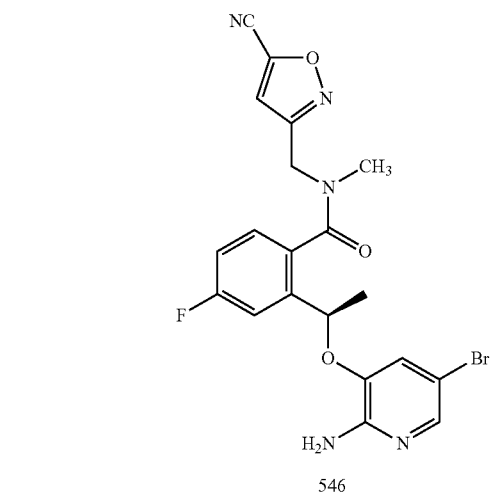

Example 100

Step 1:

To a stirred solution of compound 202 (400 mg, 1.13 mmol), compound 272 (234 mg, 1.13 mmol) and DIPEA (437 mg, 3.4 mmol) in DMF (20 mL) was added HOBt (230 mg, 1.7 mmol) and EDCI (219 mg, 1.7 mmol) at −35° C. under N2. After the addition, the mixture was stirred at room temperature for 24 hours. TLC (petroleum ether/EtOAc=1:1) indicated the reaction was complete. The mixture was poured into ice-water (20 mL), extracted with EtOAc (20 mL×5), the combined organic layers were washed with brine (20 mL×5), dried over Na$_2$SO$_4$, concentrated to give a residue, which was purified by column chromatography (silica. gel. Rf=0.2, petroleum ether/EtOAc=2:1-1:1) to give compound 546 (400 mg, 75%) as light yellow oil. $^1$H NMR (400 MHz, CDCl$_3$) δ 7.68 (s, 1H), 7.26-7.21 (m, 2H), 7.07 (s, 1H), 7.04-6.98 (m, 1H), 5.50-5.46 (m, 1H), 4.94-4.91 (d, 1H), 4.74 (s, 2H), 4.80-4.76 (d, 1H), 3.14 (s, 3H), 1.66-1.65 (d, 3H)

Step 2:

A mixture of compound 546 (170 mg, 0.358 mmol), KOAc (0.175 g, 1.8 mmol), cataCXium A (15 mg, 0.043 mmol) and Pd(OAc)$_2$ (5 mg, 0.022 mmol) in t-AmOH (20 mL) was stirred at 120° C. for 18 hours. LC-MS indicted ~30% of desire compound. The mixture was poured into ice-water (20 mL), extracted with EtOAc (30 mL×5), the combined organic layers were washed with brine (5 mL), dried over Na$_2$SO$_4$, concentrated to give a residue, which was purified by column chromatography over silica gel (Rf ~0.38, petroleum ether/EtOAc=3:1) to give Example 100 (21 mg, 15%) as a yellow solid. $^1$H NMR (400 MHz, CDCl$_3$): δ 7.92-7.91 (S, 1H), 7.32-7.26 (m, 1H), 7.24-7.23 (d, 1H), 7.07-7.02 (m, 1H), 6.84 (s, 1H), 5.72-5.70 (s, 2H), 4.59 (s, 2H), 3.18 (s, 3H), 1.81-1.79 (d, 3H). LCMS m/z 394 [M+H]$^+$.

Preparation of (10R)-7-amino-12,14-difluoro-2,10,16-trimethyl-15-oxo-10,15,16,17-tetrahydro-2H-8,4-(azeno)pyrazolo[4,3-h][2,5,11]benzoxadiazacyclotetradecine-3-carbonitrile (Example 101)

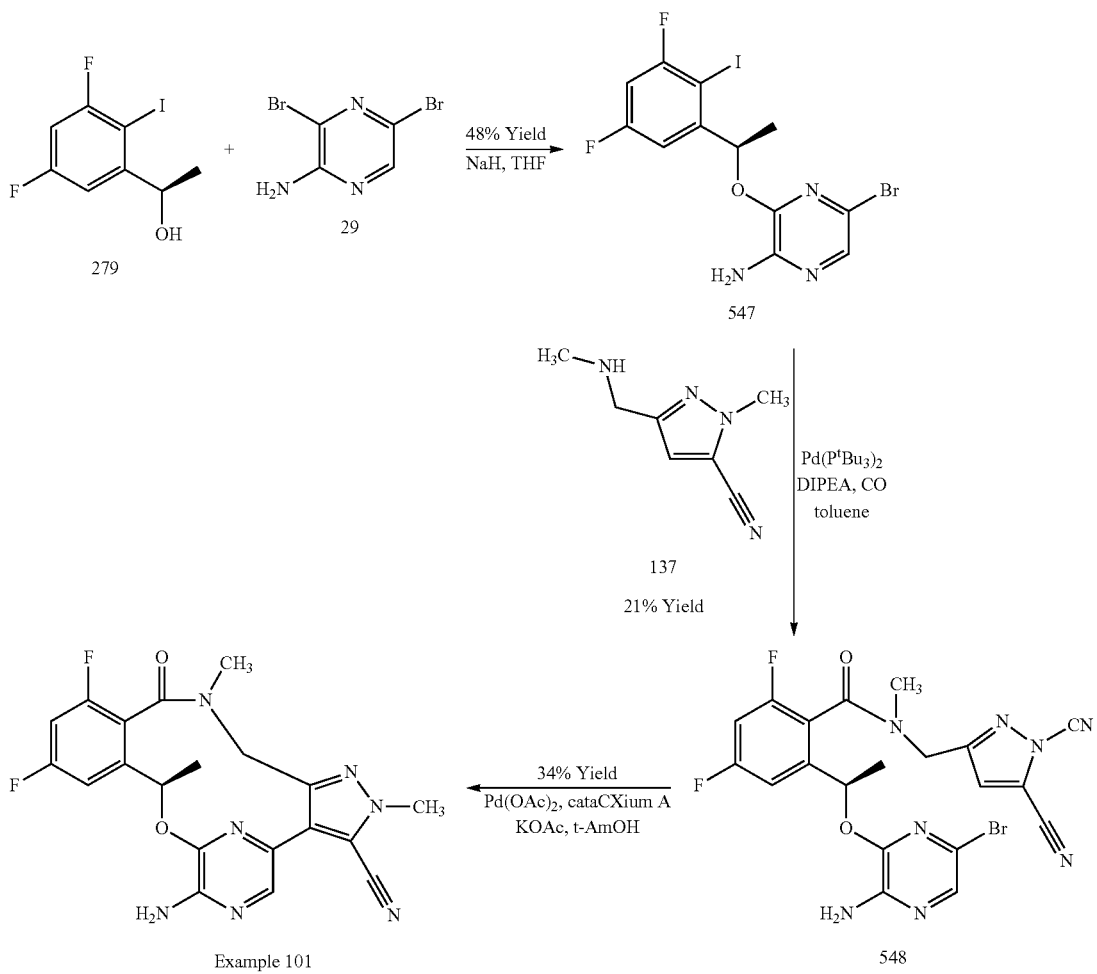

Step 1:

A solution of compound 279 (4.24 g, 14.9 mmol) in dry THF (24 mL) was added dropwise to a cooled (0° C.) suspension of NaH (60% in oil, 746 mg, 18.6 mmol) in dry THF (24 mL). The mixture was stirred 10 min at 0° C. then 30 min at room temperature before adding a solution of compound 29 (3.14 g, 12.4 mmol) in dry THF (24 mL) in one go. The mixture was stirred at 60° C. for 18 hours then was cooled to RT. Brine (200 mL) was carefully added and the mixture was extracted with EtOAc (3×200 mL). The organic phases were combined, dried over MgSO$_4$, filtered and concentrated under vacuum. The oil obtained was purified by column chromatography (eluents: heptanes/EtOAc from 98:2 to 75:25). The sticky solid obtained (4.6 g) was slurried in heptanes (~100 mL) for 72 hours. The suspension obtained was filtered and the solid dried under vacuum to give compound 547 (2.73 g, 48% yield, 99% purity by LC-MS) as a beige powder. $^1$H NMR (400 MHz, DMSO-d$_6$) δ 7.59 (s, 1H), 7.55-7.42 (m, 1H), 7.31 (td, J=8.7, 2.8 Hz, 1H), 6.75 (s, 2H), 6.23 (q, J=6.5 Hz, 1H), 1.53 (d, J=6.4 Hz, 3H). LCMS m/z 455/457 [M+H]$^+$.

Step 2:

Compound 547 (2.0 g, 4.4 mmol), compound 137 (HCl salt, 974 mg, 4.4 mmol) and DIEA (3.8 mL, 21.9 mmol) were dissolved in toluene (127 mL). Pd(P$^t$Bu$_3$)$_2$ (224 mg, 0.44 mmol) was added (the reaction becomes black) and the mixture was heated at 85° C. under CO (4 bars) for 18 hours. The mixture was cooled to RT, filtered through a pad of arbocel, rinsed with EtOAc (~100 mL) and the mother liquors concentrated. The oil obtained was purified by column chromatography over silica gel (eluents heptanes/EtOAc from 4:1 to 1:1) to give compound 548 (460 mg, 21% yield, 89% purity by LC-MS) as a colorless solid foam. $^1$H NMR (400 MHz, DMSO-d$_6$) δ 7.56 (d, J=1.1 Hz, 1H), 7.44 (m, 1H), 7.39-7.26 (m, 1H), 7.03 (s, 1H), 6.78 (d, J=4.1 Hz, 2H), 5.98 (q, J=6.5 Hz, 1H), 4.83 (d, J=15.0 Hz, 1H), 4.62 (d, J=15.0 Hz, 1H), 3.96 (d, J=1.0 Hz, 3H), 2.90 (s, 3H), 1.59 (d, J=6.5 Hz, 2H). LCMS m/z 506/508 [M+H]$^+$.

Step 3:

A solution of compound 548 (230 mg, 0.45 mmol) in tert-amyl alcohol (9 mL) was degassed (3 cycles N$_2$/vacuum) at 100° C. Pd(OAc)$_2$ (15 mg, 0.07 mmol), cataCXium A (49 mg, 0.14 mmol) and KOAc (227 mg, 2.3 mmol) were added and the mixture was degassed (3 cycles N$_2$/vacuum) at 100° C. The mixture was then heated in a microwave at 120° C. for 2 hours. The reaction was cooled to room temperature, concentrated under vacuum, and DCM (50 mL) was added and the suspension filtered. The mother liquors were concentrated under vacuum and the oil obtained was purified by column chromatography (eluents: heptanes/EtOAc from 3:1 to 1:1) to give the macrocycle as a beige powder (102 mg, 53% yield, 99% purity by LC-MS). This powder was suspended in MeOH (~2 mL) and slurried overnight. The suspension was filtered and the white solids obtained were carefully dried under vacuum (0.3 mBar) at 80° C. for 6 hours. Example 101 was obtained as a white powder (65 mg, 34% yield, 100% purity by LC-MS). $^1$H NMR (400 MHz, DMSO-d$_6$) δ 7.81 (s, 1H), 7.38 (dd, J=9.6, 2.5 Hz, 1H), 7.29 (td, J=9.3, 2.4 Hz, 1H), 6.79 (s, 2H), 5.94-5.73 (m, 1H), 4.42 (dd, J=13.8, 1.9 Hz, 1H), 4.22 (d, J=13.6 Hz, 1H), 4.04 (s, 3H), 2.90 (s, 3H), 1.63 (d, J=6.5 Hz, 3H). LCMS ES m/z 426 [M+H]$^+$.

Preparation of (10R)-7-amino-12-fluoro-2,10-dimethyl-15-oxo-10,15,16,17-tetrahydro-2H-8,4-(azeno)pyrazolo[4,3-h][2,5,11]benzoxadiazacyclotetradecine-3-carbonitrile (Example 102)

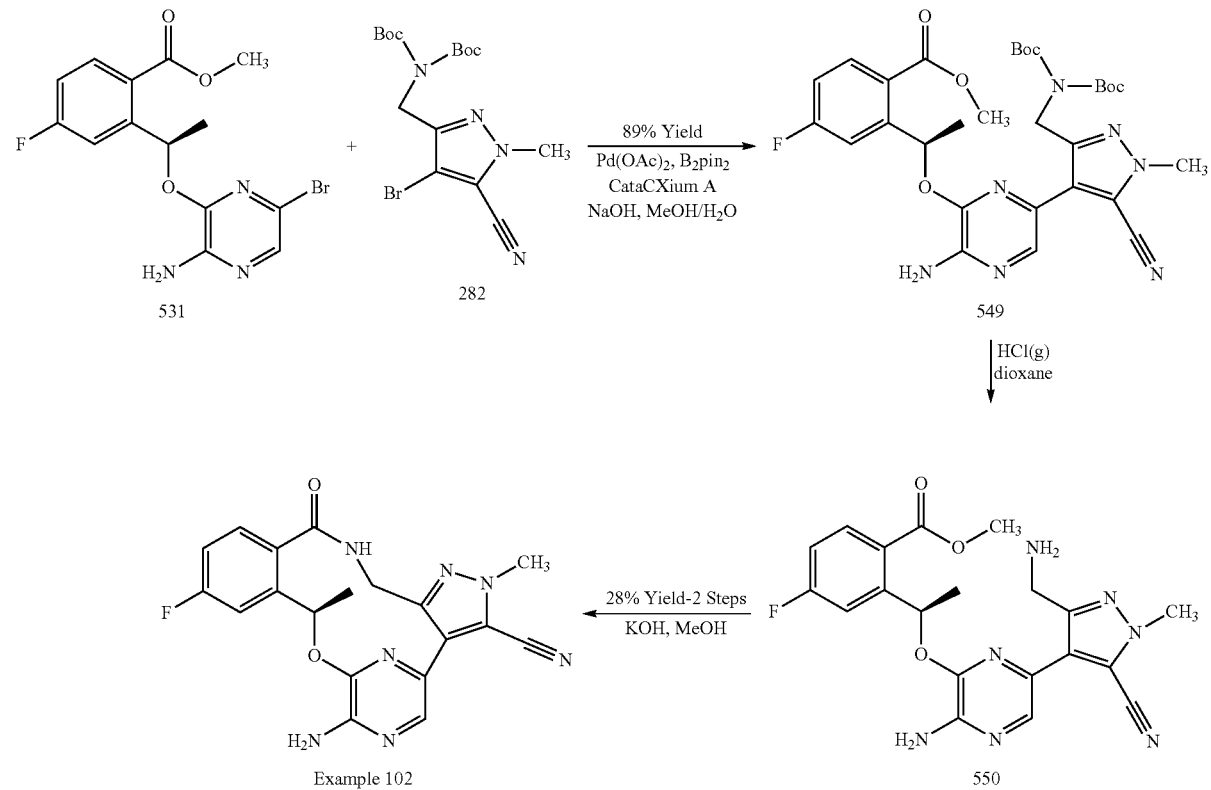 [SMILES: COC(=O)c1ccc(F)cc1[C@@H](C)Oc1nc(Br)cnc1N ; Cn1nc(CN(C(=O)OC(C)(C)C)C(=O)OC(C)(C)C)c(Br)c1C#N ; COC(=O)c1ccc(F)cc1[C@@H](C)Oc1nc(-c2c(CN(C(=O)OC(C)(C)C)C(=O)OC(C)(C)C)nn(C)c2C#N)cnc1N ; C[C@H]1Oc2nc(cnc2N)-c2c(nn(C)c2C#N)CNC(=O)c2ccc(F)cc21 ; COC(=O)c1ccc(F)cc1[C@@H](C)Oc1nc(-c2c(CN)nn(C)c2C#N)cnc1N]

Example 102

Step 1:

To a solution of compound 531 (0.2 g, 0.54 mol), compound 282 (336 mg, 0.81 mmol) and bis-(pinacalato)diboron (407 g, 1.62 mmol) in methanol (40 mL) was added cataCXium A (25 mg, 0.07 mmol) and Pd(OAc)$_2$ (16 mg, 0.07 mmol). After the mixture was degassed for three times with nitrogen, a solution of NaOH (65 mg, 1.62 mmol) in water (12 mL) was added to the above mixture under nitrogen gas at room temperature. The resulting mixture was degassed with nitrogen gas three times and was then refluxed for 16 hours. TLC (petroleum ether/EtOAc 3/1) showed the reaction was complete. The reaction mixture was diluted with EtOAc (500 mL×3). The combined EtOAc layers were washed with brine (100 mL×2), dried over Na$_2$SO$_4$ and concentrated in vacuo to give a residue, which was purified via column chromatography (silica gel, petroleum ether/EtOAc from 10/1 to 5/1) to give compound 549 (400 mg, 75% of purity, 89%) as a brown solid. LCMS m/z 648 [M+Na]$^+$.

Step 2:

To a stirred solution of compound 549 (400 mg, 75% of purity, 0.48 mmol) in DCM (2 mL) was added dropwise ~4M HCl (g) in dioxane (10 mL) at room temperature. After addition, the reaction mixture was stirred at room temperature for 2 hours. LC-MS showed the reaction mixture was complete. The reaction mixture was concentrated in vacuo to give crude compound 550, which was used for next step without any further purification. LCMS m/z 426 [M+H]$^+$.

Step 3:

A mixture of compound 550 (~300 mg) and KOH (316 mg, 5.65 mmol) in methanol (20 mL) was stirred at room temperature for 4 hours. LC-MS showed the reaction was complete. The mixture was poured into 0.5N HCl (20 mL), extracted with EtOAc (30 mL×5). The combined EtOAc layers were dried over Na$_2$SO$_4$ and concentrated in vacuo to give a residue, which was purified via column chromatography (silica gel, petroleum ether/EtOAc from 5/1-1/1) to give Example 102 (53.5 mg, 28%) as a brown solid. $^1$H NMR (400 MHz, CDCl$_3$) δ 7.96 (s, 1H), 7.32-7.28 (m, 2H), 7.05-7.00 (m, 1H), 6.19-6.14 (m, 1H), 5.08 (s, 2H), 4.30-4.26 (d, 1H), 4.22-4.18 (d, 1H), 3.49 (s, 3H), 2.17 (s, 3H). LCMS m/z 394 [M+H]$^+$.

Preparation of (11R)-8-amino-13-fluoro-11,17-dimethyl-17,18-dihydro-9,5-(metheno)-[1,5]naphthyridino[4,3-h][2,5,11]benzoxadiazacyclotetradecin-16(11H)-one (Example 103)

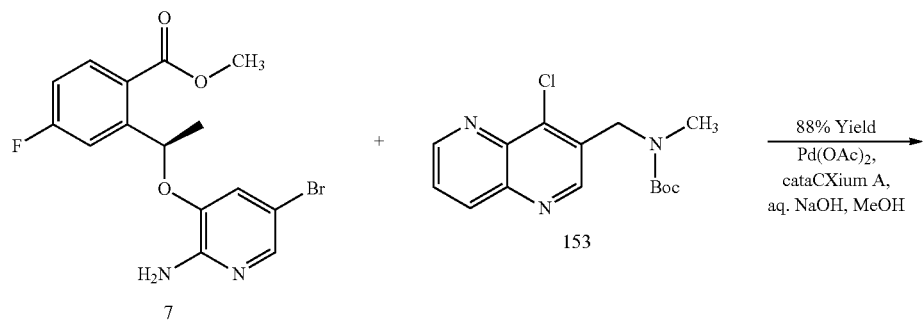

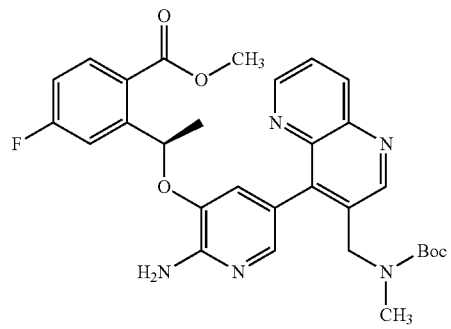

-continued

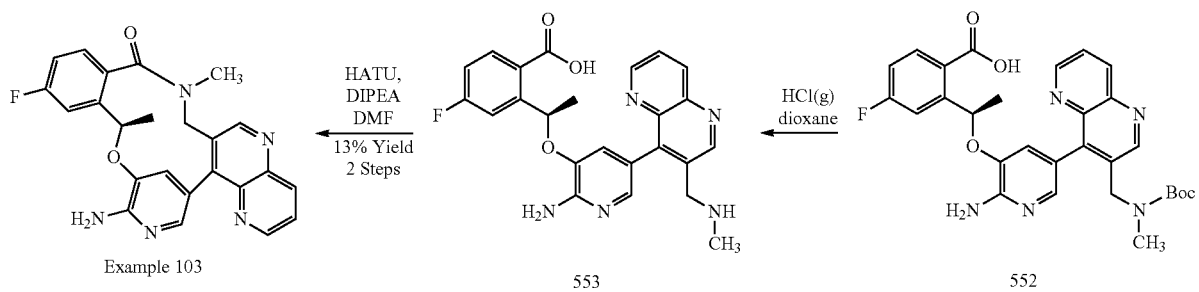

Example 103

Step 1:

To a solution of compound 7 (0.3 g, 0.81 mmol), compound 153 (400 mg, 1.29 mmol) and bis-(pinacalatodiboron) (618 mg, 2.43 mmol) in methanol (100 mL) was added cataCXium A (37.8 mg, 0.105 mmol) and Pd(OAc)$_2$ (23.7 mg, 0.105 mmol) under nitrogen at room temperature. After the mixture was degassed for three times with nitrogen, NaOH (64.8 mg, 1.62 mmol) in water (12 mL) was added. The resulting mixture was degassed with nitrogen three times and was then refluxed for 3 hours. TLC (EtOAc) showed the reaction mixture was completed. The reaction mixture was diluted with EtOAc (300 mL). The mixture was then washed with brine (100 mL×2), dried over Na$_2$SO$_4$ and concentrated in vacuo to give residue, which was purified by column chromatography over silica gel (DCM/MeOH 20:1, Rf, 0.41) to give compound 551 (400 mg, 88%) as a brown solid. LCMS m/z 308 [M+Na]$^+$.

Step 2:

A mixture of compound 551 (400 mg, 0.71 mmol) and NaOH (0.57 g, 14.2 mmol) in methanol (15 mL) and water (2 mL) was stirred at 40° C. for 3 hours. LC-MS showed the reaction mixture was completed. The reaction mixture was concentrated in vacuo to give a residue. The residue was dissolved with water (20 mL), and was extracted with MTBE (20 mL). The aqueous was then acidified with 6N HCl to pH ~5. The mixture was saturated with solid NaCl and then extracted with EtOAc (20 mL×5). The combined EtOAc layers were dried over Na$_2$SO$_4$ and concentrated in vacuo to give compound 552 (388 mg, 99%) as a yellow solid. LCMS m/z 548 [M+H]$^+$.

Step 3:

To a solution of compound 552 (388 mg, 0.7 mmol) in dioxane (5 mL) was added dropwise ~4M HCl (g) in dioxane (20 mL) at room temperature. After addition, the reaction mixture was stirred at room temperature for 14 hours. LC-MS showed the reaction mixture was completed. The reaction mixture was concentrated in vacuo to give residue, which was azeotroped with toluene three times to give crude compound 553, which was used for the next step without any further purification. LCMS m/z 448 [M+H]$^+$.

Step 4:

To a solution of HATU (400 mg, 0.313 mmol) in DMF (60 mL) was added dropwise a solution of compound 553 (~0.7 mmol) and DIEA (1.43 g, 11.2 mmol) in DMF (20 mL) at 0° C. After addition, the resulting mixture was stirred at this temperature for 1 hour. LC-MS showed the reaction was completed. The mixture was poured into ice-water (50 mL). The mixture was extracted with EtOAc (40 mL×5). The combined EtOAc layers were washed with brine (20 mL), dried over Na$_2$SO$_4$ and concentrated in vacuo to give a residue, which was purified by column chromatography over silica gel (DCM/MeOH 20:1 Rf, 0.27) to give Example 103 (40 mg, 13%) as an off-white solid. $^1$H NMR (400 MHz, CDCl$_3$) δ 9.01-9.00 (m, 2H), 8.44-8.42 (d, 1H), 7.85 (s, 1H), 7.69-7.67 (m, 1H), 7.37-7.34 (m, 1H), 7.24-7.22 (m, 2H), 7.02-6.98 (m, 1H), 5.90-5.88 (m, 1H), 4.94 (br s, 2H), 4.67-4.47 (dd, 2H), 3.18 (s, 3H), 1.83-1.81 (d, 3H). LCMS m/z 430 [M+H]$^+$.

Preparation of 7-amino-12-fluoro-2,10-dimethyl-2,10,15,17-tetrahydro-8,4-(azeno)pyrazolo[4,3-h][2,11,5]benzodioxazacyclotetradecine-3-carbonitrile (Example 104, 105 and 106)

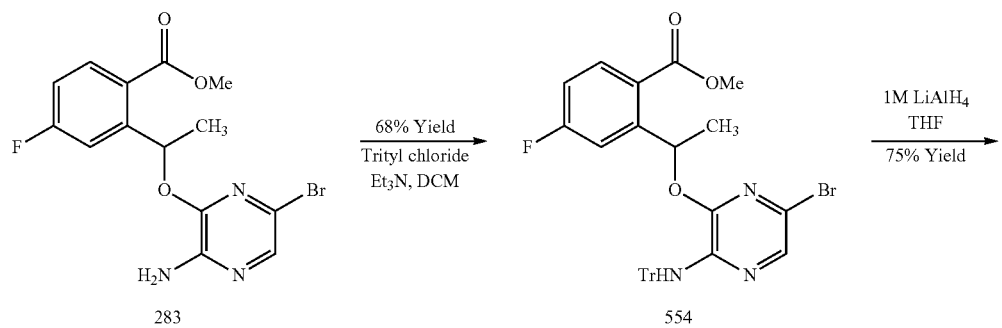

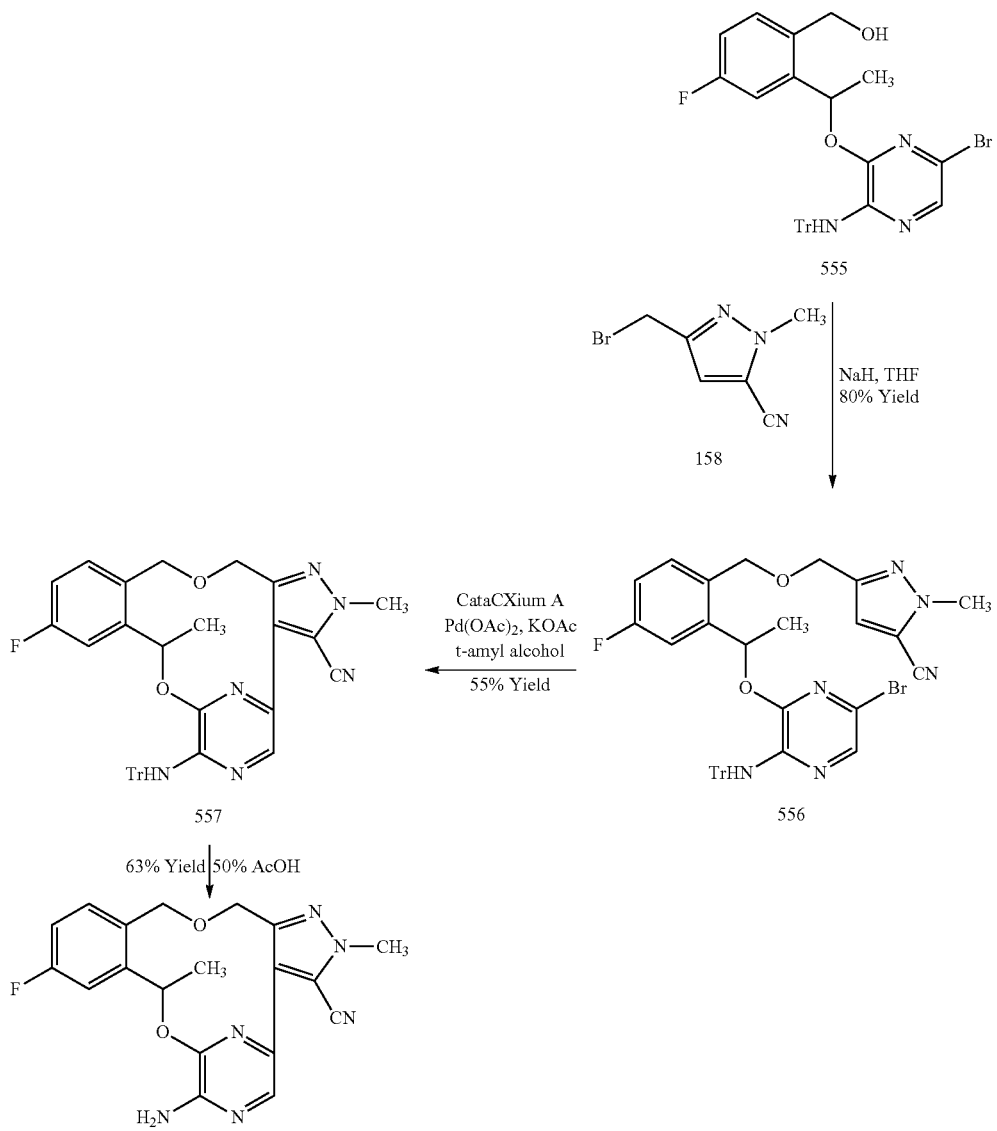

Example 104, Example 105 and Example 106

Step 1:

To the solution of compound 283 (1.48 g, 3.99 mmol) in DCM (25 mL), Et₃N (0.84 mL, 5.98 mmol) and DMAP (20 mg, 0.163 mmol) were added, followed by trityl chloride (1.68 g, 5.98 mmol). The reaction mixture was stirred for 16 hours at room temperature. An additional amount of trityl chloride (0.56 g, 1.99 mmol) was added to the reaction mixture and stirred at room temperature for 16 hours. The reaction mixture was diluted with DCM (20 mL) followed by extraction with water (10 ml) and brine (10 ml). The organic layer was removed and evaporated after drying over anhydrous sodium sulfate. The crude obtained as a yellow solid was purified by flash chromatography over silica gel (8% EtOAc in toluene) to give compound 554 as a colorless solid (1.67 g, 68% yield). $^1$H NMR (400 MHz, CDCl₃) δ 7.95 (dd, J=8.7, 5.8 Hz, 1H), 7.44-7.16 (m, 17H), 7.01 (ddd, J=8.7, 7.7, 2.7 Hz, 1H), 6.89 (qd, J=6.4, 1.3 Hz, 1H), 6.36 (s, 1H), 3.93 (s, 3H), 1.72 (d, J=6.4 Hz, 3H).

Step 2:

Compound 554 (1.6 g, 2.60 mmol) was dissolved in dry THF (15 mL) and cooled to 0° C. under nitrogen. A 1M solution of LiAlH₄ in THF (2.0 mL, 2.0 mmol) was added slowly over 15 minutes and the reaction mixture was stirred for 5 minutes at 0° C. The reaction mixture was quenched by the careful addition of H₂O (1 mL) and stirred for 10 minutes, before EtOAc (40 mL) and MgSO4 were added. The salts were filtered off, and the filtrate was evaporated to give a pale yellow oil, which was purified by column chromatography over silica gel (heptanes/EtOAc, 5:1) to give compound 555 as a colorless solid (1.13 g, 75% yield). $^1$H NMR (400 MHz, CDC₃) δ 7.38-7.20 (m, 16H), 7.09 (dd, J=9.7, 2.7 Hz, 1H), 6.96 (td, J=8.3, 2.7 Hz, 1H), 6.42 (s, 1H), 6.31 (qd, J=6.5, 1.6 Hz, 1H), 4.92 (d, J=12.1 Hz, 1H), 4.68 (dd, J=12.3, 7.1 Hz, 1H), 3.01 (d, J=8.4 Hz, 1H), 1.70 (d, J=6.5 Hz, 3H). LCMS ES m/z 584/586 [M+H]⁺.

Step 3:

To a solution of compound 555 (1.1 g, 1.189 mmol) in dry THF (15 mL) was slowly added NaH (60%, 0.15 g, 3.78 mmol) in portions at 0° C. for 3 minutes. The reaction was stirred for 30 minutes at 0° C. before adding the solution of compound 158 (0.452 g, 2.26 mmol) in dry THF (5 mL) slowly. The reaction was allowed to stir at room temperature overnight. The reaction mixture was carefully quenched with water (10 mL) followed by extraction with EtOAc (2×20 mL). The organic phase was removed, washed with water (10 mL) and brine (10 mL). The EtOAc extract was evaporated after being dried over anhydrous sodium sulfate. The crude product obtained as a light yellow gum was purified by column chromatography over silica gel using 15% acetone in heptane to provide compound 556 as a colorless solid (1.06 g, 80% yield). $^1$H NMR (400 MHz, CDCl$_3$) δ 7.36-7.19 (m, 16H), 7.14 (dd, J=9.8, 2.7 Hz, 1H), 6.94 (td, J=8.3, 2.7 Hz, 1H), 6.82 (s, 1H), 6.32-6.22 (m, 1H), 5.05 (d, J=11.5 Hz, 1H), 4.65-4.42 (m, 3H), 4.03 (s, 3H), 1.64 (d, J=6.5 Hz, 3H).

Step 4:

The reaction was done in two batches using compound 556(0.5 g, 0.71 mmol). In a microwave vial (20 ml capacity) was placed compound 556 (0.5 g, 0.71 mmol), KOAc (0.35 g, 3.55 mmol), cataCXium A (0.0763 g, 0.213 mmol) and t-amyl alcohol (degassed, 14.5 ml). The reaction mixture was further degassed for 3 minutes before adding Pd(OAc)$_2$. The vial was sealed and irradiated in the microwave for 2 hours at 120° C. The reaction mixtures were combined, diluted with EtOAc (50 ml), and filtered through celite to remove the inorganics. The clear yellow filtrate were washed with water (2×10 ml), brine (20 ml), dried over anhydrous sodium sulfate and evaporated to give the crude product as yellow solid. The solid was purified by column chromatography over silica gel using 25% acetone in heptane to give compound 557 as a light yellow solid (0.483 mg, 54.6% yield). $^1$H NMR (400 MHz, CDCl$_3$) δ 7.77 (s, 1H), 7.42-7.19 (m, 17H), 6.94 (td, J=8.2, 2.7 Hz, 1H), 6.72 (qd, J=6.7, 1.7 Hz, 1H), 6.52 (s, 1H), 5.35-5.23 (m, 1H), 4.48 (d, J=12.6 Hz, 1H), 4.24 (d, J=9.6 Hz, 1H), 4.11 (d, J=9.6 Hz, 1H), 3.97 (s, 3H), 1.65 (d, J=6.7 Hz, 3H). LCMS ES m/z 623 [M+H]$^+$.

Step 5:

A suspension of compound 557 (0.476 g, 0.76 mmol) in 50% AcOH in water (20 ml) was heated at 80° C. for 4 h. The reaction mixture was cooled to room temperature and was diluted with water (20 ml). The reaction mixture was carefully neutralized to slightly basic pH (pH=8) by slowly adding solid NaHCO$_3$ in a portionwise manner. The resultant reaction mixture was extracted with EtOAc (2×20 ml). The organic phase was removed, washed with water (5 ml), brine (10 ml). The clear yellow EtOAc extract was separated and evaporated after drying over anhydrous sodium sulfate, The crude product obtained as a light yellow solid on purification by column chromatography over silica gel using 25% acetone in heptane to give Example 104 as a colorless solid (0.183 mg, 63%). $^1$H NMR (400 MHz, DMSO-d$_6$) δ 7.84 (s, 1H), 7.49 (dd, J=10.2, 2.8 Hz, 1H), 7.38 (dd, J=8.4, 5.9 Hz, 1H), 7.07 (td, J=8.4, 2.8 Hz, 1H), 6.78 (s, 2H), 6.61 (qd, J=6.7, 1.8 Hz, 1H), 5.17 (d, J=12.3 Hz, 1H), 4.46 (d, J=12.3 Hz, 1H), 4.32 (d, J=9.9 Hz, 1H), 4.02 (d, 1H), 3.98 (s, 3H), 1.60 (d, J=6.6 Hz, 3H). LCMS ES m/z 381 [M+H]$^+$.

The chiral separation was performed by preparative SFC on a Whelk-O1 (R,R) (250×4.6 mm I.D., 3 micron particle size) column, which was eluted with 20% methanol 140 bar CO$_2$ with a flow rate of 3 mL/min. Rt$_{(Peak\,1)}$=3.77 minutes and Rt$_{(Peak\,2)}$=4.95 minutes, and gave Peak 1 as a white solid (59 mg, 20%) and Peak 2 as a white solid (58 mg, 20%).

Example 105 (Peak 1): >99% ee. $^1$H NMR (400 MHz, DMSO-d$_6$) δ 7.84 (s, 1H), 7.49 (dd, J=10.2, 2.8 Hz, 1H), 7.38 (dd, J=8.4, 5.9 Hz, 1H), 7.07 (td, J=8.4, 2.8 Hz, 1H), 6.78 (s, 2H), 6.61 (qd, J=6.7, 1.8 Hz, 1H), 5.17 (d, J=12.3 Hz, 1H), 4.46 (d, J=12.3 Hz, 1H), 4.32 (d, J=9.9 Hz, 1H), 4.02 (d, 1H), 3.98 (s, 3H), 1.60 (d, J=6.6 Hz, 3H). LCMS APCI m/z 381 [M+H]$^+$.

Example 106 (Peak 2): ~99% ee. $^1$H NMR (400 MHz, DMSO-d$_6$) δ 7.84 (s, 1H), 7.49 (dd, J=10.2, 2.8 Hz, 1H), 7.38 (dd, J=8.4, 5.9 Hz, 1H), 7.07 (td, J=8.4, 2.8 Hz, 1H), 6.78 (s, 2H), 6.61 (qd, J=6.7, 1.8 Hz, 1H), 5.17 (d, J=12.3 Hz, 1H), 4.46 (d, J=12.3 Hz, 1H), 4.32 (d, J=9.9 Hz, 1H), 4.02 (d, 1H), 3.98 (s, 3H), 1.60 (d, J=6.6 Hz, 3H). LCMS APCI m/z 381 [M+H]$^+$.

Preparation of 7-amino-12-fluoro-2-methyl-2,10,15, 17-tetrahydro-8,4-(azeno)pyrazolo[4,3-h][2,11,5] benzodioxazacyclotetradecine-3-carbonitrile (Example 107)

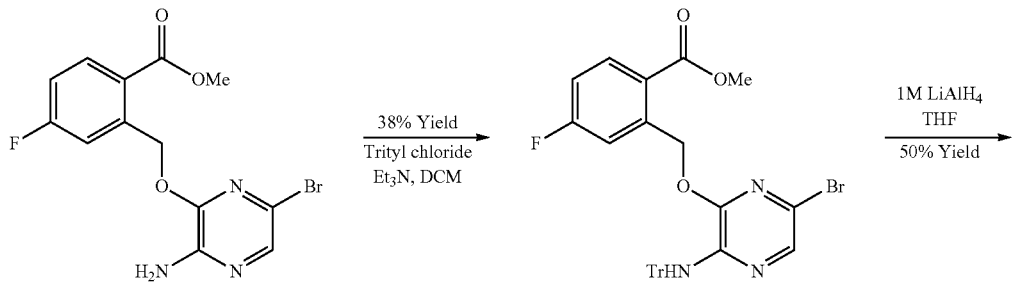

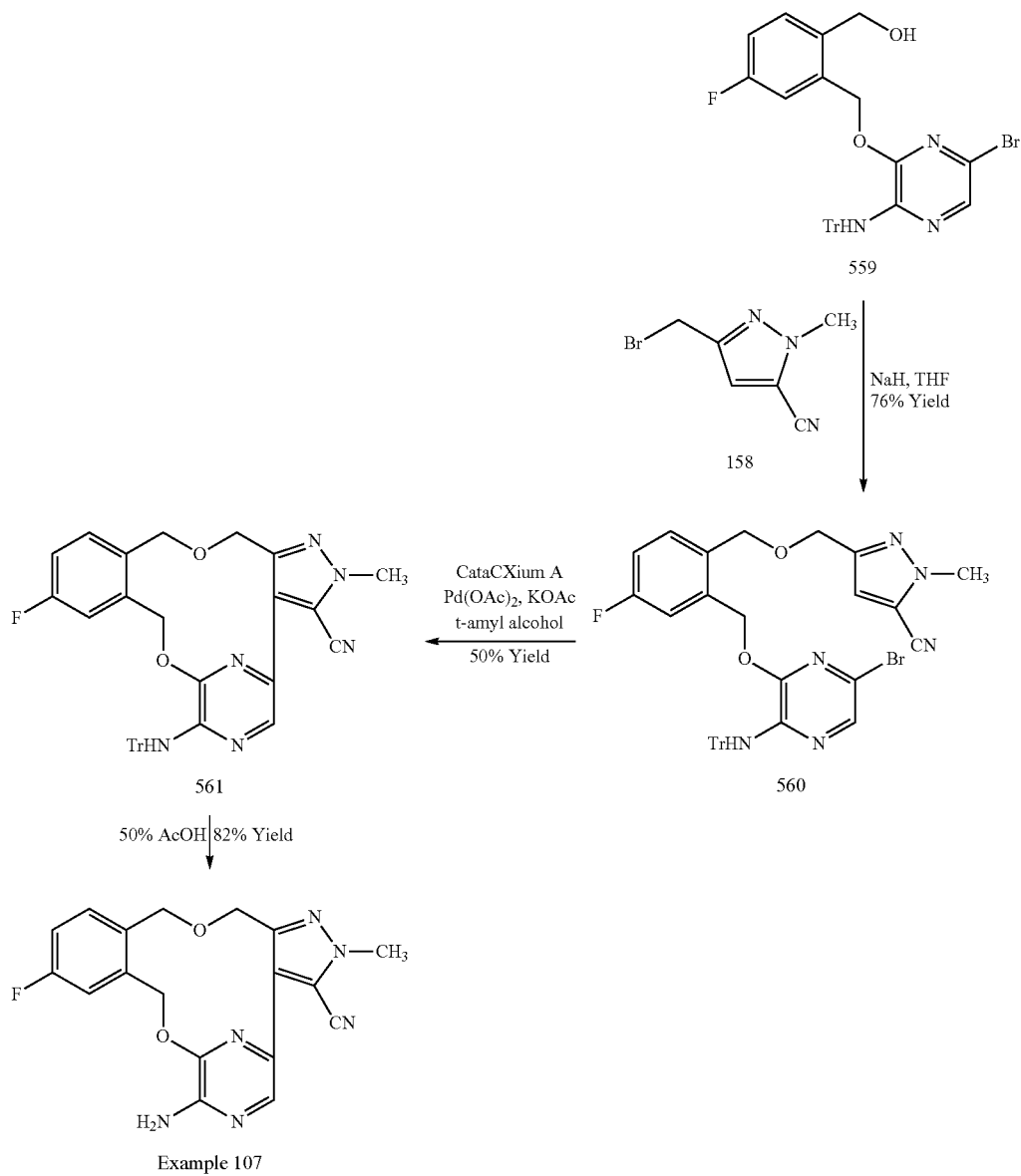

Step 1:

The procedure described in step 1 for Example 104 was used to prepare compound 558 (1.77 g, 38%) as a yellow solid. $^1$H NMR (400 MHz, CDCl$_3$) δ 8.05 (dd, J=8.7, 5.8 Hz, 1H), 7.39-7.13 (m, 17H), 7.06 (td, J=8.3, 2.7 Hz, 1H), 6.37 (s, 1H), 5.83 (s, 2H), 3.83 (s, 3H).

Step 2:

The procedure described in step 2 for Example 104 was used to prepare compound 559 (0.084 g, 50%) as a colorless solid (835 mg, 50% yield). $^1$H NMR (400 MHz, CDCl$_3$) δ 7.39 (dd, J=8.5, 5.7 Hz, 1H), 7.35 (s, 1H), 7.33-7.14 (m, 16H), 7.03 (td, J=8.3, 2.7 Hz, 1H), 6.44 (s, 1H), 5.52 (s, 2H), 4.76 (d, J=5.7 Hz, 2H), 2.01 (t, J=5.7 Hz, 1H). LCMS ES m/z 570/572 [M+H]$^+$.

Step 3:

The procedure described in step 3 for Example 104 was used to prepare compound 560 (0.77 g, 76%) as a colorless solid. $^1$H NMR (400 MHz, CDCl$_3$) δ 7.39-7.14; (m, 18H), 7.01 (td, J=8.3, 2.7 Hz, 1H), 6.82 (s, 1H), 6.35 (s, 1H), 5.48 (s, 2H), 4.64 (s, 2H), 4.51 (s, 2H), 4.00 (s, 3H). LCMS ES m/z 689/691 [M+H]$^+$.

Step 4:

The procedure described in step 4 for Example 104 was used to prepare compound 561 (0.31 g, 50%) as a yellow solid. $^1$NMR (400 MHz, DMSO-d$_6$) δ 7.67 (dd, J=10.2, 2.8 Hz, 1H), 7.55 (s, 1H), 7.47-7.16 (m, 16H), 7.10 (td, J=8.5, 2.8 Hz, 1H), 6.19-6.06 (m, 1H), 5.38-5.04 (m, 1H), 4.52-4.38 (m, 1H), 4.37-4.23 (m, 1H), 4.08-3.90 (m, 4H). LCMS ES m/z 609 [M+H]$^+$.

Step 5:

The procedure described in step 5 for Example 104 was used to prepare Example 107 (143 mg, 82%) as a pale yellow solid. $^1$H NMR (400 MHz, DMSO-d$_6$) δ 7.85 (s, 1H), 7.48-7.39 (m, 2H), 7.13 (td, J=8.5, 2.9 Hz, 1H), 6.82 (s, 2H), 6.23-5.95 (m, 1H), 5.44-5.17 (m, 1H), 5.16-4.90 (m, 1H), 4.61-4.21 (m, 2H), 4.00 (s, 3H). LCMS ES m/z 367 [M+H]$^+$.

Preparation of 8-amino-3-fluoro-5,13-dimethyl-13,15-dihydro-5H-7,11-(azeno)imidazo[1,2-k]pyrazolo[4,3-h][2,5,11]benzoxadiazacyclotetradecine-12-carbonitrile (Example 108/109)

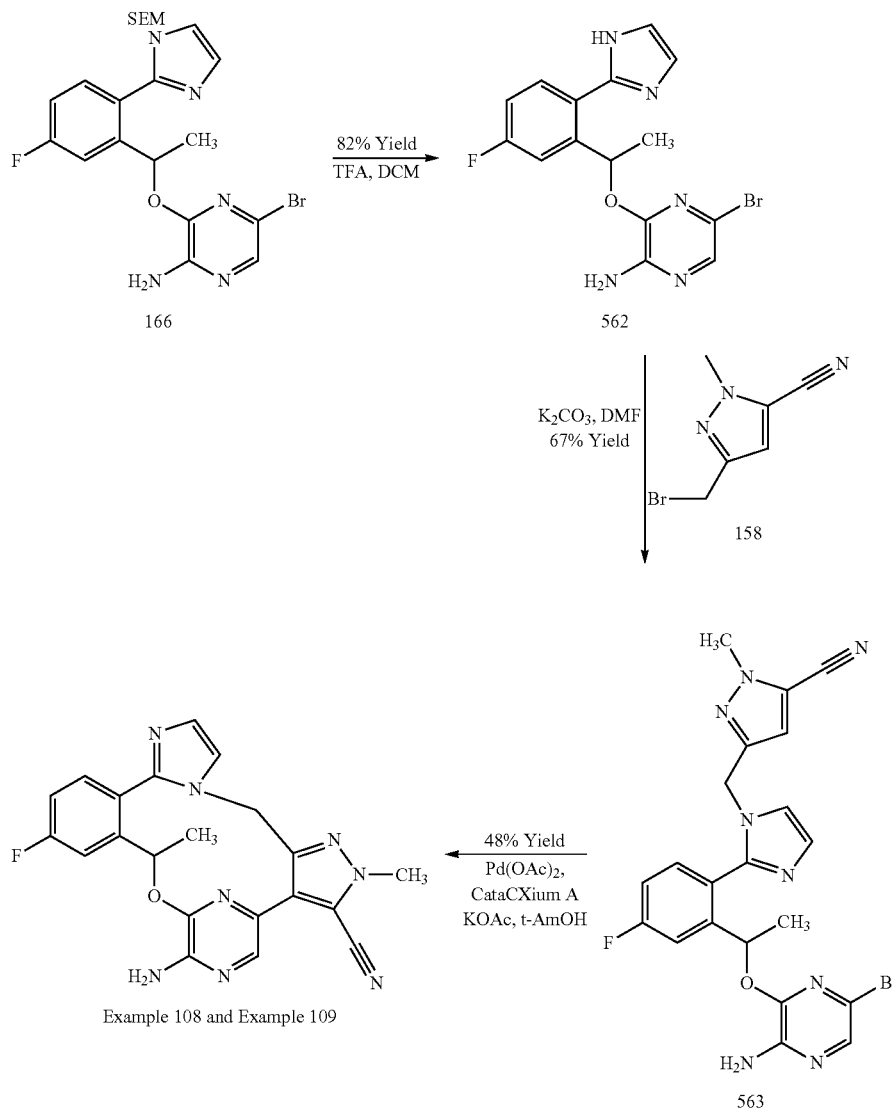

Example 108 and Example 109

Step 1:

Compound 166 (1.5 g, 2.96 mmol), was dissolved in DCM (7 mL) then TFA (15 mL) was added in a dropwise manner to this solution. The mixture was stirred at room temperature for 20 hours (TLC showed full conversion). The reaction was concentrated under vacuum, diluted with EtOAc (100 mL) and washed with a saturated aqueous solution of NaHCO$_3$ (100 mL then 50 mL). The aqueous phase was extracted with EtOAc (2×50 mL). The organic phases were combined, dried over MgSO$_4$, filtered and concentrated under vacuum. The oil obtained was purified by column chromatography over silica gel (eluents heptanes/EtOAc 1:1 to 1:2) to give compound 562 as a solid foam (919 mg, 82% yield). $^1$H NMR (400 MHz, DMSO-d$_6$) δ 12.42 (s, 1H), 7.70 (dd, J=10.5, 2.8 Hz, 1H), 7.62 (dd, J=8.7, 5.7 Hz, 1H), 7.49 (s, 1H), 7.23 (td, J=8.5, 2.8 Hz, 2H), 7.13 (s, 1H), 7.03-6.90 (m, 1H), 6.66 (s, 2H), 1.64 (d, J=6.3 Hz, 3H).

Step 2:

Compound 562 (919 mg, 2.43 mmol), compound 158 (513 mg, 2.56 mmol) and K$_2$CO$_3$ (503 mg, 3.64 mmol) were mixed in DMF (50 mL). The mixture was stirred at room temperature for 20 hours (LC-MS showed full conversion). Water (300 mL) was added and extracted with Et$_2$O (5×100 mL). The organic phases were combined, dried over MgSO$_4$, filtered and concentrated under vacuum. The oil obtained was purified by column chromatography over silica gel (eluents heptanes/EtOAc 1:1 to 0:1). Compound 563 was obtained as a white powder (805 mg, 67% yield). $^1$H NMR (400 MHz, DMSO-d$_6$) δ 7.66 (dd, J=10.2, 2.8 Hz, 1H), 7.53 (s, 1H), 7.42-7.30 (m, 2H), 7.22 (td, J=8.4, 2.7 Hz, 1H), 7.07 (d, J=1.3 Hz, 1H), 6.96 (s, 1H), 6.69 (s, 2H), 5.85 (q, J=6.3 Hz, 1H), 5.14 (d, J=15.7 Hz, 1H), 4.98 (d, J=15.7 Hz, 1H), 3.90 (s, 3H), 1.52 (d, J=6.4 Hz, 3H). LCMS m/z 497/499 [M+H]$^+$.

431

Step 3:

An identical reaction was set-up four times due to the limitation on volume of the microwave vials. Compound 563 (200 mg, 0.4 mmol) was mixed with KOAc (197 mg, 2.0 mmol) in tert-amyl alcohol (10 mL). The reaction was degassed for 30 minutes (by bubbling nitrogen through) then Pd(OAc)$_2$ (18 mg, 0.08 mmol) and cataCXium A (58 mg, 0.16 mmol) were added. The reaction was degassed again for 30 minutes, the microwave vial sealed and heated at 120° C. for 2 hours (LC-MS showed 96% of the expected product). The reaction was cooled to room temperature, filtered through a pad of celite and rinsed with EtOAc (100 mL). The filtrate was washed with water (50 mL) and brine (50 mL), dried over MgSO$_4$, filtered and concentrated under vacuum. The oil obtained was combined with the other reactions and purified by column chromatography over silica gel (eluents heptanes/EtOAc from 1:2 to 0:1). A mixture of Example 108 and Example 109 was obtained as a beige powder (320 mg, 48% yield, $^1$H NMR (400 MHz, DMSO-d$_6$) δ 7.70 (s, 1H), 7.58 (dd, J=10.0, 2.8 Hz, 1H), 7.46 (dd, J=8.5, 5.7 Hz, 1H), 7.24 (td, J=8.5, 2.8 Hz, 1H), 7.01 (s, 2H), 6.75 (s, 2H), 5.71-5.46 (m, 1H), 5.00 (d, J=14.1 Hz, 1H), 4.56 (d, J=14.1 Hz, 1H), 4.08 (s, 3H), 1.66 (d, J=6.6 Hz, 3H). LCMS m/z 417 [M+H]$^+$. The chiral separation was performed on 32 mg of material by preparative SFC on a Whelk-O1 (R,R) (250×4.6 mm I.D., 3 micron particle size) column, which was eluted with 30% methanol @ 140 bar CO$_2$ with a flow rate of 3 mL/min. Rt$_{(Peak\ 1)}$=3.00 minutes and Rt$_{(Peak\ 2)}$=3.86 minutes, and gave Peak 1 as a white solid (14.4 mg) and Peak 2 as a white solid (14.7 mg).

Example 108 (Peak 1): >99% ee. $^1$H NMR (400 MHz, DMSO-d$_6$) δ 7.71 (s, 1H), 7.58 (dd, J=2.6, 9.9 Hz, 1H), 7.46 (dd, J=5.8, 8.6 Hz, 1H), 7.24 (dt, J=2.8, 8.6 Hz, 1H), 7.01 (s, 2H), 6.73 (s, 2H), 5.62-5.51 (m, 1H), 5.00 (d, J=14.1 Hz, 1H), 4.56 (d, J=13.8 Hz, 1H), 4.08 (s, 3H), 1.66 (d, J=6.5 Hz, 3H). LCMS APCI m/z 417 [M+H]$^+$.

Example 109 (Peak 2): ~95% ee. $^1$H NMR (400 MHz, DMSO-d$_6$) δ 7.71 (s, 1H), 7.58 (dd, J=2.6, 9.9 Hz, 1H), 7.46 (dd, J=5.8, 8.6 Hz, 1H), 7.24 (dt, J=2.6, 8.5 Hz, 1H), 7.01 (s, 2H), 6.73 (s, 2H), 5.62-5.49 (m, 1H), 5.00 (d, J=14.1 Hz, 1H), 4.56 (d, J=14.1 Hz, 1H), 4.08 (s, 3H), 1.66 (d, J=6.5 Hz, 3H). LCMS APCI m/z 417 [M+H]$^+$.

Preparation of (10R)-7-amino-3-ethyl-12-fluoro-10,16-dimethyl-16,17-dihydro-8,4-(metheno)[1,2]thiazolo[4,3-h][2,5,11]benzoxadiazacyclotetradecin-15(10H)-one (Example 110)

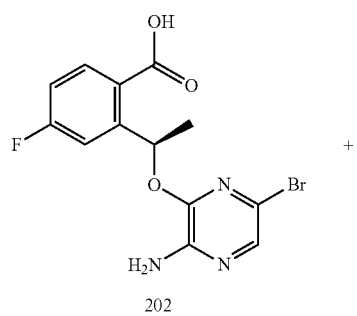

202

432

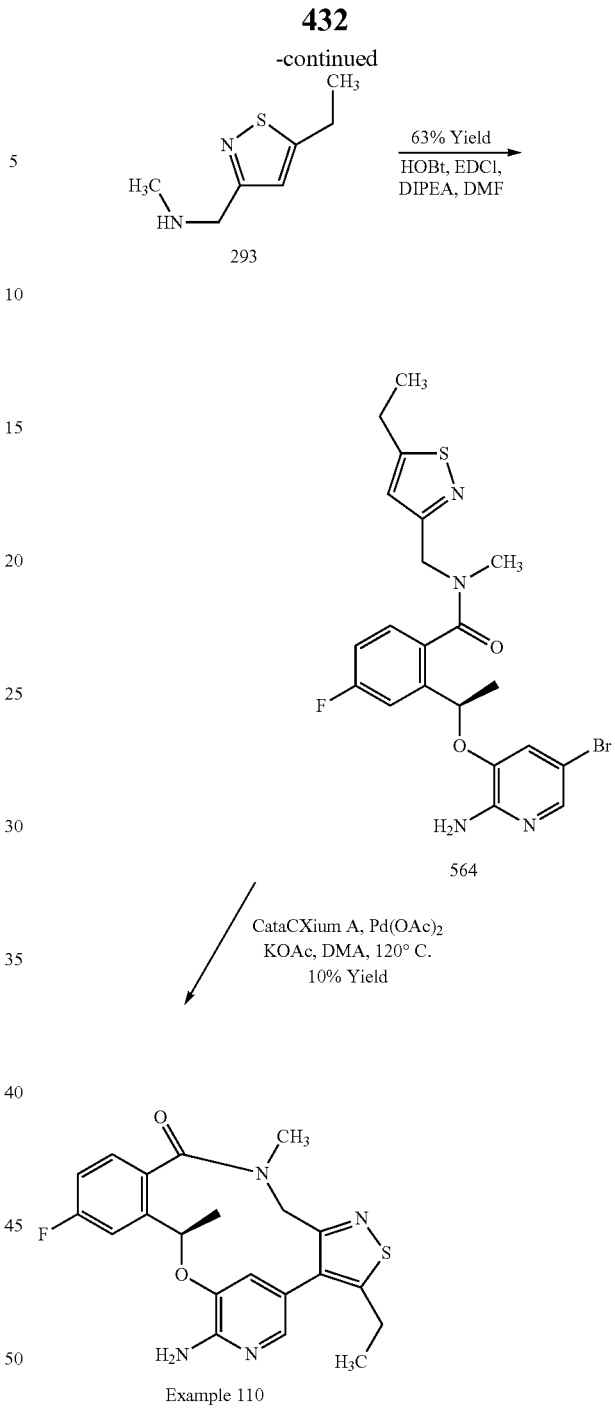

Step 1:

The procedure described in step 1 for Example 100 was used to prepare compound 564 as a yellow solid (0.5 g, 63%). LCMS m/z 493 [M+H]$^+$.

Step 2:

The procedure described in step 2 for Example 100 was used to prepare Example 110 as a yellow solid (16.8 mg, 10%). $^1$H NMR (400 MHz, Methanol-d$_4$) δ 7.59-7.56 (m, 1H), 7.48-7.42 (m, 3H), 7.19-7.14 (m, 1H), 5.99-5.98 (d, 1H), 4.56-4.47 (m, 2H), 3.18 (s, 3H), 3.09-2.99 (m, 2H), 1.88-1.87 (d, 3H), 1.38-1.35 (t, 3H). LCMS m/z 413 [M+H]$^+$.

Preparation of (10R)-7-amino-12-fluoro-3-methoxy-10,16-dimethyl-16,17-dihydro-8,4-(metheno)[1,2]oxazolo[4,5-h][2,5,11]benzoxadiazacyclotetradecin-15(10H)-one (Example 111)

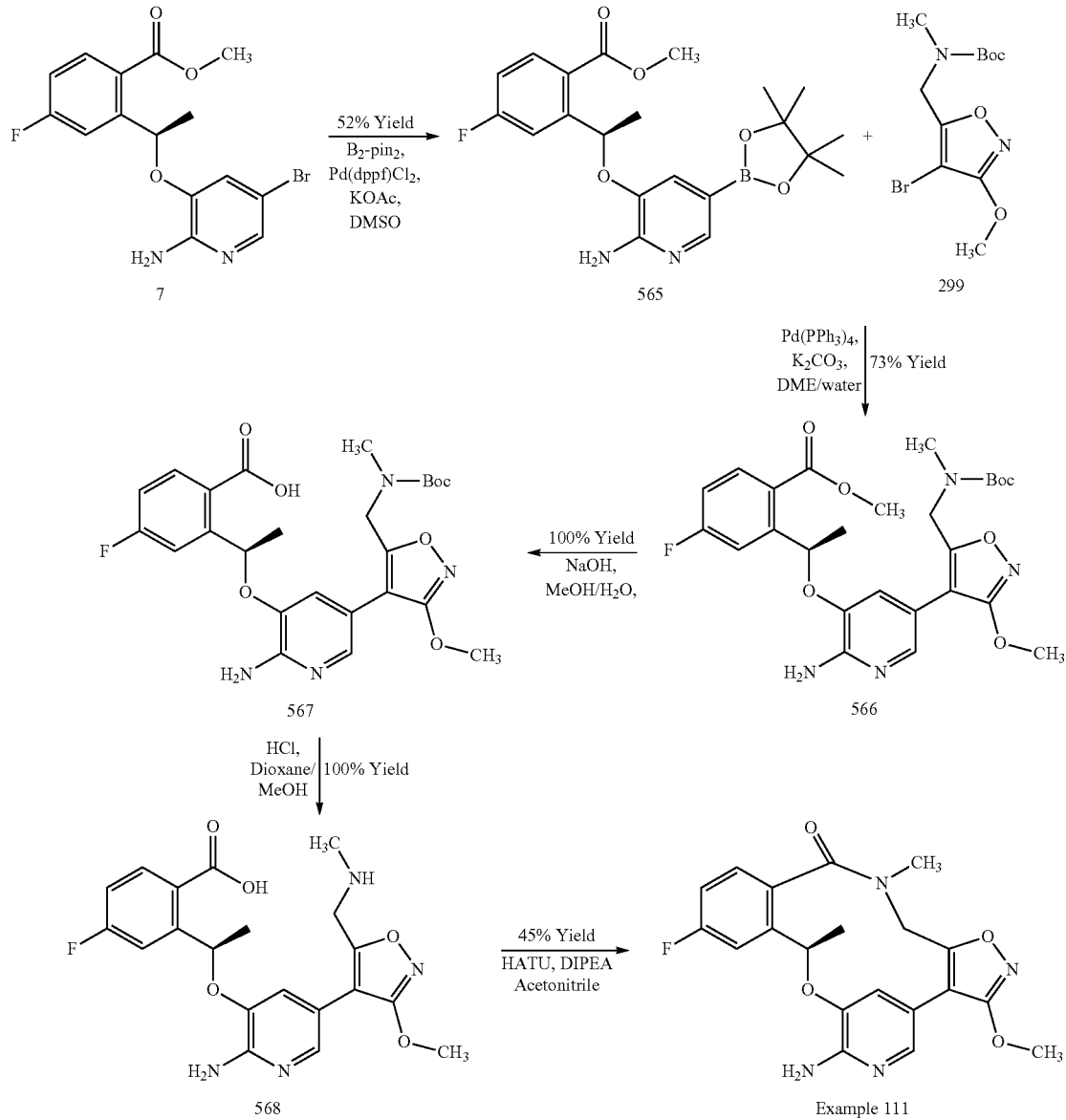

Step 1:

To a solution of compound 7 (200 mg, 0.54 mmol) in anhydrous DMSO (2 mL) was added bis-(pinacolato)diboron (635 mg, 2.5 mmol), Pd(dppf)Cl$_2$.CH$_2$Cl$_2$ (40 mg, 0.054 mmol) and then KOAc (178 mg, 1.82 mmol) and the mixture was stirred under nitrogen and heated to 80° C. for 1 hour. The mixture was cooled, EtOAc added (40 mL) and filtered through arbocel. The filtrate was washed with water then brine, then the organic layer was extracted into 1M aqueous HCl (2×). The aqueous phase was cooled in ice, neutralised to pH7 by the careful addition of 1M NaOH solution, and the resulting precipitate was extracted into EtOAc (2×). The combined organics were dried over sodium sulphate, filtered and the solvent removed under vacuum. The oily residue was redissolved in EtOAc (1 mL) and heptane (15 mL) was added forming an off white precipitate. The solvent was removed under vacuum to give 115 mg (52%) of compound 565. $^1$H NMR (400 MHz, DMSO-d$_6$) δ 7.94 (dd, 1H), 7.74 (d, 1H), 7.67 (dd, 1H), 7.25 (td, 1H), 6.87 (d, Hz, 1H), 6.35 (s, 2H), 6.26 (q, 1H), 3.91 (s, 3H), 1.57 (d, 3H), 1.21 (d, 12H). LCMS m/z 335 [M+H]$^+$.

Step 2:

A solution of compound 299 (1.26 g 3.92 mmol), potassium carbonate (811 mg, 5.88 mmol) in dimethoxyethane (20 mL) and water (15 mL) was warmed to 40° C. and degassed with bubbling nitrogen through the mixture for 20 minutes. To the mixture was added a solution of compound 565 (68 mg, 0.16 mmol) in degassed dimethoxyethane (1 mL) then Pd(PPh$_3$)$_4$. The mixture was stirred under nitrogen and warmed further to 100° C. During this time in 5 minute intervals a further 4 additions of compound 565 (68 mg, 0.16 mmol) in degassed dimethoxyethane (1 mL) was added to mixture, and after reaction reached 100° C., in 5 minute intervals a further 7 additions of compound 565 (68 mg, 0.16 mmol) in degassed dimethoxyethane (1 mL) was added to mixture. (In total 820 mg, 1.96 mmol of compound 565 was added in 12 mL DME). After the final addition the mixture was stirred at 100° C. under nitrogen for 1.5 hr, then cooled. EtOAc (120 mL) was added, then the mixture was washed with water (2×50 mL), dried over sodium sulphate, filtered and the solvent removed under vacuum. Purification of the residue by column chromatography over silica gel and eluting with heptane:EtOAc 100:0-30:70 yielded the compound 566 as a colorless solid (750 mg, 73%). $^1$H NMR (400 MHz, DMSO-d$_6$) δ 8.02-7.93 (m, 1H), 7.57-7.46 (m, 2H), 7.25 (td, 1H), 6.68 (m, 1H), 6.24 (q, 1H), 6.13 (s, 2H), 4.59-4.12 (m, 2H), 3.88 (s, 3H), 3.84 (s, 3H), 2.70 (m, 3H)*, 1.61 (d, J=6.2 Hz, 3H), 1.42-1.08 (m, 9H). LCMS m/z 531 [M+H]$^+$.

Step 3:

To a solution of compound 566 (1.05 g, 1.98 mmol) in methanol (25 mL) at room temperature was added a solution of sodium hydroxide (1.2 g, 30 mmol) in water (3.5 mL) and mixture stirred for 18 hours at room temperature. To the mixture was added water (100 mL), then the mixture was washed TBME (10 mL). The aqueous layer was adjusted to pH 4 with the careful addition of 1N HCl and a precipitate formed. The mixture was extracted with EtOAc (80 mL) then sodium chloride (20 g) was added to the aqueous layer, which was extracted further with EtOAc (80 mL). The combined organic layers were dried over sodium sulphate, filtered and the solvent removed under vacuum to give compound 567 as a pale yellow solid (1.02 g, 100%). $^1$H NMR (400 MHz, DMSO-d$_6$) δ 7.99 (dd, 1H), 7.54-7.44 (m, 2H), 7.21 (td, 1H), 6.72 (d, 1H), 6.37 (q, 1H), 6.17 (s, 2H), 4.81-3.95 (m, 2H), 3.84 (s, 3H), 2.73-2.66 (m, 3H), 1.60 (d, 3H), 1.36-1.07 (m, 9H). LCMS m/z 517 [M+H]$^+$.

Step 4:

To a solution of compound 567 (1.02 g, 1.98 mmol) in methanol (10 mL) and dioxane (10 mL) was added a solution of 4N HCl in dioxane (6 mL), and the mixture was stirred at 45° C. under nitrogen for 1.5 hours. The solvent was removed under vacuum, then azeotroped further with dioxane (2×25 mL) to give compound 568 (1.2 g, 100%) as a pale brown solid. The solid was not purified further and was taken onto the next reaction. $^1$H NMR (400 MHz, DMSO-d$_6$) δ 9.67 (s, 2H), 8.28-8.18 (m, 1H), 8.05 (dd, 1H), 7.84 (d, 1H), 7.55 (dd, 1H), 7.29 (td, 1H), 7.10 (d, 1H), 6.56 (q, 1H), 4.28 (s, 2H), 3.87 (s, 3H), 2.55 (s, 3H), 1.66 (d, 3H). LCMS m/z 417 [M+H]$^+$.

Step 5:

To a suspension of compound 568 (1.1 g, 1.654 mmol accounting for impurities) in acetonitrile (1.05 L) at room temperature was added DIEA (1.92 g, 2.59 mL, 14.88 mmol) and the mixture turned to a solution. To the mixture was added HATU (660 mg, 1.74 mmol) and the mixture was stirred under nitrogen at room temperature for 1 hour. The solvent was removed under vacuum, then the residue re-dissolved in EtOAc (200 mL), washed with water (3×40 mL), brine (20 mL), dried over sodium sulphate, filtered and the solvent removed under vacuum. Purification of the residue by column chromatography over silica gel and eluting with EtOAc, then azeotroping the fractions with hexane (30 ml) yielded the desired product as a colorless solid. 1H and 19F NMR indicated a trace of PF$_6$ salt, so the material was re-dissolved in EtOAc (100 mL), washed with 10% aqueous Na$_2$CO$_3$ (3×40 mL), brine (2×20 mL), dried over sodium sulphate, filtered and the solvent removed under vacuum. Then the residue was re-dissolved in EtOAc (2 mL), hexane added (30 mL) and white precipitate formed. the solvent was removed under vacuum to give Example 111 as a colorless solid (323 mg, 45%). $^1$H NMR (400 MHz, DMSO-d$_6$) δ 7.58 (dd, J=10.3, 2.7 Hz, 1H), 7.55 (d, J=1.8 Hz, 1H), 7.44 (dd, J=8.6, 5.7 Hz, 1H), 7.21 (td, J=8.4, 2.7 Hz, 1H), 6.67 (d, J=1.8 Hz, 1H), 6.07 (s, 2H), 5.60-5.49 (m, 1H), 4.52 (d, J=15.2 Hz, 1H), 4.33 (d, J=15.2 Hz, 1H), 3.98 (s, 3H), 3.03 (s, 3H), 1.66 (d, J=6.2 Hz, 3H). LCMS ES m/z 399 [M+H]$^+$.

Preparation of (10R)-7-amino-3-ethyl-12-fluoro-10,16-dimethyl-16,17-dihydro-8,4-(metheno)[1,2]thiazolo[4,5-h][2,5,11]benzoxadiazacyclotetradecin-15 (10H)-one (Example 112)

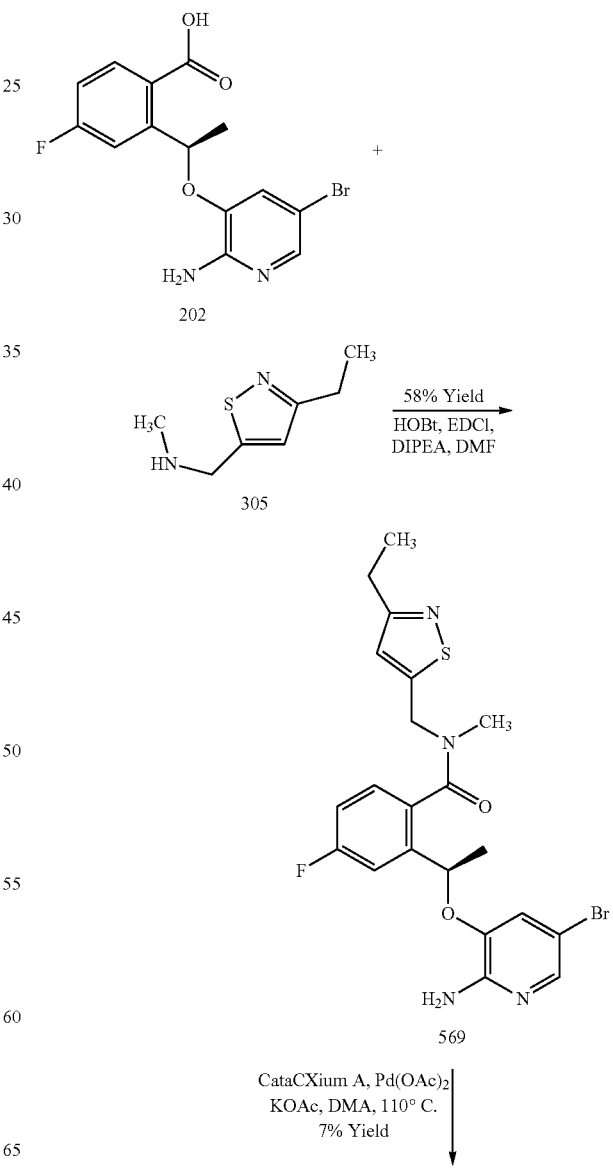

437

-continued

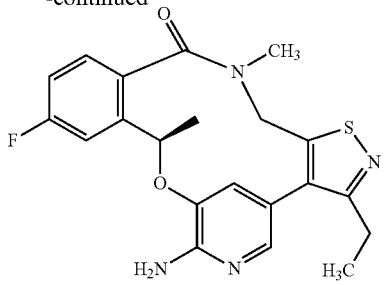

Example 112

Step 1:

The procedure described in step 1 for Example 100 was used to prepare compound 569 (0.4 g, 58%) as a yellow solid. LCMS ES m/z 493 [M+H]⁺.

438

Step 2:

The procedure described in step 2 for Example 100 was used to prepare Example 112 (12.5 mg, 7%) as a white solid. ¹NMR (400 MHz, Methanol-$d_4$) δ 7.60-7.57 (m, 1H), 7.46 (s, 1H), 7.39-7.36 (m, 1H), 7.1-7.09 (d, 1H), 7.02-7.01 (d, 1H), 5.85-5.84 (d, 1H), 4.73-4.52 (m, 2H), 3.22 (s, 3H), 2.91-2.87 (d, 2H), 1.82-1.81 (d, 3H), 1.29-1.26 (t, 3H). LCMS ES m/z 413 [M+H]⁺.

Preparation of (10R)-7-amino-12-fluoro-3-methoxy-1,10,16-trimethyl-16,17-dihydro-1H-8,4-(metheno)pyrazolo[4,3-h][2,5,11]benzoxadiazacyclotetradecin-15(10H)-one (Example 113)

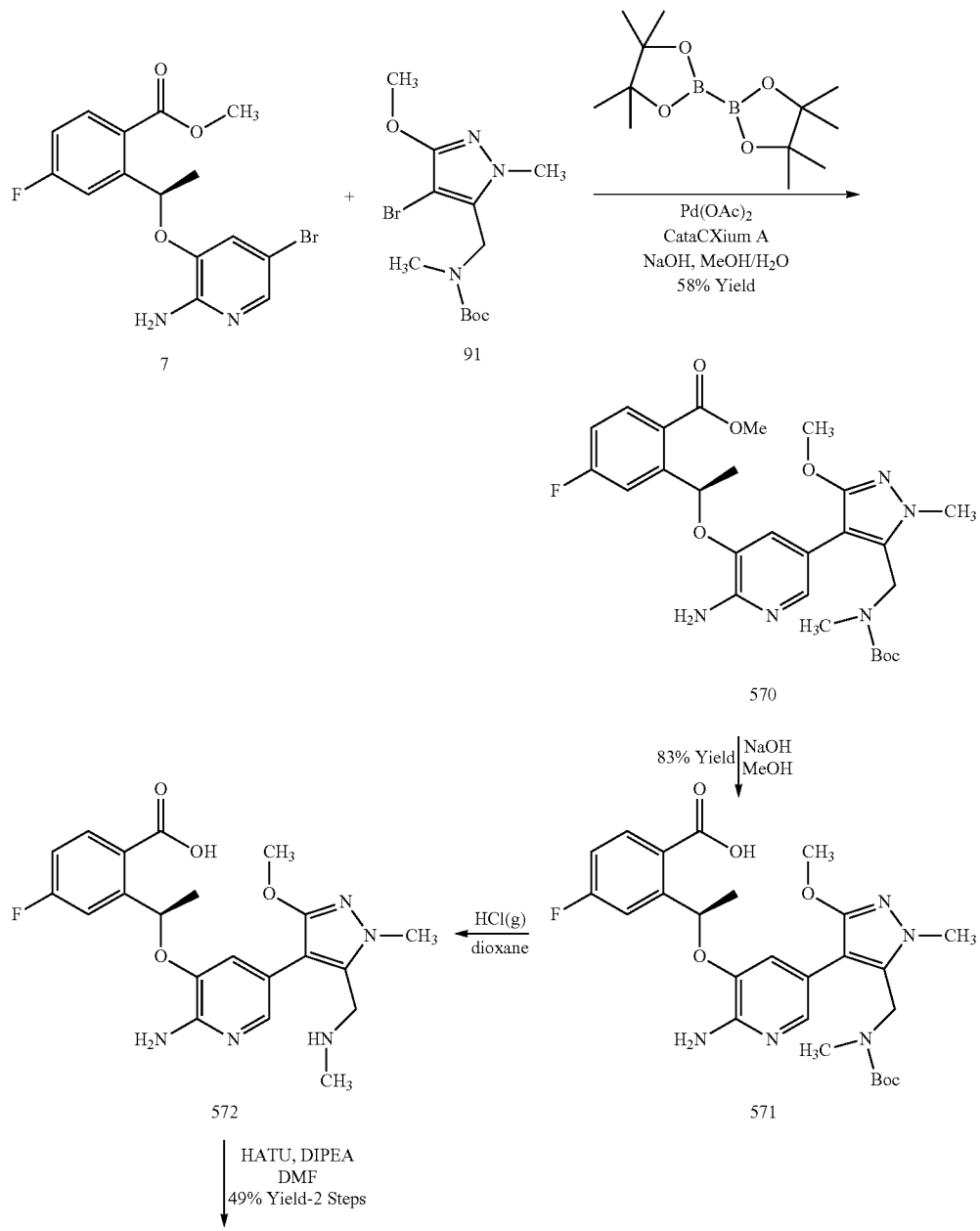

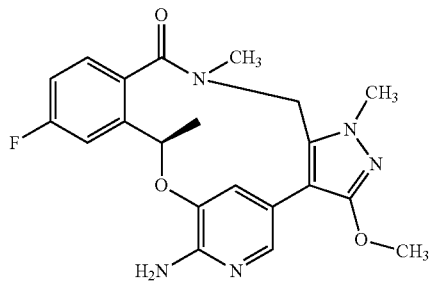
Example 113

Step 1:
The procedure described in step 1 for Example 86 and Example 87 was used to prepare compound 570 (1.4 g, 58%) as a brown solid. $^1$H NMR (400 MHz, CDCl$_3$) δ 7.99-7.95 (dd, 1H), 7.48 (s, 1H), 7.21-7.18 (dd, 1H), 6.94-6.89 (m, 1H), 6.53-6.52 (d, 1H), 6.31-6.26 (dd, 1H), 4.73 (s, 2H), 3.87-3.83 (t, 3H), 3.70 (s, 3H), 3.59 (s, 3H), 2.27 (s, 3H), 1.61-1.57 (t, 3H), 1.39 (s, 9H).

Step 2:
The procedure described in step 2 for Example 86 and Example 87 was used to prepare compound 571 (1.0 g, 83%) as a yellow solid. LCMS ES m/z 530 [M+H]$^+$.

Step 3:
The procedure described in step 3 for Example 86 and Example 87 was used to prepare compound 572, which was used in the next step directly. LCMS m/z 430 [M+H]$^+$.

Step 4:
The procedure described in step 4 for Example 86 and Example 87 was used to prepare Example 113 as an off-white solid (380 mg, 49%). $^1$H NMR (400 MHz, CDCl$_3$) δ 7.76 (d, 1H), 7.25-7.22 (m, 1H), 7.14-7.12 (m, 1H), 6.94-6.92 (d, 1H), 6.74-6.73 (d, 1H), 5.61-5.57 (m, 1H), 4.64 (s, 2H), 4.42-4.21 (dd, 2H), 3.87-3.84 (d, 3H), 3.80-3.67 (s, 3H), 3.09 (s, 3H), 1.70-1.69 (d, 3H). LCMS ES m/z 412 [M+H]$^+$.

Preparation of (10R)-7-amino-12-fluoro-1,10,16-trimethyl-15-oxo-10,15,16,17-tetrahydro-1H-8,4-(metheno)pyrazolo[4,3-h][2,5,11]benzoxadiazacyclotetradecine-3-carbonitrile (Example 114)

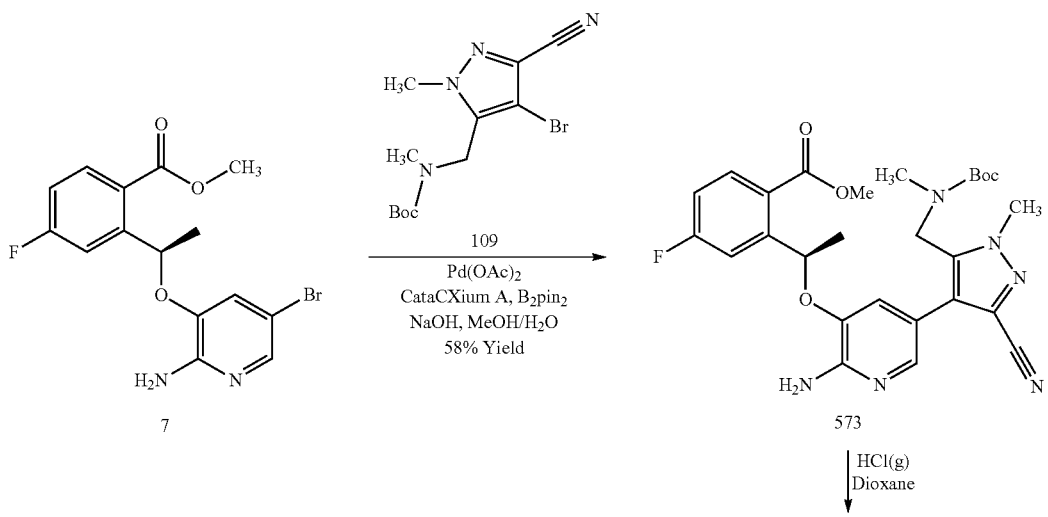

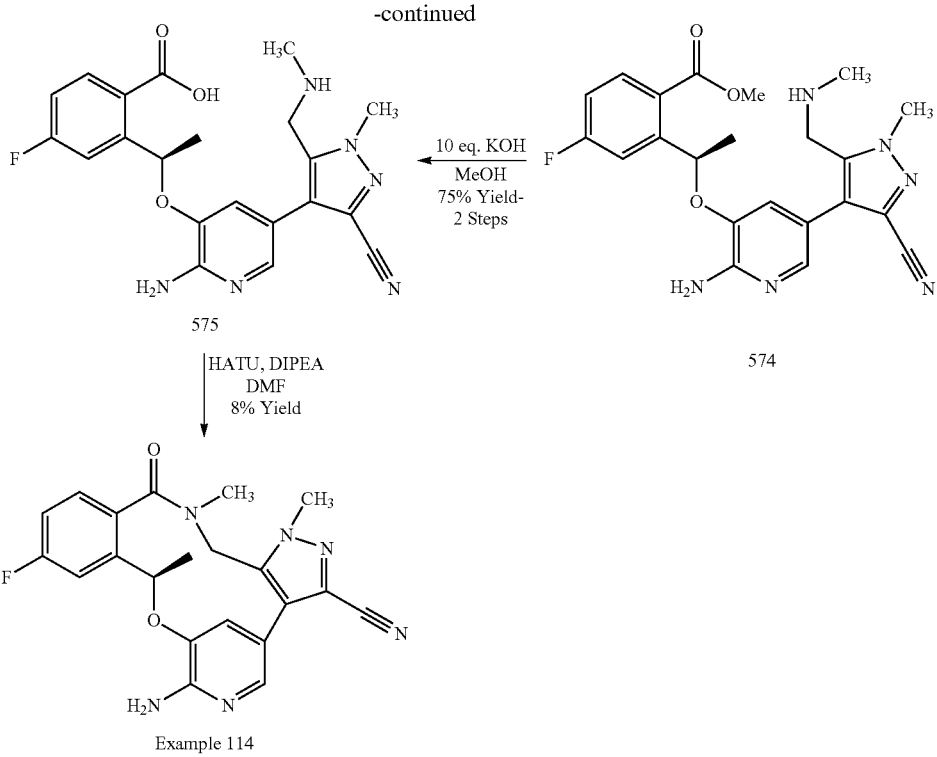

Step 1:
The procedure described in step 1 for Example 88 was used to prepare compound 573 (600 mg, 58%) as a brown solid. $^1$H NMR (400 MHz, CDCl$_3$) δ 8.04-7.99 (m, 1H), 7.57-7.56 (d, 1H), 7.24 (s, 1H), 7.03-6.97 (m, 1H), 6.63-6.62 (d, 1H), 6.42-6.40 (m, 1H), 5.01 (s, 2H), 4.54-4.31 (m, 2H), 3.99-3.95 (d, 3H), 3.94-3.86 (m, 3H), 2.307 (s, 3H), 1.69-1.64 (d, 3H), 1.29 (s, 9H)

Step 2:
The procedure described in step 2 for Example 88 was used to prepare compound 574, which was used for next step without any further purification. LCMS m/z 439 [M+H]$^+$.

Step 3:
The procedure described in step 3 for Example 88 was used to prepare compound 575 (320 mg, 75%) as a brown solid. LCMS m/z 425 [M+H]$^+$.

Step 4:
The procedure described in step 4 for Example 88 was used to prepare Example 114 (24.1 mg, 8%) as a white solid. $^1$H NMR (400 MHz, CDCl$_3$) δ 7.89 (s, 1H), 7.33-7.30 (d, 1H), 7.26-7024 (m, 1H), 7.19-7.18 (m, 1H), 7.02-7.00 (m, 1H), 5.71-5.70 (m, 1H), 4.84 (s, 2H), 4.59-4.37 (m, 2H), 4.10 (s, 3H), 3.16 (s, 3H), 1.79-1.64 (d, 3H). LCMS m/z 407 [M+H]$^+$.

Preparation of (10R)-7-amino-12-fluoro-1,10,16-trimethyl-15-oxo-10,15,16,17-tetrahydro-1H-8,4-(azeno)pyrazolo[4,3-h][2,5,11]benzoxadiazacyclotetradecine-3-carbonitrile (Example 115)

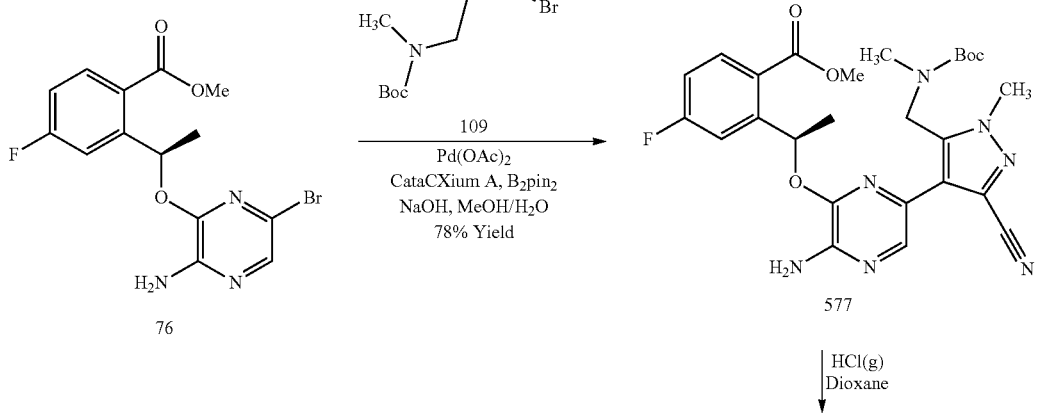

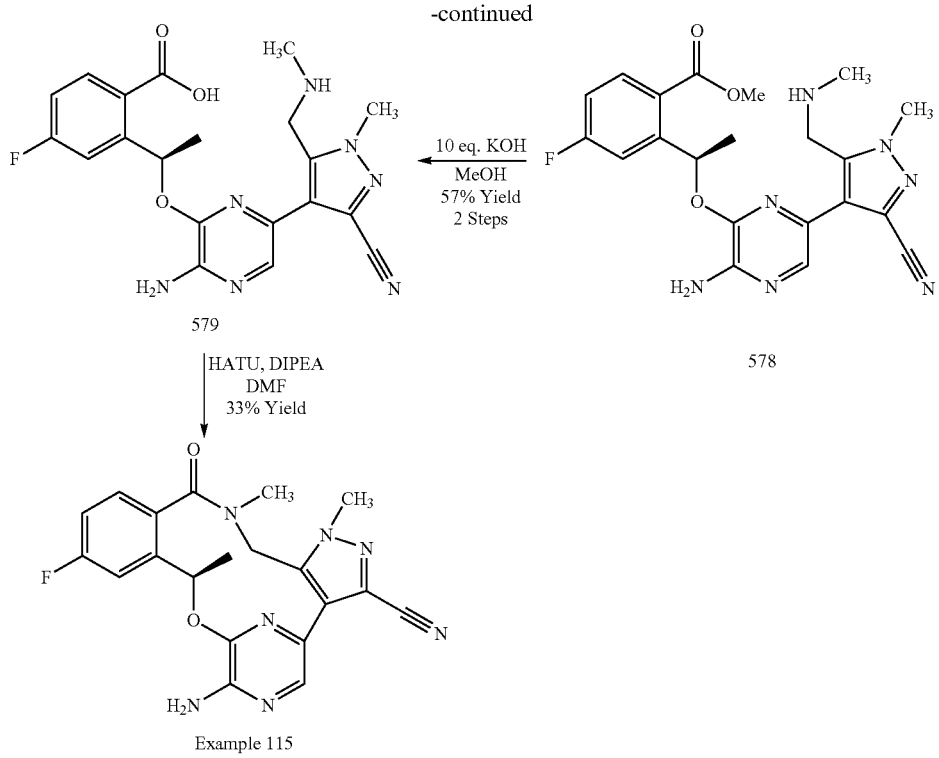

Step 1:
The procedure described in step 1 for Example 88 and was used to prepare compound 577 (400 mg, 78%) as a brown solid. LCMS m/z 562 [M+Na]⁺.

Step 2:
The procedure described in step 2 for Example 88 and was used to prepare compound 578, which was used for next step without any further purification. LCMS m/z 440 [M+H]⁺.

Step 3:
The procedure described in step 3 for Example 88 and was used to prepare compound 579 (300 mg, 65% of purity, 57%) as a brown solid. LCMS m/z 426 [M+H]⁺.

Step 4:
The procedure described in step 4 for Example 88 and was used to prepare Example 115 (61.5 mg, 33%) as a white solid. $^1$H NMR (400 MHz, CDCl$_3$) δ 8.17 (s, 1H), 7.30-7.22 (m, 1H), 7.21-7.19 (m, 1H), 7.02-6.97 (m, 1H), 6.01-5.98 (m, 1H), 5.02 (s, 2H), 4.76-4.24 (dd, 2H), 4.08 (s, 3H), 3.02 (s, 3H), 1.76-1.74 (d, 3H). LCMS ES m/z 408 [M+H]⁺.

Preparation of (1R)-4-amino-19-fluoro-9-methoxy-1,15-dimethyl-14,15-dihydro-1H-3,7:8,12-di(metheno)-2,5,11,15-benzoxatriazacyclooctadecin-16(13H)-one (Example 116)

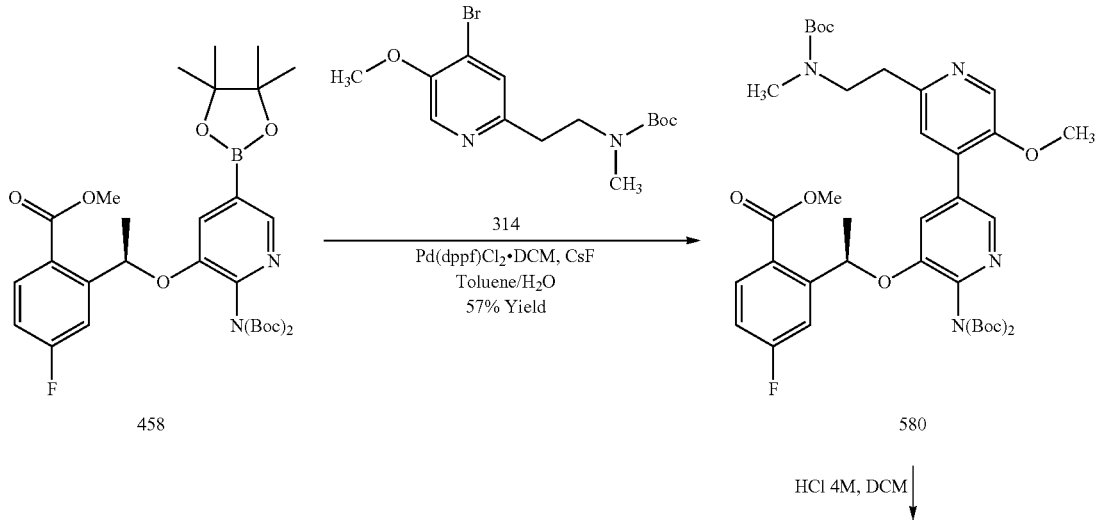

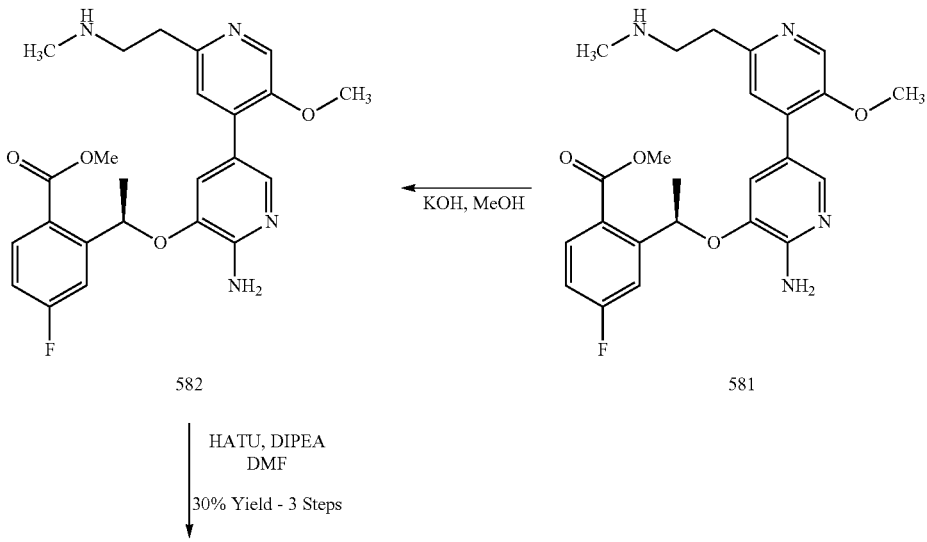

582 → KOH, MeOH → 581

HATU, DIPEA
DMF

30% Yield - 3 Steps

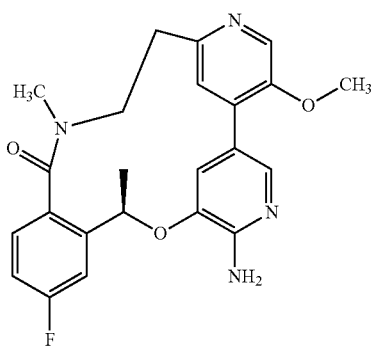

Example 116

Step 1:

Compound 458 (475 mg, 0.77 mmol), compound 314 (280 mg, 0.81 mmol) and CsF (351 mg, 2.3 mmol) were dissolved in a mixture of toluene/H2O (6.6 mL, 10:1). The solution was heated at 60° C. and degassed (3 cycles N$_2$/vacuum). Pd(dppf)Cl$_2$.CH$_2$Cl$_2$ (69 mg, 0.08 mmol) was added, the mixture was degassed (3 cycles N$_2$/vacuum) and heated at 100° C. for 18 hours. The mixture was cooled to room temperature then filtered through a pad of silica then rinsed with EtOAc (~100 mL). The phases were separated and the aqueous phase was extracted with EtOAc (2×50 mL). The combined organic phases were dried over MgSO$_4$, filtered and concentrated under vacuum to give a brown oil, which was purified by column chromatography over silica gel (eluent heptanes/EtOAc from 1:1 to 0:1). Compound 580 was obtained as orange solid foam (870 mg, 57% yield). $^1$H NMR (400 MHz, DMSO-d$_6$) δ 8.33 (s, 1H), 8.17 (d, J=6.8 Hz, 1H), 8.05 (dd, J=8.8, 5.7 Hz, 1H), 7.46-7.16 (m, 5H), 6.35 (d, J=6.3 Hz, 1H), 3.87 (d, J=1.1 Hz, 3H), 3.69 (s, 3H), 3.47 (q, J=6.4 Hz, 2H), 2.86 (t, J=6.8 Hz, 2H), 2.76 (s, 2H), 1.57 (d, J=6.2 Hz, 3H), 1.43 (s, 16H), 1.34-0.92 (m, 10H). LCMS ES m/z 755 [M+H]$^+$.

Step 2:

Compound 580 (876 mg, 1.16 mmol) was dissolved in DCM (6 mL) and the solution was cooled to 0° C. HCl 4 M in dioxane (5.8 mL) was added drop wise. The mixture was stirred at room temperature for 18 hours then concentrated under vacuum. The HCl salt of compound 581 was obtained as a white solid (713 mg, 100% purity by LC-MS) and was used in the next step without further purification. $^1$H NMR (400 MHz, DMSO-d$_6$) δ 9.48-8.90 (m, 2H), 8.38 (d, J=37.4 Hz, 3H), 7.98-7.76 (m, 2H), 7.60 (s, 1H), 7.48 (dd, J=10.2, 2.6 Hz, 1H), 7.32 (d, J=1.5 Hz, 1H), 7.18 (td, J=8.4, 2.6 Hz, 1H), 6.30 (q, J=6.2 Hz, 1H), 3.73 (s, 3H), 3.64 (s, 3H), 3.17 (d, J=6.3 Hz, 4H), 2.41 (t, J=5.2 Hz, 3H), 1.52 (d, J=6.1 Hz, 3H). LCMS ES m/z 455 [M+H]$^+$.

Step 3:

Compound 581 (713 mg, 1.16 mmol) and KOH (520 mg, 9.3 mmol) were dissolved in MeOH (12.3 mL) using ultrasound. The solution was heated at 50° C. for 5 hours, 40° C. for 18 hours then 60° C. for 2 hours. The mixture was cooled at 0° C. then acidified carefully using conc. HCl until pH 4 (formation of white solids). The suspension was filtered. Mother liquors were concentrated under vacuum to give a beige solid which was suspended in MeOH (5 mL). The solids were filtered. The mother liquors were concentrated under vacuum to give the hydrochloride salt of the compound 582 as pale brown solids (640 mg). $^1$H NMR (400 MHz, DMSO-d$_6$) δ 9.20 (s, 2H), 8.49 (d, J=22.0 Hz, 4H), 8.05 (dd, J=8.8, 5.9 Hz, 1H), 7.97 (d, J=1.7 Hz, 1H), 7.75-7.50 (m, 2H), 7.45 (d, J=1.7 Hz, 1H), 7.29 (td, J=8.4, 2.7 Hz, 1H), 6.58 (q, J=6.2 Hz, 1H), 3.79 (s, 3H), 3.36-3.19 (m, 4H), 2.56 (t, J=5.2 Hz, 3H), 1.67 (d, J=6.1 Hz, 3H). LCMS ES m/z 441 [M+H]$^+$.

Step 4:

To a cooled solution of HATU (390 mg, 1.0 mmol) in DMF (12 mL) at 0° C. was added dropwise a solution of compound 582 (450 mg, 0.82 mmol) and DIPEA (0.68 mL, 4.1 mmol) in DMF (21 mL) over 1 hour. 10 min after the end of the addition, H$_2$O (300 mL) was added and the mixture was extracted with EtOAc (6×50 mL). The organic phases were combined, dried over MgSO$_4$ and purified DIRECTLY without being concentrated by SCX-2 column (10 g, eluents:EtOAc (from the work-up) then MeOH the MeOH/NH$_3$). Fractions obtained by elution with MeOH/NH$_3$ were combined, concentrated under vacuum and purified by column chromatography over silica gel (eluents DCM/MeOH from 95:5 to 90:10) to give Example 116 as pale yellow solids (146 mg, 42% yield, 90% purity by $^1$H NMR). This sample was slurried in water (2 mL), filtered, slurried with TBME (3 mL) then dried. Example 116 was obtained as a pale yellow powder (106 mg, 30% yield over final three steps). $^1$H NMR (400 MHz, Methanol-d$_4$) δ 8.63 (s, 1H), 8.53 (s, 1H), 8.33 (d, J=1.6 Hz, 1H), 8.17 (s, 1H), 7.34 (dd, J=9.6, 2.6 Hz, 1H), 6.96 (t, J=6.8 Hz, 1H), 6.81 (dt, J=8.9, 4.5 Hz, 1H), 5.66 (q, J=6.4 Hz, 1H), 4.47 (t, J=10.6 Hz, 1H), 4.09 (s, 3H), 3.93-3.65 (m, 2H), 2.84 (s, 3H), 1.65 (d, J=6.4 Hz, 3H). LCMS ES m/z 423 [M+H]$^+$.

Preparation of (10R)-7-amino-12-fluoro-10,16-dimethyl-15-oxo-10,15,16,17-tetrahydro-8,4-(metheno)[1,2]oxazolo[4,5-h][2,5,11]benzoxadiazacyclotetradecine-3-carbonitrile (Example 117)

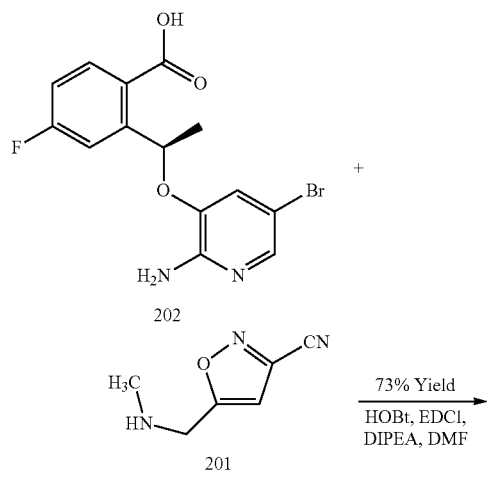

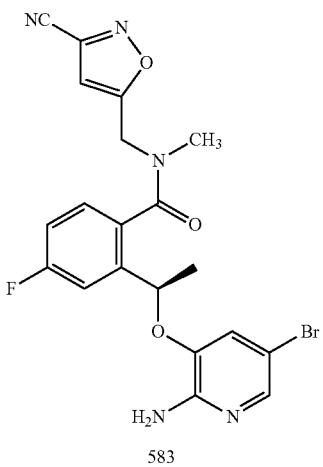

Step 1:

The procedure described in step 3 for Example 99 was used to prepare compound 583 (400 mg, 73%) as a colorless oil. $^1$H NMR (400 MHz, CDCl$_3$) δ 7.72-7.68 (s, 1H), 7.22-7.20 (m, 2H), 7.08-7.03 (m, 1H), 6.92 (s, 1H), 6.55-6.52 (s, 1H), 5.47-5.42 (m, 1H), 4.98-4.86 (dd, 2H), 4.75 (s, 2H), 2.88 (s, 3H) δ 1.66-1.64 (d, 3H)

Step 2:

The procedure described in step 3 for Example 99 was used to prepare Example 117 (4.2 mg, 3%) as a white solid. $^1$H NMR (400 MHz, Methanol-d$_4$) δ 7.79 (s, 1H), 7.56-7.59 (d, 1H), 7.39-7.49 (d, 1H), 7.12-7.21 (m, 1H), 6.89 (s, 1H), 5.79-5.71 (s, 1H), 4.7-4.65 (dd, 2H), 3.21 (s, 3H), 1.72 (s, 3H). LCMS m/z 394 [M+H]$^+$.

Preparation of 7-amino-12-fluoro-2-methyl-2,10,15, 17-tetrahydro-8,4-(metheno)pyrazolo-[4,3-h][2,11,5] benzodioxazacyclotetradecine-3-carbonitrile (Example 118)

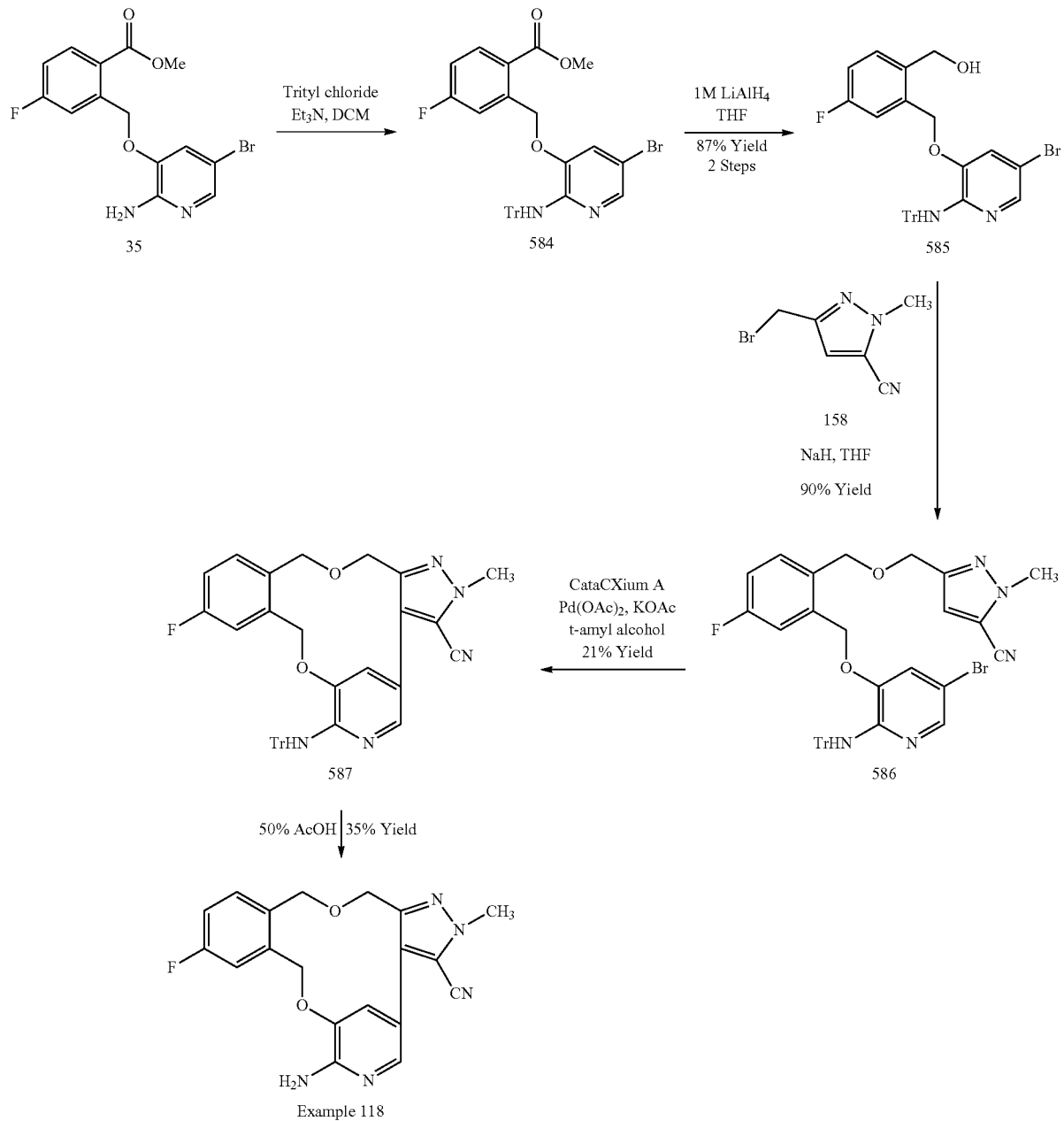

Example 118

Step 1:
The procedure described in step 1 for Example 104 was used to prepare compound 584 as an off off-white crystalline solid (5.23 g). $^1$H NMR (400 MHz, CDCl$_3$) δ 8.11 (dd, J=8.8, 5.8 Hz, 1H), 7.43 (dd, J=2.0, 0.9 Hz, 1H), 7.39-7.17 (m, 16H), 7.08 (ddd, J=8.7, 7.6, 2.7 Hz, 1H), 6.98 (d, J=2.0 Hz, 1H), 6.36 (s, 1H), 5.53 (s, 2H), 3.90 (s, 3H). LCMS ES m/z 597/599 [M+H]$^+$.

Step 2:
The procedure described in step 2 for Example 104 was used to prepare compound 585 as an off-white crystalline solid (3.86 g, 87%). $^1$H NMR (400 MHz, CDCl$_3$) δ 7.43 (d, J=2.0 Hz, 1H), 7.36 (dd, J=8.5, 5.6 Hz, 1H), 7.34-7.14 (m, 17H), 7.07-6.99 (m, 2H), 6.33 (s, 1H), 5.21 (s, 2H), 4.70 (d, J=5.6 Hz, 2H). LCMS ES m/z 569/571 [M+H]$^+$.

Step 3:
The procedure described in step 3 for Example 104 was used to prepare compound 586 as a colorless foam (1.23 g, 90%). $^1$H NMR (400 MHz, CDCl$_3$) δ 7.42 (dd, J=2.0, 0.9 Hz, 1H), 7.37-7.15 (m, 17H), 7.04-6.97 (m, 2H), 6.32 (s, 1H), 5.20 (s, 2H), 4.59 (s, 2H), 4.49 (s, 2H), 3.99 (s, 3H). LCMS ES m/z 766/768/770 [M+H]$^+$.

Step 4:
The procedure described in step 4 for Example 104 was used to prepare compound 587 (206 mg, 21%) as a yellow solid. $^1$H NMR (400 MHz, CDCl$_3$) δ 8.48 (d, J=1.9 Hz, 1H), 7.59 (d, J=1.8 Hz, 1H), 7.42-7.12 (m, 17H), 6.97 (td, J=8.1, 2.7 Hz, 1H), 6.32 (s, 1H), 5.60 (d, J=13.2 Hz, 1H), 5.34-5.16 (m, 2H), 4.46 (d, J=13.2 Hz, 1H), 4.29 (d, J=10.0 Hz, 1H), 4.03 (dd, J=12.8, 4.0 Hz, 1H), 3.95 (s, 3H). LCMS ES m/z 608 [M+H]+

Step 5:

The procedure described in step 5 for Example 104 was used to prepare Example 118 as a colorless solid (43 mg, 35%). ¹H NMR (400 MHz, Acetone-d₆) δ 8.60 (d, J=1.8 Hz, 1H), 7.80 (d, J=1.9 Hz, 1H), 7.50-7.43 (m, 2H), 7.05 (td, J=8.4, 2.8 Hz, 1H), 5.70 (d, J=13.6 Hz, 1H), 5.61 (s, 2H), 5.37 (d, J=12.1 Hz, 1H), 5.28 (d, J=13.1 Hz, 1H), 4.58 (d, J=12.3 Hz, 1H), 4.46 (d, J=10.6 Hz, 1H), 4.12 (d, J=10.5 Hz, 1H), 4.03 (s, 3H). LCMS ES m/z 366 [M+H]+.

Preparation of 7-amino-3-tert-butyl-1,10,16-trimethyl-16,17-dihydro-1H-8,4-(metheno)-pyrazolo[4,3-g]pyrido[2,3-l][1,4,10]oxadiazacyclotetradecin-15(10H)-one (Example 119 and 120)

Step 1:

The procedure described in step 1 for Example 104 was used to prepare compound 588 as a beige solid (5.82 g, quantitative). ¹H NMR (400 MHz, CDCl₃) δ 8.05 (dd, J=8.8, 5.8 Hz, 1H), 7.39-7.18 (m, 17H), 7.03 (ddd, J=8.7, 7.6, 2.7 Hz, 1H), 6.70 (d, J=2.0 Hz, 1H), 6.38 (s, 1H), 6.35 (q, J=6.4 Hz, 1H), 3.94 (s, 3H), 1.65 (d, J=6.2 Hz, 3H). LCMS ES m/z 611/613 [M+H]+.

Step 2:

The procedure described in step 2 for Example 104 was used to prepare compound 589 as a colorless solid, in two batches of slightly different purities (5.43 g, 82%). ¹H NMR (400 MHz, CDCl₃) δ 7.39-7.16 (m, 17H), 7.13 (dd, J=9.8, 2.7 Hz, 1H), 6.96 (td, J=8.2, 2.7 Hz, 1H), 6.93 (d, J=2.0 Hz, 1H), 6.37 (s, 1H), 5.70 (q, J=6.3 Hz, 1H), 4.79 (dd, J=12.3, 6.1 Hz, 1H), 4.70 (dd, J=12.3, 5.6 Hz, 1H), 1.75-1.69 (m, 1H), 1.66 (d, J=6.3 Hz, 3H). LCMS ES m/z 583/585 [M+H]+.

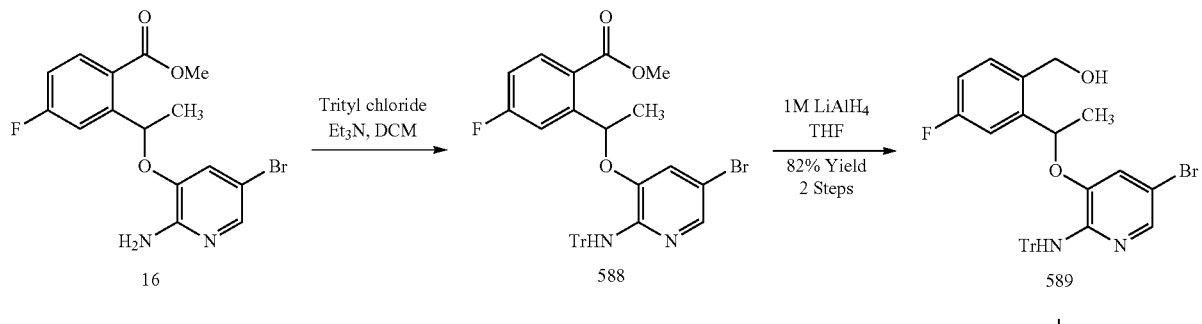

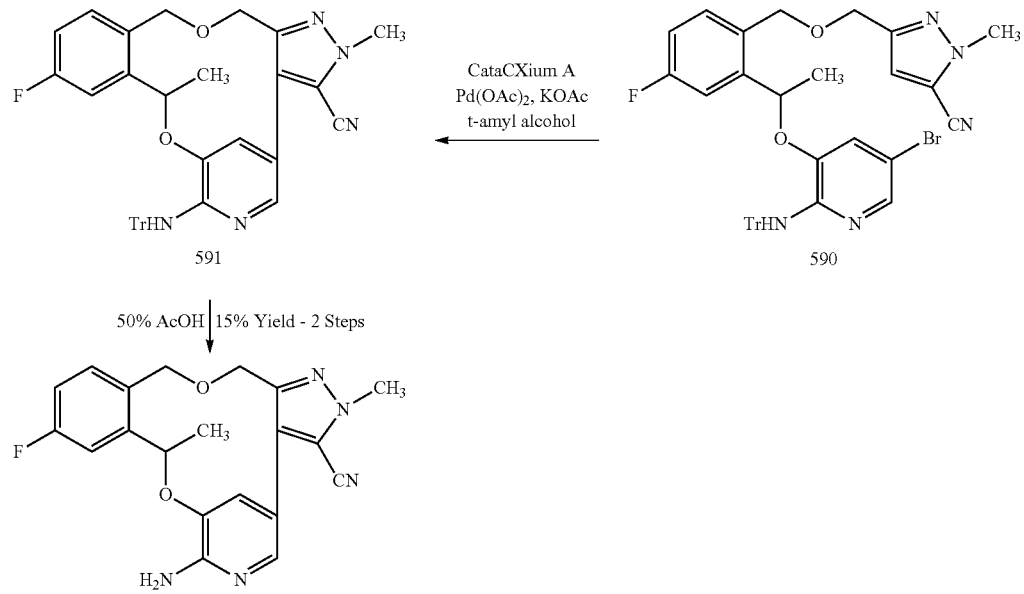

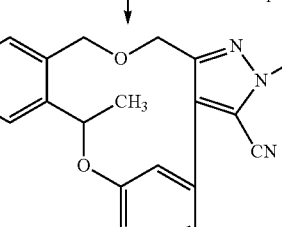

Example 119 and Example 120

Step 3:

The procedure described in step 3 for Example 104 was used to prepare compound 590 as a colorless solid (5.88 g, 88% yield). $^1$H NMR (400 MHz, CDCl$_3$) δ 7.39-7.17 (m, 17H), 7.11 (dd, J=9.7, 2.7 Hz, 1H), 6.95 (td, J=8.2, 2.7 Hz, 1H), 6.85 (d, J=2.0 Hz, 1H), 6.37 (s, 1H), 5.67 (q, J=6.3 Hz, 1H), 4.65 (d, J=11.3 Hz, 1H), 4.60 (d, J=12.1 Hz, 1H), 4.53 (d, J=12.1 Hz, 1H), 4.53 (d, J=11.2 Hz, 1H), 4.01 (s, 3H), 1.62 (d, J=6.3 Hz, 3H). LCMS ES m/z 778/780/781 [M+H]$^+$.

Step 4:

The procedure described in step 4 for Example 104 was used to prepare compound 591 (1.19 g), which was used without any further purification. LCMS ES m/z 622 [M+H]$^+$.

Step 5:

The procedure described in step 5 for Example 104 was used to prepare a mixture of Example 119 and Example 120 as a colorless solid (185 mg, 15% yield over two steps). $^1$H NMR (400 MHz, DMSO-d$_6$) δ 8.34 (d, J=1.9 Hz, 1H), 7.63 (d, J=1.8 Hz, 1H), 7.55 (dd, J=10.5, 2.8 Hz, 1H), 7.38 (dd, J=8.5, 6.0 Hz, 1H), 7.08 (td, J=8.4, 2.8 Hz, 1H), 6.17 (s, 2H), 6.02-5.92 (m, 1H), 5.24 (d, J=12.0 Hz, 1H), 4.49 (d, J=12.1 Hz, 1H), 4.45 (d, J=10.7 Hz, 1H), 3.97 (s, 3H), 3.92 (d, J=10.7 Hz, 1H), 1.64 (d, J=6.2 Hz, 3H). LCMS ES m/z 380 [M+H]$^+$.

The chiral separation of 146 mg of the material was performed by preparative SFC on a Whelk-O1 (R,R) (250×4.6 mm I.D., 3 micron particle size) column, which was eluted with 20% methanol @ 140 bar CO$_2$ with a flow rate of 3 mL/min. Rt$_{(Peak\ 1)}$=4.51 minutes and Rt$_{(Peak\ 2)}$=6.00 minutes, and gave Peak 1 as a white solid (58 mg) and Peak 2 as a white solid (57 mg).

The solids resulting from both peaks were slurried in water, and dried overnight in the vacuum oven.

Example 119 (Peak 1): >99% ee (47 mg). $^1$H NMR (400 MHz, DMSO-d6) δ 7.63 (s, 1 H) 8.35 (s, 1 H) 7.55 (dd, J=10.39, 2.57 Hz, 1 H) 7.38 (dt, J=2.20 Hz, 1 H) 7.07 (dt, J=2.60 Hz, 1 H) 6.15 (s, 2 H) 5.91-6.01 (m, 1 H) 5.24 (d, J=12.10 Hz, 1H) 4.47 (dd, J=13.63, 11.68 Hz, 2H) 3.89-4.02 (m, 4 H) 1.65 (d, J=6.11 Hz, 3 H). LCMS APCI m/z 380 [M+H]$^+$.

Example 120 (Peak 2): ~98% ee (45 mg). $^1$H NMR (400 MHz, DMSO-d6) δ 8.34 (d, J=1.52 Hz, 1 H) 7.63 (d, J=1.52 Hz, 1 H) 7.55 (dd, J=10.48, 2.65 Hz, 1 H) 7.38 (dd, J=8.59, 6.06 Hz, 1H) 7.07 (dt, J=2.50 Hz, 1 H) 6.15 (s, 2 H) 5.97 (m, J=5.80 Hz, 1 H) 5.24 (d, J=11.87 Hz, 1 H) 4.47 (dd, J=14.02, 11.49 Hz, 2 H) 3.85-4.03 (m, 4 H) 1.65 (d, J=6.06 Hz, 3 H). LCMS APCI m/z 380 [M+H]$^+$.

Preparation of (10S)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Example 121)

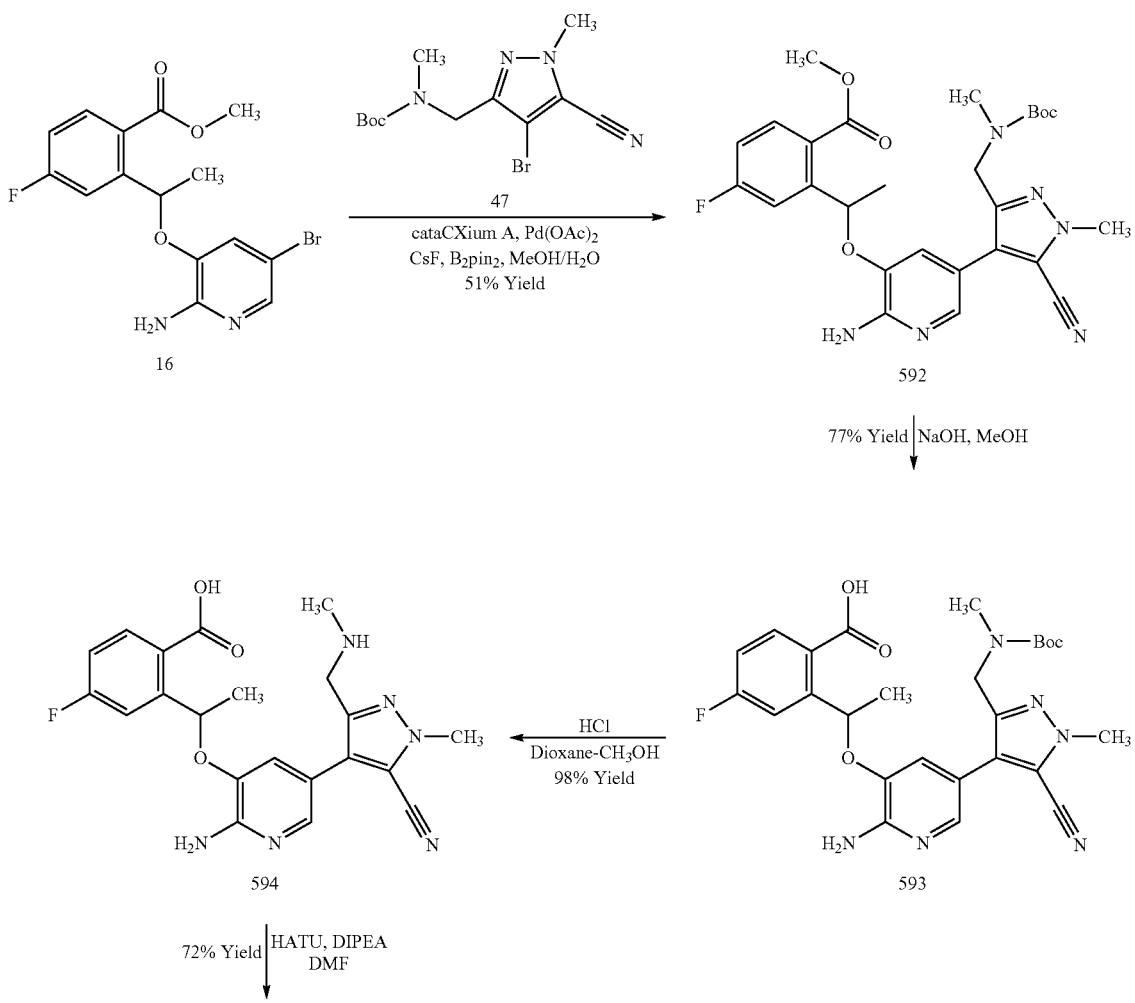

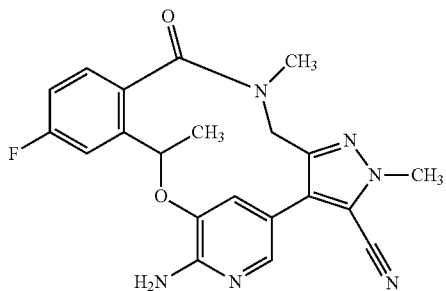

Example 2 and Example 121

Step 1:
The procedure described in step 1 for Example 2 was used to prepare compound 592 (800 mg, 51%) as a yellow foam. $^1$H NMR (400 MHz, CDCl$_3$) δ 8.02 (m, 1H), 7.58 (s, 1H), 7.23 (m, 1H), 7.03 (ddd, J=8.7, 7.6, 2.7 Hz, 1H), 6.88 (m, 1H), 6.50 (m, 1H), 6.0 (m, 1H), 5.48 (m, 1H), 4.05-4.65 (m, 2H), 3.98 (s, 3H), 3.94 (s, 3H), 2.60-2.80 (m, 4H), 1.70 (d, J=6.2 Hz, 3H), 1.25-1.45 (m, 9H). LCMS ES m/z 539 [M+H]$^+$.

Step 2:
The procedure described in step 2 for Example 2 was used to prepare compound 593 (1060 mg, 77% yield). $^1$H NMR (400 MHz, DMSO-d$_6$) δ 13.36 (s, 1H), 7.94 (t, J=6.9 Hz, 1H), 7.61-7.43 (m, 2H), 7.01-7.25 (m, 2H), 6.75-7.0 (m, 2H), 6.47 (m, 1H), 4.59-4.03 (m, 2H), 3.96 (s, 3H), 2.79-2.51 (m, 2H), 1.62 (d, J=6.2 Hz, 3H), 1.34-1.01 (m, 9H). LCMS ES m/z 525 [M+H]$^+$.

Step 3:
The procedure described in step 3 for Example 2 was used to prepare compound 594 (910 mg, 98%) as the hydrochloride salt. $^1$H NMR (400 MHz, DMSO-d$_6$) δ 13.38 (s, 1H), 9.36-9.16 (m, 2H), 7.98 (dd, J=8.8, 6.0 Hz, 1H), 7.80 (d, J=1.7 Hz, 1H), 7.58 (dd, J=10.3, 2.7 Hz, 1H), 7.26 (ddd, J=12.5, 6.6, 3.3 Hz, 2H), 7.20-7.07 (m, 2H), 6.54 (q, J=6.2 Hz, 1H), 4.24-4.07 (m, 2H), 4.05 (s, 3H), 2.18 (d, J=90.0 Hz, 2H), 1.64 (d, J=6.2 Hz, 3H). LCMS ES m/z 425 [M+H]$^+$.

Step 4:
The procedure described in step 4 for Example 2 was used to prepare a mixture of Example 2 and Example 121 as a white solid (570 mg, 72%). $^1$H NMR (400 MHz, DMSO-d$_6$) δ 7.65-7.54 (m, 2H), 7.46 (dd, J=8.6, 5.7 Hz, 1H), 7.18 (td, J=8.5, 2.7 Hz, 1H), 6.81 (d, J=1.9 Hz, 1H), 6.19 (d, J=3.4 Hz, 1H), 5.60 (dt, J=6.7, 3.4 Hz, 1H), 4.44 (d, J=14.4 Hz, 1H), 4.19 (d, J=14.4 Hz, 1H), 4.03 (s, 3H), 2.99 (s, 3H), 1.67 (d, J=6.2 Hz, 3H). LCMS ES m/z 407 [M+H]$^+$. The chiral separation of 570 mg of the material was performed by preparative SFC on a Whelk-O1 (R,R) (250×4.6 mm I.D., 3 micron particle size) column, which was eluted with 30% methanol @ 140 bar CO$_2$ with a flow rate of 3 mL/min. Rt$_{(Peak\ 1)}$=3.06 minutes and Rt$_{(Peak\ 2)}$=4.38 minutes, and gave Peak 1 as a white solid (263 mg) and Peak 2 as a white solid (262 mg).

Example 2 (Peak 1): >99% ee (263 mg).

Example 121 (Peak 2): ~98% ee (262 mg). $^1$H NMR (400 MHz, DMSO-d6) δ=7.63-7.55 (m, 2H), 7.46 (dd, J=5.8, 8.6 Hz, 1H), 7.17 (dt, J=2.8, 8.4 Hz, 1H), 6.81 (d, J=1.5 Hz, 1H), 6.17 (s, 2H), 5.66-5.55 (m, 1H), 4.43 (d, J=14.6 Hz, 1H), 4.19 (d, J=14.4 Hz, 1H), 4.03 (s, 3H), 2.99 (s, 3H), 1.68 (d, J=6.3 Hz, 3H). LCMS APCI m/z 407 [M+H]$^+$.

Preparation of 7-amino-12-fluoro-3-methoxy-1,16,17-trimethyl-16,17-dihydro-1H-8,4-(azeno)pyrazolo[4,3-h][2,5,11]benzoxadiazacyclotetradecin-15(10H)-one (Example 122 and 123)

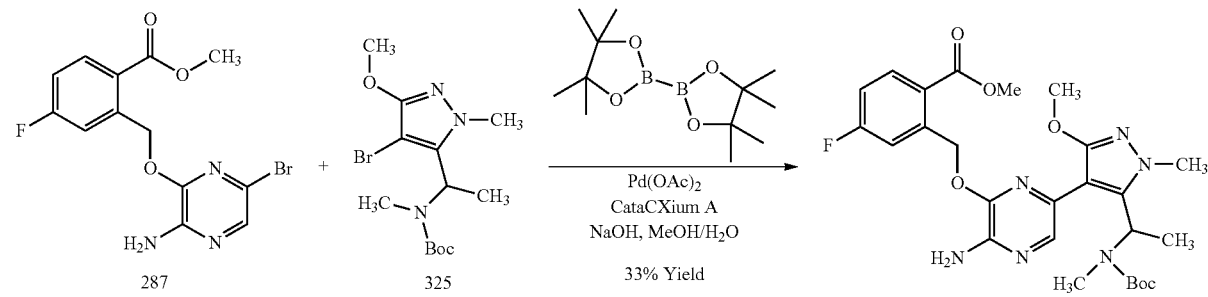

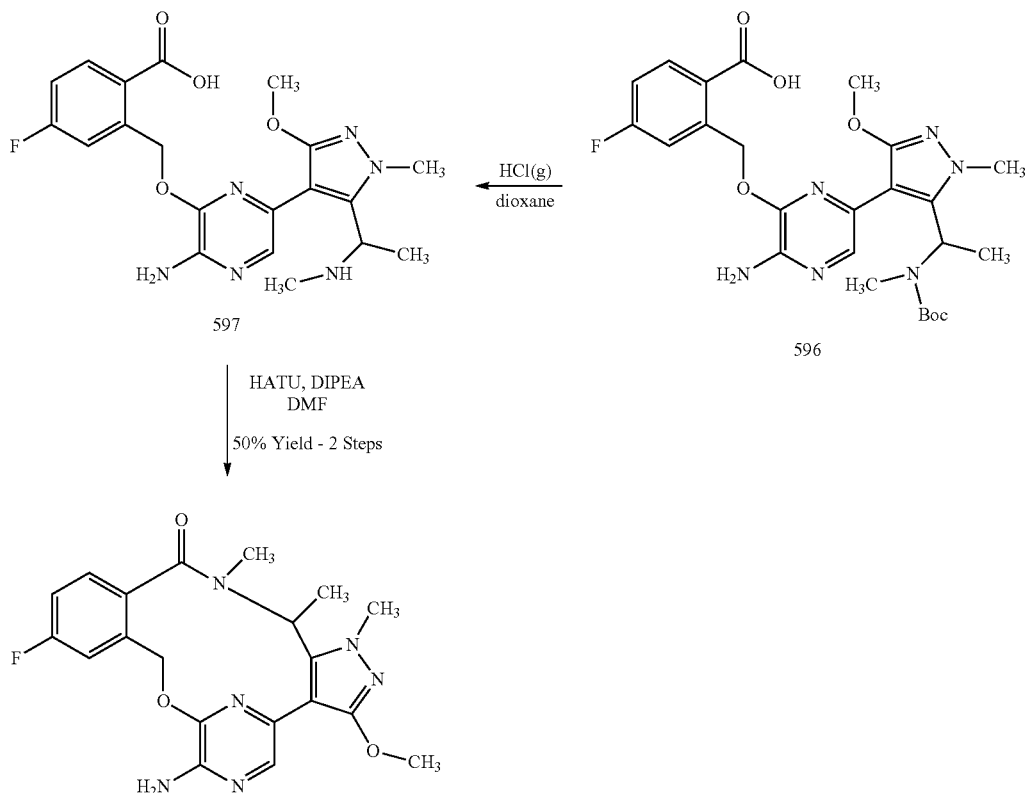

Example 122 and Example 123

Step 1:
The procedure described in step 1 for Example 86 and Example 87 was used to prepare compound 595 (500 mg, 33%, Rf=0.3) as a brown solid. LCMS m/z 567 [M+Na]+.

Step 2:
The procedure described in step 2 for Example 86 and Example 87 was used to prepare compound 596 (470 mg, 97%) as a white solid. LCMS ES m/z 531 [M+H]+.

Step 3:
The procedure described in step 3 for Example 86 and Example 87 was used to prepare compound 597, which was used in the next step directly. LCMS m/z 431 [M+H]+.

Step 4:
The procedure described in step 4 for Example 86 and Example 87 was used to prepare a mixture of Example 122 and Example 123 as an off-white solid (190.1 mg, 50% in two steps). $^1$H NMR (400 MHz, DMSO-d$_6$) δ 7.66 (s, 1H), 7.50-7.44 (m, 2H), 7.20-7.19 (m, 1H), 6.34 (s, 2H), 5.54-5.51 (d, 1H), 5.03-5.00 (d, 1H), 4.81-4.79 (d, 1H), 3.97 (s, 3H), 3.85 (s, 3H), 3.01 (s, 3H), 1.67-1.65 (d, 3H). LCMS m/z 413 [M+H]+.

The chiral separation of 70 mg of the material was performed by preparative SFC on a Chiralpak AD-H (250×4.6 mm I.D., 5 micron particle size) column, which was eluted with 5-40% ethanol (0.05% DEA) @ 140 bar CO$_2$ with a flow rate of 4 mL/min. Rt$_{(Peak\ 1)}$=6.93 minutes and Rt$_{(Peak\ 2)}$=8.52 minutes, and gave Peak 1 as a white solid (9 mg) and Peak 2 as a white solid (6 mg). Separation required two runs. Each peak on isolation equilibrated to a 90:10 mixture of atropisomers.

Example 122 (Peak 1): >99% ee. $^1$H NMR (400 MHz, Methanol-d$_4$) δ 7.79 (s, 1H), 7.54-7.51 (m, 2H), 7.16-7.11 (m, 1H), 5.68-5.65 (m, 1H), 5.07-5.01 (m, 2H), 4.06 (s, 3H), 3.98 (s, 3H), 3.15 (s, 3H), 1.78-1.76 (d, 3H). LCMS APCI m/z 413 [M+H]+.

Example 123 (Peak 2): ~98% ee. $^1$H NMR (400 MHz, Methanol-d$_4$) δ 7.79 (s, 1H), 7.54-7461 (m, 2H), 7.16-7.11 (m, 1H), 5.68-5.65 (m, 1H), 5.07-5.02 (m, 2H), 4.06 (s, 3H), 3.98 (s, 3H), 3.15 (s, 3H), 1.78-1.76 (d, 3H). LCMS APCI m/z 413 [M+H]+.

Preparation of 7-amino-12-fluoro-3-methoxy-1,16,17-trimethyl-16,17-dihydro-1H-8,4-(azeno)pyrazolo[4,3-h][2,5,11]benzoxadiazacyclotetradecin-15(10H)-one (Examples 124, 125 and 126)

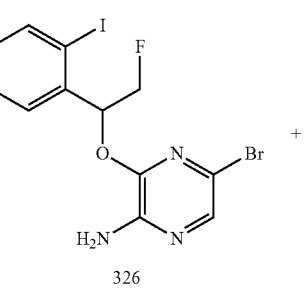

326

-continued

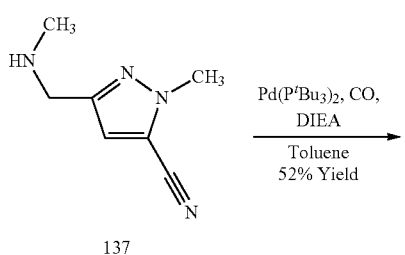

137

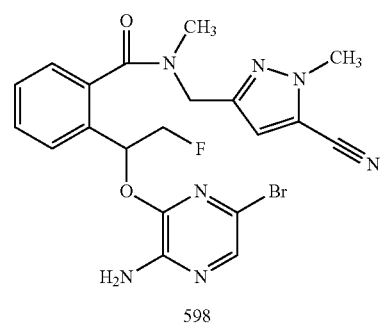

598

Pd(OAc)₂, CataCXium A
KOAc, t-AmOH
28% Yield

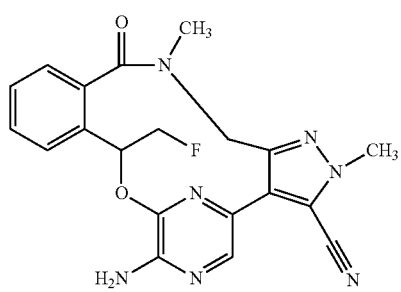

Example 124, Example 125 and Example 126

Step 1:

The procedure described in step 1 for Example 90 was used to prepare compound 598 as a white foam (117 mg, 52%). $^1$H NMR (400 MHz, Methanol-d₄, 2 rotamers) δ 7.63 (dd, J=7.0, 2.1 Hz, 1H), 7.54 and 7.51 (2×s, 1H), 7.50-7.30 (m, 3H), 6.98 and 6.79 (2×s, 1H), 6.33 (ddd, J=16.1, 7.6, 2.6 Hz) and 6.29-6.11 (m) (1H), 5.04 (d, J=15.0 Hz, 1H), 4.94-4.65 (m, 2H), 4.57 (d, J=15.0 Hz, 1H), 4.02 and 3.99 (2×s, 3H), 3.17 and 3.01 (2×s, 3H). LCMS ES m/z 488/490 [M+H]⁺

Step 2:

The procedure described in step 2 for Example 90 was used to prepare Example 124 as a colorless solid (26 mg, 28%). $^1$H NMR (400 MHz, Acetone-d₆) δ 7.90 (s, 1H), 7.65 (dd, J=7.9, 1.8 Hz, 1H), 7.48-7.34 (m, 3H), 6.21 (ddd, J=17.7, 8.1, 2.3 Hz, 1H), 4.96 (ddd, J=48.6, 10.3, 8.2 Hz, 1H), 4.71 (ddd, J=46.2, 10.3, 2.3 Hz, 1H), 4.53 (d, J=13.6 Hz, 1H), 4.36 (d, J=13.6 Hz, 1H), 4.11 (s, 3H), 2.97 (s, 3H). LCMS ES m/z 408 [M+H]⁺

The chiral separation of 23 mg of the material was carried out by preparative SFC on a Whelk-O1 (R,R) (250×4.6 mm I.D., 5 micron particle size) column, which was eluted with 35% methanol @ 120 bar CO₂ with a flow rate of 62 mL/min. Rt$_{(Peak\ 1)}$=3.06 minutes and Rt$_{(Peak\ 2)}$=4.60 minutes, and gave Peak 1 as a white solid (8 mg) and Peak 2 as a white solid (8.23 mg).

Example 125 (Peak 1): >99% ee (−). $^1$H NMR (400 MHz, Acetone-d₆) δ 7.90 (s, 1H), 7.65 (dd, J=7.9, 1.8 Hz, 1H), 7.48-7.34 (m, 3H), 6.21 (ddd, J=17.7, 8.1, 2.3 Hz, 1H), 4.96 (ddd, J=48.6, 10.3, 8.2 Hz, 1H), 4.71 (ddd, J=46.2, 10.3, 2.3 Hz, 1H), 4.53 (d, J=13.6 Hz, 1H), 4.36 (d, J=13.6 Hz, 1H), 4.11 (s, 3H), 2.97 (s, 3H). LCMS ES m/z 408 [M+H]⁺

Example 126 (Peak 2): ~98% ee (+). $^1$H NMR (400 MHz, Acetone-d₆) δ 7.90 (s, 1H), 7.65 (dd, J=7.9, 1.8 Hz, 1H), 7.48-7.34 (m, 3H), 6.21 (ddd, J=17.7, 8.1, 2.3 Hz, 1H), 4.96 (ddd, J=48.6, 10.3, 8.2 Hz, 1H), 4.71 (ddd, J=46.2, 10.3, 2.3 Hz, 1H), 4.53 (d, J=13.6 Hz, 1H), 4.36 (d, J=13.6 Hz, 1H), 4.11 (s, 3H), 2.97 (s, 3H). LCMS ES m/z 408 [M+H]⁺

Preparation of 7-amino-12-fluoro-3-methoxy-1,16,17-trimethyl-16,17-dihydro-1H-8,4-(azeno)pyrazolo[4,3-h][2,5,11]benzoxadiazacyclotetradecin-15(10H)-one (Example 127 and Example 128)

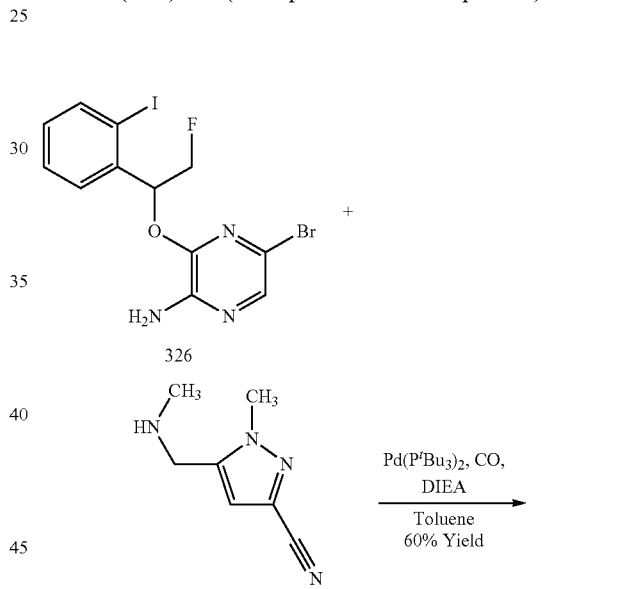

326

333

599

Pd(OAc)₂, CataCXium A
KOAc, t-AmOH
8% Yield

461

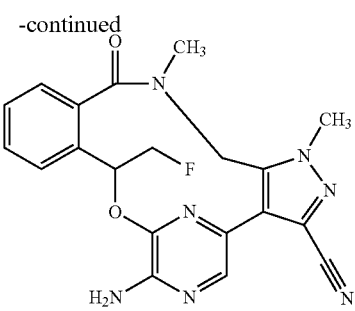

Example 127 and Example 128

Step 1:

The procedure described in step 1 for Example 90 was used to prepare compound 599 as white solid (723 mg, 60%). $^1$H NMR (400 MHz, DMSO-d$_6$) δ 7.75-7.65 (m, 1H), 7.58 (s, 1H), 7.52-7.39 (m, 3H), 7.09 (s, 1H), 6.84 (s, 2H), 6.20-6.00 (m, 1H), 5.06-4.64 (m, 4H), 3.99 (s, 3H), 2.92 (s, 3H). LCMS m/z 488/490 [M+H]$^+$.

Step 2:

The procedure described in step 2 for Example 90 was used to prepare a mixture of Example 127 and Example 128 as pale beige solids (33 mg, 8%). $^1$H NMR (400 MHz, DMSO-d$_6$) δ 7.87 (s, 1H), 7.67-7.56 (m, 1H), 7.53-7.35 (m, 3H), 6.79 (s, 2H), 6.01 (ddd, J=17.3, 8.3, 2.3 Hz, 1H), 4.98 (ddd, J=48.3, 10.2, 8.3 Hz, 1H), 4.76-4.53 (m, 2H), 4.36 (d, J=14.8 Hz, 1H), 4.08 (s, 3H), 2.91 (s, 3H). LCMS m/z 408 [M+H]$^+$.

The chiral separation of 27 mg of the material was performed by preparative SFC on a Whelk-O1 (R,R) (250×4.6 mm I.D., 5 micron particle size) column, which was eluted with 38% methanol @ 120 bar CO$_2$ with a flow rate of 62 mL/min. Rt$_{(Peak\ 1)}$=4.19 minutes and Rt$_{(Peak\ 2)}$=5.50 minutes, and gave Peak 1 as a white solid (11.99 mg) and Peak 2 as a white solid (10.99 mg).

Example 127 (Peak 1): >99% ee (−). $^1$H NMR (400 MHz, DMSO-d$_6$) δ 7.87 (s, 1H), 7.60 (d, J=6.8 Hz, 1H), 7.50-7.35 (m, 3H), 6.80 (br. s., 2H), 6.01 (dd, J=7.8, 17.4 Hz, 1H), 5.11-4.84 (m, 1H), 4.73-4.52 (m, 2H), 4.36 (d, J=15.1 Hz, 1H), 4.08 (s, 3H), 2.91 (s, 3H). LCMS APCI m/z 408 [M+H]$^+$ Example 128 (Peak 2): >99% ee (+). $^1$H NMR (400 MHz, DMSO-d$_6$) δ 7.87 (s, 1H), 7.60 (d, J=6.8 Hz, 1H), 7.50-7.35 (m, 3H), 6.80 (br. s., 2H), 6.01 (dd, J=7.8, 17.4 Hz, 1H), 5.11-4.84 (m, 1H), 4.73-4.52 (m, 2H), 4.36 (d, J=15.1 Hz, 1H), 4.08 (s, 3H), 2.91 (s, 3H). LCMS APCI m/z 408 [M+H]$^+$ Preparation of 12-fluoro-1,14-dimethyl-1,4,5,6,7,8-hexahydro-14H-16,20-(metheno)-pyrazolo-[4,3-g][1,14,11]benzodioxazacycloheptadecin-17-amine (Example 129/Example 130/Example 131)

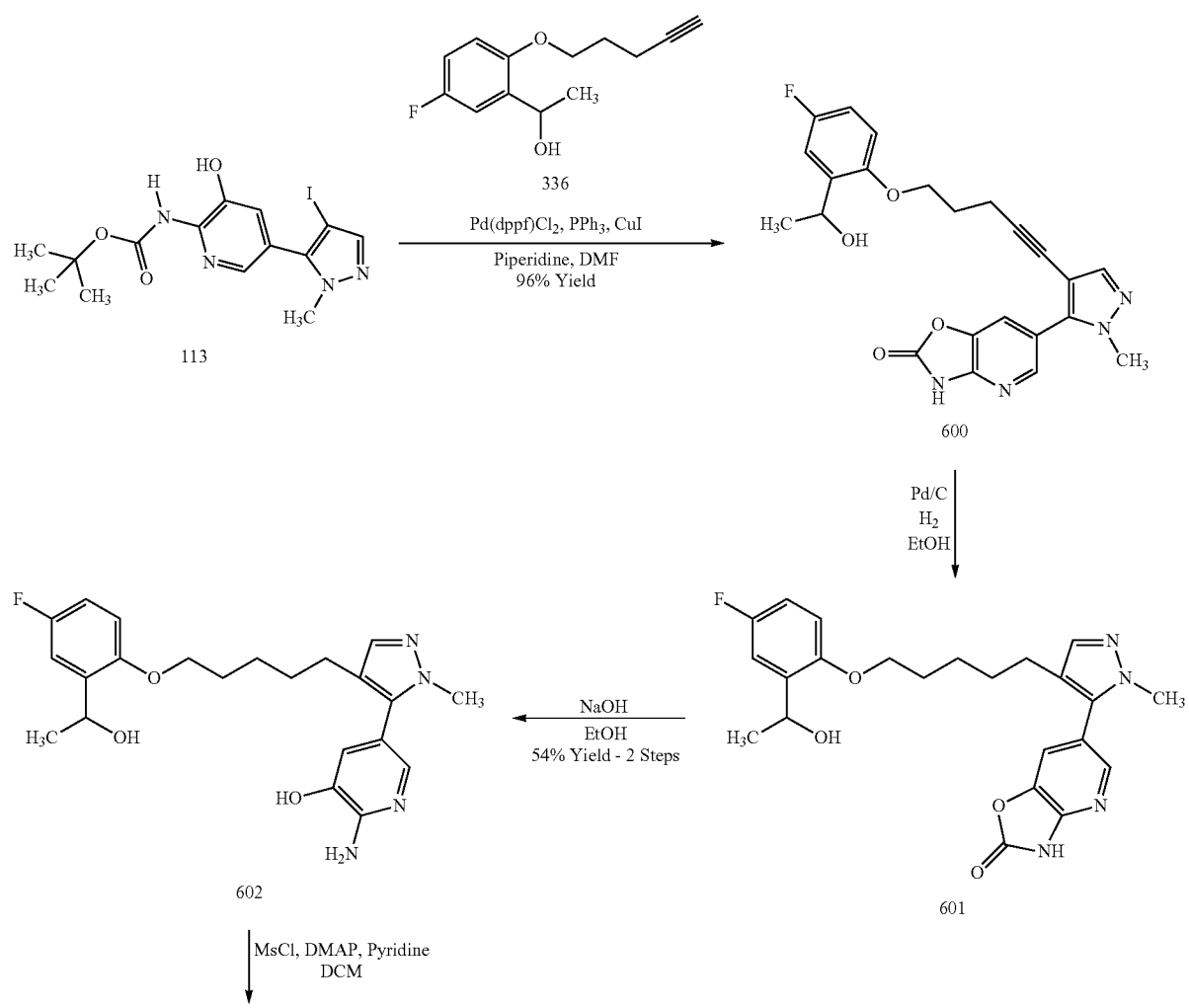

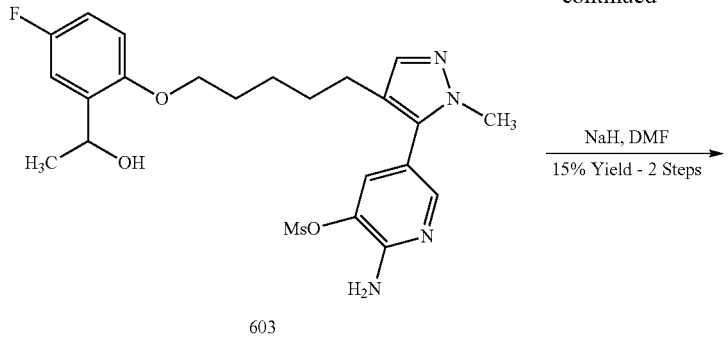

603

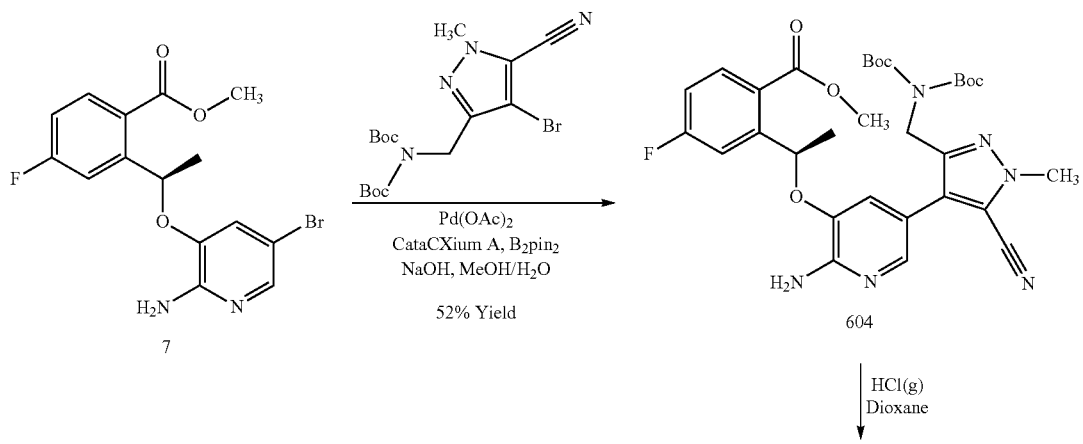

Example 129, Example 130 and Example 131

Step 1:
The procedure described in step 1 for Example 37 was used to prepare compound 600 as a yellow oil (709 mg, 96%). $^1$H NMR (400 MHz, DMSO-$d_6$) δ 8.05 (d, J=2.0 Hz, 1H), 7.63 (s, 1H), 7.45 (d, J=2.0 Hz, 1H), 7.16 (dd, J=9.7, 3.3 Hz, 1H), 6.93 (td, J=8.5, 3.3 Hz, 1H), 6.84 (dd, J=9.0, 4.6 Hz, 1H), 4.94 (q, J=6.3 Hz, 1H), 3.98 (q, J=5.7 Hz, 2H), 3.82 (s, 3H), 1.91 (p, J=6.6 Hz, 2H), 1.61 (q, J=6.0, 4.9 Hz, 2H), 1.23 (d, J=6.3 Hz, 3H). LCMS m/z 504 [M+H]$^+$ Step 2:
The procedure described in step 2 for Example 37 was used to prepare compound 601 as a yellow oil (603 mg). This was submitted to the next step without further purification. LCMS m/z 439 [M+H]$^+$ Step 3:
The procedure described in step 3 for Example 37 was used to prepare compound 602 as a white solid (350 mg, 54%). $^1$H NMR (400 MHz, DMSO-$d_6$) δ 7.40 (d, J=1.9 Hz, 1H), 7.31 (s, 1H), 7.15 (dd, J=9.7, 3.2 Hz, 1H), 6.95 (td, J=8.5, 3.2 Hz, 1H), 6.88 (dd, J=9.0, 4.6 Hz, 1H), 6.78 (d, J=2.0 Hz, 1H), 5.76 (s, 2H), 5.11 (d, J=4.4 Hz, 1H), 4.91 (p, J=6.0 Hz, 1H), 3.95-3.83 (m, 2H), 3.63 (s, 3H), 2.31 (t, J=7.4 Hz, 2H), 1.72-1.60 (m, 2H), 1.48 (d, J=7.5 Hz, 2H), 1.38 (d, J=7.1 Hz, 2H), 1.21 (d, J=6.3 Hz, 3H). LCMS m/z 413 [M+H]$^+$ Step 4:
The procedure described in step 4 for Example 37 was used to prepare compound 603 as a colorless oil (233 mg, quantitative). $^1$H NMR (400 MHz, CDCl$_3$) δ 7.91 (d, J=2.0 Hz, 1H), 7.46 (d, J=1.9 Hz, 1H), 7.38 (s, 1H), 7.12 (dd, J=9.2, 3.1 Hz, 1H), 6.87 (ddd, J=8.9, 7.9, 3.1 Hz, 1H), 6.74 (dd, J=8.9, 4.4 Hz, 1H), 5.25 (s, 2H), 5.05 (q, J=6.4 Hz, 1H), 4.00-3.86 (m, 2H), 3.74 (s, 3H), 3.56 (q, J=7.3 Hz, 2H), 3.28 (s, 3H), 2.39 (h, J=7.3 Hz, 2H), 1.77 (dd, J=14.1, 7.2 Hz, 2H), 1.44 (d, J=6.5 Hz, 3H). LCMS m/z 493 [M+H]$^+$ Step 5:
The procedure described in step 5 for Example 37 was used to prepare Example 129 as a white solid (29 mg, 15%). $^1$H NMR (400 MHz, CDCl$_3$) δ 7.47-7.38 (m, 1H), 7.34 (s, 1H), 7.03 (dd, J=8.9, 3.1 Hz, 1H), 6.91 (ddd, J=8.9, 7.9, 3.2 Hz, 1H), 6.79 (dd, J=9.0, 4.3 Hz, 1H), 6.54 (d, J=1.5 Hz, 1H), 5.73-5.65 (m, 1H), 4.29-4.16 (m, 2H), 3.94-3.84 (m, 2H), 3.76 (s, 3H), 2.64-2.43 (m, 1H), 2.13-1.99 (m, 1H), 1.83-1.66 (m, 2H), 1.63 (d, J=6.4 Hz, 3H), 1.33 (dd, J=9.7, 5.5 Hz, 2H). LCMS m/z 397 [M+H]$^+$ The chiral separation of 27 mg of the material was performed by preparative SFC on a Chiralpak AD-H (250×4.6 mm I.D., 5 micron particle size) column, which was eluted with 38% methanol @ 140 bar CO$_2$ with a flow rate of 3 mL/min. Rt$_{(Peak\ 1)}$=2.37 minutes and Rt$_{(Peak\ 2)}$=5.70 minutes, and gave Peak 1 as a white solid (4.9 mg) and Peak 2 as a white solid (4.9 mg).

Example 130 (Peak 1): >99% ee (+). $^1$H NMR (400 MHz, DMSO-$d_6$) δ 7.56 (s, 1H), 7.27 (s, 1H), 7.16 (d, J=8.6 Hz, 1H), 7.08-6.95 (m, 2H), 6.42 (s, 1H), 6.12 (s, 2H), 5.65 (d, J=6.5 Hz, 1H), 4.25 (br. s., 1H), 3.86 (t, J=10.6 Hz, 1H), 3.66 (s, 3H), 2.48-2.27 (m, 2H), 2.12-1.93 (m, 2H), 1.82-1.44 (m, 6H), 1.34-1.20 (m, 1H). LCMS APCI m/z 397 [M+H]$^+$ Example 131 (Peak 2): >99% ee (−). $^1$H NMR (400 MHz, DMSO-$d_6$) δ 7.56 (s, 1H), 7.27 (s, 1H), 7.16 (d, J=8.6 Hz, 1H), 7.08-6.95 (m, 2H), 6.42 (s, 1H), 6.12 (s, 2H), 5.65 (d, J=6.5 Hz, 1H), 4.25 (br. s., 1H), 3.86 (t, J=10.6 Hz, 1H), 3.66 (s, 3H), 2.48-2.27 (m, 2H), 2.12-1.93 (m, 2H), 1.82-1.44 (m, 6H), 1.34-1.20 (m, 1H). LCMS APCI m/z 397 [M+H]$^+$ Preparation of (10R)-7-amino-12-fluoro-2,10-dimethyl-15-oxo-10,15,16,17-tetrahydro-2H-8,4-(metheno)pyrazolo[4,3-h][2,5,11]benzoxadiazacyclotetradecine-3-carbonitrile (Example 132)

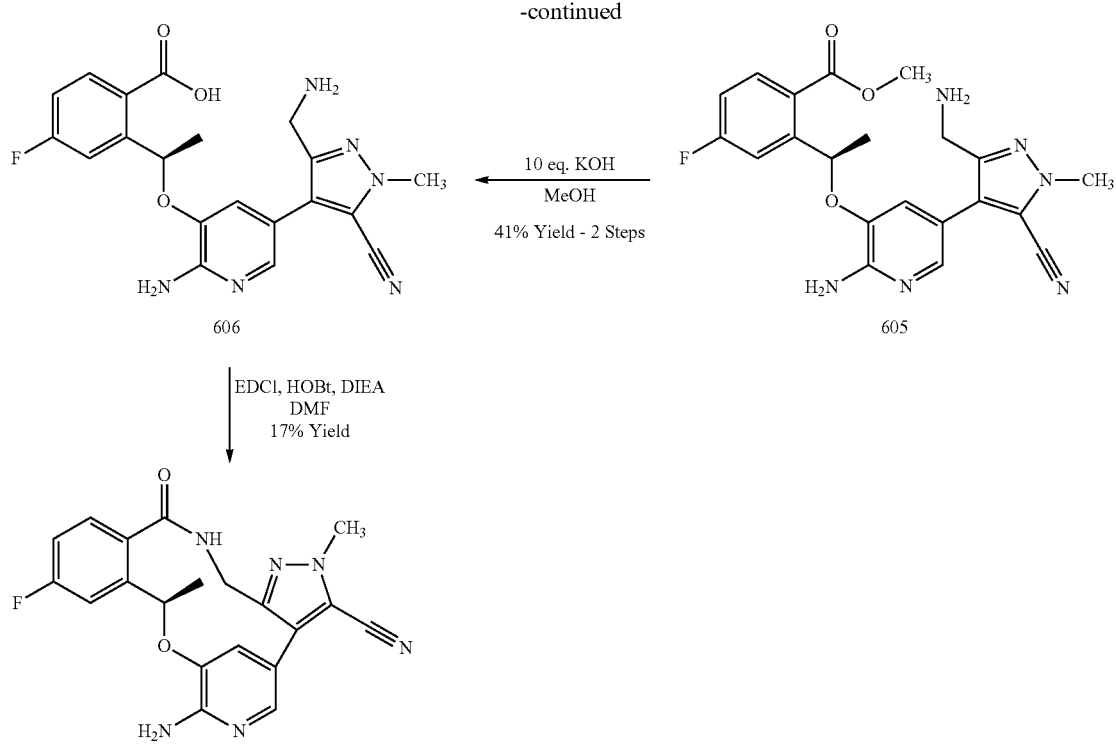

Example 132

Step 1:

The procedure described in step 1 for Example 88 was used to prepare compound 604 (340 mg, 52%) as a brown solid. LCMS m/z 647 [M+Na]⁺

Step 2:

The procedure described in step 2 for Example 88 was used to prepare compound 605, which was used for next step without any further purification. LCMS m/z 425 [M+H]⁺

Step 3:

The procedure described in step 3 for Example 88 was used to prepare compound 606 (70 mg, 41%) as a white solid. LCMS m/z 411 [M+H]⁺

Step 4:

To a solution of compound 606 (70 mg, 0.17 mmol) and DIPEA (33 mg, 0.256 mmol) in DMF (25 mL) was HOBt (35 mg, 0.256 mmol) and EDCI (33 mg, 0.256 mmol) in DMF (10 mL) at −35° C. After the addition, the resulting mixture was stirred at 80° C. for 72 hour. LC-MS showed the reaction was complete. The mixture was poured into ice-water (50 mL). The mixture was extracted with EtOAc (40 mL×5). The combined EtOAc layers were washed with brine (20 mL×5), dried over Na₂SO₄ and concentrated in vacuo to give a residue. The residue was purified via prep. TLC and then further purification by reverse phase preparative HPLC to give Example 132 (11.5 mg, 17%) as a white solid. ¹H NMR (400 MHz, Methanol-d₄—sample is a mixture of rotamers) δ 7.8-7.75 (m, 1H), 7.70-7.6 (m, 1H), 7.32-7.20 (m, 2H), 7.01-7.00 (m, 1H), 6.39-6.24 (m, 1H), 5.66-5.64 (d, 1H), 4.45-4.32 (d, 1H), 4.05-4.02 (s, 1H), 1.77-1.75 (d, 3H). LCMS m/z 392 [M+H]⁺

Preparation of (10R)-7-amino-3-ethyl-12-fluoro-10,16-dimethyl-16,17-dihydro-3H-4,8-(metheno)[1,2,3]triazolo[4,5-h][2,5,11]benzoxadiazacyclotetradecin-15(10H)-one (Example 133)

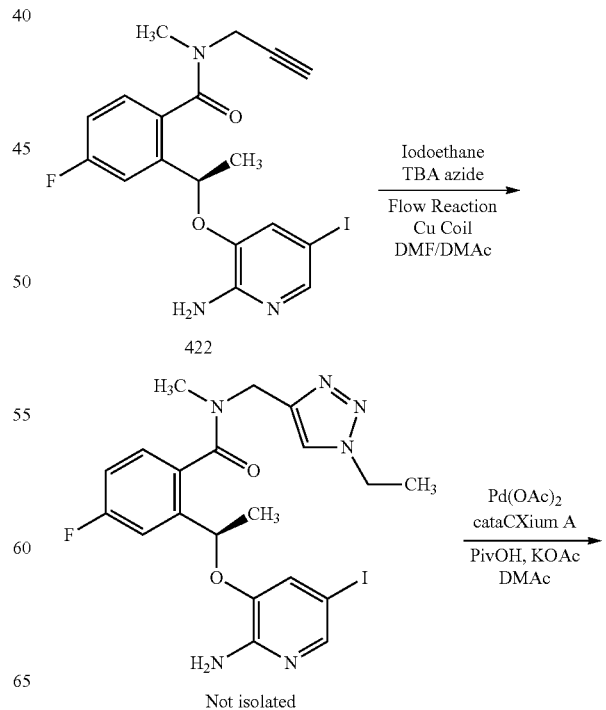

467

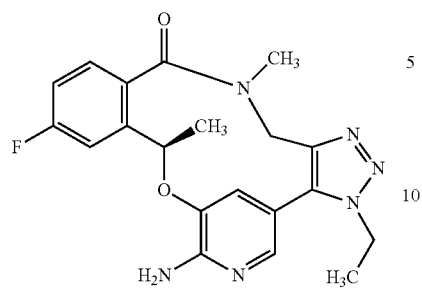

Example 133

Combining steps 3 and 4 of Example 41 in a library protocol gave Example 133 as a white solid (35.47 mg). $^1$H NMR (400 MHz, DMSO-$d_6$) δ 7.62-7.64 (m, 2 H), 7.44 (dd, J=5.7, 8.5 Hz, 1 H), 7.17 (dt, J=2.8, 8.5 Hz, 1 H), 6.77 (bs, 1 H), 6.35 (bs, 2 H), 5.65 (q, J=7.2, 3.6 Hz, 1H), 4.51 (d, J=14.4 Hz, 1 H), 4.35-4.46 (m, 2H), 4.13 (d, J=14.7 Hz, 1 H), 2.99 (s, 3 H), 1.67 (d, J=6.1 Hz, 3H), 1.40 (t, J=7.4 Hz, 3 H). LCMS APCI m/z 397 [M+H]$^+$.

Preparation of (10R)-7-amino-12-fluoro-10,16-dimethyl-3-(2-methylpropyl)-16,17-dihydro-3H-8,4-(metheno)[1,2,3]triazolo[4,5-h][2,5,11]benzoxadiazacyclotetradecin-15(10H)-one (Example 134)

468

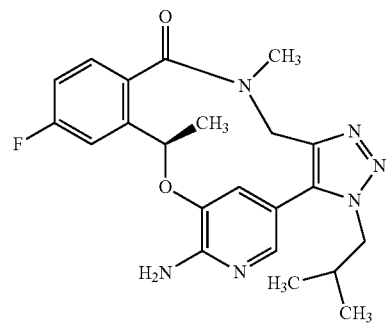

Example 134

Combining steps 3 and 4 of Example 41 in a library protocol gave Example 134 as a white solid (47.09 mg). $^1$H NMR (400 MHz, DMSO-$d_6$) δ 7.62-7.64 (m, 2 H), 7.43 (dd, J=5.7, 8.5 Hz, 1H), 7.16 (dt, J=2.8, 8.5 Hz, 1 H), 6.75 (s, 1 H), 6.33 (s, 2 H), 5.64 (q, J=7.2, 3.6 Hz, 1 H), 4.51 (d, J=14.4 Hz, 1 H), 4.27-4.31 (m, 1 H), 4.19-4.21 (m, 1 H), 4.13 (d, J=14.7 Hz, 1 H), 2.98 (s, 3 H), 2.03-2.07 (m, 1 H), 1.65 (d, J=6.1 Hz, 3 H), 0.75 (d, J=6.6 Hz, 6 H). LCMS APCI m/z 425 [M+H]$^+$.

Preparation of (10R)-7-amino-3-(cyclobutylmethyl)-12-fluoro-10,16-dimethyl-16,17-dihydro-3H-8,4-(metheno)[1,2,3]triazolo[4,5-h][2,5,11]benzoxadiazacyclotetradecin-15(10H)-one (Example 135)

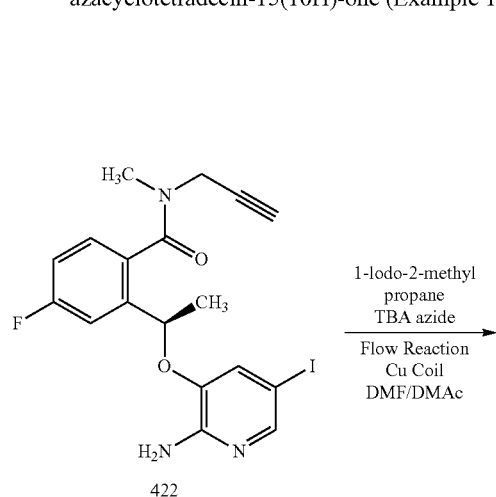

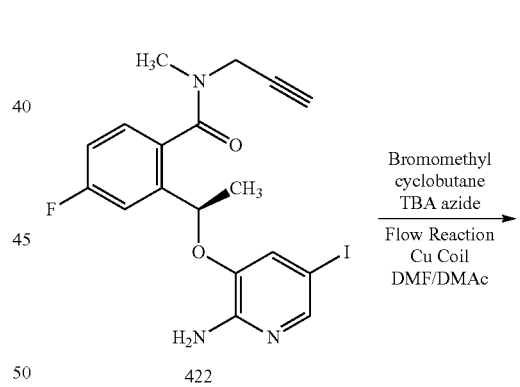

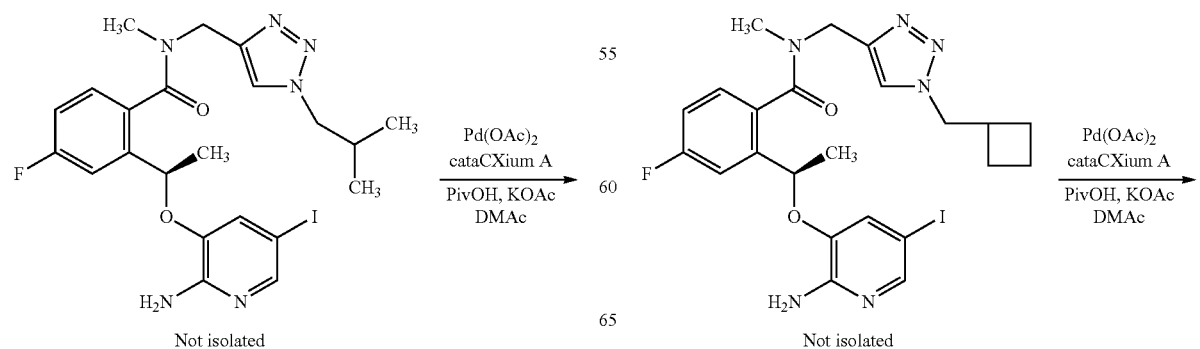

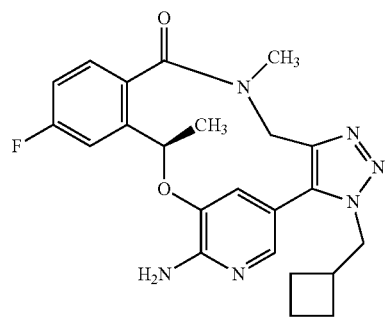

Example 135

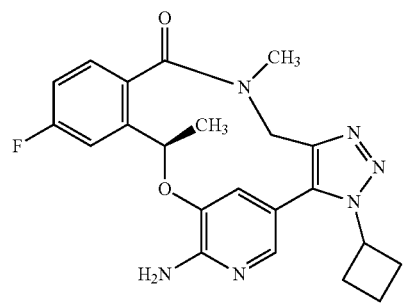

Example 136

Combining steps 3 and 4 of Example 41 in a library protocol gave Example 135 as a white solid (8.3 mg). $^1$H NMR (400 MHz, DMSO-d$_6$) δ 7.62-7.64 (m, 2 H), 7.43 (dd, J=5.7, 8.5 Hz, 1 H), 7.16 (dt, J=2.8, 8.5 Hz, 1 H), 6.77 (s, 1 H), 5.65 (q, J=7.2, 3.6 Hz, 1H), 4.51 (d, J=14.4 Hz, 1H), 4.3-8.4.47 (m, 2 H), 4.14 (d, J=14.7 Hz, 1H), 2.97 (s, 3 H), 2.71 (m, 1 H), 1.73-1.90 (m, 2H), 1.64-1.73 (m, 7 H). LCMS APCI m/z 437 [M+H]$^+$.

Preparation of (10R)-7-amino-3-cyclobutyl-12-fluoro-10,16-dimethyl-16,17-dihydro-3H-8,4-(metheno)[1,2,3]triazolo[4,5-h][2,5,11]benzoxadiazacyclotetradecin-15(10H)-one (Example 136)

Combining steps 3 and 4 of Example 41 in a library protocol gave Example 136 as a white solid (56.97 mg). $^1$H NMR (400 MHz, DMSO-d$_6$) δ 7.57-7.61 (m, 2 H), 7.44 (s, 1 H), 7.38-7.40 (m, 1 H), 7.12 (dt, J=2.8, 8.5 Hz, 1 H), 6.73 (s, 1 H), 6.31 (s, 2 H), 5.60 (q, J=7.2, 3.6 Hz, 1 H), 5.00 (m, 1 H), 4.47 (d, J=14.4 Hz, 1 H), 4.09 (d, J=14.7 Hz, 1 H), 2.95 (s, 3 H), 2.52 (m, 2 H), 2.65 (m, 1 H), 2.26 (m, 1 H), 1.82 (m, 1 H) 1.62 (d, J=6.1 Hz, 3 H), 0.78 (t, J=7.3 Hz, 3 H). LCMS APCI m/z 423 [M+H]$^+$.

Preparation of (10R)-7-amino-3-cyclopropyl-12-fluoro-10,16-dimethyl-16,17-dihydro-3H-8,4-(metheno)[1,2,3]triazolo[4,5-h][2,5,11]benzoxadiazacyclotetradecin-15(10H)-one (Example 137)

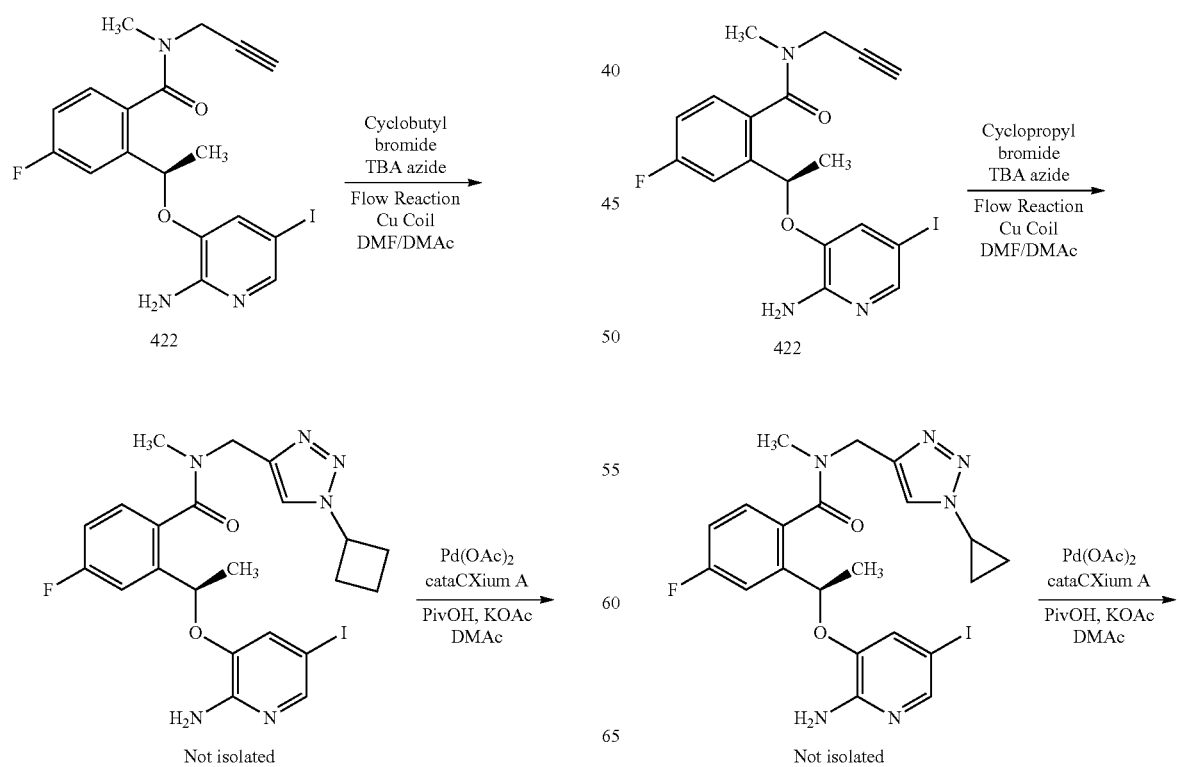

-continued

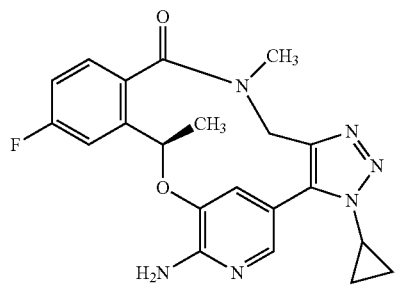

Example 137

Combining steps 3 and 4 of Example 41 in a library protocol gave Example 137 as a white solid (11.55 mg). $^1$H NMR (400 MHz, DMSO-d$_6$) δ 7.59-7.62 (m, 2 H), 7.45 (dd, J=5.7, 8.5 Hz, 1H), 7.16 (dt, J=2.8, 8.5 Hz, 1 H), 6.76 (s, 1 H), 6.35 (s, 2 H), 6.01-6.05 (m, 1 H), 5.62 (q, J=7.2, 3.6 Hz, 1 H), 5.19 (dd, J=1.2, 10.4 Hz, 1 H), 5.13-5.16 (m, 1 H), 4.98-4.99 (m, 1 H), 4.84 (dd, J=2.2, 18 Hz, 1 H), 4.53 (d, J=14.4 Hz, 1 H), 4.17 (d, J=14.7 Hz, 1 H), 3.00 (s, 3H), 1.67 (d, J=6.1 Hz, 3 H). LCMS APCI m/z 409 [M+H]$^+$.

Biological Examples
Wild-Type ALK and L1196M Mutant ALK Enzyme Assays

Wild-type ALK and L 196M mutant ALK enzyme inhibition was measured using a microfluidic mobility shift assay. The reactions were conducted in 50 μL volumes in 96-well plates, and contained preactivated human recombinant wild-type (1.3 nM) or L1196M (0.5 nM) ALK kinase domain (amino acids 1093-1411), 1.5 μM phosphoacceptor peptide, 5'FAM-KKSRGDYMTMQIG-CONH$_2$ (SEQ ID NO:1) (CPC Scientific, Sunnyvale, Calif.), test compound (11-dose 3-fold serial dilutions, 2% DMSO final) or DMSO only, 1 mM DTT, 0.002% Tween-20 and 5 mM MgCl$_2$ in 25 mM Hepes, pH 7.1, and were initiated by addition of ATP (60 μM final concentration, ~Km level) following a 20-min preincubation. The reactions were incubated for 1 h at room temperature, stopped by the addition of 0.1 M EDTA, pH 8, and the extent of reactions (~15-20% conversion with no inhibitor) was determined after electrophoretic separation of the fluorescently labeled peptide substrate and phosphorylated product on an LabChip EZ Reader II (Caliper Life Sciences, Hopkinton, Mass.). The inhibitors were shown to be ATP-competitive from kinetic and crystallographic studies. The Ki values were calculated by fitting the % conversion to the equation for competitive inhibition using non-linear regression method (GraphPad Prism, GraphPad Software, San Diego, Calif.) and experimentally measured ATP K$_m$=58 μM for wild-type and 55 μM for L1196M enzyme. ALK enzymes were produced in-house (baculoviral expression) and preactivated by auto-phosphorylation of 16 μM non-activated enzyme in the presence of 2 mM ATP, 10 mM MgCl$_2$ and 4 mM DTT in 20 mM Hepes, pH 7.5, at room temperature for ~1 h, and the full phosphorylation (~4 phosphates per protein molecule) of ALK kinase domain was verified by Q-TOF mass-spectrometry.

Cellular Phospho-ALK (Tyr1604) ELISA Assay for EML4-ALK:

Cell Lines:
NIH-3T3 EML4-ALK wt v1 and NIH-3T3 EML4-ALK v1 L1196M cells are human stable cell lines established at Pfizer—La Jolla, Calif. The cells were maintained at 37° C. in a 5% CO$_2$ incubator in DMEM (Invitrogen, Carlsbad, Calif.) medium supplemented with 1% L-glutamine, 1% penicillin and streptomycin, 1 ug/ml puromycin and 10% new born calf serum (NCS) in T-75 flasks.

Assay:
Cells were washed with PBS and re-suspended in DMEM medium supplemented with 0.5% NCS and 1% pen/strep and seeded into 96-well plates at density of 20,000 cells/well/100 μl and incubated in the incubator at 37° C. and 5% CO$_2$. After 20 hours of incubation, 100 μl of assay media (DMEM) in presence of designated PF-compounds concentrations or controls (DMSO) were added into plates and incubated for 1 hour in the incubator. Media was then removed and lysis buffer, containing phosphatase inhibitors and phenylmethanesulfonyl fluoride (PMSF), was added to wells and shaken at 4° C. for 30 minutes to generate protein lysates. Subsequently, a PathScan phospho-ALK (Tyr1604) chemiluminescent sandwich ELISA kit (Cell Signal Technology Inc., cat #7020) was used to assess the phosphorylation of ALK as follows:

A phospho-ALK (Tyr1604) rabbit antibody was coated onto the 96-well microplates. 50 μl of cell lysates were added to the antibody coated plate and incubated at room temperature for 2 hours. Following extensive washing with 0.1% Tween 20 in PBS to remove unbound materials, ALK mouse mAb was added to detect captured phospho-ALK (Tyr1604) and phospho-ALK fusion proteins. Anti-mouse IgG, HRP-linked antibody was then used to recognize the bound detection antibody. Finally, the chemiluminescent reagent was added and incubated for 10 minutes for signal development. The assay plates were read in the Envision plate reader in the luminescent mode. IC$_{50}$ values were calculated by a concentration-response curve fitting using a four-parameter analytic method.

Ki and IC$_{50}$ data obtained with the ALK enzymatic assays 1 and 2 and cellular phospho-ALK (Tyr1604) ELISA assay for WT EML4-ALK and L 196M EML4-ALK, disclosed above, are shown in the below table. In the table below, compounds that have no data indicate that those compounds were not tested against the assays listed in Table 1.

TABLE 1

| Example | WT ALK enzyme assay (Ki) | L1196M ALK enzyme assay (Ki) | ELISA assay for WT EML4-ALK (IC$_{50}$) | ELISA assay for L1196M EML4-ALK (IC$_{50}$) |
|---|---|---|---|---|
| 1 | <0.200 nM | 0.26 nM | 1.39 nM | 22.8 nM |
| 2 | <0.200 nM | 0.78 nM | 1.33 nM | 20.7 nM |
| 3 | <0.200 nM | 0.20 nM | 0.99 nM | 22.2 nM |
| 4 | <0.200 nM | 1.20 nM | 28.1 nM | 184 nM |
| 5 | 0.340 nM | 3.40 nM | 12.1 nM | 156 nM |
| 6 | <0.200 nM | 1.93 nM | 6.41 nM | 97.1 nM |
| 7 | NA | 14.0 nM | 155 nM | 2.68 μM |
| 8 | 0.90 nM | 10.0 nM | 12.1 nM | 0.68 μM |
| 9 | 0.20 nM | 1.06 nM | 0.35 nM | 9.29 nM |
| 10 | 13.0 nM | 34.0 nM | | |
| 11 | <0.200 nM | 1.10 nM | 1.21 nM | 27.7 nM |
| 12 | 10.0 nM | 29.0 nM | 34.9 nM | 0.70 μM |
| 13 | <0.200 nM | 0.29 nM | 0.70 nM | 13.9 nM |
| 14 | 17.0 nM | 61.2 nM | | |
| 15 | <0.200 nM | 2.50 nM | | |
| 16 | 213 nM | >2.27 μM | | |
| 17 | <0.200 nM | <0.100 nM | 0.30 nM | 4.25 nM |
| 18 | 5.20 nM | 24.0 nM | | |
| 19 | <0.200 nM | 0.90 nM | 4.89 nM | 110 nM |

TABLE 1-continued

| Example | WT ALK enzyme assay (Ki) | L1196M ALK enzyme assay (Ki) | ELISA assay for WT EML4-ALK (IC$_{50}$) | ELISA assay for L1196M EML4-ALK (IC$_{50}$) |
|---|---|---|---|---|
| 20 | 34.0 nM | 450 nM | | |
| 21 | <0.200 nM | <0.100 nM | 0.18 nM | 2.13 nM |
| 22 | 12.0 nM | 17.0 nM | 192 nM | 305 nM |
| 23 | <0.200 nM | 0.29 nM | 0.77 nM | 10.1 nM |
| 24 | 4.60 nM | 14.0 nM | | |
| 25 | <0.200 nM | 0.56 nM | 1.35 nM | 21.9 nM |
| 26 | 3.30 nM | 15.0 nM | 50.5 nM | 0.511 µM |
| 27 | 0.380 nM | 5.30 nM | 9.15 nM | 157 nM |
| 28 | <0.200 nM | 0.11 nM | <0.205 nM | 1.40 nM |
| 29 | 19.0 nM | 31.0 nM | | |
| 30 | <0.200 nM | 0.67 nM | 2.64 nM | 67.2 nM |
| 31 | 5.96 nM | 15.8 nM | 53.2 nM | 0.66 µM |
| 32 | <0.200 nM | <0.100 nM | 0.841 nM | 5.36 nM |
| 33 | 1.01 µM | >2.68 µM | | |
| 34 | 0.56 nM | 15.0 nM | 36.1 nM | 0.89 µM |
| 35 | <0.261 nM | 1.10 nM | 0.98 nM | 14.3 nM |
| 36 | <0.200 nM | 0.560 nM | 0.18 nM | 2.64 nM |
| 37 | 3.80 nM | 29.0 nM | 86.0 nM | 0.654 µM |
| 38 | 0.610 nM | 5.70 nM | 12.0 nM | 201 nM |
| 39 | 0.220 nM | <0.100 nM | 14.9 nM | 112 nM |
| 40 | 0.360 nM | 1.60 nM | 21.8 nM | 101 nM |
| 41 | 1.50 nM | 19.0 nM | 33.1 nM | 0.68 µM |
| 42 | 500 nM | 2.89 nM | | |
| 43 | 5.23 nM | 35.6 nM | 0.52 µM | 3.66 µM |
| 44 | 12.0 nM | 70.0 nM | | |
| 45 | >3.0 µM | 500 nM | | |
| 46 | 0.15 nM | 1.10 nM | 10.42 nM | 44.70 nM |
| 47 | 0.29 nM | 3.60 nM | 16.41 nM | 208.0 nM |
| 48 | 0.2 nM | 1.20 nM | 6.75 nM | 68.9 nM |
| 49 | 0.17 nM | 1.50 nM | 4.08 nM | 80.8 nM |
| 50 | 0.14 nM | 1.2 nM | 2.37 nM | 29.7 nM |
| 51 | 0.13 nM | 0.28 nM | 0.95 nM | 6.25 nM |
| 52 | 1.20 nM | 10.2 nM | 4.78 nM | 296.4 nM |
| 53 | 25.8 nM | 164.0 nM | | |
| 54 | <0.07 nM | 0.06 nM | 0.332 nM | 3.03 nM |
| 55 | <0.07 nM | 0.24 nM | 1.03 nM | 13.38 nM |
| 56 | 0.2 nM | 0.88 nM | 1.83 nM | 35.03 nM |
| 57 | 0.14 nM | 2.0 nM | 6.79 nM | 0.365 µM |
| 58 | <0.1 nM | <0.1 nM | 0.33 nM | 2.06 nM |
| 59 | | 14.4 nM | 12.98 nM | 155.93 nM |
| 60 | 4.6 nM | 21.5 nM | | |
| 61 | 0.15 nM | 0.17 nM | 4.82 nM | 17.07 nM |
| 62 | 137 nM | 253.0 nM | 7.605 µM | >10 µM |
| 63 | 0.12 nM | 0.13 nM | 1.95 nM | 8.70 nM |
| 64 | 34.4 nM | 33.3 nM | 0.407 µM | 1.19 µM |
| 65 | 0.88 nM | 9.8 nM | 9.36 nM | 0.313 µM |
| 66 | 19.3 nM | 122.0 nM | | |
| 67 | 411 nM | >1.5 µM | | |
| 68 | 207 nM | >1.5 µM | | |
| 69 | >3.0 µM | >3.0 µM | | |
| 70 | <0.16 nM | 0.96 nM | 6.52 nM | 78.54 nM |
| 71 | <0.249 nM | 3.73 nM | 10.16 nM | 169.09 nM |
| 72 | 5.1 nM | 28.0 nM | 0.347 µM | 4.266 µM |
| 73 | 0.33 nM | 2.4 nM | 12.75 nM | 0.169 µM |
| 74 | 0.30 nM | 0.86 nM | 11.41 nM | 51.93 nM |
| 75 | 0.065 nM | 0.095 nM | 0.902 nM | 7.06 nM |
| 76 | 3.1 nM | 1.9 nM | 95.65 nM | 108.89 nM |
| 77 | 75.0 nM | 45.8 nM | 3.39 nM | 3.32 µM |
| 78 | 2.93 nM | 9.61 nM | 40.83 nM | 0.350 µM |
| 79 | 1.18 nM | 2.9 nM | 42.79 nM | 179.84 nM |
| 80 | >3.0 µM | >3.0 µM | | |
| 81 | <1.88 nM | 3.9 nM | 2.25 nM | 51.98 nM |
| 82 | <0.2 nM | 2.39 nM | 11.15 nM | 182.59 nM |
| 83 | 47.6 nM | 74 nM | | |
| 84 | 29.3 nM | 90.2 nM | | |
| 85 | 0.070 nM | 0.13 nM | 0.55 nM | 6.72 nM |
| 86 | <0.2 nM | 0.10 nM | 0.45 nM | 2.57 nM |
| 87 | 270.0 nM | 51.0 nM | | |
| 88 | 0.2 nM | 0.39 nM | 15.51 nM | 190.94 nM |
| 89 | 0.339 nM | 0.275 nM | 6.43 nM | 56.05 nM |
| 90 | 0.079 nM | 0.249 nM | 1.32 nM | 13.00 nM |
| 91 | 0.177 nM | 0.315 nM | 0.68 nM | 5.88 nM |
| 92 | 0.23 nM | 0.21 nM | 0.47 nM | 3.66 nM |
| 93 | 0.048 nM | 0.3 nM | 3.23 nM | 31.67 nM |
| 94 | 0.93 µM | 0.698 µM | | |
| 95 | 0.35 nM | 1.9 nM | 10.37 nM | 169.25 nM |
| 97 | 3.50 nM | 24.7 nM | | |
| 98 | 0.115 nM | 0.404 nM | 2.21 nM | 32.28 nM |
| 99 | 3.2 nM | 11.7 nM | 52.38 nM | 0.531 µM |
| 100 | 3.1 nM | 24.2 nM | 146.29 nM | 1.48 µM |
| 101 | 0.12 nM | 0.41 nM | 0.92 nM | 8.77 nM |
| 102 | 0.33 nM | 1.41 nM | 11.62 nM | 83.82 nM |
| 103 | 9.1 nM | 131.0 nM | | |
| 104 | 8.4 nM | 57.5 nM | | |
| 105 | 3.0 nM | 16.7 nM | 115.04 nM | 0.642 µM |
| 106 | >3 µM | >3 µM | | |
| 107 | 88.5 nM | 179.0 nM | | |
| 108 | <0.06 nM | <0.05 nM | 0.068 nM | 0.50 nM |
| 109 | 8.1 nM | 4.7 nM | 11.029 nM | 55.56 nM |
| 110 | 0.56 nM | 7.3 nM | 9.99 nM | 0.447 µM |
| 111 | 0.059 nM | 0.54 nM | 1.42 nM | 32.49 nM |
| 112 | 0.32 nM | 3.4 nM | 9.67 nM | 247.76 nM |
| 113 | 0.20 nM | 0.46 nM | 0.68 nM | 9.56 nM |
| 114 | 0.271 nM | 1.36 nM | 3.29 nM | 78.24 nM |
| 115 | <0.08 nM | 0.09 nM | 0.96 nM | 8.18 nM |
| 116 | >1.5 µM | >3 µM | >10 µM | >10 µM |
| 117 | 2.18 nM | 17.8 nM | 35.22 nM | 393.0 nM |
| 118 | 17.8 nM | 64.7 nM | 217.23 nM | 1.402 µM |
| 119 | 1.6 nM | 13.4 nM | 7.79 nM | 264.0 nM |
| 120 | 146.0 nM | 0.821 µM | 2.11 µM | >10 µM |
| 121 | 132.0 nM | 273.0 nM | | |
| 122 | 0.27 nM | 0.70 nM | 9.27 nM | 52.31 nM |
| 123 | 205.0 nM | 333.0 nM | 4.79 µM | >10 µM |
| 124 | 2.10 nM | 7.4 nM | 56.17 nM | 0.873 µM |
| 125 | 0.11 nM | 0.49 nM | 2.30 nM | 49.08 nM |
| 126 | 0.54 µM | 1.07 µM | | |
| 127 | 0.099 nM | 0.52 nM | 2.50 nM | 64.97 nM |
| 128 | 138.0 nM | 386.0 nM | | |
| 129 | 353.0 nM | >1.5 µM | | |
| 130 | >3 µM | >3 µM | | |
| 131 | 78.3 nM | 0.794 µM | | |
| 132 | 3.32 nM | 16.52 nM | 35.27 nM | 0.892 µM |
| 133 | 3.06 nM | 32.75 nM | 95.77 nM | 0.997 µM |
| 134 | 3.0 nM | 20.5 nM | | |
| 135 | 2.1 nM | 12.6 nM | 45.89 nM | 0.814 µM |
| 136 | 0.6 nM | 4.8 nM | 28.47 nM | 0.419 µM |
| 137 | 6.1 nM | 72.4 nM | | 2.28 µM |

All publications and patent applications cited in the specification are herein incorporated by reference as if each individual publication or patent application were specifically and individually indicated to be incorporated by reference. Although the foregoing invention has been described in some detail by way of illustration and example, it will be readily apparent to those of ordinary skill in the art in light of the teachings of this invention that certain changes and modifications may be made thereto without departing from the spirit or scope of the appended claims.

We claim:
1. A compound of formula (VI)

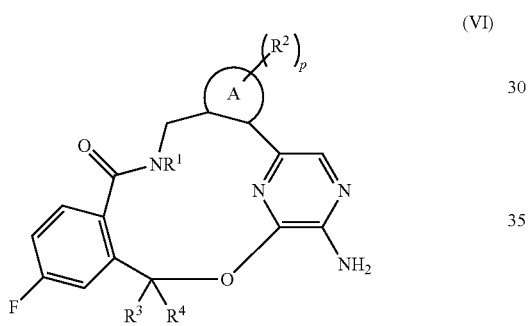

wherein:
A is a ring selected from $C_6$-$C_{12}$ aryl and 5-6 membered heteroaryl;
$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —S(O)$_r$$R^9$, —S(O)$_2$NR$^9$R$^{10}$, —S(O)$_2$OR$^9$, —NO$_2$, —CN, —OR$^9$, —C(O)R$^9$, —OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR or —C(O)NR$^9$R$^{10}$;
each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_r$R$^7$, —S(O)$_2$NR$^7$R$^8$, —S(O)$_2$OR$^7$, —NO$_2$, —(CR$^5$R$^6$)$_q$NR$^7$R$^8$, —N(CR$^5$R$^6$)(CR$^5$R$^6$)$_q$NH$^7$R$^8$, —OR$^7$, —O(CR$^5$R$^6$)(CR$^5$R$^6$)$_q$OR$^7$, —O(CR$^5$R$^6$)(CR$^5$R$^6$)$_q$R$^7$, —CN, —C(O)R$^7$, —OC(O)R$^7$, —O(CR$^5$R$^6$)$_q$R$^7$, —NR$^7$C(O)R$^8$, —(CR$^5$R$^6$)$_q$C(O)OR$^7$, —(CR$^5$R$^6$)$_q$NR$^7$R$^8$, —C(=NR$^7$)NR$^7$R$^8$, —NR$^7$C(O)NR$^7$R$^8$, —NR$^7$S(O)$_2$R$^8$ and —(CR$^5$R$^6$)$_q$C(O)NR$^7$R$^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —S(O)$_r$R$^9$, —S(O)$_2$NR$^9$R$^{10}$, —S(O)$_2$OR$^9$, —NO$_2$, —OR$^9$, —CN, —C(O)R$^9$,—OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$—NR$^9$S(O)$_2$R$^{10}$or —C(O)NR$^9$R$^{10}$;

$R^3$ and $R^4$ are each independently selected from hydrogen, $C_1$-$C_6$ alkyl and $C_3$-$C_6$ cycloalkyl, wherein each hydrogen on $C_1$-$C_6$ alkyl and $C_3$-$C_6$ cycloalkyl may be independently optionally substituted by halogen, —OH, —$NH_2$, —S(O)$_r$R$^9$, —S(O)$_2$NR$^9$R$^{10}$, —S(O)$_2$OR$^9$, —NO$_2$, —CN, —OR$^9$, —C(O)R$^9$,—OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$or —C(O)NR$^9$R$^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —$NH_2$, —S(O)$_r$R$^9$, —S(O)$_2$NR$^9$R$^{10}$, —S(O)$_2$OR$^9$, —NO$_2$, —CN, —OR$^9$, —C(O)R$^9$,—OC(O)R$^9$, —NR$^9$C(O)R$^{10}$, —C(O)OR$^9$, —C(=NR$^9$)NR$^9$R$^{10}$, —NR$^9$C(O)NR$^9$R$^{10}$, —NR$^9$S(O)$_2$R$^{10}$and —C(O)NR$^9$R$^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —$NH_2$, —S(O)$_r$R$^9$, —S(O)$_2$NR$^9$R$^{10}$, —S(O)$_2$OR$^9$, —NO$_2$, —CN, —OR$^9$, —C(O)R$^9$, —OC(O)R$^9$,—NR$^9$C(O)R$^{10}$, —C(O)OR$^9$, —C(=NR$^9$)NR$^9$R$^{10}$, —NR —NR or —C(O)NR$^9$R$^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —$NH_2$, —S(O)$_r$R$^9$, —S(O)$_2$NR$^9$R$^{10}$, —S(O)$_2$OR$^9$, —NO$_2$, —OR$^9$, —CN, —C(O)

$R^9$, —OC(O)$R^9$, —$NR^9$C(O)$R^{10}$, —C(O)O$R^9$, —C(=$NR^9$)$NR^9R^{10}$, —$NR_9$S(O)$_2R_{10}$ or —C(O)$NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3; and each t is independently 0, 1 or 2;

or a pharmaceutically acceptable salt thereof.

2. The compound of claim 1, wherein $R^1$ is selected from the group consisting of hydrogen, $C_1$-$C_6$ alkyl, and $C_3$-$C_6$ cycloalkyl, or a pharmaceutically acceptable salt thereof.

3. The compound of claim 1, wherein each $R^2$ is independently selected from the group consisting of $C_1$-$C_6$ alkyl, $C_3$-$C_6$ cycloalkyl, —S(O)$_tR^7$, —S(O)$_2NR^7R^8$, —O(C$R^5R^6$)(C$R^5R^6$)$_qOR^7$, —O(C$R^5R^6$)(C$R^5R^6$)$_qR^7$ and —CN; wherein each hydrogen on said $C_1$-$C_6$ alkyl and $C_3$-$C_6$ cycloalkyl may be independently optionally substituted by halogen, —OH, —NH$_2$, —S(O)$_tR^9$, —S(O)$_2NR^9R^{10}$, —S(O)$_2OR^9$, —NO$_2$, —O$R^9$, —CN, —C(O)$R^9$, —OC(O)$R^9$, —$NR^9$C(O)$R^{10}$, —C(O)O$R^9$, —C(=$NR^9$)$NR^9R^{10}$, —$NR^9$C(O)$NR^9R^{10}$, —$NR^9$S(O)$_2R^{10}$ and —C(O)$NR^9R^{10}$, or a pharmaceutically acceptable salt thereof.

4. The compound of claim 1, wherein A is a ring selected from the group consisting of phenyl, pyridine, pyrimidine, pyridazine, pyrazine, triazine, pyrazole, imidazole, triazole, tetrazole, thiazole, isothiazole, oxazole and isoxazole, or a pharmaceutically acceptable salt thereof.

5. The compound of claim 1, wherein $R^3$ is methyl and $R^4$ is hydrogen, or a pharmaceutically acceptable salt thereof.

6. The compound of claim 1, wherein $R^1$ is methyl, or a pharmaceutically acceptable salt thereof.

7. The compound of claim 1, wherein A is a pyrazole ring, or a pharmaceutically acceptable salt thereof.

8. The compound of claim 1, which is (10R)-7-amino-12-fluoro-2,10,16-trimethyl-15-oxo-10,15,16,17-tetrahydro-2H-8,4-(azeno)pyrazolo[4,3-h][2,5,11]benzoxadiazacyclotetradecine-3-carbonitrile, or a pharmaceutically acceptable salt thereof.

9. A pharmaceutical composition comprising a compound of claim 1, or a pharmaceutically acceptable salt thereof, and a pharmaceutically acceptable carrier or excipient.

10. A compound of the formula (XVI)

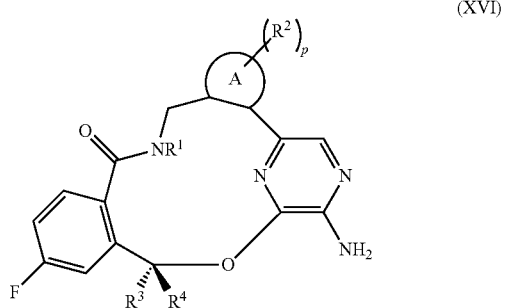

(XVI)

wherein:

A is a ring selected from $C_6$-$C_{12}$ aryl and 5-6 membered heteroaryl;

$R^1$ is selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_tR^9$, —S(O)$_2NR^9R^{10}$, —S(O)$_2OR^9$, —NO$_2$, —CN, —O$R^9$, —C(O)$R^9$, —OC(O)$R^9$, —$NR^9$C(O)$R^{10}$, —C(O)O$R^9$, —C(=$NR^9$)$NR^9R^{10}$, —$NR^9$C(O)$NR^9R^{10}$, —NR S(O)$_2R_{10}$ or —C(O)$NR^9R^{10}$;

each $R^2$ is independently selected from the group consisting of halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —S(O)$_tR^7$, —S(O)$_2NR^7R^8$, —S(O)$_2OR^7$, —NO$_2$, —(C$R^5R^6$)$_q$$NR^7R^8$, —N(C$R^5R^6$)(C$R^5R^6$)$_qNR_7R_8$—O$R^7$, —O(C$R^5R^6$)(C$R^5R^6$)$_qOR^7$, —O(C$R^5R^6$)(C$R^5R^6$)$_qNR^7R_8$, —CN, —C(O)$R^7$, —OC(O)$R^7$, —O(C$R^5R^6$)$_qR^7$, —$NR^7$C(O)$R^8$, —(C$R^5R^6$)$_qC(O)OR^7$, —(C$R^5R^6$)$_qNR^7R^8$, —C(=$NR^7$)$NR^7R^8$, —$NR^7$C(O)$NR^7R^8$, —$NR^7$S(O)$_2R^8$ and —(C$R^5R^6$)$_qC(O)NR^7R^8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_tR^9$, —S(O)$_2NR^9R^{10}$, —S(O)$_2OR^9$, —NO$_2$, —O$R^9$, —CN, —C(O)$R^9$, —OC(O)$R^9$, —$NR^9$C(O)$R^{10}$, —C(O)O$R^9$, —C(=$NR^9$)$NR^9R^{10}$, —$NR^9$C(O)$NR^9R^{10}$, —$NR^9$S(O)$_2R^{10}$ or —C(O)$NR^9R^{10}$;

$R^3$ is $C_1$-$C_6$ alkyl or $C_3$-$C_6$ cycloalkyl and $R^4$ is hydrogen, wherein each hydrogen on $C_1$-$C_6$ alkyl or $C_3$-$C_6$ cycloalkyl may be independently optionally substituted by halogen, —OH, —NH$_2$, —S(O)$_tR^9$, —S(O)$_2NR^9R^{10}$, —S(O)$_2OR^9$, —NO$_2$, —CN, —O$R^9$, —C(O)$R^9$, —OC(O)$R^9$, —$NR^9$C(O)$R^{10}$, —C(O)O$R^9$, —C(=$NR^9$)$NR^9R^{10}$, —$NR^9$C(O)$NR^9R^{10}$, —$NR^9$S(O)$_2R^{10}$ or —C(O)$NR^9R^{10}$;

each $R^5$ and $R^6$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-6 membered heteroaryl, —OH, —NH$_2$, —S(O)$_tR^9$, —S(O)$_2NR^9R^{10}$, —S(O)$_2OR^9$, —NO$_2$, —CN, —O$R^9$, —C(O)$R^9$, —OC(O)$R^9$, —$NR^9$C(O)$R^{10}$, —C(O)O$R^9$, —C(=$NR^9$)$NR^9R^{10}$, —$NR^9$C(O)$NR^9R^{10}$, —$NR^9$S(O)$_2R^{10}$ and —C(O)$NR^9R^{10}$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl may be independently optionally substituted by halogen, —OH, —NH$_2$, —S(O)$_tR^9$, —S(O)$_2NR^9R^{10}$, —S(O)$_2OR^9$, —NO$_2$, —CN, —O$R^9$, —C(O)$R^9$, —OC(O)$R^9$,—$NR^9$C(O)$R^{10}$, —C(O)O$R^9$, —C(=$NR^9$)$NR^9R^{10}$, —$NR^9$C(O)$NR^9R^{10}$, —$NR^9$S(O)$_2R^{10}$ or —C(O)$NR^9R^{10}$;

each $R^7$ and $R^8$ is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic and 5-6 membered heteroaryl may be independently optionally substituted by halogen, —OH, —NH$_2$, —S(O)$_tR^9$, —S(O)$_2NR^9R^{10}$, —S(O)$_2OR^9$, —NO$_2$, —O$R^9$, —CN, —C(O)$R^9$, —OC(O)$R^9$, —$NR^9$C(O)$R^{10}$, —C(O)O$R^9$, —C(=$NR^9$)$NR^9R^{10}$, —$NR^9$C(O)$NR^9R^{10}$, —$NR^9$S(O)$_2R^{10}$ or —C(O)$NR^9R^{10}$;

each $R^9$ and $R^{10}$ is independently selected from hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, and 5-6 membered heteroaryl;

p is 0, 1, 2, 3 or 4;

each q is independently 0, 1, 2 or 3; and each t is independently 0, 1 or 2;

or a pharmaceutically acceptable salt thereof.

11. The compound of claim 10, wherein $R^1$ is methyl, or a pharmaceutically acceptable salt thereof.

12. The compound of claim 10, wherein each $R^2$ is independently selected from the group consisting of $C_1$-$C_6$ alkyl, $C_3$-$C_6$ cycloalkyl, —S(O)$_t R^7$, —S(O)$_2$NR$^7$R$^8$, —OR$^7$, —O(CR$^5$R$^6$)(CR$^5$R$^6$)$_q$OR$^7$, —O(CR$^5$R$^6$)(CR$^5$R$^6$)$_q$, $R^7$ and —CN, or a pharmaceutically acceptable salt thereof.

13. The compound of claim 10, wherein A is a pyrazole ring, or a pharmaceutically acceptable salt thereof.

14. The compound of claim 10, wherein $R^3$ is methyl, or a pharmaceutically acceptable salt thereof.

15. The compound of claim 10, which is (10R)-7-amino-12-fluoro-2,10,16-trimethyl-15-oxo-10,15,16,17-tetrahydro-2H-8,4-(azeno) pyrazolo [4,3-h ][2,5,11]benzoxadiaza cyclotetradecine-3-carbonitrile, or a pharmaceutically acceptable salt thereof.

16. A pharmaceutical composition comprising a compound of claim 10, or a pharmaceutically acceptable salt thereof, and a pharmaceutically acceptable carrier or excipient.

17. A compound which is (10R)-7-amino-12-fluoro-2,10,16-trimethyl-15-oxo-10,15,16,17-tetrahydro-2H-8,4-(azeno)pyrazolo[4,3-h][2,5,11]benzoxadiaza cyclotetradecine-3-carbonitrile, or a pharmaceutically acceptable salt thereof.

18. A pharmaceutical composition comprising a compound of claim 17, or a pharmaceutically acceptable salt thereof, and a pharmaceutically acceptable carrier or excipient.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 5'FAM labeled Lysine
<220> FEATURE:
<221> NAME/KEY: MISC_FEATURE
<222> LOCATION: (13)..(13)
<223> OTHER INFORMATION: Glycine carboxamide

<400> SEQUENCE: 1

Lys Lys Ser Arg Gly Asp Tyr Met Thr Met Gln Ile Gly
1               5                   10